US008901133B2

(12) United States Patent
Ren et al.

(10) Patent No.: US 8,901,133 B2
(45) Date of Patent: Dec. 2, 2014

(54) HETEROCYCLIC COMPOUNDS AND USES THEREOF

(75) Inventors: Pingda Ren, San Diego, CA (US); Yi Liu, San Diego, CA (US); Liansheng Li, San Diego, CA (US); Katrina Chan, San Diego, CA (US); Troy Edward Wilson, San Marino, CA (US); Alfredo C. Castro, Winchester, MA (US); Catherine A. Evans, Somerville, MA (US); Daniel A. Snyder, Somerville, MA (US)

(73) Assignee: Infinity Pharmaceuticals, Inc., Cambridge, MA (US)

( * ) Notice: Subject to any disclaimer, the term of this patent is extended or adjusted under 35 U.S.C. 154(b) by 372 days.

(21) Appl. No.: 13/293,828

(22) Filed: Nov. 10, 2011

(65) Prior Publication Data

US 2012/0122838 A1   May 17, 2012

Related U.S. Application Data

(60) Provisional application No. 61/509,454, filed on Jul. 19, 2011, provisional application No. 61/412,384, filed on Nov. 10, 2010.

(51) Int. Cl.
*A61K 31/519* (2006.01)
*C07D 471/04* (2006.01)
*C07D 487/04* (2006.01)
*C07D 519/00* (2006.01)
*C07D 401/12* (2006.01)
*C07D 473/34* (2006.01)
*C07D 513/04* (2006.01)

(52) U.S. Cl.
CPC ............ *C07D 473/34* (2013.01); *C07D 519/00* (2013.01); *C07D 401/12* (2013.01); *C07D 471/04* (2013.01); *C07D 487/04* (2013.01); *C07D 513/04* (2013.01)
USPC ........ 514/258.1; 544/242; 544/255; 544/262; 514/247; 514/257

(58) Field of Classification Search
CPC ............................ A61K 31/519; C07D 471/04
USPC .......... 544/242, 253, 255, 262; 514/247, 257, 514/258.1
See application file for complete search history.

(56) References Cited

U.S. PATENT DOCUMENTS

| 4,547,508 A | 10/1985 | Konz et al. |
| 4,704,381 A | 11/1987 | Schaumann et al. |
| 5,240,941 A | 8/1993 | Bruneau |
| 5,310,731 A | 5/1994 | Olsson et al. |
| 5,364,862 A | 11/1994 | Spada et al. |
| 5,420,419 A | 5/1995 | Wood |
| 5,428,125 A | 6/1995 | Hefner, Jr. et al. |
| 5,442,039 A | 8/1995 | Hefner, Jr. et al. |
| 5,504,103 A | 4/1996 | Bonjouklian et al. |
| 5,506,347 A | 4/1996 | Erion et al. |
| 5,561,134 A | 10/1996 | Spada et al. |
| 5,563,257 A | 10/1996 | Zilch et al. |
| 5,593,997 A | 1/1997 | Dow et al. |
| 5,646,128 A | 7/1997 | Firestein et al. |
| 5,652,366 A | 7/1997 | Spada et al. |
| 5,654,307 A | 8/1997 | Bridges et al. |
| 5,665,721 A | 9/1997 | Bhagwat et al. |
| 5,674,998 A | 10/1997 | Boyer et al. |
| 5,686,455 A | 11/1997 | Adams et al. |
| 5,736,554 A | 4/1998 | Spada et al. |
| 5,747,235 A | 5/1998 | Farid et al. |
| 5,756,711 A | 5/1998 | Zilch et al. |
| 5,763,596 A | 6/1998 | Boyer et al. |
| 5,763,597 A | 6/1998 | Ugarkar et al. |
| 5,763,885 A | 6/1998 | Murphy et al. |
| 5,795,977 A | 8/1998 | Ugarkar et al. |
| 5,824,492 A | 10/1998 | Hiles et al. |
| 5,858,753 A | 1/1999 | Chantry et al. |
| 5,914,488 A | 6/1999 | Sone |
| 5,919,808 A | 7/1999 | Petrie et al. |
| 5,922,753 A | 7/1999 | Petrie et al. |
| 5,948,776 A | 9/1999 | Petrie et al. |
| 5,965,573 A | 10/1999 | Petrie et al. |
| 5,977,061 A | 11/1999 | Holy et al. |
| 5,981,533 A | 11/1999 | Traxler et al. |
| 5,985,589 A | 11/1999 | Chantry et al. |
| 5,990,169 A | 11/1999 | Petrie et al. |
| 5,994,358 A | 11/1999 | Petrie et al. |
| 6,001,839 A | 12/1999 | Calderwood et al. |
| 6,057,305 A | 5/2000 | Holy et al. |
| 6,084,095 A | 7/2000 | Bridges et al. |

(Continued)

FOREIGN PATENT DOCUMENTS

| CA | 1338379 C | 6/1996 |
| CN | 101602768 A | 12/2009 |
| EP | 773023 A1 | 5/1997 |
| EP | 1020445 B1 | 7/2000 |
| GB | 812366 A | 4/1959 |
| GB | 937725 A | 9/1963 |
| JP | 61109797 A | 5/1986 |
| JP | 5256693 A | 10/1993 |
| JP | 08295667 A | 11/1996 |
| JP | 09143163 A | 6/1997 |

(Continued)

OTHER PUBLICATIONS

Mayer et al., "Small molecule inhibitor of mitotic spindle bipolarity identified in a pheontype-cased screen", Science, 1999, vol. 286, pp. 971-974.

(Continued)

*Primary Examiner* — Golam M M Shameem
(74) *Attorney, Agent, or Firm* — Jones Day

(57) ABSTRACT

Compounds and pharmaceutical compositions that modulate kinase activity, including PI3 kinase activity, and compounds, pharmaceutical compositions, and methods of treatment of diseases and conditions associated with kinase activity, including PI3 kinase activity, are described herein.

54 Claims, No Drawings

(56) References Cited

U.S. PATENT DOCUMENTS

| | | |
|---|---|---|
| 6,093,737 A | 7/2000 | Anthony et al. |
| 6,127,121 A | 10/2000 | Meyer, Jr. et al. |
| 6,153,631 A | 11/2000 | Petrie et al. |
| 6,191,170 B1 | 2/2001 | Medina |
| 6,251,901 B1 | 6/2001 | Petrie et al. |
| 6,265,410 B1 | 7/2001 | Bridges et al. |
| 6,268,370 B1 | 7/2001 | Adams et al. |
| 6,312,894 B1 | 11/2001 | Hedgpeth et al. |
| 6,323,201 B1 | 11/2001 | Carson et al. |
| 6,342,514 B1 | 1/2002 | Petrie et al. |
| 6,350,741 B1 | 2/2002 | Golec et al. |
| 6,383,790 B1 | 5/2002 | Shokat |
| 6,384,039 B1 | 5/2002 | Fossa |
| 6,387,894 B1 | 5/2002 | Fossa |
| 6,390,821 B1 | 5/2002 | Shokat |
| 6,455,534 B2 | 9/2002 | Bridges et al. |
| 6,472,153 B1 | 10/2002 | Dempcy et al. |
| 6,482,623 B1 | 11/2002 | Vanhaesebroeck et al. |
| 6,485,906 B2 | 11/2002 | Meyer, Jr. et al. |
| 6,492,346 B1 | 12/2002 | Hedgpeth et al. |
| 6,506,769 B2 | 1/2003 | Snow et al. |
| 6,518,277 B1 | 2/2003 | Sadhu et al. |
| 6,521,417 B1 | 2/2003 | Shokat |
| 6,521,620 B1 | 2/2003 | Bridges et al. |
| 6,531,491 B1 | 3/2003 | Kania et al. |
| 6,534,524 B1 | 3/2003 | Kania et al. |
| 6,545,005 B1 | 4/2003 | Baxter et al. |
| 6,552,192 B1 | 4/2003 | Hanus et al. |
| 6,562,819 B2 | 5/2003 | Carson et al. |
| 6,583,161 B1 | 6/2003 | Medina |
| 6,613,798 B1 | 9/2003 | Porter et al. |
| 6,630,495 B1 | 10/2003 | Cooke et al. |
| 6,632,789 B1 | 10/2003 | June |
| 6,645,989 B2 | 11/2003 | Adams et al. |
| 6,649,631 B1 | 11/2003 | Orme et al. |
| 6,653,296 B1 | 11/2003 | Holy et al. |
| 6,653,306 B1 | 11/2003 | Alexander et al. |
| 6,660,744 B1 | 12/2003 | Hirst et al. |
| 6,660,845 B1 | 12/2003 | Gall et al. |
| 6,664,269 B2 | 12/2003 | Martin et al. |
| 6,667,300 B2 | 12/2003 | Sadhu et al. |
| 6,690,583 B1 | 2/2004 | Bergstedt et al. |
| 6,713,484 B2 | 3/2004 | Bridges et al. |
| 6,720,344 B2 | 4/2004 | Kerwin et al. |
| 6,734,187 B1 | 5/2004 | Tanaka et al. |
| 6,770,639 B2 | 8/2004 | Snow et al. |
| 6,777,425 B2 | 8/2004 | Burli et al. |
| 6,777,439 B2 | 8/2004 | Durden |
| 6,790,844 B2 | 9/2004 | Ueno et al. |
| 6,800,620 B2 | 10/2004 | Sadhu et al. |
| 6,849,420 B2 | 2/2005 | Vanhasebroeck et al. |
| 6,849,713 B2 | 2/2005 | Zhang et al. |
| 6,852,727 B2 | 2/2005 | Goulet et al. |
| 6,906,103 B2 | 6/2005 | Zhang et al. |
| 6,919,332 B2 | 7/2005 | Noe et al. |
| 6,921,763 B2 | 7/2005 | Hirst et al. |
| 6,949,535 B2 | 9/2005 | Sadhu et al. |
| 7,026,461 B1 | 4/2006 | Shokat |
| 7,041,676 B2 | 5/2006 | McDonald et al. |
| 7,049,116 B2 | 5/2006 | Shokat |
| 7,049,312 B1 | 5/2006 | Rafferty et al. |
| 7,064,218 B2 | 6/2006 | Dyatkina et al. |
| 7,071,355 B2 | 7/2006 | Leban et al. |
| 7,115,627 B2 | 10/2006 | Pinto et al. |
| 7,115,653 B2 | 10/2006 | Baxter et al. |
| 7,144,903 B2 | 12/2006 | Collins et al. |
| 7,157,487 B2 | 1/2007 | Nakayama et al. |
| 7,166,293 B2 | 1/2007 | Teng et al. |
| 7,208,601 B2 | 4/2007 | Mjalli et al. |
| 7,217,794 B2 | 5/2007 | Abdel-Meguid et al. |
| 7,244,741 B2 | 7/2007 | Simon et al. |
| 7,247,736 B2 | 7/2007 | Leban et al. |
| 7,262,204 B2 | 8/2007 | Collins et al. |
| 7,265,111 B2 | 9/2007 | Bigot et al. |
| 7,265,131 B2 | 9/2007 | Johnson et al. |
| 7,329,765 B2 | 2/2008 | Burli et al. |
| 7,332,497 B2 | 2/2008 | Hirst et al. |
| 7,348,427 B2 | 3/2008 | Burli et al. |
| 7,365,094 B2 | 4/2008 | Leban et al. |
| 7,384,967 B2 | 6/2008 | Polisetti et al. |
| 7,396,836 B2 | 7/2008 | Harada et al. |
| 7,414,036 B2 | 8/2008 | Sevillano et al. |
| 7,429,596 B2 | 9/2008 | Tanaka et al. |
| 7,439,254 B2 | 10/2008 | Bergnes |
| 7,449,477 B2 | 11/2008 | Barda et al. |
| 7,459,462 B2 | 12/2008 | Simon et al. |
| 7,459,472 B2 | 12/2008 | Mjalli et al. |
| 7,470,721 B2 | 12/2008 | Durden |
| 7,501,538 B2 | 3/2009 | Mjalli et al. |
| 7,534,797 B2 | 5/2009 | Arnold et al. |
| 7,541,373 B2 | 6/2009 | Polisetti et al. |
| 7,569,571 B2 | 8/2009 | Dong et al. |
| 7,572,913 B2 | 8/2009 | McKerracher et al. |
| 7,579,348 B2 | 8/2009 | Wang et al. |
| 7,585,868 B2 | 9/2009 | Knight et al. |
| 7,608,594 B2 | 10/2009 | Blagg et al. |
| 7,615,552 B2 | 11/2009 | Ono et al. |
| 7,622,451 B2 | 11/2009 | Blagg et al. |
| 7,678,803 B2 | 3/2010 | Huang et al. |
| 7,700,607 B2 | 4/2010 | Hu et al. |
| 7,745,485 B2 | 6/2010 | Durden |
| 7,932,260 B2 | 4/2011 | Fowler et al. |
| 8,106,146 B2 | 1/2012 | Benz et al. |
| 2001/0019829 A1 | 9/2001 | Nelson et al. |
| 2001/0027197 A1 | 10/2001 | Bridges et al. |
| 2002/0016460 A1 | 2/2002 | Snow et al. |
| 2002/0016976 A1 | 2/2002 | Shokat |
| 2002/0037856 A1 | 3/2002 | Zhang et al. |
| 2002/0102590 A1 | 8/2002 | Taing et al. |
| 2002/0127625 A1 | 9/2002 | Oxelius |
| 2002/0146690 A1 | 10/2002 | Meyer et al. |
| 2002/0147160 A1 | 10/2002 | Bhat et al. |
| 2002/0156081 A1 | 10/2002 | Hirst et al. |
| 2002/0161014 A1 | 10/2002 | Sadhu et al. |
| 2002/0173524 A1 | 11/2002 | Collins et al. |
| 2003/0001141 A1 | 1/2003 | Sun et al. |
| 2003/0008896 A1 | 1/2003 | Martin et al. |
| 2003/0018022 A1 | 1/2003 | Collins et al. |
| 2003/0022344 A1 | 1/2003 | Williams et al. |
| 2003/0064997 A1 | 4/2003 | Adams et al. |
| 2003/0073218 A1 | 4/2003 | Shokat |
| 2003/0083268 A1 | 5/2003 | Burli et al. |
| 2003/0113765 A1 | 6/2003 | Dempcy et al. |
| 2003/0119479 A1 | 6/2003 | Arima et al. |
| 2003/0119791 A1 | 6/2003 | Kerwin et al. |
| 2003/0139427 A1 | 7/2003 | Castelhano et al. |
| 2003/0143602 A1 | 7/2003 | Meyer et al. |
| 2003/0166929 A1 | 9/2003 | Snow et al. |
| 2003/0180924 A1 | 9/2003 | DeSimone |
| 2003/0186987 A1 | 10/2003 | Bridges et al. |
| 2003/0187001 A1 | 10/2003 | Calderwood et al. |
| 2003/0195211 A1 | 10/2003 | Sadhu et al. |
| 2003/0199516 A1 | 10/2003 | Moser et al. |
| 2003/0208800 A1 | 11/2003 | Eby et al. |
| 2003/0212113 A1 | 11/2003 | Dyatkina et al. |
| 2003/0232849 A1 | 12/2003 | Noe et al. |
| 2003/0235822 A1 | 12/2003 | Lokhov et al. |
| 2004/0039035 A1 | 2/2004 | Collins et al. |
| 2004/0043983 A1 | 3/2004 | Li |
| 2004/0067901 A1 | 4/2004 | Bhat et al. |
| 2004/0067915 A1 | 4/2004 | McMahon et al. |
| 2004/0072766 A1 | 4/2004 | June |
| 2004/0072788 A1 | 4/2004 | Bhat et al. |
| 2004/0102423 A1 | 5/2004 | MacLaughlan et al. |
| 2004/0102437 A1 | 5/2004 | Takami et al. |
| 2004/0110717 A1 | 6/2004 | Carroll et al. |
| 2004/0110945 A1 | 6/2004 | Nakayama et al. |
| 2004/0116689 A1 | 6/2004 | Gall et al. |
| 2004/0122235 A1 | 6/2004 | Polisetti et al. |
| 2004/0127434 A1 | 7/2004 | Bigot et al. |
| 2004/0176458 A1 | 9/2004 | Leban et al. |
| 2004/0176601 A1 | 9/2004 | Goulet et al. |
| 2004/0192758 A1 | 9/2004 | Leban et al. |
| 2004/0266780 A1 | 12/2004 | Sadhu et al. |

(56) References Cited

U.S. PATENT DOCUMENTS

| | | |
|---|---|---|
| 2005/0004149 A1 | 1/2005 | Harada et al. |
| 2005/0043239 A1 | 2/2005 | Douangpanya et al. |
| 2005/0049310 A1 | 3/2005 | Mjalli et al. |
| 2005/0054614 A1 | 3/2005 | Diacovo et al. |
| 2005/0059713 A1 | 3/2005 | Mjalli et al. |
| 2005/0085472 A1 | 4/2005 | Tanaka et al. |
| 2005/0101551 A1 | 5/2005 | Sevillano et al. |
| 2005/0124637 A1 | 6/2005 | Cheng et al. |
| 2005/0143317 A1 | 6/2005 | Abdel-Meguid et al. |
| 2005/0153997 A1 | 7/2005 | Simon et al. |
| 2005/0171148 A1 | 8/2005 | Mjalli et al. |
| 2005/0182045 A1 | 8/2005 | Nagase et al. |
| 2005/0187418 A1 | 8/2005 | Small et al. |
| 2005/0197340 A1 | 9/2005 | Arora et al. |
| 2005/0215579 A1 | 9/2005 | Simon et al. |
| 2005/0239809 A1 | 10/2005 | Watts et al. |
| 2005/0250770 A1 | 11/2005 | Ono et al. |
| 2005/0256066 A1 | 11/2005 | Abel et al. |
| 2005/0261317 A1 | 11/2005 | Sadhu et al. |
| 2005/0272751 A1 | 12/2005 | McKerracher et al. |
| 2006/0019988 A1 | 1/2006 | McDonald et al. |
| 2006/0069034 A1 | 3/2006 | Burli et al. |
| 2006/0079538 A1 | 4/2006 | Hallahan et al. |
| 2006/0106038 A1 | 5/2006 | Bouscary et al. |
| 2006/0116326 A1 | 6/2006 | Burli et al. |
| 2006/0135790 A1 | 6/2006 | Hyett et al. |
| 2006/0156485 A1 | 7/2006 | Lim |
| 2006/0183783 A1 | 8/2006 | Polisetti et al. |
| 2006/0199776 A1 | 9/2006 | Blagg et al. |
| 2006/0235031 A1 | 10/2006 | Arnold et al. |
| 2006/0276470 A1 | 12/2006 | Jackson et al. |
| 2006/0287295 A1 | 12/2006 | Barlaam et al. |
| 2007/0015773 A1 | 1/2007 | Bergeron et al. |
| 2007/0017915 A1 | 1/2007 | Weder et al. |
| 2007/0027193 A1 | 2/2007 | Leban et al. |
| 2007/0032640 A1 | 2/2007 | Varghese et al. |
| 2007/0054915 A1 | 3/2007 | Arora et al. |
| 2007/0072897 A1 | 3/2007 | Mahaney et al. |
| 2007/0099871 A1 | 5/2007 | Davis et al. |
| 2007/0142405 A1 | 6/2007 | Dong et al. |
| 2007/0224672 A1 | 9/2007 | Leban et al. |
| 2007/0249598 A1 | 10/2007 | Wang et al. |
| 2007/0270452 A1 | 11/2007 | Blagg et al. |
| 2008/0032960 A1 | 2/2008 | Knight et al. |
| 2008/0058521 A1 | 3/2008 | Krishnan et al. |
| 2008/0070935 A1 | 3/2008 | Huang et al. |
| 2008/0119454 A1 | 5/2008 | Polisetti et al. |
| 2008/0119455 A1 | 5/2008 | Polisetti et al. |
| 2008/0119461 A1 | 5/2008 | Sin et al. |
| 2008/0200465 A1 | 8/2008 | Burli et al. |
| 2008/0249090 A1 | 10/2008 | Hu et al. |
| 2008/0261956 A1 | 10/2008 | Choi et al. |
| 2008/0287469 A1 | 11/2008 | Diacovo et al. |
| 2008/0292626 A1 | 11/2008 | Wang et al. |
| 2008/0293674 A1 | 11/2008 | Schwarz et al. |
| 2008/0306053 A1 | 12/2008 | Tachdjian et al. |
| 2008/0306093 A1 | 12/2008 | Servant et al. |
| 2008/0312180 A1 | 12/2008 | Liang et al. |
| 2008/0318942 A1 | 12/2008 | Simon et al. |
| 2009/0030023 A1 | 1/2009 | Harada et al. |
| 2009/0053192 A1 | 2/2009 | Millan et al. |
| 2009/0088452 A1 | 4/2009 | Coleman et al. |
| 2009/0099214 A1 | 4/2009 | Fairhurst et al. |
| 2009/0105233 A1 | 4/2009 | Chua et al. |
| 2009/0118283 A1 | 5/2009 | Defert et al. |
| 2009/0124638 A1 | 5/2009 | Shokat et al. |
| 2009/0124654 A1 | 5/2009 | Mjalli et al. |
| 2009/0137581 A1 | 5/2009 | Chen et al. |
| 2009/0163481 A1 | 6/2009 | Murphy et al. |
| 2009/0163709 A1 | 6/2009 | Blagg |
| 2009/0170879 A1 | 7/2009 | Szucova et al. |
| 2009/0181920 A1 | 7/2009 | Watkins et al. |
| 2009/0181988 A1 | 7/2009 | Tanaka et al. |
| 2009/0187014 A1 | 7/2009 | Blagg |
| 2009/0203689 A1 | 8/2009 | Dhalla et al. |
| 2009/0232768 A1 | 9/2009 | Birkus et al. |
| 2009/0247513 A1 | 10/2009 | Burli et al. |
| 2009/0253694 A1 | 10/2009 | Ono et al. |
| 2009/0264409 A1 | 10/2009 | Dong et al. |
| 2009/0264423 A2 | 10/2009 | CHUA et al. |
| 2009/0270426 A1 | 10/2009 | Knight et al. |
| 2009/0270567 A1 | 10/2009 | Small et al. |
| 2009/0312319 A1 | 12/2009 | Ren et al. |
| 2009/0312406 A1 | 12/2009 | Hsieh et al. |
| 2009/0318411 A1 | 12/2009 | Castanedo et al. |
| 2009/0325967 A1 | 12/2009 | Fairhurst et al. |
| 2010/0009963 A1 | 1/2010 | Knight et al. |
| 2010/0022585 A1 | 1/2010 | Delong et al. |
| 2010/0029658 A1 | 2/2010 | Gavish et al. |
| 2010/0029693 A1 | 2/2010 | Douangpanya et al. |
| 2010/0048540 A1 | 2/2010 | Boyle et al. |
| 2010/0048882 A1 | 2/2010 | Blagg et al. |
| 2010/0056494 A1 | 3/2010 | Winzeler et al. |
| 2010/0105630 A1 | 4/2010 | Blagg |
| 2010/0168153 A1 | 7/2010 | Stowasser et al. |
| 2010/0190749 A1 | 7/2010 | Ren et al. |
| 2011/0046165 A1 | 2/2011 | Ren et al. |
| 2011/0124641 A1 | 5/2011 | Ren et al. |
| 2011/0144134 A1 | 6/2011 | Shokat et al. |
| 2011/0172228 A1 | 7/2011 | Ren et al. |
| 2011/0224223 A1 | 9/2011 | Shokat et al. |
| 2011/0269779 A1 | 11/2011 | Wilson et al. |
| 2011/0281866 A1 | 11/2011 | Ren et al. |
| 2011/0301144 A1 | 12/2011 | Knight et al. |
| 2012/0065154 A1 | 3/2012 | Tanaka et al. |

FOREIGN PATENT DOCUMENTS

| | | |
|---|---|---|
| JP | 10206995 A | 8/1998 |
| JP | 2000072773 A | 3/2000 |
| JP | 2002131859 A | 5/2002 |
| JP | 2003073357 A | 3/2003 |
| JP | 2004161716 A | 6/2004 |
| WO | 8301446 A1 | 4/1983 |
| WO | 9117161 A1 | 11/1991 |
| WO | 9214733 A1 | 9/1992 |
| WO | 9316091 A1 | 8/1993 |
| WO | 9316092 A1 | 8/1993 |
| WO | 9318035 A1 | 9/1993 |
| WO | 9319767 A1 | 10/1993 |
| WO | 9322443 A1 | 11/1993 |
| WO | 9413677 A1 | 6/1994 |
| WO | 9417803 A1 | 8/1994 |
| WO | 9429436 A1 | 12/1994 |
| WO | 9510628 A2 | 4/1995 |
| WO | 9512588 A1 | 5/1995 |
| WO | 9529673 A1 | 11/1995 |
| WO | 9532984 A1 | 12/1995 |
| WO | 9510628 A3 | 9/1996 |
| WO | 9640706 A1 | 12/1996 |
| WO | 9728133 A1 | 8/1997 |
| WO | 9728161 A1 | 8/1997 |
| WO | 9841525 A1 | 9/1998 |
| WO | 9852611 A1 | 11/1998 |
| WO | 9857952 A1 | 12/1998 |
| WO | 0017202 A1 | 3/2000 |
| WO | 0102369 A2 | 1/2001 |
| WO | 0116114 A2 | 3/2001 |
| WO | 0119829 A2 | 3/2001 |
| WO | 0125238 A2 | 4/2001 |
| WO | 0131063 A1 | 5/2001 |
| WO | 0138584 A2 | 5/2001 |
| WO | 0116114 A3 | 8/2001 |
| WO | 0155140 A1 | 8/2001 |
| WO | 0156988 A1 | 8/2001 |
| WO | 0119829 A3 | 9/2001 |
| WO | 0125238 A3 | 10/2001 |
| WO | 0138584 A3 | 10/2001 |
| WO | 0181346 A2 | 11/2001 |
| WO | 0206192 A1 | 1/2002 |
| WO | 0181346 A3 | 3/2002 |
| WO | 0102369 A3 | 4/2002 |
| WO | 0230944 A2 | 4/2002 |
| WO | 02057425 A2 | 7/2002 |

(56) References Cited

FOREIGN PATENT DOCUMENTS

| | | |
|---|---|---|
| WO | 02076986 A1 | 10/2002 |
| WO | 02080926 A1 | 10/2002 |
| WO | 02083143 A1 | 10/2002 |
| WO | 02088025 A1 | 11/2002 |
| WO | 02090334 A1 | 11/2002 |
| WO | 0230944 A3 | 1/2003 |
| WO | 03000187 A2 | 1/2003 |
| WO | 03016275 A1 | 2/2003 |
| WO | 03/024969 A1 | 3/2003 |
| WO | 03020880 A2 | 3/2003 |
| WO | 03028341 A2 | 4/2003 |
| WO | 03035075 A1 | 5/2003 |
| WO | 03059884 A1 | 7/2003 |
| WO | 03020880 A3 | 10/2003 |
| WO | 03082341 A1 | 10/2003 |
| WO | 03106426 A1 | 12/2003 |
| WO | 2004006906 A2 | 1/2004 |
| WO | 2004006906 A3 | 1/2004 |
| WO | 2004039774 A3 | 1/2004 |
| WO | 03000187 A3 | 3/2004 |
| WO | 2004018058 A2 | 3/2004 |
| WO | 2004031177 A1 | 4/2004 |
| WO | 2004039774 A2 | 5/2004 |
| WO | 2004018058 A3 | 7/2004 |
| WO | 2004087053 A2 | 10/2004 |
| WO | 2004111014 A1 | 12/2004 |
| WO | 2005002585 A1 | 1/2005 |
| WO | 2005007085 A2 | 1/2005 |
| WO | 2005012323 A2 | 2/2005 |
| WO | 2005016348 A1 | 2/2005 |
| WO | 2005016349 A1 | 2/2005 |
| WO | 2005016528 A2 | 2/2005 |
| WO | 2005021533 A1 | 3/2005 |
| WO | 0257425 A3 | 4/2005 |
| WO | 2005012323 A3 | 5/2005 |
| WO | 2005016528 A3 | 5/2005 |
| WO | 2005044181 A2 | 5/2005 |
| WO | 2005047289 A1 | 5/2005 |
| WO | 2005061460 A1 | 7/2005 |
| WO | 2005063258 A1 | 7/2005 |
| WO | 2005067901 A2 | 7/2005 |
| WO | 2005074603 A2 | 8/2005 |
| WO | 2005007085 A3 | 9/2005 |
| WO | 2005097800 A1 | 10/2005 |
| WO | 2005105760 A1 | 11/2005 |
| WO | 2005067901 A3 | 12/2005 |
| WO | 2005112935 A1 | 12/2005 |
| WO | 2005113556 A1 | 12/2005 |
| WO | 2005117889 A1 | 12/2005 |
| WO | 2005120511 A1 | 12/2005 |
| WO | 2005044181 A3 | 3/2006 |
| WO | 2006030032 A1 | 3/2006 |
| WO | 2006038865 A1 | 4/2006 |
| WO | 2006050501 A2 | 5/2006 |
| WO | 2006050946 A1 | 5/2006 |
| WO | 2006068760 A2 | 6/2006 |
| WO | 2004087053 A3 | 8/2006 |
| WO | 2006089106 A2 | 8/2006 |
| WO | 2006108107 A1 | 10/2006 |
| WO | 2006112666 A1 | 10/2006 |
| WO | 2005074603 A3 | 11/2006 |
| WO | 2006114064 A2 | 11/2006 |
| WO | 2006114065 A2 | 11/2006 |
| WO | 2006068760 A3 | 12/2006 |
| WO | 2006089106 A3 | 12/2006 |
| WO | 2007002293 A2 | 1/2007 |
| WO | 2007006547 A1 | 1/2007 |
| WO | 2007020046 A1 | 2/2007 |
| WO | 2007002293 A3 | 3/2007 |
| WO | 2007025090 A2 | 3/2007 |
| WO | 2006050501 A3 | 5/2007 |
| WO | 2007061737 A2 | 5/2007 |
| WO | 2006114064 A3 | 6/2007 |
| WO | 2006114065 A3 | 6/2007 |
| WO | 2007025090 A3 | 6/2007 |
| WO | 2007075554 A2 | 7/2007 |
| WO | 2007079164 A2 | 7/2007 |
| WO | 2007079164 A3 | 9/2007 |
| WO | 2007103308 A2 | 9/2007 |
| WO | 2007112005 A2 | 10/2007 |
| WO | 2007114926 A2 | 10/2007 |
| WO | 2007121453 A2 | 10/2007 |
| WO | 2007121920 A2 | 11/2007 |
| WO | 2007121924 A2 | 11/2007 |
| WO | 2007124854 A1 | 11/2007 |
| WO | 2007125310 A2 | 11/2007 |
| WO | 2007125315 A2 | 11/2007 |
| WO | 2007126841 A2 | 11/2007 |
| WO | 2007134828 A1 | 11/2007 |
| WO | 2007135380 A2 | 11/2007 |
| WO | 2007135398 A1 | 11/2007 |
| WO | 2007061737 A3 | 12/2007 |
| WO | 2007125315 A3 | 12/2007 |
| WO | 2007121920 A3 | 1/2008 |
| WO | 2008012326 A1 | 1/2008 |
| WO | 2007103308 A3 | 2/2008 |
| WO | 2007112005 A3 | 2/2008 |
| WO | 2007125310 A3 | 3/2008 |
| WO | 2008025755 A1 | 3/2008 |
| WO | 2008047821 A1 | 4/2008 |
| WO | 2008063625 A2 | 5/2008 |
| WO | 2008064018 A1 | 5/2008 |
| WO | 2007121453 A3 | 7/2008 |
| WO | 2008079028 A1 | 7/2008 |
| WO | 2008082487 A2 | 7/2008 |
| WO | 2008094737 A2 | 8/2008 |
| WO | 2007121924 A3 | 9/2008 |
| WO | 2008112715 A2 | 9/2008 |
| WO | 2007114926 A3 | 10/2008 |
| WO | 2008118454 A2 | 10/2008 |
| WO | 2008118455 A1 | 10/2008 |
| WO | 2008118468 A1 | 10/2008 |
| WO | 2008125014 A1 | 10/2008 |
| WO | 2008125207 A1 | 10/2008 |
| WO | 2008127226 A2 | 10/2008 |
| WO | 2007126841 A3 | 11/2008 |
| WO | 2008112715 A3 | 11/2008 |
| WO | 2008118454 A3 | 11/2008 |
| WO | 2008136457 A1 | 11/2008 |
| WO | 2008082487 A3 | 12/2008 |
| WO | 2008127226 A3 | 12/2008 |
| WO | 2009000412 A1 | 12/2008 |
| WO | WO 2008/157500 A1 | 12/2008 |
| WO | 2009004621 A1 | 1/2009 |
| WO | 2009010925 A2 | 1/2009 |
| WO | 2009023718 A2 | 2/2009 |
| WO | 2008094737 A3 | 3/2009 |
| WO | 2009023718 A3 | 4/2009 |
| WO | 2009044707 A1 | 4/2009 |
| WO | 2009050506 A2 | 4/2009 |
| WO | 2009064802 A2 | 5/2009 |
| WO | 2009010925 A3 | 7/2009 |
| WO | 2009064802 A3 | 7/2009 |
| WO | 2009088986 A1 | 7/2009 |
| WO | 2009088990 A1 | 7/2009 |
| WO | 2009100406 A2 | 8/2009 |
| WO | 2009117157 A1 | 9/2009 |
| WO | 2009050506 A3 | 11/2009 |
| WO | 2009100406 A3 | 11/2009 |
| WO | 2010006086 A2 | 1/2010 |
| WO | 2010009207 A1 | 1/2010 |
| WO | 2010019210 A2 | 2/2010 |
| WO | 2010036380 A1 | 4/2010 |
| WO | 2010039534 A2 | 4/2010 |
| WO | 2010019210 A3 | 5/2010 |
| WO | WO 2010/065923 A2 | 6/2010 |
| WO | 2010039534 A3 | 8/2010 |
| WO | WO 2010/129816 A2 | 11/2010 |
| WO | WO 2011/075630 A1 | 6/2011 |
| WO | 2011146882 A1 | 11/2011 |

OTHER PUBLICATIONS

Mellinghoff et al., "TORward AKTually useful mouse models", Nature Medicine, 2004, vol. 10, pp. 579-580.

(56) References Cited

OTHER PUBLICATIONS

Miyaura et al., "Palladium-catalyzed cross-coupling reactions of organoboron compounds", Chem. Rev., 1995, vol. 95, No. 7, pp. 2457-2483.
Mod! et al., "Isoquinolones; part IV-synthesis of methyl, 3-formyl & other 3-substituted N-arylisoquinolones", Indian J. Chem., 1979, vol. 18B, pp. 304-306.
Moon et al., "A novel microtubule destabilizing entity from orthogonal synthesis of triazine library and zebrafish embryo screening", J. Am. Chem. Soc., 2002, vol. 124, pp. 11608-11609.
Mosmann et al., "The expanding universe of T-cell subsets: Th1, Th2 and more", Immunology Today, 1996, pp. 138-146.
Nakanishi et al., "Cloning and sequence analysis of a cDNA encoding tetrameric corbonyl reductase of pig lung", Biochem. Biophys. Acta, 1993, vol. 194, No. 3, pp. 1311-1316.
Nemazanyi et al., "3-Amino-4aryl-1(2H)-isoquinolones", Chemistry of Heterocyclic Compounds, Mar. 1991, vol. 27, No. 3, pp. 307-308.
Niswender et al., "Protein engineering of protein kinase a catalytic subunits results in the acquisition of novel inhibitor sensitivity", The Journal of Biological Chemistry, 2002, vol. 277, No. 32, pp. 28916-28922.
Nobel et al., "Purification of full-length recombinant human and rat type 1 11b-hydroxysteroid dehydrogenases with retained oxidoreductase activities", Protein Expr. Purif., 2002, vol. 26, pp. 349-356.
Nunes et al., "Signalling Through CD28 T-Cell Activation Pathway Involves an Inositol Phospholipid-Specific Phospholipase C Activity". Biochem. J., 1993, vol. 293, pp. 835-842.
O'Shea et al., "Activaiton of human peripheral blood T lymphocytes by pharmacological induction of protein-tyrosine phosphorylation", Proc. Natl. Acad. Sci. USA, Nov. 1992, vol. 89, pp. 10306-10310.
Oda et al., "PIK3CA cooperates with other phosphatidylinositol 3'-kinase pathway mutations to effect oncogenic transformation", Cancer Research, 2008, vol. 68, pp. 8127.
Okada et al., " Essential role of phosphatidylinositol 3-kinase in insulin-induced glucose transport and antipolysis in rat adipocytes", J. Biol. Chem., Feb. 4, 1994, vol. 269, No. 5, pp. 3568-3573.
Okada et al., "Blockage of chemotactic peptide-induced stimulation of neutrophils by wortmannin as a result of selective inhibition of phosphatidylinositol 3-kinase", J. Biol. Chem., Feb. 4, 1994, vol. 269, No. 5, pp. 3568-3573.
Ozaki et al., "Studies on 4(1H)-quinazolinones. IV. Convenient synthesis of 12-methyl-6H-isoquino [2,1-a] quinazolin-6-one and 6-methyl-13H-quinazolino [3,4-a] quinazolin-13-one", Chem. Pharm. Bull., Jun. 25, 1984, vol. 32, No. 6, pp. 2160-2164.
Ozol et al., "Autoxidative transformations of 2-substituted 3-alkyl-4-hydroxy-1-oxo-1, 2-dihydroisoquinolines", Chemistry of Heterocyclic Compounds, Jun. 1978, vol. 14, No. 6, pp. 644-648.
Patel et al., "Immunopathological aspects of age-related macular degeneration", Seminars in Immunopathology, 2008, vol. 30, No. 2, pp. 97-110.
Persson, "Glucocorticoids for asthma—early contributions", Pulm. Pharmacol., 1989, vol. 2, pp. 163-166.
Pietrie et al., "Novel biotinylated adenylate analogue derived from pyrazolo[3,4-d]pyrimidine for labeling DNA probes", Bioconj. Chem., 1991, vol. 2, No. 6, pp. 441-446.
Prasad et al., "Phosphatidylinositol (PI) 3-kinase and PI 4-kinase binding to the CD4-p56Ick complex: the p56Ick SH3 domain binds to PI 3-kinase but not PI 4-kinase", Molecular and Cellular Biology, Dec. 1993, vol. 13, No. 12, pp. 7708-7717.
Prasad et al., "Src-homology 3 domain of protein kinase p59fyn mediates binding phosphatidylinositol 3-kinase in T cells", Proc. Natl. Acad. Sci. USA, Aug. 1993, vol. 90, pp. 7366-7370.
Prasad et al., "T-cell antigen CD28 interacts with the lipid kinase phosphatidylinositol 2-kinase by a cytoplasmic Tyr (P)-Met-Xaa-Met motif", Proc. Natl. Acad. Sci. USA, 1994, vol. 91, pp. 2834-2838.

Pudlo et al., "Synthesis, antiproliferative, and antiviral activity of certain 4-substituted and 4,5 disubstituted 7-[1,3- dihydroxy-2-propoxy)methyl]pyrrolo[2,3-d]pyrimidines", J. Med. Chem., 1990, vol. 33, pp. 1984-1992.
Pérez-Blas et al., "Impaired T cell signal transduction through CD28 in a patient with idiopathic thrombocytopenia", Clin. Exp. Immunol., 1991, vol. 85, pp. 424-428.
Reif et al., "Divergent regulation of phosphatidylinositol 3-kinase P85a and P85b isoforms upon T cell activation", The Journal of Biological Chemistry, 1993, vol. 268, pp. No. 15, pp. 10780-10788.
Robertson, "Eicosandoids and human disease", Harrison's Principles of Internal Medicine, Isselbacher K.J. et al. (eds.), 1994, vol. 1, pp. 431-435, McGraw-Hill, New York City.
Romero et al., "Cloning and expression of the bovine 11b-hydroxysteroid dehydrogenase type-2", J. Steroid Biochem. Mol. Biol., 2000, vol. 72, pp. 231-237.
Rott et al., "Recent development in the use of biologics in psoriasis and autoimmune disorders. The role of autoantibodies", BMJ, Mar. 26, 2005, vol. 330, No. 7493, pp. 716-720.
Schwartz et al., "Quercetin inhibition of the induction and function of cytotoxic T lymphocytes", Immunopharmacology, 1982, vol. 4, pp. 125-138.
Schwartz, "A cell culture model for T lymphocyte clonal anergy", Science, Jun. 15, 1990, vol. 248, pp. 1349-1356.
Shibasaki et al., "Different properties of monomer and heterodimer forms of phosphatidylinositol 3-kinase", Biochem. J., 1993, vol. 289, pp. 227-231.
Singer et al., "Optimization of in situ hybridization using isotopic and non-isotopic detection methods", Biotechniques, 1986, vol. 4, No. 3, pp. 230-250.
Soldan et al., "Induction of daunorubicin carbonyl reducting enzymes by daunorubicin in sensitive and resistant pancrease carcinoma cells", Biochem. Pharmacol., 1996, vol. 51, pp. 117-123.
Stanoeva et al., "Homophthalic anhydrides and their application to the synthesis of heterocyclic compounds (review)", Chemistry of Heterocyclic Compounds, Dec. 1984, vol. 20, No. 12, pp. 1305-1315.
Supplementary European Examination Report EP 07754845.1 dated Sep. 20, 2011.
Supplementary European Search Report dated Feb. 24, 2010, for EP Application No. 07754845, 4 pages.
Sykes et al., "Treatment of severe autoimmune disease by stem-cell transplantation", Nature, Jun. 2, 2005, vol. 35, No. 7042, pp. 620-627.
Takeuchi et al. "Synergistic Augmentation of Rapamycin-Induced Autophagy in Malignant Glioma Cells by Phosphatidylinositol 3-Kinase/Protein Kinase B Inhibitors". Cancer Res. 65(8):3336-46. Apr. 15, 2005.
Tanaka et al., "An unbiased cell morphology-based screen for new, biologically active small molecules", PLoS Biology, 2005, vol. 3, No. 5, pp. 0764-0776.
Truitt et al., "Stimulation of CD28 triggers an association between CD 28 and phosphatidylinositol 3-kinase in Jurkat T cells", J. Exp. Med., Mar. 1994, vol. 179, pp. 1071-1076.
U.S. Appl. No: 13/289,540, filed Nov. 4, 2011.
U.S. Appl. No. 13/016,957, filed Jan. 28, 2011.
Ugarkar et al., "Adenosine kinase inhibitors. 2. Synthesis, enzyme inhibition, and antiseizure activity of diaryltubercidin analogues", J. Med. Chem., 2000, vol. 43, pp. 2894-2805.
Vandenberghe et al., "Antibody and B7/BB1-mediated ligation of the CD28 receptor induces tyrosine phosphorylation in human T cells", J. Exp. Med., Apr. 1992, vol. 175, pp. 951-960.
Vasilevsky et al., "Study of the Heterocyclization of vic-Substituted Hydrazides of Acetylenylpyrazolecarboxylic Acids into N-Amino Pyrazolopyridinones", Journal of Heterocyclic Chemistry, Nov., 39(6): 1229-1233 (2002).
Vasilevsky et al., "Unexpected results in the heterocyclization of 5-acetylenylpyrazole-4-carboxylic acid hydrazides under the influence of CuCl: formatin of a diazepinone and dehydrodimerization into the corresponding bis(pyrazolo[4,3-d] [1,2] diazepinone)", Tetrahedron Letters, Jan., 46(26): 4457-4459 (2005).

(56) References Cited

OTHER PUBLICATIONS

Vlahos et al., "A specific inhibitor of phosphatidylinositol 3-kinase, 2-(4-morpholinyl)-8-phenyl-4H-1-benzopyran-4-one (LY294002)", The Journal of Biological Chemistry, 1994, vol. 269, No. 7, pp. 5241-5248.
International Search Report and Written Opinion for PCT/US2012/20831 dated May 2, 2012.
Berndt et al., "The P110 Structure: Mechanisms for selectivity and potency of new PI(3)K Inhibitors", Nat Chem Biol. Feb. 2010;6(2):117-24.
International Search Report & Written Opinion for PCT/US2011/60212 dated Jun. 1, 2012.
International Search Report & Written Opinion issued after Submission of Request for Additional Search for PCT/US2011/60212 dated Jul. 6, 2012.
Bansal, N., et al., "The Molecular Biology of Endometrial Cancers and the Implications for Pathogenesis, Classification, and Targeted Therapies," Cancer Control, 16(1):8-13 (2009).
Billottet, C., et al., "A Selective Inhibitor of the p110d Isoform of PI 3-Kinase Inhibits AML Cell Proliferation and Survival and Increases the Cytotoxic Effects of VP16," Oncogene, 25:6648-6659 (2006).
Billottet, C., et al., "Inhibition of Class 1 Phosphoinositide 3-Kinase Activity Impairs Proliferation and Triggers Apoptosis in Acute Promyelocytic Leukemia without Affecting Atra-Induced Differentiation," Cancer Res. 69(3):1027-36 (2009).
Chapuis, N., et al., "Dual Inhibition of P13K and mTORC1/2 Signaling by NVP-BEZ235 as a New Therapeutic Strategy for Acute Myeloid Leukemia," Clin. Cancer Res., 16(22):5424-35 (2010).
Chen, J.S., et al., "Characterization of Structurally Distinct, Isoform-Selective Phosphoinositide 3'-Kinase Inhibitors in Combination with Radiation in the Treatment of Glioblastoma," Mol. Cancer Ther., 7(4):841-50 (2008).
Courtney, K.D., et al., "The PI3K Pathway As Drug Target in Human Cancer," J. of Clinical Oncology, 28 (6):1075-1083 (2010).
Brzezianska, E., et al., "A Minireview: The Role of MAPK/ERK and PI3K/Akt Pathways in Thyroid Follicular Cell-Derived Neoplasm," Frontiers in Bioscience, 16:422-439 (2011).
Flinn, I.W., et al., "Preliminary Evidence of Clinical Activity in a Phase I Study of CAL-101, a Selective Inhibitor of the p110δ Isoform of Phosphatidylinositol 3-Kinase (PI3K), in Patients with Select Hematologic Malignancies," J. Clin. Oncol. 27:156s (Suppl: Abstr 3543) (2009).
Vara, J.A.F., et al., "PI3K/Akt Signalling Pathway and Cancer," Cancer Treat. Rev. 30(2):193-204 (2004).
Furukawa, T., "Molecular Targeting Therapy for Pancreatic Cancer: Current Knowledge and Perspectives from Bench to Bedside," J. Gastroenterol., 43:905-911 (2008).
Haluska, F., et al., "The RTK/RAS/BRAF/PI3K Pathways in Melanoma: Biology, Small Molecule Inhibitors, and Potential Applications," Semin. Oncol., 34(6):546-54 (2007).
Herman, S.E.M., et al., "Phosphatidylinositol 3-Kinase-d Inhibitor CAL-101 Shows Promising Preclinical Activity in Chronic Lymphocytic Leukemia by Antagonizing Intrinsic and Extrinsic Cellular Survival Signals," Blood, 116 (12):2078-88 (2010).
Herman, S.E.M., et al., "The Role of Phosphatidylinositol 3-Kinase-d in the Immunomodulatory Effects of Lenalidomide in Chronic Lymphocytic Leukemia," Blood, 117(16):4323-7 (2011).
Herrera, V.A., et al., "The Dual PI3K/mTOR Inhibitor BEZ235 Is Effective in Lung Cancer Cell Lines," Anticancer Research, 31:849-854 (2011).
Ikeda, H., et al., "PI3K/p110d is a Novel Therapeutic Target in Multiple Myeloma," Blood, 116(9):1460-8 (2010).
Khwaja, A., "PI3K as a Target for Therapy in Haematological Malignancies," Curr Top Microbiol immunol., 347:169-88 (2010).
Kong, D. and Yamori, T., "Advances in Development of Phosphatidylinositol 3-Kinase Inhibitors," Curr. Med. Chem., 16:2839-2854 (2009).
Markman, B., et al., "Status of PI3K Inhibition and Biomarker Development in Cancer Therapeutics," Ann. Oncol., 21 (4):683-91 (2010).
Mazzoletti, M. and Broggini, M., "PI3K/AKT/mTOR Inhibitors in Ovarian Cancer," Curr. Med. Chem., 17:4433-4447 (2010).
Meadows, S.A., et al., "CAL-101, a Potent Selective Inhibitor of the p110d Isoform of Phosphatidylinositol 3-Kinase, Attenuates Pathway Signaling, Induces Apoptosis, and Oversomces Signals From the Microenvironment in Cellular Models of Hodgkin Lymphoma," Blood (ASH Annual Meeting Abstracts), 116:Abstract 3926 (2010).
Porta, C. and Figlin, R.A., "Phsophatidylinositol-3-Kinase/Akt Signaling Pathway and Kidney Cancer, and the Therapeutic Potential of Phosphatidylinositol-3-Kinase/Akt Inhibitors," J. Urol., 182(6):2569-77 (2009).
Saif, M.W. and Chu, E., "Biology of Colorectal Cancer," Cancer J., 16(3):196-201 (2010).
Salmena, L., et al. "Tenets of PTEN Tumor Suppression," Cell, 133:403-414(2008).
Sarker, D., et al., "Targeting the PI3K/AKT Pathway for the Treatment of Prostate Cancer," Clin. Cancer Res., 15 (15):4799-805 (2009).
Shapiro, G., et al., "Phase I Dose-Escalation Study of XL147, A PI3K Inhibitor Administered Orally to Patients with Solid Tumors," J. Clin. Oncol., 27:146x (Suppl Abstr 3500) (2009).
Torbett, N.E., et al., "A Chemical Screen in Diverse Breast Cancer Cell Lines Reveals Genetic Enhancers and Suppressors of Sensitvity to PI3K Isoform-Selective Inhibition," Biochem. J., 415:97-100 (2008).
Vogt, P.K., et al., "Phosphoinositide 3-Kinase: From Viral Oncoprotein to Drug Target," Virology, 344:131-138 (2006).
Vogt, P.K., et al., "Phosphatidylinositol 3-Kinase: The Oncoprotein," Curr. Top. Microbiol. Immunol., 347:79-104 (2010).
Wagner, A.J., et al., "A First-in-Human Phase I Study to Evaluate the Pan-PI3K Inhibitor GDC-0941 Administered QD or BID in Patients with Advanced Solid Tumors," J. Clin. Oncol., 27:146s (Suppl, Abstr 3501) (2009).
Ward, S., et al., "Therapeutic Potential of Phosphoinositide 3-Kinase Inhibitors," Chem. & Biol., 10:207-213 (2003).
Zhao, L. and Vogt, P.K., "Class I PI3K in Oncogenic Cellular Transformation," Oncogene, 27:5486-5496 (2008).
Jimeno, A., et al., "Phase I Trial of PX-866, a Novel Phosphoinositide-3-Kinase (PI-3K) Inhibitor," J. Clin. Oncol., 27:15s (Suppl Abstr 3542) (2009).
International Preliminary Report on Patentability for PCT/US2009/000038 dated Jul. 6, 2010.
European Search Report for EP 07 754 845.1, dated Sep. 20, 2011.
International Preliminary Report on Patentability for PCT/US2010/002020 dated Jan. 26, 2012.
International Preliminary Report on Patentability for PCT/US2009/005380 dated Apr. 7, 2011.
Abrahamian et al. "Immunological and Clinical Profile of Adult Patients with Selective Immunoglobulin Subclass Deficiency: Response to Intravenous Immunoglobulin Therapy". Clinical & Experimental Immunology. The Journal of Translational Immunology vol. 159, pp. 344-350 (2009).
Bartholomeusz et al. "Targeting the PI3K Signaling Pathway in Cancer Therapy". Expert Opin. Ther. Targets (2012). pp. 121-130.
International Search Report and Written Opinion, International Application No. PCT/US10/33939, date of mailing Nov. 5, 2010.
Ward et al., "Inhibition of CD28-mediated T cell costimulation by the phosphoinisitide 3-kinase inhibitor wortmannin", Eur. J. Immunol., 1995, vol. 25, pp. 526-532.
Ward et al., "Ligation of CD28 receptor by B7 induces formation of D-3 phosphoinositides in T lymphocytes independently of T cell receptor/CD3 activation", Eur. J. Immunol., 1993, vol. 23, pp. 2572-2577.
Ward et al., "Regulation of D-3 phosphoinositides during T cell activation via the T cell antigen receptor/CD3 complex and CD2 antigens", Eur. J. Immunol., 1992, vol. 22, pp. 45-49.
Ward et al., "Regulation of phosphoinositide kinases in T cells", J. Biol. Chem., Nov. 25, 1992, vol. 267, No. 33, pp. 23862-23869.
White et al., "11b-hydroxysteroid dehyrdogenase and the syndrome of apparent mineralocorticoid excess", Endocr. Rev., 1997, vol. 18, No. 1, pp. 135-156.

(56) References Cited

OTHER PUBLICATIONS

Widler et al., "7-alkyl- and 7-Cycloalkyl-5-aryl-pyrrolo[2,3-d]pyrimidines—potent inhibitors of the tyrosine kinase c-Src", Bioorganis and Medicinal Chemistry Letters, 2001, vol. 11, No. 6, pp. 849-852.
Wiesinger et al., "Antiinflammatory activity of the new mold metabolite 11-desacetoxy-wortmannin and some of its derivatives", Experientia, 1974, vol. 30, pp. 135-136.
Wolff, Burger's Medicinal Chemistry, 5ed, 1995, Part 1, pp. 975-977, John Wiley & Sons.
Woscholski et al., "A comparison of demthoxyviridin and wortmannin as inhibitors of phosphatidylinositol 3-kinase", FEBS letters, 1994, vol. 342, pp. 109-114.
Yaguchi et al., "Antitumor activity of ZSTK474, a new phosphatidylinositol 3-kinase inhibitor", J. Natl. Cancer Inst., 2006, vol. 98, No. 8, pp. 545-556.
Yang et al., "A novel activation pathway for mature thymocytes", J Exp. Med., Oct. 1988, vol. 168, pp. 1457-1486.
Yano et al., "Inhibition of histamine secretion by wortmannin through the blockade of phosphatidylinositol 3-kinase in RBL-2H3 cells", J. Biol. Chem., Dec. 5, 1993, vol. 268, No. 34, pp. 25846-25856.
Yoshida et al., "Quercetin arrests human leukemic T-cells in late G1 phase of the cell cycle", 1992, vol. 52, pp. 6676-6681.
"Report of the Expert Committee on the diagnosis and classification of diabetes mellitus", Diabetes Care, 1992, vol. 2, Suppl. 1, pp. S5-S19.
Abdel-Mohsen. Synthesis, Reactions and Antimicrobial Activity of 2-Amino-4-(8-quinolinol-5-yl)-1-(p-toly1)-pyrrole-3-carbonitrile. Bull. Korean Chem. Soc. 2005;26(5):719-728.
Abe et al., "T cell receptor-mediated recognition of self-ligand induces signaling in immature thymocytes before negative selection", J. Exp. Med., Aug. 1992, vol. 176, pp. 459-468.
Ames et al., "Heterocyclic Synthesis from o-Halogen-acids. Part II. Thienopyridinones and Thienopyranones from 3-bromothiophene -2- and 4-Bromothiophene-3-Carboxylic Acids", Journal of the Chemical Society, Perkin Transactions 1, Jan., 14: 1390-1395 (1975).
Anderson et al., "Paradoxical inhibition of T-cell function in response to CTLA-4 blockade; heterogeneity within the human T-cell population", Nature, 2000, vol. 6, No. 2, pp. 211-214.
Andrews et al., "Effects of the 11b-hydroxysteroid dehydrogenase inhibitor carbenoxolone on insulin sensitive in men with type 2 diabetes", J. Clin. Endocrinol. Metab., 2003, vol. 88, No. 1, pp. 285-291.
Arcaro et al., "Wortmannin is a potent phosphatidylinositol 3-kinase inhibitor: the role of phosphatidylinositol 3,4,5-triphosphate in neutrophil responses", Biochem. J., Dec. 1, 1993, vol. 296, Pt. 2, pp. 297-301.
Arnold et al., "Pyrrolo[2,3-d]pyrimidines containing an extended 5-substituent as potent and selective inhibitors of Ick I", Bioorg. and Med. Chem. Lett., 2000, vol. 10, pp. 2167-2170.
Augustine et al., "Interleukin 2- and polyomavirus middle T antigen-induced modification of phosphatidylinositol 3-kinase activity in activated T lymphocytes", Molecular and Cellular Biology, 1991, vol. 11, No. 9, pp. 4431-4440.
Baggiolini et al., "Inhibition of the phagocytosis-induced respiratory burst by the fungal metabolite wortmannin and some analogues", Experimental Cell Research, 1987, vol. 169, pp. 408-418.
Ballell et al. "New Thiopyrazolo[3,4-d] pryimidine derivatives as anti-mycobacterial agents". Bioorganic and Medicinal Chemistry Letters. vol. 17. Dec. 22, 2006. pp. 1736-1740.
Banker et al., Modern Pharmaceutics, 1996, pp. 451-593, 3ed, Marcel Dekker, New York.
Barf et al., "Arylsulfonamidothiazoles as a new class of potential antidiabetic drugs. Discovery of potent and selective inhibitors of the 11b-hydroxysteroid dehydrogenase Type 1", J. Med. Chem., 2002, vol. 45, No. 18, pp. 3813-3815.

Barnes et al., "Efficacy and Safety of Inhaled Corticosteroids in Asthma—Report of a Workshop Held in Eze, France Oct. 1992". Am. Rev. Resir. Dis., 1993, vol. 148, pp. S1-S26.
Basotest®, "Test Kit for the Quantitative Determination of the Degranulation of Basophilic Granulocytes in Heparinized Human Whole Blood", Retreived from the Internet Nov. 29, 2011.
Beeram et al. Akt-Induced Endocrine Therapy Resistance is Reversed by Inhibition of mTOR Signaling. Ann Oncol. Aug. 2007. 18(8)1323-8.
Bell et al., "Glucokinase mutations insulin secretion, and diabetes mellitus", Annu. Reb. Physiol., 1996, vol. 58, pp. 171-186.
Bhat et al., "Pyraszolopyrimidine nucleosides. 12. Synthesis and biological activity of certain pyrazolo[3,4-d] pyrimidine nucleosides related to adenosine", J. Med. Chem., 1981, vol. 24, No. 10, pp. 1165-1172.
Bishop et al., "Generation of monospecific nanomolar tyrosine kinase inhbitors via a chemical genetic approach", Journal of the American Chemical Society, 1999, vol. 121, No. 4, pp. 627-631, Washington, DC.
Bochner et al. "Immunological aspects of allergic asthma". Annual review of Immunology 1994—Annual Reviews, pp. 295-335.
Bohren et al., "Expression, crystallization and preliminary crystallographic analysis of human carbonyl reductase", J. Mol. Biol., 1994, vol. 224, pp. 659-664.
Campora et al., "Binuclear complexes of nickel bridged by hydrocarbon ligands. Isocyanide insertion chemistry and amide formation by intramolecular coupling of acyl and imidoyl functionalities", Organometallics, Jan. 1992, vol. 11, No. 1, pp. 11-13.
Campora et al., "Isocyanide insertion chemistry. Synthesis and structural characterization of bridging imidoyl complexes of nickel and amide formation by intramolecular coupling of acyl and imidoyl functionalities", Organometallics, Oct. 1993, vol. 12, No. 10, pp. 4025-4031.
Chaisuparat et al., "Dual inhibition of P13Ka and mTOR as an alternative treatment for Kaposi's Sarcoma", Cancer Research, 2008, vol. 68, pp. 8361-8368.
Chappelow et al., "Neovascular age-related macular degeneration: potential therapies", Drugs, 2008, vol. 68, No. 8, pp. 1029-1036.
Closse et al., "2,3-dihydrobenzofuran-2-ones: a new class of highly potent antiinflammatory agents", J. Med. Chem., 1981, vol. 24, pp. 1465-1471.
Cox et al., "Human colorectal cancer cells efficiently conjugate the cyclopentenone prostaglandin, prostaglandin J2 to glutathione", Biochem. Biophys. Acta., 2002, vol. 1584, pp. 37-45.
Davies et al., "The human T3y chain is phosphorylated at Serine 126 in response to T lymphocyte activation", The Journal of Biological Chemistry, 1987, vol. 262, No. 23, pp. 10918-10921.
Davis et al., "The preparation of substituted 1(2H)-isoquinolinones from dilithiated 2-methyl-N-arylbenzamides, 2-methyl-N-(arylmethyl)-benzamides, or 2-methylbenzoic acid, 2, 2-dimethylhydrazide", Synthetic Communications, Sep. 1997, vol. 27, No. 17, pp. 2961-2969.
Diederich et al., "In search for specific inhibitors of human 11b-hydroxysteroid-dehydrogenases (11bHSDs): chenodeoxycholic acid selectively inhibits 11b-HSD-I", Eur. J. Endocrinol., 2000, vol. 142, pp. 200-207.
Dijksman et al., "271.1 : 2-dihydro-2-thianaphthalene derivatives. Part I. Preperation and reactions of 1 : 2-dihydro-1-keto-2-thianaphthalenes", J. Chem. Soc., vol. 1951, pp. 1213-1218.
Ding et al., "A combinatorial scaffold approach toward kinase-directed heterocycle libraries", J. Am. Chem. Soc., 2002, vol. 124, No. 8, pp. 1594-1596.
Ding et al., "A concise and traceless linker strategy toward combinatorial libraries of 2,6,9-substituted purines", J. Org. Chem., 2001, vol. 66, pp. 8273-8276.
Ding et al., "Resin-capture and release strategy toward combinatorial libraries of 2,6,9-substituted purines", J. Comb. Chem., 2002, vol. 4, pp. 183-186.
Donati et al., "Emerging therapies for neovascular age-related macular degeneration: state of art", Ophthalmologica, 2007, vol. 221, pp. 366-377.
European Examination Report for EP 07873406.8 dated Sep. 14, 2011.

(56) References Cited

OTHER PUBLICATIONS

European Seach Report dated Feb. 4, 2011, for EP Application No. 05857011.0.
European Seach Report dated Oct. 28, 2011, for EP Application No. 09700784.3.
European Search Report and Search Opinion for EP 09700424.6 dated Oct. 26, 2011.
European Search Report for EP 07873406.8 dated Mar. 1, 2010.
Examination Report for GB Application No. GB0819947.3 dated Oct. 27, 2010.
Extended European Search Report for EP 09816603 dated Mar. 19, 2012.
Extended European Search Report from Eureopean Application No. 09700784.3 dated Oct. 28, 2011.
Fajans et al., "Maturity onset diabetes of the young (MODY)", Diabet. Med., 1996, vol. 13, pp. S90-S95.
Feinstein et al., "Regulation of the action of hydrocotisone in airway epithelial cells by 11b-hydroxysteroid dehydrogenase", Am. J. Resp. Cell. Mol. Biol., 1999, vol. 21, pp. 403-408.
Feldman et al. Active-Site Inhibitors of mTOR Target Rapamycin-Resistant Outputs of mTORC1 and mTORC2. PLoS Biol. Feb. 10, 2009. 7(2):371-383.
Fingl et al., "General principles", The Pharmacological Basis of Therapeutics, 1975, Ch. 1, pp. 1-46, Fifth edition.
Forrest et al., "Carbonyl Reductase", Chem. Biol. Interact., 2000, vol. 129, pp. 21-40.
Forrest et al., "Induction of a human carbonyl reductase gene located on chromosome 21", Biochem. Biophys. Acta., 1990, vol. 1048, pp. 149-155.
Franzen, "The Suzuki, the Heck, and the Stille reaction—three versative methods for the introduction of new C-C bonds on solid support", Can. J. Chem., 2000, vol. 78, pp. 957-962.
Funder et al., "Mineralocorticoid action: target tissue specificity is enzyme, not receptor, mediated", Science, 1998, vol. 242, pp. 583-585.
Garber et al., "Diversity of gene expression in adenocarcinoma of the lung", Proc. Natl. Acad. Sci. USA, 2001, vol. 98, No. 24, pp. 13784-13789.
Gillespie et al. "Antagonists of the Human Adenosine A2A Receptor. Part 3. Design and Synthesis of Pyrazolo [3,4-d] Pyrimidines, Pyrrolo [2, 3-d] Pyrimidines, and 6-arylpurines". Bioorganic and Medicinal Chemistry Letters. vol. 18, No. 9. Mar. 30, 2008. pp. 2924-2929.
Gonzalez et al., "Protection against daunorubicin cytotoxicity by expression of a cloned human carbonyl reductase cDNA in K562 leukemia cells", Cancer Res., 1995, vol. 55, pp. 4646-4650.
Graber et al., "The protein tyrosine kinase inhibitor herbimycin A, but not Genistein, specifically inhibits signal transduciton by the T cell antigen receptor", International Immunology, 1992, vol. 4, No. 1, pp. 1201-1210.
Graupera et al., "Angiogenesis selectively requires the p110 isoform of PI3K to control endothelial cell migration", Nature, 2008, vol. 453, pp. 662-666.
Gunther et al., "Acute pathological effects on rats of orally administered wortmannin-containing preparations and purified wortmannin from *Fusarium oxysporum*", Fd. Chem. Toxic., 1989, vol. 27, No. 3, pp. 173-179.
Haase et al., "Detection of viral nucleic acids by in situ hybridization", Methods in Virology, 1984, vol. 7, pp. 189-226.
Hanefeld et al., "One-pot synthesis of tetrasubstituted pyrazoles proof of regiochemistry", J. Chem. Soc. Perkin Trans., 1996, vol. 1, pp. 1545-1552.
Harada et al., "Novel role of phosphatidylinositol 3-kinase in CD28-mediated costimulation", J. Biol. Chem., 2001, vol. 276, No. 12, pp. 9003-9008.
Harding et al., "CD28-mediated signalling co-stimulates murine T cells and prevents induction of anergy in T-cell clones", Nature, Apr. 16, 1992, vol. 356, pp. 607-609.

Hellwinkel et al- "Heterocyclensynthesen mit MF/Al2O3-basensystemen; 2-arylbenzofurane and 2,3-diarylisochinolin-1(2H)-one", Synthesis, 1995, vol. 1995, No. 9, pp. 1135-1141.
International Preliminary Report on Patentability and Written Opinion for PCT/US2005/042524 dated May 22, 2007.
International Preliminary Report on Patentability and Written Opinion for PCT/US2007/008355 dated Nov. 4, 2008.
International Preliminary Report on Patentability and Written Opinion for PCT/US2007/008395 dated Oct. 8, 2008.
International Preliminary Report on Patentability and Written Opinion for PCT/US2009/049969 dated Jan. 1, 2011.
International Preliminary Report on Patentability and Written Opinion for PCT/US2009/060985 dated Apr. 19, 2011.
International Preliminary Report on Patentability from International Application No. PCT/US2009/000042 issued Jul. 6, 2010.
International Search Report and Written Opinion for PCT/US2009/005380 dated Nov. 20, 2009.
International Search Report and Written Opinion for PCT/US2009/049969 dated Mar. 15, 2010.
International Search Report dated Aug. 22, 2011for PCT Application No. PCT/US2011/37412.
International Search Report dated Aug. 27, 2008 for International Applicaiton No. PCT/US07/08395, 4 pages.
International Search Report dated Mar. 11, 2009 for PCT Application No. US2009/00038.
International Search Report dated Mar. 23, 2009 for PCT/US2009/00042.
International Search Report dated Oct. 2, 2006, for International Application No. PCT/US05/042524, 7 pages.
International Search Report dated Oct. 26, 2011, for International Application No. PCT/US09/00038.
International Search Report dated Sep. 25, 2008, for International Application No. PCT/US2007/08355.
International Search Report for PCT/US2009/060985 dated Jun. 28, 2010.
International Search Report for PCT/US2010/02020 dated Nov. 2, 2010.
Ishiyama et al., "A stoichiometric aromatic C-H borylation catalyzed by iridium(I)/2,2'-bipyridine complexes at room temperature", Angew. Chem. Int. Ed., 2002, vol. 41, No. 16, pp. 3056-3058.
Ishiyama et al., "Mild iridium-catalyzed borylation of arenes. High turnover numbers, room temperature reactions, and isolation of a potential intermediate", J. Am. Chem. Soc., 2002, vol. 124, No. 3, pp. 390-391.
J.C.S. Perkin I, 1975, 1390-1395.
Johnson et al., "Accessory cell-derived signals required for T cell activation", Immunologic Research, 1993, pp. 48-64.
June et al., "Inhibition of tyrosine phosphorylation prevents T-cell receptor mediated signal transduction", Proc. Natl. Acad. Sci. USA, 1990, vol. 87, pp. 7722-7726.
Kajita et al., "Nickel-catalyzed decarbonylative addition of phthalimides to alkynes", J. Am. Chem. Soc., May 14, 2008, vol. 130, No. 19, pp. 6058-6059.
Kallberg et al., "Short-chain dehydrogenase/reductase (SDR) relationships: a large family with eight clusters common to human, animal, and plant genomes", Protein Sci., 2002, vol. 11, pp. 636-641.
Kallberg et al., "Short-Chain Dehydrogenases/Reductases (SDRs)—Coenzyme-Based Functional Assignments in Completed Genomes". Eur. J. Biochem., 2002, vol. 269, pp. 4409-4417.
Kim et al. "Activation and Function of the mTORC1 Pathway in Mast Cells". J Immunol. Apr. 1, 2008; 180(7):4586-95.
Knight et al., "A pharmacological map of the PI3-K family defines a role for p110a in insulin signaling", Cell, 2006, vol. 125, pp. 733-747.
Kost et al., "Recyclization of 3-Alkyl- and 1,3-Dialkylisoquinolinium Salts to Naphthylamines", Chemistry of Heterocyclic Compounds, Jan., 16(9): 965-970 (1981).
Kraybill et al., "Inhibitor scaffolds as new allele specific kinase substrates", Journal of the American Chemical Society, Oct. 16, 2002, vol. 124, No. 41, pp. 12118-12128, American Chemical Society, Washington, DC, US.

(56) References Cited

OTHER PUBLICATIONS

Kreutzberger et al. 5-Substituierte 4-Aminopyrimidine durch Aminomethinylierung von Acetonitrilen. Liebigs Ann. Chem. 1977: pp. 537-544.

Kumar et al., "Keten Dithioacetals. Part 11. Reaction of 3-Cyano-4-Methylthio-2(1H)-pyridones with Hydazine and Guanidine: Synthesis of Novel Substituted and Fused Pyrazolo[4,3-c]pyridone and Pyrido[4,3-d]pyrimidine derivatives", Journal of the Chemical Society, Perkin Transactions 1, Chemical Society, Letchworth, Jan., 8: 857-862 (1978).

Kundu et al., "Palladium-catalysed heteroannualation with terminal alkynes; a highly regio-and stereoselective synthesis of (Z)-3-aryl(alykl)idene isoindolin-1-ones1", Tetrahedron, Jun. 30, 2000, vol. 56, No. 27, pp. 4777-4792.

Kwok et al., "The anti-inflammatory natural product parthenolide from the medicinal herb feverfew directly binds to and inhibits IkB kinase", Chem. Biol., 2001, vol. 8, pp. 759-766.

Ledbetter et al., "Crosslinking of surface antigens cause mobilization of intracellular ionized calcium in T lymphocytes", Proc. Natl. Acad. Sci. USA, Mar. 1987, vol. 84, pp. 1384-1388.

Lee et al., "All roads lead to mTOR integrating inflammation and tumor angiogenesis", Cell Cycle, 2007, vol. 6, No. 24, pp. 3011-3014.

Ley et al., "The T cell receptor/CD3 complex and CD2 stimulate the tyrosine phosphorylation of indistinguishable patterns of polypeptides in the human T leukemic cell line Jurkat", Eur. J. Immunol., 1991, vol. 21, pp. 2203-2209.

Liu et al., "Costimulation of T-cell growth", Current Biology, 1992, pp. 265-270.

Majumder et al., "mTOR inhibition reverses Akt-dependent prostate intraepithelial neoplasia through regulation of apoptic and HIF-1-dependent pathways", Nature Medicine, 2004, vol. 10, pp. 594-601.

Basotest®, Test Kit for the Quantitative Determination of the Degranulation of Basophilic Granulocytes in Heparinized Human Whole Blood, version 04/02, pp. 1-10, [www.biocarta.com/TDS/10-0500.pdf], Retreived from the Internet Nov. 29, 2011.

Oppermann et al., "Forms and functions of human SDR enzymes," Chem. Biol. Interact. 130-132(1-3):699-705 (2001).

PubChem publication, "3-Phenylisoquinoline—Compound Summary (CID 609614)," (create date: Mar. 28, 2005), [http://pubchem.ncbi.nlm.nih.gov/summary/summary.cgi?cid=609614], retrieved from the Internet May 23, 2014.

HETEROCYCLIC COMPOUNDS AND USES THEREOF

This application claims the benefit of U.S. Provisional Application Ser. No. 61/509,454, filed on Jul. 19, 2011, and U.S. Provisional Application Ser. No. 61/412,384, filed on Nov. 10, 2010, each of which is incorporated herein by reference in its entirety.

BACKGROUND

The activity of cells can be regulated by external signals that stimulate or inhibit intracellular events. The process by which stimulatory or inhibitory signals are transmitted into and within a cell to elicit an intracellular response is referred to as signal transduction. Over the past decades, cascades of signal transduction events have been elucidated and found to play a central role in a variety of biological responses. Defects in various components of signal transduction pathways have been found to account for a vast number of diseases, including numerous forms of cancer, inflammatory disorders, metabolic disorders, vascular and neuronal diseases (Gaestel et al. *Current Medicinal Chemistry* (2007) 14:2214-2234).

Kinases represent a class of important signaling molecules. Kinases can generally be classified into protein kinases and lipid kinases, and certain kinases exhibit dual specificities. Protein kinases are enzymes that phosphorylate other proteins and/or themselves (i.e., autophosphorylation). Protein kinases can be generally classified into three major groups based upon their substrate utilization: tyrosine kinases which predominantly phosphorylate substrates on tyrosine residues (e.g., erb2, PDGF receptor, EGF receptor, VEGF receptor, src, abl), serine/threonine kinases which predominantly phosphorylate substrates on serine and/or threonine residues (e.g., mTorC1, mTorC2, ATM, ATR, DNA-PK, Akt), and dual-specificity kinases which phosphorylate substrates on tyrosine, serine and/or threonine residues.

Lipid kinases are enzymes that catalyze the phosphorylation of lipids. These enzymes, and the resulting phosphorylated lipids and lipid-derived biologically active organic molecules, play a role in many different physiological processes, including cell proliferation, migration, adhesion, and differentiation. Certain lipid kinases are membrane associated and they catalyze the phosphorylation of lipids contained in or associated with cell membranes. Examples of such enzymes include phosphoinositide(s) kinases (e.g., PI3 kinases, PI4-Kinases), diacylglycerol kinases, and sphingosine kinases.

The phosphoinositide 3-kinases (PI3Ks) signaling pathway is one of the most highly mutated systems in human cancers. PI3K signaling is also a key factor in many other diseases and disorders. PI3K signaling is involved in many disease states including allergic contact dermatitis, rheumatoid arthritis, osteoarthritis, inflammatory bowel diseases, chronic obstructive pulmonary disorder, psoriasis, multiple sclerosis, asthma, disorders related to diabetic complications, and inflammatory complications of the cardiovascular system such as acute coronary syndrome.

PI3Ks are members of a unique and conserved family of intracellular lipid kinases that phosphorylate the 3'-OH group on phosphatidylinositols or phosphoinositides. The PI3K family comprises 15 kinases with distinct substrate specificities, expression patterns, and modes of regulation. The class I PI3Ks (p110α, p110β, p110δ, and p110γ) are typically activated by tyrosine kinases or G-protein coupled receptors to generate PIP3, which engages downstream effectors such as those in the Akt/PDK1 pathway, mTOR, the Tec family kinases, and the Rho family GTPases. The class II and III PI3Ks play a key role in intracellular trafficking through the synthesis of PI(3)P and PI(3,4)P2. The PI3Ks are protein kinases that control cell growth (mTORC1) or monitor genomic integrity (ATM, ATR, DNA-PK, and hSmg-1).

The delta (δ) isoform of class I PI3K has been implicated, in particular, in a number of diseases and biological processes. PI3K δ is expressed primarily in hematopoietic cells including leukocytes such as T-cells, dendritic cells, neutrophils, mast cells, B-cells, and macrophages. PI3K δ is integrally involved in mammalian immune system functions such as T-cell function, B-cell activation, mast cell activation, dendritic cell function, and neutrophil activity. Due to its integral role in immune system function, PI3K δ is also involved in a number of diseases related to undesirable immune response such as allergic reactions, inflammatory diseases, inflammation mediated angiogenesis, rheumatoid arthritis, and autoimmune diseases such as lupus, asthma, emphysema and other respiratory diseases. Other class I PI3K involved in immune system function includes PI3K γ, which plays a role in leukocyte signaling and has been implicated in inflammation, rheumatoid arthritis, and autoimmune diseases such as lupus.

Unlike PI3K δ, the beta (β) isoform of class I PI3K appears to be ubiquitously expressed. PI3K β has been implicated primarily in various types of cancer including PTEN-negative cancer (Edgar et al. *Cancer Research* (2010) 70(3):1164-1172), and HER2-overexpressing cancer such as breast cancer and ovarian cancer.

SUMMARY

Described herein are compounds capable of selectively inhibiting certain isoform(s) of class I PI3K without substantially affecting the activity of the remaining isoforms of the same class. For example, non-limiting examples of inhibitors capable of selectively inhibiting PI3K-δ and/or PI3K-γ, but without substantially affecting the activity of PI3K-β are disclosed. Such inhibitors can be effective in ameliorating disease conditions associated with PI3K-δ/γ activity.

In one aspect, described herein are compounds of Formula (I):

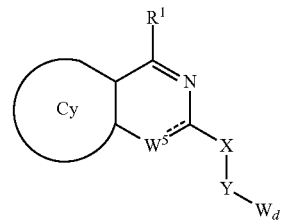

Formula (I)

or its pharmaceutically acceptable forms thereof, wherein
$W^5$ is N, $CHR^4$ or $CR^4$;
$R^4$ is hydrogen, alkyl, haloalkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R" wherein R' and R" are taken together with nitrogen to form a cyclic moiety;
Cy is aryl or heteroaryl substituted by 0-4 occurrences of $R^3$;
$R^1$ is -(L)$_n$-$R^{1'}$;
each L is independently a bond, alkylene, heteroalkylene, —N($R^2$)—, —S(O)—, —S(O)$_2$—, —S—, —C(=O)—, —P(=O)$R^2$— or —O—;

R[1'] is hydrogen, alkyl, heteroalkyl, alkenyl, alkynyl, cycloalkyl, heterocycloalkyl, aryl, arylalkyl, heteroaryl, heteroarylalkyl, alkoxy, heterocyclyloxy, heterocycloalkyloxy, amino, amido, acyl, acyloxy, alkoxycarbonyl, sulfonamido, halo, cyano, hydroxy, nitro, phosphate, urea, carbonate, —(C═O)—NR$^{a1}$R$^{a2}$ or NR$^{a1}$R$^{a2}$;

R$^{a1}$ and R$^{a2}$ are each independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or R$^{a1}$ and R$^{a2}$ are taken together with nitrogen to form a cyclic moiety;

R$^2$ is hydrogen, alkyl, cycloalkyl, heterocycloalkyl, heteroalkyl, aryl, or heteroaryl;

each R$^3$ is independently alkyl, heteroalkyl, haloalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R" wherein R' and R" are taken together with nitrogen to form a cyclic moiety;

X is absent or is —(CH(R$^{10}$))$_z$—;
Y is absent, —O—, —S—, —S(═O)—, —S(═O)$_2$—, —N(R$^9$)—, —C(═O)—(CHR$^{10}$)$_z$—, —C(═O)—, —N(R$^9$)—C(═O)—, —C(═O)—N(R$^9$)—, —N(R$^9$)—C(═O)NH—, —N(R$^9$)C(R$^{10}$)$_2$—, —C(═O)—(CHR$^{10}$)$_z$—, —C(═O)—N(R$^9$)—(CHR$^{10}$)$_z$— or —P(═O)R$_2$—;

each z is an integer of 1, 2, 3, or 4;
n is an integer of 0, 1, 2, 3, or 4;
each R$^9$ is independently hydrogen, alkyl, cycloalkyl, heterocycloalkyl, heterocycloalkylalkyl, heteroalkyl, aryl, or heteroaryl;

W$_d$ is heterocycloalkyl, aryl, cycloalkyl, or heteroaryl, wherein W$_d$ is optionally substituted with one or more R$^b$, R$^{11}$, R$^{12}$, and R$^{13}$;

each R$^b$ is independently hydrogen, halo, phosphate, urea, carbonate, alkyl, alkenyl, alkynyl, cycloalkyl, heteroalkyl, or heterocycloalkyl; and each R$^{10}$, R$^{11}$, R$^{12}$, and R$^{13}$ is independently hydrogen, alkyl, heteroalkyl, alkenyl, alkynyl, cycloalkyl, heterocycloalkyl, aryl, arylalkyl, heteroaryl, heteroarylalkyl, alkoxy, heterocyclyloxy, amido, amino, acyl, acyloxy, alkoxycarbonyl, sulfonamido, halo, haloalkyl, cyano, hydroxyl, nitro, phosphate, urea, carbonate, or NR'R" wherein R' and R" are taken together with nitrogen to form a cyclic moiety.

In some embodiments, the compound of Formula (I) has the structure of Formula (Ia):

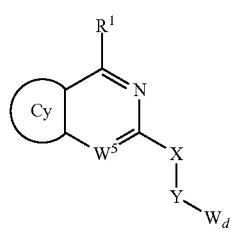

Formula (Ia)

or its pharmaceutically acceptable forms thereof, wherein n, z, R$^{a1}$, R$^{a2}$, L, R$^1$, R$^{1'}$, R$^2$, R$^3$, R$^4$, X, Y, R$^9$, R$^{10}$, R$^b$, R$^{11}$, R$^{12}$, R$^{13}$ and W$_d$ are as defined for Formula (I); and W$^5$ is N or CR$^4$.

In some embodiments, the compound of Formula (I) is a compound of Formula (II):

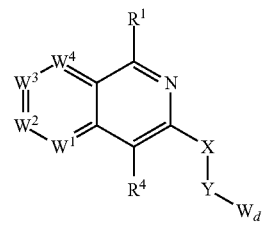

Formula (II)

or its pharmaceutically acceptable forms thereof, wherein n, z, R$^{a1}$, R$^{a2}$, L, R$^1$, R$^{1'}$, R$^2$, R$^4$, X, Y, R$^9$, R$^{10}$, R$^b$, R$^{11}$, R$^{12}$, R$^{13}$ and W$_d$ are as defined for Formula (I);

W$^1$ is N or CR$^{14}$, W$^2$ is N or CR$^6$, W$^3$ is N or CR$^7$, and W$^4$ is N or CR$^8$, wherein no more than two N atoms are adjacent; and R$^6$, R$^7$, R$^8$ and R$^{14}$ are independently hydrogen, alkyl, haloalkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R" wherein R' and R" are taken together with nitrogen to form a cyclic moiety.

In some embodiments, the compound of Formula (II) has the structure of Formula (IIa):

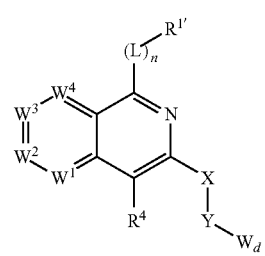

Formula (IIa)

or its pharmaceutically acceptable forms thereof, wherein
W$^1$ is N or CR$^{14}$, W$^2$ is N or CR$^6$, W$^3$ is N or CR$^7$, and W$^4$ is N or CR$^8$, wherein no more than two N atoms are adjacent;

R$^1$ is -(L)$_n$-R$^{1'}$;
each L is independently alkylene, heteroalkylene, —S(O)$_2$—, —S—, —N(R$^2$)—, or —O—;
n is an integer of 0, 1, 2, 3 or 4;
R$^{1'}$ is alkyl, substituted alkyl, a heterocyclic group comprising at least two heteroatoms chosen from O, N and S, wherein R$^{1'}$ is optionally substituted by R$^{a1}$; or R$^{1'}$ is NR$^{a1}$R$^{a2}$;

R$^{a1}$ and R$^{a2}$ are each independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or R$^{a1}$ and R$^{a2}$ are taken together with nitrogen to form a cyclic moiety;

R$^4$, R$^{14}$, R$^6$, R$^7$ and R$^8$ are each independently hydrogen, alkyl, heteroalkyl, haloalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R", wherein R' and R" are taken together with nitrogen to form a cyclic moiety;

X is absent or is —(CH($R^{10}$))$_z$—;

Y is absent, —O—, —S—, —S(=O)—, —S(=O)$_2$—, —N($R^9$)—, —C(=O)—(CHR$^{10}$)$_z$—, —C(=O)—, —N($R^9$)—C(=O)—, or —N($R^9$)—C(=O)NH—, —N($R^9$)C($R^{10}$)$_2$—, or —C(=O)—(CHR$^{10}$)$_z$—;

each z is an integer of 1, 2, 3, or 4;

each $R^2$ and $R^9$ is independently hydrogen, $C_1$-$C_{10}$ alkyl, $C_3$-$C_7$cycloalkyl, heterocycloalkyl, $C_2$-$C_{10}$ heteroalkyl, aryl, or heteroaryl;

each $R^{10}$ is independently hydrogen, alkyl, cycloalkyl, heteroalkyl, aryl, heteroaryl, arylalkyl, heteroarylalkyl or halo;

$W_d$ is heterocycloalkyl, aryl, cycloalkyl, or heteroaryl, wherein $W_d$ is substituted with one or more $R^b$, $R^{11}$, $R^{12}$, or $R^{13}$; and each $R^b$, $R^{11}$, $R^{12}$, and $R^{13}$ is independently hydrogen, alkyl, heteroalkyl, alkenyl, alkynyl, cycloalkyl, heterocycloalkyl, aryl, arylalkyl, heteroaryl, heteroarylalkyl, alkoxy, heterocyclyloxy, amido, amino, acyl, acyloxy, alkoxycarbonyl, sulfonamido, halo, haloalkyl, cyano, hydroxyl, nitro, phosphate, urea, carbonate, or NR'R", wherein R' and R" are taken together with nitrogen to form a cyclic moiety; and at least one of $R^4$, $R^{14}$, $R^6$, and $R^7$ is halo.

In some embodiments, the compound of Formula (II) has the structure of Formula (IIb):

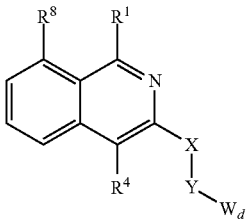

Formula (IIb)

or its pharmaceutically acceptable forms thereof, wherein $R_1$, $R_4$, $R_8$, X, Y, and $W_d$ are as defined for Formula (II).

In some embodiments, the compound of Formula (I) has the structure of Formula (III):

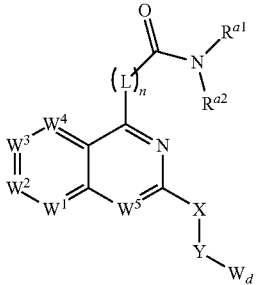

Formula (III)

or its pharmaceutically acceptable forms thereof, wherein $W^1$ is N or CR$^{14}$, $W^2$ is N or CR$^6$, $W^3$ is N or CR$^7$, $W^4$ is N or CR$^8$, and $W^5$ is N or CR$^4$, wherein no more than two N atoms are adjacent;

each L is alkylene, heteroalkylene, —S—, —N($R^2$)—, or —O—;

n is 0 or 1;

$R^{a1}$ and $R^{a2}$ are each independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or $R^{a1}$ and $R^{a2}$ are taken together with nitrogen to form a cyclic moiety;

$R^4$, $R^{14}$, $R^6$, $R^7$ and $R^8$ are independently hydrogen, alkyl, heteroalkyl, haloalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R", wherein R' and R" are taken together with nitrogen to form a cyclic moiety;

X is absent or is —(CH($R^{10}$))$_z$—;

Y is absent, —O—, —S—, —S(=O)—, —S(=O)$_2$—, —N($R^9$)—, —C(=O)—(CHR$^{10}$)$_z$—, —C(=O)—, —N($R^9$)—C(=O)—, or —N($R^9$)—C(=O)NH—, —N($R^9$)C($R^{10}$)$_2$—, or —C(=O)—(CHR$^{10}$)$_z$—;

each z is an integer of 1, 2, 3, or 4;

each $R^2$ and $R^9$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl;

each $R^{10}$ is independently hydrogen, alkyl, cycloalkyl, heteroalkyl, aryl, heteroaryl, arylalkyl, heteroarylalkyl or halo; and $W_d$ is heterocycloalkyl, aryl, cycloalkyl, or heteroaryl, wherein $W_d$ is substituted with one or more $R^b$, $R^{11}$, $R^{12}$, and $R^{13}$; and each $R^b$, $R^{11}$, $R^{12}$, and $R^{13}$ is independently hydrogen, alkyl, heteroalkyl, alkenyl, alkynyl, cycloalkyl, heterocycloalkyl, aryl, arylalkyl, heteroaryl, heteroarylalkyl, alkoxy, heterocyclyloxy, amido, amino, acyl, acyloxy, alkoxycarbonyl, sulfonamido, halo, haloalkyl, cyano, hydroxyl, nitro, phosphate, urea, carbonate, or NR'R", wherein R' and R" are taken together with nitrogen to form a cyclic moiety.

In some embodiments, the compound of Formula (III) has the structure of Formula (IIIa):

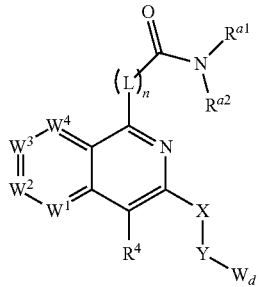

Formula (IIIa)

or its pharmaceutically acceptable forms thereof, wherein L, n, z, $R^{a1}$, $R^{a2}$, X, Y, $R^2$, $R^4$, $R^9$, $R^{10}$, $R^b$, $R^{11}$, $R^{12}$, $R^{13}$, and $W_d$ are as defined for Formula (III);

$W^1$ is N or CR$^{14}$, $W^2$ is N or CR$^6$, $W^3$ is N or CR$^7$, and $W^4$ is N or CR$^8$, wherein no more than two N atoms are adjacent; and $R^6$, $R^7$, $R^8$ and $R^{14}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R", wherein R' and R" are taken together with nitrogen to form a cyclic moiety.

In some embodiments, the compound of Formula (IIIa) has the structure of Formula (IIIb):

Formula (IIIb)

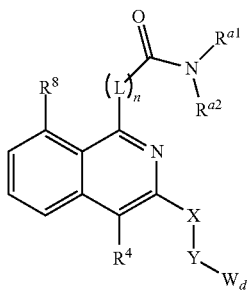

or its pharmaceutically acceptable forms thereof, wherein L, n, z, $R^{a1}$, $R^{a2}$, $R^b$, X, Y, $R^4$, $R^8$, $R^2$, $R^9$, $R^{10}$, $R^{11}$, $R^{12}$, $R^{13}$ and $W_d$ are as defined for Formula (III).

In some embodiments, the compound of Formula (I) has the structure of Formula (IV):

Formula (IV)

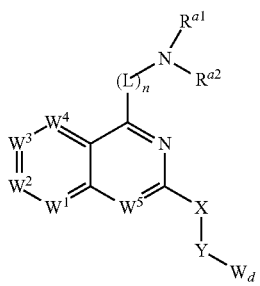

or its pharmaceutically acceptable forms thereof, wherein z, n, L, $R^{a1}$, $R^{a2}$, X, Y, $R^2$, $R^4$, $R^9$, $R^{10}$, $R^b$, $R^{11}$, $R^{12}$, $R^{13}$, and $W_d$ are as defined for Formula (I);

$W^1$ is N or $CR^{14}$, $W^2$ is N or $CR^6$, $W^3$ is N or $CR^7$, $W^4$ is N or $CR^8$, and $W^5$ is N or $CR^4$, wherein no more than two N atoms are adjacent; and $R^6$, $R^7$, $R^8$ and $R^{14}$ are independently hydrogen, alkyl, heteroalkyl, haloalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R" wherein R' and R" are taken together with nitrogen to form a cyclic moiety.

In some embodiments, the compound of Formula (IV) has the structure of Formula (IVa):

Formula (IVa)

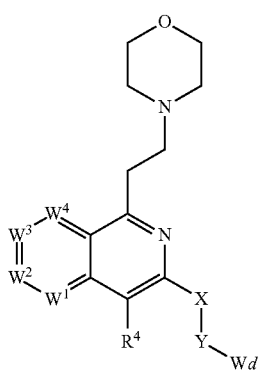

or its pharmaceutically acceptable forms thereof, wherein z, X, Y, $W^1$, $W^2$, $W^3$, $W^4$, $R^4$, $R^6$, $R^7$, $R^8$, $R^{14}$, $R^9$, $R^{10}$, $R^b$, $R^{11}$, $R^{12}$, $R^{13}$, and $W_d$ are as defined for Formula (IV).

In some embodiments, the compound of Formula (IVa) has the structure of Formula (IVb):

Formula (IVb)

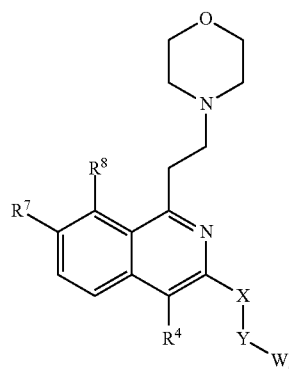

or its pharmaceutically acceptable forms thereof, wherein z, X, Y, $R^4$, $R^7$, $R^8$, $R^9$, $R^{10}$, $R^b$, $R^{11}$, $R^{12}$, $R^{13}$, and $W_d$ are as defined for Formula (IV).

In some embodiments, the compound of Formula (I) has the structure of Formula (V):

Formula (V)

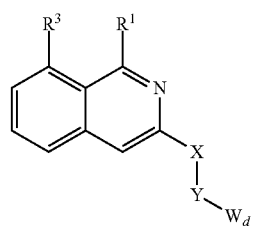

or its pharmaceutically acceptable form thereof, wherein n, z, L, X, Y, $R^1$, $R^{1'}$, $R^{a1}$, $R^{a2}$, $R^2$, $R^3$, $R^9$, $R^{10}$, $R^b$, $R^{11}$, $R^{12}$, $R^{13}$ and $W_d$ are as defined for Formula (I).

In another aspect, provided herein are compositions (e.g., a pharmaceutical composition) comprising one or more pharmaceutically acceptable excipients and a compound as described herein (e.g., a compound of Formula I, II, III, IV or V). For example, the composition is a liquid, solid, semi-solid, gel, or an aerosol form.

In another aspect, provided herein is a method of inhibiting a phosphatidyl inositol-3 kinase (PI3 kinase), comprising: contacting the PI3 kinase with an effective amount of a compound described herein.

In some embodiments, the PI3 kinase is PI3 kinase delta or PI3 kinase gamma. The step of contacting can further comprise contacting a cell that expresses said PI3 kinase. In some embodiments, the method further comprises administering a second therapeutic agent to the cell.

In another aspect, provided herein is a method for treating a condition associated with PI3 kinase, comprising administering to a subject in need thereof an effective amount of the compound described herein, such as a compound of Formula (I), (II), (III), (IV) or (V). In some embodiments, the condition associated with PI3 kinase is selected from asthma, emphysema, bronchitis, psoriasis, allergy, anaphylaxis, rheumatoid arthritis, graft versus host disease, lupus erythematosus, psoriasis, restenosis, benign prostatic hypertrophy, diabetes, pancreatitis, proliferative glomerulonephritis, diabetes—induced renal disease, inflammatory bowel disease, atherosclerosis, eczema, scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In certain embodiments, a compound as disclosed herein selectively modulates phosphatidyl inositol-3 kinase (PI3 kinase) delta isoform. In certain embodiments, the compound selectively inhibits the delta isoform over the beta isoform. By way of non-limiting example, the ratio of selectivity can be greater than a factor of about 10, greater than a factor of about 50, greater than a factor of about 100, greater than a factor of about 200, greater than a factor of about 400, greater than a factor of about 600, greater than a factor of about 800, greater than a factor of about 1000, greater than a factor of about 1500, greater than a factor of about 2000, greater than a factor of about 5000, greater than a factor of about 10,000, or greater than a factor of about 20,000, where selectivity can be measured by $IC_{50}$, among other means. In certain embodiments, the PI3 kinase delta isoform $IC_{50}$ activity of a compound as disclosed herein can be less than about 1000 nM, less than about 100 nM, less than about 10 nM, or less than about 1 nM.

In certain embodiments, provided herein is a composition (e.g., a pharmaceutical composition) comprising a compound as described herein and one or more pharmaceutically acceptable excipients. In some embodiments, provided herein is a method of inhibiting a phosphatidyl inositol-3 kinase (PI3 kinase), comprising contacting the PI3 kinase with an effective amount of a compound or pharmaceutical composition as described herein. In certain embodiments, a method is provided for inhibiting a phosphatidyl inositol-3 kinase (PI3 kinase) wherein said PI3 kinase is present in a cell. The inhibition can take place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease. In certain embodiments, a second therapeutic agent is administered to the subject.

In certain embodiments, a method is provided of selectively inhibiting a phosphatidyl inositol-3 kinase (PI3 kinase) delta isoform over PI3 kinase beta isoform wherein the inhibition takes place in a cell. Non-limiting examples of the methods disclosed herein can comprise contacting PI3 kinase delta isoform with an effective amount of a compound or pharmaceutical composition as disclosed herein. In an embodiment, such contact can occur in a cell. In certain embodiments, a method is provided of selectively inhibiting a phosphatidyl inositol-3 kinase (PI3 kinase) delta isoform over PI3 kinase beta isoform wherein the inhibition takes place in a subject suffering from a disorder selected from cancer, bone disorder, inflammatory disease, immune disease, nervous system disease (e.g., a neuropsychiatric disorder), metabolic disease, respiratory disease, thrombosis, and cardiac disease, said method comprising administering an effective amount of a compound or pharmaceutical composition to said subject. In certain embodiments, provided herein is a method of treating a subject suffering from a disorder associated with phosphatidyl inositol-3 kinase (PI3 kinase), said method comprising selectively modulating the phosphatidyl inositol-3 kinase (PI3 kinase) delta isoform over PI3 kinase beta isoform by administering an amount of a compound or pharmaceutical composition to said subject, wherein said amount is sufficient for selective modulation of PI3 kinase delta isoform over PI3 kinase beta isoform.

In some embodiments, provided herein is a method of making a compound as described herein.

In certain embodiments, provided herein is a reaction mixture comprising a compound as described herein.

In certain embodiments, provided herein is a kit comprising a compound as described herein.

In some embodiments, a method is provided for treating a disease or disorder described herein, the method comprising administering a therapeutically effective amount of a compound or pharmaceutical composition described herein to a subject.

In some embodiments, provided herein is a method for treating a PI3K mediated disorder in a subject, the method comprising administering a therapeutically effective amount of a compound or pharmaceutical composition described herein.

In certain embodiments, provided herein is the use of a compound of a pharmaceutical composition described herein in the manufacture of a medicament for the treatment of a disease or disorder described herein in a subject.

In certain embodiments, provided herein is use of a compound or a pharmaceutical composition described herein in the manufacture of a medicament for the treatment of a PI3K mediated disorder in a subject.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION

While specific embodiments of the present disclosure have been discussed, the specification is illustrative and not restrictive. Many variations of this disclosure will become apparent to those skilled in the art upon review of this specification. The full scope of the disclosure should be determined by reference to the claims, along with their full scope of equivalents, and the specification, along with such variations.

In one embodiment, provided are heterocyclyl compounds, and pharmaceutically acceptable forms, including, but not limited to, salts, hydrates, solvates, isomers, prodrugs, and isotopically labeled derivatives thereof.

In another embodiment, provided are methods of treating and/or managing various diseases and disorders, which comprises administering to a patient a therapeutically effective amount of a compound provided herein, or a pharmaceutically acceptable form (e.g., salts, hydrates, solvates, isomers, prodrugs, and isotopically labeled derivatives) thereof. Examples of diseases and disorders are described herein.

In another embodiment, provided are methods of preventing various diseases and disorders, which comprises administering to a patient in need of such prevention a prophylactically effective amount of a compound provided herein, or a pharmaceutically acceptable form (e.g., salts, hydrates, solvates, isomers, prodrugs, and isotopically labeled derivatives) thereof. Examples of diseases and disorders are described herein.

In other embodiments, a compound provided herein, or a pharmaceutically acceptable form (e.g., salts, hydrates, solvates, isomers, prodrugs, and isotopically labeled derivatives) thereof, is administered in combination with another drug ("second active agent") or treatment. Second active agents include small molecules and large molecules (e.g., proteins and antibodies), examples of which are provided herein, as well as stem cells. Other methods or therapies that can be used in combination with the administration of compounds provided herein include, but are not limited to, surgery, blood transfusions, immunotherapy, biological therapy, radiation therapy, and other non-drug based therapies presently used to treat, prevent or manage various disorders described herein.

Also provided are pharmaceutical compositions (e.g., single unit dosage forms) that can be used in the methods provided herein. In one embodiment, pharmaceutical compositions comprise a compound provided herein, or a pharmaceutically acceptable form (e.g., salts, hydrates, solvates, isomers, prodrugs, and isotopically labeled derivatives) thereof, and optionally one or more second active agents.

Unless defined otherwise, all technical and scientific terms used herein have the same meaning as is commonly understood by one of skill in the art to which this specification pertains.

As used in the specification and claims, the singular form "a", "an" and "the" includes plural references unless the context clearly dictates otherwise.

As used herein, "agent" or "biologically active agent" refers to a biological, pharmaceutical, or chemical compound or other moiety. Non-limiting examples include simple or complex organic or inorganic molecules, a peptide, a protein, an oligonucleotide, an antibody, an antibody derivative, an antibody fragment, a vitamin, a vitamin derivative, a carbohydrate, a toxin, or a chemotherapeutic compound, and metabolites thereof. Various compounds can be synthesized, for example, small molecules and oligomers (e.g., oligopeptides and oligonucleotides), and synthetic organic compounds based on various core structures. In addition, various natural sources can provide compounds for screening, such as plant or animal extracts, and the like. A skilled artisan can readily recognize that there is no limit as to the structural nature of the agents of this disclosure.

The term "agonist" as used herein refers to a compound or agent having the ability to initiate or enhance a biological function of a target protein or polypeptide, such as increasing the activity or expression of the target protein or polypeptide. Accordingly, the term "agonist" is defined in the context of the biological role of the target protein or polypeptide. While some agonists herein specifically interact with (e.g., bind to) the target, compounds and/or agents that initiate or enhance a biological activity of the target protein or polypeptide by interacting with other members of the signal transduction pathway of which the target polypeptide is a member are also specifically included within this definition.

The terms "antagonist" and "inhibitor" are used interchangeably, and they refer to a compound or agent having the ability to inhibit a biological function of a target protein or polypeptide, such as by inhibiting the activity or expression of the target protein or polypeptide. Accordingly, the terms "antagonist" and "inhibitors" are defined in the context of the biological role of the target protein or polypeptide. While some antagonists herein specifically interact with (e.g., bind to) the target, compounds that inhibit a biological activity of the target protein or polypeptide by interacting with other members of the signal transduction pathway of which the target protein or polypeptide is a member are also specifically included within this definition. Non-limiting examples of biological activity inhibited by an antagonist include those associated with the development, growth, or spread of a tumor, or an undesired immune response as manifested in autoimmune disease.

An "anti-cancer agent", "anti-tumor agent" or "chemotherapeutic agent" refers to any agent useful in the treatment of a neoplastic condition. One class of anti-cancer agents comprises chemotherapeutic agents. "Chemotherapy" means the administration of one or more chemotherapeutic drugs and/or other agents to a cancer patient by various methods, including intravenous, oral, intramuscular, intraperitoneal, intravesical, subcutaneous, transdermal, buccal, or inhalation or in the form of a suppository.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to subject so that both agents and/or their metabolites are present in the subject at the same time. Co-administration includes simultaneous administration in separate compositions, administration at different times in separate compositions, or administration in a composition in which both agents are present.

The term "effective amount" or "therapeutically effective amount" refers to that amount of a compound or pharmaceutical composition described herein that is sufficient to effect the intended application including, but not limited to, disease treatment, as illustrated below. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of platelet adhesion and/or cell migration. The specific dose will vary depending on the particular compounds chosen, the dosing regimen to be followed, whether it is administered in combination with other agents, timing of administration, the tissue to which it is administered, and the physical delivery system in which it is carried.

As used herein, the terms "treatment", "treating", "palliating" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compositions can be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

As used herein, a "pharmaceutically acceptable form" of a disclosed compound includes, but is not limited to, pharmaceutically acceptable salts, hydrates, solvates, isomers, prodrugs, and isotopically labeled derivatives of disclosed compounds.

In certain embodiments, the pharmaceutically acceptable form thereof is a pharmaceutically acceptable salt. As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Salts derived from appropriate bases include alkali metal, alkaline earth metal, ammonium and N+($C_{1-4}$ alkyl)$^4$-salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In certain embodiments, the pharmaceutically acceptable form is a "solvate" (e.g., a hydrate). As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or one to about 2, 3 or 4, solvent or water molecules. It will be understood that the term "compound" as used herein encompasses the compound and solvates of the compound, as well as mixtures thereof.

In certain embodiments, the pharmaceutically acceptable form thereof is a prodrug. As used herein, the term "prodrug" refers to compounds that are transformed in vivo to yield a disclosed compound or a pharmaceutically acceptable form of the compound. In some embodiments, a prodrug is a compound that may be converted under physiological conditions or by solvolysis to a biologically active compound described herein. Thus, the term "prodrug" refers to a precursor of a biologically active compound that is pharmaceutically acceptable. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs are typically designed to enhance pharmaceutically and/or pharmacokinetically based properties associated with the parent compound. The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it enhances absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like.

For example, if a disclosed compound or a pharmaceutically acceptable form of the compound contains a carboxylic acid functional group, a prodrug can comprise an ester formed by the replacement of the hydrogen atom of the acid group with a group such as ($C_1$-$C_8$)alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$) alkylcarbamoyl-($C_1$-$C_2$)alkyl and piperidino-, pyrrolidino- or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as $(C_1-C_6)$alkanoyloxymethyl, 1-(($C_1-C_6$)alkanoyloxy)ethyl, 1-methyl-1-(($C_1-C_6$)alkanoyloxy)ethyl ($C_1-C_6$)alkoxycarbonyloxymethyl, N—($C_1-C_6$)alkoxycarbonylaminomethyl, succinoyl, ($C_1-C_6$)alkanoyl, α-amino($C_1-C_4$)alkanoyl, arylacyl and α-aminoacyl, or α-aminoacyl-α-aminoacyl, where each -aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy$(C_1-C_6)$alkyl, amino$(C_1-C_4)$alkyl or mono-N— or di-N,N—$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino, morpholino, piperidin-1-yl or pyrrolidin-1-yl.

Geometric isomers can be represented by the symbol ------ which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

In certain embodiments, the pharmaceutically acceptable form thereof is an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include cis- and trans-isomers, E- and Z-isomers, R- and S-enantiomers, diastereomers, (d)-isomers, (l)-isomers, racemic mixtures thereof, and other mixtures thereof, as falling within the scope of this disclosure.

"Enantiomers" are a pair of stereoisomers that are non-superimposable mirror images of each other. A mixture of a pair of enantiomers in any proportion can be known as a "racemic" mixture. The term "(±)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. Optically active (R)- and (S)-isomers can be prepared, for example, using chiral synthons or chiral reagents, or resolved using conventional techniques. The optical activity of a compound can be analyzed via any suitable method, including but not limited to chiral chromatography and polarimetry, and the degree of predominance of one stereoisomer over the other isomer can be determined.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can also be used.

When desired, the (R)- and (S)-isomers of the compounds of the present invention, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

The "enantiomeric excess" or "% enantiomeric excess" of a composition can be calculated using the equation shown below. In the example shown below, a composition contains 90% of one enantiomer, e.g., the S enantiomer, and 10% of the other enantiomer, e.g., the R enantiomer.

$ee=(90-10)/100=80\%$.

Thus, a composition containing 90% of one enantiomer and 10% of the other enantiomer is said to have an enantiomeric excess of 80%. Some of the compositions described herein contain an enantiomeric excess of at least about 50%, 75%, 90%, 95%, or 99% of the S-enantiomer. In other words, the compositions contain an enantiomeric excess of the S enantiomer over the R enantiomer. In other embodiments, some compositions described herein contain an enantiomeric excess of at least about 50%, 75%, 90%, 95%, or 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least 95% by weight. In certain embodiments, the compound provided herein is made up of at least about 90% by weight of one enantiomer. In other embodiments, the compound is made up of at least about 95%, 98%, or 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In other embodiments, the compound mixture contains identical chemical entities except for their stereochemical orientations, namely (S)- or (R)-isomers. For example, if a compound disclosed herein has —CH(R)— unit, and R is not hydrogen, then the —CH(R)— is in an (S)- or (R)-stereochemical orientation for each of the identical chemical entities. In some embodiments, the mixture of identical chemical entities is a racemic mixture of (S)- and (R)-isomers. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric excess greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Enantiomers can be isolated from racemic mixtures by any method known to those skilled in the art, including chiral high pressure liquid chromatography (HPLC), the formation and crystallization of chiral salts, or prepared by asymmetric syntheses. See, for example, *Enantiomers, Racemates and Resolutions* (Jacques, Ed., Wiley Interscience, New York, 1981); Wilen et al., *Tetrahedron* 33:2725 (1977); *Stereochemistry of Carbon Compounds* (E. L. Eliel, Ed., McGraw-Hill, N.Y., 1962); and *Tables of Resolving Agents and Optical Resolutions* p. 268 (E. L. Eliel, Ed., Univ. of Notre Dame Press, Notre Dame, Ind. 1972).

In certain embodiments, the pharmaceutically acceptable form thereof is a tautomer. As used herein, the term "tautomer" includes two or more interconvertable compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

"Pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions as disclosed herein is contemplated. Supplementary active ingredients can also be incorporated into the pharmaceutical compositions.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator can augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or interact interaction with the target. For example, a compound that selectively inhibits one isoform of PI3K over another isoform of PI3K has an activity of at least 2× against a first isoform relative to the compound's activity against the second isoform (e.g., at least 3×, 5×, 10×, 20×, 50×, or 100×).

The term "B-ALL" as used herein refers to B-cell Acute Lymphoblastic Leukemia.

"Subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, and/or turkeys.

"Radiation therapy" means exposing a patient, using routine methods and compositions known to the practitioner, to radiation emitters such as, but not limited to, alpha-particle emitting radionuclides (e.g., actinium and thorium radionuclides), low linear energy transfer (LET) radiation emitters (i.e., beta emitters), conversion electron emitters (e.g., strontium-89 and samarium-153-EDTMP, or high-energy radiation, including without limitation x-rays, gamma rays, and neutrons.

The term "in vivo" refers to an event that takes place in a subject's body.

The term "in vitro" refers to an event that takes places outside of a subject's body. For example, an in vitro assay encompasses any assay conducted outside of a subject. In vitro assays encompass cell-based assays in which cells, alive or dead, are employed. In vitro assays also encompass a cell-free assay in which no intact cells are employed.

The compounds provided herein may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The disclosure also embraces isotopically labeled compounds which are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes can allow for ease of preparation and detectability. Further, substitution with heavier isotopes such as deuterium (i.e., $^2H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure.

The following abbreviations and terms have the indicated meanings throughout: PI3K=Phosphoinositide 3-kinase; PI=phosphatidylinositol; PDK=Phosphoinositide Dependent Kinase; DNA-PK=Deoxyribose Nucleic Acid Dependent Protein Kinase; PTEN=Phosphatase and Tensin homolog deleted on chromosome Ten; PIKK=Phosphoinositide Kinase Like Kinase; AIDS=Acquired Immuno Deficiency Syndrome; HIV=Human Immunodeficiency Virus; MeI=Methyl Iodide; POCl$_3$=Phosphorous Oxychloride; KCNS=Potassium Isothiocyanate; TLC=Thin Layer Chromatography; MeOH=Methanol; and CHCl$_3$=Chloroform.

"Alkyl" refers to a straight or branched hydrocarbon chain radical consisting solely of carbon and hydrogen atoms, containing no unsaturation, having from one to ten carbon atoms (e.g., $C_1$-$C_{10}$ alkyl). Whenever it appears herein, a numerical range such as "1 to 10" refers to each integer in the given range; e.g., "1 to 10 carbon atoms" means that the alkyl group can consist of 1 carbon atom, 2 carbon atoms, 3 carbon atoms, etc., up to and including 10 carbon atoms, although the present definition also covers the occurrence of the term "alkyl" where no numerical range is designated. In some embodiments, it is a $C_1$-$C_6$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like. Unless stated otherwise specifically in the specification, an alkyl group is optionally substituted by one or more of substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$ wherein each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, and each of these moieties can be optionally substituted as defined herein.

"Alkyl-cycloalkyl" refers to an -(alkyl)cycloalkyl radical where alkyl and cycloalkyl are as disclosed herein and which are optionally substituted by one or more of the substituents described as suitable substituents for alkyl and cycloalkyl respectively. The "alkyl-cycloalkyl" is bonded to the parent molecular structure through the alkyl group.

"Alkylaryl" refers to an -(alkyl)aryl radical where aryl and alkyl are as disclosed herein and which are optionally substituted by one or more of the substituents described as suitable substituents for aryl and alkyl respectively. The "alkylaryl" is bonded to the parent molecular structure through the alkyl group.

"Alkylheteroaryl" refers to an -(alkyl)heteroaryl radical where heteroaryl and alkyl are as disclosed herein and which are optionally substituted by one or more of the substituents described as suitable substituents for aryl and alkyl respectively. The "alkylheteroaryl" is bonded to the parent molecular structure through the alkyl group.

"Alkyl-heterocyclyl" refers to an -(alkyl)heterocyclyl radical where alkyl and heterocyclyl are as disclosed herein and which are optionally substituted by one or more of the substituents described as suitable substituents for heterocyclyl and alkyl respectively. The "alkyl-heterocyclyl" is bonded to the parent molecular structure through the alkyl group.

"Alkenyl" refers to a straight or branched hydrocarbon chain radical group consisting solely of carbon and hydrogen atoms, containing at least one double bond, and having from two to ten carbon atoms (i.e., $C_2$-$C_{10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In certain embodiments, an alkenyl comprises two to eight carbon atoms. In other embodiments, an alkenyl comprises two to five carbon atoms (e.g., $C_2$-$C_5$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)$^C$(O)N(R$^a$)$_2$, N(R$^a$)$^C$(NR$^a$)$^N$(R$^a$)$_2$, —N(R$^a$)S(O)$_t$R$_a$ (where t is 1 or 2), —S(O)$_t$O$_R^a$ (where t is 1 or 2), —S(O)$_t$N(R$^a$)$^2$ (where t is 1 or 2), or PO$_3$(R$^a$)$^2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Alkenyl-cycloalkyl" refers to an -(alkenyl)cycloalkyl radical where alkenyl and cyclo alkyl are as disclosed herein and which are optionally substituted by one or more of the substituents described as suitable substituents for alkenyl and cycloalkyl respectively. The "alkenyl-cycloalkyl" is bonded to the parent molecular structure through the alkenyl group.

"Alkynyl" refers to a straight or branched hydrocarbon chain radical group consisting solely of carbon and hydrogen atoms, containing at least one triple bond, having from two to ten carbon atoms (i.e., $C_2$-$C_{10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, etc., up to and including 10 carbon atoms. In certain embodiments, an alkynyl comprises two to eight carbon atoms. In other embodiments, an alkynyl has two to five carbon atoms (e.g., $C_2$-$C_5$ alkynyl). The alkynyl is attached to the parent molecular structure by a single bond, for example, ethynyl, propynyl, butynyl, pentynyl, hexynyl, and the like. Unless stated otherwise specifically in the specification, an alkynyl group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Alkynyl-cycloalkyl" refers to refers to an -(alkynyl)cycloalkyl radical where alkynyl and cycloalkyl are as disclosed herein and which are optionally substituted by one or more of the substituents described as suitable substituents for alkynyl and cycloalkyl respectively. The "alkynyl-cycloalkyl" is bonded to the parent molecular structure through the alkenyl group.

"Carbonate" refers to a —O—C(=O)—O—R$^a$ wherein each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl. In some embodiments, when R$^a$ is hydrogen and depending on the pH, the hydrogen can be replaced by an appropriately charged counter ion.

"Carboxaldehyde" refers to a —(C=O)H radical.

"Carboxyl" refers to a —(C=O)OH radical.

"Carboxylic acid" refers to a —C(=O)OH radical.

"Cyano" refers to a —CN radical.

"Cycloalkyl" refers to a monocyclic or polycyclic radical that contains only carbon and hydrogen, and can be saturated, or partially unsaturated. Cycloalkyl groups include groups having from 3 to 10 ring atoms (i.e., $C_3$-$C_{10}$ cycloalkyl). Whenever it appears herein, a numerical range such as "3 to 10" refers to each integer in the given range; e.g., "3 to 10 carbon atoms" means that the cycloalkyl group can consist of 3 carbon atoms, 4 carbon atoms, 5 carbon atoms, etc., up to and including 10 carbon atoms. In some embodiments, it is a $C_3$-$C_8$ cycloalkyl radical. In some embodiments, it is a $C_3$-$C_5$ cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like. The term "cycloalkyl" also includes bridged and spiro-fused cyclic structures containing no heteroatoms. The term also includes monocyclic or fused-ring polycyclic (i.e., rings which share adjacent pairs of ring atoms) groups. Unless stated otherwise specifically in the specification, a cycloalkyl group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Cycloalkyl-alkyl" refers to a -(cycloalkyl)alkyl radical where cycloalkyl and alkyl are as disclosed herein and which are optionally substituted by one or more of the substituents described as suitable substituents for cycloalkyl and alkyl respectively. The "cycloalkyl-alkyl" is bonded to the parent molecular structure through the cycloalkyl group.

"Cycloalkyl-heterocycloalkyl" refers to a -(cycloalkyl) heterocycyl radical where cycloalkyl and heterocycloalkyl are as disclosed herein and which are optionally substituted by one or more of the substituents described as suitable substituents for heterocycloalkyl and cycloalkyl respectively. The "cycloalkyl-heterocycloalkyl" is bonded to the parent molecular structure through the cycloalkyl group.

"Cycloalkyl-heteroaryl" refers to a -(cycloalkyl) heteroaryl radical where cycloalkyl and heteroaryl are as disclosed herein and which are optionally substituted by one or more of the substituents described as suitable substituents for heteroaryl and cycloalkyl respectively. The "cycloalkyl-heteroaryl" is bonded to the parent molecular structure through the cycloalkyl group.

The term "alkoxy" refers to the group —O-alkyl, including from 1 to 10 carbon atoms of a straight, branched, cyclic configuration and combinations thereof, attached to the parent molecular structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, C$_1$-C$_4$ alkyl is an alkyl group which encompasses both straight and branched chain alkyls of from 1 to 4 carbon atoms.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$R$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

The term "alkoxycarbonyl" refers to a group of the formula (alkoxy)(C=O)— attached to the parent molecular structure through the carbonyl carbon wherein the alkoxy group has the indicated number of carbon atoms, such as from 1-10 carbon atoms. Thus a C$_1$-C$_6$ alkoxycarbonyl group is an alkoxy group having from 1 to 6 carbon atoms attached through its oxygen to a carbonyl linker. The C$_1$-C$_6$ designation does not include the carbonyl carbon in the atom count. "Lower alkoxycarbonyl" refers to an alkoxycarbonyl group wherein the alkyl portion of the alkoxy group is a lower alkyl group. In some embodiments, C$_1$-C$_4$ alkoxy is an alkoxy group which encompasses both straight and branched chain alkoxy groups of from 1 to 4 carbon atoms.

The term "substituted alkoxycarbonyl" refers to the group (substituted alkyl)-O—C(O)— wherein the group is attached to the parent molecular structure through the carbonyl functionality. Unless stated otherwise specifically in the specification, the alkyl moiety of an alkoxycarbonyl group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Acyl" refers to R—C(O)— groups such as (alkyl)-C(O)—, (aryl)-C(O)—, (heteroaryl)-C(O)—, (heteroalkyl)-C(O)—, and (heterocycloalkyl)-C(O)—, wherein the group is attached to the parent molecular structure through the carbonyl functionality. In some embodiments, it is a C$_1$-C$_{10}$ acyl radical which refers to the total number of chain or ring atoms of the alkyl, aryl, heteroaryl or heterocycloalkyl portion of the alkyl group plus the carbonyl carbon of acyl, i.e., a C$_4$-acyl has three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(N-R$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Acyloxy" refers to a R(C=O)O— radical wherein "R" is alkyl, aryl, heteroaryl, heteroalkyl, or heterocycloalkyl, which are as described herein. The acyloxy group is attached to the parent molecular structure through the oxygen functionality. In some embodiments, it is a $C_1$-$C_4$ acyloxy radical which refers to the total number of chain or ring atoms of the alkyl, aryl, heteroaryl or heterocycloalkyl portion of the acyloxy group plus the carbonyl carbon of acyl, i.e., a $C_4$-acyloxy has three other ring or chain atoms plus carbonyl. If the R radical is heteroaryl or heterocycloalkyl, the hetero ring or chain atoms contribute to the total number of chain or ring atoms. Unless stated otherwise specifically in the specification, the "R" of an acyloxy group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Amino" or "amine" refers to a —N(R$^a$)$_2$ radical group, where each R$^a$ is independently hydrogen, alkyl, haloalkyl, carbocyclyl, carbocyclylalkyl, aryl, aralkyl, heterocycloalkyl (bonded through a chain carbon), heterocycloalkylalkyl, heteroaryl (bonded through a chain carbon), or heteroarylalkyl, unless stated otherwise specifically in the specification. When a —N(R$^a$)$_2$ group has two R$^a$ other than hydrogen, they can be combined with the nitrogen atom to form a 4-, 5-, 6-, or 7-membered ring. For example, —N(R$^a$)$_2$ is meant to include, but not be limited to, 1-pyrrolidinyl and 4-morpholinyl. Unless stated otherwise specifically in the specification, an amino group is optionally substituted by one or more substituents which independently include: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

The term "substituted amino" also refers to N-oxides of the groups —N$^+$(H)(R$^a$)O$^-$, and —N$^+$(R$^a$)(R$^a$)O$^-$, R$^a$ as described above, where the N-oxide is bonded to the parent molecular structure through the N atom. N-oxides can be prepared by treatment of the corresponding amino group with, for example, hydrogen peroxide or m-chloroperoxybenzoic acid. The person skilled in the art is familiar with reaction conditions for carrying out the N-oxidation.

"Amide" or "amido" refers to a chemical moiety with formula —C(O)N(R)$_2$ or —NRC(O)R, where R is selected from hydrogen, alkyl, cycloalkyl, aryl, heteroaryl (bonded through a ring carbon) and heteroalicyclic (bonded through a ring carbon), each of which moiety can itself be optionally substituted. In some embodiments it is a $C_1$-$C_4$ amido or amide radical, which includes the amide carbonyl in the total number of carbons in the radical. The R$_2$ of —N(R)$_2$ of the amide can optionally be taken together with the nitrogen to which it is attached to form a 4-, 5-, 6-, or 7-membered ring. Unless stated otherwise specifically in the specification, an amido group is optionally substituted independently by one or more of the substituents as described herein for alkyl, cycloalkyl, aryl, heteroaryl, or heterocycloalkyl. An amide can be an amino acid or a peptide molecule attached to a compound of Formula (I), thereby forming a prodrug. Any amine, hydroxy, or carboxyl side chain on the compounds described herein can be transformed into an amide group. The procedures and specific groups to make such amides are known to those of skill in the art and can readily be found in reference sources such as Greene and Wuts, *Protective Groups in Organic Synthesis,* 3rd Ed., John Wiley & Sons, New York, N.Y., 1999, which is incorporated herein by reference in its entirety.

"Aromatic" or "aryl" refers to a radical with six to ten ring atoms (e.g., $C_6$-$C_{10}$ aromatic or $C_6$-$C_{10}$ aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group can consist of 6 ring atoms, 7 ring atoms, etc., up to and including 10 ring atoms. The term includes monocyclic or fused-ring polycyclic (i.e., rings which share adjacent pairs of ring atoms) groups. Unless stated otherwise specifically in the specification, an aryl moiety can be optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_n$R$^a$ (where t is 1 or 2), —S(O)$_n$OR$^a$ (where t is 1 or 2), —S(O)$_n$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Aralkyl" or "arylalkyl" refers to an (aryl)alkyl-radical where aryl and alkyl are as disclosed herein and which are optionally substituted by one or more of the substituents described as suitable substituents for aryl and alkyl respectively. The "aralkyl/arylalkyl" is bonded to the parent molecular structure through the alkyl group.

As used herein, a "covalent bond" or "direct bond" refers to a single bond joining two groups.

"Ester" refers to a chemical radical of formula —COOR, where R is selected from alkyl, cycloalkyl, aryl, heteroaryl (bonded through a ring carbon) and heteroalicyclic (bonded through a ring carbon). Any amine, hydroxy, or carboxyl side chain on the compounds described herein can be esterified. The procedures and specific groups to make such esters are known to those of skill in the art and can readily be found in reference sources such as Greene and Wuts, *Protective Groups in Organic Synthesis,* 3rd Ed., John Wiley & Sons, New York, N.Y., 1999, which is incorporated herein by reference in its entirety. Unless stated otherwise specifically in the specification, an ester group can be optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, trifluoromethyl, trifluoromethoxy, nitro, trimethylsilanyl, —OR$^a$, —SR$^a$, —OC(O)—R$^a$, —N(R$^a$)$_2$, —C(O)R$^a$, —C(O)OR$^a$, —OC(O)N(R$^a$)$_2$, —C(O)N(R$^a$)$_2$, —N(R$^a$)C(O)OR$^a$, —N(R$^a$)C(O)R$^a$, —N(R$^a$)C(O)N(R$^a$)$_2$, N(R$^a$)C(NR$^a$)N(R$^a$)$_2$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical can be optionally substituted as defined above for an alkyl group.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

"Heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range can be given, e.g., $C_1$-$C_4$ heteroalkyl which refers to the chain length in total, which in this example is 4 atoms long. For example, a —CH$_2$OCH$_2$CH$_3$ radical is referred to as a "$C_4$" heteroalkyl, which includes the heteroatom center in the atom chain length description. Connection to the rest of the parent molecular structure can be through either a heteroatom or a carbon in the heteroalkyl chain. A heteroalkyl group can be substituted with one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —OC(O)—R$^a$, —N(R$^a$)$_2$, —C(O)R$^a$, —C(O)OR$^a$, —C(O)N(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$R$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

"Heteroalkylaryl" refers to an -(heteroalkyl)aryl radical where heteroalkyl and aryl are as disclosed herein and which are optionally substituted by one or more of the substituents described as suitable substituents for heteroalkyl and aryl respectively. The "heteroalkylaryl" is bonded to the parent molecular structure through a carbon atom of the heteroalkyl group.

"Heteroalkylheteroaryl" refers to an -(heteroalkyl)heteroaryl radical where heteroalkyl and heteroaryl are as disclosed herein and which are optionally substituted by one or more of the substituents described as suitable substituents for heteroalkyl and heteroaryl respectively. The "heteroalkylheteroaryl" is bonded to the parent molecular structure through a carbon atom of the heteroalkyl group.

"Heteroalkyl-heterocycloalkyl" refers to an -(heteroalkyl)heterocycloalkyl radical where heteroalkyl and heterocycloalkyl are as disclosed herein and which are optionally substituted by one or more of the substituents described as suitable substituents for heteroalkyl and heterocycloalkyl respectively. The "heteroalkyl-heterocycloalkyl" is bonded to the parent molecular structure through a carbon atom of the heteroalkyl group.

"Heteroalkylcycloalkyl" refers to an -(heteroalkyl)cycloalkyl radical where heteroalkyl and cycloalkyl are as disclosed herein and which are optionally substituted by one or more of the substituents described as suitable substituents for heteroalkyl and cycloalkyl respectively. The "heteroalkylcycloalkyl" is bonded to the parent molecular structure through a carbon atom of the heteroalkyl group.

"Heteroaryl" or, alternatively, "heteroaromatic" refers to a 5- to 18-membered aromatic radical (e.g., $C_5$-$C_{18}$ heteroaryl) that includes one or more ring heteroatoms selected from nitrogen, oxygen and sulfur, and which can be a monocyclic, bicyclic, tricyclic or tetracyclic ring system. In some embodiments, aromatic ring systems can have 6, 10 or 14 π electrons shared in a cyclic array, having ring carbon atoms and 1-6 ring heteroatoms provided in the aromatic ring system. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl polycyclic ring systems can include one or more heteroatoms in one or both rings. An N-containing "heteroaromatic" or "heteroaryl" moiety refers to an aromatic group in which at least one of the skeletal atoms of the ring is a nitrogen atom. The polycyclic heteroaryl group can be fused or non-fused. The heteroatom(s) in the heteroaryl radical is optionally oxidized. One or more nitrogen atoms, if present, are optionally quaternized. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocycyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4] oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise specifically in the specification, a heteroaryl moiety is optionally substituted by one or more substituents which are independently: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —OR$^a$, —SR$^a$, —OC(O)—R$^a$, —N(R$^a$)$_2$, —C(O)R$^a$, —C(O)OR$^a$, —C(O)$_N$(R$^a$)$_2$, —N(R$^a$)C(O)OR$^a$, —N(R$^a$)C(O)R$^a$, —N(R$^a$)S(O)$_t$R$^a$ (where t is 1 or 2), —S(O)$_t$OR$^a$ (where t is 1 or 2), —S(O)$_t$N(R$^a$)$_2$ (where t is 1 or 2), or PO$_3$(R$^a$)$_2$, where each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl and each of these moieties can be optionally substituted as defined herein.

Substituted heteroaryl also includes ring systems substituted with one or more oxide (—O—) substituents, such as pyridinyl N-oxides.

"Heteroaryl-alkyl" refers to an -(heteroaryl)alkyl radical where heteroaryl and alkyl are as disclosed herein and which are optionally substituted by one or more of the substituents described as suitable substituents for heteroaryl and alkyl respectively. The "heteroaryl-alkyl" is bonded to the parent molecular structure through any atom of the heteroaryl group.

"Heteroaryl-heterocycloalkyl" refers to an -(heteroaryl) heterocycloalkyl radical where heteroaryl and heterocycloalkyl are as disclosed herein and which are optionally substituted by one or more of the substituents described as suitable substituents for heteroaryl and heterocycloalkyl respectively. The "heteroaryl-heterocycloalkyl" is bonded to the parent molecular structure through an atom of the heteroaryl group.

"Heteroaryl-cycloalkyl" refers to an -(heteroaryl)cycloalkyl radical where heteroaryl and cycloalkyl are as disclosed herein and which are optionally substituted by one or more of the substituents described as suitable substituents for heteroaryl and cycloalkyl respectively. The "heteroaryl-cycloalkyl" is bonded to the parent molecular structure through a carbon atom of the heteroaryl group.

"Heterocyclyl", "heterocycloalkyl" or "heterocarbocyclyl" each refer refers to any 3- to 18-membered aromatic radical monocyclic or polycyclic moiety comprising at least one heteroatom selected from nitrogen, oxygen and sulfur. In some embodiments, a heterocyclyl group comprises two to twelve carbon atoms and from one to six heteroatoms selected from nitrogen, oxygen and sulfur. As used herein, heterocyclyl moieties can be aromatic or nonaromatic. A heterocyclyl group can be a monocyclic, bicyclic, tricyclic or tetracyclic ring system. Whenever it appears herein, a numerical range such as "3 to 18" refers to each integer in the given range; e.g., "5 to 18 ring atoms" means that the heterocyclyl group can consist of 5 ring atoms, 6 ring atoms, etc., up to and including 18 ring atoms. In some embodiments, it is a $C_5$-$C_{10}$ heterocycloalkyl. In some embodiments, it is a $C_4$-$C_{10}$ heterocycloalkyl. In some embodiments, it is a $C_3$-$C_{10}$ heterocycloalkyl. Bivalent radicals derived from univalent heterocyclyl radicals whose names end in "-yl" by removal of one hydrogen atom from the atom with the free valence are named by adding "-idene" to the name of the corresponding univalent radical, e.g., a piperidine group with two points of attachment is a piperidylidene. An N-containing heterocyclyl moiety refers to an non-aromatic group in which at least one of the skeletal atoms of the ring is a nitrogen atom. Unless stated otherwise specifically in the specification, the heterocycloalkyl radical is a monocyclic, bicyclic, tricyclic or tetracyclic ring system, which may include fused or bridged ring systems. The heteroatom(s) in the heterocyclyl radical is optionally oxidized. One or more nitrogen atoms, if present, are optionally quaternized. The heteroaryl is attached to the parent molecular structure through any atom of the ring(s).

"Heterocyclyl" also includes ring systems wherein the heterocycyl ring, as defined above, is fused with one or more carbocyclyl groups wherein the point of attachment is either on the carbocycyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 3-10 membered non-aromatic ring system having ring carbon atoms and 1-4 ring heteroatoms, wherein each heteroatom is independently selected from nitrogen, oxygen, and sulfur ("3-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur. In some embodiments, a heterocyclyl group is a 3-7 membered non-aromatic bicyclic ring system having at least 2 carbon atoms in addition to 1-3 heteroatoms independently selected from nitrogen, oxygen, and sulfur, as well as combinations comprising at least one of the foregoing heteroatoms; and the other ring, usually having 3 to 7 ring atoms, optionally contains 1-3 heteroatoms independently selected from nitrogen, oxygen, and sulfur and is not aromatic.

Exemplary 3-membered heterocyclyls containing 1 heteroatom include, without limitation, azirdinyl, oxiranyl, thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl and dithiolanyl. Exemplary 5-membered heterocyclyls containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

In some embodiments, heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

Unless stated otherwise, heterocyclyl moieties are optionally substituted by one or more substituents which independently are: alkyl, heteroalkyl, alkenyl, alkynyl, cycloalkyl, heterocycloalkyl, aryl, arylalkyl, heteroaryl, heteroarylalkyl, hydroxy, halo, cyano, nitro, oxo, thioxo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^a$, —N($R^a$)C(O)$R^a$, —N($R^a$)S(O)$_t R^a$ (where t is 1 or 2), —S(O)$_t$O$R^a$ (where t is 1 or 2), —S(O)$_t$N($R^a$)$_2$ (where t is 1 or 2), or PO$_3$($R^a$)$_2$, where each $R^a$ is independently hydrogen, alkyl, fluoroalkyl, carbocyclyl, carbocyclylalkyl, aryl, aralkyl, heterocycloalkyl, heteroaryl or heteroarylalkyl and each of these moieties can be optionally substituted as defined herein.

"Moiety" refers to a specific segment or functional group of a molecule. Chemical moieties are often recognized chemical entities embedded in or appended to a molecule.

"Nitro" refers to the —NO$_2$ radical.

"Oxa" refers to the —O— radical.

"Oxo" refers to the =O radical.

"Phosphate" refers to a —P=O(O$R^a$)$_2$ radical wherein each $R^a$ is independently hydrogen, alkyl, fluoroalkyl, carbocyclyl, carbocyclylalkyl, aryl, aralkyl, heterocycloalkyl (bonded through a ring carbon), heterocycloalkylalkyl, heteroaryl (bonded through a ring carbon) or heteroarylalkyl. In some embodiments, when $R^a$ is hydrogen and depending on the pH, the hydrogen can be replaced by an appropriately charged counter ion.

A "leaving group or atom" is any group or atom that will, under the reaction conditions, cleave from the starting material, thus promoting reaction at a specified site. Suitable non-limiting examples of such groups unless otherwise specified include halogen atoms, mesyloxy, p-nitrobenzensulphonyloxy and tosyloxy groups.

"Protecting group" has the meaning conventionally associated with it in organic synthesis, i.e., a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, *Protective Groups in Organic Synthesis*, Third Edition, John Wiley & Sons, New York (1999). For example, a hydroxy protected form is where at least one of the hydroxy groups present in a compound is protected with a hydroxy protecting group. Likewise, amines and other reactive groups can similarly be protected.

"Substituted" means that the referenced group can be substituted with one or more additional group(s) individually and independently selected from acyl, alkyl, alkylaryl, cycloalkyl, aralkyl, aryl, carbohydrate, carbonate, heteroaryl, heterocycloalkyl, hydroxy, alkoxy, aryloxy, mercapto, alkylthio, arylthio, cyano, halo, carbonyl, ester, thiocarbonyl, isocyanato, thiocyanato, isothiocyanato, nitro, oxo, perhaloalkyl, perfluoroalkyl, phosphate, silyl, sulfinyl, sulfonyl, sulfonamidyl, sulfonyl, sulfonate, urea, and amino, including mono- and di-substituted amino groups, and the protected derivatives thereof. Di-substituted amino groups encompass those which form a ring together with the nitrogen of the amino group, such as for instance, morpholino. The substituents themselves can be substituted, for example, a cycloalkyl substituent can have a halide substituted at one or more ring carbons, and the like. The protecting groups that can form the protective derivatives of the above substituents are known to those of skill in the art and can be found in references such as Greene and Wuts, above.

"Sulfanyl" refers to the groups: —S-(optionally substituted alkyl), —S-(optionally substituted aryl), —S-(optionally substituted heteroaryl), and —S-(optionally substituted heterocycloalkyl).

"sulfinyl" refers to the groups: —S(O)—H, —S(O)-(optionally substituted alkyl), —S(O)-(optionally substituted amino), —S(O)-(optionally substituted aryl), —S(O)-(optionally substituted heteroaryl), and —S(O)-(optionally substituted heterocycloalkyl).

"Sulfonyl" refers to the groups: —S(O$_2$)—H, —S(O$_2$)-(optionally substituted alkyl), —S(O$_2$)-(optionally substituted amino), —S(O$_2$)-(optionally substituted aryl), —S(O$_2$)-(optionally substituted heteroaryl), and —S(O$_2$)-(optionally substituted heterocycloalkyl).

"Sulfonamidyl" or "sulfonamido" refers to a —S(=O)$_2$—NRR or —N(R)—S(=O)$_2$— radical, where each R is selected independently from hydrogen, alkyl, cycloalkyl, aryl, heteroaryl (bonded through a ring carbon) and heterocycloalkyl (bonded through a ring carbon). The R groups in —NRR of the —S(=O)$_2$—NRR radical can be taken together with the nitrogen to which it is attached to form a 4-, 5-, 6-, or 7-membered ring. In some embodiments, it is a $C_1$-$C_{10}$ sulfonamido, wherein each R in sulfonamido contains 1 carbon, 2 carbons, 3 carbons, or 4 carbons total. A sulfonamido group is optionally substituted by one or more of the substituents described for alkyl, cycloalkyl, aryl, and heteroaryl respectively "Sulfoxyl" refers to a —S(=O)$_2$OH radical.

"Sulfonate" refers to a —S(=O)$_2$—OR radical, where R is selected from alkyl, cycloalkyl, aryl, heteroaryl (bonded through a ring carbon) and heteroalicyclic (bonded through a ring carbon). A sulfonate group is optionally substituted on R by one or more of the substituents described for alkyl, cycloalkyl, aryl, and heteroaryl respectively.

"Thio" or "thiol" refers to a —S— radical.

"Thioxo" refers to a =S radical.

"Urea" refers to a —N(R$^a$)—C(=O)—N(R$^a$)— radical wherein each R$^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl.

Where substituent groups are specified by their conventional chemical formulae, written from left to right, they equally encompass the chemically identical substituents that would result from writing the structure from right to left, e.g., —CH$_2$O— is equivalent to —OCH$_2$—.

Compounds

As noted above, provided herein are various compounds that are useful as antagonists for one or more lipid kinases and/or protein kinases.

In one aspect, described herein are compounds of Formula (I):

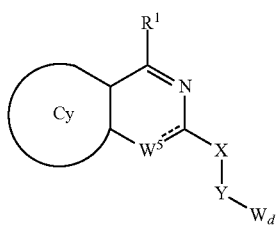

Formula (I)

or its pharmaceutically acceptable forms thereof, wherein
W$^5$ is N, CHR$^4$ or CR$^4$;
R$^4$ is hydrogen, alkyl, haloalkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R", wherein R' and R" are taken together with nitrogen to form a cyclic moiety.
Cy is aryl or heteroaryl substituted by 0-4 occurrences of R$^3$;

R$^1$ is -(L)$_n$-R$^{1'}$;
each L is independently a bond, alkylene, heteroalkylene, —N(R$^2$)—, —S(O)—, —S(O)$_2$—, —S—, —C(=O)—, —P(=O)R$^2$—, or —O—;
R$^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocyclyloxy, amino, amido, acyl, acyloxy, alkoxycarbonyl, sulfonamido, halo, cyano, hydroxy, nitro, phosphate, urea, carbonate, —(C=O)—NR$^{a1}$R$^{a2}$, or NR$^{a1}$R$^{a2}$;

R$^{a1}$ and R$^{a2}$ are each independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or R$^{a1}$ and R$^{a2}$ are taken together with nitrogen to form a cyclic moiety;

R$^2$ is hydrogen, alkyl, cycloalkyl, heterocycloalkyl, heteroalkyl, aryl, or heteroaryl;

each R$^3$ is independently alkyl, heteroalkyl, haloalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R", wherein R' and R" are taken together with nitrogen to form a cyclic moiety;

X is absent or is —(CH(R$^{10}$))$_z$—;
Y is absent, —O—, —S—, —S(=O)—, —S(=O)$_2$—, —N(R$^9$)—, —C(=O)—(CHR$^{10}$)$_z$—, —C(=O)—, —N(R$^9$)—C(=O)—, —N(R$^9$)—C(=O)NH—, —N(R$^9$)C(R$^{10}$)$_2$—, —C(=O)—(CHR$^{10}$)$_z$—, —C(=O)—N(R$^9$)—(CHR$^{10}$)$_z$—, or —P(=O)R$_2$—;
each z is an integer of 1, 2, 3, or 4;
n is an integer of 0, 1, 2, 3, or 4;
each R$^9$ is independently hydrogen, alkyl, cycloalkyl, heterocycloalkyl, heterocycloalkylalkyl, heteroalkyl, aryl, or heteroaryl;

W$_d$ is heterocycloalkyl, aryl, cycloalkyl, or heteroaryl, wherein W$_d$ is optionally substituted with one or more R$^b$, R$^{11}$, R$^{12}$, and R$^{13}$; and each R$_b$, R$^{10}$, R$^{11}$, R$^{12}$, and R$^{13}$ is independently hydrogen, alkyl, heteroalkyl, alkenyl, alkynyl, cycloalkyl, heterocycloalkyl, aryl, arylalkyl, heteroaryl, heteroarylalkyl, alkoxy, heterocyclyloxy, amido, amino, acyl, acyloxy, alkoxycarbonyl, sulfonamido, halo, haloalkyl, cyano, hydroxyl, nitro, phosphate, urea, carbonate, or NR'R", wherein R' and R" are taken together with nitrogen to form a cyclic moiety.

In some embodiments, the compound of Formula (I) has the structure of Formula (Ia):

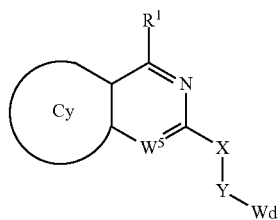

Formula (Ia)

or its pharmaceutically acceptable forms thereof, wherein n, z, R$^{a1}$, R$^{a2}$, L, R$^1$, R$^{1'}$, R$^2$, R$^3$, R$^4$, X, Y, R$^9$, R$^{10}$, R$^b$, R$^{11}$, R$^{12}$, R$^{13}$ and W$_d$ are as defined for Formula (I); and
W$^5$ is N or CR$^4$.

In some embodiments, each L is independently a bond, alkylene, —N(R$^2$)—, —S(O)—, —S(O)$_2$—, —S—, —C(=O)—, or —O—.

In some embodiments, L is —O—, —C(═O)—, —S— or a bond. In some embodiments, L is a bond. In some embodiments, L is —O—. In some embodiments, L is —S—. In some embodiments, L is —C(═O)—. In some embodiments, L is alkylene (e.g., methylene, ethylene or propylene). In some embodiments, n is 1.

In some embodiments, n is 2. In some embodiments, one L is alkylene (e.g., methylene) and one L is —C(═O)—. In some embodiments, one L is —O— and one L is alkylene (e.g., methylene or ethylene). In some embodiments, one L is —S— and one L is alkylene (e.g., ethylene). In some embodiments, one L is —S(O)— and one L is alkylene (e.g., ethylene). In some embodiments, one L is —S(O)$_2$— and one L is alkylene (e.g., ethylene).

In some embodiments, n is 3. In some embodiments, one L is —O—, one L is alkylene (e.g., methylene) and one L is —C(O)—.

In some embodiments, $R^{1'}$ is —$NR^{a1}R^{a2}$. In some embodiments, $R^{1'}$ is —(C═O)—$NR^{a1}R^{a2}$. In some embodiments, $R^{a1}$ and $R^{a2}$ are taken together with nitrogen to form a cyclic moiety (e.g., a heterocyclic moiety), such as N-pyrollyl, N-(3,3-difluoro)pyrolyl, N-azetidinyl, N-(2,2-difluoro)azetidinyl, N-morpholinyl, 2-methyl-N-morpholinyl, N-methyl-N-piperazinyl, N-(2-methyl)-piperazinyl, N-(2,2-difluoro)pyrollyl, N-(2-hydroxy)azetidinyl, 4-hydroxy-N-piperidinyl, N-isopropyl-4-piperidinyl, 4-tetrahydropyran, 4-isopropyl-N-piperazinyl, 4-ethyl-N-piperazinyl, N-methyl-4-piperidinyl, N-(methylsulfonyl)-4-piperidinyl, 4-piperidinyl, N-methyl-4-piperidinyl, 3-tetrahydrofuranyl, N-piperazinyl-2-one, 3-methyl-N-morpholinyl, N-(1,4)-oxazepanyl, N-((1R,5S)-3-oxa-8-azabicyclo[3.2.1]octanyl), N-((1R,5S)-8-oxa-3-azabicyclo[3.2.1]octanyl) or 4,4-difluoro-N-piperidinyl).

In some embodiments, $R^{a1}$ is hydrogen. In some embodiments, $R^{a1}$ is alkyl (e.g., methyl).

In some embodiments, $R^{a2}$ is alkyl (e.g., methyl). In some embodiments, $R^{a2}$ is cycloalkyl (e.g., cyclopentyl, cyclohexyl or 4-hydroxycyclohexyl). In some embodiments, $R^{a2}$ is aryl (e.g., phenyl). In some embodiments, $R^{a2}$ is aralkyl (e.g., benzyl). In some embodiments, $R^{a2}$ is heterocycloalkyl (e.g., 2-tetrahydrofuranyl, 4-piperidyl, N-methyl-4-piperidyl or tetrahydropyranyl). In some embodiments, $R^{a2}$ is heterocycloalkylalkyl (e.g., methyl-4-tetrahydropyranyl). In some embodiments, $R^{a2}$ is acyl (e.g., —C(O)CH$_3$).

In some embodiments, $R^{1''}$ is heteroaryl (e.g., 5-methyl-2-(1,2,4-oxadiazolyl) or 5-hydroxymethyl-3-isoxazolyl). In some embodiments, $R^{1'}$ is alkyl (e.g., methyl, isopropyl or hydroxyisopropyl). In some embodiments, $R^{1'}$ is hydroxy.

In some embodiments, $W^5$ is N. In some embodiments, $W^5$ is $CR^4$. In some embodiments, $W^5$ is $CHR^4$. In some embodiments, $R^4$ is hydrogen, alkyl, alkenyl, alkynyl, cycloalkyl, heteroalkyl, alkoxy, amido, amino, acyl, acyloxy or NR'R''. In some embodiments, $R^4$ is hydrogen.

In some embodiments, X is absent or is —(CH($R^{10}$))$_z$—. In some embodiments, z is 1. In some embodiments, $R^{10}$ is methyl or hydrogen. In some instances, X is —CH$_2$— or —CH(CH$_3$)—. In some embodiments, the —CH(CH$_3$)— moiety has a (S) stereochemical configuration. Alternatively, the carbon of the —CH(CH$_3$)— moiety has a (R) stereochemical configuration. In some embodiments, Y is absent, —O—, —N($R^9$)—, or —S(═O)$_2$—. In some embodiments, X—Y is —CH$_2$—N(CH$_3$)—. Alternatively, X—Y is (S)—CH(CH$_3$)—NH— or (R)—CH(CH$_3$)—NH—.

In some embodiments, each $R^3$ is alkyl, alkenyl, alkynyl, cycloalkyl, heterocycloalkyl, haloalkyl, heteroalkyl, alkoxy, amido, amino, acyl, acyloxy, sulfonamido, halo, cyano, heteroaryl, aryl, hydroxyl, or nitro.

In some embodiments, each $R^3$ is alkyl, heteroalkyl, alkenyl, alkynyl, cycloalkyl, heterocycloalkyl, aryl, arylalkyl, heteroaryl, heteroarylalkyl, alkoxy, heterocyclyloxy, amido, amino, acyl, acyloxy, alkoxycarbonyl, sulfonamido, halo, haloalkyl, cyano, hydroxyl, nitro, phosphate, urea, carbonate, or NR'R'', wherein R' and R'' are taken together with nitrogen to form a heterocyclic moiety.

In some embodiments of the compound of Formula (I), Cy is aryl substituted with 0-4 occurrences of $R^3$. In some embodiments, Cy is phenyl substituted with 0-4 occurrences of $R^3$. In some embodiments, Cy is phenyl substituted with 0 occurrences of $R^3$. In some embodiments, Cy is phenyl substituted with 1 occurrence of $R^3$. In some embodiments, $R^3$ is halo (e.g., fluoro or chloro). In some embodiments, $R^3$ is alkyl (e.g., methyl). In some embodiments, $R^3$ is haloalkyl (e.g., trifluoromethyl). In some embodiments, $R^3$ is heteroaryl (e.g., 1-methyl-4-pyrazolyl or 3-pyridyl). In some embodiments, $R^3$ is acyl (e.g., —C(═O)—N-morphonlinyl, —C(═O)—N-methyl-N-piperizinyl, or N-((1R,5S)-3-oxa-8-azabicyclo[3.2.1]octanyl)).

In some embodiments, Cy is phenyl substituted with 2 occurrences of $R^3$. In some embodiments, each $R^3$ is halo (e.g., chloro or fluoro).

In some embodiments, $W_d$ is heteroaryl optionally substituted with one or more $R^b$, $R^{11}$, $R^{10}$, $R^{12}$, or $R^{13}$ (e.g., a monocyclic heteroaryl).

In some embodiments, $W_d$ is:

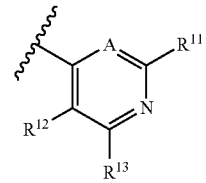

wherein A is N or $CR^{10}$.

In some embodiments, $W_d$ is

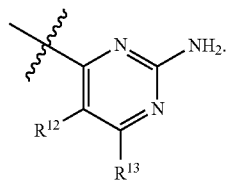

In some embodiments, $W_d$ is

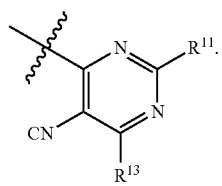

In some embodiments, $W_d$ is

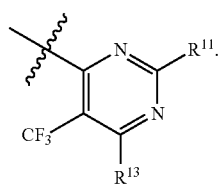

In some embodiments, $W_d$ is

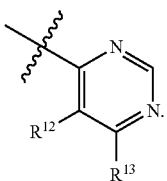

In some embodiments, $W_d$ is

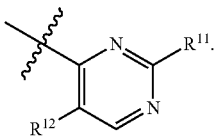

In some embodiments, $W_d$ is

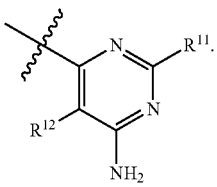

In some embodiments, $W_d$ is

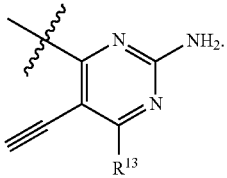

In some embodiments, $W_d$ is

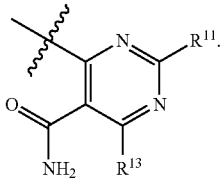

In certain embodiments, $W_d$ is selected from:

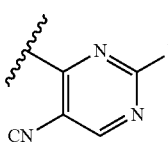 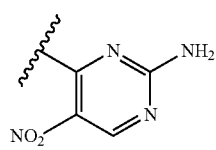

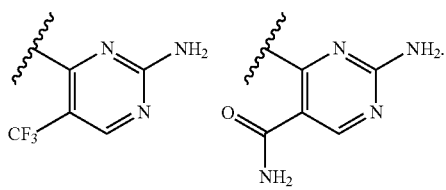

In some embodiments, $W_d$ is aryl optionally substituted with one or more $R^b$, $R^{11}$, $R^{12}$, or $R^{13}$. In some embodiments, $W_d$ is heteroaryl optionally substituted with one or more $R^b$, $R^{11}$, $R^{12}$, or $R^{13}$ (e.g., a bicyclic heteroaryl). In some embodiments, $W_d$ is selected from:

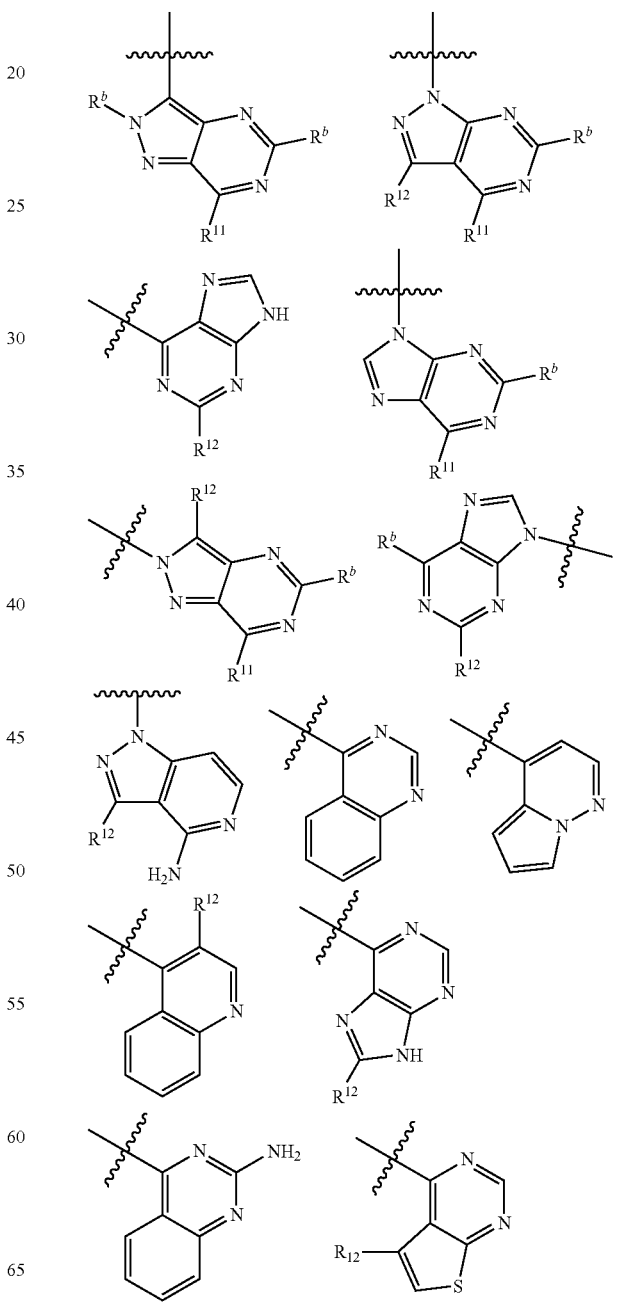

-continued

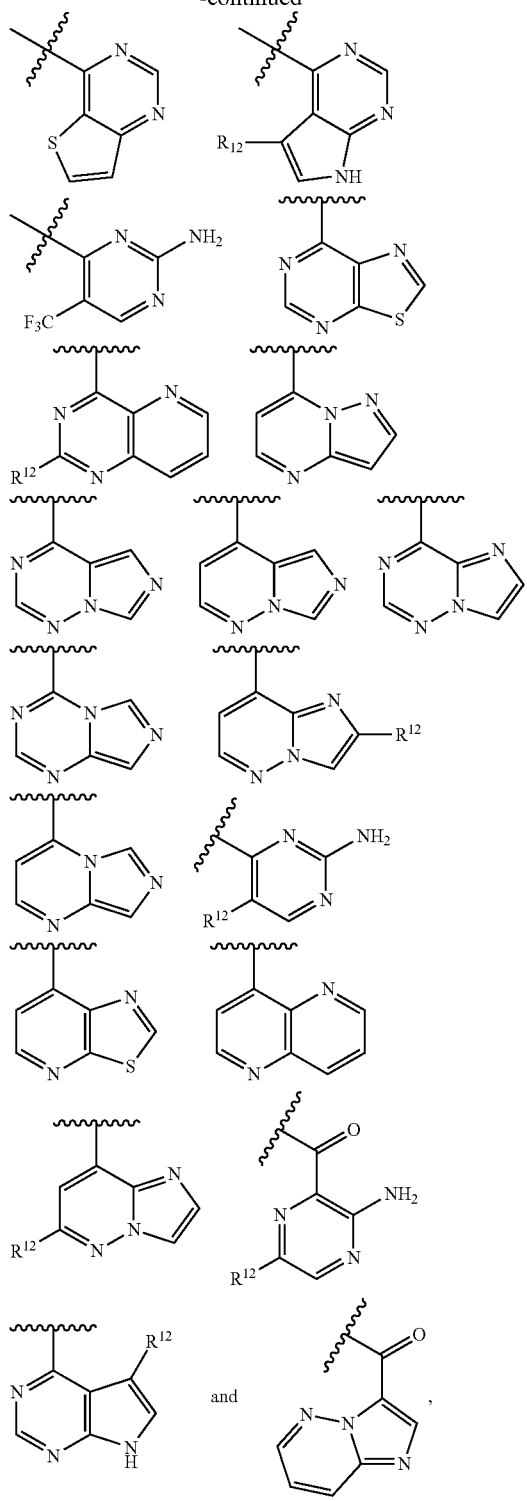

wherein each $W_d$ is optionally further substituted with one or more $R^b$, $R^{11}$, $R^{12}$, and $R^{13}$.

In some embodiments, $R^b$ is hydrogen, halo, alkyl, cycloalkyl or heterocycloalkyl.

In some embodiments, each $R^{11}$ and $R^{12}$ is independently hydrogen, alkyl, cycloalkyl, heterocycloalkyl, aryl, heteroaryl, alkoxy, amino, cyano, halo or hydroxyl.

In some embodiments, $W_d$ is

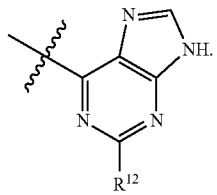

In some embodiments, $W_d$ is

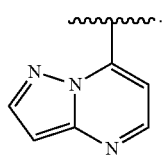

In other embodiments, $W_d$ is

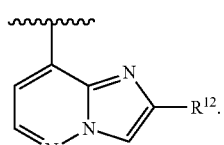

In other embodiments, $W_d$ is

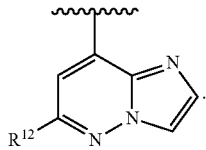

In yet other embodiments, $W_d$ is

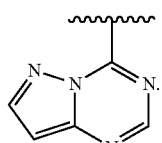

In some embodiments, $W_d$ is

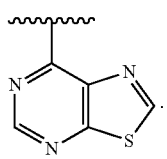 [SMILES: *c1ncnc2scnc12]

In some embodiments, $W_d$ is

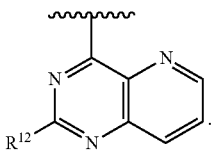

In some embodiments, $W_d$ is

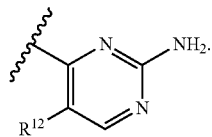

In some embodiments, $W_d$ is

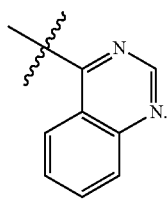 [SMILES: *c1ncnc2ccccc12]

In some embodiments, $W_d$ is

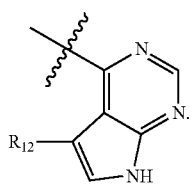

In some embodiments, $W_d$ is

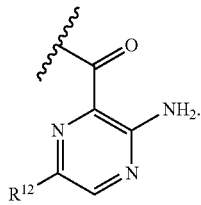

In some embodiments, $W_d$ is

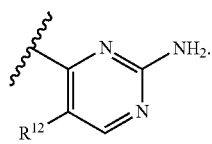

In some embodiments, $W_d$ is

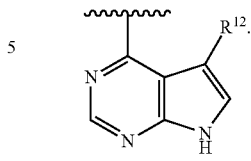

In some embodiments, $R^{11}$ is hydrogen.

In some embodiments, $R^{12}$ is hydrogen. In some embodiments, $R^{12}$ is halo (e.g., fluoro or chloro). In some embodiments, $R^{12}$ is haloalkyl (e.g., trifluoromethyl). In some embodiments, $R^{12}$ is cyano. In some embodiments, $R^{12}$ is amido (e.g., $-C(O)NH_2$). In some embodiments, $R^{12}$ is amino (e.g., $-NH_2$).

In some embodiments, $R^4$ is hydrogen, alkyl, alkenyl, alkynyl, cycloalkyl, heteroalkyl, alkoxy, heterocycloalkyloxy, amido, amino, acyl, acyloxy, sulfonamido, halo, cyano, hydroxyl or nitro.

In some embodiments, the compound of Formula (I) has the structure of Formula (Ia):

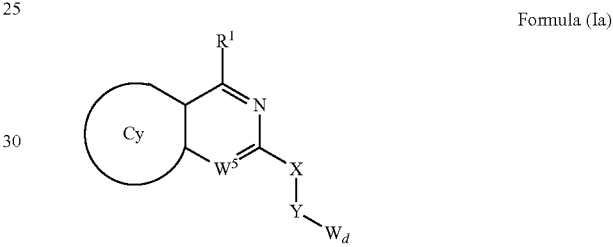

Formula (Ia)

or its pharmaceutically acceptable forms thereof, wherein n, z, $R^{a1}$, $R^{a2}$, L, $R^1$, $R^{1'}$, $R^2$, $R^3$, $R^4$, X, Y, $R^9$, $R^{10}$, $R^b$, $R^{11}$, $R^{12}$, $R^{13}$ and $W_d$ are as defined for Formula (I); and $W^5$ is N or $CR^4$.

In some embodiments, the compound of Formula (I) has the structure of Formula (II):

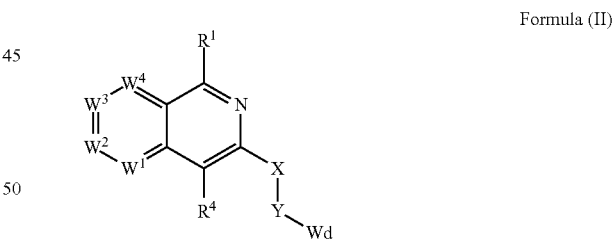

Formula (II)

or its pharmaceutically acceptable forms thereof, wherein n, z, $R^{a1}$, $R^{a2}$, L, $R^1$, $R^{1'}$, $R^2$, $R^4$, X, Y, $R^9$, $R^{10}$, $R^b$, $R^{11}$, $R^{12}$, $R^{13}$ and $W_d$ are as defined for Formula (I);

$W^1$ is N or $CR^{14}$, $W^2$ is N or $CR^6$, $W^3$ is N or $CR^7$, and $W^4$ is N or $CR^8$, wherein no more than two N atoms are adjacent; and $R^6$, $R^7$, $R^8$ and $R^{14}$ are independently hydrogen, alkyl, haloalkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R" wherein R' and R" are taken together with nitrogen to form a cyclic moiety.

In yet other embodiments, the compound of Formula (II) has the structure of Formula (IIa):

Formula (IIa)

or its pharmaceutically acceptable forms thereof, wherein $W^1$ is N or $CR^{14}$, $W^2$ is N or $CR^6$, $W^3$ is N or $CR^7$, and $W^4$ is N or $CR^8$, wherein no more than two N atoms are adjacent;

$R^1$ is $-(L)_n-R^{1'}$;

each L is independently alkylene, heteroalkylene, $-S(O)_2-$, $-S-$, $-N(R^2)-$, or $-O-$;

n is an integer of 0, 1, 2, 3 or 4;

$R^{1'}$ is alkyl, substituted alkyl, a heterocyclic group comprising at least two heteroatoms chosen from O, N and S, wherein $R^{1'}$ is optionally substituted by $R^{a1}$; or $R^{1'}$ is $NR^{a1}R^{a2}$;

$R^{a1}$ and $R^{a2}$ are each independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or $R^{a1}$ and $R^{a2}$ are taken together with nitrogen to form a cyclic moiety;

$R^4$, $R^{14}$, $R^6$, $R^7$ and $R^8$ are each independently hydrogen, alkyl, heteroalkyl, haloalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R", wherein R' and R" are taken together with nitrogen to form a cyclic moiety;

X is absent or is $-(CH(R^{10}))_z-$;

Y is absent, $-O-$, $-S-$, $-S(=O)-$, $-S(=O)_2-$, $-N(R^9)-$, $-C(=O)-(CHR^{10})_z-$, $-C(=O)-$, $-N(R^9)-C(=O)-$, or $-N(R^9)-C(=O)NH-$, $-N(R^9)C(R^{10})_2-$, or $-C(=O)-(CHR^{10})_z-$;

each z is an integer of 1, 2, 3, or 4;

each $R^2$ and $R^9$ is independently hydrogen, $C_1$-$C_{10}$ alkyl, $C_3$-$C_7$ cycloalkyl, heterocycloalkyl, $C_2$-$C_{10}$ heteroalkyl, aryl, or heteroaryl;

each $R^{10}$ is independently hydrogen, alkyl, cycloalkyl, heteroalkyl, aryl, heteroaryl, arylalkyl, heteroarylalkyl or halo;

$W_d$ is heterocycloalkyl, aryl, cycloalkyl, or heteroaryl, wherein $W_d$ is substituted with one or more $R^b$, $R^{11}$, $R^{12}$, or $R^{13}$; and each $R^b$, $R^{11}$, $R^{12}$, and $R^{13}$ is independently hydrogen, alkyl, heteroalkyl, alkenyl, alkynyl, cycloalkyl, heterocycloalkyl, aryl, arylalkyl, heteroaryl, heteroarylalkyl, alkoxy, heterocyclyloxy, amido, amino, acyl, acyloxy, alkoxycarbonyl, sulfonamido, halo, haloalkyl, cyano, hydroxyl, nitro, phosphate, urea, carbonate, or NR'R", wherein R' and R" are taken together with nitrogen to form a cyclic moiety; and at least one of $R^4$, $R^{14}$, $R^6$, and $R^7$ is halo.

In some embodiments, the compound of Formula (II) has the structure of Formula (IIb):

Formula (IIb)

or its pharmaceutically acceptable forms thereof, wherein $R_1$, $R_4$, $R_8$, X, Y, and $W_d$ are as defined for Formula (II).

In some embodiments, L is a bond and $R^{1'}$ is an optionally substituted 5-membered heterocyclic group comprising at least two heteroatoms chosen from O and N.

In some embodiments, X is absent or is $-(CH(R^{10})_z-$ and z is an integer of 1, 2, 3, or 4.

In some embodiments, each $R^9$ is independently hydrogen, $C_1$-$C_{10}$ alkyl, $C_3$-$C_7$ cycloalkyl, heterocycloalkyl, $C_2$-$C_{10}$ heteroalkyl, aryl, or heteroaryl.

In some embodiments, each $R^{10}$ is independently hydrogen, alkyl, cycloalkyl, heteroalkyl, aryl, heteroaryl, arylalkyl, heteroarylalkyl or halo.

In some embodiments, $W^1$ is $CR^{14}$, $W^2$ is $CR^6$, $W^3$ is $CR^7$, and $W^4$ is $CR^8$. In some embodiments, $W^1$ is N, $W^2$ is $CR^6$, $W^3$ is $CR^7$, and $W^4$ is $CR^8$. In some embodiments, $W^1$ is $CR^{14}$, $W^2$ is N, $W^3$ is $CR^7$, and $W^4$ is $CR^8$. In some embodiments, $W^1$ is $CR^{14}$, $W^2$ is $CR^6$, $W^3$ is N, and $W^4$ is $CR^8$. In some embodiments, $W^1$ is $CR^{14}$, $W^2$ is $CR^6$, $W^3$ is $CR^7$, and $W^4$ is N. In some embodiments, $W^1$ is N, $W^2$ is $CR^6$, $W^3$ is N, and $W^4$ is $CR^8$. In some embodiments, $W^1$ is N, $W^2$ is $CR^6$, $W^3$ is N, and $W^4$ is $CR^8$. In some embodiments, $W^1$ is N, $W^2$ is $CR^6$, $W^3$ is $CR^7$, and $W^4$ is N. In some embodiments, $W^1$ is $CR^{14}$, $W^2$ is N, $W^3$ is N, and $W^4$ is $CR^8$. In some embodiments, $W^1$ is $CR^{14}$, $W^2$ is N, $W^3$ is $CR^7$, and $W^4$ is N. In some embodiments, $W^1$ is $CR^{14}$, $W^2$ is $CR^6$, $W^3$ is N, and $W^4$ is N.

In other embodiments of compounds of Formula (II), $R^{1'}$ is hydrogen, alkoxy, alkyl, heterocycloalkyl, aryl, or NR'R", wherein R' and R" are taken together with nitrogen to form a cyclic moiety. In some embodiments, $R^{1'}$ is amino, alkoxy, alkyl, or NR'R", wherein R' and R" are taken together with nitrogen to form a cyclic moiety.

In some embodiments, $R^8$ is hydrogen, alkyl, haloalkyl, heteroalkyl, alkenyl, alkynyl, cycloalkyl, heterocycloalkyl, alkoxy, sulfonamido, thio, sulfoxide, sulfone, halo, cyano, hydroxy, amino or NR'R", wherein R' and R" taken together with nitrogen to form a cyclic moiety. For example, $R^8$ is hydrogen or alkyl. In other embodiments, $R^8$ is haloalkyl (e.g., trifluoromethyl). In some embodiments, $R^8$ is halo (e.g., chloro).

In still other embodiments, X is $-CH_2-$, $-CH(CH_3)-$, $-CH(C_6H_5)-$ or $-CH(CH_2CH_3)-$. In some embodiments, $-CH(CH_3)-$ or $-CH(CH_2CH_3)-$ has a predominately (S) stereochemical configuration.

In some embodiments, Y is absent, $-O-$, $-N(R^9)-$, $-N(R^9)C(R^{10})_2-$, or $-S(=O)_2-$, where each $R^9$ is independently hydrogen, methyl or ethyl.

Alternatively, X is $-CH(R^{10}))_z-$, z is 1, Y is $-N(R^9)-$, and $R^9$ is hydrogen; or Y is $-N(CH_2CH_3)CH_2-$ or $-N(CH_3)CH_2-$. In some embodiments, X—Y is $-CH_2-N(CH_3)-$, or $-CH_2-N(CH_2CH_3)-$.

Also contemplated herein are compounds wherein $W_d$ is a monocyclic or polycyclic heteroaryl which is unsubstituted or substituted with one or more substituents selected from alkyl, alkynyl, alkenyl, halo, aryl, heteroaryl, heterocycloalkyl, cycloalkyl, cyano, amino, hydroxy, alkoxy, acyloxy, alkoxycarbonyl, and amido.

For example, $W_d$ is a bicyclic heteroaryl. In some embodiments, $W_d$ is a pyrazolopyrimidine, thiazolo[5,4-d]pyrimidine, pyrido[3,2-d]pyrimidine, pyrazolo[1,5-a]pyrimidine, quinazoline, imidazo[1,2-b]pyridazine, or a purine.

In some embodiments, $W_d$ is purine, and X—Y is —(CH($R^{10}$))N($R^9$)—. $R^9$ is, for example, hydrogen.

In other embodiments, $W_d$ is one of the following formulae:

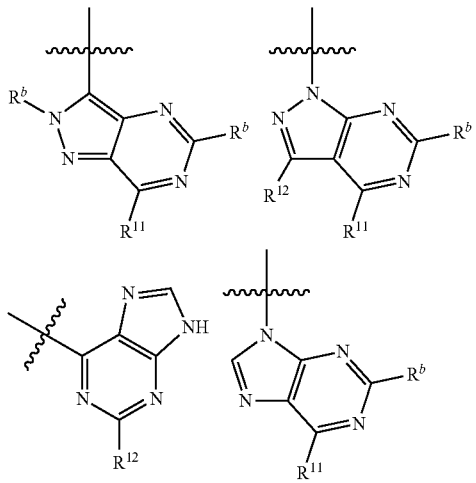

wherein each $R^b$ is independently hydrogen or alkyl;

$R^{11}$ is hydrogen, alkyl, halo, amino, amido, hydroxy, or alkoxy, and $R^{12}$ is hydrogen, alkyl, haloalkyl, cyano, alkynyl, alkenyl, halo, aryl, heteroaryl, heterocycloalkyl, cycloalkyl, amino, alkoxycarbonyl, or amido.

In some embodiments, $W_d$ is Formula (X):

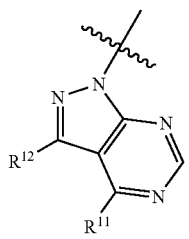

Formula (X)

wherein $R^{11}$ is H, alkyl, halo, amino, amido, hydroxy, or alkoxy, and $R^{12}$ is H, alkyl, alkynyl, alkenyl, halo, aryl, heteroaryl, heterocycloalkyl, cycloalkyl, cyano, amino, acyloxy, alkoxycarbonyl, or amido.

In other embodiments, $W_d$ is Formula (XVI):

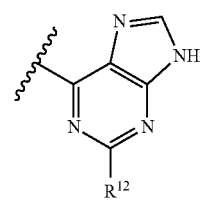

Formula (XVI)

wherein $R^{12}$ is H, alkyl, alkynyl, alkenyl, halo, aryl, heteroaryl, heterocycloalkyl, cycloalkyl, cyano, amino, acyloxy, alkoxycarbonyl, or amido.

In some embodiments, $R^{11}$ is amino. In other embodiments, $R^{12}$ is a monocyclic heteroaryl, a bicyclic heteroaryl, or a heterocycloalkyl. In still other embodiments, $R^{12}$ is hydrogen.

In some embodiments of the compounds of Formula II, R' and R" are taken together with nitrogen to form a cyclic moiety. For example, the cyclic moiety is 5- or 6-membered.

In some embodiments of the compounds of Formula II, n is 1 and L is alkylene (e.g., methylene or ethylene). In other embodiments, L is alkyl substituted by $R^{15}$, wherein $R^{15}$ is aryl, heteroaryl or halo.

In one aspect, the compound of Formula (I) has the structure of Formula (III):

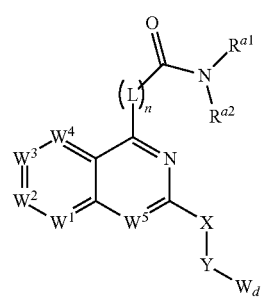

Formula (III)

or its pharmaceutically acceptable forms thereof, wherein
$W^1$ is N or $CR^{14}$, $W^2$ is N or $CR^6$, $W^3$ is N or $CR^7$, $W^4$ is N or $CR^8$, and $W^5$ is N or $CR^4$, wherein no more than two N atoms are adjacent;

each L is alkylene, heteroalkylene, —S—, —N($R^2$)—, or —O—;

n is 0 or 1;

$R^{a1}$ and $R^{a2}$ are each independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or $R^{a1}$ and $R^{a2}$ are taken together with nitrogen to form a cyclic moiety;

$R^4$, $R^{14}$, $R^6$, $R^7$ and $R^8$ are independently hydrogen, alkyl, heteroalkyl, haloalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R", wherein R' and R" are taken together with nitrogen to form a cyclic moiety;

X is absent or is —(CH($R^{10}$))$_z$—;

Y is absent, —O—, —S—, —S(=O)—, —S(=O)$_2$—, —N($R^9$)—, —C(=O)—(CHR$^{10}$)$_z$—, —C(=O)—, —N($R^9$)—C(=O)—, or —N($R^9$)—C(=O)NH—, —N($R^9$)C($R^{10}$)$_2$—, or —C(=O)—(CHR$^{10}$)$_z$—;

each z is an integer of 1, 2, 3, or 4;

each $R^2$ and $R^9$ is independently hydrogen, $C_1$-$C_{10}$alkyl, $C_3$-$C_7$cycloalkyl, heterocycloalkyl, $C_2$-$C_{10}$heteroalkyl, aryl, or heteroaryl;

each $R^{10}$ is independently hydrogen, alkyl, cycloalkyl, heteroalkyl, aryl, heteroaryl, arylalkyl, heteroarylalkyl or halo; and $W_d$ is heterocycloalkyl, aryl, cycloalkyl, or heteroaryl, wherein $W_d$ is substituted with one or more $R^b$, $R^{11}$, $R^{12}$, and $R^{13}$; and each $R^b$, $R^{11}$, $R^{12}$, and $R^{13}$ is independently hydrogen, alkyl, heteroalkyl, alkenyl, alkynyl, cycloalkyl, heterocycloalkyl, aryl, arylalkyl, heteroaryl, heteroarylalkyl, alkoxy, heterocyclyloxy, amido, amino, acyl, acyloxy, alkoxycarbonyl, sulfonamido, halo, haloalkyl, cyano, hydroxyl, nitro, phosphate, urea, carbonate, or NR'R", wherein R' and R" are taken together with nitrogen to form a cyclic moiety.

In some embodiments, the compound of Formula (III) has the structure of Formula (IIIa):

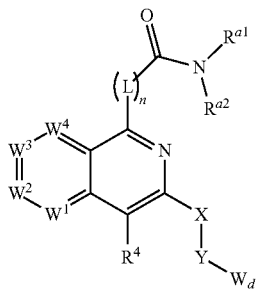

Formula (IIIa)

or its pharmaceutically acceptable forms thereof, wherein L, n, z, $R^{a1}$, $R^{a2}$, X, Y, $R^2$, $R^4$, $R^9$, $R^{10}$, $R^b$, $R^{11}$, $R^{12}$, $R^{13}$, and $W_d$ are as defined for Formula (III);

$W^1$ is N or CR$^{14}$, $W^2$ is N or CR$^6$, $W^3$ is N or CR$^7$, and $W^4$ is N or CR$^8$, wherein no more than two N atoms are adjacent; and $R^6$, $R^7$, $R^8$ and $R^{14}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R", wherein R' and R" are taken together with nitrogen to form a cyclic moiety.

In some embodiments, the compound of Formula (IIIa) has the structure of Formula (IIIb):

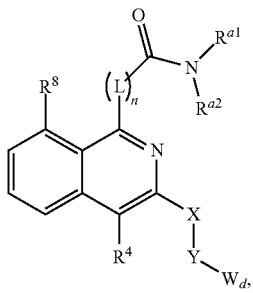

Formula (IIIb)

or its pharmaceutically acceptable forms thereof, wherein L, n, z, $R^{a1}$, $R^{a2}$, $R^b$, X, Y, $R^4$, $R^8$, $R^2$, $R^9$, $R^{10}$, $R^{11}$, $R^{12}$, $R^{13}$, and $W_d$ are as defined for Formula (III).

In some embodiments, n is 0 or 1.

In some embodiments, X is absent or is —(CH($R^{10}$))$_z$— and z is an integer of 1, 2, 3, or 4.

In some embodiments, L is alkylene (e.g., methylene or ethylene), heteroalkylene, —S—, —N($R^2$)—, or —O—.

In some embodiments, $R^{10}$ is hydrogen, alkyl, cycloalkyl, heteroalkyl, aryl, heteroaryl, arylalkyl, heteroarylalkyl or halo.

In some embodiments, $W^1$ is CR$^{14}$, $W^2$ is CR$^6$, $W^3$ is CR$^7$, and $W^4$ is CR$^8$. In some embodiments, $R^{14}$ is hydrogen. In some embodiments, $R^6$ is hydrogen. In some embodiments, $R^7$ is hydrogen. In some embodiments, $R^{14}$, $R^6$ and $R^7$ are hydrogen.

In some embodiments, $R^8$ is halo (e.g., chloro). In some embodiments, $R^8$ is alkyl (e.g., methyl). In some embodiments, $R^8$ is heteroaryl (e.g., 1-methyl-4-pyrazolyl).

In some embodiments, the compound of Formula (I) has the structure of Formula (IV):

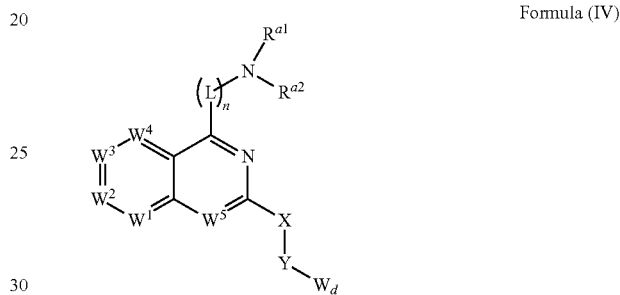

Formula (IV)

or its pharmaceutically acceptable forms thereof, wherein z, n, L, $R^{a1}$, $R^{a2}$, $R^2$, $R^4$, X, Y, $R^9$, $R^{10}$, $R^b$, $R^{11}$, $R^{12}$, $R^{13}$, and $W_d$ are as defined for Formula (I);

$W^1$ is N or CR$^{14}$, $W^2$ is N or CR$^6$, $W^3$ is N or CR$^7$, $W^4$ is N or CR$^8$, and $W^5$ is N or CR$^4$, wherein no more than two N atoms are adjacent; and $R^6$, $R^7$, $R^8$ and $R^{14}$ are independently hydrogen, alkyl, heteroalkyl, haloalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R" wherein R' and R" are taken together with nitrogen to form a cyclic moiety.

In some embodiments, the compound of Formula (IV) has the structure of Formula (IVa):

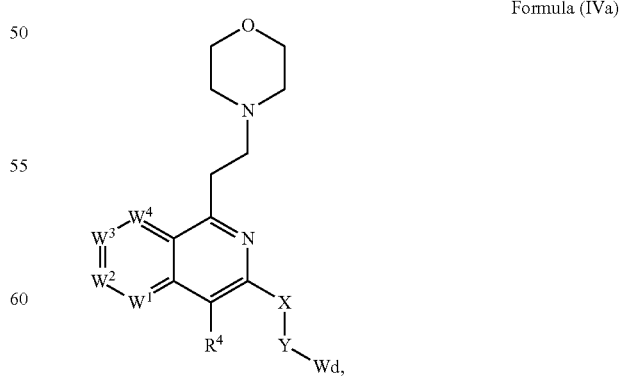

Formula (IVa)

or its pharmaceutically acceptable forms thereof, wherein z, X, Y, $W^1$, $W^2$, $W^3$, $W^4$, $R^4$, $R^6$, $R^7$, $R^8$, $R^{14}$, $R^9$, $R^{10}$, $R^b$, $R^{11}$, $R^{12}$, $R^{13}$, and $W_d$ are as defined for Formula (IV).

In some embodiments, the compound of Formula (IVa) has the structure of Formula (IVb):

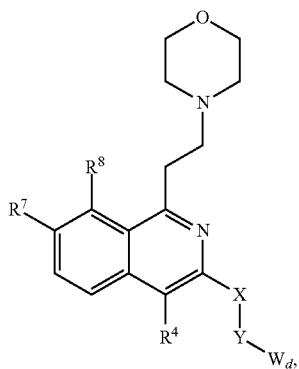

Formula (IVb)

or its pharmaceutically acceptable forms thereof, wherein z, X, Y, $R^4$, $R^7$, $R^8$, $R^9$, $R^{10}$, $R^b$, $R^{11}$, $R^{12}$, $R^{13}$, and $W_d$ are as defined for Formula (IV).

In some embodiments, X is —(CH($R^{10}$))$_z$— and z is an integer of 1, 2, 3, or 4.

In some embodiments, each $R^9$ is independently hydrogen, $C_1$-$C_{10}$ alkyl, $C_3$-$C_7$ cycloalkyl, heterocycloalkyl, $C_2$-$C_{10}$ heteroalkyl, aryl, or heteroaryl.

In some embodiments, each $R^{10}$ is independently hydrogen, alkyl, cycloalkyl, heteroalkyl, aryl, heteroaryl, arylalkyl, heteroarylalkyl or halo.

In some embodiments, at least one of $R^4$, $R^{14}$, $R^6$, $R^7$ and $R^8$ is halo (e.g., chloro or fluoro).

In some embodiments, the compound of Formula (I) has the structure of Formula (V):

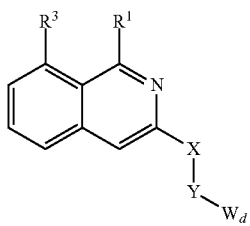

Formula (V)

or its pharmaceutically acceptable forms thereof, wherein n, z, L, X, Y, $R^1$, $R^{1'}$, $R^{a1}$, $R^{a2}$, $R^2$, $R^3$, $R^9$, $R_{10}$, $R^b$, $R^{11}$, $R^{12}$, $R^{13}$ and $W_d$ are as defined for Formula (I).

In some embodiments, $R^3$ is halo, alkyl, heteroalkyl, haloalkyl, alkenyl, alkynyl, cycloalkyl, heteroaryl, or heterocycloalkyl. In some embodiments, $R^3$ is halo, alkyl, haloalkyl, acyl, or heteroaryl. In some embodiments, $R^3$ is alkyl (e.g., methyl) or halo (e.g., chloro or fluoro).

In other embodiments, each L is —O—, —C(=O)—, —S(=O)—, —S(=O)$_2$—, —S—, alkylene, or a bond. In some embodiments, L is —(C(=O))— or —O—.

In some embodiments, $R^{1'}$ is alkyl, hydroxy, aryl, heteroaryl, aralkyl, —(C=O)—NR$^{a1}$R$^{a2}$, or NR$^{a1}$R$^{a2}$. In some embodiments, $R^{1'}$ is substituted alkyl, —(C=O)—NR$^{a1}$R$^{a2}$, NR$^{a1}$R$^{a2}$, a it wherein $R^{a1}$ and $R^{a2}$ are taken together with nitrogen to form a cyclic moiety. For instance, the cyclic moiety is a heterocyclic or heteroaryl group such as a morpholino group. In other instances, $R^{1'}$ is substituted alkyl, including alkyl which is substituted with a heterocycloalkyl group.

In some embodiments, X is absent or is —(CH($R^{10}$))$_z$—. In some embodiments, $R^{10}$ is methyl or hydrogen. In some embodiments, z is 1. In some instances, X is —CH$_2$— or —CH(CH$_3$)—. In some embodiments, the —CH(CH$_3$)— moiety has a (S) stereochemical configuration. Alternatively, the CH carbon of the —CH(CH$_3$)— moiety has a (R) stereochemical configuration. In some embodiments, Y is absent, —O—, —N($R^9$)—, or —S(=O)$_2$—. In some embodiments, X—Y is —CH$_2$—N(CH$_3$). Alternatively, X—Y is (S)—CH(CH$_3$)—NH— or (R)—CH(CH$_3$)—NH—.

In some embodiments, $R^{10}$ is selected from hydrogen, alkyl, heteroalkyl, alkenyl, alkynyl, alkoxy, amido, amino, acyl, acyloxy, alkoxycarbonyl, sulfonamido, halo, cyano, and hydroxyl. For example, $R^{10}$ is selected from hydrogen, amino, and chloro. In one instance, $R^{10}$ is selected from amino and chloro.

In some embodiments of compounds described herein, L is a bond and $R^{1'}$ is a heteroaryl group.

In some embodiments, the compound is a compound of Formula (V), wherein:

each L is —O—, —C(=O)—, —S(=O)—, —S(=O)$_2$—, —S—, or alkylene (e.g. —O— or alkylene);

$R^{1'}$ is alkyl, hydroxy, aryl, heteroaryl, aralkyl, —(C=O)—NR$^{a1}$R$^{a2}$, or —NR$^{a1}$R$^{a2}$;

$W_d$ is:

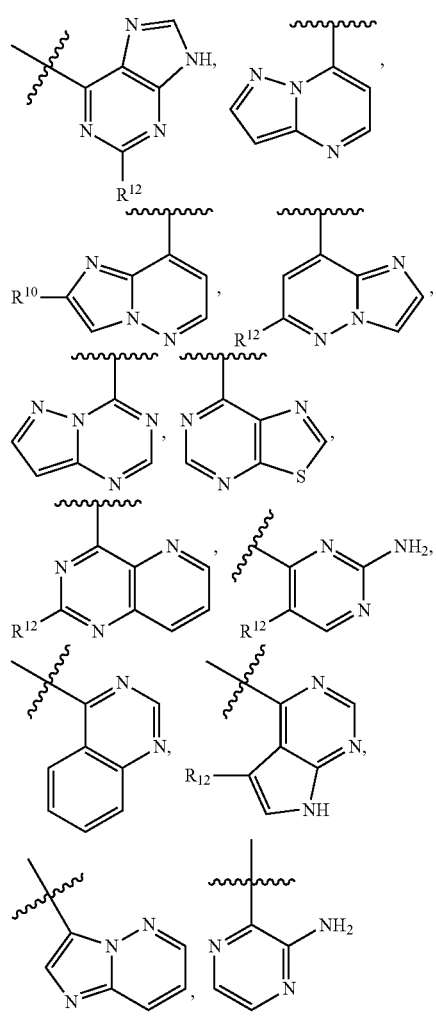

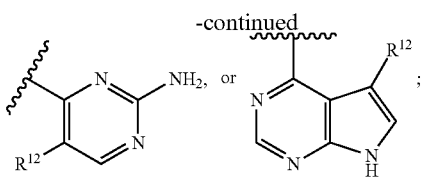

$R^{10}$ it is hydrogen;
$R^{12}$ is hydrogen, halo, haloalkyl, cyano, amino, or amido; and
n is 0, 1, 2, 3, or 4 (e.g. 0, 1, or 2).

In some embodiments, the compounds described herein can exist as a tautomer, and such tautomers are contemplated herein.

In some embodiments of the compounds described herein, $W^1$ is $CR^{14}$, $W^2$ is $CR^6$, $W^3$ is $CR^7$, $W^4$ is $CR^8$; $W^1$ is N, $W^2$ is $CR^6$, $W^3$ is $CR^7$, $W^4$ is $CR^8$; $W^1$ is $CR^{14}$, $W^2$ is N, $W^3$ is $CR^7$, $W^4$ is $CR^8$; $W^1$ is $CR^{14}$; $W^2$ is $CR^6$, $W^3$ is N, $W^4$ is $CR^8$; $W^1$ is $CR^{14}$, $W^2$ is $CR^6$, $W^3$ is $CR^7$, $W^4$ is N; $W^1$ is N, $W^2$ is $CR^6$, $W^3$ is N, $W^4$ is $CR^8$; $W^1$ is N, $W^2$ is $CR^6$, $W^3$ is N, $W^4$ is $CR^8$; $W^1$ is N, $W^2$ is $CR^6$, $W^3$ is $CR^7$, $W^4$ is N; $W^1$ is $CR^{14}$, $W^2$ is N, $W^3$ is N, $W^4$ is $CR^8$; $W^1$ is $CR^{14}$; $W^2$ is N, $W^3$ is $CR^7$, $W^4$ is N; or $W^1$ is $CR^{14}$, $W^2$ is $CR^6$, $W^3$ is N, $W^4$ is N.

In some embodiments of the compounds of Formulas (I) and (III), $R^{a1}$ or $R^{a2}$ can be hydrogen, or unsubstituted or substituted alkyl (including, but not limited to, —CH$_3$, —CH$_2$CH$_3$, n-propyl, isopropyl, n-butyl, tert-butyl, sec-butyl, pentyl, hexyl, and heptyl). In other embodiments, $R^{a1}$ or $R^{a2}$ is unsubstituted or substituted alkenyl (including, but not limited to, unsubstituted or substituted $C_2$-$C_5$ alkenyl such as, vinyl, allyl, 1-methyl propen-1-yl, butenyl, or pentenyl) or unsubstituted or substituted alkynyl (including, but not limited to, unsubstituted or substituted $C_2$-$C_5$ alkynyl such as acetylenyl, propargyl, butynyl, or pentynyl). Alternatively, $R^{a1}$ or $R^{a2}$ is unsubstituted or substituted aryl (including, but not limited to, monocyclic or bicyclic aryl) or unsubstituted or substituted arylalkyl (including, but not limited to, monocyclic or bicyclic aryl linked to alkyl wherein alkyl includes, but is not limited to, —CH$_3$, —CH$_2$CH$_3$, n-propyl, isopropyl, n-butyl, sec-butyl, and pentyl). In some other embodiments, $R^{a1}$ or $R^{a2}$ is unsubstituted or substituted heteroaryl, including, but not limited to, monocyclic and bicyclic heteroaryl. Monocyclic heteroaryl $R^{a1}$ or $R^{a2}$ includes, but is not limited to, pyrrolyl, thienyl, furyl, pyridinyl, pyranyl, pyrimidinyl, pyrazinyl, pyridazinyl, imidazolyl, thiazolyl, pyrazolyl, and oxazolyl. Bicyclic heteroaryl $R^{a1}$ or $R^{a2}$ includes, but is not limited to, benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. In some embodiments, $R^{a1}$ or $R^{a2}$ is unsubstituted or substituted heteroarylalkyl, including, but not limited to, monocyclic and bicyclic heteroaryl as described above, that are linked to alkyl, which in turn includes, but is not limited to, —CH$_3$, —CH$_2$CH$_3$, n-propyl, isopropyl, n-butyl, sec-butyl, and pentyl. In some embodiments, $R^{a1}$ or $R^{a2}$ is unsubstituted or substituted cycloalkyl (including, but not limited to, cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^{a1}$ or $R^{a2}$ is unsubstituted or substituted heterocycloalkyl which includes, but is not limited to, pyrrolidinyl, tetrahydrofuranyl, piperidinyl, tetrahydropyranyl, thiazolidinyl, imidazolidinyl, morpholinyl, and piperazinyl. In yet other embodiments, $R^{a1}$ or $R^{a2}$ is unsubstituted or substituted alkoxy including, but not limited to, $C_1$-$C_4$ alkoxy such as methoxy, ethoxy, propoxy or butoxy. In some embodiments, $R^{a1}$ can also be unsubstituted or substituted heterocycloalkyloxy, including, but not limited to, 4-NHpiperidin-1-yl-oxy, 4-methylpiperidin-1-yl-oxy, 4-ethylpiperidin-1-yl-oxy, 4-isopropylpiperidin-1-yl-oxy, and pyrrolidin-3-yl-oxy. In other embodiments, $R^{a1}$ is unsubstituted or substituted amino, wherein the substituted amino includes, but is not limited to, dimethylamino, diethylamino, di-isopropyl amino, N-methyl N-ethyl amino, and dibutylamino. In some embodiments, $R^{a1}$ or $R^{a2}$ is unsubstituted or substituted acyl, unsubstituted or substituted acyloxy, unsubstituted or substituted $C_1$-$C_4$ acyloxy, unsubstituted or substituted alkoxycarbonyl, unsubstituted or substituted amido, or unsubstituted or substituted sulfonamido. In other embodiments, $R^{a1}$ or $R^{a2}$ is halo, selected from —I, —F, —Cl, or —Br. In some embodiments, $R^{a1}$ or $R^{a2}$ is selected from cyano, hydroxy, nitro, phosphate, urea, or carbonate. Also contemplated are $R^{a1}$ or $R^{a2}$ being —CH$_3$, —CH$_2$CH$_3$, n-propyl, isopropyl, n-butyl, tert-butyl, sec-butyl, pentyl, hexyl, heptyl, —OCH$_3$, —OCH$_2$CH$_3$, or —CF$_3$.

In some embodiments of the compounds of Formulas (I) and (V), $R^{a1}$ and $R^{a2}$ are taken together with the nitrogen to form a cyclic moiety having from 3 to 8 ring atoms. In some embodiments, the cyclic moiety so formed can further include one or more heteroatoms which are selected from S, O, or N. In other embodiments, the cyclic moiety so formed is unsubstituted or substituted, including, but not limited to, morpholinyl, azetidinyl, pyrrolidinyl, piperidinyl, piperazinyl, isothiazolidinyl-1,1-dioxide, and thiomorpholinyl. Further non-limiting exemplary cyclic moieties include the following:

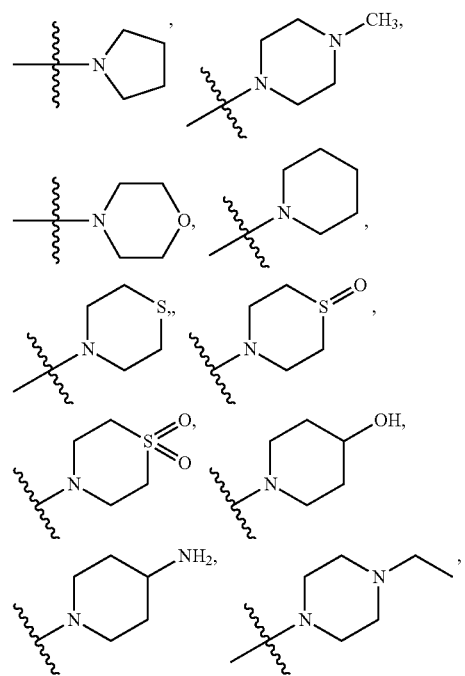

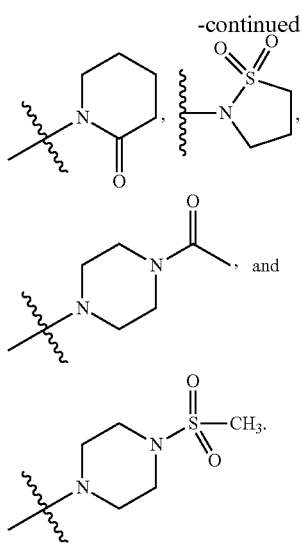

In some embodiments of compounds of Formulas (I) and (V), wherein when $R^{a1}$ or $R^{a2}$ is alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, or alkoxycarbonyl, then $R^{a1}$ or $R^{a2}$ is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, heterocycloalkyloxy, alkoxy, amido, amino, sulfonamido, acyloxy, alkoxycarbonyl, halo, cyano, hydroxy, nitro, phosphate, urea, carbonate, or NR'R", wherein R' and R" are taken together with nitrogen to form a cyclic moiety. Each of the above substituents can be further substituted with one or more substituents chosen from alkyl, alkoxy, amido, amino, sulfonamido, acyloxy, alkoxycarbonyl, halo, cyano, hydroxy, nitro, oxo, phosphate, urea, and carbonate.

For example, in some embodiments are compounds of Formulas (I) and (V), wherein when $R^{a1}$ or $R^{a2}$ is alkyl, the alkyl is substituted with NR'R", wherein R' and R" are taken together with the nitrogen to form a cyclic moiety. In some embodiments, the cyclic moiety so formed can be unsubstituted or substituted. Non-limiting exemplary cyclic moieties include, but are not limited to, morpholinyl, azetidinyl, pyrrolidinyl, piperidinyl, piperazinyl, and thiomorpholinyl. In other examples, when R' is alkyl, the alkyl is substituted with heterocycloalkyl, which includes oxetanyl, azetidinyl, tetrahydrofuranyl, pyrrolyl, tetrahydropyranyl, piperidinyl, morpholinyl, and piperazinyl. All of the above listed heterocycloalkyl substituents can be unsubstituted or substituted.

In yet other examples of the compounds of Formula (I) and (V), when $R^{a1}$ or $R^{a2}$ is alkyl, the alkyl is substituted with a 5, 6, 7, 8, 9, or 10 membered monocyclic or bicyclic heteroaryl, which is unsubstituted or substituted. In some embodiments, the monocyclic heteroaryl includes, but is not limited to, pyrrolyl, thienyl, furyl, pyridinyl, pyranyl, pyrimidinyl, pyrazinyl, pyridazinyl, imidazolyl, thiazolyl, pyrazolyl, and oxazolyl. In other embodiments, the bicyclic heteroaryl includes, but is not limited to, benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some embodiments of the compounds of Formula (I) and (V), L is —N($R^2$)—, wherein $R^2$ is hydrogen, unsubstituted or substituted $C_1$-$C_{10}$ alkyl (which includes, but is not limited to, —$CH_3$, —$CH_2CH_3$, n-propyl, isopropyl, n-butyl, tert-butyl, sec-butyl, pentyl, hexyl, and heptyl), or unsubstituted or substituted $C_3$-$C_7$ cycloalkyl (which includes, but is not limited to, cyclopropyl, cyclobutyl, cyclopentyl, and cyclohexyl). In other embodiments, $R^2$ is unsubstituted or substituted heterocycloalkyl (which includes, but is not limited to, oxetanyl, tetrahydrofuranyl, pyrrolidinyl, tetrahydropyranyl, piperidinyl, and piperazinyl), or unsubstituted or substituted $C_2$-$C_{10}$ heteroalkyl (which includes, but is not limited to, methoxyethoxy, methoxymethyl, and diethylaminoethyl). Alternatively, $R^2$ is unsubstituted or substituted monocyclic heteroaryl (which includes, but is not limited to, pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In some embodiments of the compounds of Formulas (I) and (V), L is alkylene (e.g., —C($R^{16}$)$_2$—). In some embodiments of the compounds of Formulas (I) and (V), L is —C($R^{16}$)$_2$—, wherein $R^{16}$ is hydrogen, unsubstituted or substituted $C_1$-$C_{10}$ alkyl (including, but not limited to, —$CH_3$, —$CH_2CH_3$, n-propyl, isopropyl, n-butyl, tert-butyl, sec-butyl, pentyl, hexyl, and heptyl), or halo selected from —I, —F, —Cl, or —Br. In further embodiments, $R^{16}$ is unsubstituted or substituted monocyclic heteroaryl (including, but not limited to, pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In some embodiments of the compounds of Formula (I) and (V), L is heteroalkylene (e.g., —C($R^{16}$)$_2$—). In some embodiments of the compound of Formulas (I) and (V), L is —O—C($R^{16}$)$_2$—, wherein $R^{16}$ is hydrogen, unsubstituted or substituted $C_1$-$C_{10}$ alkyl (including, but not limited to, —$CH_3$, —$CH_2CH_3$, n-propyl, isopropyl, n-butyl, tert-butyl, sec-butyl, pentyl, hexyl, and heptyl), or halo selected from —I, —F, —Cl, or —Br. In further embodiments, $R^{16}$ is unsubstituted or substituted monocyclic heteroaryl (including, but not limited to, pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl.

In some embodiments of the compound of Formulas (III) and (IV), L is a bond and $R^{1'}$ is an optionally substituted 5-membered heterocyclic group comprising at least two heteroatoms chosen from O and N. For example, $R^{1'}$ can be oxazole. In other embodiments, $R^{1'}$ is isoxazole.

In some embodiments of compounds of Formulas (I) and (III), $R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, —(C=O)—NR$^{a1}$R$^{a2}$, or NR$^{a1}$R$^{a2}$, wherein $R^{a1}$ or $R^{a2}$ are taken together with nitrogen to form a cyclic moiety.

In some embodiments of the compounds of Formulas (I), (II) and (III), $R^{1'}$ can be hydrogen, or unsubstituted or substituted alkyl (including, but not limited to, —$CH_3$, —$CH_2CH_3$, n-propyl, isopropyl, n-butyl, tert-butyl, sec-butyl, pentyl, hexyl, and heptyl). In other embodiments, $R^{1'}$ is unsubstituted or substituted alkenyl (including, but not limited to, unsubstituted or substituted $C_2$-$C_5$ alkenyl such as, vinyl, allyl, 1-methyl propen-1-yl, butenyl, or pentenyl) or unsubstituted or substituted alkynyl (including, but not limited to, unsubstituted or substituted $C_2$-$C_5$ alkynyl such as acetylenyl, propargyl, butynyl, or pentynyl). Alternatively, R¹' is unsubstituted or substituted aryl (including, but not limited to, monocyclic or bicyclic aryl) or unsubstituted or substituted arylalkyl (including but not limited to monocyclic or bicyclic aryl linked to alkyl wherein alkyl includes, but is not limited to, —CH₃, —CH₂CH₃, n-propyl, isopropyl, n-butyl, sec-butyl, and pentyl). In some other embodiments, R¹' is unsubstituted or substituted heteroaryl, including, but not limited to, monocyclic and bicyclic heteroaryl. In some embodiments, monocyclic heteroaryl R¹' includes, but is not limited to, pyrrolyl, thienyl, furyl, pyridinyl, pyranyl, pyrimidinyl, pyrazinyl, pyridazinyl, imidazolyl, thiazolyl, pyrazolyl, and oxazolyl. In some embodiments, bicyclic heteroaryl R¹' includes, but is not limited to, benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. Also provided herein are compounds which are unsubstituted or substituted heteroarylalkyl, including, but not limited to, monocyclic and bicyclic heteroaryl as described above, that are linked to alkyl, which in turn includes, but is not limited to, —CH₃, —CH₂CH₃, n-propyl, isopropyl, n-butyl, sec-butyl, and pentyl. In some embodiments, R¹' is unsubstituted or substituted cycloalkyl (including, but not limited to, cyclopropyl, cyclobutyl, and cyclopentyl) or unsubstituted or substituted heteroalkyl (non-limiting examples include ethoxymethyl, methoxymethyl, and diethylaminomethyl). In some further embodiments, R¹' is unsubstituted or substituted heterocycloalkyl which includes, but is not limited to, pyrrolidinyl, tetrahydrofuranyl, piperidinyl, tetrahydropyranyl, thiazolidinyl, imidazolidinyl, morpholinyl, and piperazinyl. In yet other embodiments of the compounds described herein, R¹' is unsubstituted or substituted alkoxy including, but not limited to, C₁-C₄ alkoxy such as methoxy, ethoxy, propoxy or butoxy. R¹' can also be unsubstituted or substituted heterocycloalkyloxy, including, but not limited to, 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, R¹' is unsubstituted or substituted amino, wherein the substituted amino includes, but is not limited to, dimethylamino, diethylamino, di-isopropyl amino, N-methyl N-ethyl amino, and dibutylamino. In some embodiments, R¹' is unsubstituted or substituted acyl, unsubstituted or substituted acyloxy, unsubstituted or substituted C₁-C₄ acyloxy, unsubstituted or substituted alkoxycarbonyl, unsubstituted or substituted amido, or unsubstituted or substituted sulfonamido. In other embodiments, R¹' is halo, selected from —I, —F, —Cl, or —Br. In some embodiments, R¹' is selected from cyano, hydroxy, nitro, phosphate, urea, or carbonate. Also contemplated are R¹' being —CH₃, —CH₂CH₃, n-propyl, isopropyl, n-butyl, tert-butyl, sec-butyl, pentyl, hexyl, heptyl, —OCH₃, —OCH₂CH₃, or —CF₃.

In some embodiments of the compounds of Formulas (I), (II) or (III), R¹' is NR^{a1}R^{a2}, where R^{a1} or R^{a2} are taken together with the nitrogen to form a cyclic moiety having from 3 to 8 ring atoms. The cyclic moiety so formed can further include one or more heteroatoms which are selected from S, O, and N. The cyclic moiety so formed is unsubstituted or substituted, including but not limited to morpholinyl, azetidinyl, pyrrolidinyl, piperidinyl, piperazinyl, isothiazolidinyl-1,1-dioxide, and thiomorpholinyl. Further non-limiting exemplary cyclic moieties are the following:

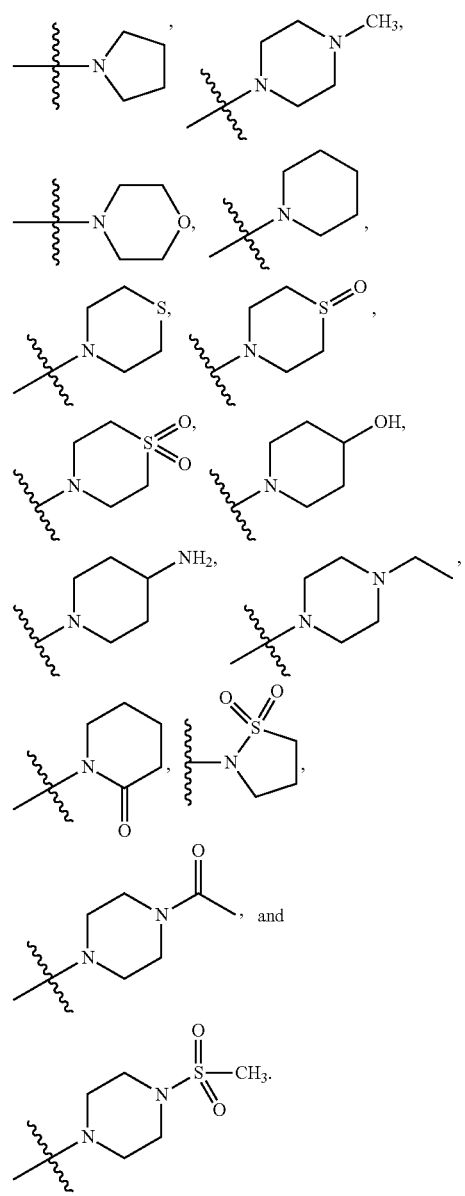

Also provided are compounds of Formulas (I), (II) or (III), wherein when R¹' is alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, or alkoxycarbonyl, then R¹' is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, heterocycloalkyloxy, alkoxy, amido, amino, sulfonamido, acyloxy, alkoxycarbonyl, halo, cyano, hydroxy, nitro, phosphate, urea, carbonate, or NR'R'', wherein R' and R'' are taken together with nitrogen to form a cyclic moiety. Each of the above substituents can be further substituted with one or more substituents chosen from alkyl, alkoxy, amido, amino, sulfonamido, acyloxy, alkoxycarbonyl, halo, cyano, hydroxy, nitro, oxo, phosphate, urea, and carbonate.

For example, provided herein are compounds of Formulas (I), (II) or (III), wherein when R¹' is alkyl, the alkyl is substituted with NR'R", wherein R' and R" are taken together with the nitrogen to form a cyclic moiety. The cyclic moiety so formed can be unsubstituted or substituted. Non-limiting exemplary cyclic moieties include, but are not limited to, morpholinyl, azetidinyl, pyrrolidinyl, piperidinyl, piperazinyl, and thiomorpholinyl. In other examples of the compounds disclosed herein, when $R^{1'}$ is alkyl, the alkyl is substituted with heterocycloalkyl, which includes, but is not limited to, oxetanyl, azetidinyl, tetrahydrofuranyl, pyrrolyl, tetrahydropyranyl, piperidinyl, morpholinyl, and piperazinyl. All of the above listed heterocycloaklyl substituents can be unsubstituted or substituted.

In yet other examples of the compounds of Formulas (I), (II) or (III), when $R^{1'}$ is alkyl, the alkyl is substituted with a 5, 6, 7, 8, 9, or 10 membered monocyclic or bicyclic heteroaryl, which is unsubstituted or substituted. In some embodiments, the monocyclic heteroaryl includes, but is not limited to, pyrrolyl, thienyl, furyl, pyridinyl, pyranyl, pyrimidinyl, pyrazinyl, pyridazinyl, imidazolyl, thiazolyl, pyrazolyl, and oxazolyl. In other embodiments, the bicyclic heteroaryl includes, but is not limited to, benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some embodiments of the compound disclosed herein, $R^4$ can be hydrogen, or unsubstituted or substituted alkyl (including, but not limited to, —$CH_3$, —$CH_2CH_3$, n-propyl, isopropyl, n-butyl, tert-butyl, sec-butyl, pentyl, hexyl, and heptyl). In other embodiments, $R^4$ is unsubstituted or substituted alkenyl (including, but not limited to, unsubstituted or substituted $C_2$-$C_5$ alkenyl such as, vinyl, allyl, 1-methyl propen-1-yl, butenyl, or pentenyl) or unsubstituted or substituted alkynyl (including, but not limited to, unsubstituted or substituted $C_2$-$C_5$ alkynyl such as acetylenyl, propargyl, butynyl, or pentynyl). Alternatively, $R^4$ is unsubstituted or substituted aryl (including, but not limited to, monocyclic or bicyclic aryl) or unsubstituted or substituted arylalkyl (including, but not limited to, monocyclic or bicyclic aryl linked to alkyl wherein alkyl includes, but is not limited to, —$CH_3$, —$CH_2CH_3$, n-propyl, isopropyl, n-butyl, sec-butyl, and pentyl). In some other embodiments, $R^4$ is unsubstituted or substituted heteroaryl, including but not limited to, monocyclic and bicyclic heteroaryl. In other embodiments, monocyclic heteroaryl $R^4$ includes, but is not limited to, pyrrolyl, thienyl, furyl, pyridinyl, pyranyl, pyrimidinyl, pyrazinyl, pyridazinyl, imidazolyl, thiazolyl, pyrazolyl, and oxazolyl. In some embodiments, bicyclic heteroaryl $R^4$ includes, but is not limited to, benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some embodiments, provided herein are compounds wherein $R^4$ is unsubstituted or substituted heteroarylalkyl, including, but not limited to, monocyclic and bicyclic heteroaryl as described above, that are linked to alkyl, which in turn includes but is not limited to, —$CH_3$, —$CH_2CH_3$, n-propyl, isopropyl, n-butyl, sec-butyl, and pentyl. In some embodiments, $R^4$ is unsubstituted or substituted cycloalkyl (including, but not limited to, cyclopropyl, cyclobutyl, and cyclopentyl) or unsubstituted or substituted heteroalkyl (non-limiting examples include ethoxymethyl, methoxymethyl, and diethylaminomethyl). In some further embodiments, $R^4$ is unsubstituted or substituted heterocycloalkyl which includes, but is not limited to, pyrrolidinyl, tetrahydrofuranyl, piperidinyl, tetrahydropyranyl, thiazolidinyl, imidazolidinyl, morpholinyl, and piperazinyl. In yet other embodiments of the compounds described herein, $R^4$ is unsubstituted or substituted alkoxy including, but not limited to, $C_1$-$C_4$ alkoxy such as methoxy, ethoxy, propoxy or butoxy. In some embodiments, $R^4$ can also be unsubstituted or substituted heterocycloalkyloxy, including, but not limited to, 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In some embodiments, $R^4$ is unsubstituted or substituted acyl, unsubstituted or substituted acyloxy, unsubstituted or substituted $C_1$-$C_4$ acyloxy, unsubstituted or substituted alkoxycarbonyl, unsubstituted or substituted amido, or unsubstituted or substituted sulfonamido. In some embodiments, $R^4$ is selected from cyano, hydroxy, nitro, phosphate, urea, or carbonate. Also contemplated is $R^4$ being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$.

In some embodiments, $R^4$ can also be NR'R", wherein R' and R" are taken together with the nitrogen to form a cyclic moiety having from 3 to 8 ring atoms. The cyclic moiety so formed can further include one or more heteroatoms which are selected from S, O, and N. The cyclic moiety so formed is unsubstituted or substituted, including, but not limited to, morpholinyl, azetidinyl, pyrrolidinyl, piperidinyl, piperazinyl, isothiazolidinyl-1,1,-dioxide, and thiomorpholinyl. Further non-limiting exemplary cyclic moieties include the following:

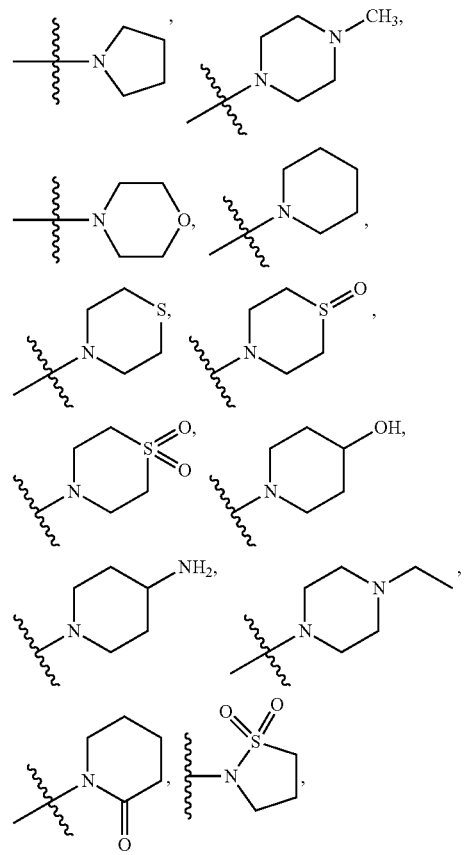

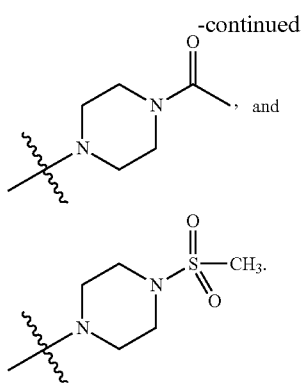

In some embodiments, provided herein are compounds wherein when R⁴ is alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, or NR'R" (wherein R' and R" are taken together with nitrogen to form a cyclic moiety), then R⁴ is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, halo, cyano, hydroxy, nitro, phosphate, urea, carbonate, or NR'R", wherein R' and R" are taken together with nitrogen to form a cyclic moiety. Each of the above substituents can be further substituted with one or more substituents chosen from alkyl, alkoxy, amido, amino, sulfonamido, acyloxy, alkoxycarbonyl, halo, cyano, hydroxy, nitro, oxo, phosphate, urea, and carbonate.

For example, provided herein are compounds wherein when R⁴ is alkyl, the alkyl is substituted with NR'R", wherein R' and R" are taken together with the nitrogen to form a cyclic moiety. The cyclic moiety so formed can be unsubstituted or substituted. Non-limiting exemplary cyclic moieties include, but are not limited to, morpholinyl, azetidinyl, pyrrolidinyl, piperidinyl, piperazinyl, isothiazolidinyl-1,1-dioxide, and thiomorpholinyl. In other examples of the compounds described herein, when R⁴ is alkyl, the alkyl is substituted with heterocycloalkyl, which includes, but is not limited to, oxetanyl, azetidinyl, tetrahydrofuranyl, pyrrolyl, tetrahydropyranyl, piperidinyl, morpholinyl, and piperazinyl. All of the above listed heterocycloaklyl substituents can be unsubstituted or substituted.

In yet other examples of the compounds described herein, when R⁴ is alkyl, the alkyl is substituted with a 5, 6, 7, 8, 9, or 10 membered monocyclic or bicyclic heteroaryl, which is unsubstituted or substituted. In some embodiments, the monocyclic heteroaryl includes, but is not limited to, pyrrolyl, thienyl, furyl, pyridinyl, pyranyl, pyrimidinyl, pyrazinyl, pyridazinyl, imidazolyl, thiazolyl, pyrazolyl, and oxazolyl. In other embodiments, the bicyclic heteroaryl includes, but is not limited to, benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some of the embodiments of the compounds of Formulas (II), (III), and (IV), W¹ is CR¹⁴, W² is CR⁶, W³ is CR⁷, and W⁴ is CR⁸. Each of R¹⁴, R⁶, R⁷, and R⁸ can independently be hydrogen, or unsubstituted or substituted alkyl (including, but not limited to, —CH₃, —CH₂CH₃, n-propyl, isopropyl, n-butyl, tert-butyl, sec-butyl, pentyl, hexyl, and heptyl). In other embodiments, each of R¹⁴, R⁶, and R⁷ independently is unsubstituted or substituted alkenyl (including, but not limited to, unsubstituted or substituted C₂-C₅ alkenyl such as, vinyl, allyl, 1-methyl propen-1-yl, butenyl, or pentenyl) or unsubstituted or substituted alkynyl (including, but not limited to, unsubstituted or substituted C₂-C₅ alkynyl such as acetylenyl, propargyl, butynyl, or pentynyl). Alternatively, each of R¹⁴, R⁶, R⁷, and R⁸ independently is unsubstituted or substituted aryl (including, but not limited to, monocyclic or bicyclic aryl) or unsubstituted or substituted arylalkyl (including, but not limited to, monocyclic or bicyclic aryl linked to alkyl wherein alkyl includes, but is not limited to, —CH₃, —CH₂CH₃, n-propyl, isopropyl, n-butyl, sec-butyl, and pentyl). In some other embodiments, each of R¹⁴, R⁶, and R⁷ independently is unsubstituted or substituted heteroaryl, including, but not limited to, monocyclic and bicyclic heteroaryl. In some embodiments, monocyclic heteroaryl for each of R¹⁴, R⁶, R⁷, and R⁸ includes, but is not limited to, pyrrolyl, thienyl, furyl, pyridinyl, pyranyl, pyrimidinyl, pyrazinyl, pyridazinyl, imidazolyl, thiazolyl, pyrazolyl, and oxazolyl. In other embodiments, bicyclic heteroaryl for each of R¹⁴, R⁶, R⁷, and R⁸ includes, but is not limited to, benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. In some embodiments, provided herein are compounds of Formulas (II), (III), and (IV), wherein each of R¹⁴, R⁶, R⁷, and R⁸ independently is unsubstituted or substituted heteroarylalkyl, including but not limited to, monocyclic and bicyclic heteroaryl as described above, that are linked to alkyl, which in turn includes, but is not limited to, —CH₃, —CH₂CH₃, n-propyl, isopropyl, n-butyl, sec-butyl, and pentyl. In some embodiments, each of R¹⁴, R⁶, R⁷, and R⁸ independently is unsubstituted or substituted cycloalkyl (including, but not limited to, cyclopropyl, cyclobutyl, and cyclopentyl) or unsubstituted or substituted heteroalkyl (non-limiting examples include ethoxymethyl, methoxymethyl, and diethylaminomethyl). In some further embodiments, each of R¹⁴, R⁶, R⁷, and R⁸ independently is unsubstituted or substituted heterocycloalkyl which includes, but is not limited to, pyrrolidinyl, tetrahydrofuranyl, piperidinyl, tetrahydropyranyl, thiazolidinyl, imidazolidinyl, morpholinyl, isothiazolidinyl-1,1-dioxide, and piperazinyl. In yet other embodiments of the compounds disclosed herein, each of R¹⁴, R⁶, R⁷, and R⁸ independently is unsubstituted or substituted alkoxy including, but not limited to, C₁-C₄ alkoxy such as methoxy, ethoxy, propoxy or butoxy. In some embodiments, each of R¹⁴, R⁶, R⁷, and R⁸ can also independently be unsubstituted or substituted heterocycloalkyloxy, including, but not limited to, 4-NH piperidin-1-yl-oxy, 4-methyl piperidin-1-yl-oxy, 4-ethyl piperidin-1-yl-oxy, 4-isopropyl-piperidin-1-yl-oxy, and pyrrolidin-3-yl-oxy. In other embodiments, each of R¹⁴, R⁶, R⁷, and R⁸ independently is unsubstituted or substituted amino, wherein the substituted amino includes, but is not limited to, dimethylamino, diethylamino, di-isopropyl amino, N-methyl N-ethyl amino, and dibutylamino. In some embodiments, each of R¹⁴, R⁶, R⁷, and R⁸ independently is unsubstituted or substituted acyl, unsubstituted or substituted acyloxy, unsubstituted or substituted C₁-C₄ acyloxy, unsubstituted or substituted alkoxycarbonyl, unsubstituted or substituted amido, or unsubstituted or substituted sulfonamido. In some embodiments, each of R¹⁴, R⁶, R⁷, and R⁸ independently is halo, selected from —I, —F, —Cl, or —Br. In some embodiments, each of R¹⁴, R⁶, R⁷, and R⁸ independently is selected from cyano, hydroxy, nitro, phosphate, urea, or carbonate. Also contemplated are each of $R^{14}$, $R^6$, and $R^7$ independently being —$CH_3$, —$CH_2CH_3$, n-propyl, isopropyl, n-butyl, tert-butyl, sec-butyl, pentyl, hexyl, heptyl, —$OCH_3$, —$OCH_2CH_3$, or —$CF_3$.

In some embodiments, each of $R^{14}$, $R^6$, $R^7$, and $R^8$ can also independently be NR'R", wherein R' and R" are taken together with the nitrogen to form a cyclic moiety having from 3 to 8 ring atoms. The cyclic moiety so formed can further include one or more heteroatoms which are selected from S, O, and N. The cyclic moiety so formed is unsubstituted or substituted, including, but not limited to, morpholinyl, azetidinyl, pyrrolidinyl, piperidinyl, piperazinyl, isothiazolidinyl-1,1-dioxide, and thiomorpholinyl. Further non-limiting exemplary cyclic moieties include the following:

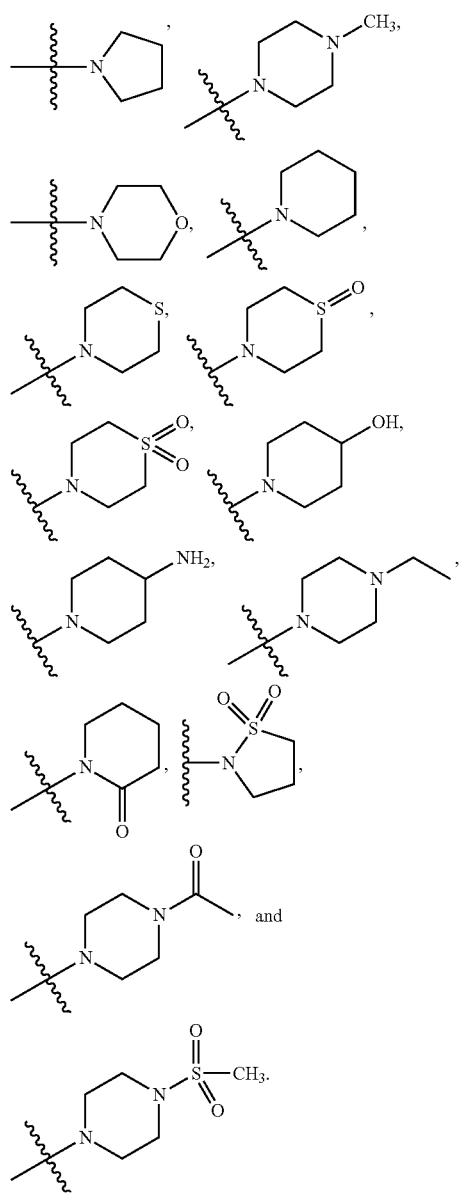

In some embodiments, provided herein are compounds wherein when each of $R^{14}$, $R^6$, $R^7$, and $R^8$ independently is alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, or NR'R" (wherein R' and R" are taken together with nitrogen to form a cyclic moiety), then each of $R^{14}$, $R^6$, $R^7$, and $R^8$ independently is optionally substituted with one or more of the following substituents: alkyl, alkenyl, alkynyl, cycloalkyl, heteroalkyl, heterocycloalkyl, heterocycloalkyloxy, aryl, arylalkyl, heteroaryl, heteroarylalkyl, acyl, alkoxy, amido, amino, sulfonamido, acyloxy, alkoxycarbonyl, halo, cyano, hydroxy, nitro, phosphate, urea, carbonate, or NR'R", wherein R' and R" are taken together with nitrogen to form a cyclic moiety. Each of the above substituents can be further substituted with one or more substituents chosen from alkyl, alkoxy, amido, amino, sulfonamido, acyloxy, alkoxycarbonyl, halo, cyano, hydroxy, nitro, oxo, phosphate, urea, and carbonate.

For example, provided herein are compounds wherein when each of $R^{14}$, $R^6$, $R^7$, and $R^8$ independently is alkyl, the alkyl is substituted with NR'R", wherein R' and R" are taken together with the nitrogen to form a cyclic moiety. The cyclic moiety so formed can be unsubstituted or substituted. Non-limiting exemplary cyclic moieties include, but are not limited to, morpholinyl, azetidinyl, pyrrolidinyl, piperidinyl, piperazinyl, isothiazolidinyl-1,1-dioxide, and thiomorpholinyl. In other examples of the compounds disclosed herein, when each of $R^{14}$, $R^6$, $R^7$, and $R^8$ independently is alkyl, the alkyl is substituted with heterocycloalkyl, which includes, but is not limited to, oxetanyl, azetidinyl, tetrahydrofuranyl, pyrrolyl, tetrahydropyranyl, piperidinyl, morpholinyl, and piperazinyl. All of the above listed heterocycloaklyl substituents can be unsubstituted or substituted.

In yet other examples of the compounds disclosed herein, when each of $R^{14}$, $R^6$, $R^7$, and $R^8$ independently is alkyl, the alkyl is substituted with a 5, 6, 7, 8, 9, or 10 membered monocyclic or bicyclic heteroaryl, which is unsubstituted or substituted. In some embodiments, the monocyclic heteroaryl for each of $R^{14}$, $R^6$, $R^7$, and $R^8$ includes, but is not limited to, pyrrolyl, thienyl, furyl, pyridinyl, pyranyl, pyrimidinyl, pyrazinyl, pyridazinyl, imidazolyl, thiazolyl, pyrazolyl, and oxazolyl. In other embodiments, the bicyclic heteroaryl for each of $R^{14}$, $R^6$, $R^7$, and $R^8$ includes, but is not limited to, benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl.

In some embodiments of the compounds disclosed herein, $W^1$ is $CR^{14}$, $W^2$ is $CR^6$, $W^3$ is $CR^7$, $W^4$ is $CR^8$ and $R^8$, $R^{14}$, $R^6$, and $R^7$ are hydrogen.

In some embodiments of the compounds disclosed herein, at least one X or Y is present.

In some embodiments, provided here are compounds wherein Y is —N($R^9$)—, —N($R^9$)(C=O)—, —N($R^9$)(C=O)NH—, —N($R^9$)C($R^{10}$)$_2$—, or —C(=O)—(CH$R^{10}$)$_z$— and z is an integer of 1, 2, 3, or 4. In some embodiments, $R^9$ is hydrogen, unsubstituted or substituted $C_1$-$C_{10}$ alkyl (including, but not limited to, —$CH_3$, —$CH_2CH_3$, n-propyl, isopropyl, n-butyl, tert-butyl, sec-butyl, pentyl, hexyl, and heptyl), or unsubstituted or substituted $C_3$-$C_7$ cycloalkyl (non-limiting examples include cyclopropyl, cyclobutyl, cyclopentyl, and cyclohexyl). In other embodiments, $R^9$ is unsubstituted or substituted heterocycloalkyl (including, but not limited to, oxetanyl, tetrahydrofuranyl, pyrrolidinyl, tetrahydropyranyl, piperidinyl, and piperazinyl), or unsubstituted or substituted $C_2$-$C_{10}$heteroalkyl ($C_2$-$C_{10}$heteroalkyl includes, but is not limited to, methoxyethoxy, methoxymethyl, and diethylaminoethyl).

Alternatively, $R^9$ is unsubstituted or substituted monocyclic heteroaryl (non-limiting examples include pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl. For example, Y is —N(CH$_3$)CH$_2$—, —N(CH(CH$_3$)$_2$)CH$_2$—, N(CH$_2$CH$_3$)CH$_2$—, —N(CH$_3$)—, —N(CH$_2$CH$_3$)—, or —N(CH(CH$_3$)$_2$)—. In some embodiments, Y is —NH—.

In other embodiments, X is —(CH(R$^{10}$))$_z$—, and z is an integer of 1 or 2. In some embodiments, provided herein are compounds wherein R$^{10}$ is hydrogen or unsubstituted or substituted C$_1$-C$_{10}$ alkyl (non-limiting exemplary alkyl substituents include, but are not limited to, —CH$_3$, —CH$_2$CH$_3$, n-propyl, isopropyl, n-butyl, tert-butyl, sec-butyl, pentyl, hexyl, and heptyl), or halo (such as —I, —F, —Cl, or —Br). In further embodiments, R$^{10}$ is unsubstituted or substituted monocyclic heteroaryl (including, but not limited to, pyrrolyl, thienyl, furyl, pyridinyl, pyranyl, pyrimidinyl, pyrazinyl, pyridazinyl, imidazolyl, thiazolyl, pyrazolyl, and oxazolyl) or unsubstituted or substituted monocyclic aryl. For example, X is —CH$_2$—, —CH$_2$CH$_2$—, —CH$_2$CH$_2$CH$_2$—, —CH(CH$_3$)—, —CH(CH$_2$CH$_3$), —CH(CH$_3$)—, —CH(CH$_2$CH$_3$)— or —CH(C$_6$H$_6$)— or —CH(C$_6$H$_6$)—. In some embodiments, when X is —CH(CH$_3$)—, —CH(CH$_2$CH$_3$)— or —CH(C$_6$H$_6$)—, the asymmetric carbon center is predominately in the (S)- or predominately in the (R)-stereochemical configuration. In some embodiments, an asymmetric carbon center is predominately (S)- or predominately (R)- when the predominate stereoisomer is present in greater than about 60%, 65%, 70%, 75%, 80%, 85%, 90%, 95%, 97%, 95%, or 99% of the total proportion of the two possible stereoisomers at that asymmetric center.

In some embodiments, X—Y is —CH$_2$—, —CH$_2$—NH—, —CH$_2$—N(CH$_3$)—, —CH(CH$_3$)—NH—, —CH(CH$_2$CH$_3$)—NH—, —CH(C$_6$H$_6$)—NH—, (S)—CH(CH$_3$)—NH—, (R)—CH(CH$_3$)—NH—, (S)—CH(CH$_2$CH$_3$)—NH—, (R)—CH(CH$_2$CH$_3$)—NH—, (S)—CH(C$_6$H$_6$)—NH—, or (R)—CH(C$_6$H$_6$)—NH—. In some embodiments, X—Y is —N(CH$_3$)_CH$_2$—, —N(CH$_2$CH$_3$)CH$_2$—, —N(CH(CH$_3$)$_2$)CH$_2$—, or —NHCH$_2$—.

In some embodiments of the compounds disclosed herein, W$_d$ is unsubstituted or substituted heterocycloalkyl, wherein the heterocycloalkyl includes, but is not limited to, morpholinyl, piperidinyl, piperazinyl, tetrahydro-2H-pyranyl, and pyrrolidinyl. In some embodiments, also provided herein are compounds wherein W$_d$ is unsubstituted or substituted cycloalkyl wherein the cycloalkyl includes, but is not limited to, cyclobutyl, cyclopentyl, and cyclohexyl. Alternatively, W$_d$ is monocyclic aryl (for example, phenyl) or bicyclic aryl (for example, naphthyl), wherein the monocyclic aryl or bicyclic aryl is unsubstituted or substituted. In some embodiments, W$_d$ is unsubstituted or substituted monocyclic heteroaryl. Non-limiting exemplary monocyclic heteroaryls include pyrrolyl, thienyl, furyl, pyridinyl, pyranyl, pyrimidinyl, pyrazinyl, pyridazinyl, imidazolyl, isothiazolyl, isoxazolyl, thiazolyl, triazinyl, pyrazolyl, and oxazolyl. In some embodiments, also provided herein are compounds wherein W$_d$ is unsubstituted or substituted bicyclic heteroaryl, including, but not limited to, benzothiophenyl, benzofuryl, indolyl, quinolinyl, isoquinolinyl, benzimidazolyl, benzoxazolyl, benzothiazolyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. In some embodiments, the quinolinyl W$_d$ bicyclic heteroaryl is 4-quinolinyl. In some embodiments, the W$_d$ bicyclic heteroaryl has at least one heteroatom, including, but not limited to, indolyl, quinolinyl, benzothiazolyl, pyrazolopyridinyl, pyrazolopyrimidinyl, or isoquinolinyl. Additionally, the W$_d$ bicyclic heteroaryl can have at least two nitrogen ring atoms, such as indazole, pyrrolopyridinyl, pyrazolopyridinyl, pyrazolopyrimidinyl, benzimidazolyl, benzothiazolyl, azaindolyl, quinazolinyl, benzoxazolyl, or pyrazolopyrimidinyl. In yet other embodiments, W$_d$ is a bicyclic heteroaryl having at least three nitrogen ring atoms, such as pyrazolopyridinyl, pyrrolopyrimidinyl, thiazolylpyrimidinyl, pyrrolo[1,2-b]pyridazinyl, or imidazo[1,2-a]pyridinyl. Alternatively, W$_d$ is a bicyclic heteroaryl having at least four nitrogen ring atoms, including, but not limited to, pyrazolopyrimidinyl, purinyl, or pyrrolo[1,2-f][1,2,4]triazinyl. In some embodiments, W$_d$ is a bicyclic heteroaryl having two heteroatoms in the ring which is connected to XY.

In some embodiments, W$_d$ is one of the following:

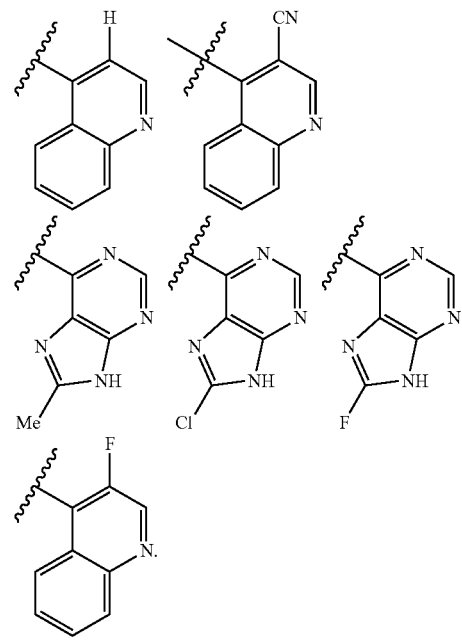

In some embodiments of W$_d$, R$^b$ is selected from hydrogen, halo, phosphate, urea, carbonate, unsubstituted or substituted alkyl, unsubstituted or substituted alkenyl, unsubstituted or substituted alkynyl, unsubstituted or substituted cycloalkyl, unsubstituted or substituted heteroalkyl, and unsubstituted or substituted heterocycloalkyl.

In some embodiments of W$_d$, when R$^b$ is alkyl, alkynyl, cycloalkyl, heteroalkyl, or heterocycloalkyl, it is substituted by phosphate, urea, carbonate, or combinations thereof.

In the compounds disclosed herein, W$_d$ can be substituted by R$^{11}$ wherein R$^{11}$ is hydrogen, unsubstituted or substituted alkyl, and halo (such as —I, —F, —Cl, and —Br). In some embodiments, R$^{11}$ is unsubstituted or substituted amino, unsubstituted or substituted amido, hydroxy, or unsubstituted or substituted alkoxy. In some embodiments, R$^{11}$ can also be phosphate, unsubstituted or substituted urea, or carbonate.

Additionally, when R$^{11}$ is alkyl, amino, amido, hydroxy, or alkoxy, R$^{11}$ can be substituted by phosphate, urea, or carbonate.

In some embodiments of the compound disclosed herein, when W$_d$ is purinyl, X is —(CH(R$^{10}$))$_z$—, z is 1, and Y is —N(R$^9$)—, then R$^9$ is —NH—.

In some embodiments of the compound disclosed herein, —X—Y—W$_d$ is one of the following moieties:
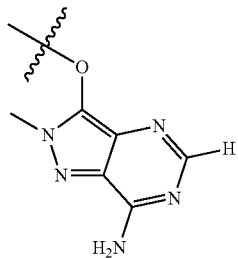 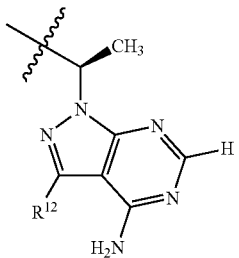
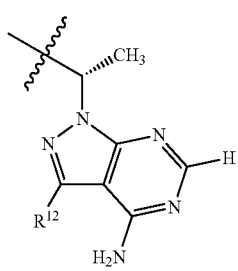 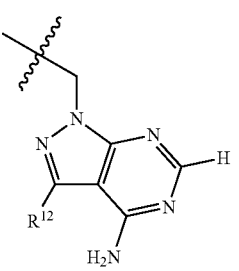
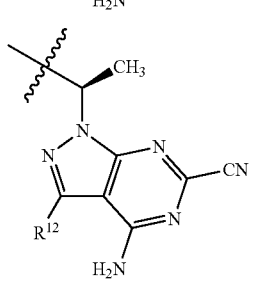 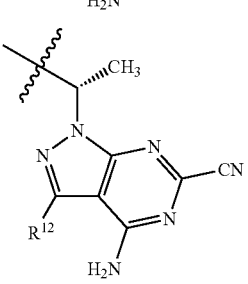
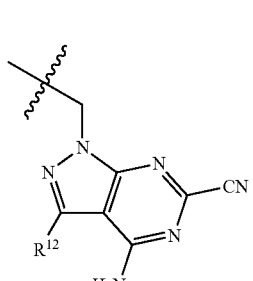 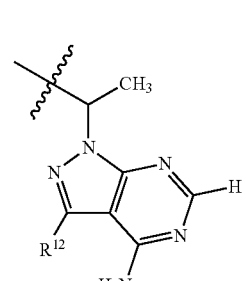
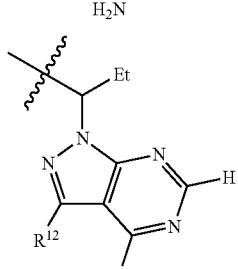 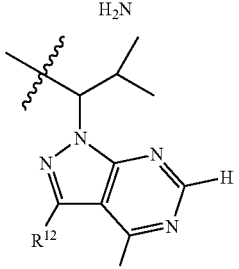
 
-continued
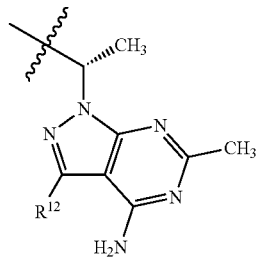
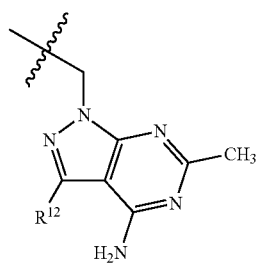
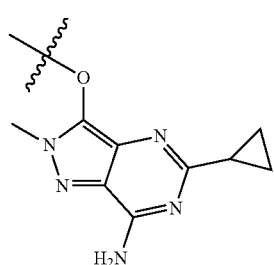
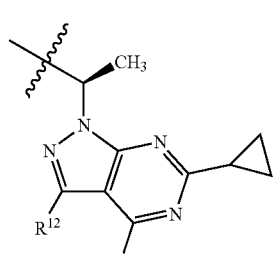
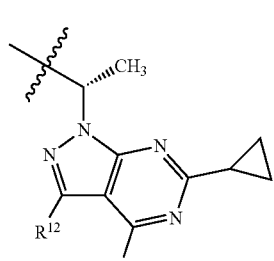
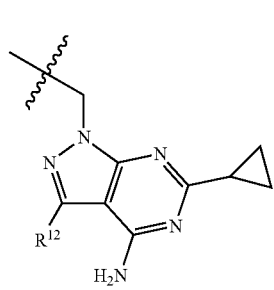

67
-continued
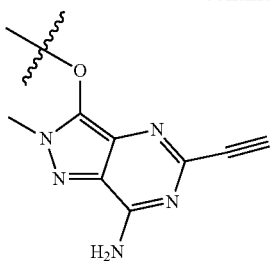
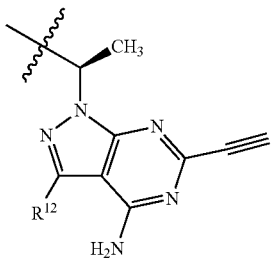
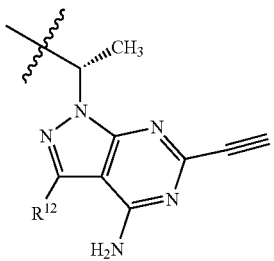
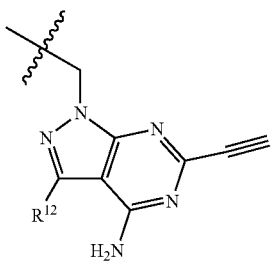
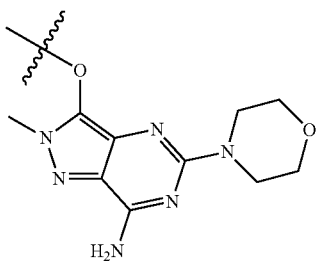
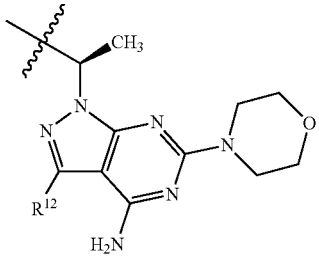
68
-continued
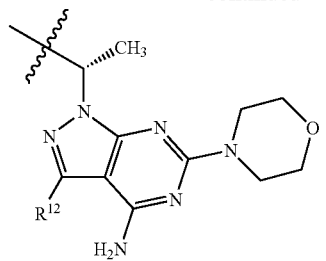
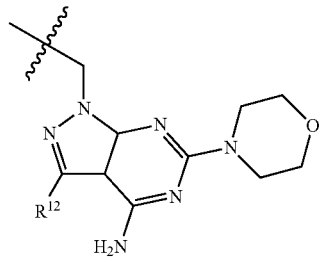
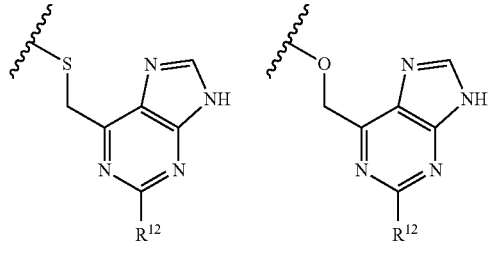
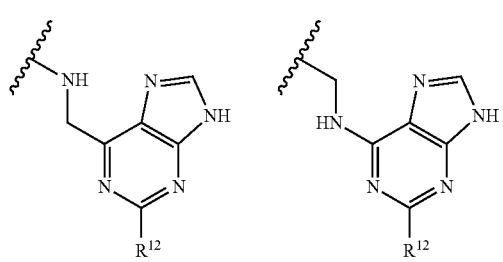
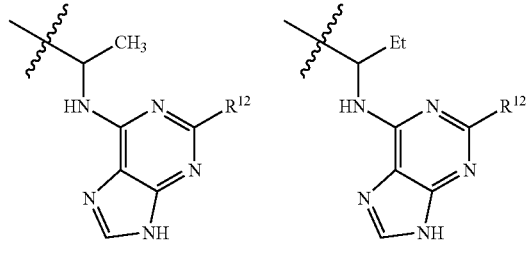
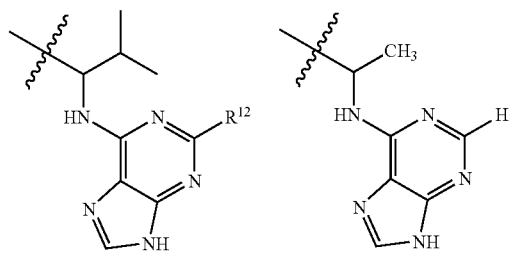

-continued
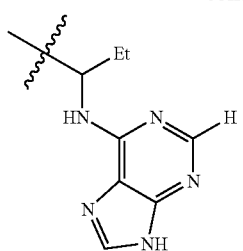 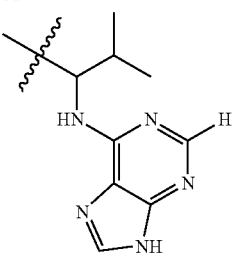 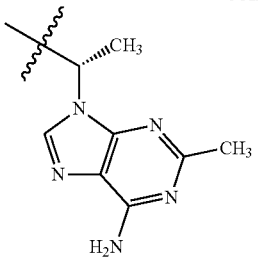 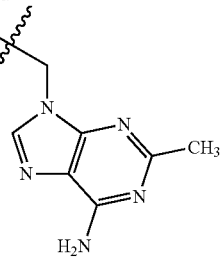
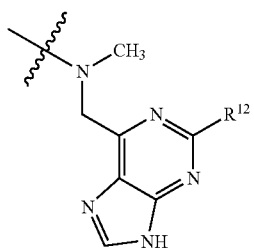 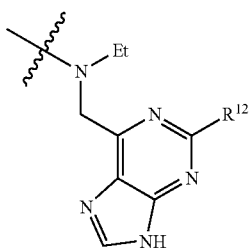 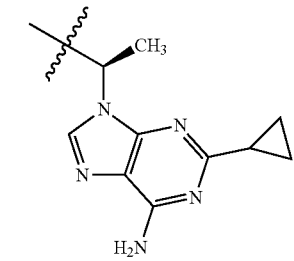
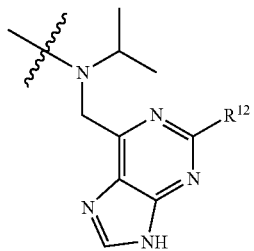 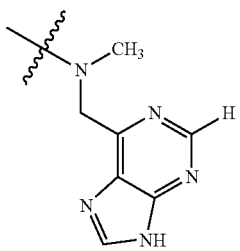 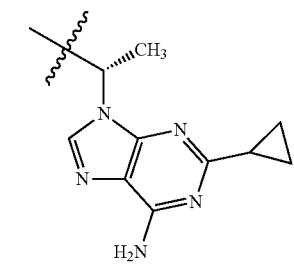
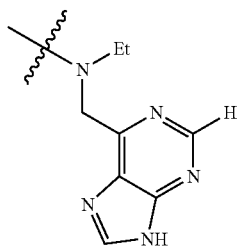 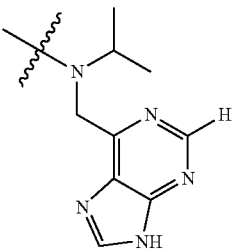 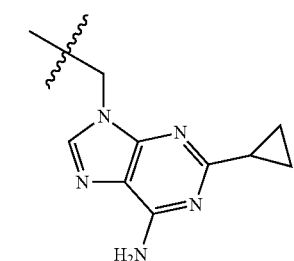
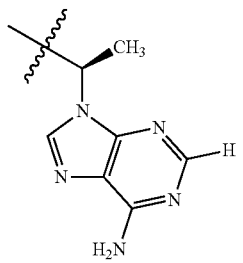 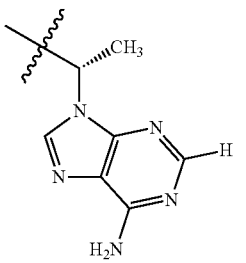 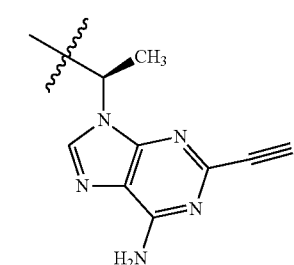
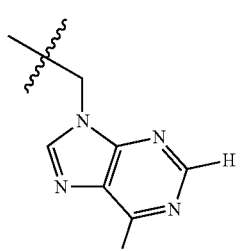 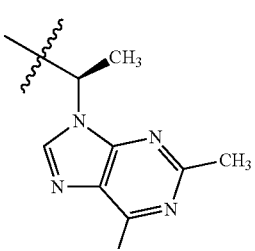 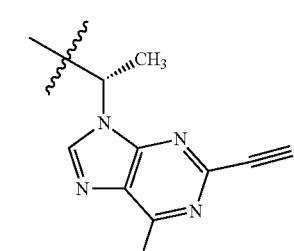

-continued
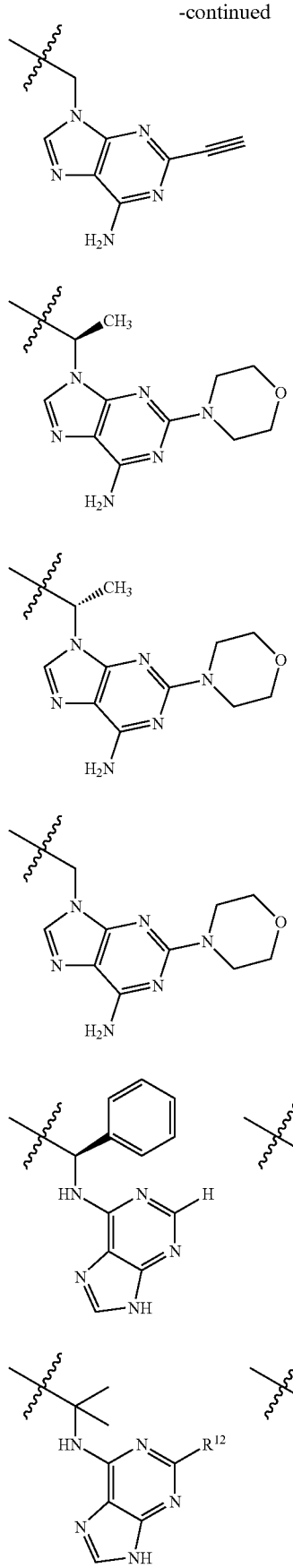
-continued
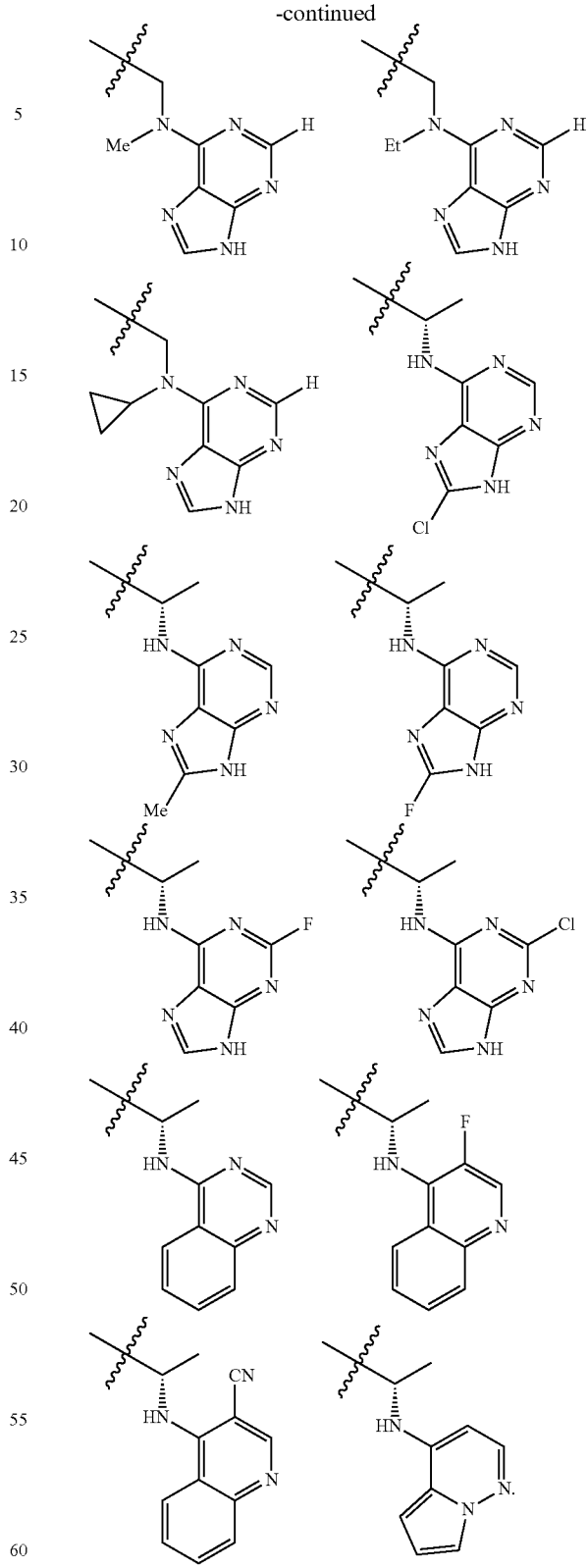
In some embodiments of the compounds disclosed herein, $W_d$ can be substituted by $R^{12}$ wherein $R^{12}$ is hydrogen, cyano, halo, unsubstituted or substituted alkenyl (including, but not limited to, unsubstituted or substituted $C_2$-$C_5$ alkenyl such as, vinyl, allyl, 1-methyl propen-1-yl, butenyl, or pentenyl) or unsubstituted or substituted alkynyl (including, but not limited to, unsubstituted or substituted $C_2$-$C_5$ alkynyl such as acetylenyl, propargyl, butynyl, or pentynyl). In other embodiments, $R^{12}$ is unsubstituted or substituted alkyl (including, but not limited to, —$CH_3$, —$CH_2CH_3$, n-propyl, isopropyl, n-butyl, tert-butyl, sec-butyl, pentyl, hexyl, and heptyl). Additionally, $R^{12}$ can be unsubstituted or substituted aryl (including, but not limited to, monocyclic or bicyclic aryl). In some embodiments, $R^{12}$ is unsubstituted or substituted heteroaryl, wherein the heteroaryl has a 5 membered ring (including, but not limited to, imidazolyl, furyl, thienyl, pyrrolyl, pyrazolyl, isothiazolyl, isoxazolyl, oxazolyl, and thiazolyl). In some embodiments, the $R^{12}$ heteroaryl can be heteroaryl having a six membered ring, including, but not limited to, pyridinyl, pyranyl, pyrazinyl, pyrimidinyl, pyridazinyl, or triazinyl. In other embodiments, the $R^{12}$ heteroaryl can also be heteroaryl with at least one nitrogen ring atom, including, but not limited to, pyrrolyl, thiazolyl, pyrazolyl, imidazolyl, pyrimidinyl, pyridinyl, indolyl, benzoxazolyl, or pyrazinyl. Alternatively, the $R^{12}$ heteroaryl is heteroaryl with two nitrogen ring atoms, where non-limiting exemplary heteroaryls include pyrazolyl, indazolyl, benzimidazolyl, and imidazolyl. In some embodiments, the $R^{12}$ heteroaryl can be monocylic heteroaryl, including, but not limited to, imidazolyl, pyrrolyl, and thiazolyl. In further embodiments, the $R^{12}$ heteroaryl is bicylic heteroaryl, wherein non-limiting exemplary bicyclic heteroaryls include, but are not limited to, benzoxazolyl, benzoisoxazolyl benzothiazolyl, benzimidazolyl, benzothiophenyl, benzofuryl, indolyl, quinolinyl, isoquinolinyl, quinazolinyl, azaindolyl, pyrazolopyrimidinyl, purinyl, pyrrolo[1,2-b]pyridazinyl, pyrrolopyrimidinyl, indazolyl, pyrazolylpyridinyl, imidazo[1,2-a]pyridinyl, and pyrrolo[1,2-f][1,2,4]triazinyl. In some embodiments, $R^{12}$ can also be unsubstituted or substituted heterocycloalkyl, wherein the $R^{12}$ heterocycloalkyl is a heterocycloalkyl with one nitrogen ring atom (including, but not limited to, pyrrolidinyl, piperidinyl, morpholinyl, isothiazolidinyl-1,1-dioxide, or caprolactam). In other embodiments, the $R^{12}$ heterocycloalkyl is heterocycloalkyl with one oxygen ring atom, including, but not limited to, tetrahydrofuranyl, tetrahydropyranyl, morpholinyl, or oxetanyl. Alternatively, the $R^{12}$ heterocycloalkyl is heterocycloalkyl with one sulfur ring atom, including, but not limited to, thiomorpholinyl and isothiazolidinyl-1,1-dioxide. In yet other embodiments, the $R^{12}$ heterocyloalkyl is a 5 membered heterocycloalkyl, including, but not limited to, tetrahydrofuranyl, imidazolidinyl, isothiazolidinyl-1,1-dioxide, or pyrrolidinyl. In some embodiments, the $R^{12}$ heterocycloalkyl is a 6 membered heterocycloalkyl (non-limiting exemplary 6 membered heterocycloalkyls include tetrahydropyranyl, piperidinyl, piperazinyl, morpholinyl, or thiomorpholinyl). In some embodiments, the $R^{12}$ heterocycloalkyl is saturated heterocycloalkyl, including, but not limited to, tetrahydrofuranyl, tetrahydropyranyl, morpholinyl, oxetanyl, pyrrolidinyl, piperidinyl, morpholinyl, piperazinyl, or azetidinyl. In other embodiments, the $R^{12}$ heterocyloalkyl is heterocycloalkyl having an unsaturated moiety connected to the heterocycloalkyl ring, including, but not limited to, cyano, imidazolyl, or pyrazolyl moieties. Alternatively, the $R^{12}$ heterocycloalkyl is heterocycloalkyl substituted by oxo, including, but not limited to, one of the following:

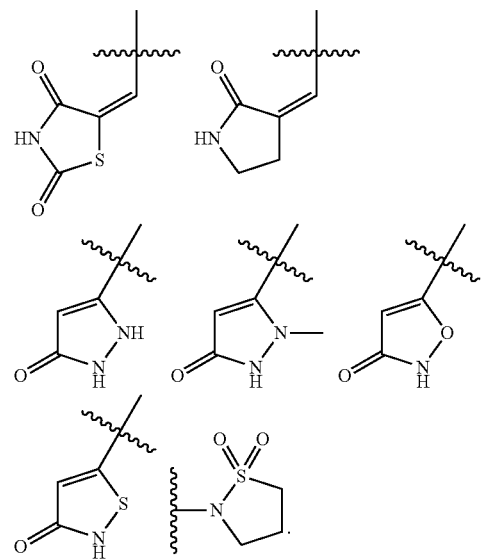

Additionally, $R^{12}$ can be unsubstituted or substituted cycloalkyl (including, but not limited to, cyclopropyl, cyclobutyl, cyclopentyl, or cyclohexyl). In other embodiments, $R^{12}$ is cycloalkyl substituted by one oxo (including but not limited to, 2-oxo-cyclobutyl, 3-oxo-cyclopentyl, and 4-oxo-cyclohexyl). In yet other embodiments, $R^{12}$ is unsubstituted or substituted amido, unsubstituted or substituted acyloxy, or unsubstituted or substituted alkoxycarbonyl.

In some embodiments, when $R^{12}$ is alkyl, alkynyl, alkenyl, aryl, heteroaryl, heterocycloalkyl, or cycloalkyl, the $R^{12}$ moiety is substituted with phosphate. In some embodiments, when $R^{12}$ is alkyl, alkynyl, alkenyl, aryl, heteroaryl, heterocycloalkyl, or cycloalkyl, the $R^{12}$ moiety is substituted with urea. In some embodiments, when $R^{12}$ is alkyl, alkynyl, alkenyl, aryl, heteroaryl, heterocycloalkyl, or cycloalkyl, the $R^{12}$ moiety is substituted with carbonate.

In other embodiments, when $R^{12}$ is alkyl, alkynyl, alkenyl, aryl, heteroaryl, heterocycloalkyl, cycloalkyl, alkoxycarbonyl, amido, or acyloxy, the $R^{12}$ moiety is substituted with one or more of alkyl, heteroalkyl, alkenyl, alkynyl, cycloalkyl, heterocycloalkyl, aryl, heteroaryl, alkoxy, amido, amino, acyl, acyloxy, alkoxycarbonyl, sulfonamido, thio, sulfoxide, sulfone, halo, cyano, hydroxy or nitro. Each of the substituents selected from alkyl, heteroalkyl, alkenyl, alkynyl, cycloalkyl, heterocycloalkyl, aryl, heteroaryl, alkoxy, amido, amino, acyl, acyloxy, aloxycarbonyl, and sulfonamido, can be further substituted by one or more of alkyl, alkoxy, amido, amino, acyl, acyloxy, alkoxycarbonyl, sulfonamido, thio, sulfoxide, sulfone, halo, cyano, hydroxy or nitro substituents.

In some embodiments, $R^{12}$ of $W_d$ is one of the following moieties:

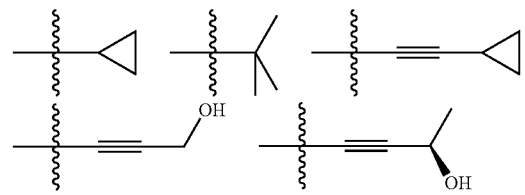

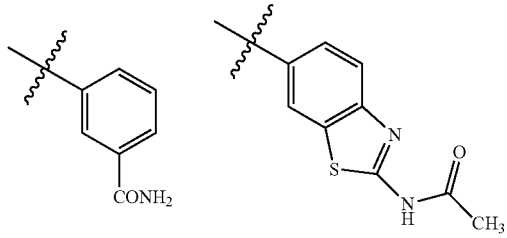
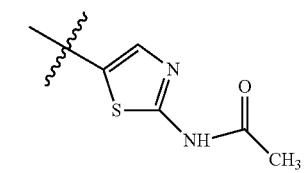
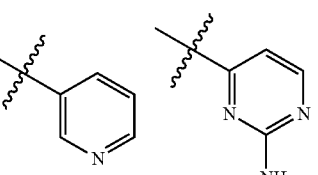
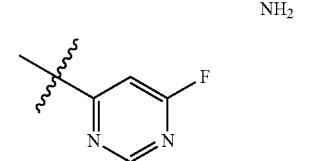
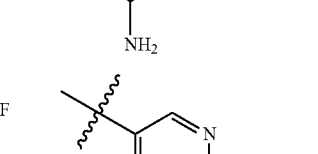
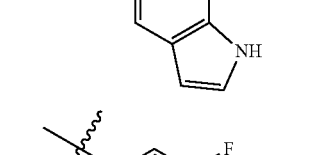
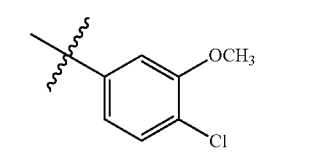
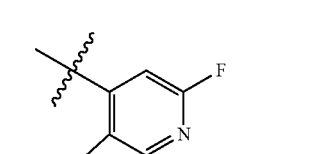
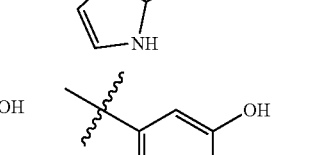
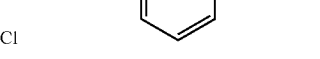
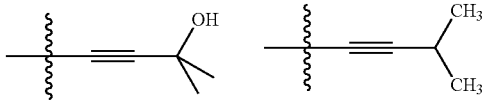
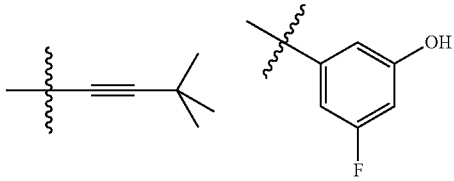
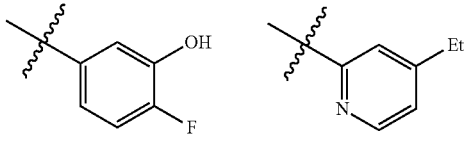
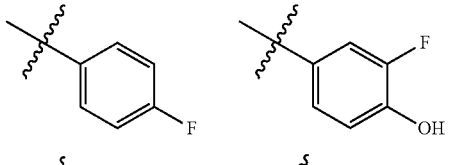
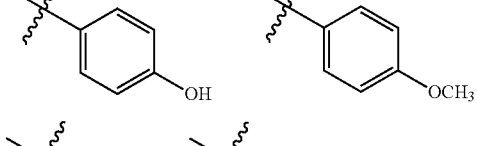
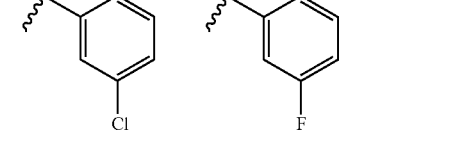
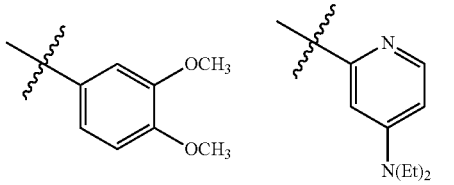
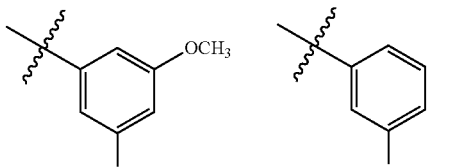
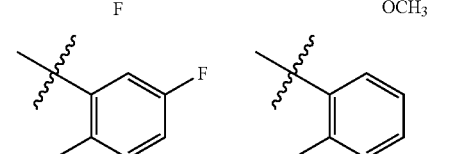
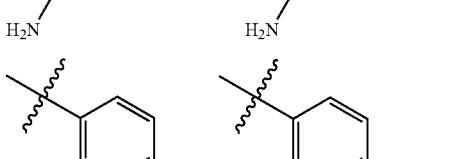

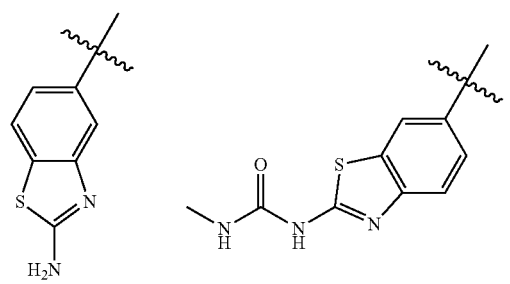
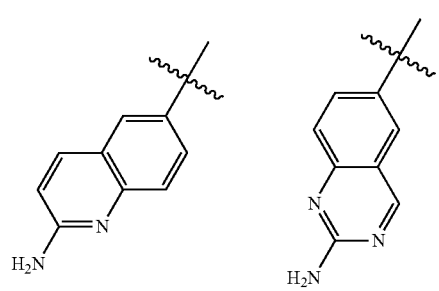
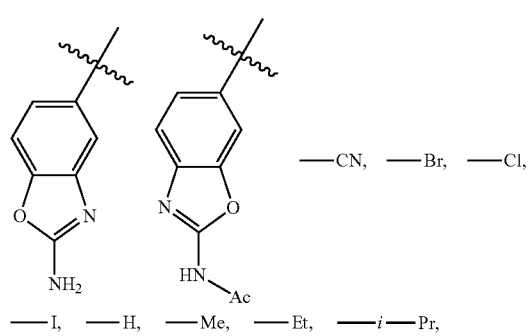
—CN, —Br, —Cl,
—I, —H, —Me, —Et, —i—Pr,
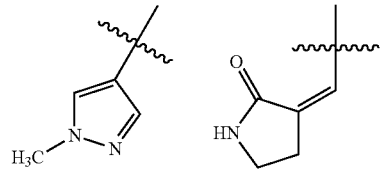
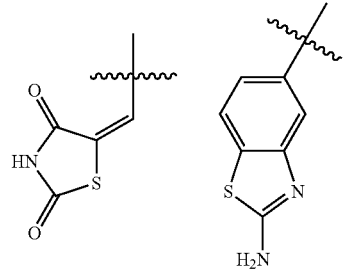
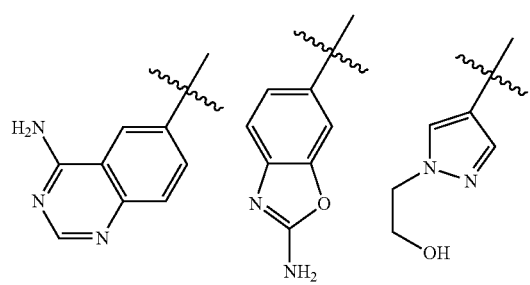
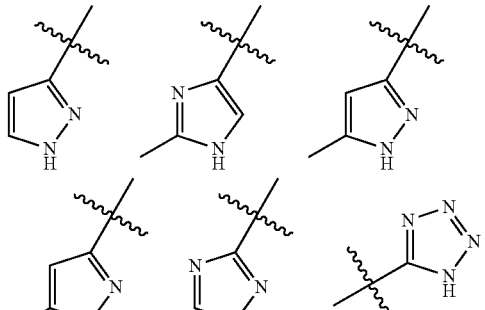
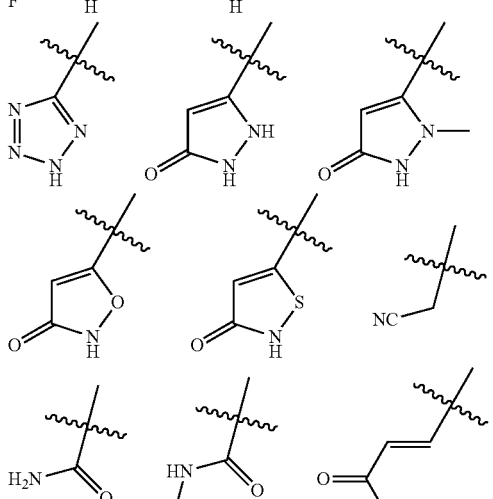
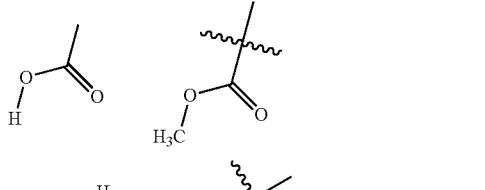
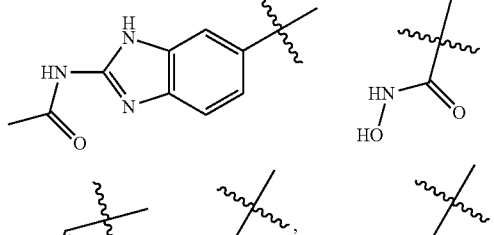
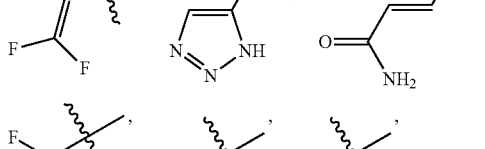
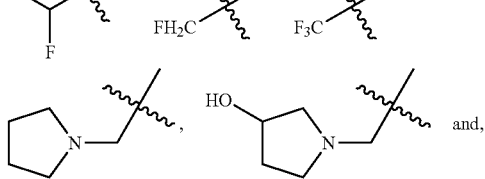
and, -continued

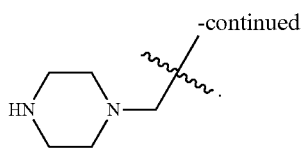

In some embodiments, $W_d$ is a pyrazolopyrimidine of Formula XIII:

Formula (XIII)

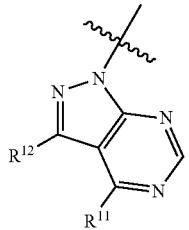

wherein $R^{11}$ is hydrogen, alkyl, halo, amino, amido, hydroxy, or alkoxy; and $R^{12}$ is hydrogen, alkyl, alkynyl, alkenyl, halo, aryl, heteroaryl, heterocycloalkyl, cycloalkyl, cyano, amino, acyloxy, alkoxycarbonyl, or amido.

In some embodiments, $R^{11}$ is amino and $R^{12}$ is hydrogen, alkyl, alkynyl, alkenyl, halo, aryl, heteroaryl, heterocycloalkyl, or cycloalkyl. In some embodiments, $R^{11}$ is amino and $R^{12}$ is alkyl, halo, aryl, heteroaryl, heterocycloalkyl, or cycloalkyl. In some embodiments, $R^{11}$ is amino and $R^{12}$ is monocyclic heteroaryl. In some embodiments, $R^{11}$ is amino and $R^{12}$ is bicyclic heteroaryl. In some embodiments, $R^{11}$ is amino and $R^{12}$ is cyano, amino, acyloxy, alkoxycarbonyl or amido.

In some embodiments, $W_d$ is a purine of the following Formula XIV:

Formula XIV

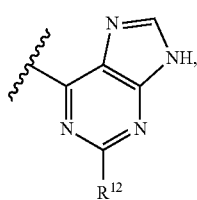

wherein $R^{12}$ is H, alkyl, alkynyl, alkenyl, halo, aryl, heteroaryl, heterocycloalkyl, cycloalkyl, cyano, amino, acyloxy, alkoxycarbonyl, or amido.

In some embodiments, provided herein are compounds of Formula (IIb), (IIIb) and (IVb):

Formula (IIb)

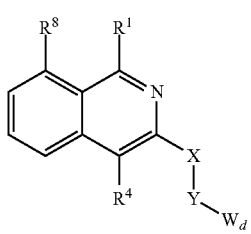

Formula (IIIb)

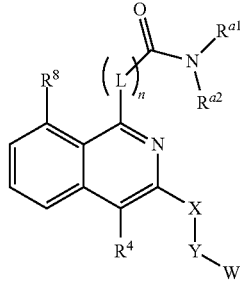

Formula (IVb)

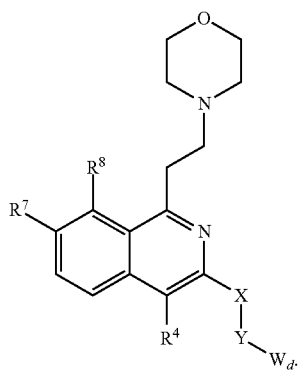

In some embodiments of compounds of Formulas (IIb), (IIIb) or (IVb), $R^8$ is methyl or halo. For example, $R^8$ is halo. In some embodiments of compounds of Formulas (IIb), (IIIb) or (IVb), $R^8$ is Cl.

In some embodiments, provided herein are compounds of Formula (IVb), wherein $R^7$ is halo. For example, $R^7$ is Cl or F.

In some embodiments of compounds of Formula (IIb), $R^{1'}$ is $NR^{a1}R^{a2}$. In other embodiments of compounds of Formula (IIb), n is 0 or 1.

Some illustrative compounds include those in which $R^8$ is —H, —CH$_3$, —CH$_2$CH$_3$, or —CF$_3$ in combination with any $R^{a1}$ or $R^{a2}$ moiety described in Table 1, and any $R^{12}$ as described in Table 2. A compound disclosed herein includes any combination of $R^8$, $R^{a1}$, $R^{a2}$ and $R^{12}$. Additional exemplary compounds are illustrated in Table 3.

TABLE 1

$R^{a1}$ moieties of the compounds disclosed herein, include but are not limited to the following:

| Subclass # | $R^{a1}$ or $R^{a2}$ |
|---|---|
| $R^{a1}$-1 | 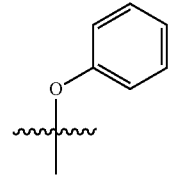 [SMILES: *Oc1ccccc1] |
| $R^{a1}$-2 | 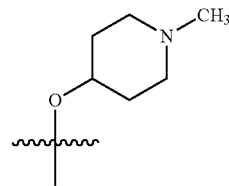 [SMILES: *OC1CCN(C)CC1] |

TABLE 1-continued

R$^{a1}$ moieties of the compounds disclosed herein, include but are not limited to the following:

| Sub-class # | R$^{a1}$ or R$^{a2}$ |
|---|---|
| R$^{a1}$-3 | 1-isopropyl-4-piperidinyloxy |
| R$^{a1}$-4 | 4-piperidinyloxy (NH) |
| R$^{a1}$-5 | pyrrolidin-1-yl |
| R$^{a1}$-6 | isopropoxy |
| R$^{a1}$-7 | 4-methylpiperazin-1-yl |
| R$^{1}$-8 | benzyl |
| R$^{a1}$-9 | —CH(CH$_3$)$_2$ |
| R$^{a1}$-10 | N-methyl-N-cyclopropylamino |
| R$^{a1}$-11 | N,N-dimethylamino |
| R$^{a1}$-12 | N,N-diisopropylamino |
| R$^{a1}$-13 | 2-(pyrrolidin-1-yl)ethyl (gem-dimethyl) |
| R$^{a1}$-14 | (3-methylpyridin-2-yl)amino |
| R$^{a1}$-15 | 2-(morpholin-4-yl)ethyl (gem-dimethyl) |
| R$^{a1}$-16 | 2-methylphenoxy |
| R$^{a1}$-17 | 2-chlorophenoxy |
| R$^{a1}$-18 | 3-(4-methylpiperazin-1-yl)propyl |
| R$^{a1}$-19 | N-methyl-N-(4-cyanophenyl)amino |
| R$^{a1}$-20 | morpholin-4-yl |
| R$^{a1}$-21 | N-methyl-N-(tetrahydropyran-4-yl)amino |

TABLE 1-continued

R$^{a1}$ moieties of the compounds disclosed herein, include but are not limited to the following:

| Sub-class # | R$^{a1}$ or R$^{a2}$ |
|---|---|
| R$^{a1}$-22 | 5-oxy-1H-indazole |
| R$^{a1}$-23 | 2-methoxyphenoxy |
| R$^{a1}$-24 | 3-(2-methylthiazol-4-yl)propyl |
| R$^{a1}$-25 | 1-acetylpiperidin-4-yloxy |
| R$^{a1}$-26 | 5-(N-methylamino)-1H-indazole |
| R$^{a1}$-27 | 3-(1H-indazol-5-yl)propyl |
| R$^{a1}$-28 | 3-(4-ethylpiperazin-1-yl)propyl |
| R$^{a1}$-29 | 3-(1-(2-cyanoethyl)piperidin-4-yl)propyl |
| R$^{a1}$-30 | 1-(2-cyanoethyl)piperidin-4-yloxy |
| R$^{a1}$-31 | 3-(1-acetylpiperidin-4-yl)propyl |
| R$^{a1}$-32 | 1-acetylpiperidin-4-yloxy |
| R$^{a1}$-33 | 1-(2-hydroxyethyl)-4-methoxypiperidin-4-yl |
| R$^{a1}$-34 | 3-(1-(2-hydroxyethyl)piperidin-4-yl)propyl |
| R$^{a1}$-35 | 1-(2-(methylsulfonyl)ethyl)piperidin-4-yloxy |

TABLE 1-continued

R$^{a1}$ moieties of the compounds disclosed herein, include but are not limited to the following:

| Sub-class # | R$^{a1}$ or R$^{a2}$ |
|---|---|
| R$^{a1}$-36 | 4-(2-(methylsulfonyl)ethyl)piperidine linked via ethyl |
| R$^{a1}$-37 | 2-pyridyloxy |
| R$^{a1}$-38 | 2-(2-pyridyl)ethyl |
| R$^{a1}$-39 | thiazol-4-yl |
| R$^{a1}$-40 | H |
| R$^{a1}$-41 | 2-(diethylamino)thiazol-4-yl |
| R$^{a1}$-42 | 2-(imidazol-1-yl)thiazol-4-yl |
| R$^{a1}$-43 | piperidin-1-yl |
| R$^{a1}$-44 | 2-oxopiperidin-1-yl |
| R$^{a1}$-45 | thiomorpholin-4-yl |
| R$^{a1}$-46 | 4-ethylpiperazin-1-yl |
| R$^{a1}$-47 | 1-(methylsulfonyl)piperidin-4-yloxy |
| R$^{a1}$-48 | tetrahydro-2H-pyran-4-yloxy |
| R$^{1}$-49 | (tetrahydro-2H-pyran-4-yl)methoxy |
| R$^{1}$-50 | (1-acetylpiperidin-4-yl)methoxy |
| R$^{1}$-51 | (1-(methylsulfonyl)piperidin-4-yl)methoxy |
| R$^{a1}$-52 | 2-(pyrrolidin-1-yl)ethoxy |

TABLE 1-continued
R$^{a1}$ moieties of the compounds disclosed herein, include but are not limited to the following:
| Subclass # | R$^{a1}$ or R$^{a2}$ |
|---|---|
| R$^{a1}$-53 | 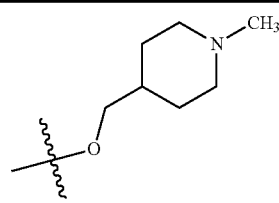 |
| R$^{a1}$-54 | 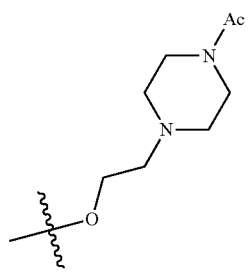 [SMILES: *OCCN1CCN(C(C)=O)CC1] |
| R$^{a1}$-55 | 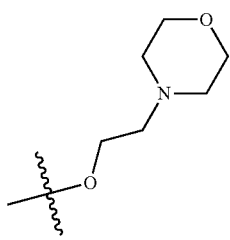 [SMILES: *OCCN1CCOCC1] |
| R$^{a1}$-56 | 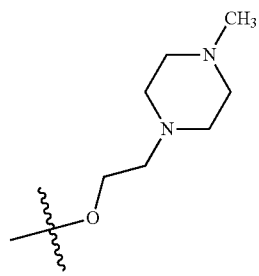 [SMILES: *OCCN1CCN(C)CC1] |
| R$^{a1}$-57 | 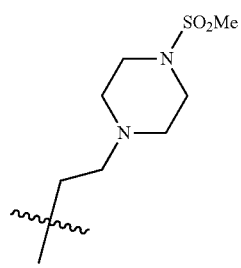 [SMILES: *CCN1CCN(S(C)(=O)=O)CC1] |
| R$^{a1}$-58 | 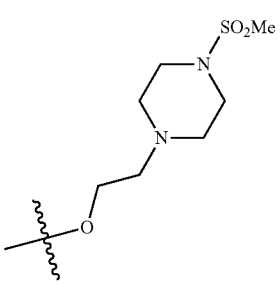 [SMILES: *OCCN1CCN(S(C)(=O)=O)CC1] |
| R$^{a1}$-59 | 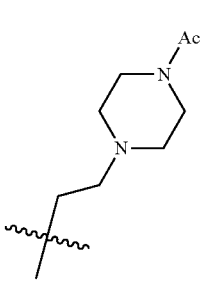 |
| R$^{a1}$-60 | 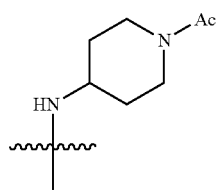 [SMILES: *NC1CCN(C(C)=O)CC1] |
| R$^{a1}$-61 | 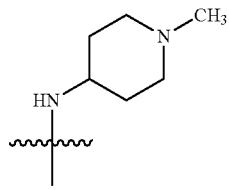 [SMILES: *NC1CCN(C)CC1] |
| R$^{a1}$-62 | 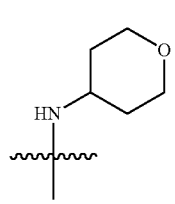 [SMILES: *NC1CCOCC1] |
| R$^{a1}$-63 | 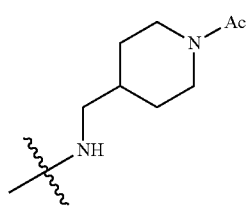 [SMILES: *NCC1CCN(C(C)=O)CC1] |

TABLE 1-continued
R^{a1} moieties of the compounds disclosed herein, include but are not limited to the following:
| Sub-class # | R^{a1} or R^{a2} |
|---|---|
| R^{a1}-64 | 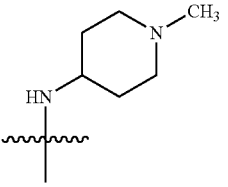 [SMILES: *NC1CCN(C)CC1] |
| R^{a1}-65 | 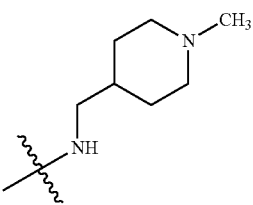 [SMILES: *NCC1CCN(C)CC1] |
| R^{a1}-66 | 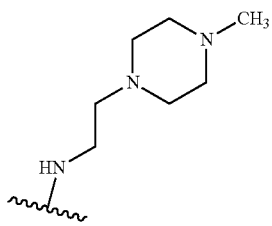 [SMILES: *NCCN1CCN(C)CC1] |
| R^{a1}-67 | 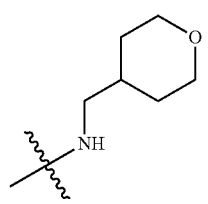 [SMILES: *NCC1CCOCC1] |
| R^{a1}-68 | 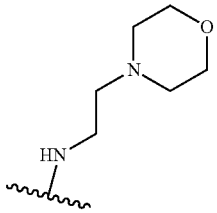 [SMILES: *NCCN1CCOCC1] |
| R^{a1}-69 | 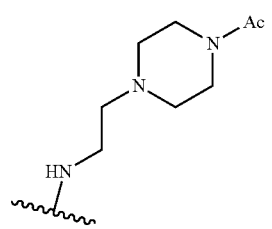 [SMILES: *NCCN1CCN(C(C)=O)CC1] |
| R^{a1}-70 | 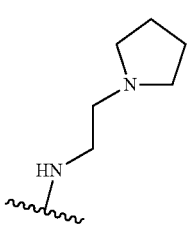 [SMILES: *NCCN1CCCC1] |
| R^{a1}-71 | 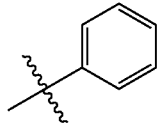 [SMILES: *c1ccccc1] |
| R^{a1}-72 | 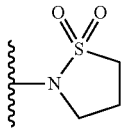 [SMILES: *N1CCCS1(=O)=O] |
| R^{a1}-73 | 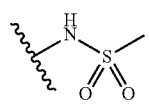 [SMILES: *NS(C)(=O)=O] |
| R^{a1}-74 | 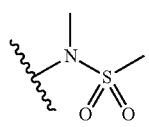 [SMILES: *N(C)S(C)(=O)=O] |
| R^{a1}-75 | 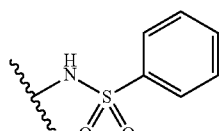 |
| R^{a1}-76 | 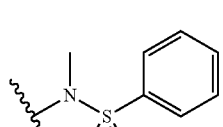 |
| R^{a1}-77 | 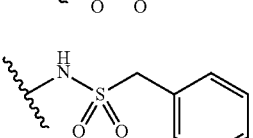 |
| R^{a1}-78 | 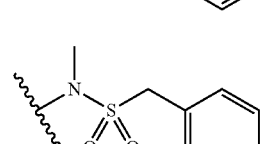 |
| R^{a1}-79 | 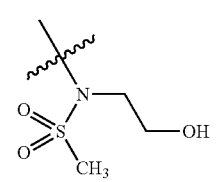 |
| R^{a1}-80 | 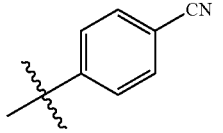 [SMILES: *c1ccc(C#N)cc1] |

TABLE 1-continued

R$^{a1}$ moieties of the compounds disclosed herein, include but are not limited to the following:

| Subclass # | R$^{a1}$ or R$^{a2}$ |
|---|---|
| R$^{a1}$-81 | 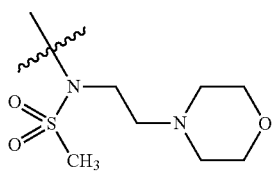 [SMILES: *N(CCN1CCOCC1)S(C)(=O)=O] |

TABLE 2

Illustrative R$^{12}$ of compounds of Formula I, include but are not limited to the following:

| Subclass # | R$^{12}$ |
|---|---|
| 12-1 | —CN |
| 12-2 | —Br |
| 12-3 | —Cl |
| 12-4 | —CH$_2$CH$_3$ |
| 12-5 | —CH$_3$ |
| 12-6 | —CH(CH$_3$)$_2$ |
| 12-7 | cyclopropyl |
| 12-8 | tert-butyl |
| 12-9 | 3-pyridyl |
| 12-10 | —C≡C—CH$_2$OH |
| 12-11 | —C≡C—CH(OH)CH$_3$ |
| 12-12 | —C≡C-cyclopropyl |
| 12-13 | 1H-pyrazol-4-yl |
| 12-14 | 3-carbamoylphenyl |
| 12-15 | 2-acetamidothiazol-5-yl |
| 12-16 | 2-acetamidobenzothiazol-6-yl |
| 12-17 | 2-aminothiazol-5-yl |
| 12-18 | 2-aminopyridin-4-yl |
| 12-19 | 2-amino-6-fluoropyridin-4-yl |
| 12-20 | 2-aminopyrimidin-4-yl |

TABLE 2-continued

Illustrative R[12] of compounds of Formula I, include but are not limited to the following:

| Sub-class # | R[12] |
|---|---|
| 12-21 | 4-fluoro-2-aminopyrimidin-6-yl |
| 12-22 | 1H-pyrrolo[2,3-b]pyridin-5-yl |
| 12-23 | 1H-indazol-6-yl |
| 12-24 | 4-fluoro-1H-indazol-6-yl |
| 12-25 | 1H-pyrrolo[2,3-b]pyridin-4-yl |
| 12-26 | 3-methoxyphenyl |
| 12-27 | 6-fluoro-1H-pyrrolo[2,3-b]pyridin-4-yl |
| 12-28 | 4-hydroxy-4-methylpent-2-yn-1-yl |
| 12-29 | 3,3-dimethylbut-1-yn-1-yl |
| 12-30 | 4-ethylpyridin-2-yl |
| 12-31 | 4-chloro-3-methoxyphenyl |
| 12-32 | 4-chloro-3-hydroxyphenyl |
| 12-33 | 4-fluorophenyl |
| 12-34 | 3-fluoro-4-hydroxyphenyl |
| 12-35 | —H |
| 12-36 | 4-hydroxyphenyl |
| 12-37 | 4-fluorophenyl |
| 12-38 | 3-fluoro-4-hydroxyphenyl |
| 12-39 | 4-hydroxyphenyl |

TABLE 2-continued
Illustrative R$^{12}$ of compounds of Formula I, include but are not limited to the following:
| Sub-class # | R$^{12}$ |
|---|---|
| 12-40 | 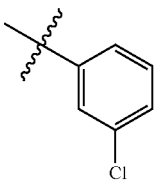 [SMILES: *c1cccc(Cl)c1] |
| 12-41 | 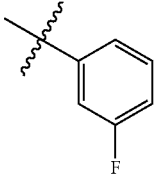 |
| 12-42 | 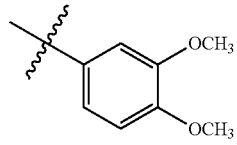 [SMILES: *c1ccc(OC)c(OC)c1] |
| 12-43 | 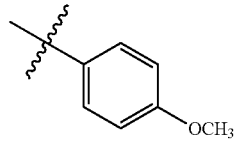 |
| 12-44 | 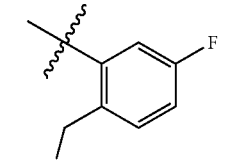 |
| 12-45 | 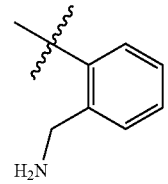 |
| 12-46 | 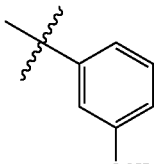 |
| 12-47 | 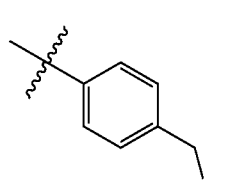 |
| 12-48 | 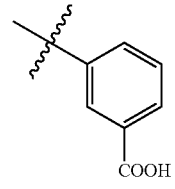 |
| 12-49 | 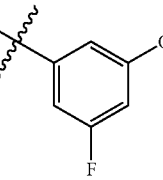 |
| 12-50 | 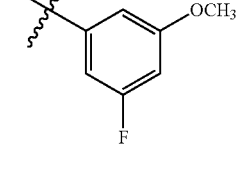 |
| 12-51 | 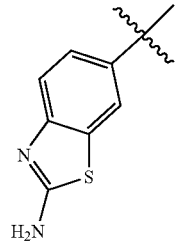 [SMILES: *c1ccc2nc(N)sc2c1] |
| 12-52 | 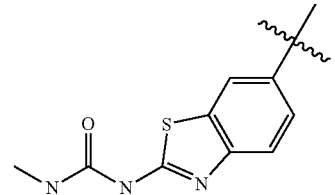 |
| 12-53 | 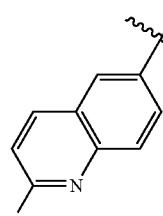 |

TABLE 2-continued
Illustrative $R^{12}$ of compounds of Formula I, include but are not limited to the following:
| Sub-class # | $R^{12}$ |
|---|---|
| 12-54 | 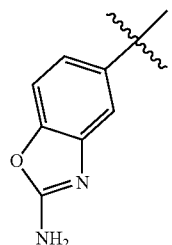 |
| 12-55 | 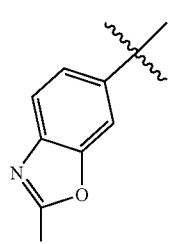 |
| 12-56 | 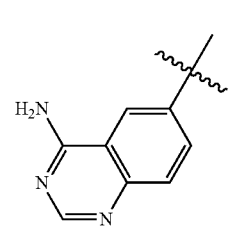 [SMILES: *c1ccc2ncnc(N)c2c1] |
| 12-57 | 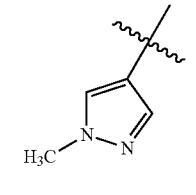 [SMILES: *c1cnn(C)c1] |
| 12-58 | 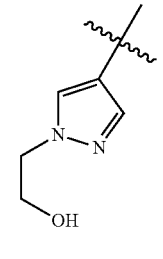 [SMILES: *c1cnn(CCO)c1] |
| 12-59 | 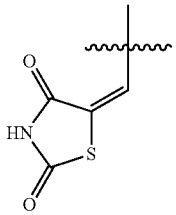 |
| 12-60 | 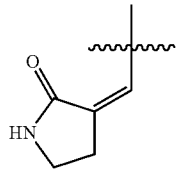 |
| 12-61 | —I |
| 12-62 | 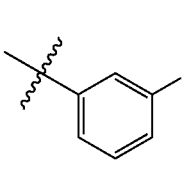 |
| 12-63 | 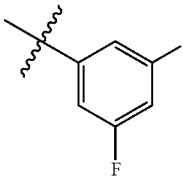 |
| 12-64 | 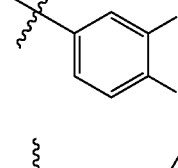 |
| 12-65 | 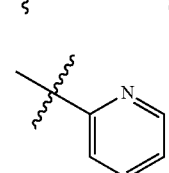 |
| 12-66 | 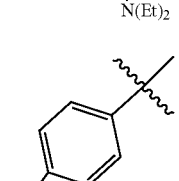 |
| 12-67 | 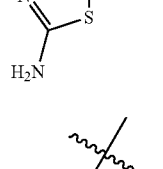 |
| 12-68 | 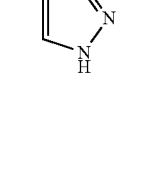 |

US 8,901,133 B2
TABLE 2-continued
Illustrative R$^{12}$ of compounds of Formula I, include but are not limited to the following:
| Sub-class # | R$^{12}$ |
|---|---|
| 12-69 | 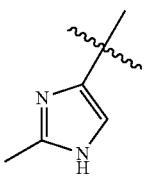 [SMILES: *c1c[nH]c(C)n1] |
| 12-70 | 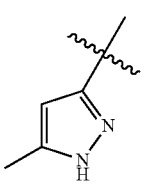 [SMILES: *c1cc(C)[nH]n1] |
| 12-71 | 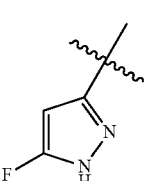 |
| 12-72 | 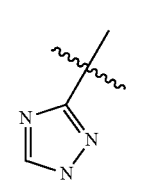 |
| 12-73 | 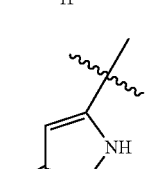 |
| 12-74 | 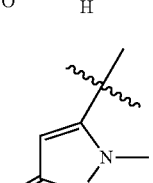 |
| 12-75 | 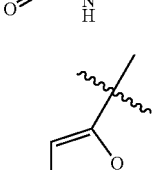 |
| 12-76 | 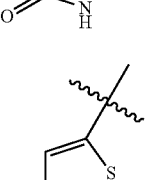 |
| 12-77 | 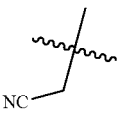 |
| 12-78 | 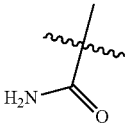 |
| 12-79 | 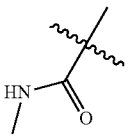 |
| 12-80 | 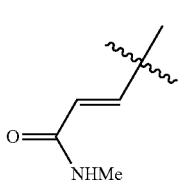 [SMILES: */C=C/C(=O)NC] |
| 12-81 | 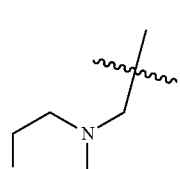 |
| 12-82 | 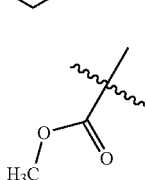 |
| 12-83 | 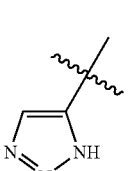 |
| 12-84 | 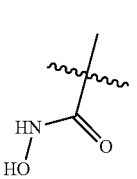 |
| 12-85 | 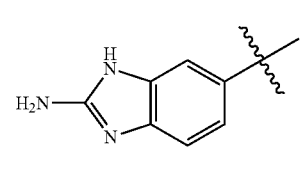 [SMILES: *c1ccc2nc(N)[nH]c2c1] |

TABLE 2-continued

Illustrative R$^{12}$ of compounds of Formula I, include but are not limited to the following:

| Sub-class # | R$^{12}$ |
|---|---|
| 12-86 | 2-acetamido-1H-benzimidazol-6-yl |
| 12-87 | 2,2-difluorovinyl |
| 12-88 | 1H-pyrazol-3-yl |
| 12-89 | 1-methyl-1H-pyrazol-5-yl |
| 12-90 | –CH$_2$CH$_2$C(O)NH$_2$ |
| 12-91 | 2-acetamidobenzo[d]oxazol-6-yl |
| 12-92 | (E)-3-(morpholin-4-yl)-3-oxoprop-1-en-1-yl |
| 12-93 | 3-(morpholin-4-yl)-3-oxopropyl |
| 12-94 | (E)-3-amino-3-oxoprop-1-en-1-yl |
| 12-95 | 1H-tetrazol-5-yl |
| 12-96 | 1H-tetrazol-5-yl |
| 12-97 | –CHF$_2$ (difluoromethyl, substituted) |
| 12-98 | –CH$_2$F |
| 12-99 | –CF$_3$ |
| 12-100 | (pyrrolidin-1-yl)methyl |
| 12-101 | (3-hydroxypyrrolidin-1-yl)methyl |
| 12-102 | (piperazin-1-yl)methyl |

In some embodiments, one or more subject compounds bind specifically to a PI3 kinase.

In some embodiments, the $IC_{50}$ of a subject compound for p110α, p110β, p110γ, or p110δ is less than about 1 uM, less than about 100 nM, less than about 50 nM, less than about 10 nM, less than about 1 nM, less than about 0.5 nM, less than about 100 pM, or less than about 50 pM. In some embodiments, the $IC_{50}$ of a subject compound for mTor is less than about 1 μM, less than about 100 nM, less than about 50 nM, less than about 10 nM, less than 1 nM or even less than about 0.5 nM. In some other embodiments, one or more subject compounds exhibit dual binding specificity and are capable of inhibiting a PI3 kinase (e.g., a class I PI3 kinase) as well as a protein kinase (e.g., mTor) with an $IC_{50}$ value less than about 1 μM, less than about 100 nM, less than about 50 nM, less than about 10 nM, less than 1 nM or even less than about 0.5 nM. One or more subject compounds are capable of inhibiting tyrosine kinases including, for example, DNA-dependent protein kinase DNA-dependent protein kinase (Pubmed protein accession number (PPAN) AAA79184), Abl tyrosine kinase (CAA52387), Bcr-Abl, hemopoietic cell kinase (PPAN CAI19695), Src (PPAN CAA24495), vascular endothelial growth factor receptor 2 (PPAN ABB82619), vascular endothelial growth factor receptor-2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and functional mutants thereof. In some embodiments, the tyrosine kinase is Abl, Bcr-Abl, EGFR, or Flt-3, and any other kinases listed in the Tables herein.

In some embodiments, non-limiting exemplary compounds exhibit one or more functional characteristics disclosed herein. For example, one or more subject compounds bind specifically to a PI3 kinase. In some embodiments, the $IC_{50}$ of a subject compound for p110α, p110β, p110γ, or p110δ is less than about 1 μM, less than about 100 nM, less than about 50 nM, less than about 10 nM, less than about 1 nM, less than about 0.5 nM, less than about 100 pM, or less than about 50 pM.

In some embodiments, one or more of the subject compound can selectively inhibit one or more members of type I or class I phosphatidylinositol 3-kinases (PI3 kinase) with an IC50 value of about 100 nM, 50 nM, 10 nM, 5 nM, 100 pM, 10 pM or 1 pM, or less as measured in an in vitro kinase assay.

In some embodiments, one or more of the subject compound can selectively inhibit one or two members of type I or class I phosphatidylinositol 3-kinases (PI3 kinase) consisting of PI3 kinase α, PI3 kinase β, PI3 kinase γ, and PI3 kinase δ. In some aspects, some of the subject compounds selectively inhibit PI3 kinase δ as compared to all other type I PI3 kinases. In other aspects, some of the subject compounds selectively inhibit PI3 kinase δ and PI3 kinase γ as compared to the rest of the type I PI3 kinases. In yet other aspects, some of the subject compounds selectively inhibit PI3 kinase α and PI3 kinase β as compared to the rest of the type I PI3 kinases. In still yet some other aspects, some of the subject compounds selectively inhibit PI3 kinase δ and PI3 kinase α as compared to the rest of the type I PI3 kinases. In still yet some other aspects, some of the subject compounds selectively inhibit PI3 kinase δ and PI3 kinase β as compared to the rest of the type I PI3 kinases, or selectively inhibit PI3 kinase δ and PI3 kinase α as compared to the rest of the type I PI3 kinases, or selectively inhibit PI3 kinase α and PI3 kinase γ as compared to the rest of the type I PI3 kinases, or selectively inhibit PI3 kinase γ and PI3 kinase β as compared to the rest of the type I PI3 kinases.

In yet another aspect, an inhibitor that selectively inhibits one or more members of type I PI3 kinases, or an inhibitor that selectively inhibits one or more type I PI3 kinase mediated signaling pathways, alternatively can be understood to refer to a compound that exhibits a 50% inhibitory concentration (IC50) with respect to a given type I PI3 kinase, that is at least at least 10-fold, at least 20-fold, at least 50-fold, at least 100-fold, at least 1000-fold, at least 10,000-fold, or lower, than the inhibitor's IC50 with respect to the rest of the other type I PI3 kinases. In one embodiment, an inhibitor selectively inhibits PI3 kinase δ as compared to PI3 kinase β with at least about 10-fold lower $IC_{50}$ for PI3 kinase δ. In certain embodiments, the $IC_{50}$ for PI3 kinase δ is below about 100 nM, while the $IC_{50}$ for PI3 kinase β is above about 1000 nM. In certain embodiments, the $IC_{50}$ for PI3 kinase δ is below about 50 nM, while the $IC_{50}$ for PI3 kinase β is above about 5000 nM. In certain embodiments, the $IC_{50}$ for PI3 kinase δ is below about 10 nM, while the $IC_{50}$ for PI3 kinase β is above about 1000 nM, above about 5,000 nM, or above about 10,000 nM.

Pharmaceutical Compositions

In some embodiments, provided herein are compositions (e.g., pharmaceutical compositions) comprising one or more compounds as disclosed herein. In some embodiments, the one or more compounds can each independently be a pharmaceutically acceptable form thereof (e.g., pharmaceutically acceptable salts, hydrates, solvates, isomers, prodrugs, and isotopically labeled derivatives). In other embodiments, provided herein are pharmaceutical compositions comprising one or more compounds as disclosed herein, or a pharmaceutically acceptable form thereof (e.g., pharmaceutically acceptable salts, hydrates, solvates, isomers, prodrugs, and isotopically labeled derivatives), and one or more pharmaceutically acceptable excipients carriers, including inert solid diluents and fillers, diluents, including sterile aqueous solution and various organic solvents, permeation enhancers, solubilizers and adjuvants. In some embodiments, a pharmaceutical composition described herein includes an second active agent such as an additional therapeutic agent, (e.g., a chemotherapeutic).

In some embodiments, provided herein are pharmaceutical compositions for the treatment of disorders such as hyperproliferative disorder including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related AIDS-Related (e.g. Lymphoma and Kaposi's Sarcoma) or Viral-Induced cancer. In some embodiments, said pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

In some embodiments, provided herein are pharmaceutical compositions for treating diseases or conditions related to an undesirable, over-active, harmful or deleterious immune response in a subject. Such undesirable immune response can be associated with or result in, e.g., asthma, emphysema, bronchitis, psoriasis, allergy, anaphylaxsis, auto-immune diseases, rhuematoid arthritis, graft versus host disease, and lupus erythematosus. The pharmaceutical compositions disclosed herein can be used to treat other respiratory diseases including but not limited to diseases affecting the lobes of lung, pleural cavity, bronchial tubes, trachea, upper respiratory tract, or the nerves and muscle for breathing.

In some embodiments, provided herein are pharmaceutical compositions for the treatment of multiorgan failure. Also provided herein are pharmaceutical compositions for the treatment of liver diseases (including diabetes), gall bladder disease (including gallstones), pancreatitis or kidney disease (including proliferative glomerulonephritis and diabetes—induced renal disease) or pain in a subject.

In some embodiments, provided herein are pharmaceutical compositions for the prevention of blastocyte implantation in a subject.

In some embodiments, provided herein are pharmaceutical compositions for treating a disease related to vasculogenesis or angiogenesis in a subject which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In some embodiments, provided herein are pharmaceutical compositions for the treatment of disorders involving platelet aggregation or platelet adhesion, including but not limited to Idiopathic thrombocytopenic purpura, Bernard-Soulier syndrome, Glanzmann's thrombasthenia, Scott's syndrome, von Willebrand disease, Hermansky-Pudlak Syndrome, and Gray platelet syndrome.

In some embodiments, pharmaceutical compositions are provided for treating a disease which is skeletal muscle atrophy, skeletal or muscle hypertrophy. In some embodiments, provided herein are pharmaceutical compositions for the treatment of disorders that include, but are not limited to, cancers as discussed herein, transplantation-related disorders (e.g., lowering rejection rates, graft-versus-host disease, etc.), muscular sclerosis (MS), allergic disorders (e.g., arthritis, allergic encephalomyelitis) and other immunosuppressive-related disorders, metabolic disorders (e.g., diabetes), reducing intimal thickening following vascular injury, and misfolded protein disorders (e.g., Alzheimer's Disease, Gaucher's Disease, Parkinson's Disease, Huntington's Disease, cystic fibrosis, macular degeneration, retinitis pigmentosa, and prion disorders) (as mTOR inhibition can alleviate the effects of misfolded protein aggregates). The disorders also include hamartoma syndromes, such as tuberous sclerosis and Cowden Disease (also termed Cowden syndrome and multiple hamartoma syndrome).

1. Formulations

The subject pharmaceutical compositions are typically formulated to provide a therapeutically effective amount of a compound described herein as the active ingredient, or a pharmaceutically acceptable form thereof (e.g., pharmaceutically acceptable salts, hydrates, solvates, isomers, prodrugs, and isotopically labeled derivatives). Where desired, the pharmaceutical compositions can contain one or more disclosed compounds or its pharmaceutically acceptable form thereof (e.g., pharmaceutically acceptable salts, hydrates, solvates, isomers, prodrugs, and isotopically labeled derivatives), and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the subject compounds and other agent(s) can be mixed into a preparation or both components can be formulated into separate preparations to use them in combination separately or at the same time.

The subject pharmaceutical composition can, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition can be in unit dosage forms suitable for single administration of precise dosages. The pharmaceutical composition will include a conventional pharmaceutical carrier or excipient and a compound as disclosed herein as an active ingredient. In addition, it can include other medicinal or pharmaceutical agents, carriers, adjuvants, etc.

Pharmaceutical compositions can be specially formulated for administration in solid or liquid form, including those adapted for the following: oral administration, for example, drenches (aqueous or non-aqueous solutions or suspensions), tablets (e.g., those targeted for buccal, sublingual, and systemic absorption), capsules, boluses, powders, granules, pastes for application to the tongue, and intraduodenal routes; parenteral administration, including intravenous, intraarterial, subcutaneous, intramuscular, intravascular, intraperitoneal or infusion as, for example, a sterile solution or suspension, or sustained-release formulation; topical application, for example, as a cream, ointment, or a controlled-release patch or spray applied to the skin; intravaginally or intrarectally, for example, as a pessary, cream, stent or foam; sublingually; ocularly; pulmonarily; local delivery by catheter or stent; intrathecally, or nasally.

Examples of suitable aqueous and nonaqueous carriers which can be employed in pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions can also contain adjuvants such as preservatives, wetting agents, emulsifying agents, dispersing agents, lubricants, and/or antioxidants. Prevention of the action of microorganisms upon the compounds described herein can be ensured by the inclusion of various antibacterial and antifungal agents, for example, paraben, chlorobutanol, phenol sorbic acid, and the like. It can also be desirable to include isotonic agents, such as sugars, sodium chloride, and the like into the compositions. In addition, prolonged absorption of the injectable pharmaceutical form can be brought about by the inclusion of agents which delay absorption such as aluminum monostearate and gelatin.

Methods of preparing these formulations or compositions include the step of bringing into association a compound described herein and/or the chemotherapeutic with the carrier and, optionally, one or more accessory ingredients. In general, the formulations are prepared by uniformly and intimately bringing into association a compound as disclosed herein with liquid carriers, or finely divided solid carriers, or both, and then, if necessary, shaping the product.

Preparations for such pharmaceutical compositions are well-known in the art. See, e.g., Anderson, Philip O.; Knoben, James E.; Troutman, William G, eds., *Handbook of Clinical Drug Data*, Tenth Edition, McGraw-Hill, 2002; Pratt and Taylor, eds., *Principles of Drug Action*, Third Edition, Churchill Livingston, New York, 1990; Katzung, ed., *Basic and Clinical Pharmacology*, Ninth Edition, McGraw Hill, 20037ybg; Goodman and Gilman, eds., *The Pharmacological Basis of Therapeutics*, Tenth Edition, McGraw Hill, 2001; *Remingtons Pharmaceutical Sciences*, 20th Ed., Lippincott Williams & Wilkins., 2000; Martindale, *The Extra Pharmacopoeia*, Thirty-Second Edition (The Pharmaceutical Press, London, 1999); all of which are incorporated by reference herein in their entirety. Except insofar as any conventional excipient medium is incompatible with the compounds provided herein, such as by producing any undesirable biological effect or otherwise interacting in a deleterious manner with any other component(s) of the pharmaceutically acceptable composition, the excipient's use is contemplated to be within the scope of this disclosure.

In some embodiments, the concentration of one or more of the compounds provided in the pharmaceutical compositions is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, the concentration of one or more of the compounds as disclosed herein is greater than 90%, 80%, 70%, 60%, 50%, 40%, 30%, 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v, or v/v.

In some embodiments, the concentration of one or more of the compounds as disclosed herein is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. v/v.

In some embodiments, the concentration of one or more of the compounds as disclosed herein is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more of the compounds as disclosed herein is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g.

In some embodiments, the amount of one or more of the compounds as disclosed herein is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g.

In some embodiments, the amount of one or more of the compounds as disclosed herein is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds as disclosed herein are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that can be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition disclosed herein typically contains an active ingredient (e.g., a compound disclosed herein or a pharmaceutically acceptable form and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants).

Described below are non-limiting exemplary pharmaceutical compositions and methods for preparing the same.

1A. Formulations for Oral Administration

In some embodiments, provided herein are pharmaceutical compositions for oral administration containing a compound as disclosed herein, and a pharmaceutical excipient suitable for oral administration.

In some embodiments, provided herein are solid pharmaceutical compositions for oral administration containing: (i) an effective amount of a compound disclosed herein; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition can be a liquid pharmaceutical composition suitable for oral consumption. Pharmaceutical compositions as disclosed herein suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. Pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the pharmaceutical compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants can be used in the pharmaceutical compositions as provided herein to provide tablets that disintegrate when exposed to an aqueous environment. Too much of a disintegrant can produce tablets which can disintegrate in the bottle. Too little can be insufficient for disintegration to occur and can thus alter the rate and extent of release of the active ingredient(s) from the dosage form. Thus, a sufficient amount of disintegrant that is neither too little nor too much to detrimentally alter the release of the active ingredient(s) can be used to form the dosage forms of the compounds disclosed herein. The amount of disintegrant used can vary based upon the type of formulation and mode of administration, and can be readily discernible to those of ordinary skill in the art. About 0.5 to about 15 weight percent of disintegrant, or about 1 to about 5 weight percent of disintegrant, can be used in the pharmaceutical composition. Disintegrants that can be used to form pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethylaureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the essential active ingredient therein can be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms include, but are not limited to, hydrophilic surfactants, lipophilic surfactants, and mixtures thereof. That is, a mixture of hydrophilic surfactants can be employed, a mixture of lipophilic surfactants can be employed, or a mixture of at least one hydrophilic surfactant and at least one lipophilic surfactant can be employed.

A suitable hydrophilic surfactant can generally have an HLB value of at least 10, while suitable lipophilic surfactants can generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions. Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants can be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants can be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants can include, but not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol can be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10oleate, Tween 40, Tween 60, sucrose monostearate, sucrose monolaurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the pharmaceutical composition can include a solubilizer to ensure good solubilization and/or dissolution of the compound disclosed herein and to minimize precipitation of the compound. This can be especially important for pharmaceutical compositions for non-oral use, e.g., compositions for injection. A solubilizer can also be added to increase the solubility of the hydrophilic drug and/or other components, such as surfactants, or to maintain the pharmaceutical composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers known in the art, such as dimethyl acetamide, dimethyl isosorbide, N-methylpyrrolidones, monooctanoin, diethylene glycol monoethyl ether, and water.

Mixtures of solubilizers can also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. In some embodiments, solubilizers include sorbitol, glycerol, triacetin, ethyl alcohol, PEG-400, glycofurol and propylene glycol.

The amount of solubilizer that can be included is not particularly limited. The amount of a given solubilizer can be limited to a bioacceptable amount, which can be readily determined by one of skill in the art. In some circumstances, it can be advantageous to include amounts of solubilizers far in excess of bioacceptable amounts, for example to maximize the concentration of the drug, with excess solubilizer removed prior to providing the pharmaceutical composition to a subject (e.g., a patient) using conventional techniques, such as distillation or evaporation. Thus, if present, the solubilizer can be in a weight ratio of 10%, 25%, 50%, 100%, or up to about 200% by weight, based on the combined weight of the drug, and other excipients. If desired, very small amounts of solubilizer can also be used, such as 5%, 2%, 1% or even less. Typically, the solubilizer can be present in an amount of about 1% to about 100%, more typically about 5% to about 25% by weight.

The pharmaceutical composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

Exemplary preservatives can include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, beta-carotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

In addition, an acid or a base can be incorporated into the pharmaceutical composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl)aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example can include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

1B. Formulations for Parenteral Administration

In some embodiments, provided herein are pharmaceutical compositions for parenteral administration containing a compound as disclosed herein and a pharmaceutical excipient suitable for parenteral administration. Components and amounts of agents in the pharmaceutical compositions are as described herein. In some embodiments, provided herein are pharmaceutical compositions for parenteral administration containing: (i) an effective amount of a disclosed compound; optionally (ii) an effective amount of one or more second agents; and (iii) one or more pharmaceutical excipients suitable for parenteral administration. In some embodiments, the pharmaceutical composition further contains: (iv) an effective amount of a third agent.

The forms in which the disclosed pharmaceutical compositions disclosed herein can be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Exemplary parenteral administration forms include solutions or suspensions of active compound in sterile aqueous solutions, for example, aqueous propylene glycol or dextrose solutions. Such dosage forms can be suitably buffered, if desired.

Aqueous solutions in saline are also conventionally used for injection. Ethanol, glycerol, propylene glycol, liquid polyethylene glycol, and the like (and suitable mixtures thereof), cyclodextrin derivatives, and vegetable oils can also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound as disclosed herein in the required amount in the appropriate solvent with various other ingredients as enumerated above, as appropriate, followed by filtered sterilization. Generally, dispersions are prepared by incorporating the various sterilized active ingredients into a sterile vehicle which contains the basic dispersion medium and the appropriate other ingredients from those enumerated above. In the case of sterile powders for the preparation of sterile injectable solutions, certain methods of preparation are vacuum-drying and freeze-drying techniques which yield a powder of the active ingredient plus any additional ingredient from a previously sterile-filtered solution thereof.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. Injectable compositions can contain from about 0.1 to about 5% w/w of a compound as disclosed herein.

The pharmaceutical compositions provided herein can also be delivered via an impregnated or coated device such as a stent, for example, or an artery-inserted cylindrical polymer. Such a method of administration can, for example, aid in the prevention or amelioration of restenosis following procedures such as balloon angioplasty. Without being bound by theory, compounds disclosed herein can slow or inhibit the migration and proliferation of smooth muscle cells in the arterial wall which contribute to restenosis. A compound as disclosed herein can be administered, for example, by local delivery from the struts of a stent, from a stent graft, from grafts, or from the cover or sheath of a stent. In some embodiments, a compound as disclosed herein is admixed with a matrix. Such a matrix can be a polymeric matrix, and can serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly(ether-ester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices can be nondegrading or can degrade with time, releasing the compound or compounds. Compounds described herein can be applied to the surface of the stent by various methods such as dip/spin coating, spray coating, dip-coating, and/or brush-coating. The compounds can be applied in a solvent and the solvent can be allowed to evaporate, thus forming a layer of compound onto the stent. Alternatively, the compound can be located in the body of the stent or graft, for example in microchannels or micropores. When implanted, the compound diffuses out of the body of the stent to contact the arterial wall. Such stents can be prepared by dipping a stent manufactured to contain such micropores or microchannels into a solution of the compound as disclosed herein in a suitable solvent, followed by evaporation of the solvent. Excess drug on the surface of the stent can be removed via an additional brief solvent wash. In yet other embodiments, compounds described herein can be covalently linked to a stent or graft. A covalent linker can be used which degrades in vivo, leading to the release of the compound. Any bio-labile linkage can be used for such a purpose, such as ester, amide or anhydride linkages Compounds described herein can additionally be administered intravascularly from a balloon used during angioplasty. Extravascular administration of the compounds via the pericard or via advential application of formulations can also be performed to decrease restenosis.

A variety of stent devices which can be used as described are disclosed, for example, in the following references, all of which are hereby incorporated by reference: U.S. Pat. No. 5,451,233; U.S. Pat. No. 5,040,548; U.S. Pat. No. 5,061,273; U.S. Pat. No. 5,496,346; U.S. Pat. No. 5,292,331; U.S. Pat. No. 5,674,278; U.S. Pat. No. 3,657,744; U.S. Pat. No. 4,739,762; U.S. Pat. No. 5,195,984; U.S. Pat. No. 5,292,331; U.S. Pat. No. 5,674,278; U.S. Pat. No. 5,879,382; U.S. Pat. No. 6,344,053.

1C. Formulations for Topical Administration

In some embodiments, provided herein are pharmaceutical compositions for transdermal delivery containing a compound as disclosed herein and a pharmaceutical excipient suitable for transdermal delivery. In some embodiments, provided herein are pharmaceutical compositions for topical administration containing: (i) an effective amount of a disclosed compound; optionally (ii) an effective amount of one or more second agents; and (iii) one or more pharmaceutical excipients suitable for topical administration. In some embodiments, the pharmaceutical composition further contains: (iv) an effective amount of a third agent.

Pharmaceutical compositions provided herein can be formulated into preparations in solid, semi-solid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation can provide more immediate exposure of the active ingredient to the chosen area.

The pharmaceutical compositions also can comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the disclosed methods employs transdermal delivery devices ("patches"). Such transdermal patches can be used to provide continuous or discontinuous infusion of a compound as disclosed herein in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches can be constructed for continuous, pulsatile, or on demand delivery of pharmaceutical agents.

Suitable devices for use in delivering intradermal pharmaceutically acceptable compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Topically-administrable formulations can, for example, comprise from about 1% to about 10% (w/w) compound of formula (I), although the concentration of the compound of formula (I) can be as high as the solubility limit of the compound of formula (I) in the solvent. In some embodiments, topically-administrable formulations can, for example, comprise from about 1% to about 9% (w/w) compound of formula (I), such as from about 1% to about 8% (w/w), further such as from about 1% to about 7% (w/w), further such as from about 1% to about 6% (w/w), further such as from about 1% to about 5% (w/w), further such as from about 1% to about 4% (w/w), further such as from about 1% to about 3% (w/w), and further such as from about 1% to about 2% (w/w) compound of formula (I). Formulations for topical administration can further comprise one or more of the additional pharmaceutically acceptable excipients described herein.

1D. Formulations for Inhalation Administration

In some embodiments, provided herein are pharmaceutical compositions for inhalation administration containing a compound as disclosed herein, and a pharmaceutical excipient suitable for topical administration. In some embodiments, provided herein are pharmaceutical compositions for inhalation administration containing: (i) an effective amount of a disclosed compound; optionally (ii) an effective amount of one or more second agents; and (iii) one or more pharmaceutical excipients suitable for inhalation administration. In some embodiments, the pharmaceutical composition further contains: (iv) an effective amount of a third agent.

Pharmaceutical compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described supra. In some embodiments, the compositions are administered by the oral or nasal respiratory route for local or systemic effect. Pharmaceutical compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can be administered, e.g., orally or nasally, from devices that deliver the formulation in an appropriate manner 1E. Formulations for Ocular Administration In some embodiments, the disclosure provides a pharmaceutical composition for treating ophthalmic disorders. The pharmaceutical composition can contain an effective amount of a compound as disclosed herein and a pharmaceutical excipient suitable for ocular administration. Pharmaceutical compositions suitable for ocular administration can be presented as discrete dosage forms, such as drops or sprays each containing a predetermined amount of an active ingredient a solution, or a suspension in an aqueous or non-aqueous liquid, an oil-in-water emulsion, or a water-in-oil liquid emulsion. Other administration forms include intraocular injection, intravitreal injection, topically, or through the use of a drug eluting device, microcapsule, implant, or microfluidic device. In some cases, the compounds as disclosed herein are administered with a carrier or excipient that increases the intraocular penetrance of the compound such as an oil and water emulsion with colloid particles having an oily core surrounded by an interfacial film. It is contemplated that all local routes to the eye can be used including topical, subconjunctival, periocular, retrobulbar, subtenon, intracameral, intravitreal, intraocular, subretinal, juxtascleral and suprachoroidal administration. Systemic or parenteral administration can be feasible including but not limited to intravenous, subcutaneous, and oral delivery. An exemplary method of administration will be intravitreal or subtenon injection of solutions or suspensions, or intravitreal or subtenon placement of bioerodible or non-bioerodible devices, or by topical ocular administration of solutions or suspensions, or posterior juxtascleral administration of a gel or cream formulation.

Eye drops can be prepared by dissolving the active ingredient in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

In some cases, the colloid particles include at least one cationic agent and at least one non-ionic surfactant such as a poloxamer, tyloxapol, a polysorbate, a polyoxyethylene castor oil derivative, a sorbitan ester, or a polyoxyl stearate. In some cases, the cationic agent is an alkylamine, a tertiary alkyl amine, a quarternary ammonium compound, a cationic lipid, an amino alcohol, a biguanidine salt, a cationic compound or a mixture thereof. In some cases, the cationic agent is a biguanidine salt such as chlorhexidine, polyaminopropyl biguanidine, phenformin, alkylbiguanidine, or a mixture thereof. In some cases, the quaternary ammonium compound is a benzalkonium halide, lauralkonium halide, cetrimide, hexadecyltrimethylammonium halide, tetradecyltrimethylammonium halide, dodecyltrimethylammonium halide, cetrimonium halide, benzethonium halide, behenalkonium halide, cetalkonium halide, cetethyldimonium halide, cetylpyridinium halide, benzododecinium halide, chlorallyl methenamine halide, rnyristylalkonium halide, stearalkonium halide or a mixture of two or more thereof. In some cases, cationic agent is a benzalkonium chloride, lauralkonium chloride, benzododecinium bromide, benzethenium chloride, hexadecyltrimethylammonium bromide, tetradecyltrimethylammonium bromide, dodecyltrimethylammonium bromide or a mixture of two or more thereof. In some cases, the oil phase is mineral oil and light mineral oil, medium chain triglycerides (MCT), coconut oil; hydrogenated oils comprising hydrogenated cottonseed oil, hydrogenated palm oil, hydrogenate castor oil or hydrogenated soybean oil; polyoxyethylene hydrogenated castor oil derivatives comprising polyoxyl-40 hydrogenated castor oil, polyoxyl-60 hydrogenated castor oil or polyoxyl-100 hydrogenated castor oil.

1F. Formulations for Controlled Release Administration

In some embodiments, provided herein are pharmaceutical compositions for controlled release administration containing a compound as disclosed herein, and a pharmaceutical excipient suitable for controlled release administration. In some embodiments, provided herein are pharmaceutical compositions for controlled release administration containing: (i) an effective amount of a disclosed compound; optionally (ii) an effective amount of one or more second agents; and (iii) one or more pharmaceutical excipients suitable for controlled release administration. In some embodiments, the pharmaceutical composition further contains: (iv) an effective amount of a third agent.

Active agents such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active agents using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active agents provided herein. Thus, the pharmaceutical compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. In some embodiments, the use of a controlled release preparation in medical treatment is characterized by a minimum of drug substance being employed to cure or control the disease, disorder, or condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

In some embodiments, controlled release formulations are designed to initially release an amount of a compound as disclosed herein that promptly produces the desired therapeutic effect, and gradually and continually release other amounts of the compound to maintain this level of therapeutic or prophylactic effect over an extended period of time. In order to maintain this constant level of the compound in the body, the compound should be released from the dosage form at a rate that will replace the amount of drug being metabolized and excreted from the body. Controlled release of an active agent can be stimulated by various conditions including, but not limited to, pH, temperature, enzymes, water, or other physiological conditions or compounds.

In certain embodiments, the pharmaceutical composition can be administered using intravenous infusion, an implantable osmotic pump, a transdermal patch, liposomes, or other modes of administration. In one embodiment, a pump can be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release,* 115-138 (vol. 2, 1984). Other controlled release systems are discussed in the review by Langer, *Science* 249:1527-1533 (1990). The one or more active agents can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The one or more active agents then diffuse through the outer polymeric membrane in a release rate controlling step. The percentage of active agent in such parenteral compositions is highly dependent on the specific nature thereof, as well as the needs of the subject.

2. Dosage

A compound described herein can be delivered in the form of pharmaceutically acceptable compositions which comprise a therapeutically effective amount of one or more compounds described herein and/or one or more additional therapeutic agents such as a chemotherapeutic, formulated together with one or more pharmaceutically acceptable excipients. In some instances, the compound described herein and the additional therapeutic agent are administered in separate pharmaceutical compositions and can (e.g., because of different physical and/or chemical characteristics) be administered by different routes (e.g., one therapeutic is administered orally, while the other is administered intravenously). In other instances, the compound described herein and the additional therapeutic agent can be administered separately, but via the same route (e.g., both orally or both intravenously). In still other instances, the compound described herein and the additional therapeutic agent can be administered in the same pharmaceutical composition.

The selected dosage level will depend upon a variety of factors including, for example, the activity of the particular compound employed, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

In general, a suitable daily dose of a compound described herein and/or a chemotherapeutic will be that amount of the compound which, in some embodiments, can be the lowest dose effective to produce a therapeutic effect. Such an effective dose will generally depend upon the factors described above. Generally, doses of the compounds described herein for a patient, when used for the indicated effects, will range from about 0.0001 mg to about 100 mg per day, or about 0.001 mg to about 100 mg per day, or about 0.01 mg to about 100 mg per day, or about 0.1 mg to about 100 mg per day, or about 0.0001 mg to about 500 mg per day, or about 0.001 mg to about 500 mg per day, or about 0.01 mg to 1000 mg, or about 0.01 mg to about 500 mg per day, or about 0.1 mg to about 500 mg per day, or about 1 mg to 50 mg per day, or about 5 mg to 40 mg.

The amount of the compound administered will be dependent on the subject being treated, the severity of the disorder or condition, the rate of administration, the disposition of the compound and the discretion of the prescribing physician. However, an effective dosage can be in the range of about 0.001 to about 100 mg per kg body weight per day, such as from about 1 to about 35 mg/kg/day, in single or divided doses. For a 70 kg human, this would amount to about 0.05 to about 7 g/day, such as about 0.05 to about 2.5 g/day. In some instances, dosage levels below the lower limit of the aforesaid range can be more than adequate, while in other cases still larger doses can be employed without causing any harmful side effect, e.g. by dividing such larger doses into several small doses for administration throughout the day.

In some embodiments, a compound as disclosed herein is administered in a single dose. Typically, such administration will be by injection, e.g., intravenous injection, in order to introduce the agent quickly. However, other routes can be used as appropriate. A single dose of a compound as provided herein can also be used for treatment of an acute condition.

In some embodiments, the compounds can be administered daily, every other day, three times a week, twice a week, weekly, or bi-weekly. The dosing schedule can include a "drug holiday," i.e., the drug can be administered for two weeks on, one week off, or three weeks on, one week off, or four weeks on, one week off, etc., or continuously, without a drug holiday. The compounds can be administered orally, intravenously, intraperitoneally, topically, transdermally, intramuscularly, subcutaneously, intranasally, sublingually, or by any other route.

In some embodiments, a compound as provided herein is administered in multiple doses. Dosing can be about once, twice, three times, four times, five times, six times, or more than six times per day. Dosing can be about once a month, once every two weeks, once a week, or once every other day. In another embodiment a compound as disclosed herein and another agent are administered together about once per day to about 6 times per day. In another embodiment the administration of a compound as disclosed herein and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents as disclosed herein can continue as long as necessary. In some embodiments, an agent as disclosed herein is administered for more than 1, 2, 3, 4, 5, 6, 7, 14, or 28 days. In some embodiments, an agent as disclosed herein is administered for less than 28, 14, 7, 6, 5, 4, 3, 2, or 1 day. In some embodiments, an agent as disclosed herein is administered chronically on an ongoing basis, e.g., for the treatment of chronic effects.

An effective amount of a compound as disclosed herein can be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

Since the compounds described herein can be administered in combination with other treatments (such as additional chemotherapeutics, radiation or surgery), the doses of each agent or therapy can be lower than the corresponding dose for single-agent therapy. The dose for single-agent therapy can range from, for example, about 0.0001 to about 200 mg, or about 0.001 to about 100 mg, or about 0.01 to about 100 mg, or about 0.1 to about 100 mg, or about 1 to about 50 mg per kilogram of body weight per day.

When a compound provided herein, is administered in a pharmaceutical composition that comprises one or more agents, and the agent has a shorter half-life than the compound provided herein unit dose forms of the agent and the compound provided herein can be adjusted accordingly.

The compounds provided herein can be administered in dosages. It is known in the art that due to intersubject variability in compound pharmacokinetics, individualization of dosing regimen is necessary for optimal therapy. Dosing for a compound as disclosed herein can be found by routine experimentation in light of the instant disclosure.

3. Kits

In some embodiments, provided herein are kits. The kits can include a compound or compounds as described herein, in suitable packaging, and written material that can include instructions for use, discussion of clinical studies, listing of side effects, and the like. In some embodiments, the kits can contain one or more pharmaceutical compositions as described herein. Such kits can also include information, such as scientific literature references, package insert materials, clinical trial results, and/or summaries of these and the like, which indicate or establish the activities and/or advantages of the pharmaceutical composition, and/or which describe dosing, administration, side effects, drug interactions, or other information useful to the health care provider. Such information can be based on the results of various studies, for example, studies using experimental animals involving in vivo models and studies based on human clinical trials. The kit can further contain another agent. In some embodiments, the compound as disclosed herein and the agent are provided as separate pharmaceutical compositions in separate containers within the kit. In some embodiments, the compound described herein and the agent are provided as a single pharmaceutical composition within a container in the kit. Suitable packaging and additional articles for use (e.g., measuring cup for liquid preparations, foil wrapping to minimize exposure to air, and the like) are known in the art and can be included in the kit. Kits described herein can be provided, marketed and/or promoted to health providers, including physicians, nurses, pharmacists, formulary officials, and the like. Kits can also, in some embodiments, be marketed directly to the consumer.

In some embodiments, a memory aid is provided with the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . . Second Week, Monday, Tuesday, . . . " etc. Other variations of memory aids will be readily apparent. A "daily dose" can be a single tablet or capsule or several tablets or capsules to be taken on a given day.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. The strength of the sheet is such that the tablets or capsules can be removed from the blister pack by manually applying pressure on the recesses whereby an opening is formed in the sheet at the place of the recess. The tablet or capsule can then be removed via said opening.

Kits can further comprise pharmaceutically acceptable vehicles that can be used to administer one or more active agents. For example, if an active agent is provided in a solid form that must be reconstituted for parenteral administration, the kit can comprise a sealed container of a suitable vehicle in which the active agent can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

The present disclosure further encompasses anhydrous pharmaceutical compositions and dosage forms comprising an active ingredient, since water can facilitate the degradation of some compounds. For example, water can be added (e.g., about 5%) in the pharmaceutical arts as a means of simulating long-term storage in order to determine characteristics such as shelf-life or the stability of formulations over time. Anhydrous pharmaceutical compositions and dosage forms can be prepared using anhydrous or low moisture containing ingredients and low moisture or low humidity conditions. For example, pharmaceutical compositions and dosage forms which contain lactose can be made anhydrous if substantial contact with moisture and/or humidity during manufacturing, packaging, and/or storage is expected. An anhydrous pharmaceutical composition can be prepared and stored such that its anhydrous nature is maintained. Accordingly, anhydrous pharmaceutical compositions can be packaged using materials known to prevent exposure to water such that they can be included in suitable formulary kits. Examples of suitable packaging include, but are not limited to, hermetically sealed foils, plastic or the like, unit dose containers, blister packs, and strip packs.

4. Therapeutic Methods

Phosphoinositide 3-kinases (PI3Ks) are members of a conserved family of lipid kinases that regulate numerous cell functions, including proliferation, differentiation, cell survival and metabolism. Several classes of PI3Ks exist in cells (e.g., mammalian cells), including Class IA subgroup (e.g., PI3K-α, β, δ), which are generally activated by receptor tyrosine kinases (RTKs); Class IB (e.g., PI3K-γ), which is activated by G-protein coupled receptors, among others. PI3Ks exert their biological activities via a "PI3K-mediated signaling pathway" that includes several components that directly and/or indirectly transduce a signal triggered by a PI3K, including the generation of secondary messenger phophotidylinositol, 3,4,5-triphosphate (PIP3) at the plasma membrane, activation of heterotrimeric G protein signaling, and generation of further second messengers such as cAMP, DAG, and IP3, all of which leads to an extensive cascade of protein kinase activation (reviewed in Vanhaesebroeck, B. et al. (2001) *Annu Rev Biochem*. 70:535-602). For example, PI3K-δ is activated by cellular receptors through interaction between the PI3K regulatory subunit (p85) SH2 domains, or through direct interaction with RAS. PIP3 produced by PI3K activates effector pathways downstream through interaction with plextrin homology (PH) domain containing enzymes (e.g., PDK-1 and AKT [PKB]). (Fung-Leung W P. (2011) *Cell Signal*. 23(4):603-8). Unlike PI3K-δ, PI3K-γ is not a Class IA PI3K, and is not associated with a regulatory subunit of the P85 family, but rather with a regulatory subunit in the p101 family. PI3K-γ is associated with G-protein coupled receptors (GPCRs), and is responsible for the very rapid induction of PIP3, and can be also activated by RAS.

As used herein, a "PI3K-mediated disorder" refers to a disease or condition involving aberrant PI3K-mediated signaling pathway. In one embodiment, provided herein is a method of treating a PI3K mediated disorder in a subject, the method comprising administering a therapeutically effective amount of a compound or a pharmaceutical composition as disclosed herein. In some embodiments, provided herein is a method of treating a PI3K-δ or PI3K-γ mediated disorder in a subject, the method comprising administering a therapeutically effective amount of a compound or a pharmaceutical composition as disclosed herein. In some embodiments, provided herein is a method for inhibiting at least one of PI3K-δ or PI3K-γ, the method comprising contacting a cell expressing PI3K in vitro or in vivo with an effective amount of the compound or composition disclosed herein PI3Ks have been associated with a wide range of conditions, including immunity, cancer and thrombosis (reviewed in Vanhaesebroeck, B. et al. (2010) *Current Topics in Microbiology and Immunology*, DOI 10.1007/82_2010_65). For example, Class I PI3Ks, particularly PI3Kγ and PI3Kδ isoforms, are highly expressed in leukocytes and have been associated with adaptive and innate immunity; thus, these PI3Ks are believed to be important mediators in inflammatory disorders and hematologic malignancies (reviewed in Harris, S J et al. (2009) *Curr Opin Investig Drugs* 10(11):1151-62); Rommel C. et al. (2007) *Nat Rev Immunol* 7(3):191-201; Durand C A et al. (2009) *J Immunol*. 183(9):5673-84; Dil N, Marshall A J. (2009) *Mol Immunol*. 46(10):1970-8; Al-Alwan M M et al. (2007) *J Immunol*. 178(4):2328-35; Zhang T T, et al. (2008) *J Allergy Clin Immunol*. 2008; 122(4):811-819.e2; Srinivasan L, et al. (2009) *Cell* 139(3):573-86).

Numerous publications support roles of PI3K-δ, PI3K-γ, and PI3K-β in the differentiation, maintenance, and activation of immune and malignant cells, as described in more detail below.

The importance of PI3K-δ in the development and function of B-cells is supported from inhibitor studies and genetic models. PI3K-δ is an important mediator of B-cell receptor (BCR) signaling, and is upstream of AKT, calcium flux, PLCγ, MAP kinase, P70S6k, and FOXO3a activation. PI3K-δ is also important in IL4R, S1P, and CXCR5 signaling, and has been shown to modulate responses to toll-like receptors 4 and 9 Inhibitors of PI3K-δ have shown the importance of PI3K-δ in B-cell development (Marginal zone and B1 cells), B-cell activation, chemotaxis, migration and homing to lymphoid tissue, and in the control of immunoglobulin class switching leading to the production of IgE. Clayton E et al. (2002) *J Exp Med*. 196(6):753-63; Bilancio A, et al. (2006) *Blood* 107(2):642-50; Okkenhaug K. et al. (2002) *Science* 297(5583):1031-4; Al-Alwan M M et al. (2007) *J Immunol*. 178(4):2328-35; Zhang T T, et al. (2008) *J Allergy Clin Immunol*. 2008; 122(4):811-819.e2; Srinivasan L, et al. (2009) *Cell* 139(3):573-86)

In T-cells, PI3K-δ has been demonstrated to have a role in T-cell receptor and cytokine signaling, and is upstream of AKT, PLCγ, and GSK3b. In PI3K-δ deletion or kinase-dead knock-in mice, or in inhibitor studies, T-cell defects including proliferation, activation, and differentiation have been observed, leading to reduced T helper cell 2 (TH2) response, memory T-cell specific defects (DTH reduction), defects in antigen dependent cellular trafficking, and defects in chemotaxis/migration to chemokines (e.g., S1P, CCR7, CD62L). (Garçon F. et al. (2008) *Blood* 111(3):1464-71; Okkenhaug K et al. (2006). *J Immunol*. 177(8):5122-8; Soond D R, et al. (2010) *Blood* 115(11):2203-13; Reif K, (2004). *J Immunol*. 2004; 173(4):2236-40; Ji H. et al. (2007) *Blood* 110(8):2940-7; Webb L M, et al. (2005) *J Immunol*. 175(5):2783-7; Liu D, et al. (2010) *J Immunol*. 184(6):3098-105; Haylock-Jacobs S, et al. (2011) *J Autoimmun*. 2011; 36(3-4):278-87; Jarmin S J, et al. (2008) *J Clin Invest*. 118(3):1154-64).

In neutrophils, PI3K-δ along with PI3K-γ, and PI3K-β, contribute to the responses to immune complexes, FCgRII signaling, including migration and neutrophil respiratory burst. Human neutrophils undergo rapid induction of PIP3 in response to formyl peptide receptor (FMLP) or complement component C5a (C5a) in a PI3K-γ dependent manner, followed by a longer PIP3 production period that is PI3K-δ dependent, and is essential for respiratory burst. The response to immune complexes is contributed by PI3K-δ, PI3K-γ, and PI3K-β, and is an important mediator of tissue damage in models of autoimmune disease (Randis T M et al. (2008) *Eur J Immunol*. 38(5):1215-24; Pinho V, (2007) *J Immunol*. 179 (11):7891-8; Sadhu C. et al. (2003) *J Immunol*. 170(5):2647-54; Condliffe A M et al. (2005) *Blood* 106(4):1432-40).

In macrophages collected from patients with chronic obstructive pulmonary disease (COPD), glucocorticoid responsiveness can be restored by treatment of the cells with inhibitors of PI3K-δ. Macrophages also rely on PI3K-δ and PI3K-γ for responses to immune complexes through the arthus reaction (FCgR and C5a signaling) (Randis T M, et al. (2008) *Eur J Immunol*. 38(5):1215-24; Marwick J A et al. (2009) *Am J Respir Crit Care Med*. 179(7):542-8; Konrad S, et al. (2008) *J Biol Chem*. 283(48):33296-303).

In mast cells, stem cell factor-(SCF) and IL3-dependent proliferation, differentiation and function are PI3K-δ dependent, as is chemotaxis. The allergen/IgE crosslinking of FCgR1 resulting in cytokine release and degranulation of the mast cells is severely inhibited by treatment with PI3K-δ inhibitors, suggesting a role for PI3K-δ in allergic disease (Ali K et al. (2004) *Nature* 431(7011):1007-11; Lee K S, et al. (2006) *FASEB J.* 20(3):455-65; Kim M S, et al. (2008) *Trends Immunol.* 29(10):493-501).

Natural killer (NK) cells are dependent on both PI3K-δ and PI3K-γ for efficient migration towards chemokines including CXCL10, CCL3, S1P and CXCL12, or in response to LPS in the peritoneum (Guo H, et al. (2008) *J Exp Med.* 205(10): 2419-35; Tassi I, et al. (2007) *Immunity* 27(2):214-27; Saudemont A, (2009) *Proc Natl Acad Sci USA.* 106(14):5795-800; Kim N, et al. (2007) *Blood* 110(9):3202-8).

The roles of PI3K-δ, PI3K-γ, and PI3K-β in the differentiation, maintenance, and activation of immune cells support a role for these enzymes in inflammatory disorders ranging from autoimmune diseases (e.g., rheumatoid arthritis, multiple sclerosis) to allergic inflammatory disorders, such as asthma and COPD. Extensive evidence is available in experimental animal models, or can be evaluated using art-recognized animal models. In an embodiment, described herein is a method of treating inflammatory disorders ranging from autoimmune diseases (e.g., rheumatoid arthritis, multiple sclerosis) to allergic inflammatory disorders, such as asthma and COPD using a compound described herein.

For example, inhibitors of PI3Kδ and/or γ have been shown to have anti-inflammatory activity in several autoimmune animal models for rheumatoid arthritis (Williams, O. et al. (2010) Chem Biol, 17(2):123-34; WO 2009/088986; WO2009/088880; WO 2011/008302). PI3Kδ is expressed in the RA synovial tissue (especially in the synovial lining which contains fibroblast-like synoviocytes (FLS), and selective PI3Kd inhibitors have been shown to be effective in inhibiting synoviocyte growth and survival (Bartok et al. (2010) *Arthritis Rheum* 62 Suppl 10:362). Several PI3K δ and γ inhibitors have been shown to ameliorate arthritic symptoms (e.g., swelling of joints, reduction of serum-induced collagen levels, reduction of joint pathology and/or inflammation), in art-recognized models for RA, such as collagen-induced arthritis and adjuvant induced arthritis (WO 2009/088986; WO2009/088880; WO 2011/008302).

The role of PI3K-δ has also been shown in models of T-cell dependent response, including the DTH model. In the murine experimental autoimmune encephalomyelitis (EAE) model of multiple sclerosis, the PI3K-g/d-double mutant mice are resistant. PI3K-δ inhibitors have also been shown to block EAE disease induction and development of TH-17 cells both in vitro and in vivo (Haylock-Jacobs, S. et al. (2011) *J. Autoimmunity* 36(3-4):278-87).

Systemic lupus erythematosus (SLE) is a complex disease that at different stages requires memory T-cells, B-cell polyclonal expansion and differentiation into plasma cells, and the innate immune response to endogenous damage associated molecular pattern molecules (DAMPS), and the inflammatory responses to immune complexes through the complement system as well as the $F_C$ receptors. The role of PI3K-δ and PI3K-γ together in these pathways and cell types suggest that blockade with an inhibitor would be effective in these diseases. A role for PI3K in lupus is also predicted by two genetic models of lupus. The deletion of phosphatase and tensin homolog (PTEN) leads to a lupus-like phenotype, as does a transgenic activation of Class1A PI3Ks, which includes PI3K-δ. The deletion of PI3K-γ in the transgenically activated class 1A lupus model is protective, and treatment with a PI3K-γ selective inhibitor in the murine MLR/lpr model of lupus improves symptoms (Barber, D F et al. (2006) *J. Immunol.* 176(1): 589-93).

In allergic disease, PI3K-δ has been shown by genetic models and by inhibitor treatment to be essential for mast-cell activation in a passive cutaneous anaphalaxis assay (Ali K et al. (2008) *J Immunol.* 180(4):2538-44; Ali K, (2004) *Nature* 431(7011):1007-11). In a pulmonary measure of response to immune complexes (Arthus reaction) a PI3K-δ knockout is resistant, showing a defect in macrophage activation and C5a production. Knockout studies and studies with inhibitors for both PI3K-δ and PI3K-γ support a role for both of these enzymes in the ovalbumin induced allergic airway inflammation and hyper-responsiveness model (Lee K S et al. (2006) *FASEB J.* 20(3):455-65). Reductions of infiltration of eosinophils, neutrophils, and lymphocytes as well as TH2 cytokines (IL4, IL5, and IL13) were seen with both PI3K-δ specific and dual PI3K-δ and PI3K-γ inhibitors in the Ova induced asthma model (Lee K S et al. (2006) *J Allergy Clin Immunol* 118(2): 403-9).

PI3K-δ and PI3K-γ inhibition can be used in treating COPD. In the smoked mouse model of COPD, the PI3K-δ knockoutdoes not develop smoke induced glucocorticoid resistance, while wild-type and PI3K-γ knockout mice do. An inhaled formulation of dual PI3K-δ and PI3K-γ inhibitor blocked inflammation in a LPS or smoke COPD models as measured by neutrophilia and glucocorticoid resistance (Doukas J, et al. (2009) *J Pharmacol Exp Ther.* 328(3):758-65).

Class I PI3Ks, particularly PI3Kδ and PI3Kγ isoforms, are also associated with cancers (reviewed, e.g., in Vogt, P K et al. (2010) Curr Top Microbiol Immunol. 347:79-104; Fresno Vara, J A et al. (2004) *Cancer Treat Rev.* 30(2):193-204; Zhao, L and Vogt, P K. (2008) Oncogene 27(41):5486-96). Inhibitors of PI3K, e.g., PI3Kδ and/or γ, have been shown to have anti-cancer activity (e.g., Courtney, K D et al. (2010) *J Clin Oncol.* 28(6):1075-1083); Markman, B et al. (2010) Ann Oncol. 21(4):683-91; Kong, D and Yamori, T (2009) Curr Med. Chem. 16(22):2839-54; Jimeno, A et al. (2009) J Clin Oncol. 27:156s (suppl; abstr 3542); Flinn, I W et al. (2009) *J Clin Oncol.* 27:156s (suppl; abstr 3543); Shapiro, G et al. (2009) J Clin Oncol. 27:146s (suppl; abstr 3500); Wagner, A T et al. (2009) *J Clin Oncol.* 27:146s (suppl; abstr 3501); Vogt, P K et al. (2006) Virology 344(1):131-8; Ward, S et al. (2003) *Chem. Biol.* 10(3):207-13; WO 2011/041399; US 2010/0029693; US 2010/0305096; US 2010/0305084). In an embodiment, described herein is a method of treating cancer.

Types of cancer that can be treated with an inhibitor of PI3K (particularly, PI3Kδ and/or γ) include, e.g., leukemia, chronic lymphocytic leukemia, acute myeloid leukemia, chronic myeloid leukemia (e.g., Salmena, L et al. (2008) *Cell* 133:403-414; Chapuis, N et al. (2010) *Clin Cancer Res.* 16(22):5424-35; Khwaja, A (2010) *Curr Top Microbiol Immunol.* 347:169-88); lymphoma, e.g., non-Hodgkin's lymphoma (e.g., Salmena, L et al. (2008) *Cell* 133:403-414); lung cancer, e.g., non-small cell lung cancer, small cell lung cancer (e.g., Herrera, V A et al. (2011) *Anticancer Res.* 31(3):849-54); melanoma (e.g., Haluska, F et al. (2007) *Semin Oncol.* 34(6):546-54); prostate cancer (e.g., Sarker, D et al. (2009) *Clin Cancer Res.* 15(15):4799-805); glioblastoma (e.g., Chen, J S et al. (2008) Mol Cancer Ther. 7:841-850); endometrial cancer (e.g., Bansal, N et al. (2009) Cancer Control. 16(1):8-13); pancreatic cancer (e.g., Furukawa, T (2008) *J Gastroenterol.* 43(12):905-11); renal cell carcinoma (e.g., Porta, C and Figlin, R A (2009) *J Urol.* 182(6):2569-77); colorectal cancer (e.g., Saif, M W and Chu, E (2010) Cancer J. 16(3):196-201); breast cancer (e.g., Torbett, N E et al. (2008) *Biochem J.* 415:97-100); thyroid cancer (e.g., Brzezianska, E and Pastuszak-Lewandoska, D (2011) *Front Biosci.* 16:422-39); and ovarian cancer (e.g., Mazzoletti, M and Broggini, M (2010) *Curr Med Chem.* 17(36):4433-47).

Numerous publications support a role of PI3K-δ and PI3K-γ in treating hematological cancers. PI3K-δ and PI3K-γ are highly expressed in the heme compartment, and some solid tumors, including prostate, breast and glioblastomas (Chen J. S. et al. (2008) *Mol Cancer Ther.* 7(4):841-50; Ikeda H. et al. (2010) *Blood* 116(9):1460-8). In hematological cancers including acute myeloid leukemia (AML), multiple myeloma (MM), and chronic lymphocytic leukemia (CLL), overexpression and constitutive activation of PI3K-δ supports the model that PI3K-δ inhibition would be therapeutic Billottet C, et al. (2006) *Oncogene* 25(50):6648-59; Billottet C, et al. (2009) *Cancer Res.* 69(3):1027-36; Meadows, S A, $52^{nd}$ Annual ASH Meeting and Exposition; 2010 Dec. 4-7; Orlando, Fla.; Ikeda H, et al. (2010) *Blood* 116(9):1460-8; Herman S E et al. (2010) *Blood* 116(12):2078-88; Herman S E et al. (2011). *Blood* 117(16):4323-7. In an embodiment, described herein is a method of treating hematological cancers including, but not limited to acute myeloid leukemia (AML), multiple myeloma (MM), and chronic lymphocytic leukemia (CLL).

A PI3K-δ inhibitor (CAL-101) has been evaluated in a phase 1 trial in patients with haematological malignancies, and showed activity in CLL in patients with poor prognostic characteristics. In CLL, inhibition of PI3K-δ not only affects tumor cells directly, but it also affects the ability of the tumor cells to interact with their microenvironment. This microenvironment includes contact with and factors from stromal cells, T-cells, nurse like cells, as well as other tumor cells. CAL-101 suppresses the expression of stromal and T-cell derived factors including CCL3, CCL4, and CXCL13, as well as the CLL tumor cells' ability to respond to these factors. CAL-101 treatment in CLL patients induces rapid lymph node reduction and redistribution of lymphocytes into the circulation, and affects tonic survival signals through the BCR, leading to reduced cell viability, and an increase in apoptosis. Single agent CAL-101 treatment was also active in mantle cell lymphoma and refractory non Hodgkin's lymphoma (Furman, R R, et al. $52^{nd}$ Annual ASH Meeting and Exposition; 2010 Dec. 4-7; Orlando, Fla.; Hoellenriegel, J, et al. $52^{nd}$ Annual ASH Meeting and Exposition; 2010 Dec. 4-7; Orlando, Fla.; Webb, H K, et al. $52^{nd}$ Annual ASH Meeting and Exposition; 2010 Dec. 4-7; Orlando, Fla.; Meadows, et al. $52^{nd}$ Annual ASH Meeting and Exposition; 2010 Dec. 4-7; Orlando, Fla.; Kahl, B, et al. $52^{nd}$ Annual ASH Meeting and Exposition; 2010 Dec. 4-7; Orlando, Fla.; Lannutti B J, et al. (2011) *Blood* 117(2):591-4).

PI3K-δ inhibitors have shown activity against PI3K-δ positive gliomas in vitro (Kashishian A, et al. Poster presented at: The American Association of Cancer Research $102^{nd}$ Annual Meeting; 2011 Apr. 2-6; Orlando, Fla.). PI3K-β is the PI3K isoform that is most commonly activated in tumors where the PTEN tumor suppressor is mutated (Ward S, et al. (2003) *Chem. Biol.* 10(3):207-13). In this subset of tumors, treatment with the PI3K-δ inhibitor either alone or in combination with a cytotoxic agent can be effective.

Another mechanism for PI3K-δ inhibitors to have an affect in solid tumors involves the tumor cells' interaction with their micro-environment. PI3K-δ, PI3K-γ, and PI3K-β are expressed in the immune cells that infiltrate tumors, including tumor infiltrating lymphocytes, macrophages, and neutrophils. PI3K-δ inhibitors can modify the function of these tumor-associated immune cells and how they respond to signals from the stroma, the tumor, and each other, and in this way affect tumor cells and metastasis (Hoellenriegel, J, et al. $52^{nd}$ Annual ASH Meeting and Exposition; 2010 Dec. 4-7; Orlando, Fla.).

PI3K-δ is also expressed in endothelial cells. It has been shown that tumors in mice treated with PI3K-δ selective inhibitors are killed more readily by radiation therapy. In this same study, capillary network formation is impaired by the PI3K inhibitor, and it is postulated that this defect contributes to the greater killing with radiation. PI3K-δ inhibitors can affect the way in which tumors interact with their microenvironment, including stromal cells, immune cells, and endothelial cells and be therapeutic either on its own or in conjunction with another therapy (Meadows, S A, et al. Paper presented at: $52^{nd}$ Annual ASH Meeting and Exposition; 2010 Dec. 4-7; Orlando, Fla.; Geng L, et al. (2004) *Cancer Res.* 64(14):4893-9).

In other embodiments, inhibition of PI3K (such as PI3K-δ and/or -γ) can be used to treat a neuropsychiatric disorder, e.g., an autoimmune brain disorder. Infectious and immune factors have been implicated in the pathogenesis of several neuropsychiatric disorders, including, but not limited to, Sydenham's chorea (SC) (Garvey, M. A. et al. (2005) *J. Child Neurol.* 20:424-429), Tourette's syndrome (TS), obsessive compulsive disorder (OCD) (Asbahr, F. R. et al. (1998) *Am. J. Psychiatry* 155:1122-1124), attention deficit/hyperactivity disorder (AD/HD) (Hirschtritt, M. E. et al. (2008) *Child Neuropsychol.* 1:1-16; Peterson, B. S. et al. (2000) *Arch. Gen. Psychiatry* 57:364-372), anorexia nervosa (Sokol, M. S. (2000) *J. Child Adolesc. Psychopharmacol.* 10:133-145; Sokol, M. S. et al. (2002) *Am. J. Psychiatry* 159:1430-1432), depression (Leslie, D. L. et al. (2008) *J. Am. Acad. Child Adolesc. Psychiatry* 47:1166-1172), and autism spectrum disorders (ASD) (Hollander, E. et al. (1999) *Am. J. Psychiatry* 156:317-320; Margutti, P. et al. (2006) *Curr. Neurovasc. Res.* 3:149-157). A subset of childhood obsessive compulsive disorders and tic disorders has been grouped as Pediatric Autoimmune Neuropsychiatric Disorders Associated with Streptococci (PANDAS). PANDAS disorders provide an example of disorders where the onset and exacerbation of neuropsychiatric symptoms is preceded by a streptococcal infection (Kurlan, R., Kaplan, E. L. (2004) *Pediatrics* 113: 883-886; Garvey, M. A. et al. (1998) *J. Clin. Neurol.* 13:413-423). Many of the PANDAS disorders share a common mechanism of action resulting from antibody responses against streptococcal associated epitopes, such as GlcNAc, which produces neurological effects (Kirvan. C. A. et al. (2006) *J. Neuroimmunol.* 179:173-179). Autoantibodies recognizing central nervous system (CNS) epitopes are also found in sera of most PANDAS subjects (Yaddanapudi, K. et al. (2010) *Mol. Psychiatry.* 15:712-726). Thus, several neuropsychiatric disorders have been associated with immune and autoimmune components, making them suitable for therapies that include PI3K-δ and/or -γ inhibition.

In certain embodiments, a method of treating (e.g., reducing or ameliorating one or more symptoms of) a neuropsychiatric disorder, (e.g., an autoimmune brain disorder), using a PI3K-δ and/or -γ inhibitor is described, alone or in combination therapy. For example, one or more PI3K-δ and/or -γ inhibitors described herein can be used alone or in combination with any suitable therapeutic agent and/or modalities, e.g., dietary supplement, for treatment of neuropsychiatric disorders. Exemplary neuropsychiatric disorders that can be treated with the PI3K-δ and/or -γ inhibitors described herein include, but are not limited to, PANDAS disorders, Sydenham's chorea, Tourette's syndrome, obsessive compulsive disorder, attention deficit/hyperactivity disorder, anorexia nervosa, depression, and autism spectrum disorders. Pervasive Developmental Disorder (PDD) is an exemplary class of autism spectrum disorders that includes Autistic Disorder, Asperger's Disorder, Childhood Disintegrative Disorder (CDD), Rett's Disorder and PDD-Not Otherwise Specified (PDD-NOS). Animal models for evaluating the activity of the PI3K-δ and/or -γ inhibitor are known in the art. For example, a mouse model of PANDAS disorders is described in, e.g., Yaddanapudi, K. et al. (2010) supra; and Hoffman, K. I. et al. (2004) *J. Neurosci.* 24:1780-1791.

In some embodiments, provided herein are methods of using the compounds or pharmaceutical compositions as disclosed herein to treat disease conditions, including, but not limited to, diseases associated with malfunctioning of one or more types of PI3 kinase and/or mTOR. A detailed description of conditions and disorders mediated by p110δ kinase activity is set forth in Sadu et al., WO 01/81346, which is incorporated herein by reference in its entirety for all purposes.

The treatment methods provided herein comprise administering to the subject a therapeutically effective amount of a compound as disclosed herein.

In some embodiments, the disclosure relates to a method of treating a hyperproliferative disorder in a subject that comprises administering to said subject a therapeutically effective amount of a compound as disclosed herein, or a pharmaceutically acceptable salt, ester, prodrug or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

In one embodiment, provided herein is a method of treating an inflammation disorder, including autoimmune diseases in a subject. The method comprises administering to said subject a therapeutically effective amount of a compound as disclosed herein, or a pharmaceutically acceptable salt, ester, prodrug or derivative thereof. Examples of autoimmune diseases includes but is not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barré syndrome (GBS), Hashimoto's disease, lupus erythematosus, multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, and vulvodynia. Other disorders include bone-resorption disorders and thrombosis.

In some embodiments, provided herein are methods for treating disorders or conditions in which the δ isoform of PI3K is implicated to a greater extent than other PI3K isoforms such as PI3K α and/or β. Selective inhibition of PI3K-δ and/or PI3K-γ can provide advantages over using less selective compounds which inhibit PI3K α and/or β, such as an improved side effects profile or lessened reduction in the ability to reduce a bacterial, viral, and/or fungal infection.

In some embodiments, the method of treating inflammatory or autoimmune diseases includes administering to a subject (e.g. a mammal) a therapeutically effective amount of one or more compounds of that selectively inhibit PI3K-δ and/or PI3K-γ as compared to all other type I PI3 kinases. Such selective inhibition of PI3K-δ and/or PI3K-γ can be advantageous for treating any of the diseases or conditions described herein. For example, selective inhibition of PI3K-δ can inhibit inflammatory responses associated with inflammatory diseases, autoimmune disease, or diseases related to an undesirable immune response including but not limited to asthma, emphysema, allergy, dermatitis, rhuematoid arthritis, psoriasis, lupus erythematosus, or graft versus host disease. Selective inhibition of PI3K-δ can further provide for a reduction in the inflammatory or undesirable immune response without a concomitant reduction in the ability to reduce a bacterial, viral, and/or fungal infection. Selective inhibition of both PI3K-δ and PI3K-γ can be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one of more of the subject methods are effective in ameliorating symptoms associated with rhuematoid arthritis including but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In other embodiments, provided herein are methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term include, but are not limited to: chronic bronchitis, emphysema, and bronchiectasis.

In another embodiment, the compounds described herein are used for the treatment of asthma. Also, the compounds or pharmaceutical compositions described herein can be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

In some embodiments, the disclosure provides a method of treating diseases related to vasculogenesis or angiogenesis in a subject that comprises administering to said subject a therapeutically effective amount of a compound as disclosed herein, or a pharmaceutically acceptable form (e.g., pharmaceutically acceptable salts, hydrates, solvates, isomers, prodrugs, and isotopically labeled derivatives) thereof. In some embodiments, said method is for treating a disease selected tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Subjects (e.g., patients) that can be treated with compounds as disclosed herein, or a pharmaceutically acceptable form (e.g., pharmaceutically acceptable salts, hydrates, solvates, isomers, prodrugs, and isotopically labeled derivatives) thereof of said compounds, according to the methods as disclosed herein include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-1) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

Patients that can be treated with compounds disclosed herein, or pharmaceutically acceptable form (e.g., pharmaceutically acceptable salts, hydrates, solvates, isomers, prodrugs, and isotopically labeled derivatives) thereof of said compounds, according to the methods disclosed herein include, for example, patients that have been diagnosed as having conditions including, but not limited to, acoustic neuroma, adenocarcinoma, adrenal gland cancer, anal cancer, angiosarcoma (e.g., lymphangiosarcoma, lymphangioendotheliosarcoma, hemangiosarcoma), benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer, esophageal cancer (e.g., adenocarcinoma of the esophagus, Barrett's adenocarinoma), Ewing sarcoma, familiar hypereosinophilia, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leukemia (e.g., acute lymphocytic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM); peripheral T cell lymphomas (PTCL), adult T cell leukemia/lymphoma (ATL), cutaneous T-cell lymphoma (CTCL), large granular lymphocytic leukemia (LGF), Hodgkin's disease and Reed-Stemberg disease; acute myelocytic leukemia (AML), chronic myelocytic leukemia (CML), chronic lymphocytic leukemia (CLL)), lymphoma (e.g., Hodgkin lymphoma (HL), non-Hodgkin lymphoma (NHL), follicular lymphoma, diffuse large B-cell lymphoma (DLBCL), mantle cell lymphoma (MCL)), leiomyosarcoma (LMS), mastocytosis (e.g., systemic mastocytosis), multiple myeloma (MM), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), Paget's disease of the vulva, Paget's disease of the penis, papillary adenocarcinoma, pancreatic cancer (e.g., pancreatic andenocarcinoma, intraductal papillary mucinous neoplasm (IPMN)), pinealoma, primitive neuroectodermal tumor (PNT), prostate cancer (e.g., prostate adenocarcinoma), rhabdomyosarcoma, retinoblastoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), and Waldenström's macroglobulinemia.

In some embodiments, the disclosure relates to a method of treating diabetes in a subject that comprises administering to said subject a therapeutically effective amount of a compound disclosed herein, or a pharmaceutically acceptable form (e.g., pharmaceutically acceptable salts, hydrates, solvates, isomers, prodrugs, and isotopically labeled derivatives) thereof.

In addition, the compounds described herein can be used to treat acne.

In addition, the compounds described herein can be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein can be used for the treatment of glomerulonephritis. Glomerulonephritis is a primary or secondary autoimmune renal disease characterized by inflammation of the glomeruli. It can be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein can be used for the treatment of bursitis, lupus, acute disseminated encephalomyelitis (ADEM), addison's disease, antiphospholipid antibody syndrome (APS), aplastic anemia, autoimmune hepatitis, coeliac disease, crohn's disease, diabetes mellitus (type 1), goodpasture's syndrome, graves' disease, guillain-barré syndrome (GBS), hashimoto's disease, inflammatory bowel disease, lupus erythematosus, myasthenia gravis, opsoclonus myoclonus syndrome (OMS), optic neuritis, ord's thyroiditis, ostheoarthritis, uveoretinitis, pemphigus, polyarthritis, primary biliary cirrhosis, reiter's syndrome, takayasu's arteritis, temporal arteritis, warm autoimmune hemolytic anemia, wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

Further, the compounds disclosed herein can be used for the treatment of Perennial allergic rhinitis, Mesenteritis, Peritonitis, Acrodermatitis, Angiodermatitis, Atopic dermatitis, Contact dermatitis, Eczema, Erythema multiforme, Intertrigo, Stevens Johnson syndrome, Toxic epidermal necrolysis, Skin allergy, Severe allergic reaction/anaphylaxis, Allergic granulomatosis, Wegener granulomatosis, Allergic conjunctivitis, Chorioretinitis, Conjunctivitis, Infectious keratoconjunctivitis, Keratoconjunctivitis, Ophthalmia neonatorum, Trachoma, Uveitis, Ocular inflammation, Blepharoconjunctivitis, Mastitis, Gingivitis, Pericoronitis, Pharyngitis, Rhinopharyngitis, Sialadenitis, Musculoskeletal system inflammation, Adult onset Stills disease, Behcets disease, Bursitis, Chondrocalcinosis, Dactylitis, Felty syndrome, Gout, Infectious arthritis, Lyme disease, Inflammatory osteoarthritis, Periarthritis, Reiter syndrome, Ross River virus infection, Acute Respiratory, Distress Syndrome, Acute bronchitis, Acute sinusitis, Allergic rhinitis, Asthma, Severe refractory asthma, Pharyngitis, Pleurisy, Rhinopharyngitis, Seasonal allergic rhinitis, Sinusitis, Status asthmaticus, Tracheobronchitis, Rhinitis, Serositis, Meningitis, Neuromyelitis optica, Poliovirus infection, Alport syndrome, Balanitis, Epididymitis, Epididymo orchitis, Focal segmental, Glomerulosclerosis, Glomerulonephritis, IgA Nephropathy (Berger's Disease), Orchitis, Parametritis, Pelvic inflammatory disease, Prostatitis, Pyelitis, Pyelocystitis, Pyelonephritis, Wegener granulomatosis, Hyperuricemia, Aortitis, Arteritis, Chylopericarditis, Dressler syndrome, Endarteritis, Endocarditis, Extracranial temporal arteritis, HIV associated arteritis, Intracranial temporal arteritis, Kawasaki disease, Lymphangiophlebitis, Mondor disease, Periarteritis, or Pericarditis.

In other aspects, the compounds disclosed herein are used for the treatment of Autoimmune hepatitis, Jejunitis, Mesenteritis, Mucositis, Non alcoholic steatohepatitis, Non viral hepatitis, Autoimmune pancreatitis, Perihepatitis, Peritonitis, Pouchitis, Proctitis, Pseudomembranous colitis, Rectosigmoiditis, Salpingoperitonitis, Sigmoiditis, Steatohepatitis, Ulcerative colitis, Churg Strauss syndrome, Ulcerative proctitis, Irritable bowel syndrome, Gastrointestinal inflammation, Acute enterocolitis, Anusitis, Balser necrosis, Cholecystitis, Colitis, Crohns disease, Diverticulitis, Enteritis, Enterocolitis, Enterohepatitis, Eosinophilic esophagitis, Esophagitis, Gastritis, Hemorrhagic enteritis, Hepatitis, Hepatitis virus infection, Hepatocholangitis, Hypertrophic gastritis, Ileitis, Ileocecitis, Sarcoidosis, Inflammatory bowel disease, Ankylosing spondylitis, Rheumatoid arthritis, Juvenile rheumatoid arthritis, Psoriasis, Psoriatic arthritis, Lupus (cutaneous/systemic/nephritis), AIDS, Agammaglobulinemia, AIDS related complex, Bretons disease, Chediak Higashi syndrome, Common variable immunodeficiency, DiGeorge syndrome, Dysgammaglobulinemia, Immunoglobulindeficiency, Job syndrome, Nezelof syndrome, Phagocyte bactericidal disorder, Wiskott Aldrich syndrome, Asplenia, Elephantiasis, Hypersplenism, Kawasaki disease, Lymphadenopathy, Lymphedema, Lymphocele, Norme Milroy Meige syndrome, Spleen disease, Splenomegaly, Thymoma, Thymus disease, Perivasculitis, Phlebitis, Pleuropericarditis, Polyarteritis nodosa, Vasculitis, Takayasus arteritis, Temporal arteritis, Thromboangiitis, Thromboangiitis obliterans, Thromboendocarditis, Thrombophlebitis, or COPD.

In some embodiments, provided herein is a method of treating a cardiovascular disease in a subject that comprises administering to said subject a therapeutically effective amount of a compound as disclosed herein, or a pharmaceutically acceptable form (e.g., pharmaceutically acceptable salts, hydrates, solvates, isomers, prodrugs, and isotopically labeled derivatives) thereof. Examples of cardiovascular conditions include, but are not limited to, atherosclerosis, restenosis, vascular occlusion and carotid obstructive disease.

In another aspect, provided herein are methods of disrupting the function of a leukocyte or disrupting a function of an osteoclast. The method includes contacting the leukocyte or the osteoclast with a function disrupting amount of a compound as described herein.

In another aspect, methods are provided for treating ophthalmic disease by administering one or more of the subject compounds or pharmaceutical compositions to the eye of a subject.

In some embodiments, provided herein are methods of modulating a PI3K and/or mTor kinase activity by contacting the kinase with an amount of an effective amount of compound as disclosed herein. Modulate can be inhibiting or activating kinase activity. In some embodiments, provided herein are methods of inhibiting kinase activity by contacting the kinase with an amount of an effective amount of a compound disclosed herein in solution. In some embodiments, provided herein are methods of inhibiting the kinase activity by contacting a cell, tissue, organ that express the kinase of interest. In some embodiments, provided herein are methods of inhibiting kinase activity in a subject (e.g., a human) by administering into the subject an effective amount of a compound as disclosed herein. In some embodiments, the percentage of inhibiting exceeds 50%, 60%, 70%, 80%, or 90%.

In some embodiments, the kinase is a lipid kinase or a protein kinase. In some embodiments, the kinase is selected from a PI3 kinase including different isoforms such as PI3 kinase α, PI3 kinase β, PI3 kinase γ, PI3 kinase δ; DNA-PK; mTor; Abl, VEGFR, Ephrin receptor B4 (EphB4); TEK receptor tyrosine kinase (TIE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulsin Receptor (1R) and IGFR. In some embodiments, disclosed herein are methods of modulating PI3 kinase activity by contacting a PI3 kinase with an amount of a compound as disclosed herein sufficient to modulate the activity of the PI3 kinase. Modulate can be inhibiting or activating PI3 kinase activity. In some embodiments, provided herein are methods of inhibiting PI3 kinase activity by contacting a PI3 kinase with an amount of a compound as disclosed herein coefficient to inhibit the activity of the PI3 kinase. In some embodiments, provided herein are methods of inhibiting PI3 kinase activity. Such inhibition can take place in solution, in a cell expressing one or more PI3 kinases, in a tissue comprising a cell expressing one or more PI3 kinases, or in an organism expressing one or more PI3 kinases. In some embodiments, provided herein are methods of inhibiting PI3 kinase activity in a subject (including mammals such as humans) by contacting said subject with an amount of a compound as disclosed herein sufficient to inhibit the activity of the PI3 kinase in said subject.

5. Combination Therapy

In some embodiments, provided herein are methods for combination therapies in which an agent known to modulate other pathways, or other components of the same pathway, or even overlapping sets of target enzymes are used in combination with a compound as disclosed herein, or a pharmaceutically acceptable salt, ester, prodrug or derivative thereof. In one aspect, such therapy includes but is not limited to the combination of the subject compound with chemotherapeutic agents, therapeutic antibodies, and radiation treatment, to provide a synergistic or additive therapeutic effect.

In one aspect, the compounds or pharmaceutical compositions as disclosed herein can present synergistic or additive efficacy when administered in combination with agents that inhibit IgE production or activity. Such combination can reduce the undesired effect of high level of IgE associated with the use of one or more PI3Kδ inhibitors, if such effect occurs. This can be particularly useful in treatment of autoimmune and inflammatory disorders (AIID) such as rheumatoid arthritis. Additionally, the administration of PI3Kδ or PI3Kγ inhibitors as disclosed herein in combination with inhibitors of mTOR can also exhibit synergy through enhanced inhibition of the PI3K pathway.

In a separate but related aspect, provided herein is a combination treatment of a disease associated with PI3Kδ comprising administering to a PI3Kδ inhibitor and an agent that inhibits IgE production or activity. Other exemplary PI3Kδ inhibitors are applicable and they are described, e.g., U.S. Pat. No. 6,800,620. Such combination treatment is particularly useful for treating autoimmune and inflammatory diseases (AIID) including but not limited to rheumatoid arthritis.

Agents that inhibit IgE production are known in the art and they include but are not limited to one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as for example Omalizumab and TNX-901.

For treatment of autoimmune diseases, the subject compounds or pharmaceutical compositions can be used in combination with commonly prescribed drugs including but not limited to Enbrel®, Remicade®, Humira®, Avonex®, and Rebif®. For treatment of respiratory diseases, the subject compounds or pharmaceutical compositions can be administered in combination with commonly prescribed drugs including but not limited to Xolair®, Advair®, Singulair®, and Spiriva®.

The compounds as disclosed herein can be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. A commonly prescribed drug of this type is Prednisone. Chloroquine (Aralen) or hydroxychloroquine (Plaquenil) can also be very useful in some individuals with lupus. They can be prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin. Other compounds used in the treatment of lupus include belimumab (Benlysta®).

In another aspect, provided herein are pharmaceutical compositions for inhibiting abnormal cell growth in a subject which comprises an amount of a compound as disclosed herein, or a pharmaceutically acceptable form (e.g., pharmaceutically acceptable salts, hydrates, solvates, isomers, prodrugs, and isotopically labeled derivatives) thereof, in combination with an amount of an anti-cancer agent (e.g. a biotherapeutic chemotherapeutic agent). Many chemotherapeutics are presently known in the art and can be used in combination with the compounds described herein. Other cancer therapies can also be used in combination with the compounds described herein and include, but are not limited to, surgery and surgical treatments, and radiation therapy.

In some embodiments, the chemotherapeutic is selected from mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec® (Imatinib Mesylate), Velcade® (bortezomib), Casodex (bicalutamide), Iressa®, and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethyla-mine; urethan; vindesine; dacarbazine; mannomustine; mitobronitol; mitolactol; pipobroman; gacytosine; arabinoside ("Ara-C"); cyclophosphamide; thiotepa; taxanes, e.g., paclitaxel (TAXOL™, Bristol-Myers Squibb Oncology, Princeton, N.J.) and docetaxel (TAXOTERE™, Rhone-Poulenc Rorer, Antony, France) and ABRAXANE® (paclitaxel protein-bound particles); retinoic acid; esperamicins; capecitabine; and pharmaceutically acceptable forms, salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). Where desired, the compounds or pharmaceutical composition as disclosed herein can be used in combination with commonly prescribed anti-cancer drugs such as Herceptin®, Avastin®, Erbitux®, Rituxan®, Taxol®, Arimidex®, Taxotere®, ABVD, AVICINE, Abagovomab, Acridine carboxamide, Adecatumumab, 17-N-Allylamino-17-demethoxygeldanamycin, Alpharadin, Alvocidib, 3-Aminopyridine-2-carboxaldehyde thiosemicarbazone, Amonafide, Anthracenedione, Anti-CD22 immunotoxins, Antineoplastic, Antitumorigenic herbs, Apaziquone, Atiprimod, Azathioprine, Belotecan, Bendamustine, BIBW 2992, Biricodar, Brostallicin, Bryostatin, Buthionine sulfoximine, CBV (chemotherapy), Calyculin, cell-cycle nonspecific antineoplastic agents, Dichloroacetic acid, Discodermolide, Elsamitrucin, Enocitabine, Epothilone, Eribulin, Everolimus, Exatecan, Exisulind, Ferruginol, Forodesine, Fosfestrol, ICE chemotherapy regimen, IT-101, Imexon, Imiquimod, Indolocarbazole, Irofulven, Laniquidar, Larotaxel, Lenalidomide, Lucanthone, Lurtotecan, Mafosfamide, Mitozolomide, Nafoxidine, Nedaplatin, Olaparib, Ortataxel, PAC-1, Pawpaw, Pixantrone, Proteasome inhibitor, Rebeccamycin, Resiquimod, Rubitecan, SN-38, Salinosporamide A, Sapacitabine, Stanford V, Swainsonine, Talaporfin, Tariquidar, Tegafur-uracil, Temodar, Tesetaxel, Triplatin tetranitrate, Tris (2-chloroethyl)amine, Troxacitabine, Uramustine, Vadimezan, Vinflunine, ZD6126, and Zosuquidar.

In some embodiments, the chemotherapeutic is selected from hedgehog inhibitors including, but not limited to IPI-926 (See U.S. Pat. No. 7,812,164). Other suitable hedgehog inhibitors include, for example, those described and disclosed in U.S. Pat. No. 7,230,004, U.S. Patent Application Publication No. 2008/0293754, U.S. Patent Application Publication No. 2008/0287420, and U.S. Patent Application Publication No. 2008/0293755, the entire disclosures of which are incorporated by reference herein. Examples of other suitable hedgehog inhibitors include those described in U.S. Patent Application Publication Nos. US 2002/0006931, US 2007/0021493 and US 2007/0060546, and International Application Publication Nos. WO 2001/19800, WO 2001/26644, WO 2001/27135, WO 2001/49279, WO 2001/74344, WO 2003/011219, WO 2003/088970, WO 2004/020599, WO 2005/013800, WO 2005/033288, WO 2005/032343, WO 2005/042700, WO 2006/028958, WO 2006/050351, WO 2006/078283, WO 2007/054623, WO 2007/059157, WO 2007/120827, WO 2007/131201, WO 2008/070357, WO 2008/110611, WO 2008/112913, and WO 2008/131354. Additional examples of hedgehog inhibitors include, but are not limited to, GDC-0449 (also known as RG3616 or vismodegib) described in, e.g., Von Hoff D. et al., *N. Engl. J. Med.* 2009; 361(12):1164-72; Robarge K. D. et al., *Bioorg Med Chem Lett.* 2009; 19(19):5576-81; Yauch, R. L. et al. (2009) *Science* 326: 572-574; Sciencexpress: 1-3 (10.1126/science.1179386); Rudin, C. et al. (2009) *New England J of Medicine* 361-366 (10.1056/nejma0902903); BMS-833923 (also known as XL139) described in, e.g., in Siu L. et al., *J. Clin. Oncol.* 2010; 28:15s (suppl; abstr 2501); and National Institute of Health Clinical Trial Identifier No. NCT006701891; LDE-225 described, e.g., in Pan S. et al., *ACS Med. Chem. Lett.*, 2010; 1(3): 130-134; LEQ-506 described, e.g., in National Institute of Health Clinical Trial Identifier No. NCT01106508; PF-04449913 described, e.g., in National Institute of Health Clinical Trial Identifier No. NCT00953758; Hedgehog pathway antagonists disclosed in U.S. Patent Application Publication No. 2010/0286114; SMOi2-17 described, e.g., U.S. Patent Application Publication No. 2010/0093625; SANT-1 and SANT-2 described, e.g., in Rominger C. M. et al., *J. Pharmacol. Exp. Ther.* 2009; 329(3):995-1005; 1-piperazinyl-4-arylphthalazines or analogues thereof, described in Lucas B. S. et al., *Bioorg. Med. Chem. Lett.* 2010; 20(12):3618-22.

Other chemotherapeutic agents include, but are not limited to, anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (Abraxane), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), Ca2+ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (Velcade)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, caminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, caminomycin, aminopterin, and hexamethyl melamine.

Exemplary biotherapeutic agents include, but are not limited to, interferons, cytokines (e.g., tumor necrosis factor, interferon α, interferon γ), vaccines, hematopoietic growth factors, monoclonal serotherapy, immunostimulants and/or immunodulatory agents (e.g., IL-1,2,4,6, or 12), immune cell growth factors (e.g., GM-CSF) and antibodies (e.g. Herceptin (trastuzumab), T-DM1, AVASTIN (bevacizumab), ERBITUX (cetuximab), Vectibix (panitumumab), Rituxan (rituximab), Bexxar (tositumomab)).

In some embodiments, the chemotherapeutic is selected from HSP90 inhibitors. The HSP90 inhibitor can be a geldanamycin derivative, e.g., a benzoquinone or hygroquinone ansamycin HSP90 inhibitor (e.g., IPI-493 and/or IPI-504). Non-limiting examples of HSP90 inhibitors include IPI-493, IPI-504, 17-AAG (also known as tanespimycin or CNF-1010), BIIB-021 (CNF-2024), BIIB-028, AUY-922 (also known as VER-49009), SNX-5422, STA-9090, AT-13387, XL-888, MPC-3100, CU-0305, 17-DMAG, CNF- 1010, Macbecin (e.g., Macbecin I, Macbecin II), CCT-018159, CCT-129397, PU-H71, or PF-04928473 (SNX-2112).

In some embodiments, the chemotherapeutic is selected from PI3K inhibitors (e.g., including those PI3K inhibitors disclosed herein and those PI3K inhibitors not disclosed herein). In some embodiment, the PI3K inhibitor is an inhibitor of delta and gamma isoforms of PI3K. In some embodiments, the PI3K inhibitor is an inhibitor of alpha isoforms of PI3K. In other embodiments, the PI3K inhibitor is an inhibitor of one or more alpha, beta, delta and gamma isoforms of PI3K. Exemplary PI3K inhibitors that can be used in combination are described in, WO 09/088,990, WO 09/088,086, WO 2011/008302, WO 2010/036380, WO 2010/006086, WO 09/114,870, WO 05/113556; US 2009/0312310, and US 2011/0046165. Additional PI3K inhibitors that can be used in combination with the pharmaceutical compositions, include but are not limited to, GSK 2126458, GDC-0980, GDC-0941, Sanofi XL147, XL756, XL147, PF-46915032, BKM 120, CAL-101, CAL 263, SF1126, PX-886, and a dual PI3K inhibitor (e.g., Novartis BEZ235). In one embodiment, the PI3K inhibitor is an isoquinolinone.

In some embodiments, provided herein is a method for using the compounds or pharmaceutical composition in combination with radiation therapy in inhibiting abnormal cell growth or treating the hyperproliferative disorder in the subject. Techniques for administering radiation therapy are known in the art, and these techniques can be used in the combination therapy described herein. The administration of the compound as disclosed herein in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds as disclosed herein can render abnormal cells more sensitive to treatment with radiation for purposes of killing and/or inhibiting the growth of such cells. Accordingly, provided herein is a method for sensitizing abnormal cells in a subject to treatment with radiation which comprises administering to the subject an amount of a compound as disclosed herein or pharmaceutically acceptable forms (e.g., pharmaceutically acceptable salts, hydrates, solvates, isomers, prodrugs, and isotopically labeled derivatives) thereof, which amount is effective is sensitizing abnormal cells to treatment with radiation. The amount of the compound or pharmaceutically acceptable form in this method can be determined according to the means for ascertaining effective amounts of such compounds described herein.

The compounds or pharmaceutical compositions as disclosed herein can be used in combination with an amount of one or more substances selected from anti-angiogenesis agents, signal transduction inhibitors, and antiproliferative agents, glycolysis inhibitors, or autophagy inhibitors.

Anti-angiogenesis agents, such as MMP-2 (matrix-metalloproteinase 2) inhibitors, MMP-9 (matrix-metalloprotienase 9) inhibitors, and COX-11 (cyclooxygenase 11) inhibitors, can be used in conjunction with a compound as disclosed herein and pharmaceutical compositions described herein. Anti-angiogenesis agents include, for example, rapamycin, temsirolimus (CCI-779), everolimus (RAD001), sorafenib, sunitinib, and bevacizumab. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published Can 31,1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. In some embodiments, MMP-2 and MMP-9 inhibitors are those that have little or no activity inhibiting MMP-1. In other embodiments, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors are AG-3340, RO 32-3555, and RS 13-0830.

Autophagy inhibitors include, but are not limited to, chloroquine, 3-methyladenine, hydroxychloroquine (Plaquenil™), bafilomycin A1, 5-amino-4-imidazole carboxamide riboside (AICAR), okadaic acid, autophagy-suppressive algal toxins which inhibit protein phosphatases of type 2A or type 1, analogues of cAMP, and drugs which elevate cAMP levels such as adenosine, LY204002, $N^6$-mercaptopurine riboside, and vinblastine. In addition, antisense or siRNA that inhibits expression of proteins including but not limited to ATG5 (which are implicated in autophagy), can also be used.

In some embodiments, disclosed herein is a method of and/or a pharmaceutical composition for treating a cardiovascular disease in a subject which comprises an amount of a compound as disclosed herein, or a pharmaceutically acceptable forms (e.g., pharmaceutically acceptable salts, hydrates, solvates, isomers, prodrugs, and isotopically labeled derivatives) thereof, and an amount of one or more therapeutic agents use for the treatment of cardiovascular diseases.

Exemplary agents for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, anti-proliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings. Moreover, a coating can be used to effect therapeutic delivery focally within the vessel wall. By incorporation of the active agent in a swellable polymer, the active agent will be released upon swelling of the polymer.

The compounds described herein can be formulated or administered in conjunction with liquid or solid tissue barriers also known as lubricants. Examples of tissue barriers include, but are not limited to, polysaccharides, polyglycans, seprafilm, interceed and hyaluronic acid.

Medicaments which can be administered in conjunction with the compounds described herein include any suitable drugs usefully delivered by inhalation for example, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamine, pirbuterol, reproterol, rimiterol, salbutamol, salmeterol, terbutalin, isoetharine, tulobuterol, orciprenaline or (−)-4-amino-3,5-dichloro-α-[[[6-[2-(2-pyridinyl)ethoxy]hexyl]-amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be clear to a person skilled in the art that, where appropriate, the medicaments can be used in the form of salts (e.g. as alkali metal or amine salts or as acid addition salts) or as esters (e.g. lower alkyl esters) to optimize the activity and/or stability of the medicament.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat malaria, amebiasis, giardiasis, trichomoniasis, trypanosomiasis, and/or leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-lactam antibiotics, an agent containing an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

For treating renal carcinoma, one can combine a compound as disclosed herein with sorafenib and/or avastin. For treating an endometrial disorder, one can combine a compound as disclosed herein with doxorubincin, taxotere (taxol), and/or cisplatin (carboplatin). For treating ovarian cancer, one can combine a compound as disclosed herein with cisplatin (carboplatin), taxotere, doxorubincin, topotecan, and/or tamoxifen. For treating breast cancer, one can combine a compound as disclosed herein with taxotere (taxol), gemcitabine (capecitabine), tamoxifen, letrozole, tarceva, lapatinib, PD0325901, avastin, herceptin, OSI-906, and/or OSI-930. For treating lung cancer, one can combine a compound as disclosed herein with taxotere (taxol), gemcitabine, cisplatin, pemetrexed, Tarceva, PD0325901, and/or avastin.

Further therapeutic agents that can be combined with a subject compound can be found in Goodman and Gilman's "*The Pharmacological Basis of Therapeutics*" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the compounds described herein will be co-administered with other agents as described above. When used in combination therapy, the compounds described herein can be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound as disclosed herein and any of the agents described above can be simultaneously administered, wherein both the agents are present in separate formulations. In another alternative, a compound as disclosed herein can be administered just followed by and any of the agents described above, or vice versa. In the separate administration protocol, a compound as disclosed herein and any of the agents described above can be administered a few minutes apart, or a few hours apart, or a few days apart.

Administration of the compounds as disclosed herein can be effected by any method that enables delivery of the compounds to the site of action. An effective amount of a compound disclosed herein can be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

When a compound as disclosed herein is administered in a pharmaceutical composition that comprises one or more agents, and the agent has a shorter half-life than the compound unit dose forms of the agent and the compound can be adjusted accordingly.

The examples and preparations provided below further illustrate and exemplify the compounds as disclosed herein and methods of preparing such compounds. It is to be understood that the scope of the present disclosure is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers can be obtained by methods known to those skilled in the art.

EXAMPLES

Chemical Examples

The chemical entities described herein can be synthesized according to one or more illustrative schemes herein and/or techniques known in the art.

Unless specified to the contrary, the reactions described herein take place at atmospheric pressure, generally within a temperature range from $-10°$ C. to $200°$ C. Further, except as otherwise specified, reaction times and conditions are intended to be approximate, e.g., taking place at about atmospheric pressure within a temperature range of about $-10°$ C. to about $110°$ C. over a period of about 1 to about 24 hours; reactions left to run overnight average a period of about 16 hours.

The terms "solvent," "organic solvent," or "inert solvent" each mean a solvent inert under the conditions of the reaction being described in conjunction therewith including, for example, benzene, toluene, acetonitrile, tetrahydrofuran ("THF"), dimethylformamide ("DMF"), chloroform, methylene chloride (or dichloromethane), diethyl ether, methanol, N-methylpyrrolidone ("NMP"), pyridine and the like. Unless specified to the contrary, the solvents used in the reactions described herein are inert organic solvents. Unless specified to the contrary, for each gram of the limiting reagent, one cc (or mL) of solvent constitutes a volume equivalent.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures are given by reference to the examples hereinbelow. However, other equivalent separation or isolation procedures can also be used.

When desired, the (R)- and (S)-isomers of the non-limiting exemplary compounds, if present, can be resolved by methods known to those skilled in the art, for example by formation of diastereoisomeric salts or complexes which can be separated, for example, by crystallization; via formation of diastereoisomeric derivatives which can be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer can be synthesized by asymmetric synthesis using optically active reagents, substrates, catalysts or solvents, or by converting one enantiomer to the other by asymmetric transformation.

The compounds described herein can be optionally contacted with a pharmaceutically acceptable acid to form the corresponding acid addition salts. Also, the compounds described herein can be optionally contacted with a pharmaceutically acceptable base to form the corresponding basic addition salts.

In some embodiments, disclosed compounds can generally be synthesized by an appropriate combination of generally well known synthetic methods. Techniques useful in synthesizing these chemical entities are both readily apparent and accessible to those of skill in the relevant art, based on the instant disclosure. Many of the optionally substituted starting compounds and other reactants are commercially available, e.g., from Aldrich Chemical Company (Milwaukee, Wis.) or can be readily prepared by those skilled in the art using commonly employed synthetic methodology.

The discussion below is offered to illustrate certain of the diverse methods available for use in making the disclosed compounds and is not intended to limit the scope of reactions or reaction sequences that can be used in preparing the compounds provided herein.

General Synthetic Methods

The compounds now being generally described, it will be more readily understood by reference to the following examples, which are included merely for purposes of illustration of certain aspects and embodiments of the embodiments disclosed herein, and are not intended to limit these embodiments.

(i) General Methods for the Synthesis of Cl—$W_d$ and TsO—$W_d$ Heterocycles

Method A:

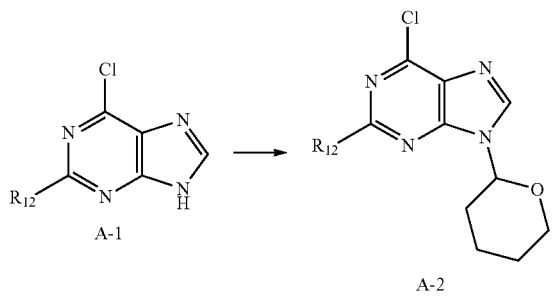

General conditions for the preparation of 6-chloro-9-(tetrahydro-2H-pyran-2-yl)-9H-purines To a solution of 6-chloro-9H-purine (A-1) (1.29 mol, 1 eq) and anhydrous TsOH (0.02 mol, 0.015 eq) in ethyl acetate (1000 mL), 3,4-dihydro-2H-pyran (1.94 mol, 1.5 eq) is added and the resulting mixture is stirred at reflux for 2 h. The reaction mixture is allowed to cool to RT, aqueous $Na_2CO_3$ solution (3%, 500 mL) is added and the resulting mixture is stirred for 10 min. The organic layer is separated, washed with water (2×500 mL) and brine (500 mL), dried over anhydrous $Na_2SO_4$, and filtered. The filtrate is concentrated in vacuo. The product is dissolved in ethyl acetate (50 mL), and then n-heptane (500 mL) is added. The resulting mixture is stirred at RT for 1 h. The precipitate is collected by filtration, rinsed with heptane (100 mL) and dried in vacuo to afford the product, 6-chloro-9-(tetrahydro-2H-pyran-2-yl)-9H-purine (A-2).

Method B:

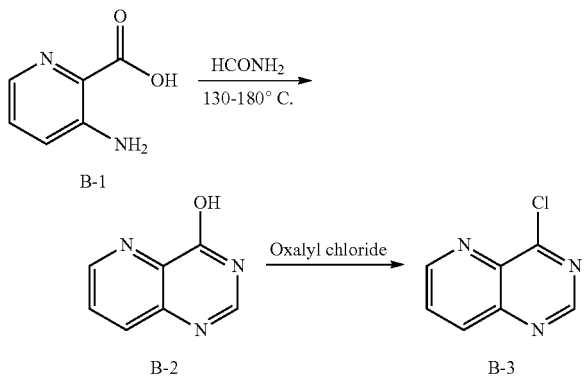

General conditions for the preparation of 4-chloropyrido[3,2-d]pyrimidine

3-Aminopicolinic acid (B-1) (30 g, 217 mmol, 1.0 eq) is suspended in formamide (75 mL, 1.88 mol, 8.66 eq). The resulting mixture is stirred at 140° C. for 1 h and at 170° C. for 1 h and then at 180° C. for an additional 1 h. The mixture is cooled to RT and filtered. The filter cake is washed with water, and dried in vacuo to afford the product, pyrido[3,2-d]pyrimidin-4-ol (B-2).

To a stirred solution pyrido[3,2-d]pyrimidin-4-ol (B-2) (16 g, 109 mmol, 1.0 eq) in DCM (200 mL) and DMF (0.4 mL) at RT, oxalyl chloride (23.2 mL, 272 mmol, 2.5 eq) is added dropwise (over 5 min) and the resulting mixture is stirred at reflux overnight. The mixture is allowed to cool to RT and concentrated in vacuo. The residue is diluted with water (200 mL), neutralized with saturated aqueous $NaHCO_3$ solution below 10° C. to adjust the pH to 8-9 and then extracted with ethyl acetate (4×100 mL). The combined organic layers are washed with brine, dried over $Na_2SO_4$ and filtered. The filtrate is concentrated in vacuo. The residue is purified by flash column chromatography on silica gel (16-50% ethyl acetate-petroleum ether) to afford the product, 4-chloropyrido[3,2-d]pyrimidine (B-3).

Method C:

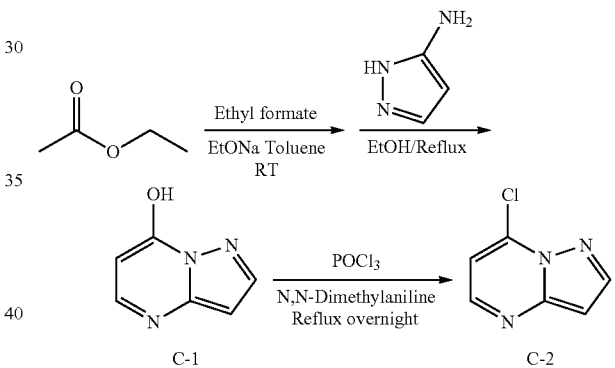

General conditions for the preparation of 7-chloropyrazolo[1,5-a]pyrimidine

To a mixture of ethyl acetate (88 g, 1.0 mol, 1.0 eq) and ethyl formate (74 g, 1.0 mol, 1.0 eq) in toluene (100 mL), sodium ethoxide (68 g, 1.0 mol, 1.0 eq) is added and the resulting mixture is stirred at RT overnight. The reaction mixture is concentrated in vacuo to remove the solvent. The resulting residue is suspended in EtOH (100 mL) and then 1H-pyrazol-5-amine (41.5 g, 0.5 mol, 0.5 eq) is added in portions to the mixture. The resulting mixture is stirred at reflux for 5 h and concentrated in vacuo. The residue is suspended in ice-water (200 mL) and neutralized with conc. HCl to adjust pH to 1. The resulting solid is collected by filtration and dried in vacuo to afford the product, pyrazolo[1,5-a]pyrimidin-7-ol (C-1).

To a solution of pyrazolo[1,5-a]pyrimidin-7-ol (C-1) (19.0 g, 14.1 mmol, 1.0 eq) in phosphoroxychloride (100 mL, 1.06 mol, 76 eq) at RT, N,N-dimethylaniline (7.0 g, 58.0 mmol, 4.1 eq) is added dropwise and the resulting mixture is stirred at reflux overnight. The mixture is allowed to cool to RT and concentrated in vacuo to remove the phosphoroxychloride. The residue is poured into ice water (200 mL), neutralized with saturated aqueous NaHCO$_3$ solution to adjust the pH to 8-9 while keeping the temperature below 5° C. The mixture is stirred at RT for 30 min and then extracted with ethyl acetate (4×200 mL). The combined organic layers are washed with brine, dried over Na$_2$SO$_4$ and filtered. The filtrate is concentrated in vacuo and the residue is purified by flash column chromatography on silica gel (1-3% ethyl acetate-petroleum ether) to afford the product, 7-chloropyrazolo[1,5-a]pyrimidine (C-2).

Method D:

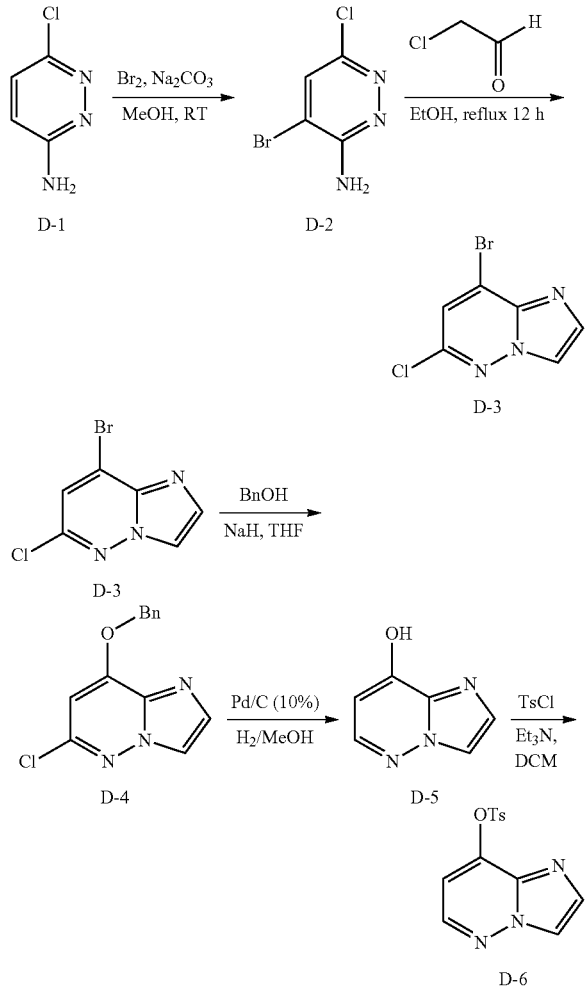

General conditions for the preparation of 6,8-dichloroimidazo[1,2-b]pyridazine and imidazo[1,2-b]pyridazin-8-yl-4-methylbenzenesulfonate To a stirred mixture of 6-chloropyridazin-3-amine (D-1) (52.0 g, 0.4 mol, 1.0 eq) and sodium carbonate (84.8 g, 0.8 mol, 2.0 eq) in MeOH (500 mL) at RT, bromine (70.6 g, 0.44 mol, 1.1 eq) is added dropwise and the resulting mixture is stirred overnight. The reaction mixture is filtered and the filter cake is washed with ethyl acetate. The filtrate is concentrated in vacuo and the residue is poured into water (300 mL). The resulting mixture is extracted with ethyl acetate (2×300 mL). The combined organic layers are dried over Na$_2$SO$_4$ and filtered. The filtrate is concentrated in vacuo and the residue is purified by flash column chromatography on silica gel (0-50% ethyl acetate-petroleum ether) to afford the product, 4-bromo-6-chloropyridazin-3-amine (D-2).

To a stirred solution of 4-bromo-6-chloropyridazin-3-amine (D-2) (16 g, 77.3 mmol, 1.0 eq) in EtOH (200 mL), 2-chloroacetaldehyde (45% in water, 67.4 g, 386.6 mmol, 5.0 eq) is added and the resulting mixture is stirred at reflux overnight. The mixture is allowed to cool to RT and concentrated in vacuo to remove EtOH. The residue is slurried in acetone. The solid is collected by filtration and washed with acetone. The solid is suspended in water, neutralized with aqueous ammonia to adjust the pH to 8 at 0-5° C. and then extracted with ethyl acetate (2×150 mL). The combined layers are washed with brine, dried over Na$_2$SO$_4$ and filtered. The filtrate is concentrated in vacuo to afford the product, 8-bromo-6-chloroimidazo[1,2-b]pyridazine (D-3).

To a stirred solution of phenylmethanol (3.35 g, 31 mmol, 1.2 eq) in THF (80 mL), NaH (60% dispersion in mineral oil, 1.34 g, 33.5 mmol, 1.3 eq) is added in portions. The resulting mixture is stirred at RT for 30 min and then 8-bromo-6-chloroimidazo[1,2-b]pyridazine (D-3) (6 g, 25.8 mmol, 1.0 eq) is added. The resulting mixture is stirred at RT for an additional 2 h and then poured into water (30 mL). The mixture is extracted with ethyl acetate (2×100 mL). The combined organic layers are washed with brine, dried over Na$_2$SO$_4$ and filtered. The filtrate is concentrated in vacuo to afford the product, 8-(benzyloxy)-6-chloroimidazo[1,2-b] pyridazine (D-4).

To a stirred solution of 8-(benzyloxy)-6-chloroimidazo[1,2-b]pyridazine (D-4) (6.2 g, 23.8 mmol, 1.0 eq) in MeOH (100 mL), Pd/C (10%, 620 mg) is added. The resulting mixture is degassed and back-filled with hydrogen three times and then stirred at 50° C. under hydrogen for 24 h. The resulting mixture is filtered and concentrated in vacuo to afford the product, imidazo[1,2-b]pyridazin-8-ol hydrochloride (D-5).

To a stirred solution of imidazo[1,2-b]pyridazin-8-ol hydrochloride (D-5) (4 g, 23.3 mmol, 1.0 eq) and triethylamine (7.1 g, 70.0 mmol, 3.0 eq) in DCM (50 mL), 4-toluenesulfonyl chloride (5.3 g, 28.0 mmol, 1.2 eq) is added in portions and the resulting mixture is stirred at RT for 1 h. The mixture is washed with brine, dried over Na$_2$SO$_4$ and filtered. The filtrate is concentrated in vacuo and the residue is purified by flash column chromatography on silica gel (10-50% ethyl acetate-petro ether) to afford the product, imidazo[1,2-b]pyridazin-8-yl-4-methylbenzenesulfonate (D-6).

Method E:

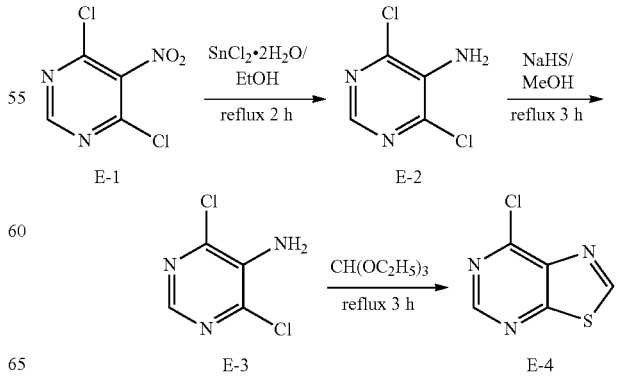

General conditions for the preparation of 7-chlorothiazolo[5,4-d]pyrimidine

A mixture of 4,6-dichloro-5-nitroprimidine (E-1) (20.0 g, 104 mmol) and stannous chloride dihydrate (117.7 g, 520 mmol) in EtOH (300 mL) is stirred at reflux for 2 h. The resulting mixture is allowed to cool to RT and then concentrated in vacuo. The residue is poured into ice water (300 mL) and neutralized with saturated NaHCO₃ aqueous solution to adjust the pH value to 5-6. The resulting mixture is stirred at RT for 30 min and then extracted with ethyl acetate (3×200 mL). The combined organic layers are washed with brine, dried over Na₂SO₄ and filtered. The filtrate is concentrated in vacuo to afford the product, 4,6-dichloropyrimidine-5-amine (E-2).

A mixture of 4,6-dichloropyrimidine-5-amine (E-2) (16.0 g, 98.2 mmol) and sodium hydrosulphide (7.15 g, 128 mmol) in MeOH (320 mL) is stirred at reflux for 3 h. The resulting mixture is allowed to cool to RT and then concentrated in vacuo. The residue is poured into aqueous NaOH solution (200 mL, 1 M) and then neutralized with acetic acid to adjust the pH value to 5-6. The resulting mixture is stirred at RT for 30 min. The solid is collected by filtration, rinsed with water (2×50 mL) and dried in vacuo to afford the product, 5-amino-6-chloropyrimidine-4-thiol (E-3).

5-Amino-6-chloropyrimidine-4-thiol (E-3) (14.0 g, 86.9 mmol) is dissolved in triethoxy methane (180 mL) and the resulting mixture is stirred at reflux for 3 h. The mixture is allowed to cool to RT and then concentrated in vacuo. The residue is purified by flash column chromatography on silica gel (5-10% ethyl acetate-petro ether) to afford the product, 7-chlorothiazolo[5,4-d]pyrimidine (E-4).

Method F:

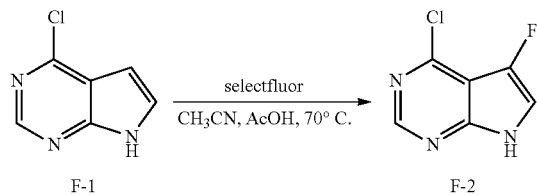

General conditions for the preparation of 4-chloro-5-fluoro-7H-pyrrolo[2,3-d]pyrimidine 4-Chloro-7H-pyrrolo[2,3-d]pyrimidine (F-1) (5.01 g, 32.6 mmol, 1 eq) and selectfluor (17.32 g, 48.9 mmol, 1.5 eq) are dissolved in a mixture of anhydrous acetonitrile (250 mL) and AcOH (50 mL). The resulting mixture is stirred at 70° C. under argon for 16 h. The mixture is concentrated in vacuo. The residue is dissolved in a mixture of DCM-ethyl acetate (v/v=1/1, 50 mL) and filtered through celite. The filtrate is concentrated in vacuo and the residue is purified by flash chromatography on silica gel (0-0.7% MeOH-DCM) to afford the product, 4-chloro-5-fluoro-7H-pyrrolo[2,3-d]pyrimidine (F-2).

Method G:

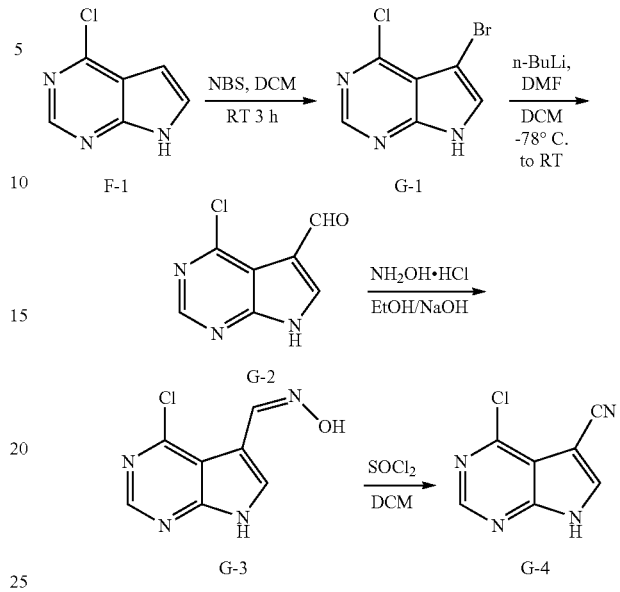

General conditions for the preparation of 4-chloro-7H-pyrrolo[2,3-d]pyrimidine-5-carbonitrile

[To a suspension of 4-chloro-7H-pyrrolo[2,3-d]pyrimidine (F-1) (3.99 g, 26.0 mmol, 1.0 eq) in anhydrous DCM (150 mL) under argon, N-bromosuccinimide (6.02 g, 33.8 mmol, 1.3 eq) is added and the resulting mixture is stirred at RT for 3 h. The reaction mixture is diluted with MeOH (30 mL) and then concentrated in vacuo. The residue is triturated with H₂O (150 mL). This is collected by filtration and then re-crystallized in MeOH to afford the product, 5-bromo-4-chloro-7H-pyrrolo[2,3-d]pyrimidine (G-1).

To a solution of 5-bromo-4-chloro-7H-pyrrolo[2,3-d]pyrimidine (G-1) (2.33 g, 10.0 mmol, 1.0 eq) in anhydrous THF (100 mL) at -78° C. under argon, n-BuLi solution (2.5 M in THF, 8.8 mL, 22.0 mmol, 2.2 eq) is added dropwise (over 10 min). The resulting mixture is stirred at -78° C. for 1 h and then DMF (2.0 g, 11.0 mmol, 1.1 eq) is added dropwise (over 10 min). The mixture is stirred at -78° C. for an additional 30 min and then stirred at RT overnight. The reaction mixture is quenched with H₂O (50 mL) and then concentrated in vacuo. The residue is triturated with saturated aqueous NH₄Cl solution. The solid is collected by filtration, rinsed with ethyl acetate, and dried in vacuo to afford the product, 4-chloro-7H-pyrrolo[2,3-d]pyrimidine-5-carbaldehyde (G-2).

To a suspension of 4-chloro-7H-pyrrolo[2,3-d]pyrimidine-5-carbaldehyde (G-2) (1.17 g, 6.47 mmol, 1.0 eq) and hydroxylamine hydrochloride (0.54 g, 7.77 mmol, 1.2 eq) in EtOH (25 mL), aqueous NaOH solution (0.31 g, 7.77 mmol, 1.2 eq) in H₂O (4 mL) is added dropwise. The resulting mixture is stirred at RT for 30 min and then is diluted with a sufficient amount of EtOH to allow stirring for additional 30 min. The solid is collected by filtration, rinsed with H₂O and dried in vacuo to afford the product, 4-chloro-7H-pyrrolo[2,3-d]pyrimidine-5-carbaldehyde oxime (G-3) as a mixture of isomers.

To a suspension of 4-chloro-7H-pyrrolo[2,3-d]pyrimidine-5-carbaldehyde oxime (G-3) (865 mg, 4.40 mmol, 1.0 eq) in DCM (20 mL), thionyl chloride (3.1 mL, 43.7 mmol, 10.0 eq) is added and the resulting mixture is stirred at RT overnight.

The reaction mixture is concentrated in vacuo. The residue is suspended in water (60 mL) and saturated aqueous NaHCO₃ is added to adjust the pH to 4. The solid is collected by filtration, rinsed with water and followed by ethyl acetate to afford the first batch of product. The filtrate is extracted with ethyl acetate (3×50 mL). The combined organic layers are washed with brine, dried over Na₂SO₄ and filtered. The filtrate is concentrated in vacuo and the residue is combined with the above-obtained solid. The product is re-crystallized in ethyl acetate/hexanes (v/v=1/1) and dried in vacuo to afford the product, 4-chloro-7H-pyrrolo[2,3-d]pyrimidine-5-carbonitrile (G-4).

Method H:

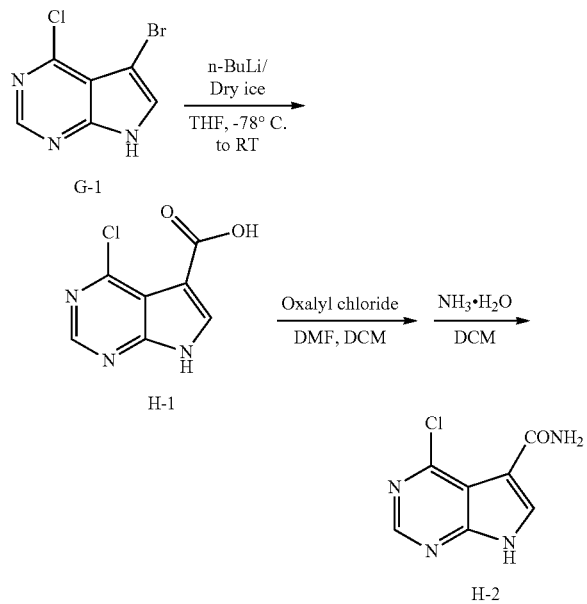

General method for the synthesis of
4-chloro-7H-pyrrolo[2,3-d]pyrimidine-5-carboxamide To a mixture of 5-bromo-4-chloro-7H-pyrrolo[2,3-d]pyrimidine (G-1) (6.24 g, 26.8 mmol, 1.0 eq) in anhydrous THF (100 mL) at −78° C. under argon, n-BuLi solution (2.5 M in THF, 23.6 mL, 59.0 mmol, 2.2 eq) is added dropwise over 30 min. The reaction mixture is stirred at −78° C. for 1 h and then dry ice (300 g) is added in portions under an argon atmosphere. The resulting mixture is allowed to warm to RT and then stirred at RT overnight. The reaction mixture is diluted with H₂O (200 mL) and extracted with ethyl acetate (50 mL×4). The aqueous layer is acidified with conc. HCl to adjust the pH to 3-4. The precipitate is collected by filtration, rinsed with H₂O (30 mL) and dried in vacuo to afford the product, 4-chloro-7H-pyrrolo[2,3-d]pyrimidine-5-carboxylic acid (H-1).

To a stirred suspension of 4-chloro-7H-pyrrolo[2,3-d]pyrimidine-5-carboxylic acid (H-1) (3.11 g, 15.7 mmol, 1.0 eq) and a catalytic amount of DMF in a mixture of DCM (40 mL) and THF (40 mL) at RT, oxalyl chloride (2.0 mL, 23.5 mmol, 1.5 eq) is added dropwise. The resulting mixture is stirred for 2 h and then concentrated in vacuo. The residue is dissolved in DCM (50 mL) and the resulting solution is added dropwise to saturated aqueous ammonium hydroxide (200 mL) at RT. The resulting mixture is stirred for 30 min and then filtered. The filter cake is rinsed with H₂O (30 mL×2). The filtrate is acidified with conc. HCl to adjust the pH to 4-5. The solid is collected by filtration, rinsed with water and dried in vacuo to afford the product, 4-chloro-7H-pyrrolo[2,3-d]pyrimidine-5-carboxamide (H-2).

(ii) General Method for the Synthesis of Isoquinolinyl Amine Core Precursors

Method I:

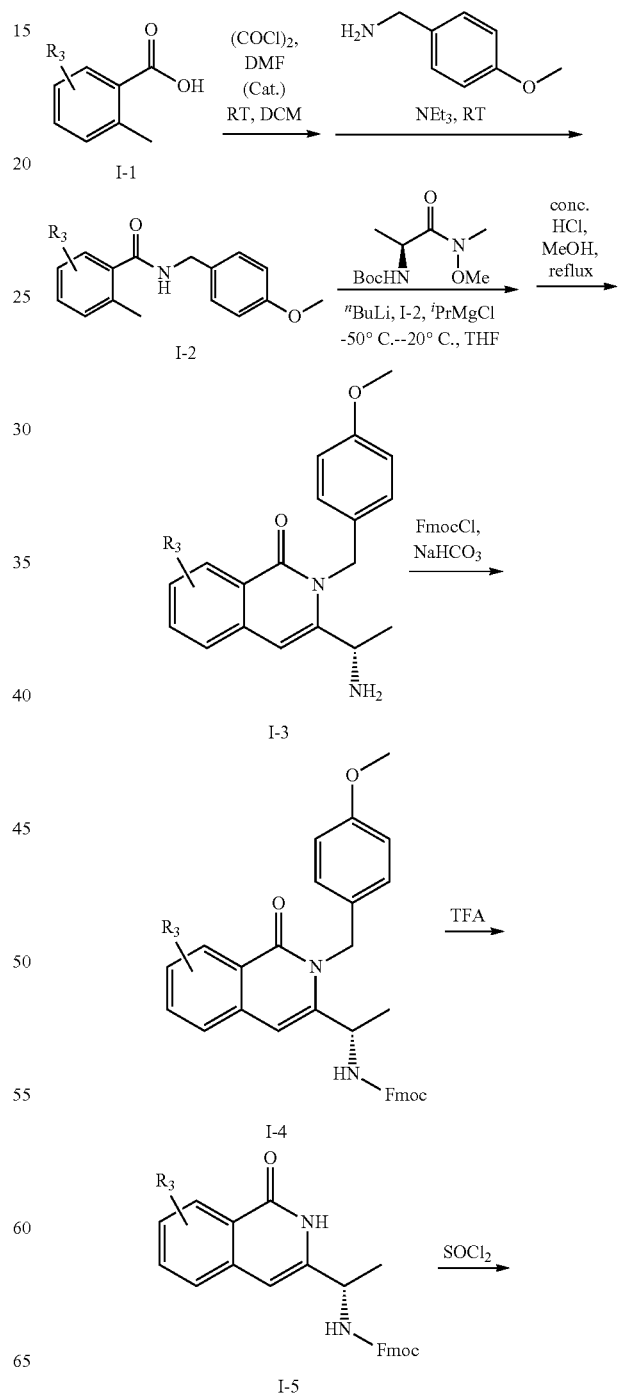

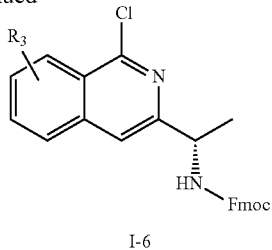

I-6

General conditions for the preparation of (S)-(9H-fluoren-9-yl)methyl 1-(1-chloroisoquinolin-3-yl) ethylcarbamates To a stirred mixture of methylbenzoic acid (I-1) (0.41 mol, 1 eq) and DMF (0.5 mL) in DCM (500 mL) at RT, oxalyl chloride (0.45 mol, 1.1 eq) is added slowly over 5 min. The resulting mixture is stirred at RT for 2 h and then concentrated in vacuo to afford the product, methylbenzoyl chloride. The product is used directly in the next step.

To a stirred mixture of 4-methoxybenzylamine (0.45 mol, 1.1 eq) and triethylamine (0.86 mol, 2.1 eq) in DCM (600 mL), a solution of methylbenzoyl chloride in DCM (50 mL) is added dropwise while keeping the reaction temperature between 25° C. and 40° C. (controlling by an ice-water bath). The resulting mixture is stirred at RT for 2 h and then water (200 mL) is added. The organic layer is separated, washed with water (2×200 mL), dried over anhydrous Na$_2$SO$_4$ and filtered. The filtrate is concentrated in vacuo and the residue is suspended in n-heptane (200 mL) and stirred at RT for 30 min. The precipitate is collected by filtration, rinsed with heptane (100 mL) and further dried in vacuo to afford the product amide (I-2).

To a stirred mixture of amide (I-2) (173 mmol, 1 eq) in anhydrous THF (250 mL) at −30° C. under an argon atmosphere, a solution of n-butyllithium in hexanes (2.5 M, 173 mL, 432 mol, 2.5 eq) is added dropwise over 30 min while keeping inner temperature between −30° C. and −10° C. The resulting mixture A is stirred at −30° C. for 30 min To a stirred mixture of (S)-tert-butyl 1-(methoxy(methyl)amino)-1-oxo-propan-2-ylcarbamate (60.3 g, 260 mmol, 1.5 eq) in anhydrous THF (250 mL) at −30° C. under an argon atmosphere, a solution of isopropylmagnesium chloride in THF (2 M, 143 mL, 286 mmol, 1.65 eq) is added dropwise over 30 min while keeping the inner temperature between −30° C. and −10° C. The resulting mixture is stirred at −30° C. for 30 min. This solution is then slowly added to above reaction mixture A while keeping the inner temperature between −30° C. and −10° C. The resulting mixture is stirred at −15° C. for 1 h. The reaction mixture is then quenched with water (50 mL) and then acidified with conc. HCl (80 mL) at −10-0° C. to adjust the pH to 1-3. The mixture is allowed to warm to RT and concentrated in vacuo to afford the product.

This solid is dissolved in MeOH (480 mL), and then conc. HCl (240 mL) is added quickly at RT. The resulting mixture is stirred at reflux for 1 h. The reaction mixture is concentrated in vacuo to reduce the volume to ca. 450 mL. The residue is extracted with a mixture of heptanes and ethyl acetate (v/v=2/1, 2×500 mL). The aqueous layer is basified with concentrated ammonium hydroxide to adjust the pH value to 9-10 while keeping the inner temperature between −10° C. and 0° C. The mixture is then extracted with DCM (3×300 mL), washed with brine, dried over MgSO$_4$ and filtered. The filtrate is concentrated in vacuo and the residue is dissolved in MeOH (1200 mL) at RT. To this solution, D-(−)-tartaric acid (21 g, 140 mmol, 0.8 eq) is added in one portion at RT. After stirring at RT for 30 min, solid precipitates and the mixture is slurried at RT for 10 h. The solid is collected by filtration and rinsed with MeOH (3×50 mL). The collected solid is suspended in water (500 mL) and then neutralized with concentrated ammonium hydroxide solution at RT to adjust the pH value to 9-10. The mixture is extracted with DCM (3×200 mL). The combined organic layers are washed with brine, dried over MgSO$_4$ and filtered. The filtrate is concentrated in vacuo to afford the product (I-3).

To a stirred mixture of (I-3) (10.0 mmol, 1.0 eq) in DCM (20 mL), saturated aqueous NaHCO$_3$ solution (2.8 mL) is added. The mixture is cooled to 0° C. and 9-fluorenylmethyl chloroformate (10.5 mmol, 1.05 eq) is added in one portion. The resulting mixture is allowed to warm to RT and stirred at RT for 1 h. The organic layers are separated, washed with water (2×50 mL), dried over anhydrous MgSO$_4$ and filtered. The filtrate is concentrated in vacuo to afford the product (I-4).

Compound (I-4) (10.0 mmol, 1.0 eq) is dissolved in TFA (25 mL) and the resulting mixture is stirred at reflux for 1 h. The mixture is allowed to cool to RT and concentrated in vacuo to remove TFA. The resulting residue is partitioned between DCM (50 mL) and saturated aqueous NaHCO$_3$ (50 mL) solution. The organic layer is washed with water (2×20 mL), dried over anhydrous MgSO$_4$ and filtered. The filtrate is concentrated in vacuo to afford the product (I-5).

A mixture of compound (I-5) (45.0 mmol) and DMF (0.3 mL) in SOCl$_2$ (100 mL) is stirred at reflux for 2 h. The mixture is allowed to cool to RT and concentrated in vacuo. The residue is purified by flash column chromatography on silica gel to afford the product (I-6).

(iii) General Conditions for Attachment of W$_d$ Substituents

Method J:

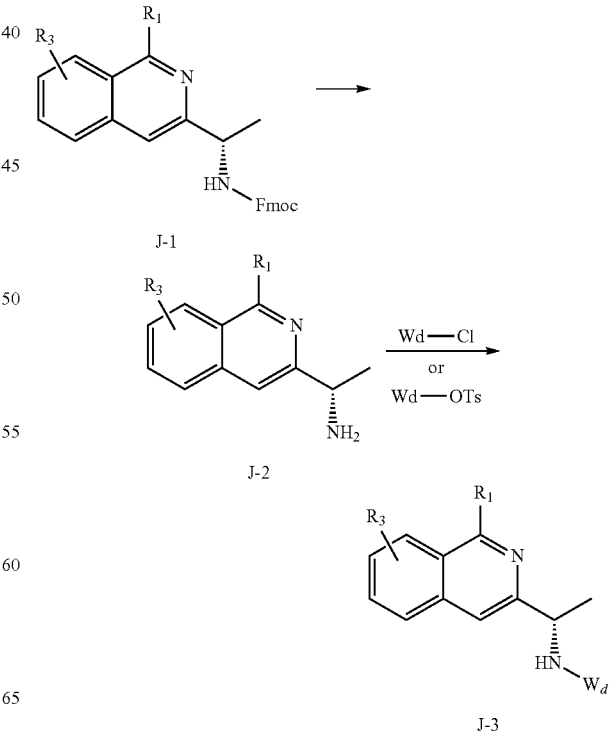

A mixture of compound (J-1) (0.961 mmol, 1.0 eq) in morpholine (45.68 mmol, 47.5 eq) is stirred at RT for 30 min. The reaction mixture is diluted with 1,4-dioxane (10 mL) and then evaporated in vacuo. The residue is purified by flash column chromatography on silica gel (eluting with a mixture solvent of MeOH and DCM) to give the product (J-2).

A mixture of compound (J-2) (1.0 mmol, 1.0 eq), Wd-Cl or Wd-OTs (1.50 mmol, 1.5 eq) and triethylamine (3.0 mmol, 3.0 eq) in n-BuOH (5 mL) is stirred at reflux for 1-5 h. The reaction mixture is allowed to cool to RT and then concentrated in vacuo. The residue is purified by flash column chromatography on silica gel (eluting with a mixture solvent of MeOH and DCM) to afford the product (J-3).

(iv) General method for the synthesis of (S)-1-(1-chloroisoquinolin-3-yl)ethanamine cores Method K:

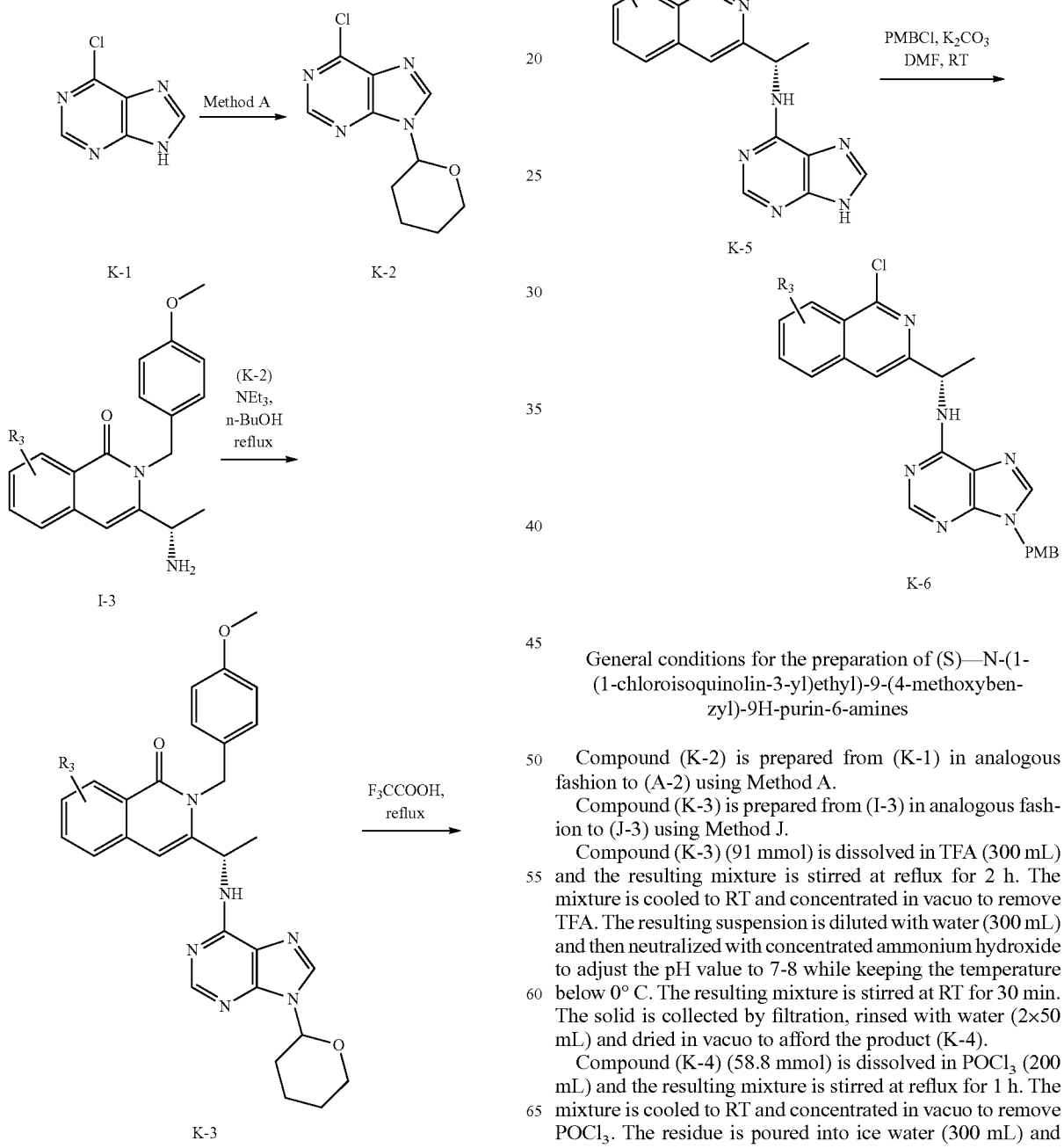

General conditions for the preparation of (S)—N-(1-(1-chloroisoquinolin-3-yl)ethyl)-9-(4-methoxybenzyl)-9H-purin-6-amines Compound (K-2) is prepared from (K-1) in analogous fashion to (A-2) using Method A.

Compound (K-3) is prepared from (I-3) in analogous fashion to (J-3) using Method J.

Compound (K-3) (91 mmol) is dissolved in TFA (300 mL) and the resulting mixture is stirred at reflux for 2 h. The mixture is cooled to RT and concentrated in vacuo to remove TFA. The resulting suspension is diluted with water (300 mL) and then neutralized with concentrated ammonium hydroxide to adjust the pH value to 7-8 while keeping the temperature below 0° C. The resulting mixture is stirred at RT for 30 min. The solid is collected by filtration, rinsed with water (2×50 mL) and dried in vacuo to afford the product (K-4).

Compound (K-4) (58.8 mmol) is dissolved in POCl₃ (200 mL) and the resulting mixture is stirred at reflux for 1 h. The mixture is cooled to RT and concentrated in vacuo to remove POCl₃. The residue is poured into ice water (300 mL) and neutralized with saturated aqueous Na₂CO₃ solution to adjust the pH value to 7-8 while keeping the temperature below 0° C. The resulting mixture is stirred at RT for 30 min and then extracted with a mixture of DCM and MeOH (v/v=10/1, 3×200 mL). The combined organic layers are washed with brine, dried over Na$_2$SO$_4$ and filtered. The filtrate is concentrated in vacuo and the residue is purified by flash column chromatography on silica gel (2-10% MeOH-DCM) to afford the product (K-5).

To a stirred solution of (K-5) (22 mmol, 1.0 eq) and K$_2$CO$_3$ (9.1 g, 66 mmol, 3 eq) in DMF (100 mL) at RT, 1-(chloromethyl)-4-methoxybenzene (4 g, 25.6 mmol, 1.1 eq) is slowly added, and the resulting mixture is stirred at RT overnight. The reaction mixture is poured into water (200 mL) and extracted with DCM (3×100 mL). The combined organic layers are washed with brine, dried over Na$_2$SO$_4$ and filtered. The filtrate is concentrated in vacuo and the residue is purified by flash column chromatography on silica gel (1-5% MeOH-DCM) to afford the product (K-6).

(v) PMB Deprotection Procedure

Method A:

General conditions for the PMB deprotection of (S)—N-(1-(isoquinolin-3-yl)ethyl)-9-(4-methoxybenzyl)-9H-purin-6-amines Compound (L-1) (0.27 mmol) is dissolved in TFA (30 mL) and the resulting mixture is stirred at reflux for 30 min. The mixture is allowed to cool to RT and then concentrated in vacuo to remove TFA. The residue is diluted with water (50 mL), neutralized with concentrated ammonium hydroxide to adjust the pH to 7-8 and then stirred at RT for 30 min. The solid is collected by filtration and further purified by flash column chromatography on silica gel to afford the product (L-2).

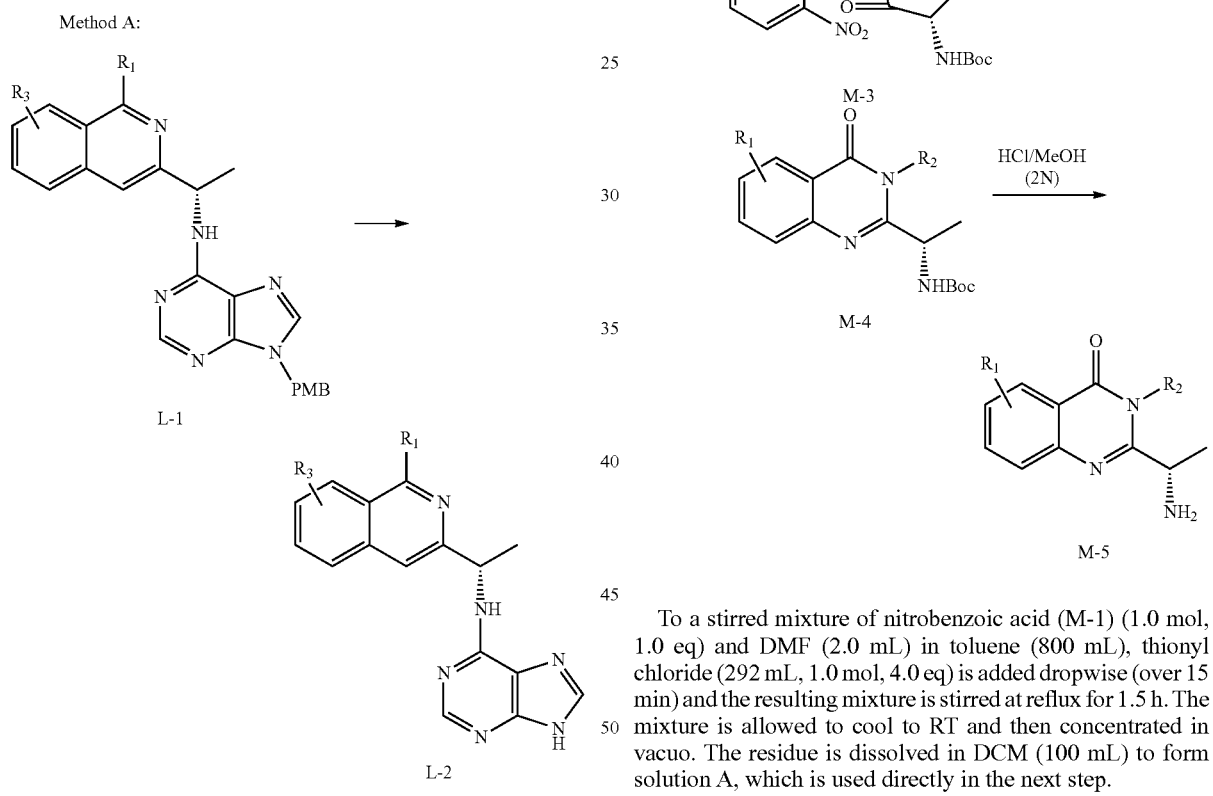

Method M:

To a stirred mixture of nitrobenzoic acid (M-1) (1.0 mol, 1.0 eq) and DMF (2.0 mL) in toluene (800 mL), thionyl chloride (292 mL, 1.0 mol, 4.0 eq) is added dropwise (over 15 min) and the resulting mixture is stirred at reflux for 1.5 h. The mixture is allowed to cool to RT and then concentrated in vacuo. The residue is dissolved in DCM (100 mL) to form solution A, which is used directly in the next step.

To a stirred mixture of a given amine R$_2$—NH$_2$ (102.4 g, 1.1 mol, 1.1 eq) and triethylamine (280 mL, 2.0 mol, 2.0 eq) in DCM (700 mL), solution A is added dropwise while keeping the reaction temperature below 10° C. The resulting mixture is allowed to warm to RT and then stirred at RT overnight. The reaction mixture is diluted with ice-water (1.0 L) and stirred for 15 min. The precipitate is collected by filtration, rinsed with isopropyl ether (3×100 mL) and petroleum ether (3×100 mL), and then dried in vacuo to afford product amide (M-2).

A mixture of nitro-benzamide (M-2) (20.0 mmol, 1.0 eq) and DMF (cat.) in toluene (60 mL) at RT, thionyl chloride (12 mL, 164 mmol, 8.2 eq) is added dropwise (over 5 min) and the resulting mixture is stirred at reflux for 2 h. The mixture is allowed to cool to RT and then concentrated in vacuo. The residue is dissolved in DCM (10 mL) to form solution B, which is used directly in the next step.

To a stirred mixture of N-(tert-butoxycarbonyl)-L-alanine (16.0 mmol, 0.8 eq) and N,N-diisopropylethylamine (4.0 g, 31.0 mol, 1.5 eq) in DCM (20 mL), solution B is added dropwise while keeping the reaction temperature between 0-10° C. The resulting mixture is stirred at this temperature for 1 h and then stirred at RT overnight. The reaction mixture is quenched with ice-water (100 mL). The organic layer is separated and the aqueous layer is extracted with DCM (2×80 mL). The combined organic layers are washed with brine, dried over Na₂SO₄ and filtered. The filtrate is concentrated in vacuo and the residue is slurried in isopropyl ether (100 mL) for 15 min. The solid is collected by filtration and dried in vacuo to afford product (M-3).

To a suspension of zinc dust (7.2 g, 110 mmol, 10.0 eq) in glacial acetic acid (40 mL) at 15° C., a solution of M-3 (11.0 mmol, 1.0 eq) in glacial acetic acid (40 mL) is added and the resulting mixture is stirred at RT for 4 h. The mixture is poured into ice-water (200 mL) and neutralized with saturated aqueous NaHCO₃ solution to adjust the pH to 8. The resulting mixture is extracted with DCM (3×150 mL). The combined organic layers are washed with brine, dried over Na₂SO₄ and filtered. The filtrate is concentrated in vacuo and the residue is purified by flash chromatography on silica gel (7% ethyl acetate-petroleum ether) to afford product (M-4).

Compound (M-4) (0.5 mmol, 1.0 eq) is dissolved in hydrochloric methanol solution (2N, 20 mL) and the resulting mixture is stirred at RT for 2 h. The mixture is concentrated in vacuo. The residue is diluted with water (30 mL) and then neutralized with saturated aqueous NaHCO₃ to adjust the pH to 8 while keeping the temperature below 5° C. The resulting mixture is extracted with DCM (3×30 mL). The combined organic layers are washed with brine, dried over Na₂SO₄ and filtered. The filtrate is concentrated in vacuo and the residue is slurried in petroleum ether (10 mL). The solid is collected by filtration and dried in vacuo to afford product (M-5).

The quinazolinone (M-5) can be used to synthesize compounds described herein using, for example, Method J to couple the amine to $W_d$ groups.

Example 1

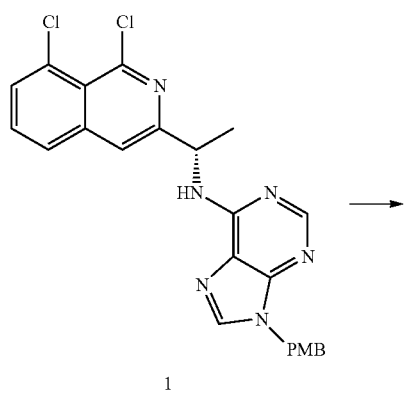

1

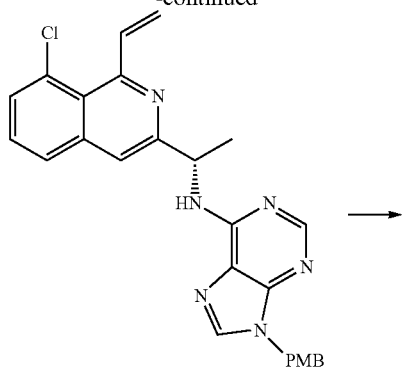

2

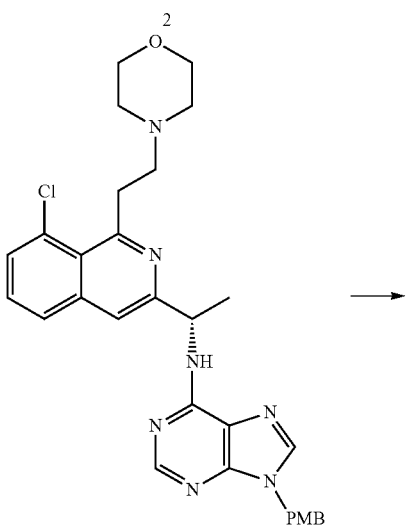

3

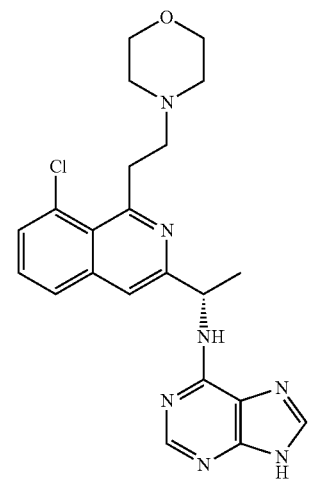

4

Compound 1 was prepared according to Method K and was then converted to compound 2 by the following method:

To a stirred mixture of (S)—N-(1-(1,8-dichloroisoquinolin-3-yl)ethyl)-9-(4-methoxybenzyl)-9H-purin-6-amine 1 (2.58 g, 5.4 mmol, 1 eq), Pd(OAc)₂ (363 mg, 1.62 mmol, 0.3 eq) and PPh₃ (846 mg, 3.24 mol, 0.6 eq) in THF (50 mL) at RT, tributyl(vinyl)tin (1.97 g, 5.94 mmol, 1.1 eq) was added and the resulting mixture was stirred at reflux overnight. The mixture was allowed to cool to RT and filtered through silica gel (10 g). The filtrate was concentrated in vacuo and the residue was purified by flash column chromatography on silica gel (1-5% MeOH-DCM) to afford the product (S)—N-(1-(8-chloro-1-vinylisoquinolin-3-yl)ethyl)-9-(4-methoxybenzyl)-9H-purin-6-amine 2.

Compound 2 was then converted to compound 4 in two steps: To a stirred mixture of (S)—N-(1-(8-chloro-1-vinyl-isoquinolin-3-yl)ethyl)-9-(4-methoxybenzyl)-9H-purin-6-amine 2 (200 mg, 0.42 mmol, 1 eq) in EtOH (50 mL) at RT, morpholine (183 mg, 2.1 mmol, 5 eq) and triethylamine (213 mg, 2.1 mmol, 5 eq) were added sequentially. The resulting mixture was stirred at reflux for 4 h. The mixture was allowed to cool to RT and then concentrated in vacuo and the residue was purified by flash column chromatography on silica gel (1-5% MeOH-DCM) to afford the product (S)—N-(1-(8-chloro-1-(2-morpholinoethyl)isoquinolin-3-yl)ethyl)-9-(4-methoxybenzyl)-9H-purin-6-amine 3. The PMB group was then subsequently deprotected using Method L to provide compound 4. ESI-MS m/z: 438.8 [M+H]$^+$.

Example 2

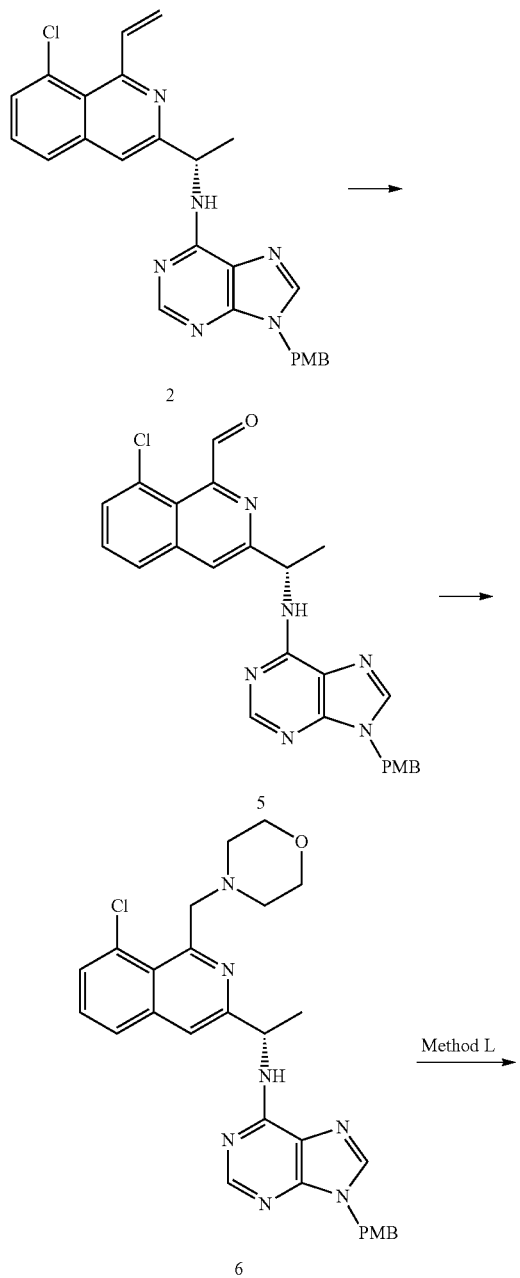

Compound 7 was prepared from compound 2 in 3 steps according to the following procedures:

To a stirred mixture of (S)—N-(1-(8-chloro-1-vinylisoquinolin-3-yl)ethyl)-9-(4-methoxybenzyl)-9H-purin-6-amine 2 (3.6 g, 7.6 mmol, 1 eq) in a mixture of 1,4-dioxane (40 mL) and H$_2$O (40 mL) at RT, osmium tetraoxide (5 mg) was added and the resulting mixture was stirred at RT for 30 min. To this mixture, sodium periodate (3.3 g, 15.2 mmol, 2 eq) was added and the resulting mixture was stirred at RT overnight. The reaction mixture was filtered through silica gel (10 g). The filtrate was extracted with DCM (3×60 mL), washed with brine, dried over Na$_2$SO$_4$ and filtered. The filtrate was concentrated in vacuo and the residue was purified by flash column chromatography on silica gel (1-5% MeOH-DCM) to afford the product, (S)-8-chloro-3-(1-((9-(4-methoxybenzyl)-9H-purin-6-yl)amino)ethyl)isoquinoline-1-carbaldehyde 5.

To a stirred solution of (S)-8-chloro-3-(1-((4-methoxybenzyl)-9H-purin-6-yl)amino)ethyl)isoquinoline-1-carbaldehyde 5 (150 mg, 0.317 mmol, 1 eq), H$_2$O (1 mL) and AcOH (a drop) in DCM (30 mL), NaB(OAc)$_3$H (134 mg, 0.634 mmol, 2 eq) was added and the resulting mixture was stirred at RT for 2 h. The mixture was concentrated in vacuo and the residue was purified by flash column chromatography on silica gel (1-5% MeOH-DCM) to afford the product, (S)—N-(1-(8-chloro-1-(morpholinomethyl)isoquinolin-3-yl)ethyl)-9-(4-methoxybenzyl)-9H-purin-6-amine 6. Compound 6 was then deprotected using Method L to provide compound 7. ESI-MS m/z: 424.8 [M+H]$^+$.

Example 3

Compound 8 was prepared in analogous fashion to compound 7 in Example 2 except that 3,3-difluoropyrrolidine was used in place of morpholine. ESI-MS m/z: 458.0 [M+H]$^+$.

Example 4

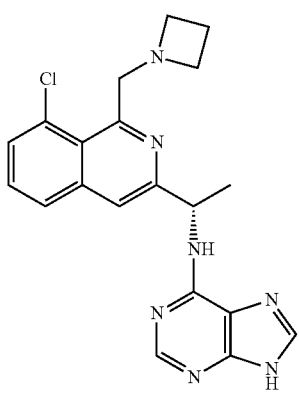

Compound 9 was prepared in analogous fashion to compound 7 in Example 2 except that azetidine was used in place of morpholine. ESI-MS m/z: 394.0 [M+H]+.

Example 5

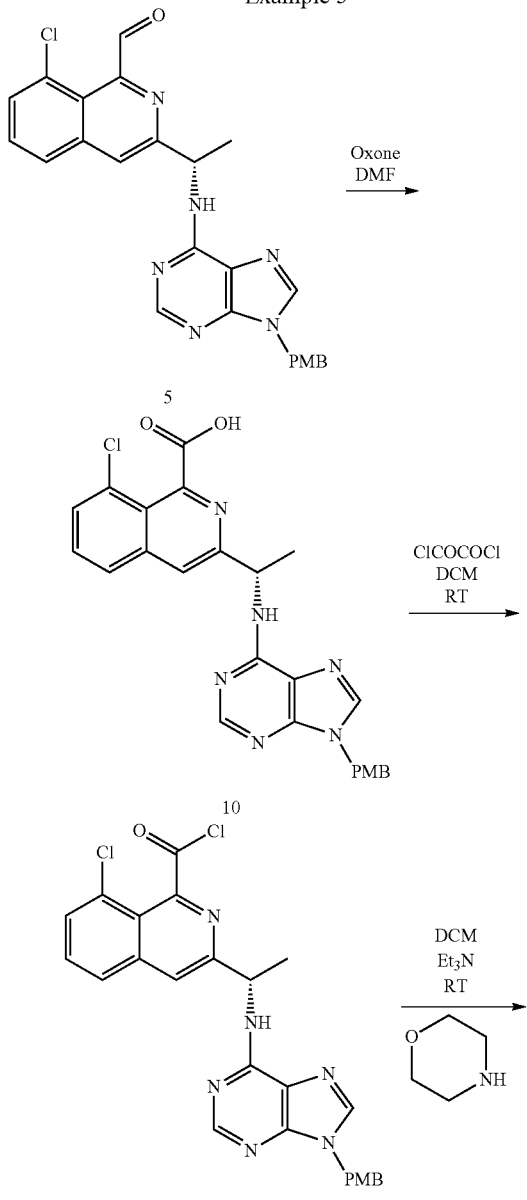

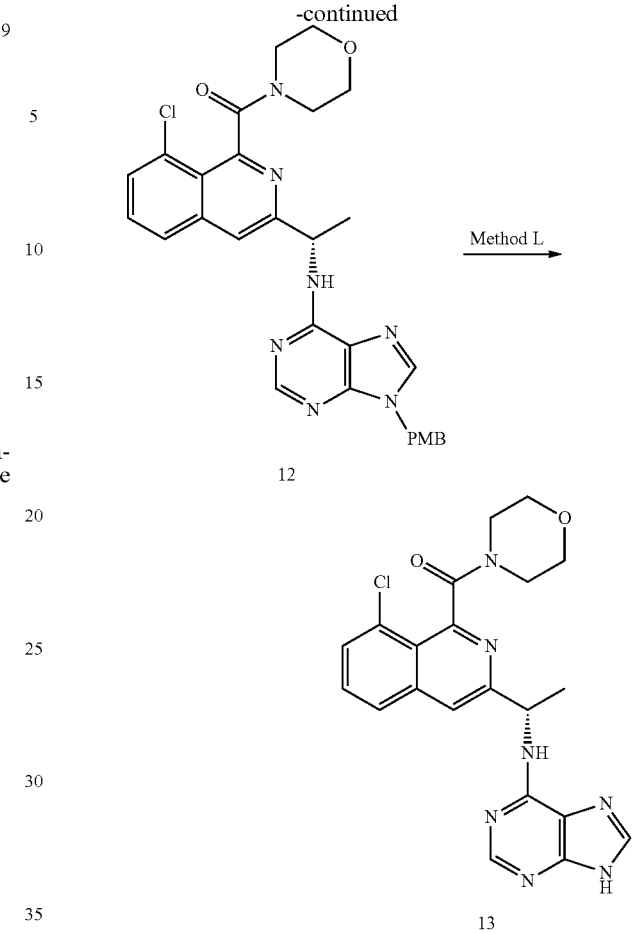

Amide 13 was prepared in 4 steps from aldehyde 5 according to the following procedures:

To a solution of (S)-8-chloro-3-(1-((9-(4-methoxybenzyl)-9H-purin-6-yl)amino)ethyl)isoquinoline-1-carbaldehyde 5 (1.67 g, 3.53 mmol, 1 eq) in DMF (40 mL) at RT, oxone (6.5 g, 10.59 mmol, 3 eq) was slowly added and the resulting mixture was stirred at RT overnight. The reaction was complete based on TLC analysis. The reaction mixture was poured into water (50 mL) and neutralized with concentrated ammonium hydroxide to adjust the pH value to 7-8. The mixture was stirred at RT for 30 min and then extracted with ethyl acetate (3×50 mL). The combined organic layers were washed with brine, dried over $Na_2SO_4$ and filtered. The filtrate was concentrated in vacuo and the residue was purified by flash column chromatography on silica gel (1-5% MeOH-DCM) to afford the product (S)-8-chloro-3-(1-((9-(4-methoxybenzyl)-9H-purin-6-yl)amino)ethyl)isoquinoline-1-carboxylic acid 10.

To a solution of (S)-8-chloro-3-(1-((9-(4-methoxybenzyl)-9H-purin-6-yl)amino)ethyl)isoquinoline-1-carboxylic acid 10 (160 mg, 0.327 mol, 1 eq) and DMF (0.1 mL) in DCM (10 mL), oxalyl chloride (83.1 mg, 0.654 mmol, 2 eq) was added and the resulting mixture was stirred at RT for 1 h. The mixture was concentrated in vacuo to afford the product (S)-8-chloro-3-(1-((9-(4-methoxybenzyl)-9H-purin-6-yl)amino) ethyl) isoquinoline-1-carbonyl chloride 11. The product obtained was used directly in the next step without purification.

To a solution of morpholine (34 mg, 0.392 mmol, 1.3 eq) and triethylamine (100 mg, 0.981 mol, 3 eq) in DCM (20 mL), (S)-8-chloro-3-(1-((9-(4-methoxybenzyl)-9H-purin-6-yl)amino)ethyl) isoquinoline-1-carbonyl chloride 11 was added at RT. The resulting mixture was stirred at RT for 1 h. The reaction mixture was poured into water (50 mL) and extracted with DCM (3×50 mL). The combined organic layers were washed with brine, dried over $Na_2SO_4$ and filtered. The filtrate was concentrated in vacuo and the residue was purified by flash column chromatography on silica gel (1-5% MeOH-DCM) to afford the product (S)-(8-chloro-3-(1-((9-(4-methoxybenzyl)-9H-purin-6-yl)amino)ethyl)isoquinolin-1-yl)(morpholino)methanone 12.

Compound 12 was then deprotected using Method L to provide compound 13. ESI-MS m/z: 438.0 $[M+H]^+$.

Example 6

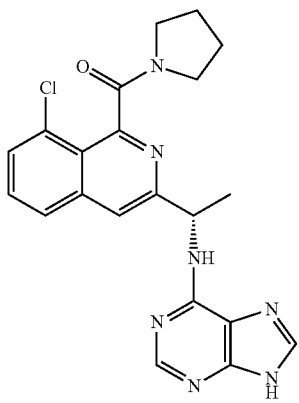

14

Compound 14 was prepared in analogous fashion to compound 13 in Example 5 except that pyrollidine was used in place of morpholine. ESI-MS m/z: 422.0 $[M+H]^+$.

Example 7

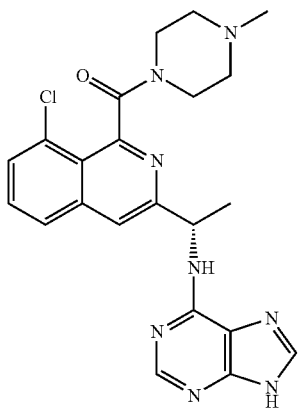

15

Compound 15 was prepared in analogous fashion to compound 13 in Example 5 except that N-methylpiperidine was used in place of morpholine. ESI-MS m/z: 451.2 $[M+H]^+$.

Example 8

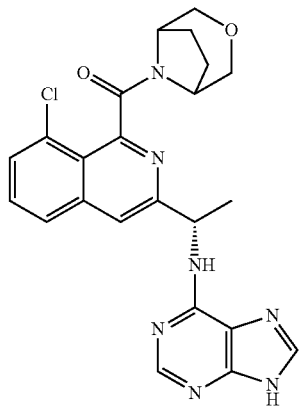

16

Compound 16 was prepared in analogous fashion to compound 13 in Example 5 except that 3-oxa-8-azabicyclo[3.2.1]octane was used in place of morpholine. ESI-MS m/z: 464.0 $[M+H]^+$.

Example 9

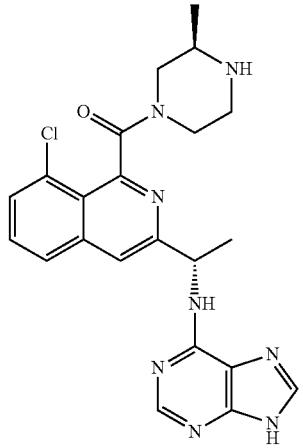

17

Compound 17 was prepared in analogous fashion to compound 13 in Example 5 except that (R)-2-methylpiperazine was used in place of morpholine. ESI-MS m/z: 451.0 $[M+H]^+$.

Example 10

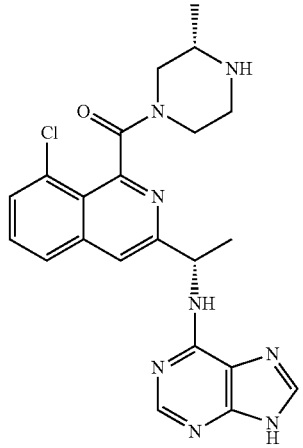

18

Compound 18 was prepared in analogous fashion to compound 13 in Example 5 except that (S)-2-methylpiperazine was used in place of morpholine. ESI-MS m/z: 451.0 $[M+H]^+$.

Example 11

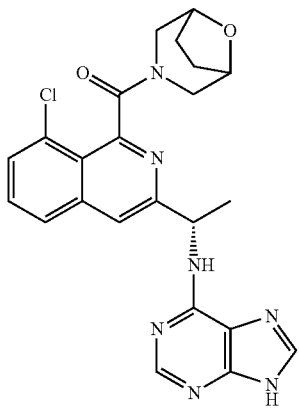

Compound 19 was prepared in analogous fashion to compound 13 in Example 5 except that 8-oxa-3-azabicyclo[3.2.1]octane was used in place of morpholine. ESI-MS m/z: 464.0 [M+H]+.

Example 12

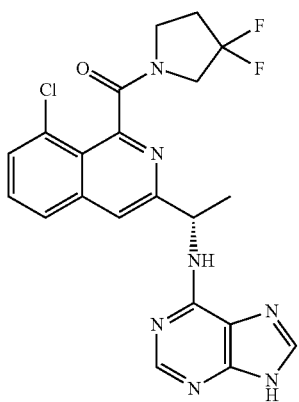

Compound 20 was prepared in analogous fashion to compound 13 in Example 5 except that 3,3-difluoropyrrolidine was used in place of morpholine. ESI-MS m/z: 458.0 [M+H]+.

Example 13

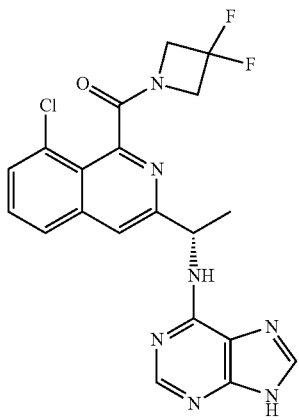

Compound 21 was prepared in analogous fashion to compound 13 in Example 5 except that 2,2-difluoro azetidine was used in place of morpholine. ESI-MS m/z: 444.0 [M+H]+.

Example 14

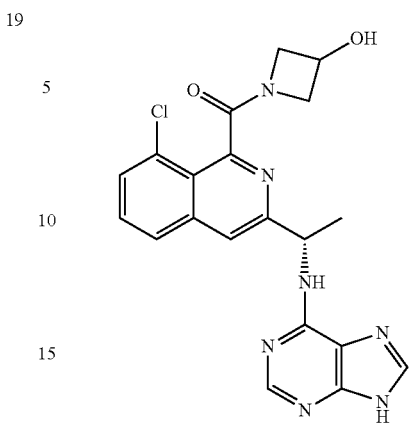

Compound 22 was prepared in analogous fashion to compound 13 in Example 5 except that 2-hydroxyazetidine was used in place of morpholine. ESI-MS m/z: 424.0 [M+H]+.

Example 15

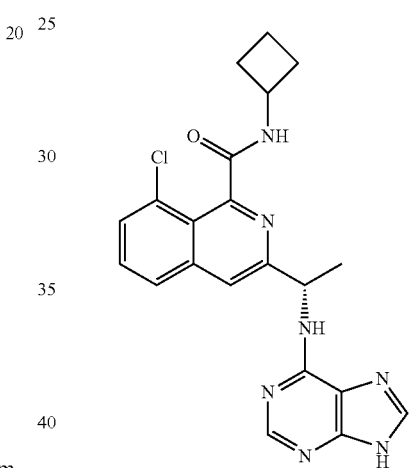

Compound 23 was prepared in analogous fashion to compound 13 in Example 5 except that cyclobutylamine was used in place of morpholine. ESI-MS m/z: 422.0 [M+H]+.

Example 16

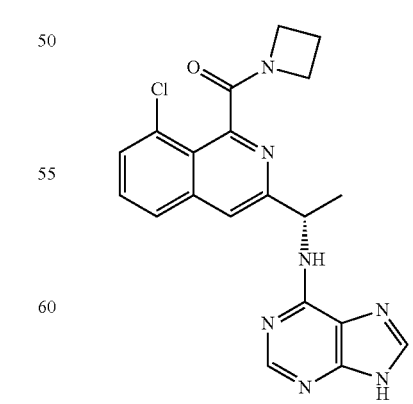

Compound 24 was prepared in analogous fashion to compound 13 in Example 5 except that azetidine was used in place of morpholine. ESI-MS m/z: 408.2 [M+H]+.

Example 17

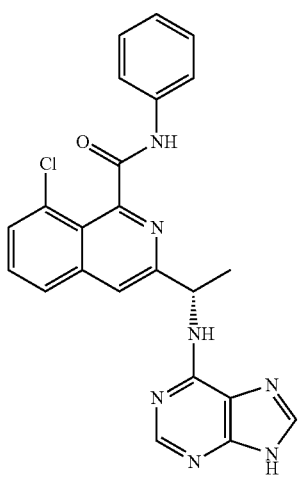

25

Compound 25 was prepared in analogous fashion to compound 13 in Example 5 except that aniline was used in place of morpholine. ESI-MS m/z: 444.2 [M+H]⁺.

Example 18

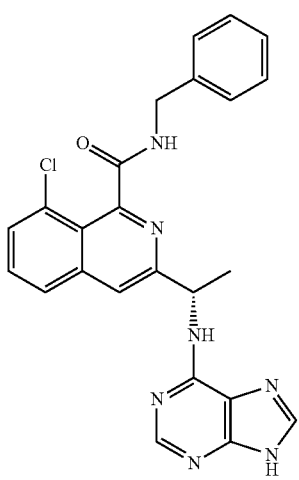

26

Compound 26 was prepared in analogous fashion to compound 13 in Example 5 except that benzylamine was used in place of morpholine. ESI-MS m/z: 458.0 [M+H]⁺.

Example 19

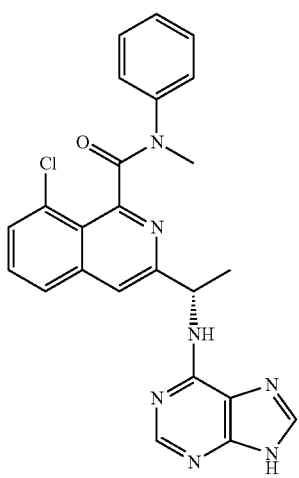

27

Compound 27 was prepared in analogous fashion to compound 13 in Example 5 except that N-methylaniline was used in place of morpholine. ESI-MS m/z: 458.0 [M+H]⁺.

Example 20

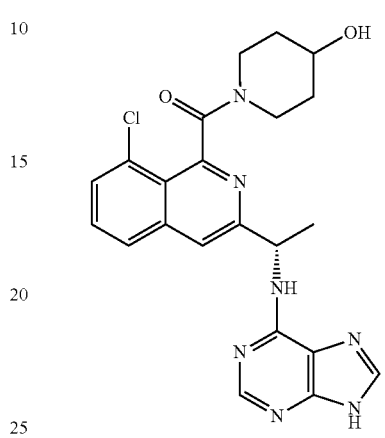

28

Compound 28 was prepared in analogous fashion to compound 13 in Example 5 except that 4-hydroxypiperidine was used in place of morpholine. ESI-MS m/z: 452.2 [M+H]⁺.

Example 21

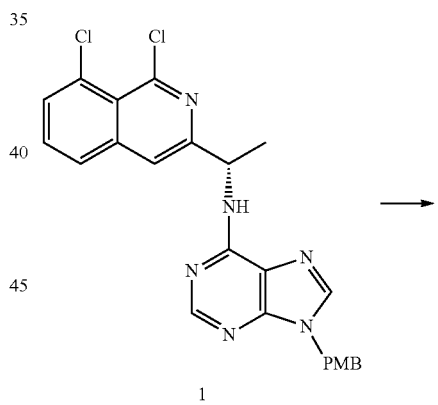

1

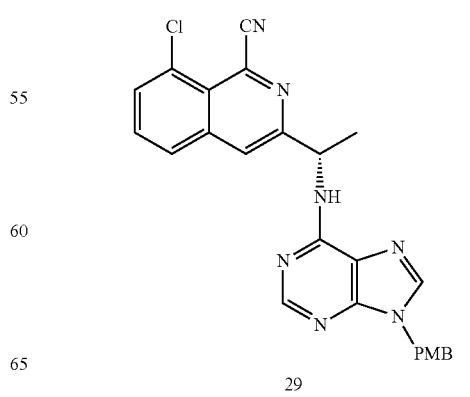

29

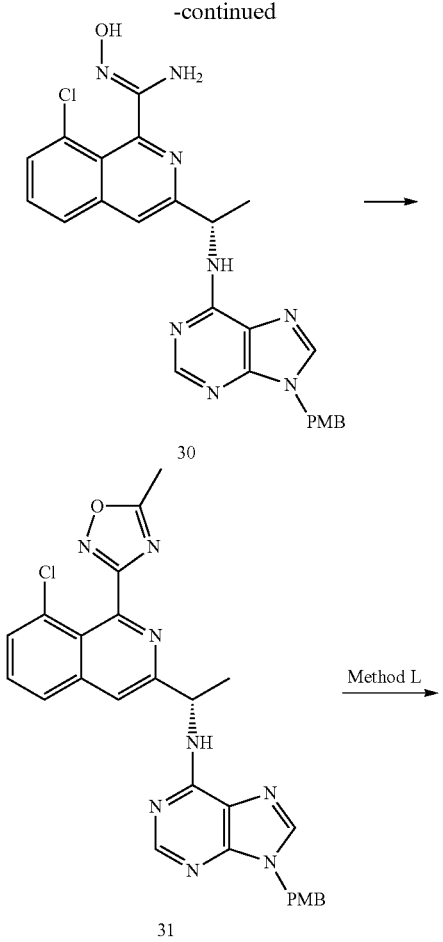

was purified by flash column chromatography on silica gel (1-10% MeOH-DCM) to afford the product (S)-8-chloro-3-(1-((9-(4-methoxybenzyl)-9H-purin-6-yl)amino)ethyl)isoquinoline-1-carbonitrile 29.

A mixture of (S)-8-chloro-3-(1-((9-(4-methoxybenzyl)-9H-purin-6-yl)amino)ethyl) isoquinoline-1-carbonitrile 29 (600 mg, 1.28 mmol, 1.0 eq), hydroxylamine hydrochloride (269 mg, 3.84 mmol, 3 eq) and NaOH (154 mg, 3.84 mmol, 3 eq) in EtOH (15 mL) was stirred at reflux 4 h. The mixture was cooled to RT, poured into water (100 mL) and then extracted with DCM (3×100 mL). The combined organic layers were washed with brine, dried over Na$_2$SO$_4$ and filtered. The filtrate was concentrated in vacuo and the residue was purified by flash column chromatography on silica gel (1-10% MeOH-DCM) to afford the product (S,Z)-8-chloro-N'-hydroxy-3-(1-((9-(4-methoxybenzyl)-9H-purin-6-yl)amino)ethyl)isoquinoline-1-carboximidamide 30.

(S,Z)-8-chloro-N'-hydroxy-3-(1-((9-(4-methoxybenzyl)-9H-purin-6-yl)amino)ethyl)isoquinoline-1-carboximidamide 30 (502 mg, 1 mmol, 1.0 eq) was dissolved in acetic anhydride (10 mL) and the resulting mixture was stirred at reflux overnight. The mixture was cooled to RT and concentrated in vacuo to remove acetic anhydride. The resulting suspension was diluted with water (50 mL) and neutralized with concentrated ammonium hydroxide to adjust the pH value to 7-8. The mixture was extracted with DCM (3×100 mL). The combined organic layers were washed with brine, dried over Na$_2$SO$_4$ and filtered. The filtrate was concentrated in vacuo and the residue was purified by flash column chromatography on silica gel (1-10% MeOH-DCM) to afford the product ((S)—N-(1-(8-chloro-1-(5-methyl-1,2,4-oxadiazol-3-yl)isoquinolin-3-yl)ethyl)-9-(4-methoxybenzyl)-9H-purin-6-amine 31.

Oxadiazole 31 was then deprotected to using Method L to provide compound 32. ESI-MS m/z: 407.0 [M+H]$^+$.

Example 22

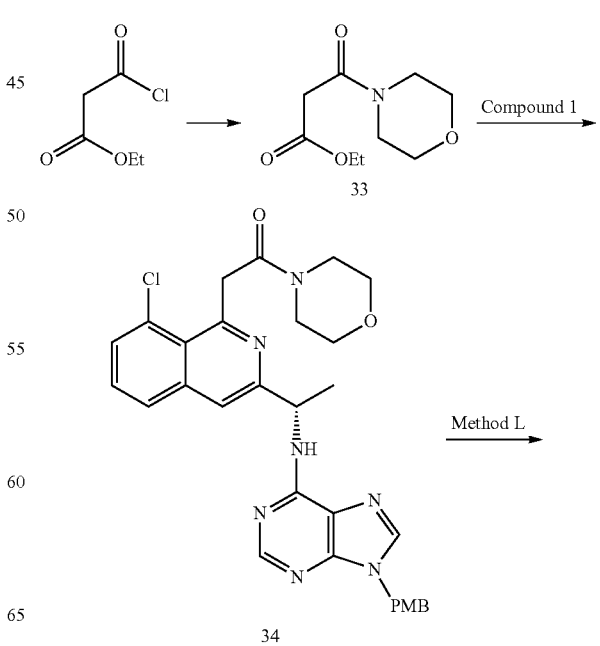

Compound 32 was prepared in 4 steps from compound 1 according to the following procedures:

To a stirred solution of ((S)—N-(1-(1,8-dichloroisoquinolin-3-yl)ethyl)-9-(4-methoxybenzyl)-9H-purin-6-amine 1 (1.5 g, 3.1 mmol, 1.0 eq) and tetrakis(triphenylphosphine) palladium (181 mg, 0.16 mmol, 0.05 eq) in DMF (50 mL) at RT, dicyanozinc (476 mg, 4.06 mmol, 1.3 eq) was added and the resulting mixture was stirred at 100° C. overnight. The reaction mixture was poured into water (100 mL) and extracted with DCM (3×100 mL). The combined organic layers were washed with brine, dried over Na$_2$SO$_4$ and filtered. The filtrate was concentrated in vacuo and the residue

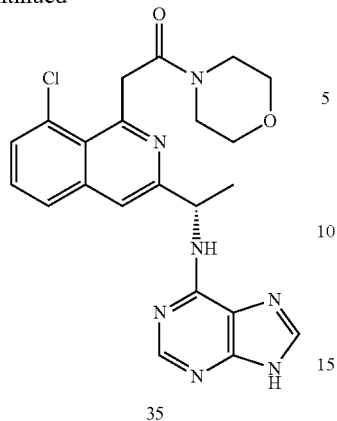

35

Amide 35 was prepared in 3 steps from ethyl 3-chloro-3-oxopropanate according to the following procedures:

To a stirred solution of morpholine (479 mg, 5.5 mmol, 1.1 eq) and triethylamine (1.01 g, 10 mmol, 10 eq) in DCM (20 mL) at 0° C., ethyl 3-chloro-3-oxopropanoate (750 mg, 5 mmol, 1.0 eq) was added and the resulting mixture was stirred at RT for 1 h. The reaction mixture was poured into water (50 mL) and extracted with ethyl acetate (3×50 mL). The combined organic layers were washed with brine, dried over $Na_2SO_4$ and filtered. The filtrate was concentrated in vacuo and the residue was purified by flash column chromatography on silica gel (1-50% ethyl acetate-hexanes) to afford the product ethyl 3-morpholino-3-oxopropanoate 33.

To a mixture of ethyl 3-morpholino-3-oxopropanoate 33 (402 mg, 2 mmol, 1.0 eq) and NaH (144 mg, 3 mmol, 1.5 eq) in THF (3 mL) at RT, (S)—N-(1-(1,8-dichloroisoquinolin-3-yl)ethyl)-9-(4-methoxybenzyl)-9H-purin-6-amine 1 (765 mg, 1.6 mmol, 0.8 eq) was added and the resulting mixture was stirred at reflux overnight. The reaction mixture was poured into water (50 mL) and extracted with DCM (3×50 mL). The combined organic layers were washed with brine, dried over $Na_2SO_4$ and filtered. The filtrate was concentrated in vacuo and the residue was purified by flash column chromatography on silica gel (1-5% MeOH-DCM) to afford the product (S)-2-(8-chloro-3-(1-((9-(4-methoxybenzyl)-9H-purin-6-yl)amino)ethyl)isoquinolin-1-yl)-1-morpholinoethanone 34.

Amide 34 was then deprotected to provide the compound 35 using Method L. ESI-MS m/z: 452.2 $[M+H]^+$.

Example 23

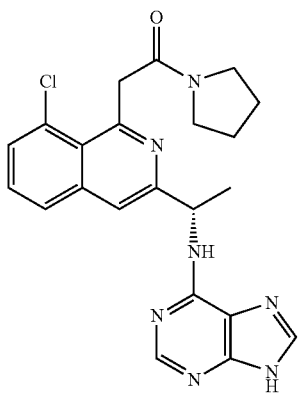

36

Compound 36 was prepared in analogous fashion to compound 35 in Example 22 except that pyrollidine was used in place of morpholine in step 1. ESI-MS m/z: 436.0 $[M+H]^+$.

Example 24

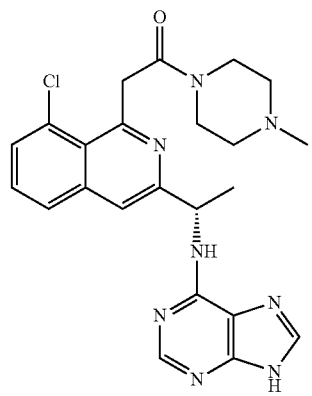

37

Compound 37 was prepared in analogous fashion to compound 35 in Example 22 except that N-methylpiperazine was used in place of morpholine in step 1. ESI-MS m/z: 465.2 $[M+H]^+$.

Example 25

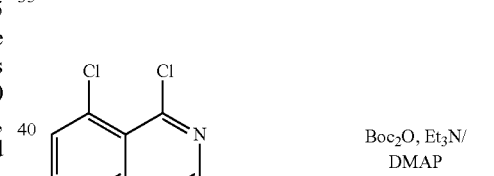

38

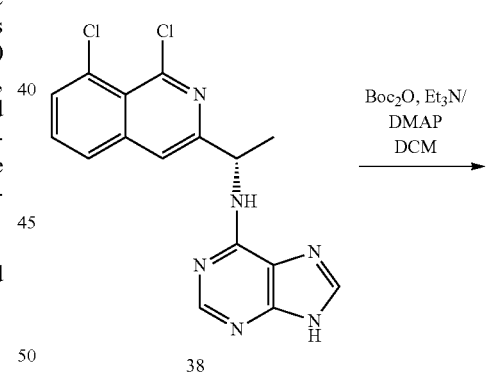

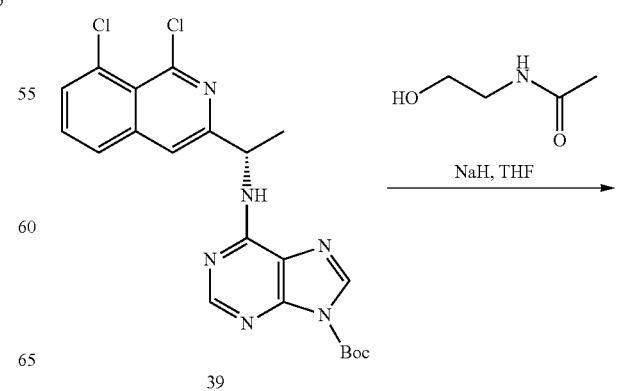

39

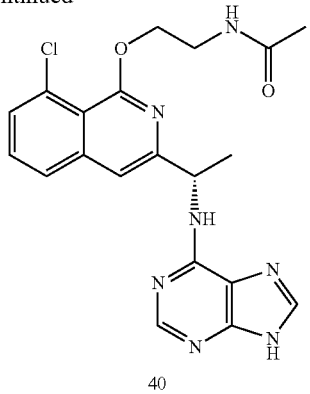

40

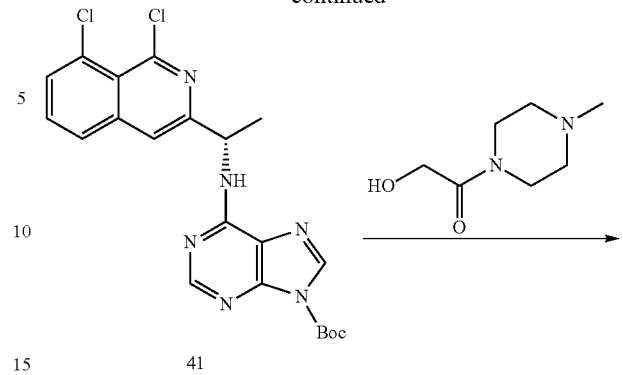

41

Compound 38 was prepared from compound 1 using Method J and then converted to compound 40 according to the following procedures:

To a stirred mixture of (S)—N-(1-(1,8-dichloroisoquinolin-3-yl)ethyl)-9H-purin-6-amine 38 (4.7 g, 13.1 mmol, 1.0 eq) in THF (20 mL) at 0° C., triethylamine (1.8 mL, 13.0 mmol, 0.99 eq), N,N-dimethylpyridin-4-amine (0.16 g, 1.31 mmol, 0.1 eq) and di-tert-butyl dicarbonate (3.0 g, 13.75 mmol, 1.05 eq) were added sequentially. The resulting mixture was stirred at 0-5° C. for 10 min and then at RT for an additional 2 h. The mixture was concentrated in vacuo and the residue was purified by flash column chromatography on silica gel (3% MeOH-DCM) to afford the product (S)-tert-butyl 6-(1-(1,8-dichloroisoquinolin-3-yl)ethylamino)-9H-purine-9-carboxylate 39.

To a stirred mixture of N-(2-hydroxyethyl)acetamide (110 mg, 1.07 mmol, 2.43 eq) in THF (20 mL) at 0° C., NaH (60% in mineral oil, 110 mg, 2.75 mmol, 6.25 eq) was added and the resulting mixture was stirred for 15 min. To this mixture, (S)-tert-butyl 6-(1-(1,8-dichloroisoquinolin-3-yl)ethylamino)-9H-purine-9-carboxylate 39 (200 mg, 0.44 mmol, 1.0 eq) was added. The resulting mixture was stirred at reflux for 2 h, cooled to RT and then poured into water (30 mL). The mixture was extracted with DCM (3×30 mL). The combined organic layers were washed with brine, dried over Na$_2$SO$_4$ and filtered. The filtrate was concentrated in vacuo and the residue was purified by flash column chromatography on silica gel (3% MeOH-DCM) to afford the product (S)—N-(2-(3-(1-(9H-purin-6-ylamino)ethyl)-8-chloroisoquinolin-1-yloxy)ethyl)acetamide 40. ESI-MS m/z: 426.0 [M+H]$^+$.

Example 26

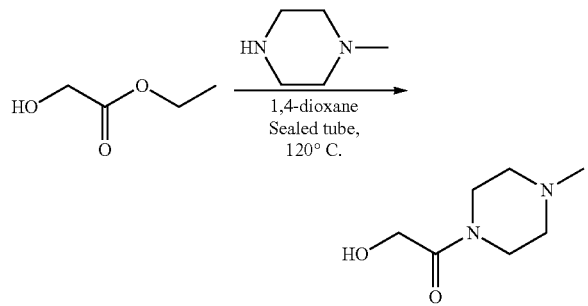

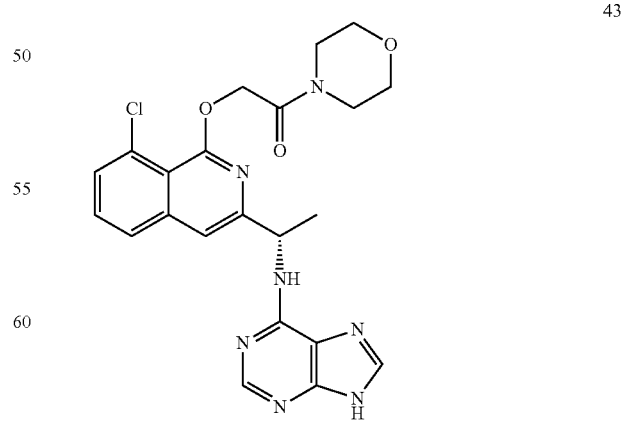

42

2-Hydroxy-1-(4-methyl piperazin-1-yl)ethanone was prepared according to the following procedure: Ethyl 2-hydroxyacetate (6.85 g, 65.8 mmol, 1.0 eq) and 1-methylpiperazine (5.26 g, 52.6 mmol, 0.8 eq) were dissolved in 1,4-dioxane (10 mL) in a sealed tube and the mixture was stirred at 120° C. overnight. The mixture was allowed to cool to RT and then concentrated in vacuo. The residue was purified by flash column chromatography on silica gel (2% MeOH-DCM) to afford the product 2-hydroxy-1-(4-methyl piperazin-1-yl)ethanone.

Compound 42 was prepared in analogous fashion to compound 40 in Example 25 except that 2-hydroxy-1-(4-methylpiperazin-1-yl)ethanone was used in place of N-(2-hydroxyethyl)acetamide in step 2. ESI-MS m/z: 481.0 [M+H]$^+$.

Example 27

43

Compound 43 was prepared in analogous fashion to compound 42 in Example 26 except that morpholine was used in place of N-methylpiperidine. ESI-MS m/z: 468.0 [M+H]$^+$.

Example 28

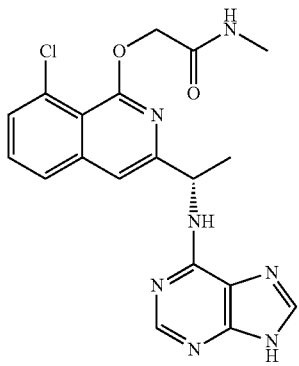

44

Compound 44 was prepared in analogous fashion to compound 42 in Example 26 except that methylamine was used in place of N-methylpiperidine. ESI-MS m/z: 412.0 [M+H]+.

Example 29

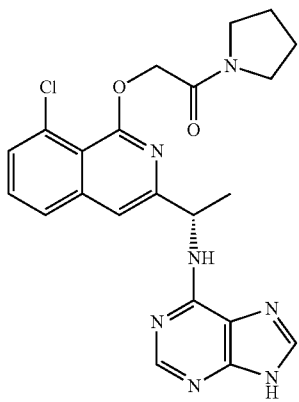

45

Compound 45 was prepared in analogous fashion to compound 42 in Example 26 except that pyrrolidine was used in place of N-methylpiperidine. ESI-MS m/z: 452.2 [M+H]+.

Example 30

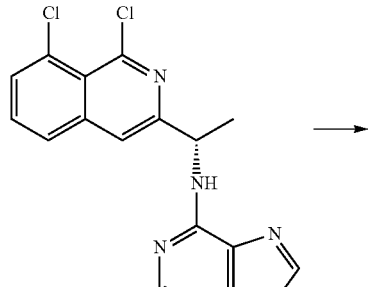

38

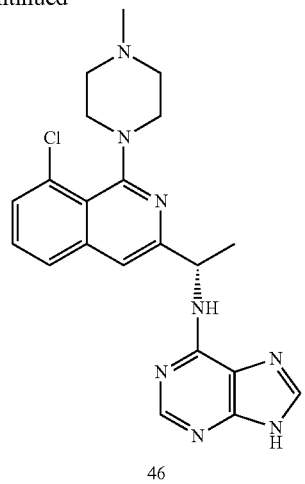

46

Compound 46 was prepared from compound 38 according to the following procedure:

To a mixture of (S)—N-(1-(1,8-dichloroisoquinolin-3-yl)ethyl)-9H-purin-6-amine 38 (300 mg, 0.84 mmol, 1 eq) in 1,4-dioxane (10 mL) at RT, 1-methylpiperazine (167 mg, 1.68 mmol, 2 eq) was added and the resulting mixture was stirred at reflux for 8 h. The mixture was allowed to cool to RT, concentrated in vacuo and the residue was purified by flash column chromatography on silica gel (1-5% MeOH-DCM) to afford the product, (S)—N-(1-(8-chloro-1-(4-methylpiperazin-1-yl)isoquinolin-3-yl)ethyl)-9H-purin-6-amine 46. ESI-MS m/z: 423.2 [M+H]+.

Example 31

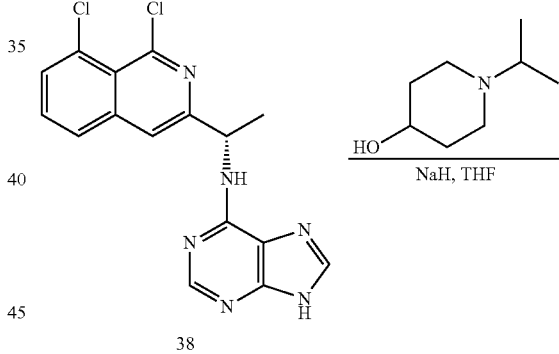

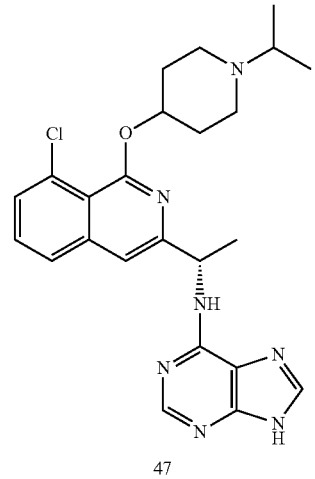

47

Compound 47 was prepared from 38 according to the following procedure:

To a stirred mixture of 1-isopropylpiperidin-4-ol (120 mg, 0.83 mmol, 1.2 eq) in THF (10 mL) at 0° C., NaH (60% in mineral oil, 33.2 mg, 0.83 mmol, 1.2 eq) was added and the resulting mixture was stirred for 10 min. To this mixture, (S)—N-(1-(1,8-dichloroisoquinolin-3-yl)ethyl)-9H-purin-6-amine 38 (250 mg, 0.70 mmol, 1.0 eq) was added. The resulting mixture was stirred at reflux overnight, cooled to RT and then poured into water (20 mL). The mixture was extracted with ethyl acetate (3×20 mL). The combined organic layers were washed with brine, dried over $Na_2SO_4$, and filtered. The filtrate was concentrated in vacuo and the residue was purified by flash column chromatography on silica gel (5% MeOH-DCM) to afford the product, (S)—N-(1-(8-chloro-1-(1-isopropylpiperidin-4-yloxy)isoquinolin-3-yl)ethyl)-9H-purin-6-amine 47. ESI-MS m/z: 466.2 $[M+H]^+$.

Example 32

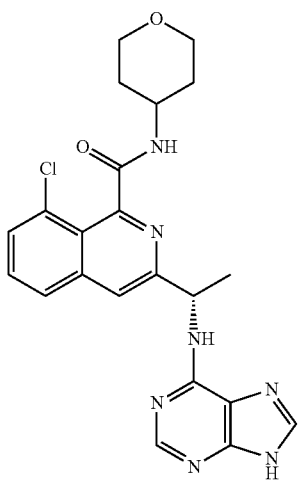

48

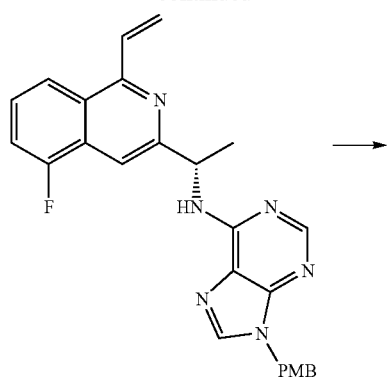

51

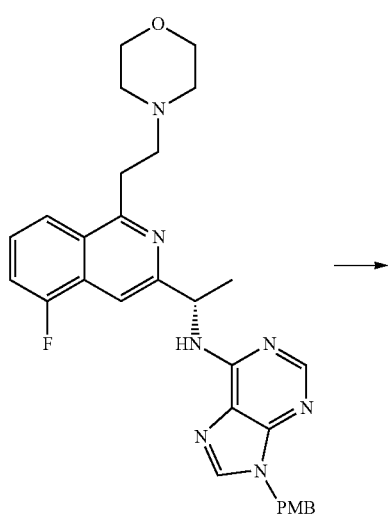

52

Compound 48 was prepared in analogous fashion to compound 13 in Example 5 except that tetrahydro-2H-pyran-4-amine was used in place of morpholine. ESI-MS m/z: 452.2 $[M+H]^+$.

Example 33

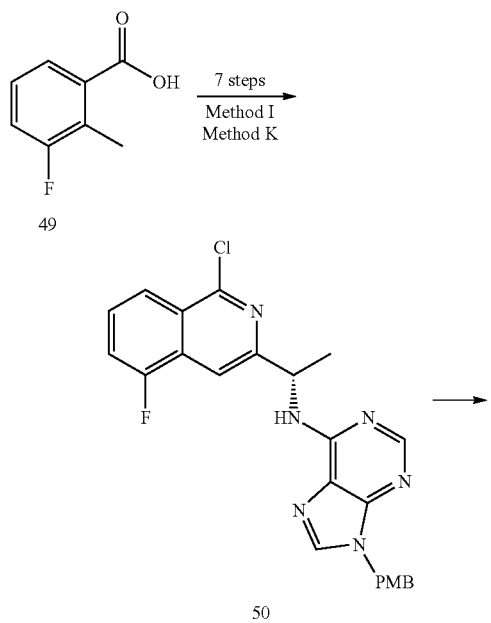

49

50

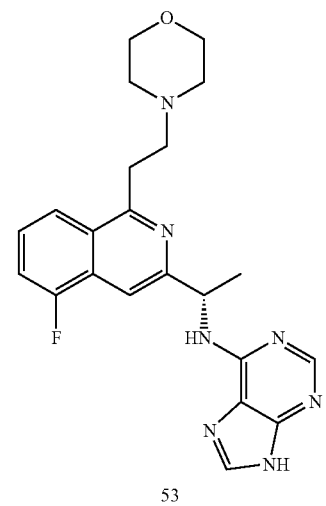 [SMILES: C[C@H](Nc1ncnc2[nH]cnc12)c1cc2c(F)cccc2c(CCN2CCOCC2)n1]

53

Compound 50 was prepared in 7 steps from commercially available material 49 using Method I (steps transforming (I-1) to (I-3)) and Method K (steps transforming (I-3) to (K-6)). Compound 53 was then prepared from 50 in analogous fashion to compound 4 in Example 1. ESI-MS m/z: 422.2 $[M+H]^+$.

Example 34

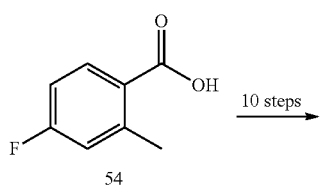

Compound 55 was prepared in 10 steps from commercially available material 54 in analogous fashion to compound 53 in Example 33. ESI-MS m/z: 422.2 [M+H]+.

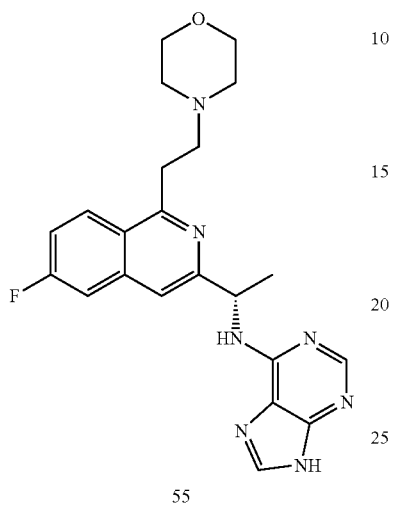

Example 35

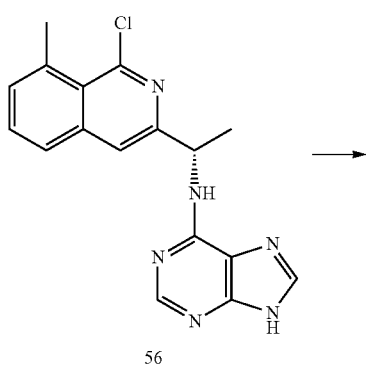

Compound 56 was prepared from dimethylbenzoic acid using Method I (steps transforming (I-1) to (I-3)) followed by Method K (steps transforming (I-3) to (K-5)). Compound 56 was converted to 57 in analogous fashion to compound 47 in Example 31. ESI-MS m/z: 446.2 [M+H]+.

Example 36

Compound 58 was prepared in analogous fashion to compound 13 in Example 5 except that 4-hydroxypiperidine was used in place of morpholine. ESI-MS m/z: 466.2 [M+H]+.

Example 37

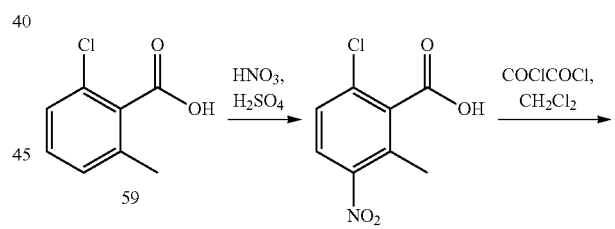

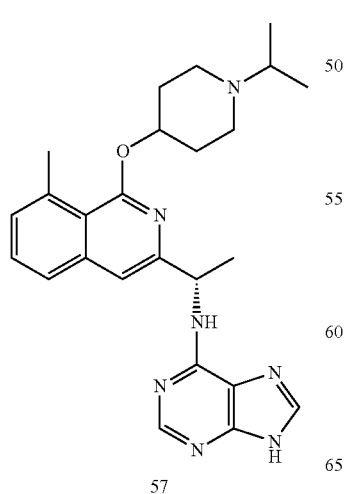

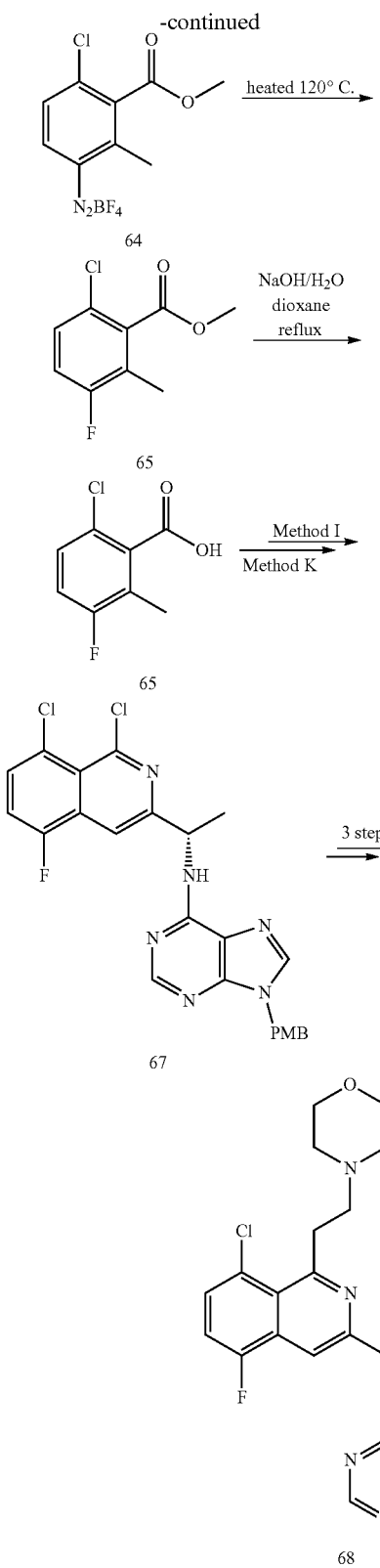

1.1 eq) was added slowly. The reaction mixture was stirred at 0° C. for 5 min and then stirred at RT for 2 h. The reaction mixture was poured into ice-water (800 mL) and extracted with ethyl acetate (3×500 mL). The combined organic layers were washed with brine, dried over $Na_2SO_4$ and filtered. The filtrate was concentrated in vacuo to afford the product as a mixture of two regio-isomers, 6-chloro-2-methyl-3-nitrobenzoic acid 60 (70%) and 6-chloro-2-methyl-5-nitrobenzoic acid (30%). The mixture was used directly in the next step.

To a stirred solution of the above obtained regio-isomer mixture of 6-chloro-2-methyl-3-nitrobenzoic acid 60 and 6-chloro-2-methyl-5-nitrobenzoic acid (58 g, 270 mmol, 1 eq) and DMF (0.5 mL) in DCM (250 mL) at RT, oxalyl chloride (34 mL, 405 mmol, 1.5 eq) was added slowly (over 5 min). The resulting mixture was stirred at RT for 2 h and then concentrated in vacuo to afford the product as a mixture of two regio-isomers, 6-chloro-2-methyl-3-nitrobenzoyl chloride 61 and 6-chloro-2-methyl-5-nitrobenzoyl chloride. The mixture was used directly in the next step.

The above obtained regio-isomer mixture of 6-chloro-2-methyl-3-nitrobenzoyl chloride 61 and 6-chloro-2-methyl-5-nitrobenzoyl chloride was dissolved in MeOH and stirred at RT for 30 min. The mixture was concentrated in vacuo to afford the product as a mixture of two regio-isomers, methyl 6-chloro-2-methyl-3-nitrobenzoate 62 and methyl 6-chloro-2-methyl-5-nitrobenzoate. The mixture was used directly in the next step.

To above stirred mixture of methyl 6-chloro-2-methyl-3-nitrobenzoate 62 and methyl 6-chloro-2-methyl-5-nitrobenzoate in EtOH (500 mL), $SnCl_2 \cdot 2H_2O$ (224 g, 992 mmol, 4 eq) was added and the resulting mixture was stirred at reflux for 3 h. The reaction mixture was allowed to cool to RT and concentrated in vacuo. The residue was poured into water (1 L) and extracted with ethyl acetate (5×500 mL). The combined organic layers were washed with brine, dried over $Na_2SO_4$ and filtered. The filtrate was concentrated in vacuo and the residue was purified by flash column chromatography on silica gel (2-10% ethyl acetate-hexanes) to afford the regio-isomer methyl 3-amino-6-chloro-2-methylbenzoate 63.

To a stirred mixture of methyl 3-amino-6-chloro-2-methylbenzoate 63 (22 g, 110 mmol, 1 eq) in fluoroboric acid (42%, 200 mL) at 0° C., a solution of sodium nitrate (15.2 g, 220 mmol, 2 eq) in $H_2O$ (20 mL) was added dropwise (over 30 min) while keeping the reaction temperature between 5° C. and 10° C. The resulting mixture was stirred at RT for 1 h. The precipitate was collected by filtration, rinsed with cold water (2×5 mL), and dried in vacuo to afford the product 64. The product was used directly in the next step.

Product 64 (30 g, 99 mmol) was heated to 120° C. and stirred for 30 min. while maintaining the temperature at 120-130° C. The mixture was cooled to 50° C., poured into ice-water (100 mL) and then extracted with ethyl acetate (3×100 mL). The combined organic layers were washed with brine, dried over $Na_2SO_4$ and filtered. The filtrate was concentrated in vacuo and the residue was purified by flash column chromatography on silica gel (2-20% ethyl acetate-hexanes) to afford the product methyl 6-chloro-3-fluoro-2-methylbenzoate 65.

Methyl 6-chloro-3-fluoro-2-methylbenzoate 65 (14 g, 69 mmol, 1 eq) and NaOH (13.8 g, 345 mmol, 5 eq) were dissolved in a mixture of 1,4-dioxane (10 mL) and $H_2O$ (130 mL), and the resulting mixture was stirred at reflux overnight. The reaction mixture was cooled to RT and neutralized with conc. HCl to adjust the pH value to 1. The mixture was extracted with DCM (3×60 mL). The combined organic layers were washed with brine, dried over $Na_2SO_4$ and filtered.

Compound 68 was prepared from 2-chloro-6-methylbenzoic acid 59 according to the following procedures: 2-Chloro-6-methylbenzoic acid 59 (50 g, 294 mmol, 1 eq) was dissolved in conc. $H_2SO_4$ (500 mL) and cooled to 0° C. with an ice bath. To this solution, fuming $HNO_3$ (20.4 g, 324 mmol, The filtrate was concentrated in vacuo to afford the product 6-chloro-3-fluoro-2-methylbenzoic acid 66. The product was used directly in the next step.

Compound 67 was then prepared using Method I (steps transforming (I-1) to (I-3)) followed by Method K (steps transforming (I-3) to (K-6)) from the prepared intermediate 6-chloro-3-fluoro-2-methylbenzoic acid 66. Compound 68 was prepared from compound 67 using an analogous procedure to compound 53 in Example 33. ESI-MS m/z: 456.2 [M+H]$^+$.

Example 38

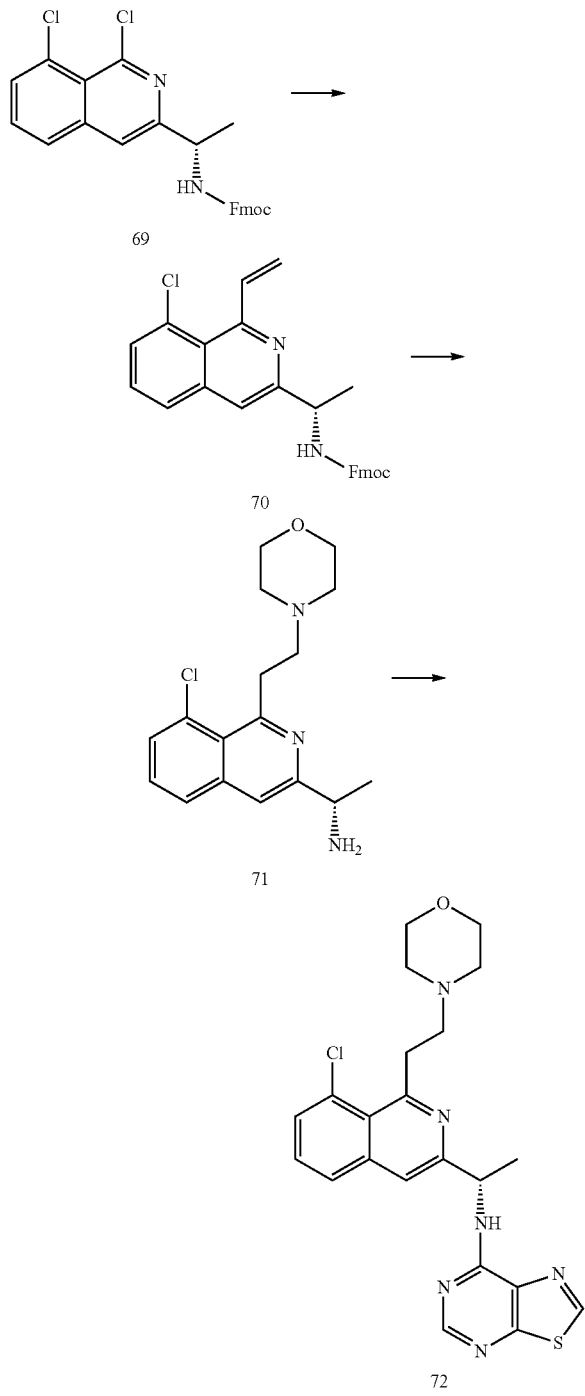

Compound 69 was prepared from 2-chloro-5-methylbenzoic acid according to Method I. Compound 69 was then converted to compound 72 in 3 steps according to the following procedures:

To a stirred mixture of (S)-(9H-fluoren-9-yl)methyl (1-(1,8-dichloroisoquinolin-3-yl)ethyl)carbamate 69 (5.2 g, 11.2 mmol, 1 eq), Pd(OAc)$_2$ (780 mg, 3.48 mmol, 0.31 eq) and PPh$_3$ (1.8 g, 6.89 mmol, 0.61 eq) in THF (200 mL) at RT under argon, tributyl(vinyl)tin (4.0 g, 12.1 mmol, 1.08 eq) was added and the resulting mixture was stirred at reflux overnight. The reaction mixture was allowed to cool to RT and filtered through silica gel. The filtrate was concentrated in vacuo and the residue was purified by flash column chromatography on silica gel (1-10% ethyl acetate-hexanes) to afford the product (S)-(9H-fluoren-9-yl)methyl (1-(8-chloro-1-vinylisoquinolin-3-yl)ethyl) carbamate 70.

To a stirred mixture of (S)-(9H-fluoren-9-yl)methyl (1-(8-chloro-1-vinylisoquinolin-3-yl)ethyl) carbamate 70 (800 mg, 1.76 mmol, 1 eq) in EtOH (50 mL) at RT, morpholine (3.05 g, 35.2 mmol, 20 eq) was added and the resulting mixture was stirred at reflux for 4 h. The mixture was allowed to cool to RT and then concentrated in vacuo. The residue was purified by flash column chromatography on silica gel (1-10% MeOH-DCM) to afford the product, (S)-1-(8-chloro-1-(2-morpholinoethyl)isoquinolin-3-yl)ethanamine 71.

A mixture of (S)-1-(8-chloro-1-(2-morpholinoethyl)isoquinolin-3-yl)ethanamine 71 (100 mg, 0.31 mmol, 1 eq), 7-chlorothiazolo[5,4-d]pyrimidine (E-4) (108 mg, 0.63 mmol, 2 eq) and triethylamine (130 mg, 1.25 mmol, 4.0 eq) in n-BuOH (40 mL) was stirred at reflux for 16 h. The reaction mixture was cooled to RT and concentrated in vacuo. The residue was purified by flash column chromatography on silica gel (1-5% MeOH-DCM) to afford the product (S)—N-(1-(8-chloro-1-(2-morpholinoethyl)isoquinolin-3-yl)ethyl)thiazolo[5,4-d]pyrimidin-7-amine 72. ESI-MS m/z: 455.0 [M+H]$^+$.

Example 39

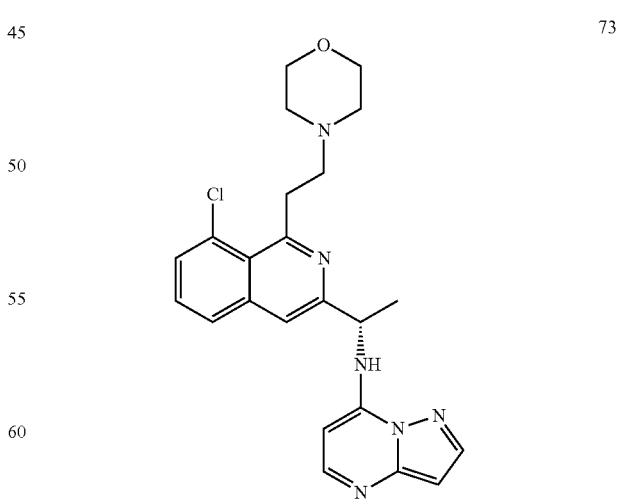

Compound 73 was prepared in analogous fashion to compound 72 in Example 38 except that (C-2) was used in place of (E-4). ESI-MS m/z: 437.2 [M+H]$^+$.

Example 40

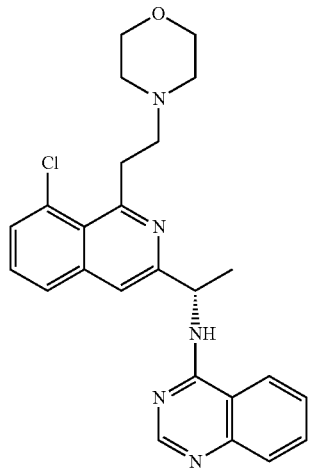

74

Compound 74 was prepared in analogous fashion to compound 72 in Example 38 except that 4-chloroquinazoline was used in place of (E-4). ESI-MS m/z: 448.2 [M+H]$^+$.

Example 41

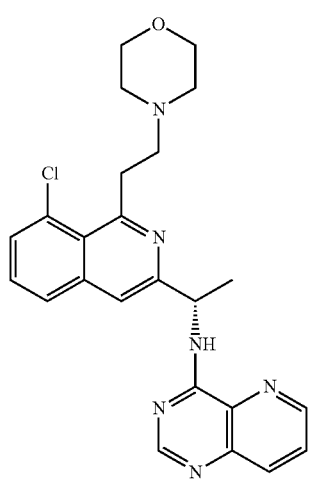

75

Compound 75 was prepared in analogous fashion to 72 in Example 38 except that (B-3) was used in place of (E-4). ESI-MS m/z: 449.2 [M+H]$^+$.

Example 42

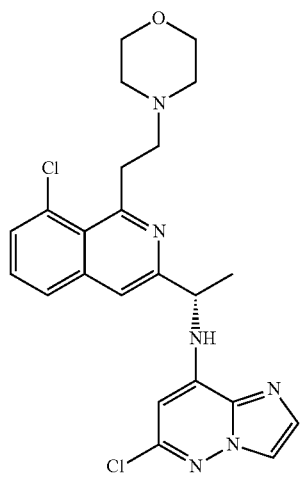

76

Compound 76 was prepared in analogous fashion to 72 in Example 38 except that (D-3) was used in place of (E-4). ESI-MS m/z: 471.0 [M+H]$^+$.

Example 43

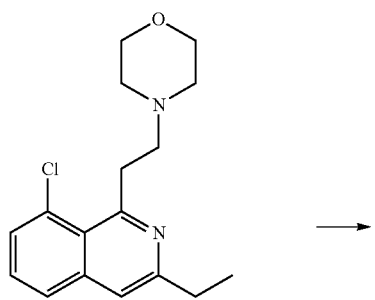

76

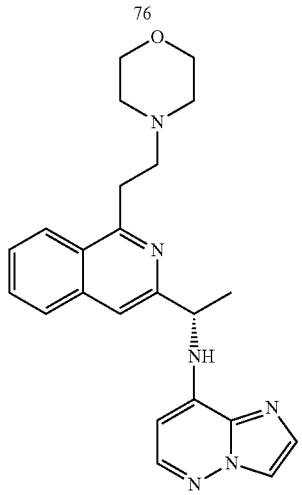

77

Compound 77 was prepared from 76 according to the following procedure:

Palladium on carbon (10%, 10 mg) was added to a mixture of (S)-6-chloro-N-(1-(8-chloro-1-(2-morpholinoethyl)isoquinolin-3-yl)ethyl)imidazo[1,2-b]pyridazin-8-amine 76 (40 mg, 0.085 mmol, 1.0 eq) and triethylamine (0.2 mL, 1.5 mmol, 17.6 eq) in MeOH (10 mL). The resulting mixture was degassed and back-filled with hydrogen three times and then stirred at RT under hydrogen for 5 h. The mixture was filtered and the filtrate was concentrated in vacuo. The residue was purified by flash column chromatography on silica gel (1-4% MeOH-DCM) to afford the product (S)—N-(1-(1-(2-morpholinoethyl)isoquinolin-3-yl)ethyl)imidazo[1,2-b]pyridazin-8-amine 77. ESI-MS m/z: 403.2 [M+H]+.

Example 44

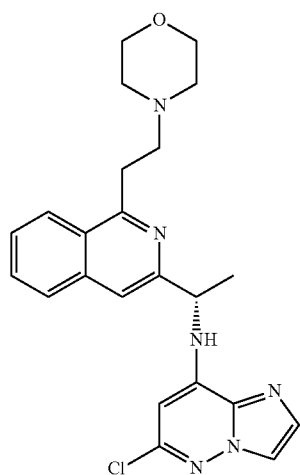

78

Compound 78 was also isolated from the reaction described in Example 43. ESI-MS m/z: 437.2 [M+H]+.

Example 45

79

80

-continued

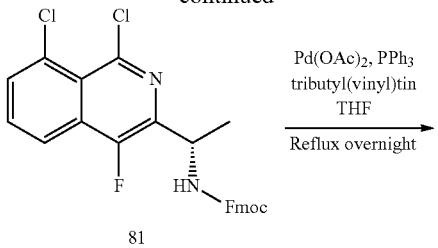

81

82

83

84

Example 46

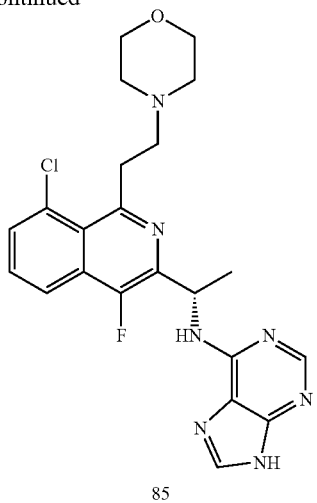
85

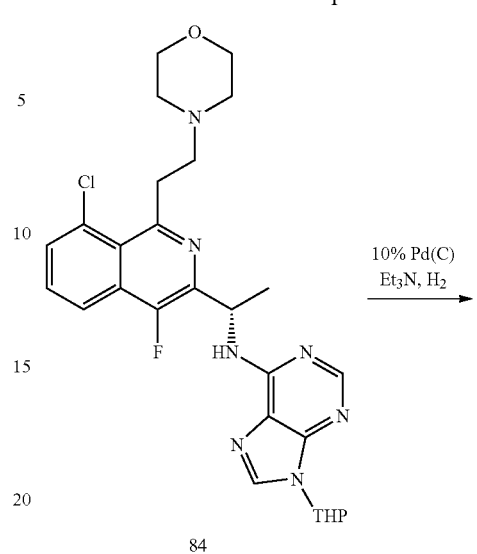

Compound 79 was prepared from 2-chloro-5-methylbenzoic acid using Method I. Compound 79 was then converted to compound 80 according to the following procedures:

A mixture of (S)-(9H-fluoren-9-yl)methyl 1-(8-chloro-1-oxo-1,2-dihydroisoquinolin-3-yl)ethylcarbamate 79 (2.75 g, 6.1 mmol, 1.0 eq) and selectfluor (2.16 g, 6.1 mmol, 1.0 eq) in anhydrous acetonitrile (100 mL) was stirred at reflux under argon for 12 h. The mixture was allowed to cool to RT and then concentrated in vacuo. The residue was dissolved in ethyl acetate (100 mL) and filtered through celite. The filtrate was washed with water, dried over anhydrous $Na_2SO_4$ and filtered. The filtrate was concentrated in vacuo and the residue was purified by flash column chromatography on silica gel (10-50% ethyl acetate-hexanes) to afford the product (S)-(9H-fluoren-9-yl)methyl 1-(8-chloro-4-fluoro-1-oxo-1,2-dihydroisoquinolin-3-yl)ethylcarbamate 80.

Compound 81 was prepared from compound 80 using step 7 in Method I. Compound 81 was converted to 83 in analogous fashion to compound 71 in Example 38.

Compound 83 was coupled with intermediate 6-chloro-9-(tetrahydro-2H-pyran-2-yl)-9H-purine (K-2, prepared by Method K) to afford compound 84 according to Method J.

A mixture of N—((S)-1-(8-chloro-4-fluoro-1-(2-morpholinoethyl)isoquinolin-3-yl)ethyl)-9-(tetrahydro-2H-pyran-2-yl)-9H-purin-6-amine 84 (60 mg, 0.11 mmol) in hydrogen chloride/methanol solution (4 N, 20 mL) was stirred at RT for 0.5 h and then concentrated in vacuo. The residue was suspended in water (20 mL), neutralized with concentrated ammonium hydroxide to adjust the pH to 8-9 and then extracted with DCM (3×10 mL). The combined organic layers were washed with brine, dried over $Na_2SO_4$ and filtered. The filtrate was concentrated in vacuo and the residue was purified by flash column chromatography on silica gel (2-10% MeOH-DCM) to afford the product (S)—N-(1-(8-chloro-4-fluoro-1-(2-morpholinoethyl)isoquinolin-3-yl)ethyl)-9H-purin-6-amine 85. ESI-MS m/z: 456.2 [M+H]$^+$.

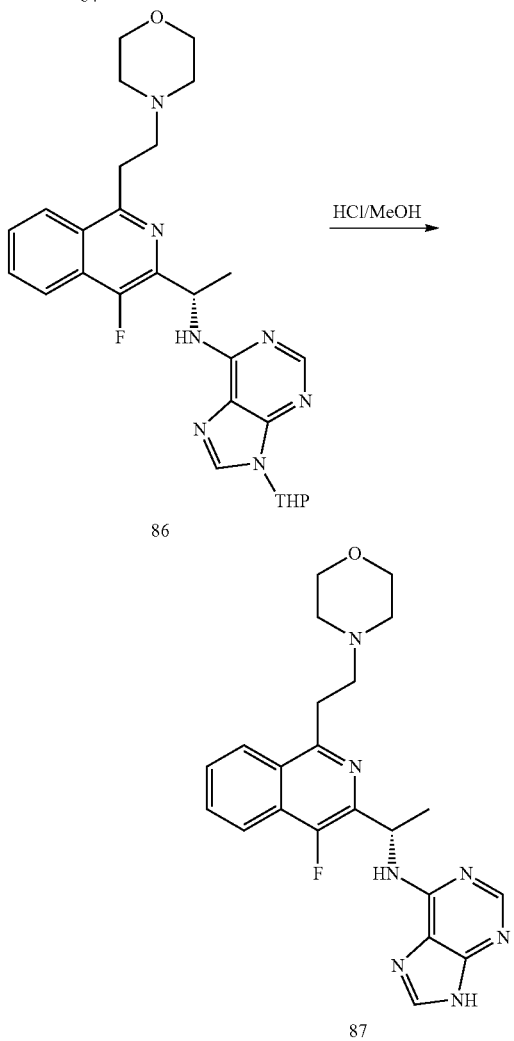

Compound 86 was prepared in an analogous fashion to compound 77 in Example 43 from compound 84. Compound 87 was then prepared in an analogous fashion to compound 85 in Example 45 from compound 86. ESI-MS m/z: 422.2 [M+H]$^+$.

Example 47

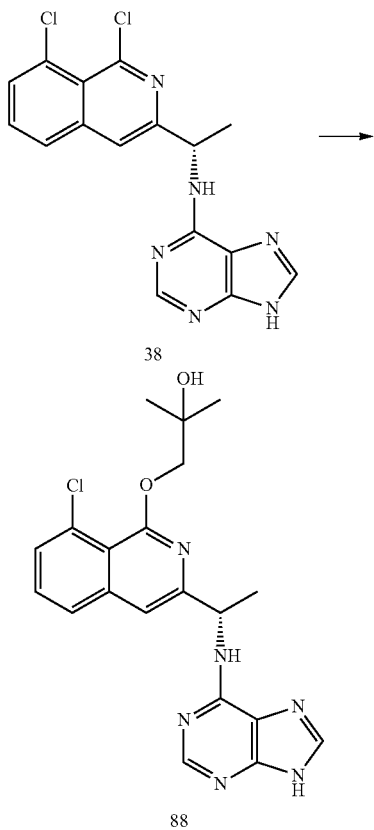

Compound 88 was prepared from compound 38 in analogous fashion to compound 47 in Example 31 except that 2-methylpropane-1,2-diol was used in place of 1-isopropylpiperidin-4-ol. ESI-MS m/z: 413.2 [M+H]+.

Example 48

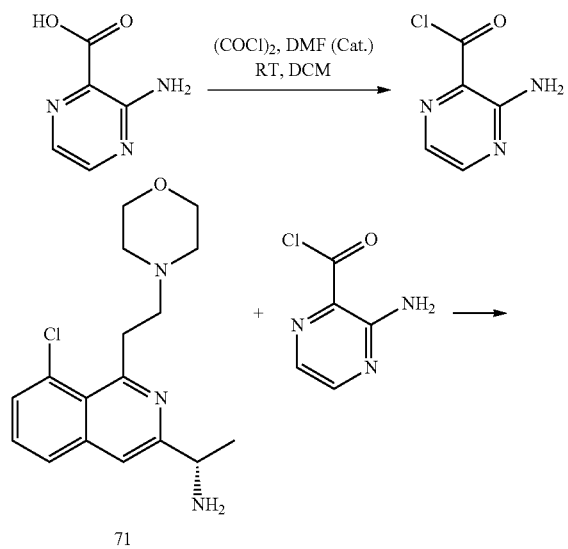

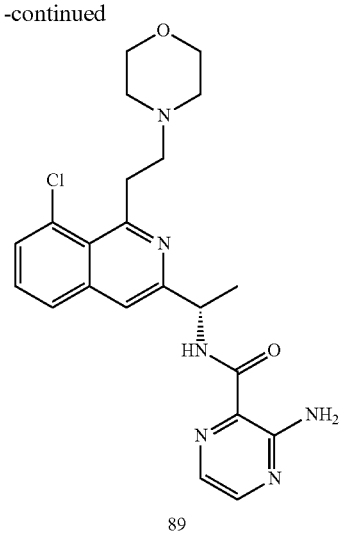

Compound 71 was prepared from compound 69 according to Example 38. Compound 89 was prepared from compound 71 according to the following procedure:

To a stirred mixture of 3-aminopyrazine-2-carboxylic acid (70 mg, 0.5 mmol, 1.6 eq) and DMF (cat.) in anhydrous DCM (10 mL) at RT, oxalyl chloride (0.13 mL, 4.8 eq) was added and the resulting mixture was stirred at RT for 2 h. The mixture was concentrated in vacuo. The residue was dissolved in DCM (10 mL) and the resulting solution (solution A) was used directly in the next step.

To a stirred mixture of (S)-1-(8-chloro-1-(2-morpholino-ethyl)isoquinolin-3-yl)ethanamine 71 (100 mg, 0.31 mol, 1.0 eq) in DCM (5 mL), solution A was added dropwise and the resulting mixture was stirred at RT for 1 h. Water (10 mL) was added to the reaction mixture. The organic layer was separated and washed with water (2×10 mL), dried over Na₂SO₄ and filtered. The filtrate was concentrated in vacuo. The residue was purified by flash column chromatography on silica gel (2-6% MeOH-DCM) to afford the product (S)-3-amino-N-(1-(8-chloro-1-(2-morpholinoethyl)isoquinolin-3-yl)ethyl)pyrazine-2-carboxamide 89. ESI-MS m/z: 441.2 [M+H]+.

Example 49

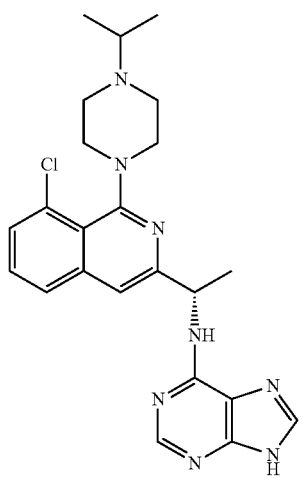

Compound 90 was prepared in analogous fashion to compound 46 in Example 30 except that N-isopropylpiperidine was used in place of N-methylpiperidine. ESI-MS m/z: 451.2 [M+H]+.

Example 50

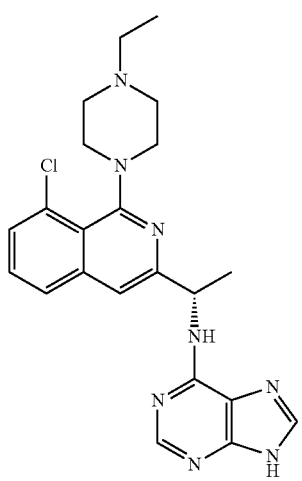

91

Compound 91 was prepared in analogous fashion to compound 46 in Example 30 except that N-ethylpiperidine was used in place of N-methylpiperidine. ESI-MS m/z: 437.2 [M+H]$^+$.

Example 51

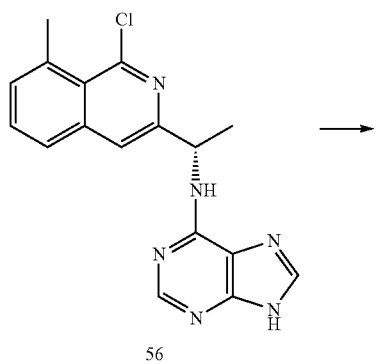

56

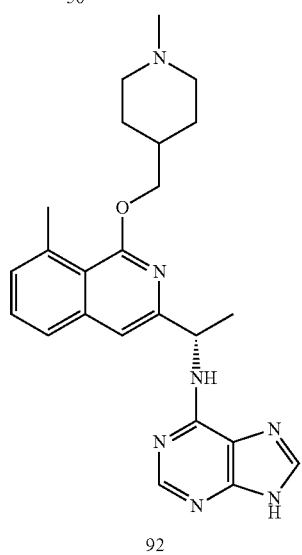

92

Compound 92 was synthesized from compound 56 using the analogous procedure for compound 47 in Example 31 except that (1-methylpiperidin-4-yl)methanol was used in place of 1-isopropylpiperidin-4-ol. ESI-MS m/z: 432.0 [M+H]$^+$.

Example 52

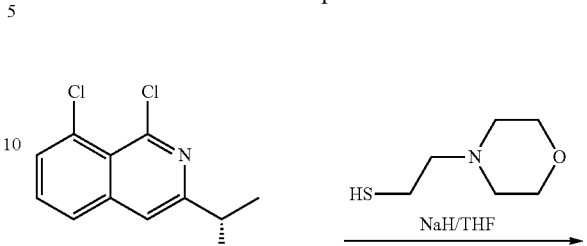

38

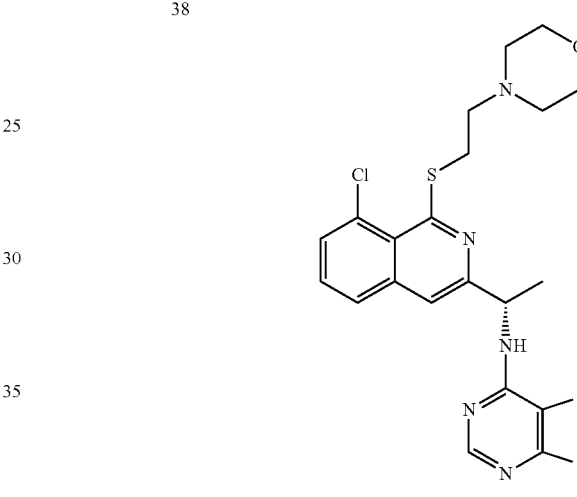

93

Compound 93 was prepared from compound 38 in analogous fashion to compound 47 in Example 31 except that 2-morpholinoethanethiol was used in place of 1-isopropylpiperidin-4-ol. ESI-MS m/z: 470.0 [M+H]$^+$.

Example 53

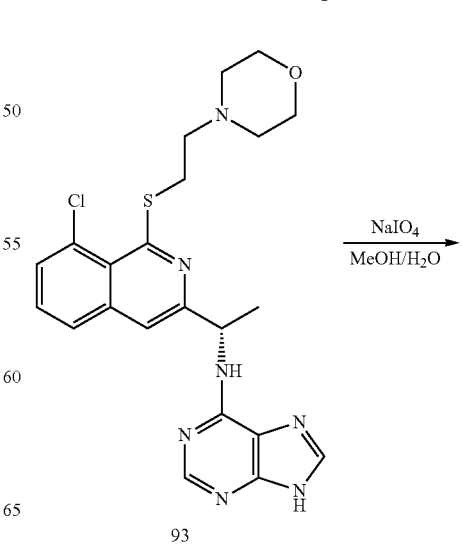

93

-continued

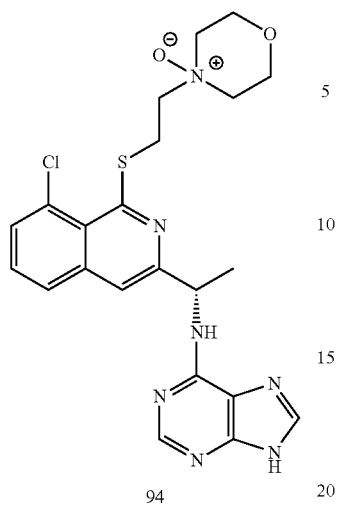

94

Compound 94 was prepared according to the following procedure:

To a stirred mixture of (S)—N-(1-(8-chloro-1-(2-morpholinoethylthio)isoquinolin-3-yl)ethyl)-9H-purin-6-amine 93 (100 mg, 0.21 mmol, 1.0 eq) in MeOH (15 mL) and H$_2$O (2 mL) at 0° C., sodium periodate (184 mg, 0.84 mmol, 4.0 eq) was added in portions. The resulting mixture was allowed to warm to RT over 30 min and stirred at RT overnight. The reaction mixture was poured into water (40 mL) and extracted with DCM (3×30 mL). The combined organic layers were washed with brine, dried over Na$_2$SO$_4$ and filtered. The filtrate was concentrated in vacuo and the residue was purified by flash column chromatography on silica gel (1-7% MeOH-DCM) to afford the product 94. ESI-MS m/z: 486.2 [M+H]$^+$.

Example 54

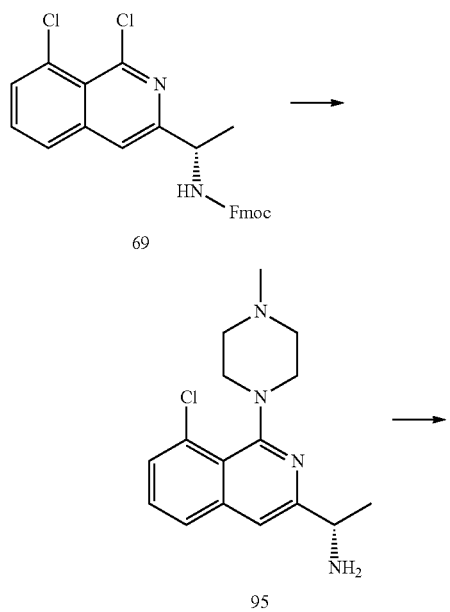

-continued

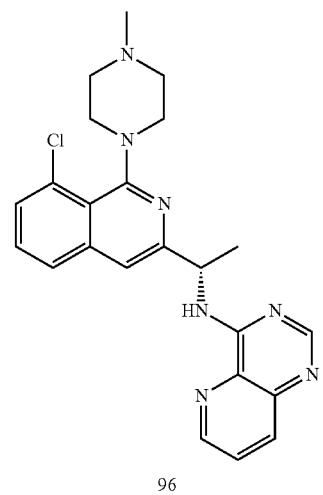

96

Compound 96 was prepared from 69 according to the following procedure:

A solution of (S)-(9H-fluoren-9-yl)methyl 1-(1,8-dichloroisoquinolin-3-yl)ethylcarbamate 69 (250 mg, 0.539 mmol, 1.0 eq) and 1-methylpiperazine (108 mg, 1.079 mmol, 2.0 eq) in 1,4-dioxane (5 mL) was stirred at reflux overnight. The reaction mixture was allowed to cool to RT and concentrated in vacuo. The residue was purified by flash column chromatography on silica gel (3.3% MeOH-DCM) to afford the product (S)-1-(8-chloro-1-(4-methylpiperazin-1-yl) isoquinolin-3-yl)ethanamine 95.

Compound 95 was then converted to compound 96 in analogous fashion to compound 72 in Example 38 except that (B-3) was used in place of (E-4). ESI-MS m/z: 434.2 [M+H]$^+$.

Example 55

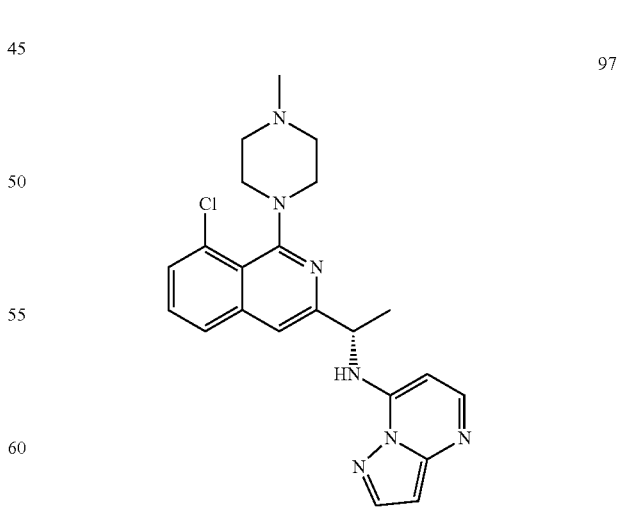

Compound 97 was synthesized from compound 95 in analogous fashion to compound 72 in Example 38 except that (C-2) was used in place of (E-4). ESI-MS m/z: 422.2 [M+H]$^+$.

Example 56

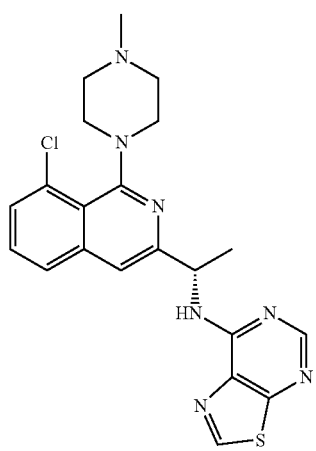

Compound 98 was synthesized from compound 95 in analogous fashion to compound 72 in Example 38. ESI-MS m/z: 440.0 [M+H]+.

Example 57

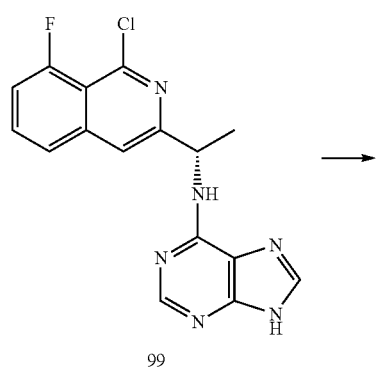

Compound 99 was prepared from 2-fluoro-5-methylbenzoic acid using Method I (steps transforming (I-1) to (I-3)) followed by Method K (steps transforming (I-3) to (K-5)).

Compound 99 was then converted to compound 100 in analogous fashion to compound 46 in Example 30. ESI-MS m/z: 407.2 [M+H]+.

Example 58

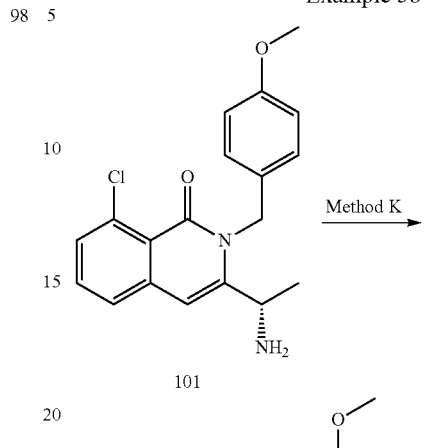

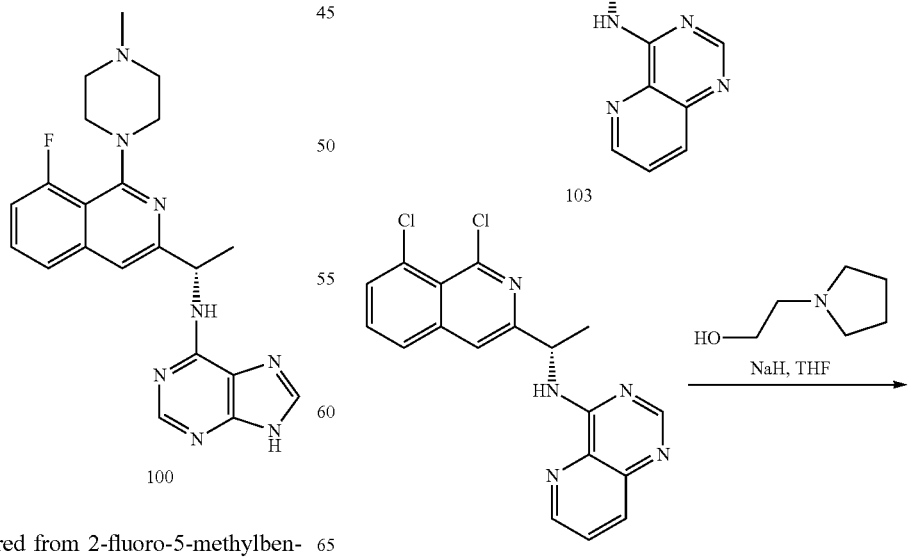

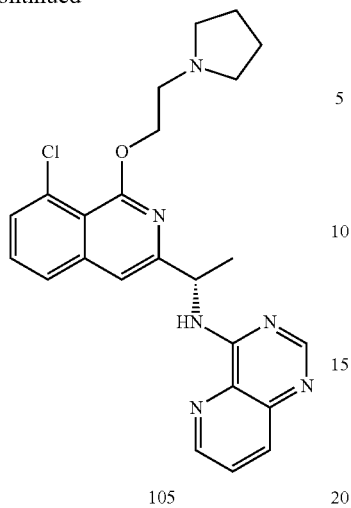

105

Compound 105 was prepared from compound 101 according to the following 4-step procedure:

Compound 101 was prepared by using method I (steps transforming (I-1) to (I-3)). Compound 101 was then converted to compound 104 in a 3-step procedure analogous to the conversion of compound (I-3) to (K-5) in Method K except that (B-3) was used in place of (K-2). Compound 105 was then prepared from 104 in analogous fashion to compound 47 in Example 31 except that 2-(pyrrolidin-1-yl)ethanol was used in place of 1-isopropylpiperidin-4-ol. ESI-MS m/z: 449.2 [M+H]⁺.

Example 59

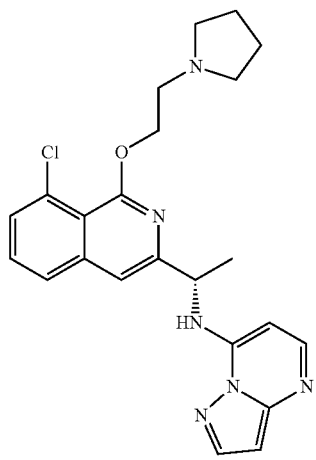

106

Compound 106 was synthesized from compound 101 in analogous fashion to compound 105 in Example 58 except that (C-2) was used in place of (B-3). ESI-MS m/z: 437.2 [M+H]⁺.

Example 60

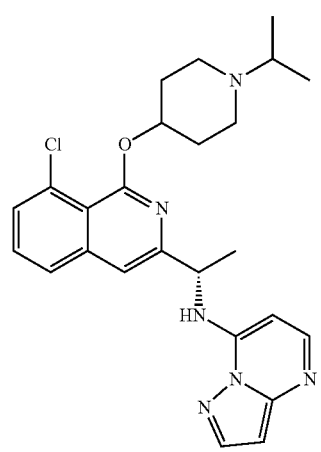

107

Compound 107 was prepared in analogous fashion to compound 106 in Example 59 except that 1-isopropylpiperidin-4-ol was used in place of 2-(pyrrolidin-1-yl)ethanol. ESI-MS m/z: 465.2 [M+H]⁺.

Example 61

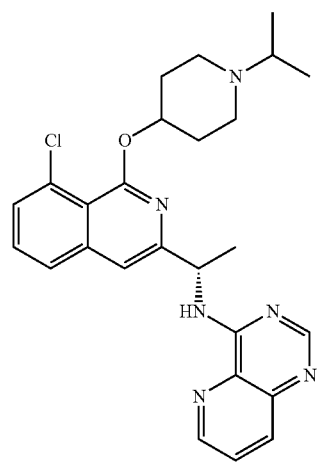

108

Compound 108 was prepared in analogous fashion to compound 105 in Example 58 except that 1-isopropylpiperidin-4-ol was used in place of 2-(pyrrolidin-1-yl)ethanol. ESI-MS m/z: 477.2 [M+H]⁺.

Example 62

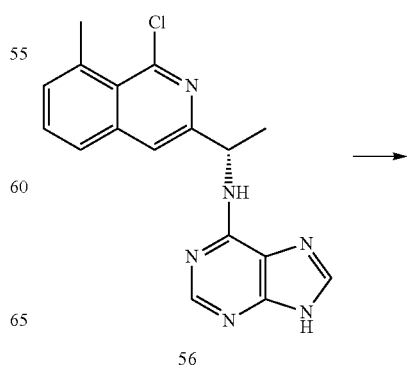

56

Example 64

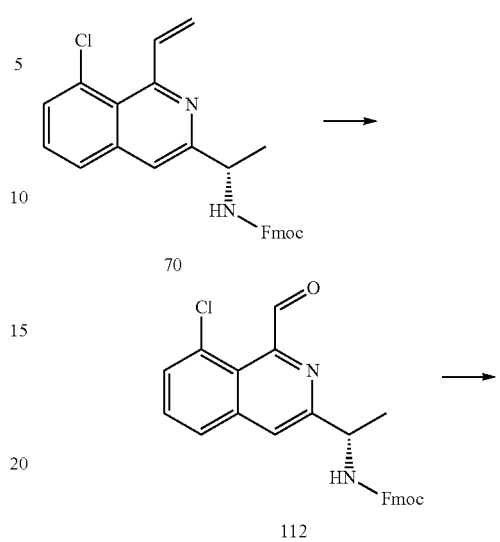

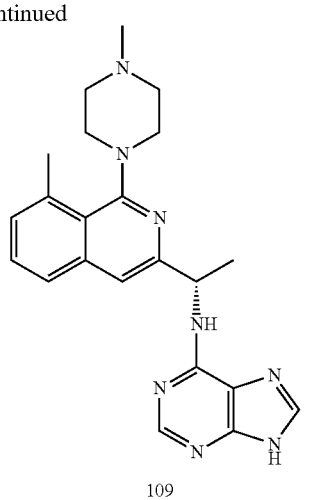

109

Compound 109 was prepared from 56 in analogous fashion to compound 46 in Example 30. ESI-MS m/z: 403.2 [M+H]+.

Example 63

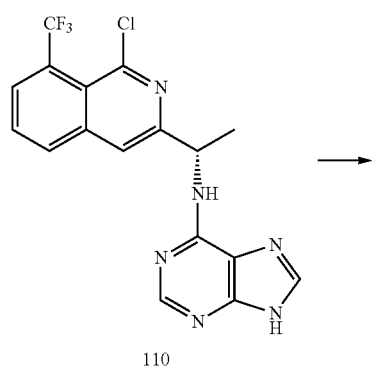

110

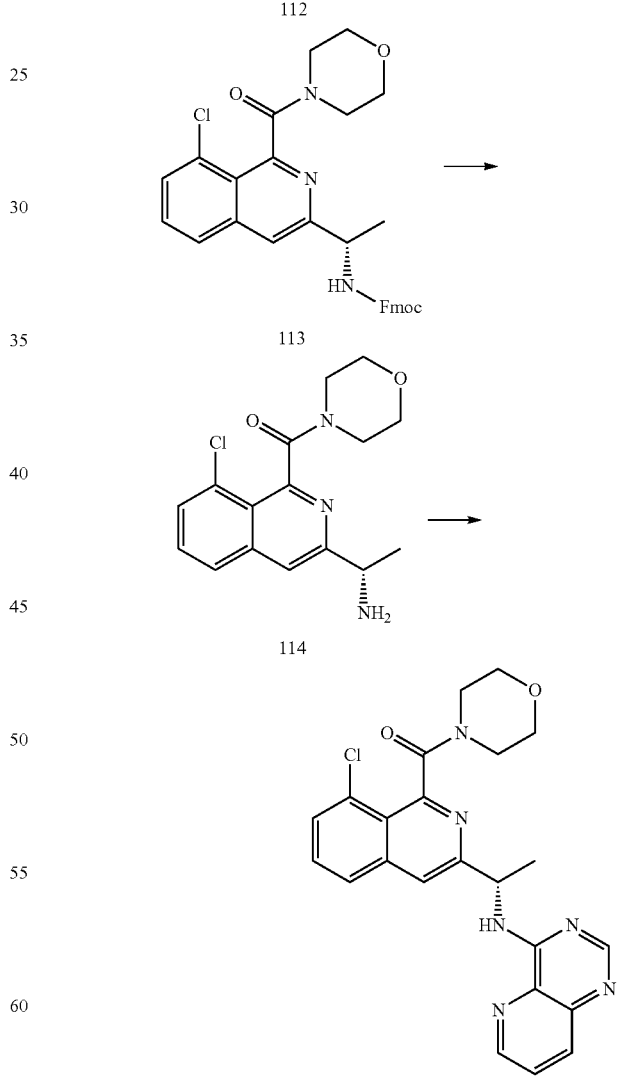

111

Compound 110 was prepared from trifluoromethylbenzoic acid by using method I (steps transforming (I-1) to (I-3)) then method K (steps transforming (I-3) to (K-5)). Compound 110 was then converted to 111 using the analogous procedure for 46 in Example 30. ESI-MS m/z: 457.2 [M+H]+.

Compound 115 was prepared in 4 steps from compound 70 according to the following procedures:

Compound 70 was prepared in analogous fashion to compound 2 in Example 1. Oxidation and amide formation using the analogous procedures for compound 12 in Example 5 provided compound 113, which was Fmoc-deprotected under standard conditions to provide compound 114. This amine 114 was then converted to compound 115 in analogous fashion to compound 72 in Example 38 except that (B-3) was used in place of (E-4). ESI-MS m/z: 449.2 [M+H]$^+$.

Example 65

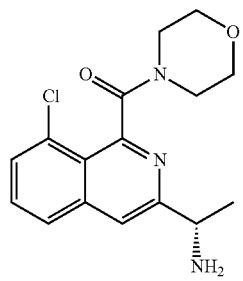
114

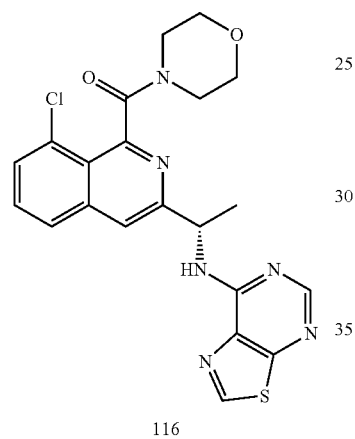
116

Compound 116 was prepared from compound 114 in analogous fashion to compound 73 in Example 38. ESI-MS m/z: 455.0 [M+H]$^+$.

Example 66

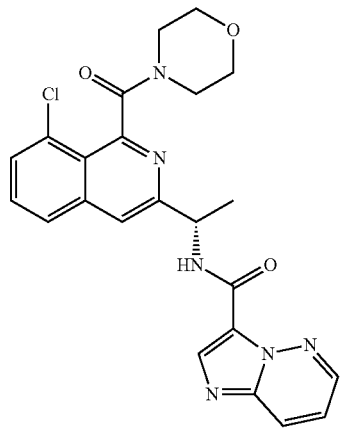
117

Compound 117 was prepared from compound 114 in analogous fashion to compound 90 in Example 48 except that imidazo[1,2-b]pyridazine-3-carboxylic acid was used in place of 3-aminopyrazine-2-carboxylic acid. ESI-MS m/z: 465.0 [M+H]$^+$.

Example 67

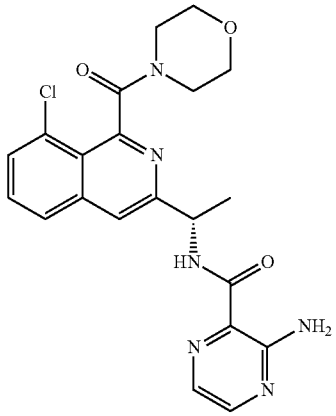
118

Compound 118 was prepared from compound 115 in analogous fashion to compound 90 in Example 48. ESI-MS m/z: 441.2 [M+H]$^+$.

Example 68

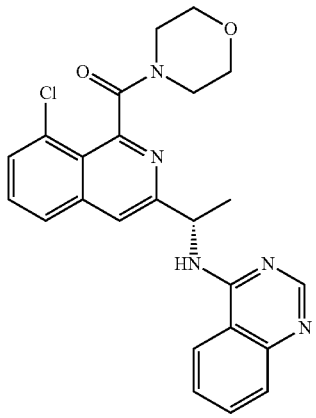
119

Compound 119 was prepared from compound 114 in analogous fashion to compound 72 in Example 38 except that 4-chloroquinazoline was used in place of (E-4). ESI-MS m/z: 448.2 [M+H]$^+$.

Example 69

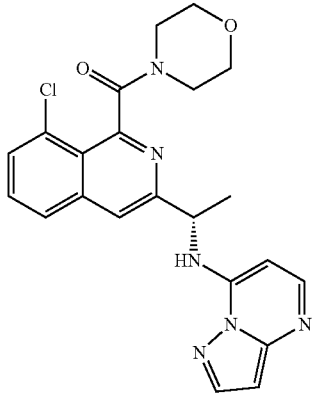
120

Compound 120 was prepared from compound 114 in analogous fashion to compound 72 in Example 38 except that (C-2) was used in place of (E-4). ESI-MS m/z: 437.2 [M+H]$^+$.

Example 70

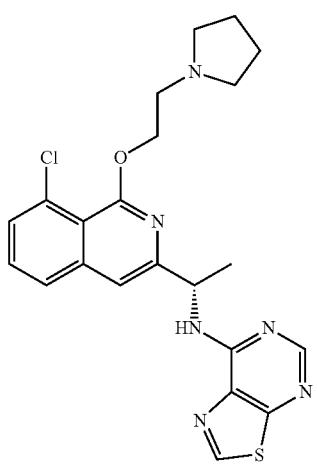

121

Compound 121 was prepared from compound 101 in analogous fashion to compound 105 in Example 58 except that (E-4) was used in place of (B-3). ESI-MS m/z: 437.2 [M+H]⁺.

Example 71

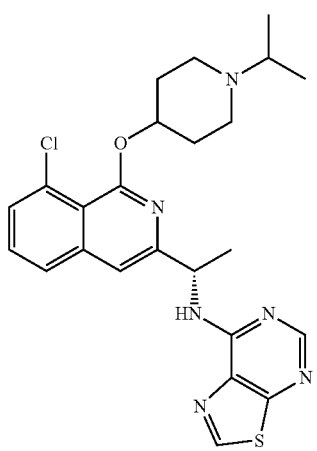

122

Compound 122 was prepared from compound 101 in analogous fashion to compound 105 in Example 59 except that 1-isopropylpiperidin-4-ol was used in place of 2-(pyrrolidin-1-yl)ethanol and (E-4) was used in place of (B-3). ESI-MS m/z: 483.2 [M+H]⁺.

Example 72

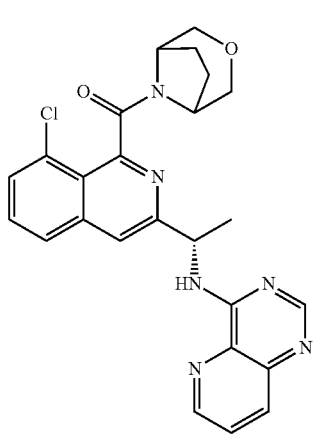

123

Compound 123 was prepared from compound 70 in analogous fashion to compound 115 in Example 64 except that 3-oxa-8-azabicyclo[3.2.1]octane was used in place of morpholine for the coupling. ESI-MS m/z: 475.2 [M+H]⁺.

Example 73

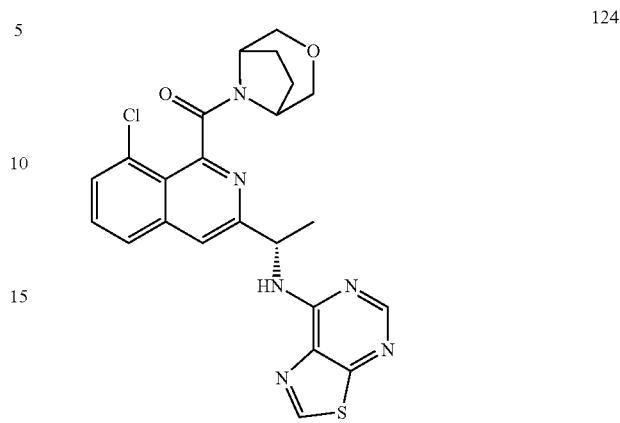

124

Compound 124 was prepared from compound 70 in analogous fashion to compound 115 in Example 64 except that 3-oxa-8-azabicyclo[3.2.1]octane was used in place of morpholine for the coupling and (E-4) was used in place of (B-3). ESI-MS m/z: 481.2 [M+H]⁺.

Example 74

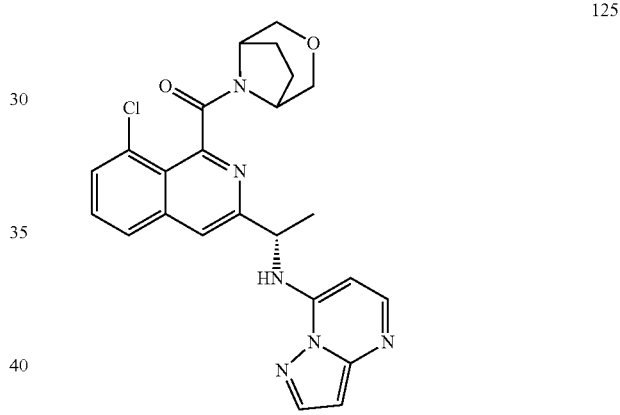

125

Compound 125 was prepared from compound 70 in analogous fashion to compound 115 in Example 64 except that 3-oxa-8-azabicyclo[3.2.1]octane was used in place of morpholine for the coupling and (C-2) was used in place of (B-3). ESI-MS m/z: 463.2 [M+H]⁺.

Example 75

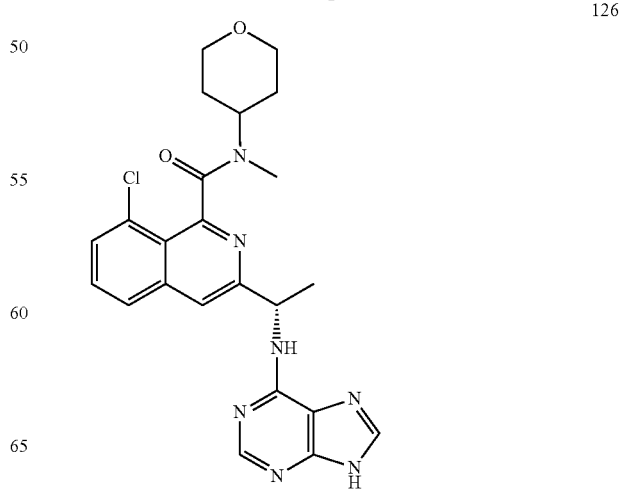

126

Compound 126 was prepared from compound 5 in analogous fashion to compound 13 in Example 5 except that N-methyltetrahydro-2H-pyran-4-amine was used in place of morpholine. ESI-MS m/z: 466.2 [M+H]⁺.

Example 76

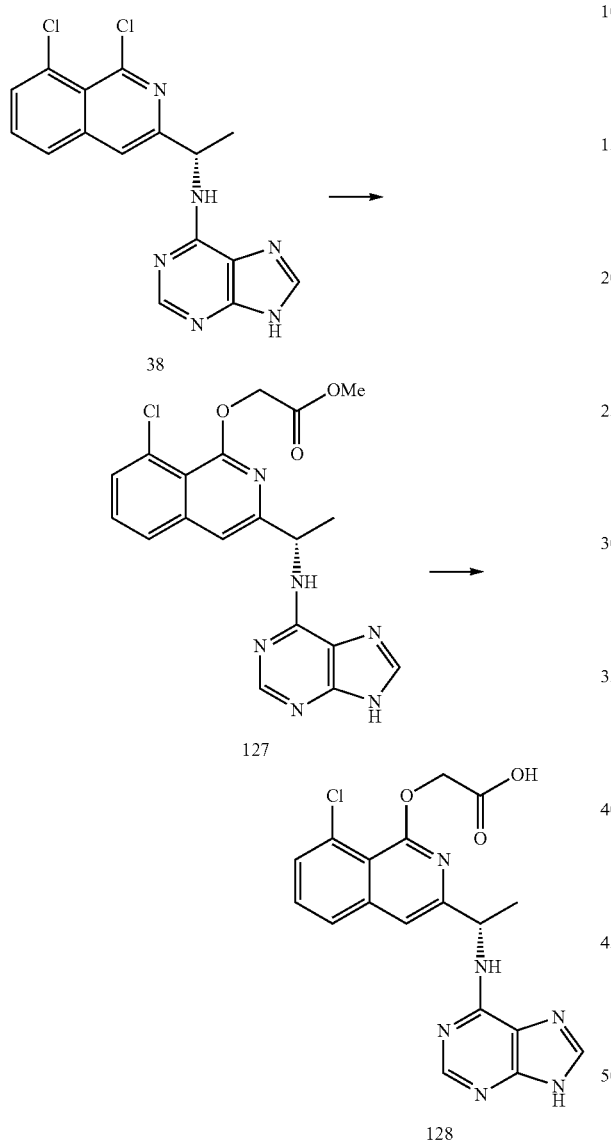

Compound 128 was prepared from compound 38 according to the following procedures:

Compound 38 was converted to compound 127 in analogous fashion to compound 47 in Example 31 except that methyl 2-hydroxyacetate was used in place of 1-isopropylpiperidin-4-ol.

To a mixture of (S)-methyl 2-(3-(1-(9H-purin-6-ylamino) ethyl)-8-chloroisoquinolin-1-yloxy)acetate 127 (200 mg, 0.47 mmol, 1.0 eq) in EtOH (5 mL) and H₂O (2 mL), LiOH (78 mg, 3.25 mmol, 6.9 eq) was added in one portion. The resulting mixture was stirred at 60° C. for 2 h and then concentrated in vacuo. The residue was suspended in ice-water (15 mL) and the resulting mixture was neutralized with acetic acid at 0-5° C. to adjust pH to 7-8. The precipitate was collected by filtration and dried in vacuo to afford the product (S)-2-(3-(1-(9H-purin-6-ylamino)ethyl)-8-chloroisoquinolin-1-yloxy)acetic acid 128. ESI-MS m/z: 399.0 [M+H]⁺.

Example 77

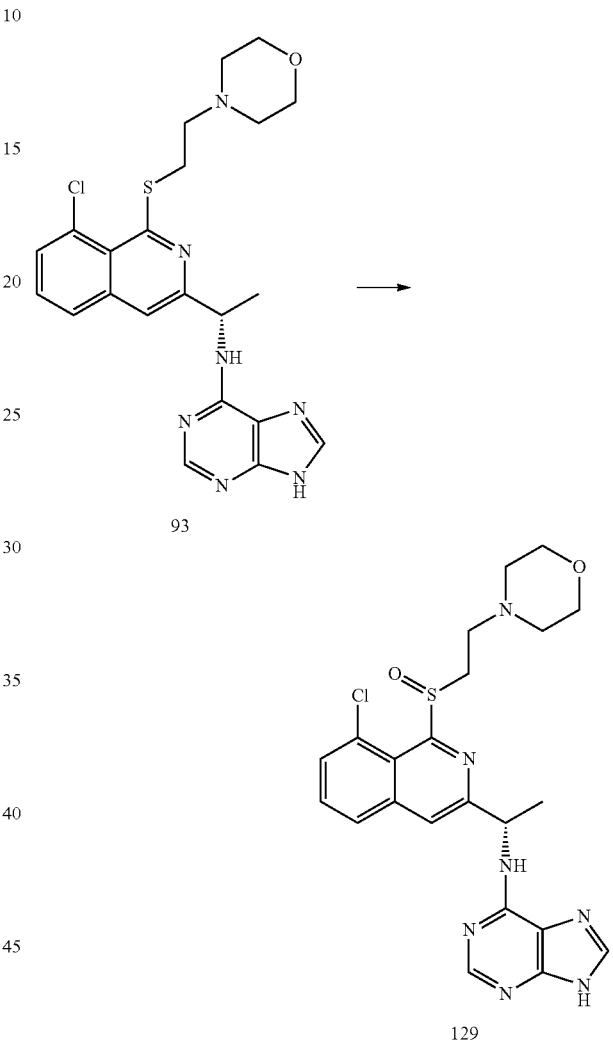

Compound 129 was prepared from compound 93 according to the following procedure:

To a mixture of (S)—N-(1-(8-chloro-1-(2-morpholinoethylthio)isoquinolin-3-yl)ethyl)-9H-purin-6-amine 93 (100 mg, 0.21 mmol, 1.0 eq) in acetic acid (10 mL) at 0° C., hydrogen peroxide (30%, 24 mg, 0.21 mmol, 1.0 eq) was added dropwise. The resulting mixture was allowed to warm to RT over 5 min and then stirred at RT for 1.5 h. The reaction mixture was poured into ice-water (50 mL) and neutralized with concentrated ammonium hydroxide to adjust the pH to 8-9. The resulting mixture was extracted with DCM (3×30 mL). The combined organic layers were washed with brine, dried over Na₂SO₄ and filtered. The filtrate was concentrated in vacuo and the residue was purified by flash column chromatography on silica gel (1-8% MeOH-DCM) to afford the product 129. ESI-MS m/z: 486.2 [M+H]⁺.

Example 78

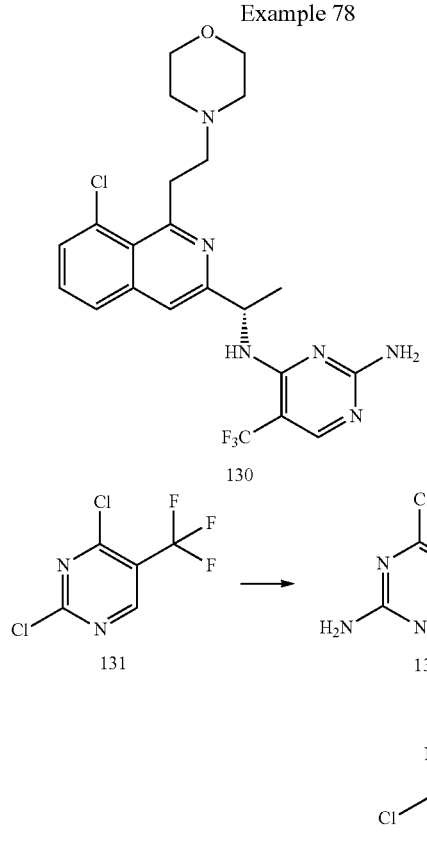

Ammonia in methanol (7 N solution, 15 mL) was added dropwise to stirred neat 2,4-dichloro-5-(trifluoromethyl)pyrimidine 131 (5.0 g, 23.04 mmol) under argon, and the resulting mixture was stirred at RT for 2 h. The reaction mixture was quenched with water and then extracted with ethyl acetate (2×200 mL). The combined organic layers were washed with brine, dried over $Na_2SO_4$ and filtered. The filtrate was concentrated in vacuo and the residue was purified by flash chromatography on silica gel (0-20% ethyl acetate-hexanes) to afford the product 4-chloro-5-(trifluoromethyl)pyrimidin-2-amine 132. The regio-isomer 2-chloro-5-(trifluoromethyl)pyrimidin-4-amine 133 can also be isolated.

Compound 130 was prepared in analogous fashion to compound 72 in Example 38 except that 132 was used in place of (E-4). ESI-MS m/z: 481.2 $[M+H]^+$.

Example 79

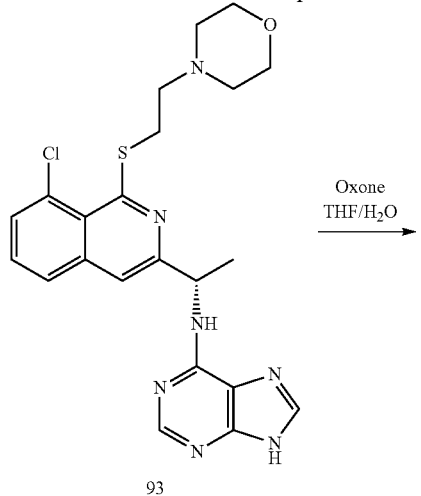

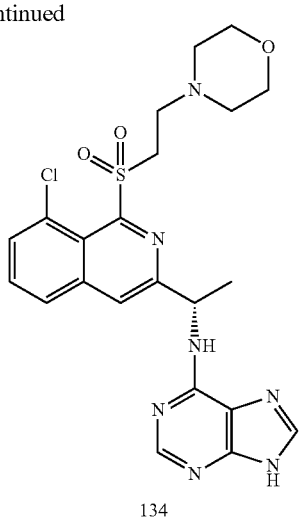

Compound 134 was prepared from 93 according to the following procedure:

To a mixture of (S)—N-(1-(8-chloro-1-(2-morpholinoethylthio)isoquinolin-3-yl)ethyl)-9H-purin-6-amine 93 (150 mg, 0.32 mmol, 1.0 eq) in THF (10 mL) and water (3 mL) at RT, ozone (393 mg, 0.64 mmol, 2.0 eq) was added in one portion and the resulting mixture was stirred overnight. The reaction was quenched with ice-water (20 mL), neutralized with concentrated ammonium hydroxide to adjust the pH to 8 and then extracted with DCM (3×30 mL). The combined organic layers were washed with brine, dried over $Na_2SO_4$ and filtered. The filtrate was concentrated in vacuo and the residue was purified by flash column chromatography on silica gel (1-7% MeOH-DCM) to afford the product 134. ESI-MS m/z: 502.2 $[M+H]^+$.

Example 80

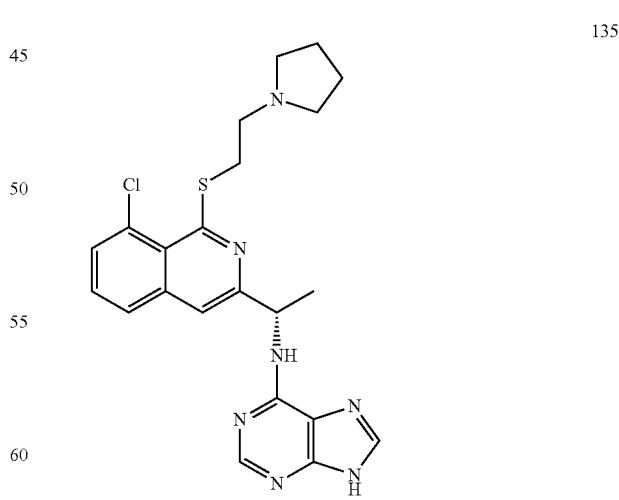

Compound 135 was prepared from compound 38 in analogous fashion to compound 93 in Example 52 except that 2-(pyrrolidin-1-yl)ethanethiol was used in place of 2-morpholinoethanethiol. ESI-MS m/z: 454.2 $[M+H]^+$.

Example 81

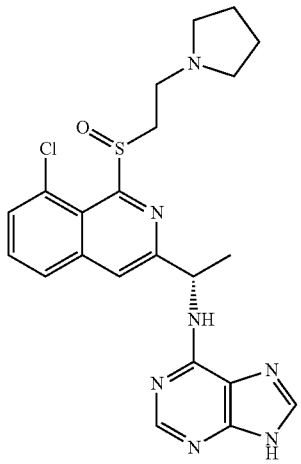

Compound 136 was prepared from compound 135 in analogous fashion to compound 129 in Example 77. ESI-MS m/z: 470.2 [M+H]$^+$.

Example 82

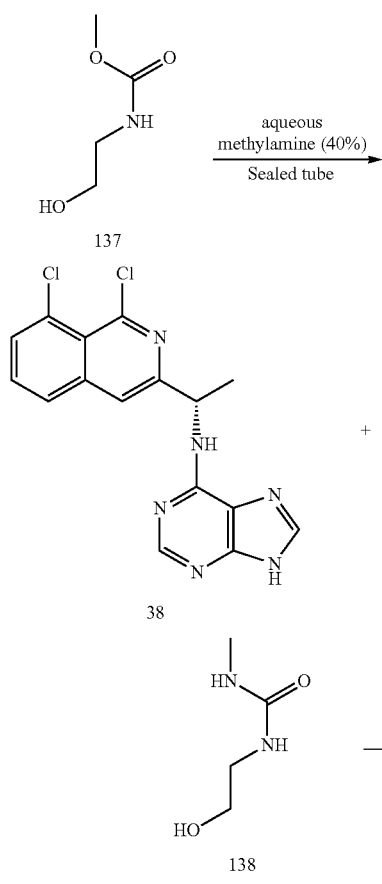

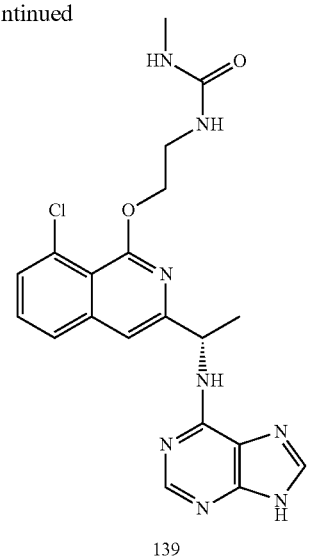

Compound 139 was prepared according the following procedure:

Methyl 2-hydroxyethylcarbamate 137 (2.0 g, 16.8 mmol, 1.0 eq) and aqueous methylamine (40%, 5 mL, 45.0 mmol, 2.7 eq) were mixed in a sealed tube and the mixture was stirred at 120° C. overnight. The mixture was allowed to cool to RT and concentrated in vacuo. The residue was purified by flash column chromatography on silica gel (3% MeOH-DCM) to afford the product 1-(2-hydroxyethyl)-3-methylurea 138. Compound 139 was prepared from compound 38 in analogous fashion to compound 47 in Example 31 except that 1-(2-hydroxyethyl)-3-methylurea 138 was used in place of 1-isopropylpiperidin-4-ol. ESI-MS m/z: 441.2 [M+H]$^+$.

Example 83

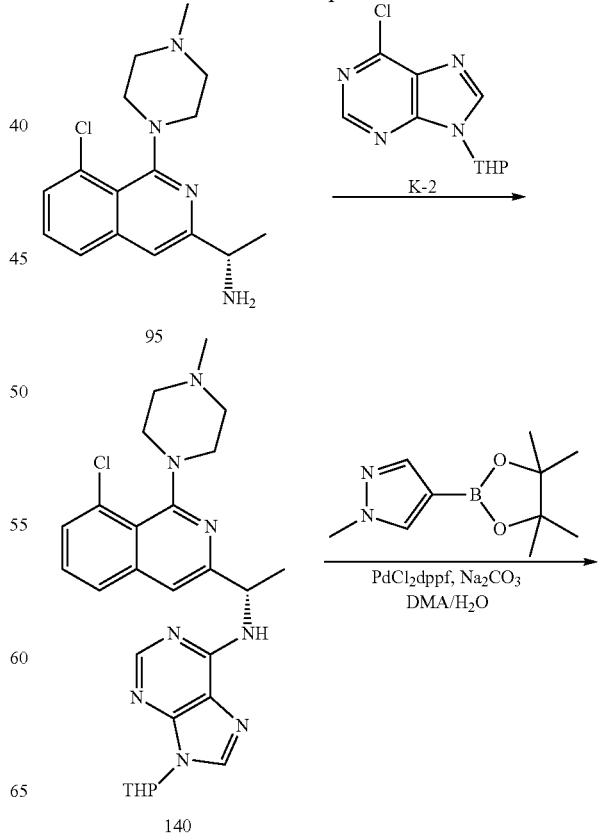

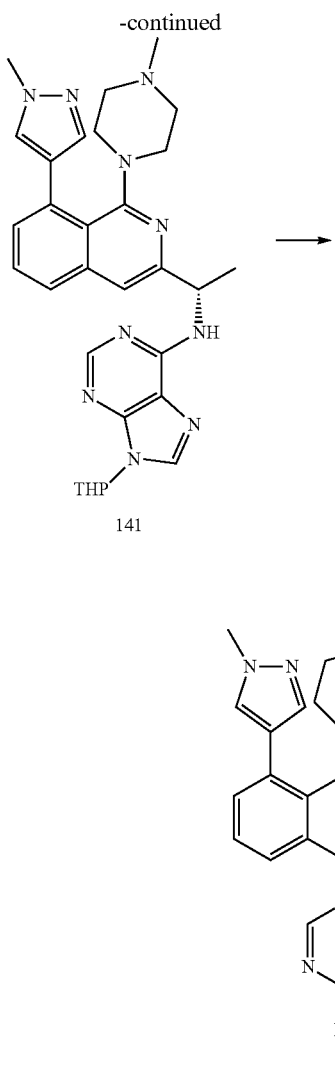

141

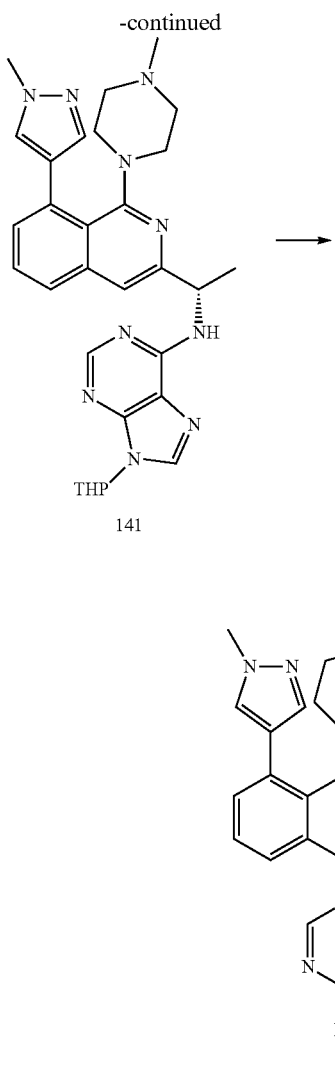

142

Compound 142 was prepared according the following procedures:

Compound 140, prepared from compound 95 in analogous fashion to compound 96 in Example 54 except that (K-2) was used in place of (E-4), was converted to compound 142 by the following procedure:

N—((S)-1-(8-chloro-1-(4-methylpiperazin-1-yl)isoquinolin-3-yl)ethyl)-9-(tetrahydro-2H-pyran-2-yl)-9H-purin-6-amine 140 (80 mg, 0.16 mmol, 1.0 eq), 1-methyl-4-(4,4,5,5-tetramethyl-1,3,2-dioxaborolan-2-yl)-1H-pyrazole (66 mg, 0.32 mmol, 2.0 eq), PdCl$_2$(dppf) (13 mg, 0.016 mmol, 0.1 eq) and Na$_2$CO$_3$ (84 mg, 0.79 mmol, 5.0 eq) were suspended in a mixture of N,N-dimethylacetamide (5 mL) and water (2 mL). The resulting mixture was degassed and back-filled with argon three times and then stirred at 80° C. under argon overnight. The mixture was concentrated in vacuo and the residue was purified by flash column chromatography on silica gel (1-5% MeOH-DCM) to afford the product, N—((S)-1-(8-(1-methyl-1H-pyrazol-4-yl)-1-(4-methylpiperazin-1-yl)isoquinolin-3-yl)ethyl)-9-(tetrahydro-2H-pyran-2-yl)-9H-purin-6-amine 141.

The THP group of compound 141 was then subsequently de-protected in analogous fashion to compound 85 in Example 45 to give compound 142. ESI-MS m/z: 469.2 [M+H]$^+$.

Example 84

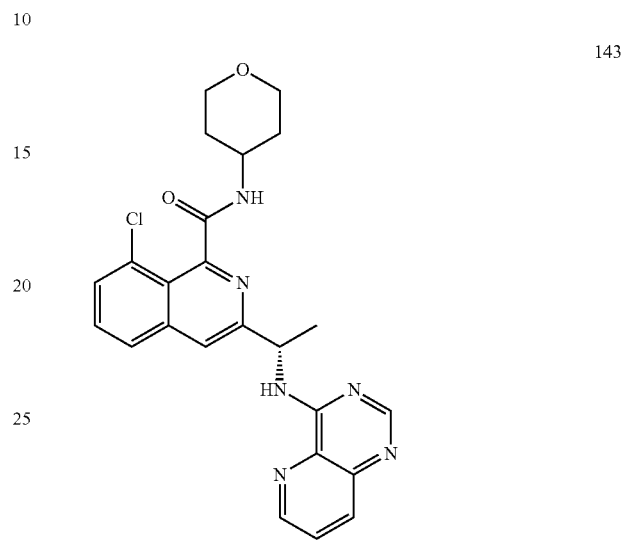

143

Compound 143 was prepared in analogous fashion to compound 115 in Example 64 except that tetrahydro-2H-pyran-4-amine was used in place of morpholine for the coupling reaction. ESI-MS m/z: 463.2 [M+H]$^+$.

Example 85

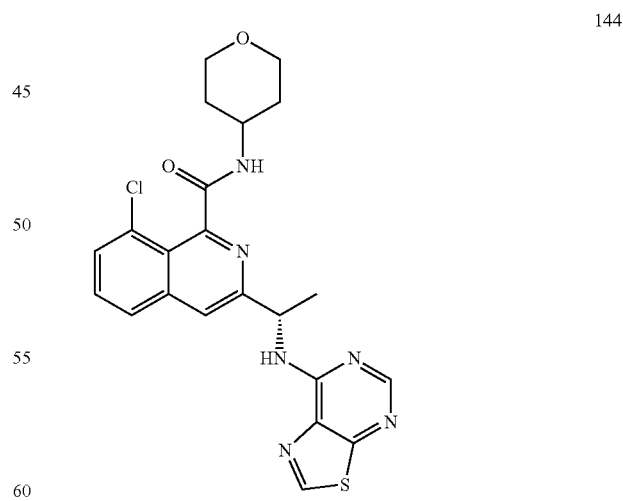

144

Compound 144 was prepared in analogous fashion to compound 115 in Example 64 except that tetrahydro-2H-pyran-4-amine was used in place of morpholine for the coupling reaction and (E-4) was used in place of (B-3). ESI-MS m/z: 469.0 [M+H]$^+$.

Example 86

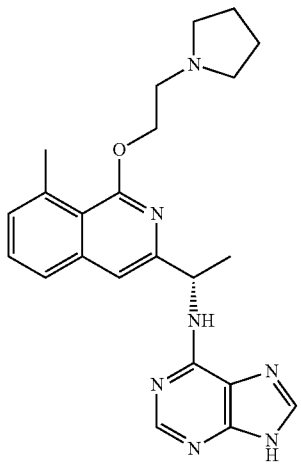

145

Compound 145 was synthesized from compound 56 using the analogous procedure for compound 47 in Example 31 except that 2-(pyrrolidin-1-yl) ethanol was used in place of 1-isopropylpiperidin-4-ol. ESI-MS m/z: 418.2 [M+H]$^+$.

Example 87

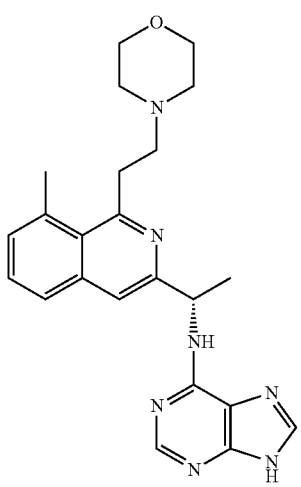

146

Compound 146 was prepared from compound 56 in analogous fashion to compound 4 from Example 1. ESI-MS m/z: 418.2 [M+H]$^+$.

Example 88

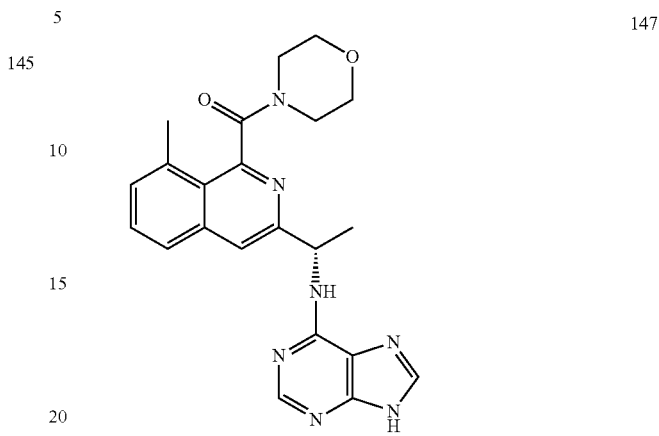

147

Compound 147 was prepared from compound 56 in analogous fashion to compound 13 in Example 5. ESI-MS m/z: 418.2 [M+H]$^+$.

Example 89

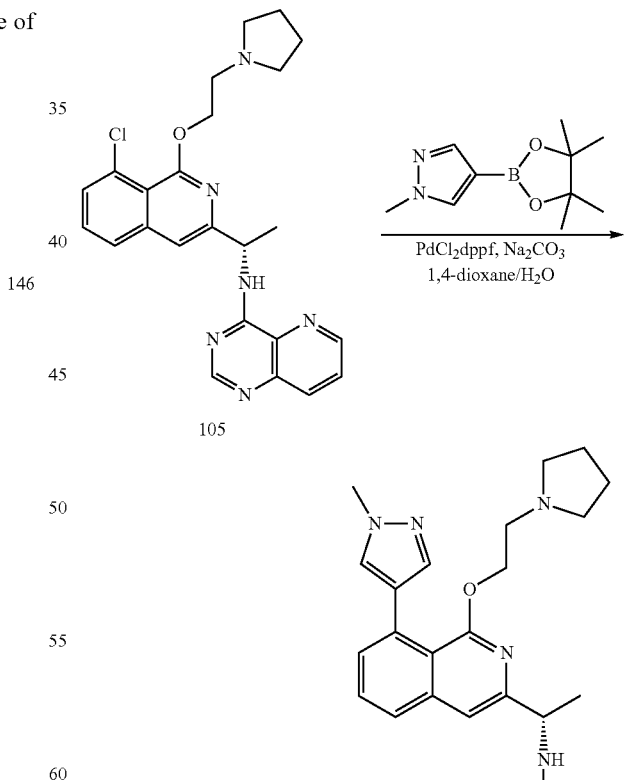

105

148

Compound 148 was prepared from compound 105 using the analogous Suzuki coupling conditions to obtain compound 141 in Example 83 except that the reaction solvent 1,4-dioxane was used in place of N,N-dimethylacetamide. ESI-MS m/z: 495.2 [M+H]⁺.

Example 90

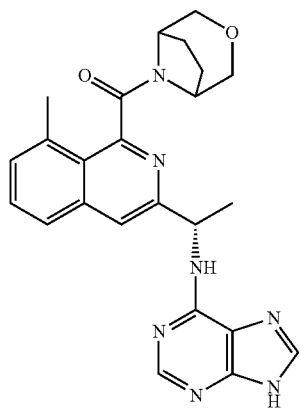

149

Compound 149 was prepared from compound 56 in analogous fashion to compound 13 in Example 5 except that 3-oxa-8-azabicyclo[3.2.1]octane was used in place of morpholine. ESI-MS m/z: 444.2 [M+H]⁺.

Example 91

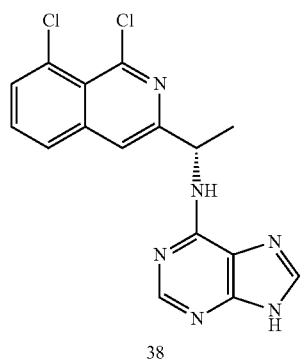

38

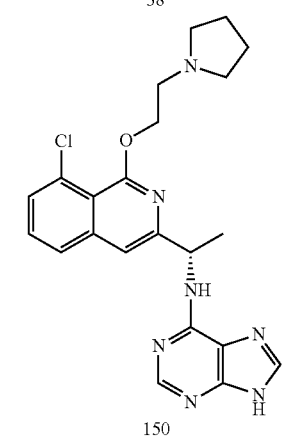

150

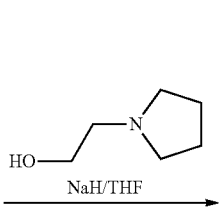

NaH/THF

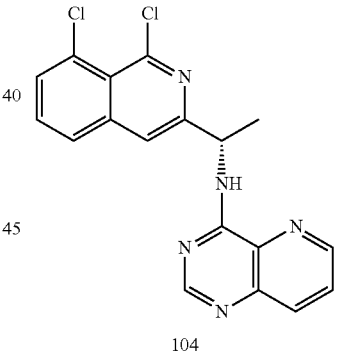

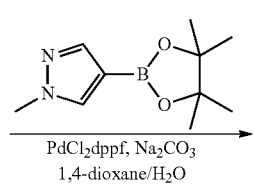

PdCl₂dppf, Na₂CO₃
1,4-dioxane/H₂O

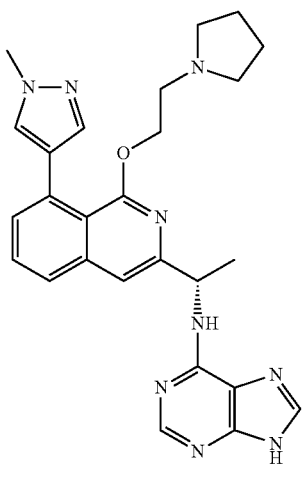

151

Compound 150, prepared from compound 38 in analogous fashion to compound 47 in Example 31 except that 2-(pyrrolidin-1-yl)ethanol was used in place of 1-isopropylpiperidin-4-ol, was converted to 151 using the analogous Suzuki coupling conditions for compound 148 in Example 89. ESI-MS m/z: 484.2 [M+H]⁺.

Example 92

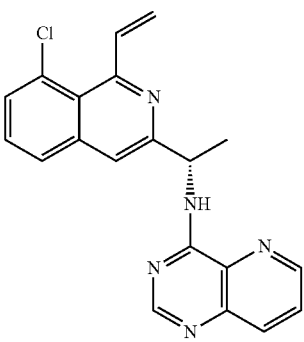

104

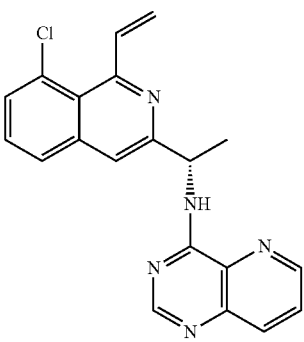

152

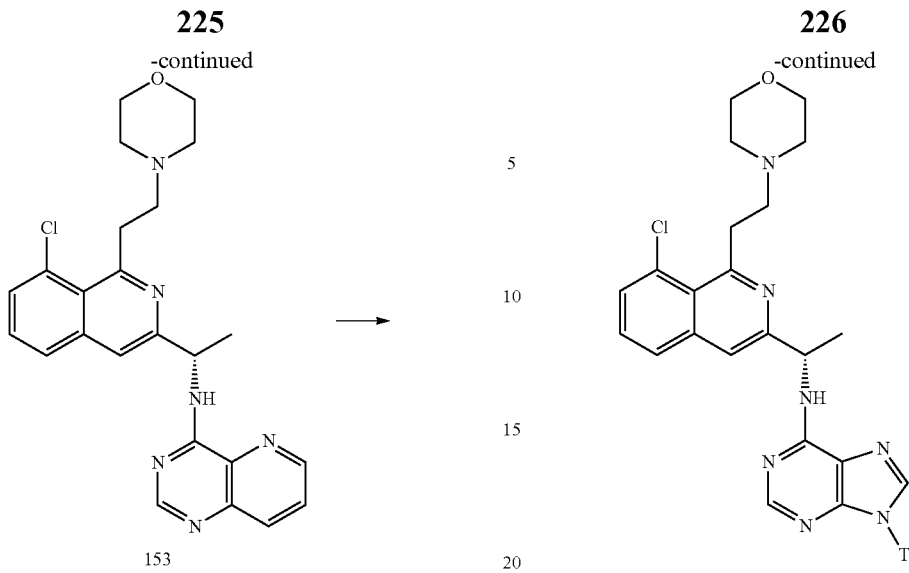

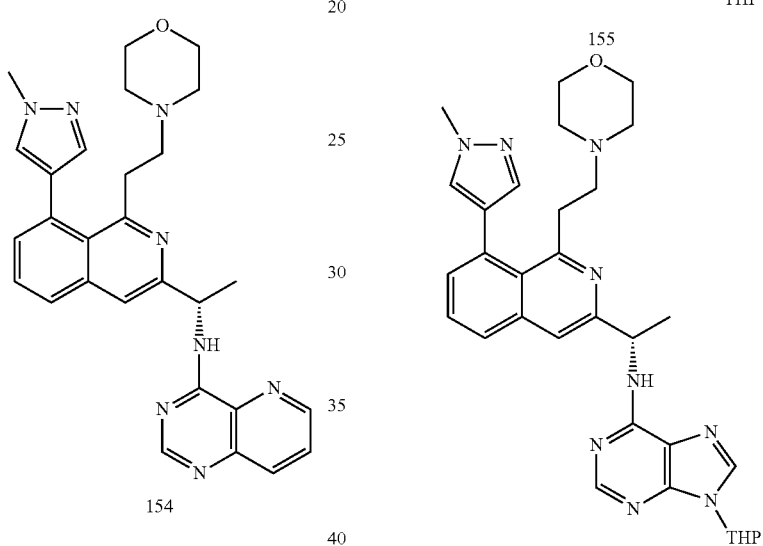

Compound 104 was converted to compound 153 by two steps in analogous fashion to compound 3 in example 1. Compound 154 was prepared from compound 153 using Suzuki coupling conditions analogous to compound 151 in example 91. ESI-MS m/z: 495.2 [M+H]$^+$.

Example 93

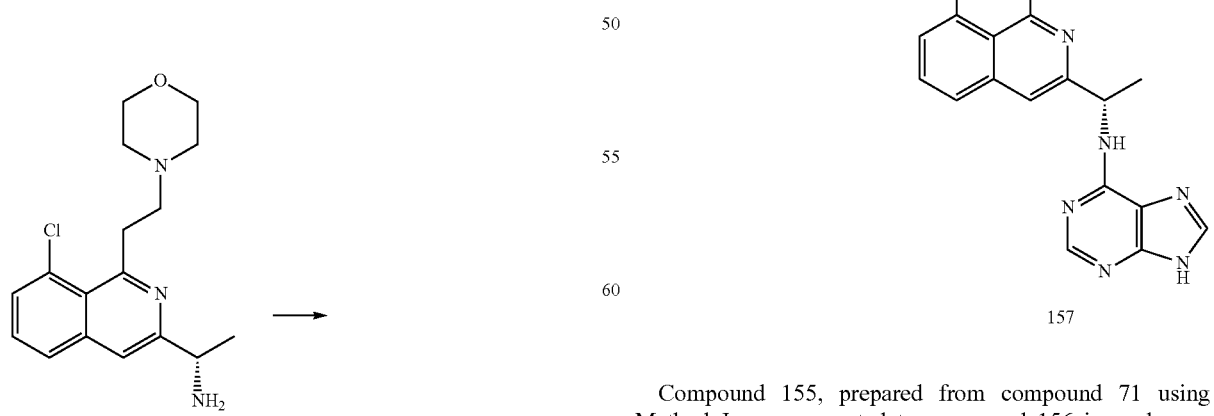

Compound 155, prepared from compound 71 using Method J, was converted to compound 156 in analogous fashion to compound 151 in example 91. The THP group of compound 156 was then subsequently de-protected in analogous fashion to compound 85 in Example 45 to provide compound 157. ESI-MS m/z: 484.2 [M+H]+.

Example 94

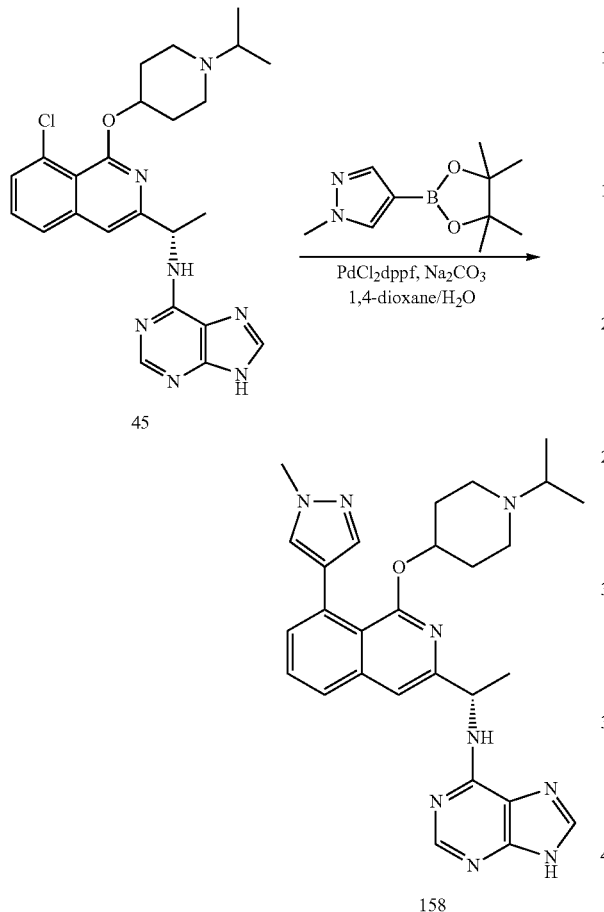

Compound 158 was prepared from compound 45 in analogous fashion to compound 148 in Example 89. ESI-MS m/z: 512.2 [M+H]+.

Example 95

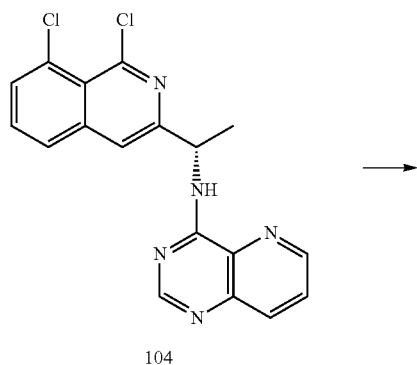

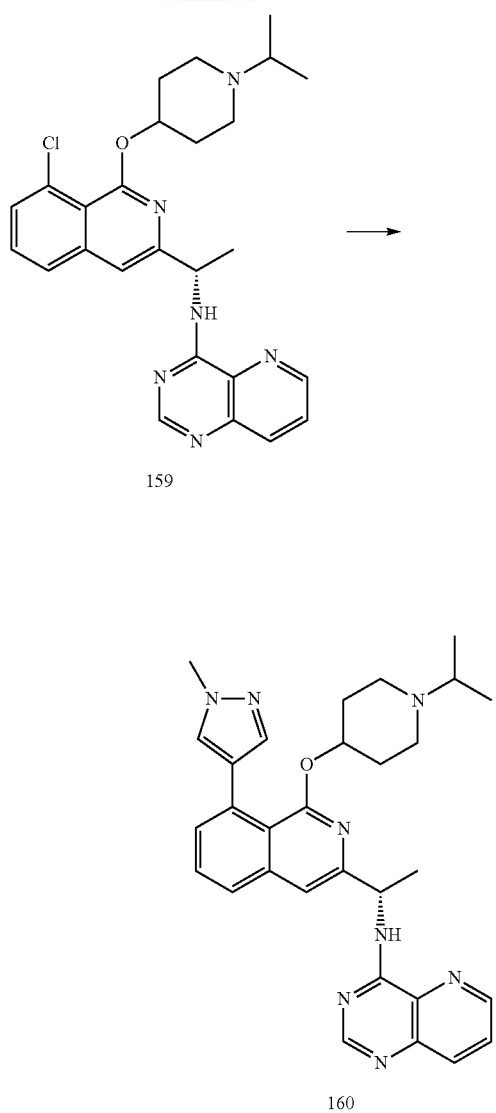

Compound 159 was prepared from compound 104 in analogous fashion to compound 107 in Example 60. Compound 159 was converted to compound 160 in analogous fashion to compound 151 in Example 91. ESI-MS m/z: 523.2 [M+H]+.

Example 96

Example 97

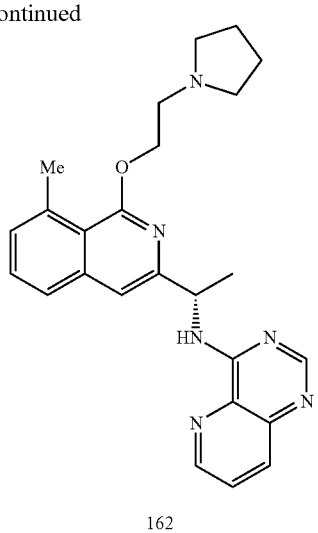

162

Compound 161 was prepared according to Method I and then converted to compound 162 using the analogous procedures for the synthesis of compound 105 in Example 58. ESI-MS m/z: 429.2 [M+H]$^+$.

Example 97

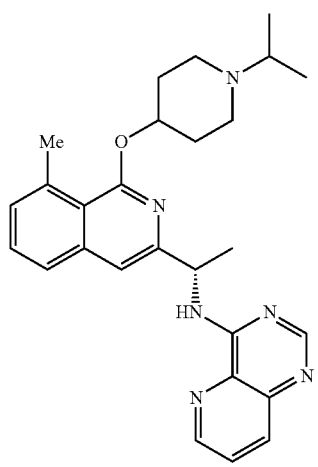

163

Compound 163 was prepared from compound 161 using the analogous procedures for the synthesis of compound 105 in Example 58 except that 1-isopropylpiperidin-4-ol was used in place of 2-(pyrrolidin-1-yl)ethanol. ESI-MS m/z: 457.0 [M+H]$^+$.

Example 98

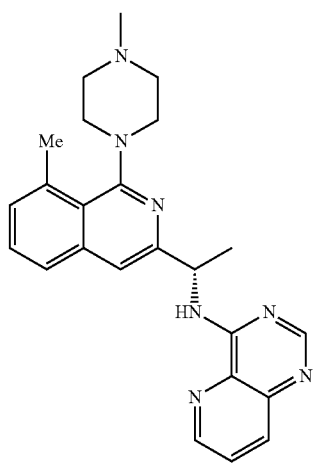

164

Compound 164 was prepared from compound 161 using the analogous procedures for the synthesis of compound 96 in Example 54. ESI-MS m/z: 414.2 [M+H]$^+$.

Example 99

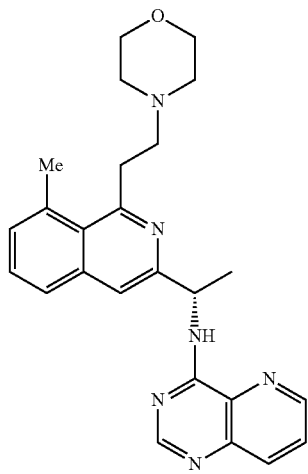

165

Compound 165 was prepared from compound 161 using the analogous procedures for the synthesis of compound 70 in Example 38 except that (B-3) was used in place of (E-4). ESI-MS m/z: 429.2 [M+H]$^+$.

Example 100

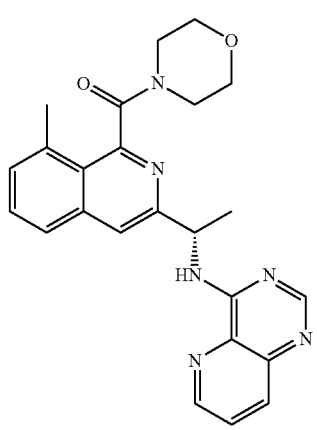

166

Compound 166 was prepared from compound 161 using the analogous procedures for the synthesis of compound 115 in Example 64. ESI-MS m/z: 429.2 [M+H]+.

Example 101

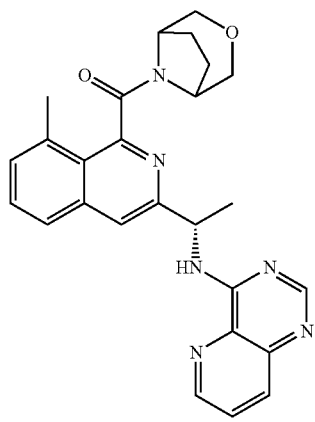
167

Compound 167 was prepared in analogous fashion to compound 166 in Example 100 except that 3-oxa-8-azabicyclo[3.2.1]octane was used in place of morpholine. ESI-MS m/z: 455.2 [M+H]+.

Example 102

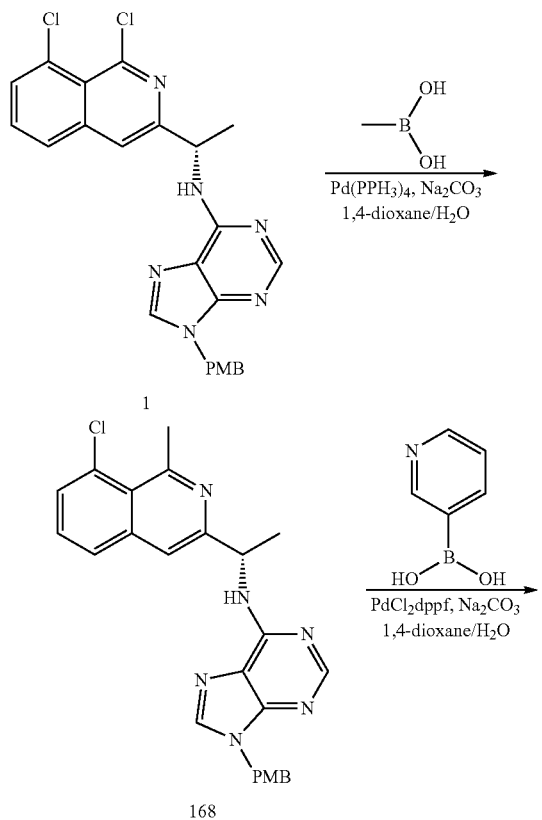

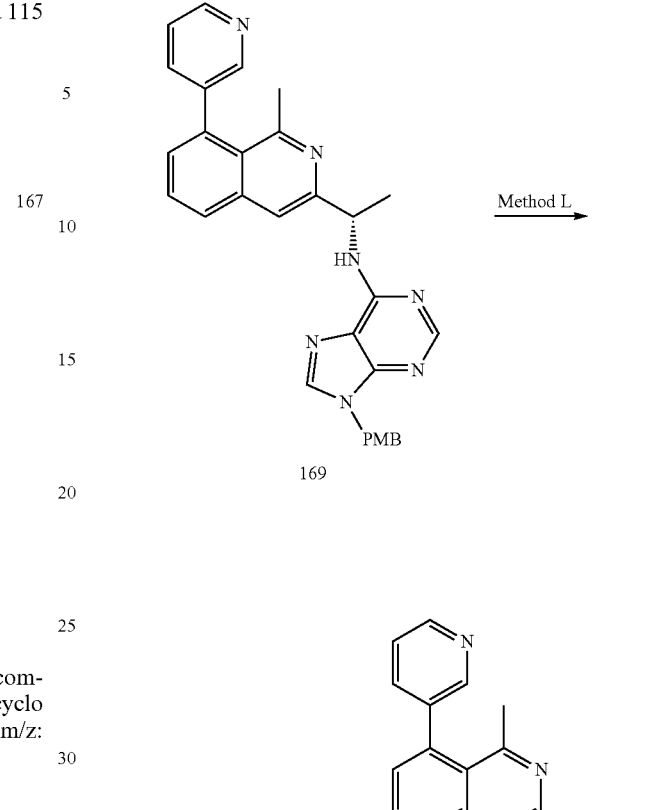

(S)-9-(4-Methoxybenzyl)-N-(1-(1,8-dichloroisoquinolin-3-yl)ethyl)-9H-purin-6-amine (1) (2.0 g, 4.2 mmol, 1.0 eq), methylboronic acid (277 mg, 4.62 mmol, 1.1 eq), Pd(PPh₃)₄ (485 mg, 0.42 mmol, 0.1 eq) and Na₂CO₃ (1.34 g, 12.6 mmol, 3.0 eq) were suspended in a mixture of 1,4-dioxane (30 mL) and water (10 mL). The resulting mixture was degassed and back-filled with argon three times and then stirred at reflux under argon for 16 h. The mixture was allowed to cool to RT, concentrated in vacuo and the residue was purified by column chromatography on silica gel (1-3% MeOH-DCM) to afford the product, (S)-9-(4-methoxybenzyl)-N-(1-(8-chloro-1-methylisoquinolin-3-yl)ethyl)-9H-purin-6-amine (168). Compound 168 was then converted to compound 169 using the analogous procedures for the synthesis of 151 in Example 91 except that pyridin-3-ylboronic acid was used in place of 1-methyl-4-(4,4,5,5-tetramethyl-1,3,2-dioxaborolan-2-yl)-1H-pyrazole. The PMB group of compound 169 was then subsequently deprotected using Method L to afford compound 170. ESI-MS m/z: 382.2 [M+H]+.

Example 103

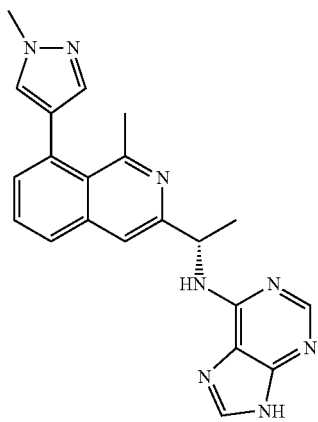

171

Compound 171 was prepared in analogous fashion to 170 in Example 102 except that (1-methyl-1H-pyrazol-4-yl)boronic acid was used in place of 3-pyridylboronic acid. ESI-MS m/z: 385.2 [M+H]⁺.

Example 104

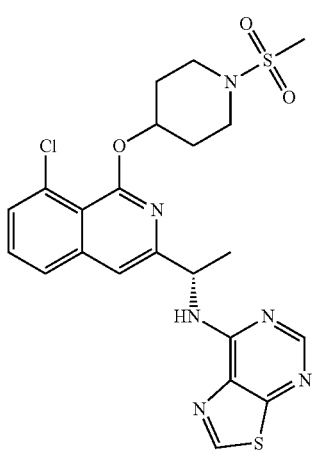

172

Compound 172 was prepared from compound 101 in analogous fashion to 105 in Example 58 except that (E-4) was used in place of (B-3) and 1-(methylsulfonyl)piperidin-4-ol was used in place of 2-(pyrrolidin-1-yl)ethanol. ESI-MS m/z: 519.0 [M+H]⁺.

Example 105

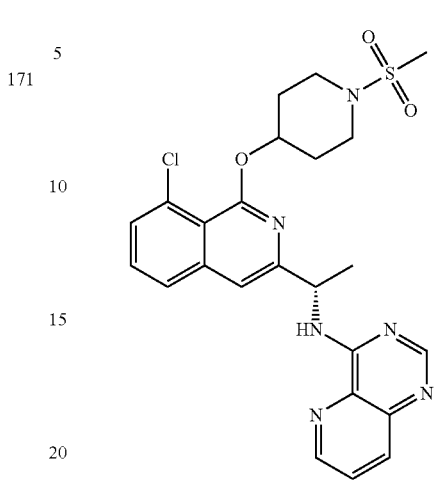

173

Compound 173 was prepared from compound 101 in analogous fashion to compound 105 in Example 58 except 1-(methylsulfonyl)piperidin-4-ol was used in place of 2-(pyrrolidin-1-yl)ethanol. ESI-MS m/z: 513.2 [M+H]⁺.

Example 106

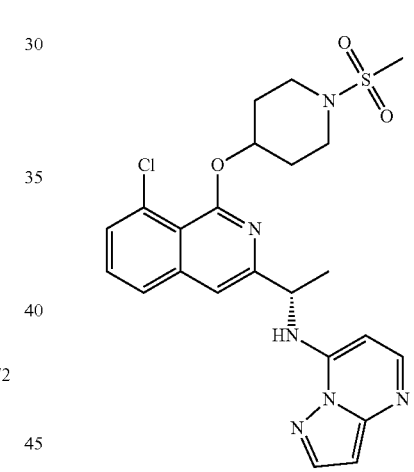

174

Compound 174 was prepared from compound 101 in analogous fashion to 105 in Example 58 except that (E-4) was used in place of (B-2) and 1-(methylsulfonyl)piperidin-4-ol was used in place of 2-(pyrrolidin-1-yl)ethanol. ESI-MS m/z: 501.0 [M+H]⁺.

Example 107

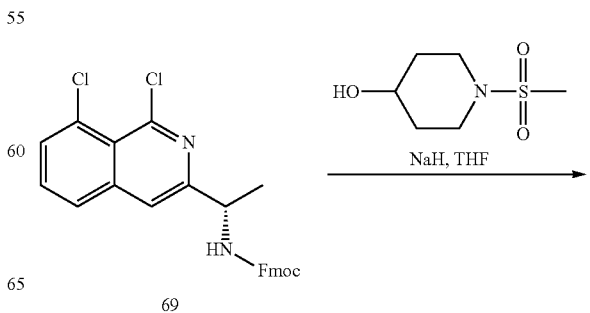

69

Example 108

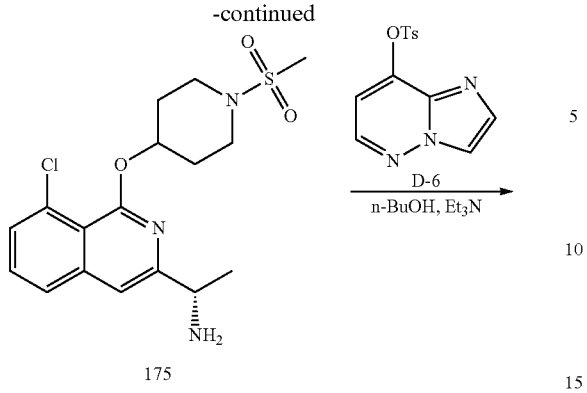
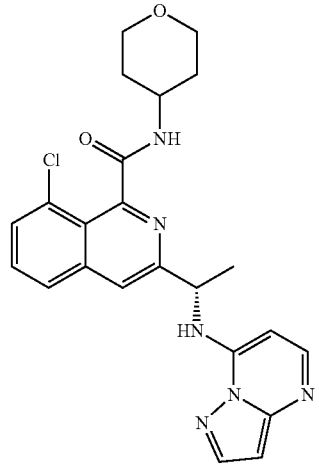

Compound 177 was prepared in analogous fashion to compound 115 in Example 64 except that tetrahydro-2H-pyran-4-amine was used in place of morpholine for the coupling and (C-2) was used in place of (B-3). ESI-MS m/z: 451.2 [M+H]+.

Example 109

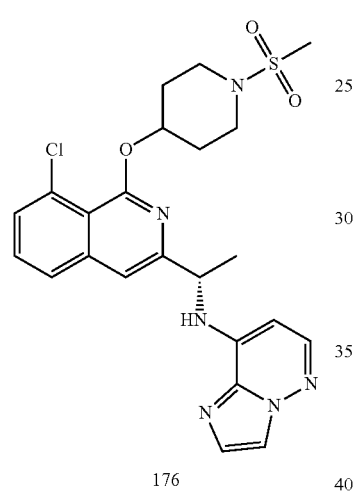

Compound 69 was converted to 176 in 2 steps according to the following procedures:

To a mixture of 1-(methylsulfonyl)piperidin-4-ol (618 mg, 3.45 mmol, 1.6 eq) in THF (5 mL) at 0° C., NaH (60% in mineral oil, 173 mg, 4.32 mmol, 2.0 eq) was added and the resulting mixture was stirred for 10 min. To this mixture, (S)-(9H-fluoren-9-yl)methyl 1-(1,8-dichloroisoquinolin-3-yl)ethylcarbamate 69 (1.0 g, 2.16 mmol, 1.0 eq) was added and the resulting mixture was stirred at reflux for 2 h. The mixture was cooled to RT and poured into water (20 mL). The mixture was extracted with ethyl acetate (3×20 mL). The combined organic layer was washed with brine, dried over Na₂SO₄ and filtered. The filtrate was concentrated in vacuo and the residue was purified by flash column chromatography on silica gel (3% MeOH-DCM) to afford the product (S)-1-(8-chloro-1-(1-(methylsulfonyl)piperidin-4-yloxy)isoquinolin-3-yl)ethanamine (175).

Compound 175 was converted to 176 according to Method J. ESI-MS m/z: 501.2 [M+H]+.

237

-continued

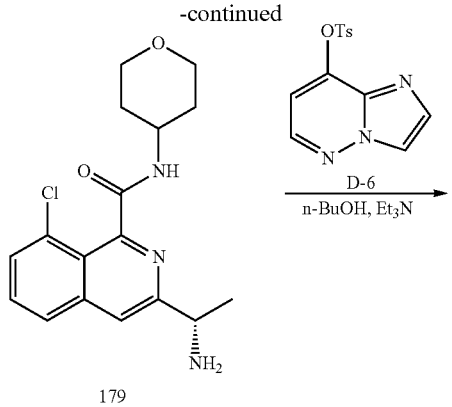

179

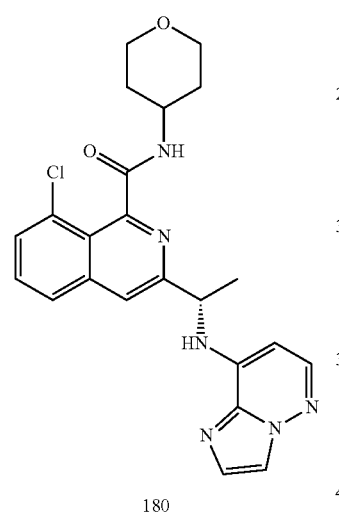

180

Compound 179 was prepared by a three-step procedure from compound 112 in analogous fashion to compound 113 in example 64 except that tetrahydro-2H-pyran-4-amine was used in place of morpholine in the second step. Compound 179 was then converted to compound 180 in analogous fashion to 176 in Example 107. ESI-MS m/z: 451.0 [M+H]$^+$.

Example 110

238

-continued

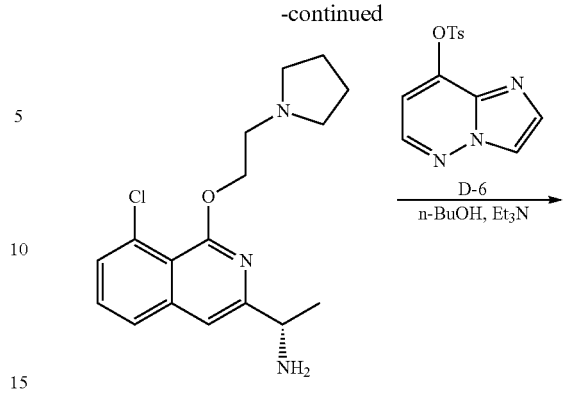

181

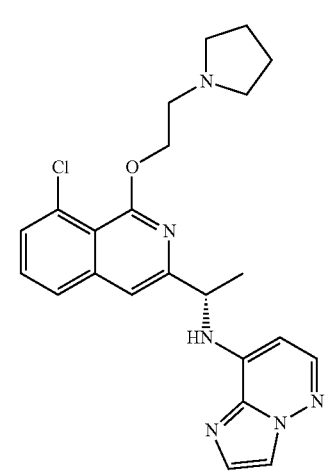

182

Compound 181 was prepared from compound 69 in analogous fashion to compound 175 in Example 107 except that 2-(pyrrolidin-1-yl)ethanol was used in place of 1-(methylsulfonyl)piperidin-4-ol. Compound 181 was then converted to compound 182 using the analogous procedure for 176 in Example 107. ESI-MS m/z: 437.2 [M+H]$^+$.

Example 111

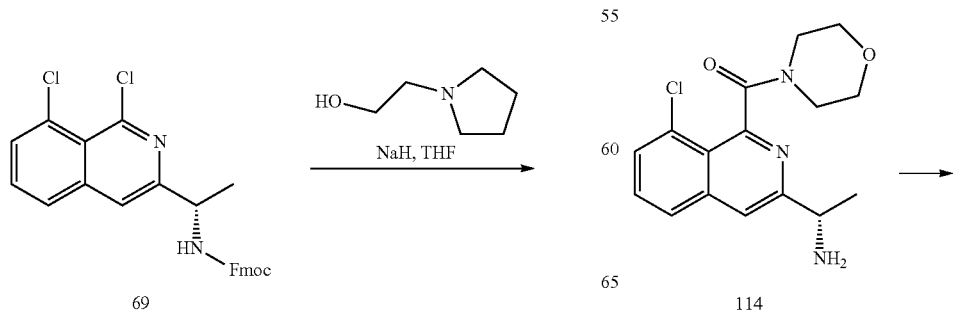

Example 112

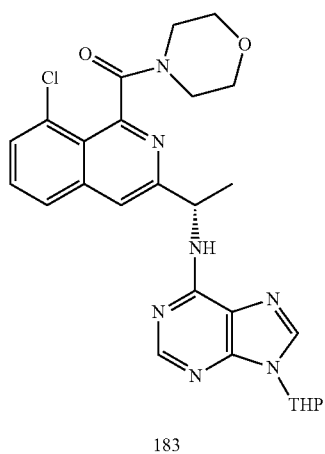
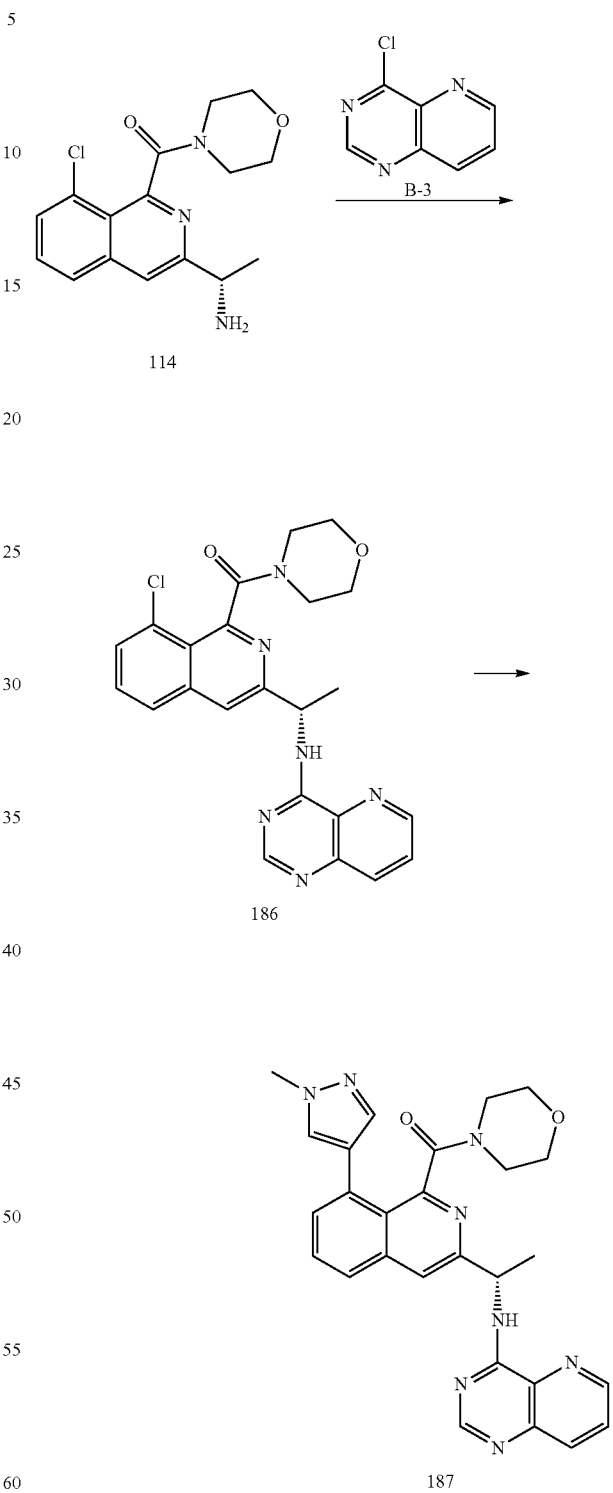

Compound 114 was coupled to (K-2) in analogous fashion to compound 72 in Example 38 except that (K-2) was used in place of (E-4) to give compound 183. The following Suzuki coupling of compound 183 to afford compound 184 was analogous to the preparation of compound 158 in Example 94. The THP group of compound 184 was then subsequently de-protected using an analogous procedure for compound 85 in Example 45 to provide compound 185. ESI-MS m/z: 484.2 [M+H]$^+$.

Compound 187 was prepared from compound 114 in analogous fashion to compound 185 in Example 111 except that (B-3) was used in place of (K-2). ESI-MS m/z: 495.2 [M+H]$^+$.

Example 113
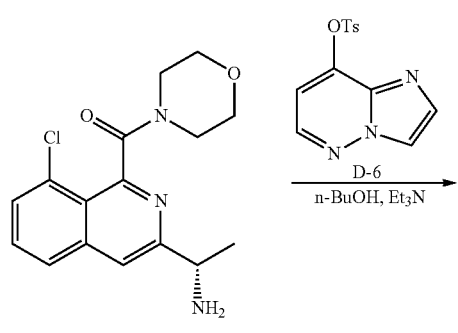
114
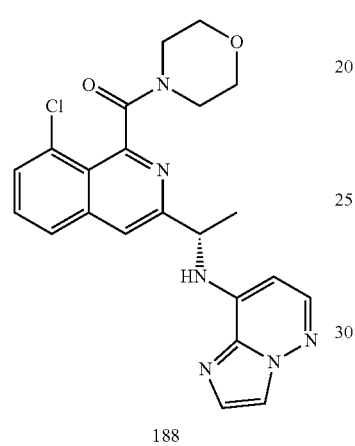
188
Compound 188 was prepared from compound 114 in analogous fashion to compound 182 in Example 110. ESI-MS m/z: 437.2 [M+H]$^+$.
Example 114
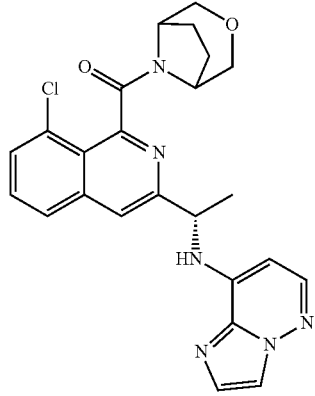
189
Compound 189 was prepared in analogous fashion to compound 188 in Example 113 except that 3-oxa-8-azabicyclo[3.2.1]octane was used in place of morpholine. ESI-MS m/z: 463.2 [M+H]$^+$.
Example 115
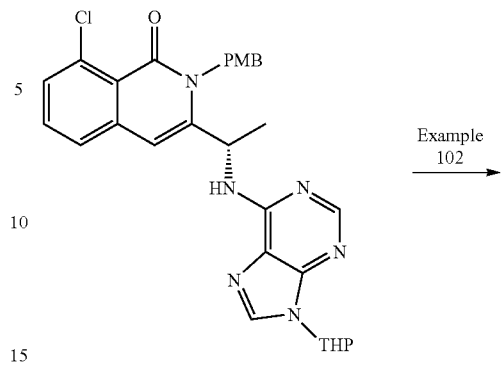
K-3 (R$_5$ = Cl)
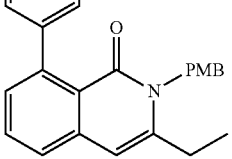
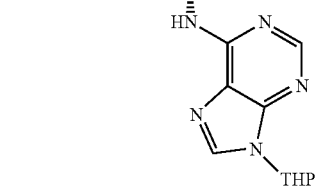
190
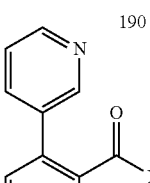
191
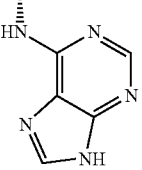
192

Compound 190 was prepared from K-3 (R3=Cl) in analogous fashion to compound 169 in Example 102. Compound 190 was converted to compound 192 in 2 steps according to Method K. ESI-MS m/z: 402.2 [M+H]⁺.
Example 116
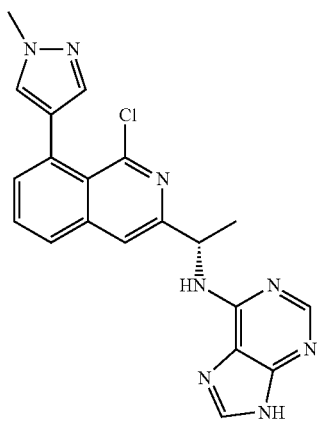
193
Compound 193 was prepared in analogous fashion to compound 192 in Example 115 except that (1-methyl-1H-pyrazol-4-yl)boronic acid was used in place of 3-pyridylboronic acid. ESI-MS m/z: 405.2 [M+H]⁺.
Example 117
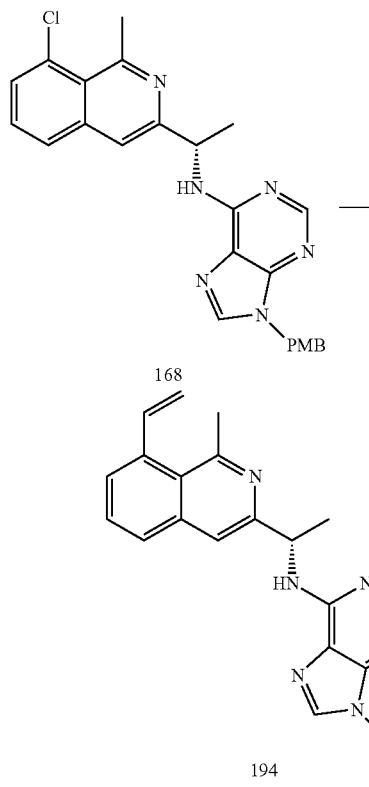
-continued
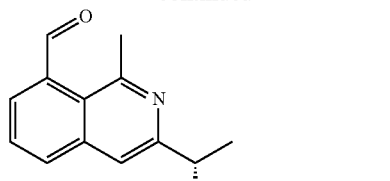
195
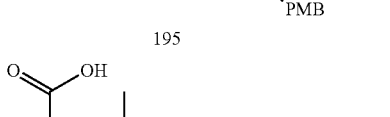
196
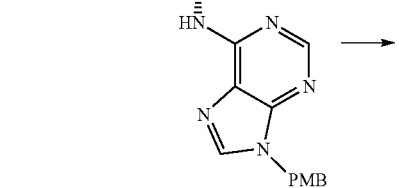
197
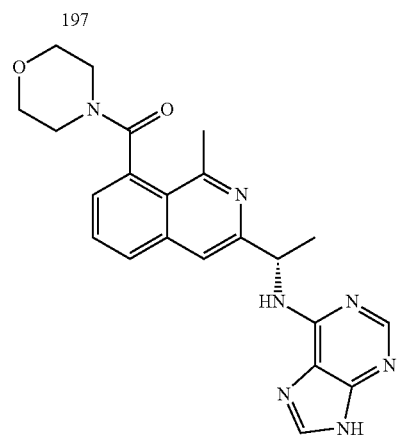
198

Compound 195 was prepared from 168 in 2 steps in analogous fashion to compound 2 in Example 1 followed by compound 5 in Example 2. The following 2 steps (oxidation and amide formation) using the analogous procedures for compound 12 in Example 5 provided compound 197. The last step of removing the PMB group using Method K gave compound 198. ESI-MS m/z: 418.2 [M+H]$^+$.

Example 118

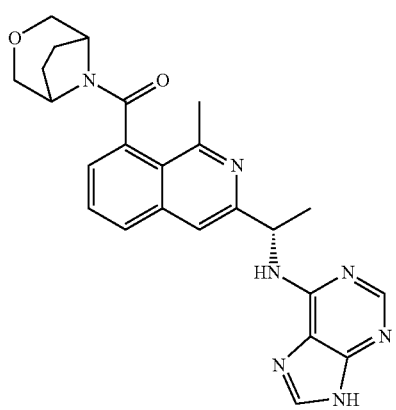

199

Compound 199 was prepared in analogous fashion to compound 198 in Example 117 except that 3-oxa-8-azabicyclo[3.2.1]octane is used in place of morpholine. ESI-MS m/z: 444.2 [M+H]$^+$.

Example 119

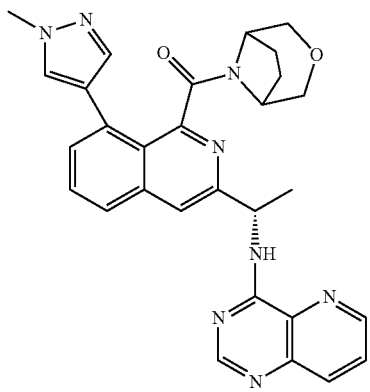

200

Compound 200 is prepared in analogous fashion to compound 187 in Example 112 except that 3-oxa-8-azabicyclo[3.2.1]octane is used in place of morpholine. ESI-MS m/z: 521.2 [M+H]$^+$.

Example 120

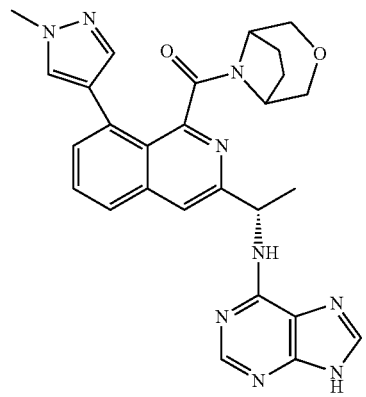

201

Compound 201 was prepared in analogous fashion to compound 185 in Example 111 except that 3-oxa-8-azabicyclo[3.2.1]octane is used in place of morpholine. ESI-MS m/z: 510.2 [M+H]$^+$.

Example 121

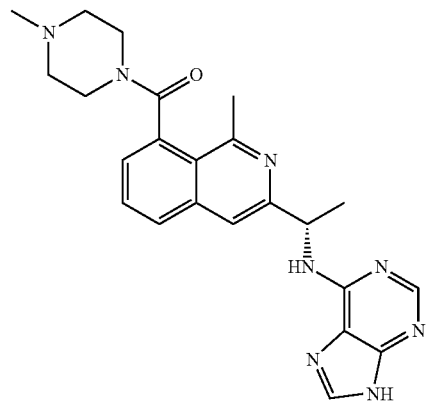

202

Compound 202 was prepared in analogous fashion to compound 198 in Example 117 except that N-methylpiperidine is used in place of morpholine. ESI-MS m/z: 431.2 [M+H]$^+$.

Example 122

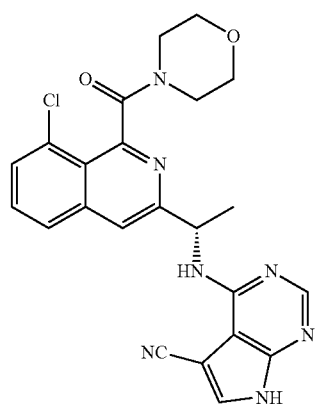

203

Compound 203 was prepared from compound 114 in analogous fashion to compound 72 in Example 38 except that (G-4) was used in place of (E-4). ESI-MS m/z: 462.0 [M+H]$^+$.

Example 123

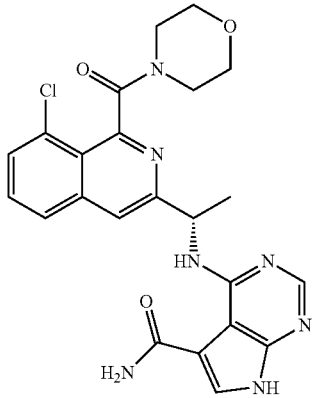

204

Compound 204 was prepared from compound 114 in analogous fashion to compound 72 in Example 38 except that (H-2) was used in place of (E-4). ESI-MS m/z: 480.2 [M+H]+.

Example 124

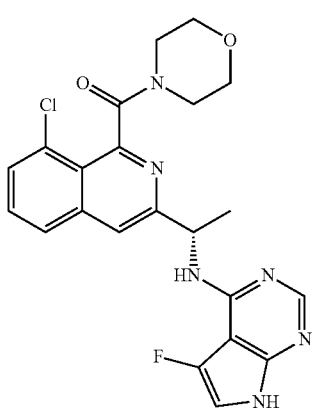

205

Compound 205 was prepared from compound 114 in analogous fashion to compound 72 in Example 38 except that (F-2) was used in place of (E-4). ESI-MS m/z: 455.2 [M+H]+.

Example 125

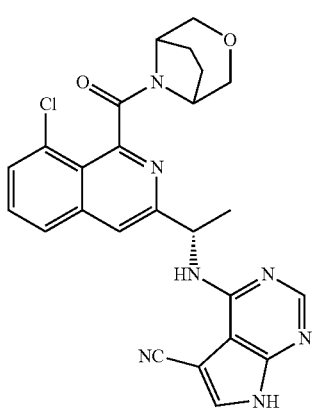

206

Compound 206 was prepared in analogous fashion to compound 203 in Example 122 except that except that 3-oxa-8-azabicyclo[3.2.1]octane is used in place of morpholine. ESI-MS m/z: 488.2 [M+H]+.

Example 126

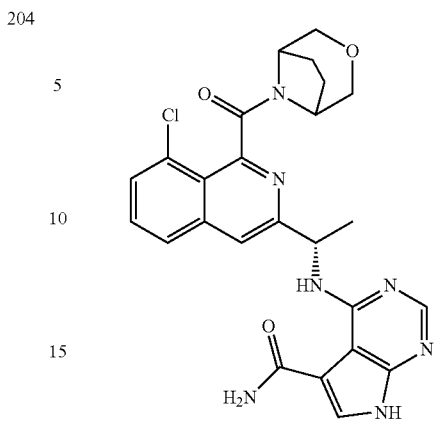

207

Compound 207 was prepared in analogous fashion as compound 204 in Example 123 except that except that 3-oxa-8-azabicyclo[3.2.1]octane is used in place of morpholine. ESI-MS m/z: 506.2 [M+H]+.

Example 127

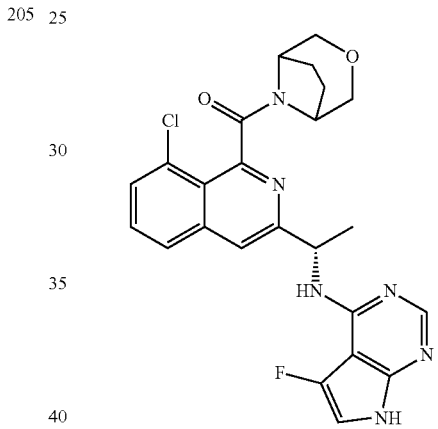

208

Compound 208 was prepared in analogous fashion to compound 205 in Example 124 except that except that 3-oxa-8-azabicyclo[3.2.1]octane is used in place of morpholine. ESI-MS m/z: 481.2 [M+H]+.

Example 128

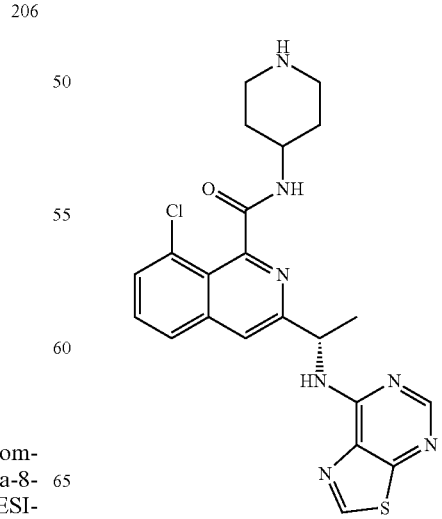

209

Compound 209 was prepared in analogous fashion to compound 115 in Example 64 except that piperidin-4-amine was used in place of morpholine for the coupling and (E-4) was used in place of (B-3). ESI-MS m/z: 468.2 [M+H]⁺.

Example 129

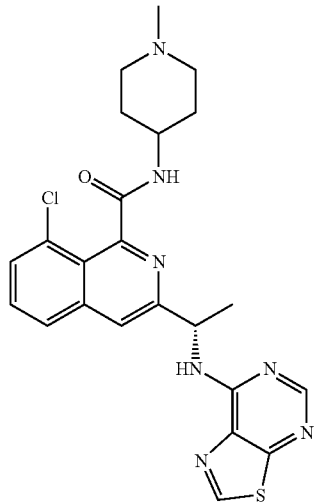

Compound 210 was prepared in analogous fashion to compound 115 in Example 64 except that 1-methylpiperidin-4-amine was used in place of morpholine for the coupling and (E-4) was used in place of (B-3). ESI-MS m/z: 482.2 [M+H]⁺.

Example 130

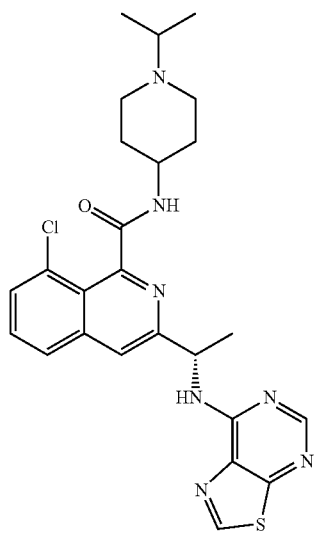

Compound 211 was prepared in analogous fashion to compound 115 in Example 64 except that 1-isopropylpiperidin-4-amine was used in place of morpholine for the coupling and (E-4) was used in place of (B-3). ESI-MS m/z: 510.2 [M+H]⁺.

Example 131

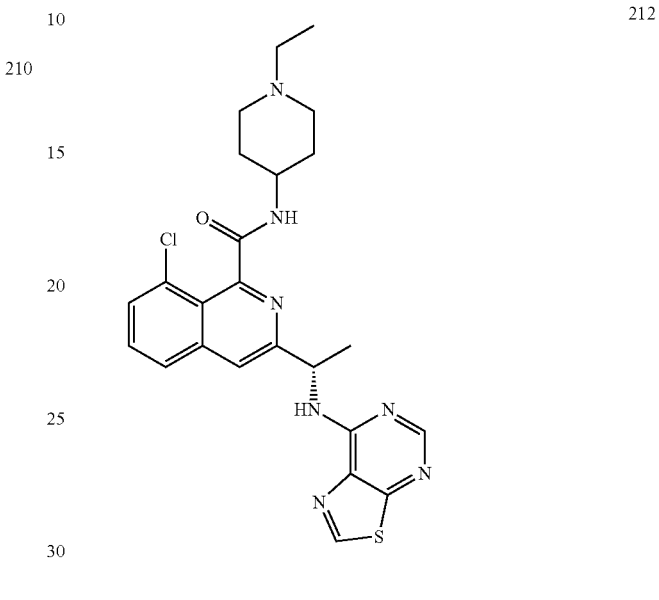

Compound 212 was prepared in analogous fashion to compound 115 in Example 64 except that 1-ethylpiperidin-4-amine was used in place of morpholine for the coupling and (E-4) was used in place of (B-3). ESI-MS m/z: 496.2 [M+H]⁺.

Example 132

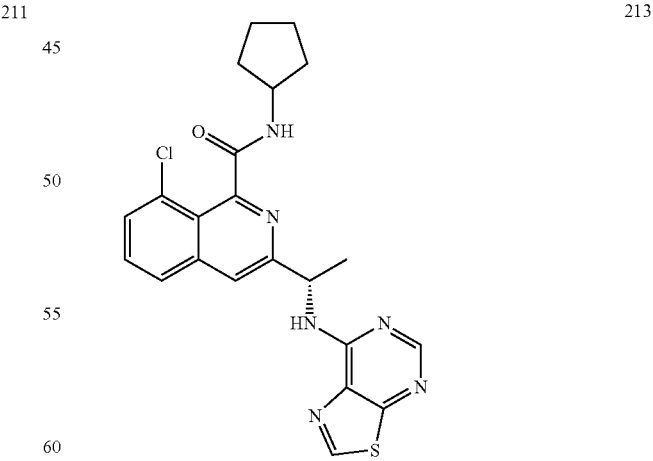

Compound 213 was prepared in analogous fashion to compound 115 in Example 64 except that cylcopentylamine was used in place of morpholine for the coupling and (E-4) was used in place of (B-3). ESI-MS m/z: 453.0 [M+H]⁺.

Example 133

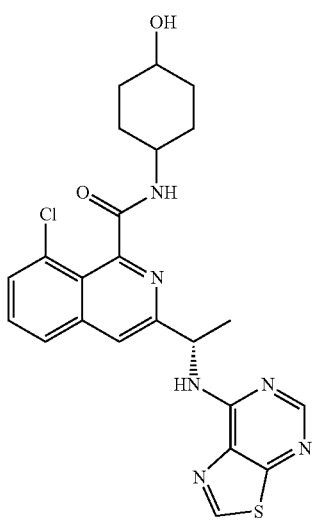

214

Compound 214 was prepared in analogous fashion to compound 115 in Example 64 except that 4-aminocyclohexanol was used in place of morpholine for the coupling and (E-4) was used in place of (B-3). ESI-MS m/z: 483.2 [M+H]$^+$.

Example 134

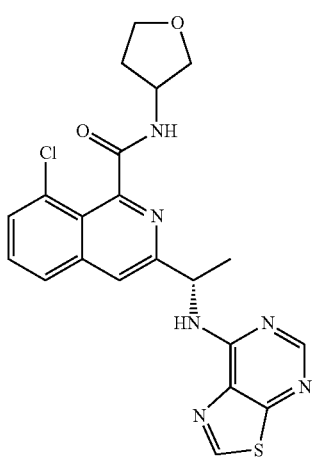

215

Compound 215 was prepared in analogous fashion to compound 115 in Example 64 except that tetrahydrofuran-3-amine was used in place of morpholine for the coupling and (E-4) was used in place of (B-3). ESI-MS m/z: 455.0 [M+H]$^+$.

Example 135

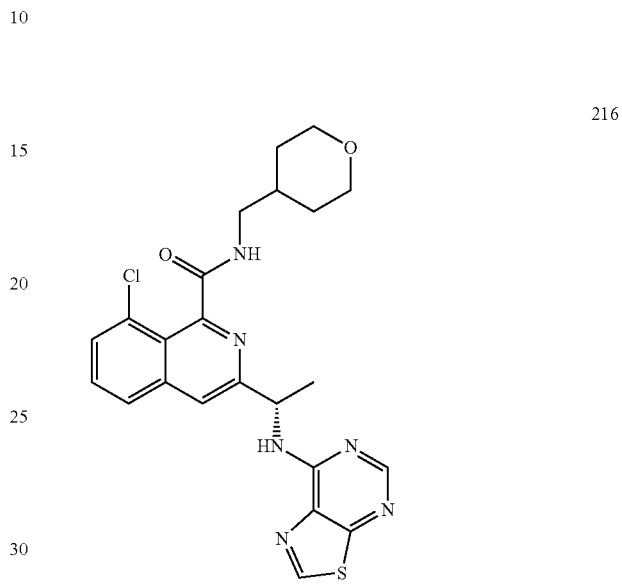

216

Compound 216 was prepared in analogous fashion to compound 115 in Example 64 except that (tetrahydro-2H-pyran-4-yl)methanamine was used in place of morpholine for the coupling and (E-4) was used in place of (B-3). ESI-MS m/z: 483.2 [M+H]$^+$.

The following compounds were also prepared in analogous fashion to compound 115 in Example 64:

| Example | Compound | Amine | Wd-Cl or Wd-OTs | ESI-MS m/z |
|---|---|---|---|---|
| 136 | 217 | morpholine | 132 | 481.2 [M + H]$^+$ |

-continued

| Example | Compound | Amine | Wd-Cl or Wd-OTs | ESI-MS m/z |
|---|---|---|---|---|
| 137 | 218 | | E-4 | 468.0 [M + H]⁺ |
| 138 | 219 | | B-3 | 497.0 [M + H]⁺ |
| 139 | 220 | | E-4 | 503.0 [M + H]⁺ |

-continued
| Example | Compound | Amine | Wd-Cl or Wd-OTs | ESI-MS m/z |
|---|---|---|---|---|
| 140 | 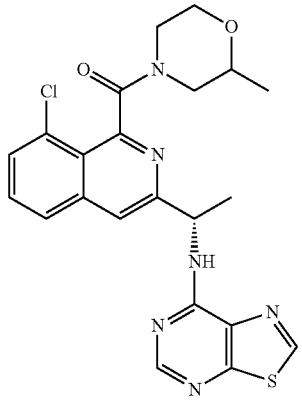<br>221 | 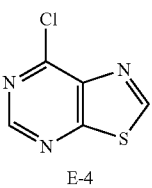 | E-4 | 469.0 [M + H]+ |
| 141 | 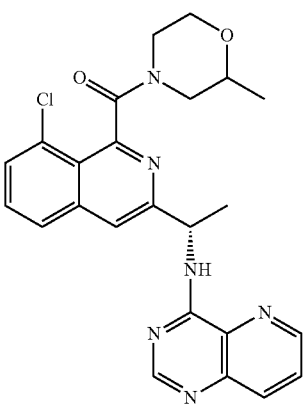<br>222 |  | B-3 | 463.0 [M + H]+ |
| 142 | 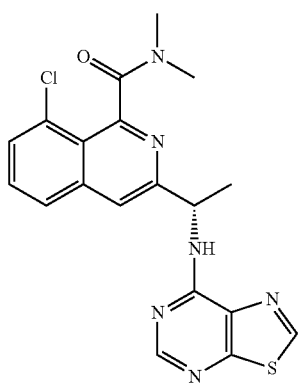<br>223 |  | E-4 | 413.0 [M + H]+ |

-continued

| Example | Compound | Amine | Wd-Cl or Wd-OTs | ESI-MS m/z |
|---|---|---|---|---|
| 143 | 224 | | B-3 | 407.2 [M + H]+ |
| 144 | 225 | | B-3 | 462.2 [M + H]+ |
| 145 | 226 | | B-3 | 483.2 [M + H]+ |

| Example | Compound | Amine | Wd-Cl or Wd-OTs | ESI-MS m/z |
| --- | --- | --- | --- | --- |
| 146 | 227 | | E-4 | 469.0 [M + H]⁺ |
| 147 | 228 | | E-4 | 489.0 [M + H]⁺ |
| 148 | 229 | | E-4 | 453.0 [M + H]⁺ |

-continued
| Example | Compound | Amine | Wd-Cl or Wd-OTs | ESI-MS m/z |
|---|---|---|---|---|
| 149 | 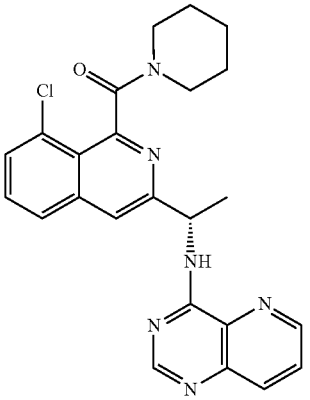<br>230 |  | 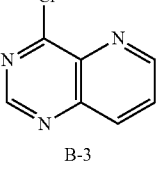<br>B-3 | 447.2 [M + H]⁺ |
| 150 | 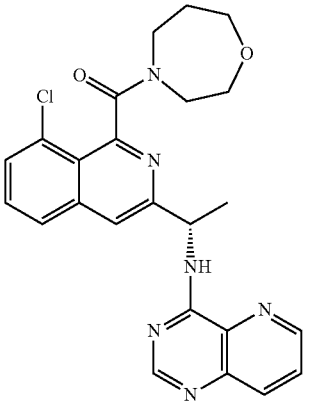<br>231 | 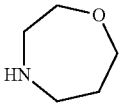 | 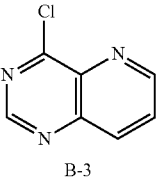<br>B-3 | 463.2 [M + H]⁺ |
| 151 | 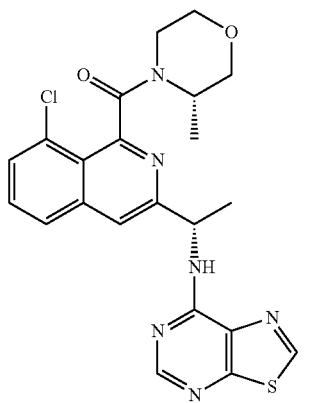<br>232 | 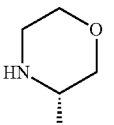 | 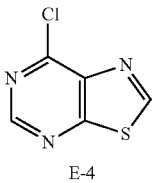<br>E-4 | 469.0 [M + H]⁺ |

-continued
| Example | Compound | Amine | Wd-Cl or Wd-OTs | ESI-MS m/z |
|---|---|---|---|---|
| 152 | 233 | 4-hydroxypiperidine | B-3 (4-chloropyrido[3,2-d]pyrimidine) | 463.2 [M + H]+ |
| 153 | 234 | 4-hydroxypiperidine | E-4 (7-chlorothiazolo[5,4-d]pyrimidine) | 469.0 [M + H]+ |
Example 154
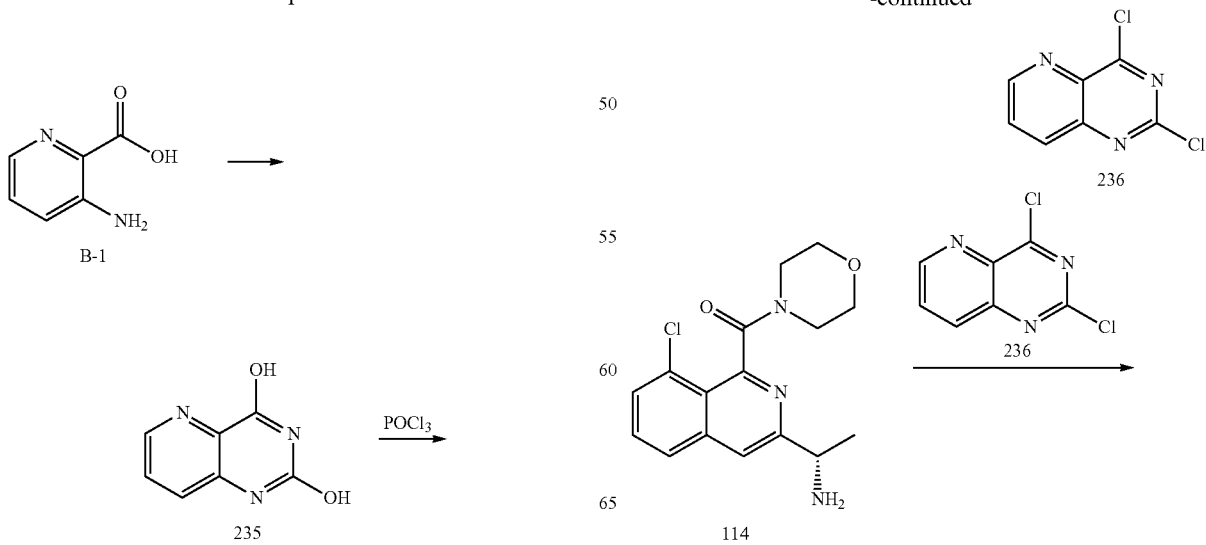

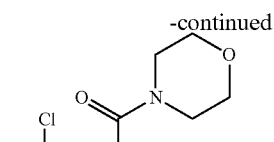

237

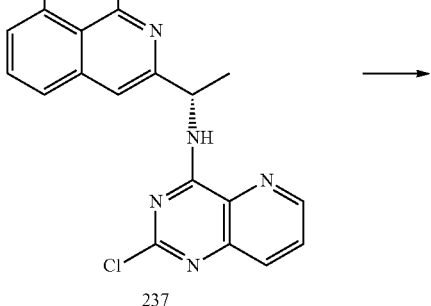

238

3-Aminopicolinic acid (B-1) (1.0 g, 7.24 mmol, 1.0 eq), potassium cyanate (2.94 g, 36.2 mmol, 5.0 eq) and ammonium chloride (3.87 g, 72.4 mmol, 10.0 eq) were suspended in water (40 mL). The slurry was heated to 160° C. and mixed manually for 2 h as water vapor was expelled from the reaction vessel. The reaction temperature was then increased to 200° C. and stirred for 40 min. After cooling to 90° C., hot water was added and then the mixture was allowed to cool to RT. The mixture was acidified with concentrated HCl to pH=3-4. The precipitate was collected by filtration, rinsed with water (2×10 mL) and dried in vacuo to afford the product pyrido[3,2-d]pyrimidine-2,4-diol 235.

A mixture of pyrido[3,2-d]pyrimidine-2,4-diol 235 (360 mg, 2.21 mmol, 1.0 eq) and $PCl_5$ (1.84 g, 8.83 mmol, 8.0 eq) in $POCl_3$ (20 mL) was stirred at reflux for 8 h. An additional amount of $PCl_5$ (1.84 g, 8.83 mmol, 8.0 eq) and $POCl_3$ (20 mL) were added, and the resulting mixture was stirred at reflux for 16 h. After cooling to RT, the mixture was concentrated in vacuo and the residue was poured into ice-water. The mixture was neutralized with saturated $Na_2CO_3$ aq to pH=8-9, and then extracted with DCM (3×20 mL). The combined organic layers were washed with brine, dried over $Na_2SO_4$ and filtered. The filtrate was concentrated in vacuo and the residue was purified by column chromatography on silica gel (10-12% ethyl acetate/petroether) to afford the product 2,4-dichloropyrido[3,2-d]pyrimidine 236.

Compound 237 was prepared from amine 114 and compound 236 using Method J and then converted to compound 238 according to the following procedure:

Quinolinone 237 (0.11 mmol, 1.0 eq) was suspended in ammonium hydroxide (10-35% solution, 20 mL) in a sealed tube and the resulting mixture was stirred at 140° C. overnight. The mixture was allowed to cool to RT and then extracted with DCM (3×15 mL). The combined organic layers were washed with brine, dried over $Na_2SO_4$ and filtered. The filtrate was concentrated in vacuo and the residue was purified by column chromatography on silica gel (1-2% MeOH-DCM) to afford compound 238. ESI-MS m/z: 464.2 $[M+H]^+$.

Example 155

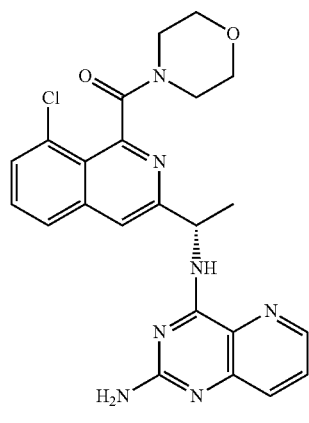

239

Compound 239 was prepared in analogous fashion to compound 14 in Example 6 except that pyrrolidine was used in place of morpholine and that (R)-tert-butyl 1-(methoxy(methyl)amino)-1-oxopropan-2-ylcarbamate was used in place of (S)-tert-butyl 1-(methoxy(methyl)amino)-1-oxopropan-2-ylcarbamate. ESI-MS m/z: 408.0 $[M+H]^+$.

Example 156

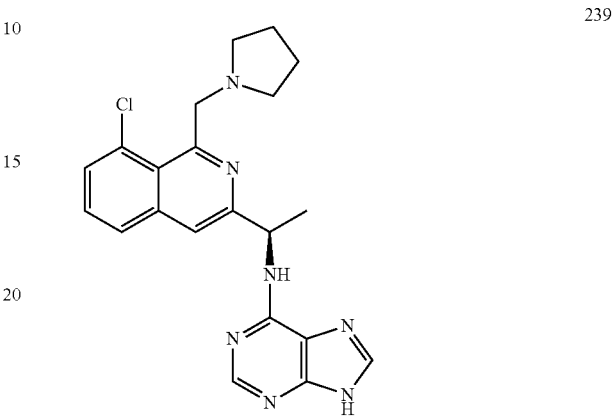

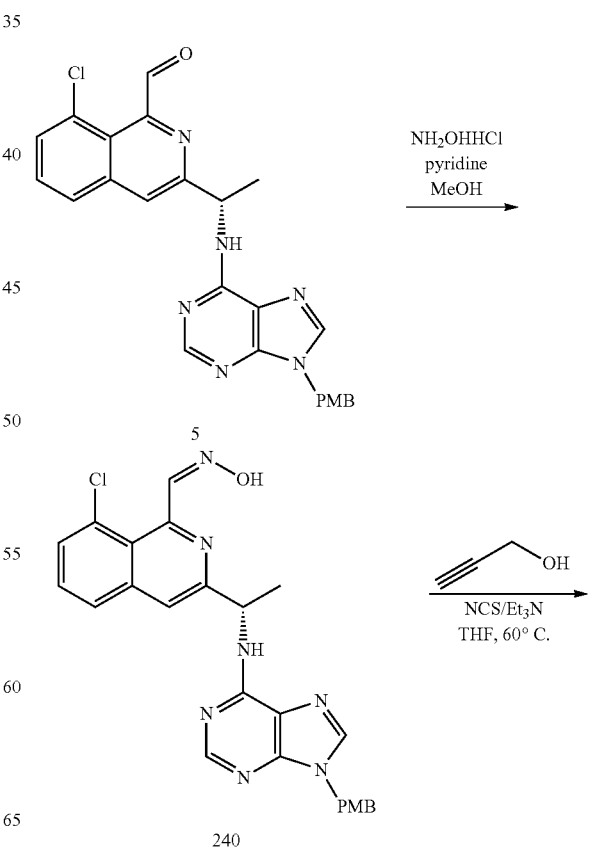

240

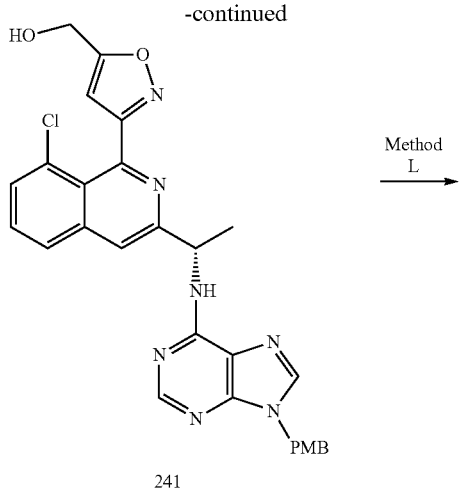

241

Method L
→

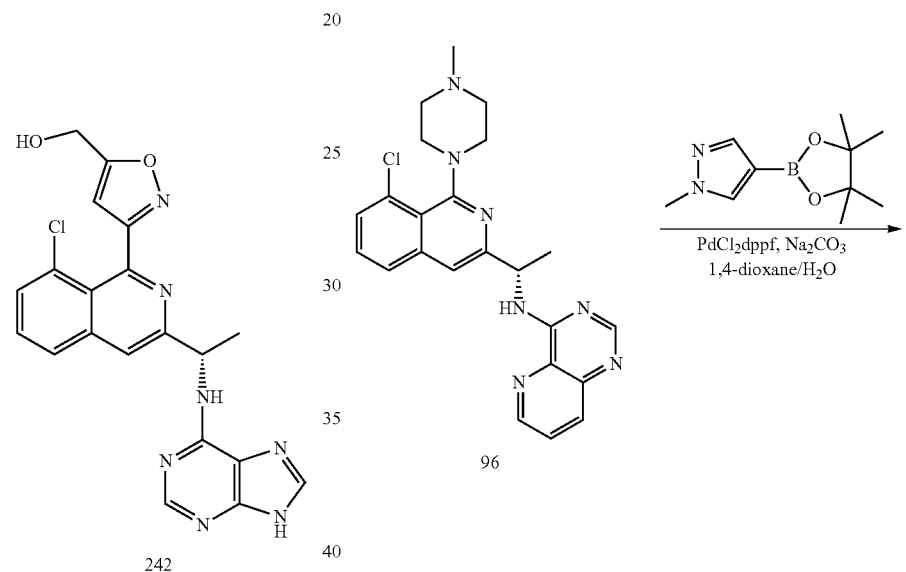

242

96 eq) and triethylamine (105 mg, 1 mmol, 2 eq) were slowly added. The resulting mixture was stirred at 50° C. for 2 h. The mixture was cooled to RT, poured into water (20 mL) and extracted with DCM (3×20 mL). The combined organic layers were washed with brine, dried over $Na_2SO_4$ and filtered. The filtrate was concentrated in vacuo and the residue was purified by flash column chromatography on silica gel (1-5% MeOH-DCM) to afford the product, (S)-(3-(8-chloro-3-(1-((9-(4-methoxybenzyl)-9H-purin-6-yl)amino)ethyl)isoquinolin-1-yl)isoxazol-5-yl)MeOH 241.

Compound 241 was converted to 242 according to Method L. ESI-MS m/z: 422.0 [M+H]+.

Example 157

Compound 242 was prepared in 3 steps from aldehyde 5 according to the following procedures:

A mixture of (S)-8-chloro-3-(1-((9-(4-methoxybenzyl)-9H-purin-6-yl)amino)ethyl)isoquinoline-1-carbaldehyde 5 (270 mg, 0.57 mmol, 1.0 eq) and hydroxylamine hydrochloride (495 mg, 7.1 mmol, 13 eq) in pyridine (4 mL) and MeOH (20 mL) was stirred at RT overnight. The reaction mixture was poured into water (50 mL) and extracted with DCM (3×30 mL). The combined organic layers were washed with brine, dried over $Na_2SO_4$ and filtered. The filtrate was concentrated in vacuo and the residue was purified by flash column chromatography on silica gel (1-10% MeOH-DCM) to afford the product, (S,Z)-8-chloro-3-(1-((9-(4-methoxybenzyl)-9H-purin-6-yl)amino)ethyl)isoquinoline-1-carbaldehyde oxime (240).

To a solution of (S,Z)-8-chloro-3-(1-((9-(4-methoxybenzyl)-9H-purin-6-yl)amino)ethyl)isoquinoline-1-carbaldehyde oxime 240 (250 mg, 0.5 mmol, 1.0 eq), pyridine (40 mg, 0.5 mmol, 1 eq) and NCS (90 mg, 0.6 mmol, 1.2 eq) in THF (100 mL) at 60° C., propargyl alcohol (45 mg, 0.75 mmol, 1.5

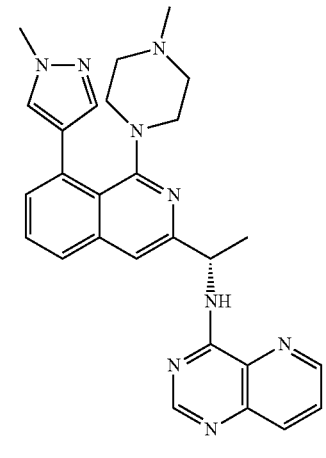

243

Compound 243 was prepared from compound 96 using the analogous Suzuki coupling conditions to obtain compound 141 in Example 83 except that the reaction solvent 1,4-dioxane was used in place of N,N-dimethylacetamide. ESI-MS m/z: 480.2 [M+H]+.

Example 158

Structures and In Vitro IC50 Values for Selected Compounds

TABLE 3

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 239 | 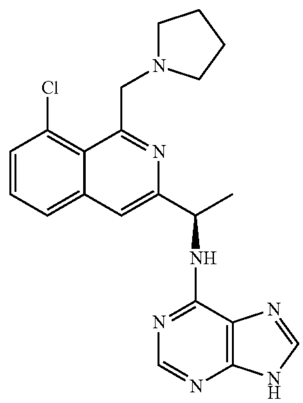 [SMILES: C[C@@H](Nc1ncnc2[nH]cnc12)c1cc2cccc(Cl)c2c(CN2CCCC2)n1] | + | + | + | + | | Calcd: 407.16 Found: 408.0 [M + H]$^+$ |
| 8 | 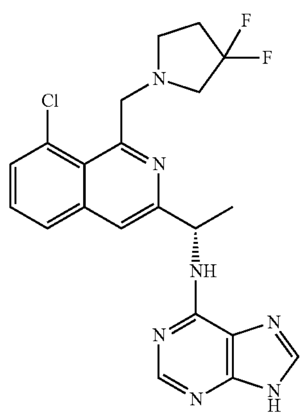 [SMILES: C[C@H](Nc1ncnc2[nH]cnc12)c1cc2cccc(Cl)c2c(CN2CCC(F)(F)C2)n1] | +++ | +++ | ++ | ++ | +++ | Calcd: 443.14 Found: 444.0 [M + H]$^+$ |
| 9 | 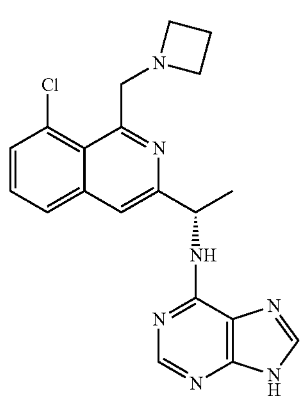 [SMILES: C[C@H](Nc1ncnc2[nH]cnc12)c1cc2cccc(Cl)c2c(CN2CCC2)n1] | +++ | ++ | + | ++ | | Calcd: 393.15 Found: 394.0 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 13 | 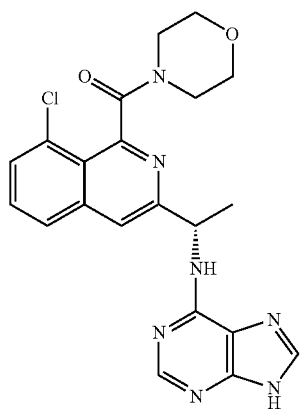 [SMILES: C[C@H](Nc1ncnc2[nH]cnc12)c1cc2cccc(Cl)c2c(C(=O)N2CCOCC2)n1] | ++++ | ++++ | + | ++ | ++++ | Calcd: 437.14 Found: 438.0 [M + H]$^+$ |
| 14 | 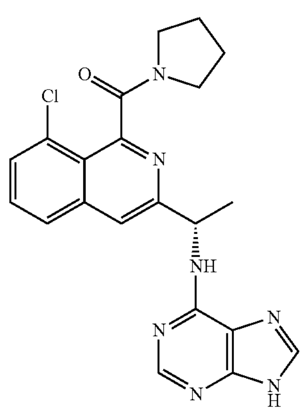 [SMILES: C[C@H](Nc1ncnc2[nH]cnc12)c1cc2cccc(Cl)c2c(C(=O)N2CCCC2)n1] | ++++ | ++ | + | + | ++++ | Calcd: 421.14 Found: 422.0 [M + H]$^+$ |
| 4 | 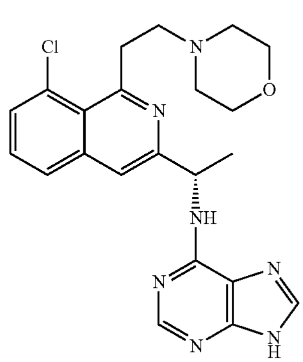 | ++++ | ++ | ++ | ++ | ++++ | Calcd: 437.17 Found: 438.0 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 7 | 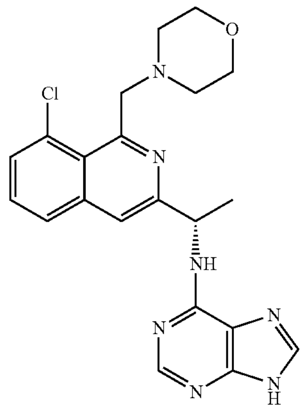 [SMILES: C[C@H](Nc1ncnc2[nH]cnc12)c1cc2cccc(Cl)c2c(CN2CCOCC2)n1] | ++++ | ++ | + | + | ++++ | Calcd: 423.26<br>Found: 424.0<br>[M + H]$^+$ |
| 15 | 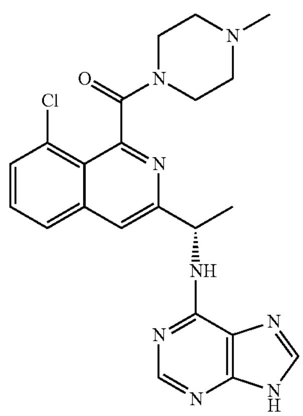 [SMILES: C[C@H](Nc1ncnc2[nH]cnc12)c1cc2cccc(Cl)c2c(C(=O)N2CCN(C)CC2)n1] | ++++ | ++ | ++ | + | ++++ | Calcd: 450.17<br>Found: 451.2<br>[M + H]$^+$ |
| 16 | 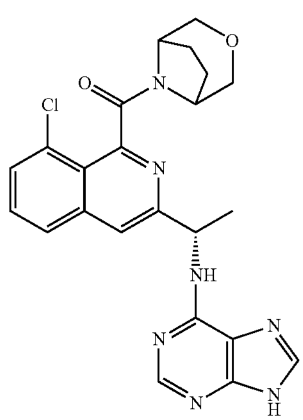 [SMILES: C[C@H](Nc1ncnc2[nH]cnc12)c1cc2cccc(Cl)c2c(C(=O)N2C3CCC2COC3)n1] | ++++ | ++ | + | ++ | ++++ | Calcd: 463.15<br>Found: 464.0<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 17 | 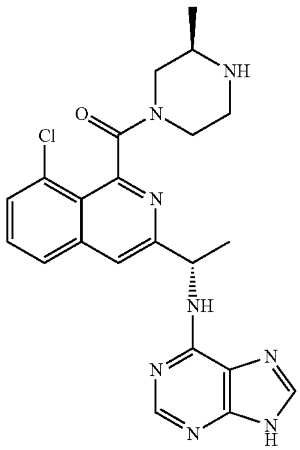 [SMILES: C[C@@H]1CN(C(=O)c2nc([C@H](C)Nc3ncnc4[nH]cnc34)cc3cccc(Cl)c23)CCN1] | ++++ | + | + | ++ | +++ | Calcd: 450.17 Found: 451.0 [M + H]$^+$ |
| 18 | 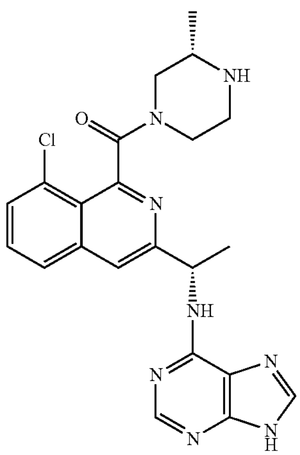 [SMILES: C[C@H](Nc1ncnc2[nH]cnc12)c1cc2cccc(Cl)c2c(C(=O)N2CCN[C@@H](C)C2)n1] | ++++ | ++ | ++ | +++ | +++ | Calcd: 450.17 Found: 451.0 [M + H]$^+$ |
| 19 | 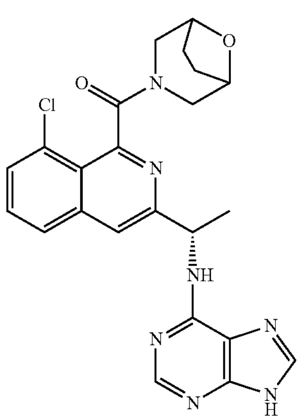 [SMILES: C[C@H](Nc1ncnc2[nH]cnc12)c1cc2cccc(Cl)c2c(C(=O)N2CC3CCC(C2)O3)n1] | ++++ | +++ | + | ++ | ++++ | Calcd: 463.15 Found: 464.0 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 20 | 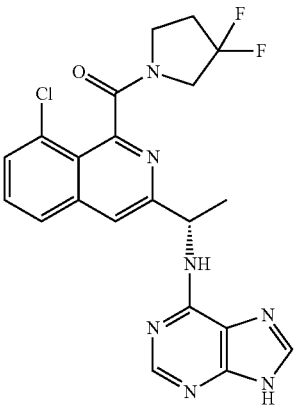 [SMILES: C[C@H](Nc1ncnc2[nH]cnc12)c1cc2cccc(Cl)c2c(C(=O)N2CCC(F)(F)C2)n1] | ++++ | +++ | + | + | ++++ | Calcd: 457.12<br>Found: 458.0<br>[M + H]$^+$ |
| 21 | 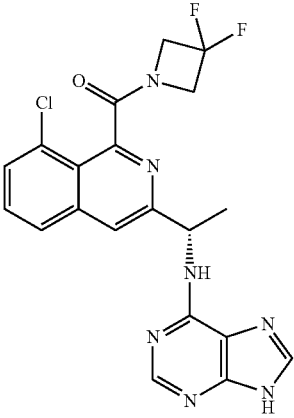 [SMILES: C[C@H](Nc1ncnc2[nH]cnc12)c1cc2cccc(Cl)c2c(C(=O)N2CC(F)(F)C2)n1] | ++++ | +++ | + | + | ++++ | Calcd: 443.11<br>Found: 444.0<br>[M + H]$^+$ |
| 22 | 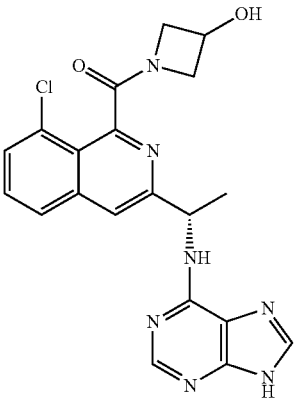 [SMILES: C[C@H](Nc1ncnc2[nH]cnc12)c1cc2cccc(Cl)c2c(C(=O)N2CC(O)C2)n1] | ++++ | +++ | + | ++ | | Calcd: 423.12<br>Found: 424.0<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 23 | [structure] | ++++ | ++ | + | + | ++++ | Calcd: 421.14<br>Found: 422.0<br>[M + H]$^+$ |
| 32 | [structure] | +++ | ++ | + | ++ | | Calcd: 406.11<br>Found: 407.0<br>[M + H]$^+$ |
| 24 | [structure] | +++ | ++ | + | ++ | +++ | Calcd: 407.13<br>Found: 408.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 25 | 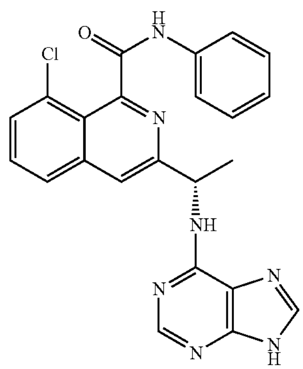 [SMILES: C[C@H](Nc1ncnc2[nH]cnc12)c1cc2cccc(Cl)c2c(C(=O)Nc2ccccc2)n1] | ++++ | ++ | + | ++ | +++ | Calcd: 443.13<br>Found: 444.2<br>[M + H]$^+$ |
| 26 | 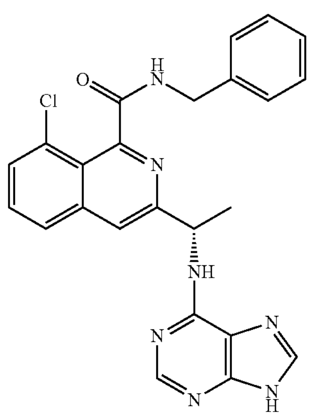 [SMILES: C[C@H](Nc1ncnc2[nH]cnc12)c1cc2cccc(Cl)c2c(C(=O)NCc2ccccc2)n1] | ++++ | +++ | + | ++ | ++++ | Calcd: 457.14<br>Found: 458.0<br>[M + H]$^+$ |
| 27 | 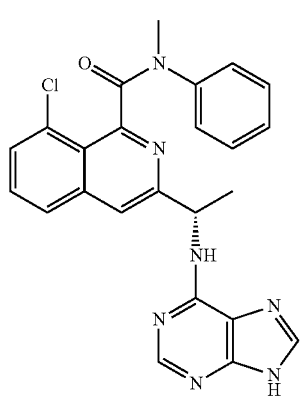 [SMILES: C[C@H](Nc1ncnc2[nH]cnc12)c1cc2cccc(Cl)c2c(C(=O)N(C)c2ccccc2)n1] | +++ | ++ | + | + | | Calcd: 457.14<br>Found: 458.0<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 28 | 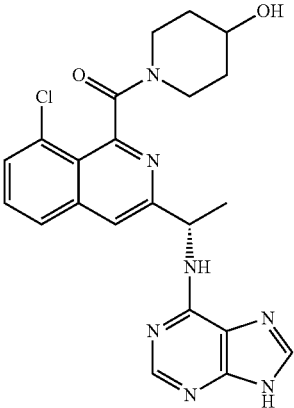 [SMILES: C[C@H](Nc1ncnc2[nH]cnc12)c1cc2cccc(Cl)c2c(C(=O)N2CCC(O)CC2)n1] | ++++ | +++ | + | + | | Calcd: 451.15<br>Found: 452.2<br>[M + H]$^+$ |
| 35 | 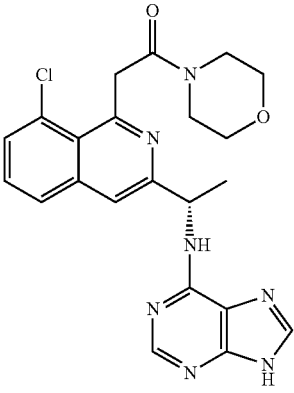 [SMILES: C[C@H](Nc1ncnc2[nH]cnc12)c1cc2cccc(Cl)c2c(CC(=O)N2CCOCC2)n1] | +++ | ++ | + | + | | Calcd: 451.15<br>Found: 452.2<br>[M + H]$^+$ |
| 36 | 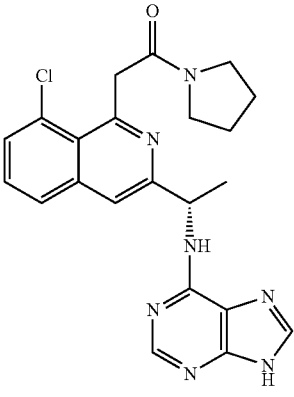 [SMILES: C[C@H](Nc1ncnc2[nH]cnc12)c1cc2cccc(Cl)c2c(CC(=O)N2CCCC2)n1] | ++++ | ++ | + | ++ | +++ | Calcd: 435.16<br>Found: 436.0<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 242 | 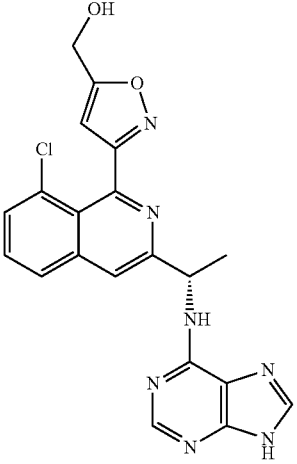 [SMILES: C[C@H](Nc1ncnc2[nH]cnc12)c1cc2cccc(Cl)c2c(-c2cc(CO)on2)n1] | ++++ | +++ | ++ | +++ | ++++ | Calcd: 421.11<br>Found: 422.0<br>[M + H]$^+$ |
| 37 | 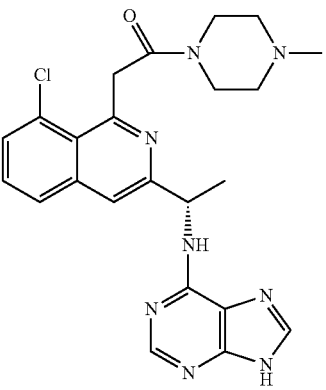 [SMILES: C[C@H](Nc1ncnc2[nH]cnc12)c1cc2cccc(Cl)c2c(CC(=O)N2CCN(C)CC2)n1] | +++ | + | + | + | +++ | Calcd: 464.18<br>Found: 465.2<br>[M + H]$^+$ |
| 40 | 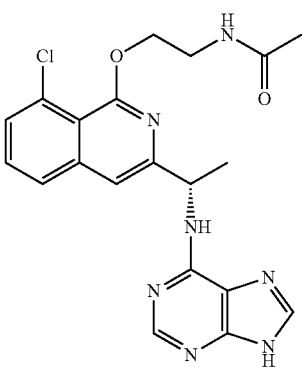 [SMILES: CC(=O)NCCOc1nc([C@H](C)Nc2ncnc3[nH]cnc23)cc2cccc(Cl)c12] | ++++ | +++ | ++ | ++ | ++++ | Calcd: 425.14<br>Found: 426.0<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 42 | 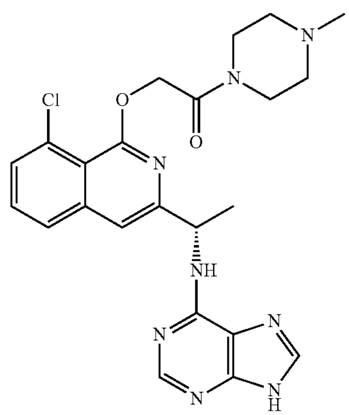 [SMILES: C[C@H](Nc1ncnc2[nH]cnc12)c1cc2cccc(Cl)c2c(OCC(=O)N2CCN(C)CC2)n1] | ++++ | + | + | ++ | +++ | Calcd: 480.18 Found: 481.0 [M + H]$^+$ |
| 43 | 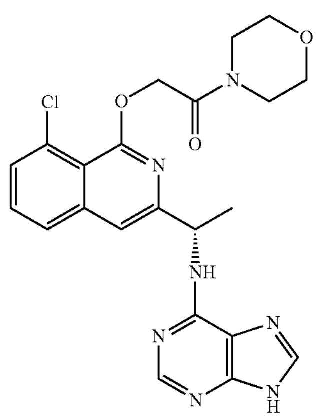 [SMILES: C[C@H](Nc1ncnc2[nH]cnc12)c1cc2cccc(Cl)c2c(OCC(=O)N2CCOCC2)n1] | ++++ | +++ | ++ | + | ++++ | Calcd: 467.15 Found: 468.0 [M + H]$^+$ |
| 44 | 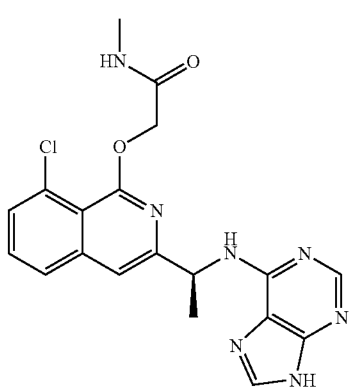 [SMILES: CNC(=O)COc1nc([C@H](C)Nc2ncnc3[nH]cnc23)cc2cccc(Cl)c12] | ++++ | +++ | ++ | ++ | +++ | Calcd: 411.12 Found: 412.0 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 45 | 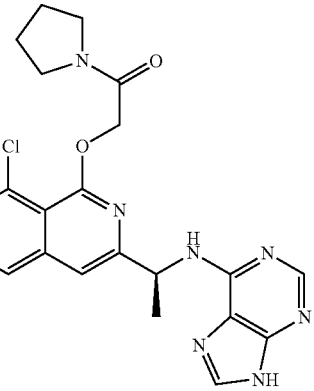 | ++++ | ++ | + | + | +++ | Calcd: 451.15<br>Found: 452.2<br>[M + H]$^+$ |
| 46 | 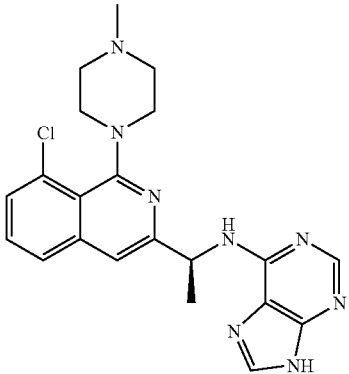 [SMILES: C[C@H](Nc1ncnc2[nH]cnc12)c1cc2cccc(Cl)c2c(N2CCN(C)CC2)n1] | ++++ | + | + | ++ | ++++ | Calcd: 422.17<br>Found: 423.2<br>[M + H]$^+$ |
| 53 | 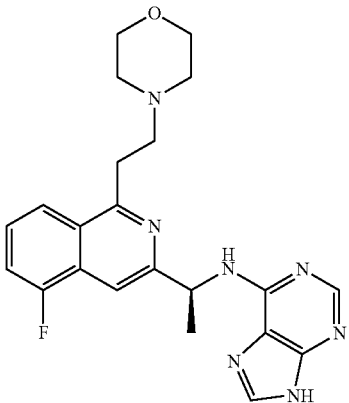 [SMILES: C[C@H](Nc1ncnc2[nH]cnc12)c1cc2c(F)cccc2c(CCN2CCOCC2)n1] | ++++ | + | + | + | ++++ | Calcd: 421.20<br>Found: 422.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 48 | 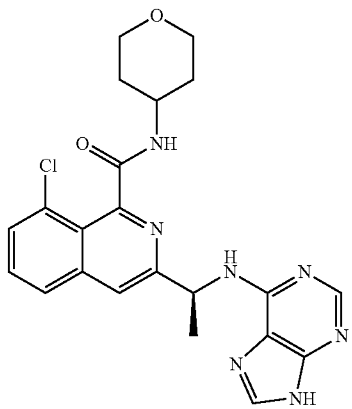 [SMILES: C[C@H](Nc1ncnc2[nH]cnc12)c1cc2cccc(Cl)c2c(C(=O)NC2CCOCC2)n1] | ++++ | ++ | + | + | | Calcd: 451.15 Found: 452.2 [M + H]$^+$ |
| 47 | 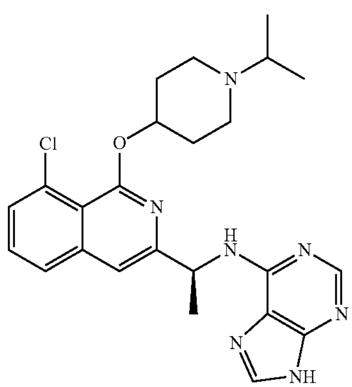 [SMILES: CC(C)N1CCC(Oc2nc([C@H](C)Nc3ncnc4[nH]cnc34)cc3cccc(Cl)c23)CC1] | ++++ | + | ++ | ++ | ++++ | Calcd: 465.20 Found: 466.2 [M + H]$^+$ |
| 57 | 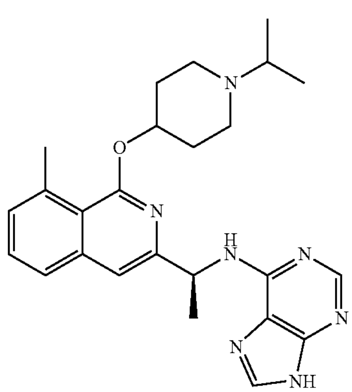 [SMILES: Cc1cccc2cc([C@H](C)Nc3ncnc4[nH]cnc34)nc(OC3CCN(C(C)C)CC3)c12] | ++++ | + | + | ++ | +++ | Calcd: 445.26 Found: 446.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 55 | 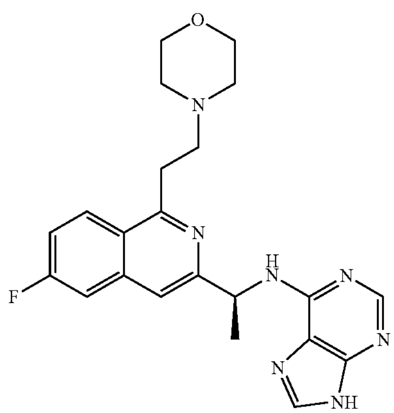 [SMILES: C[C@H](Nc1ncnc2[nH]cnc12)c1cc2cc(F)ccc2c(CCN2CCOCC2)n1] | +++ | + | + | + | | Calcd: 421.20 Found: 422.2 [M + H]$^+$ |
| 68 | 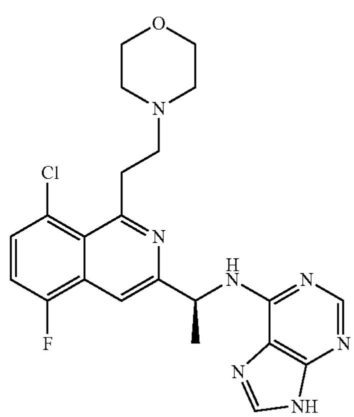 [SMILES: C[C@H](Nc1ncnc2[nH]cnc12)c1cc2c(F)ccc(Cl)c2c(CCN2CCOCC2)n1] | ++++ | ++ | ++ | + | ++++ | Calcd: 455.16 Found: 456.2 [M + H]$^+$ |
| 58 | 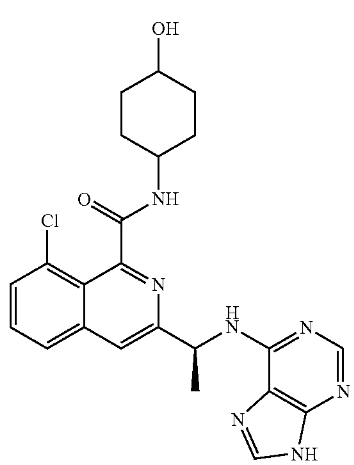 [SMILES: C[C@H](Nc1ncnc2[nH]cnc12)c1cc2cccc(Cl)c2c(C(=O)NC2CCC(O)CC2)n1] | ++++ | ++ | + | + | | Calcd: 465.17 Found: 466.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 73 | 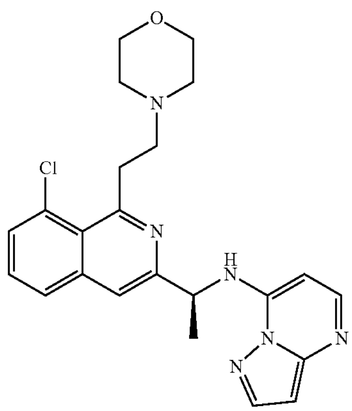 [SMILES: C[C@H](Nc1ccnc2ccnn12)c1cc2cccc(Cl)c2c(CCN2CCOCC2)n1] | ++++ | ++ | ++ | +++ | ++++ | Calcd: 436.18<br>Found: 437.2<br>[M + H]$^+$ |
| 74 | 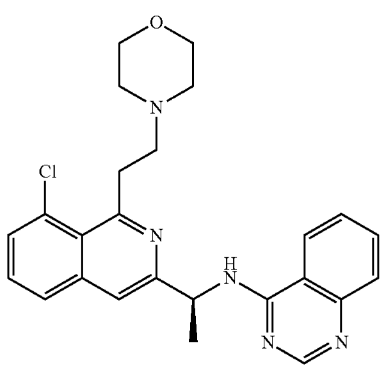 [SMILES: C[C@H](Nc1ncnc2ccccc12)c1cc2cccc(Cl)c2c(CCN2CCOCC2)n1] | ++++ | ++ | ++ | ++ | +++ | Calcd: 447.18<br>Found: 448.2<br>[M + H]$^+$ |
| 75 | 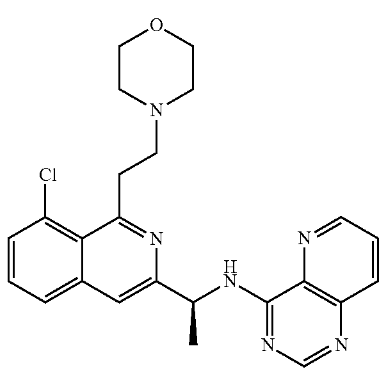 [SMILES: C[C@H](Nc1ncnc2cccnc12)c1cc2cccc(Cl)c2c(CCN2CCOCC2)n1] | ++++ | +++ | +++ | +++ | ++++ | Calcd: 448.18<br>Found: 449.2<br>[M + H]$^+$ |

… TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 85 | 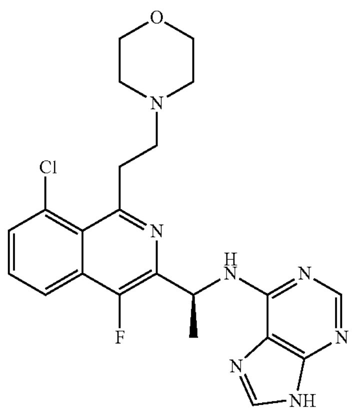 [SMILES: C[C@H](Nc1ncnc2[nH]cnc12)c1nc(CCN2CCOCC2)c2c(Cl)cccc2c1F] | +++ | + | + | + | +++ | Calcd: 455.16<br>Found: 456.2<br>[M + H]$^+$ |
| 87 | 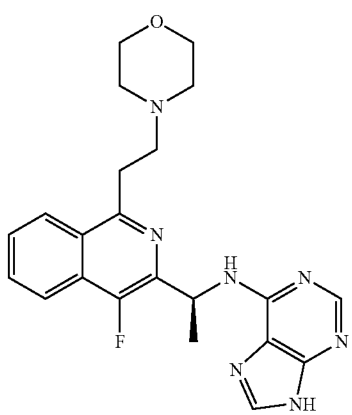 [SMILES: C[C@H](Nc1ncnc2[nH]cnc12)c1nc(CCN2CCOCC2)c2ccccc2c1F] | +++ | + | + | + | | Calcd: 421.20<br>Found: 422.2<br>[M + H]$^+$ |
| 72 | 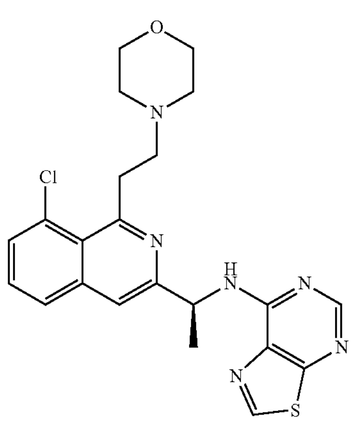 [SMILES: C[C@H](Nc1ncnc2scnc12)c1cc2cccc(Cl)c2c(CCN2CCOCC2)n1] | ++++ | ++ | ++ | +++ | | Calcd: 454.13<br>Found: 455.0<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 88 | *structure* | +++ | ++ | ++ | ++ | | Calcd: 412.1 Found: 413.2 [M + H]$^+$ |
| 76 | *structure* | ++ | + | + | + | | Calcd: 470.14 Found: 471.0 [M]$^+$ |
| 78 | *structure* | ++ | + | + | + | | Calcd: 436.18 Found: 437.2 [M + H]$^+$ |
| 77 | *structure* | ++++ | + | + | + | ++++ | Calcd: 402.22 Found: 403.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 89 | 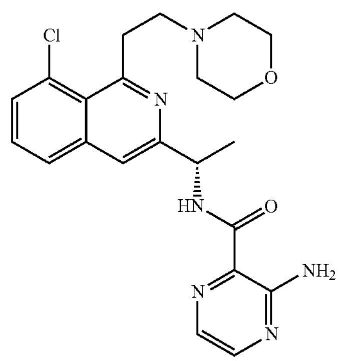 [SMILES: C[C@H](NC(=O)c1nccnc1N)c1cc2cccc(Cl)c2c(CCN2CCOCC2)n1] | +++ | ++ | + | ++ | | Calcd: 440.17 Found: 441.2 [M + H]$^+$ |
| 90 | 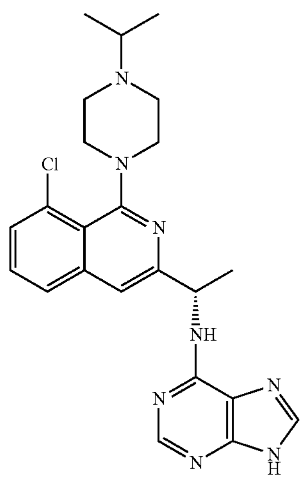 [SMILES: CC(C)N1CCN(c2nc([C@H](C)Nc3ncnc4[nH]cnc34)cc3cccc(Cl)c23)CC1] | ++++ | ++ | ++ | ++ | ++++ | Calcd: 450.20 Found: 451.2 [M + H]$^+$ |
| 91 | 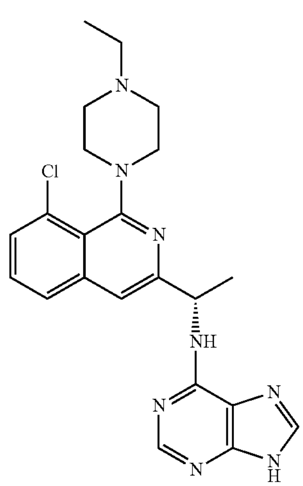 [SMILES: CCN1CCN(c2nc([C@H](C)Nc3ncnc4[nH]cnc34)cc3cccc(Cl)c23)CC1] | ++++ | ++ | ++ | ++ | ++++ | Calcd: 436.19 Found: 437.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 92 | 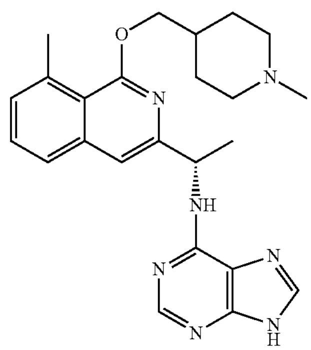 [SMILES: Cc1cccc2cc([C@H](C)Nc3ncnc4[nH]cnc34)nc(OCC3CCN(C)CC3)c12] | ++++ | ++ | ++ | ++ | ++++ | Calcd: 431.24 Found: 432.0 [M + H]$^+$ |
| 93 | 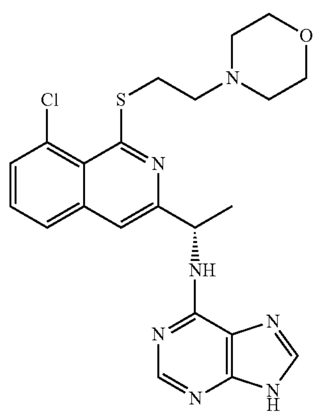 [SMILES: C[C@H](Nc1ncnc2[nH]cnc12)c1cc2cccc(Cl)c2c(SCCN2CCOCC2)n1] | ++++ | +++ | ++ | +++ | ++++ | Calcd: 469.15 Found: 470.0 [M + H]$^+$ |
| 94 | 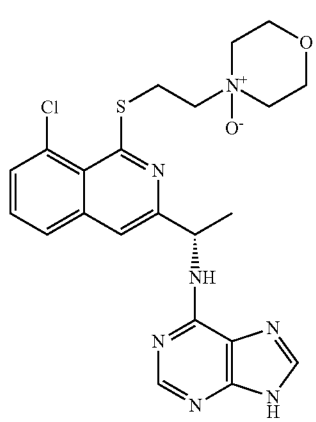 [SMILES: C[C@H](Nc1ncnc2[nH]cnc12)c1cc2cccc(Cl)c2c(SCC[N+]2([O-])CCOCC2)n1] | ++++ | +++ | ++ | ++ | | Calcd: 485.14 Found: 486.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 96 | 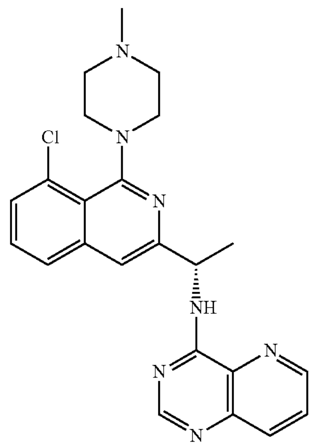 [SMILES: C[C@H](Nc1ncnc2cccnc12)c1cc2cccc(Cl)c2c(N2CCN(C)CC2)n1] | ++++ | ++++ | +++ | +++ | | Calcd: 433.18<br>Found: 434.2<br>[M + H]$^+$ |
| 97 | 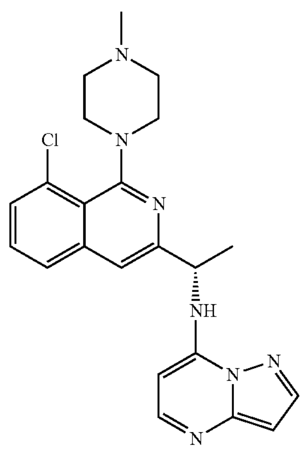 [SMILES: C[C@H](Nc1ccnc2ccnn12)c1cc2cccc(Cl)c2c(N2CCN(C)CC2)n1] | ++++ | + | + | ++ | | Calcd: 421.18<br>Found: 422.2<br>[M + H]$^+$ |
| 100 | 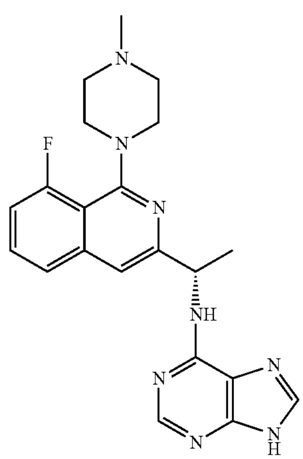 | ++++ | + | + | + | | Calcd: 406.20<br>Found: 407.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 105 | 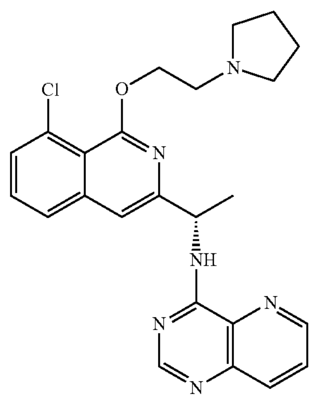 [SMILES: C[C@H](Nc1ncnc2cccnc12)c1cc2cccc(Cl)c2c(OCCN2CCCC2)n1] | ++++ | +++ | +++ | ++ | | Calcd: 448.18<br>Found: 449.2<br>[M + H]$^+$ |
| 106 | 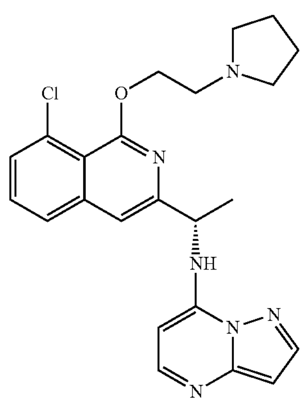 [SMILES: C[C@H](Nc1ccnc2ccnn12)c1cc2cccc(Cl)c2c(OCCN2CCCC2)n1] | ++++ | ++ | + | ++ | | Calcd: 436.18<br>Found: 437.2<br>[M + H]$^+$ |
| 115 | 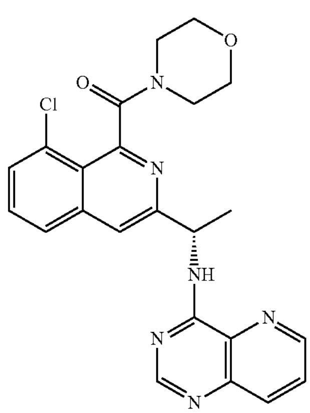 [SMILES: C[C@H](Nc1ncnc2cccnc12)c1cc2cccc(Cl)c2c(C(=O)N2CCOCC2)n1] | ++++ | +++ | ++ | ++ | | Calcd: 448.14<br>Found: 449.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 109 | 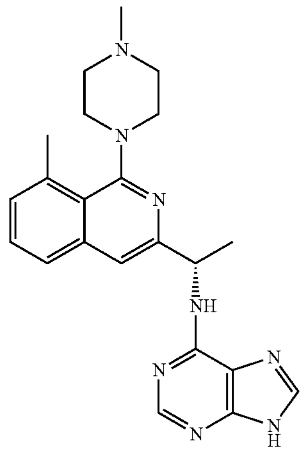 [SMILES: Cc1cccc2cc([C@H](C)Nc3ncnc4[nH]cnc34)nc(N3CCN(C)CC3)c12] | ++++ | ++ | + | ++ | | Calcd: 402.23 Found: 403.2 [M + H]$^+$ |
| 107 | 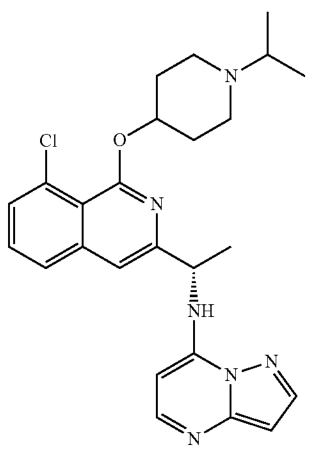 [SMILES: CC(C)N1CCC(Oc2nc([C@H](C)Nc3ccnc4ccnn34)cc3cccc(Cl)c23)CC1] | ++++ | ++ | ++ | ++ | ++++ | Calcd: 464.21 Found: 465.2 [M + H]$^+$ |
| 98 | 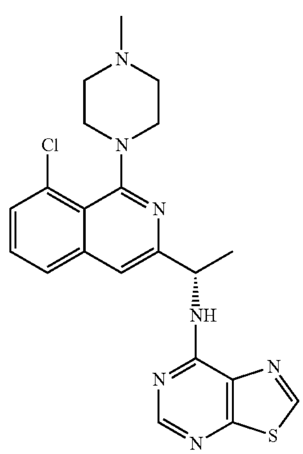 [SMILES: C[C@H](Nc1ncnc2scnc12)c1cc2cccc(Cl)c2c(N2CCN(C)CC2)n1] | ++++ | ++ | ++ | +++ | ++++ | Calcd: 439.13 Found: 440.0 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 116 | 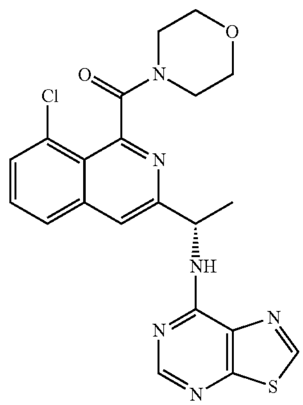 [SMILES: C[C@H](Nc1ncnc2scnc12)c1cc2cccc(Cl)c2c(C(=O)N2CCOCC2)n1] | ++++ | +++ | ++ | +++ | ++++ | Calcd: 454.10<br>Found: 455.0<br>[M + H]$^+$ |
| 117 | 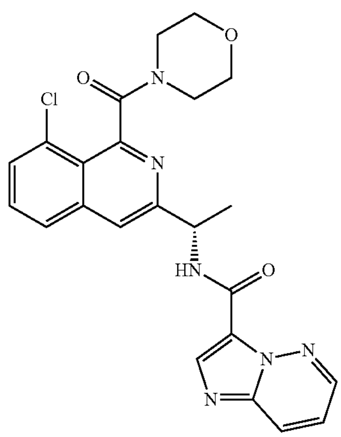 [SMILES: C[C@H](NC(=O)c1cnc2cccnn12)c1cc2cccc(Cl)c2c(C(=O)N2CCOCC2)n1] | +++ | ++ | + | ++ | | Calcd: 464.14<br>Found: 465.0<br>[M + H]$^+$ |
| 108 | 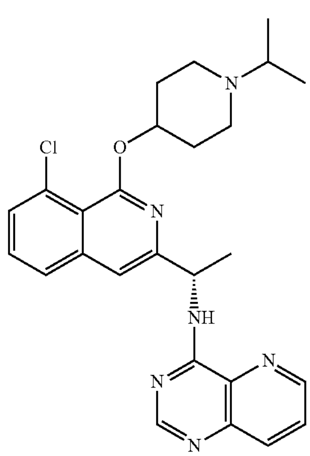 [SMILES: CC(C)N1CCC(Oc2nc([C@H](C)Nc3ncnc4cccnc34)cc3cccc(Cl)c23)CC1] | ++++ | ++++ | ++ | + | +++ | Calcd: 476.21<br>Found: 477.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 119 | 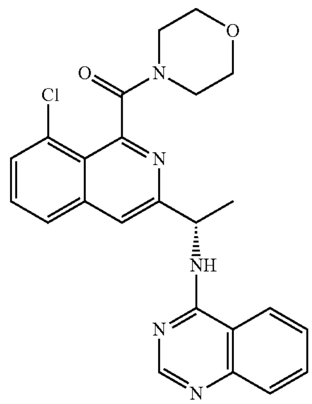 [SMILES: C[C@H](Nc1ncnc2ccccc12)c1cc2cccc(Cl)c2c(C(=O)N2CCOCC2)n1] | ++++ | +++ | ++ | + | +++ | Calcd: 447.15<br>Found: 448.2<br>[M + H]$^+$ |
| 120 | 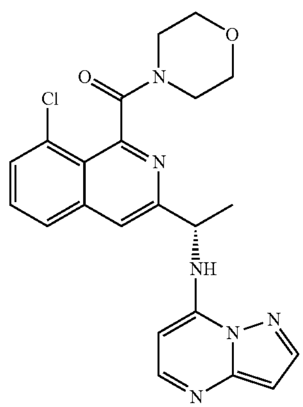 [SMILES: C[C@H](Nc1ccnc2ccnn12)c1cc2cccc(Cl)c2c(C(=O)N2CCOCC2)n1] | ++++ | +++ | ++ | ++ | ++++ | Calcd: 436.14<br>Found: 437.2<br>[M + H]$^+$ |
| 121 | 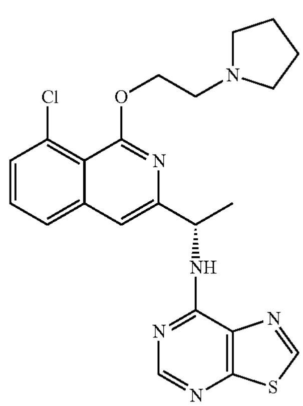 [SMILES: C[C@H](Nc1ncnc2scnc12)c1cc2cccc(Cl)c2c(OCCN2CCCC2)n1] | ++++ | +++ | +++ | +++ | ++++ | Calcd: 454.13<br>Found: 455.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 111 | 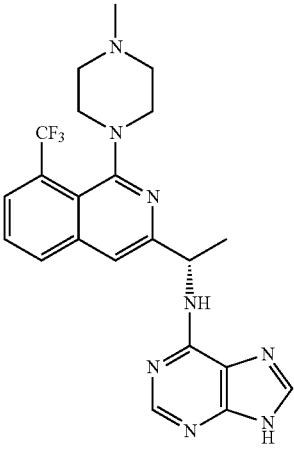 [SMILES: C[C@H](Nc1ncnc2[nH]cnc12)c1cc2cccc(C(F)(F)F)c2c(N2CCN(C)CC2)n1] | +++ | ++ | + | ++ | | Calcd: 456.2<br>Found: 457.2<br>[M + H]$^+$ |
| 122 | 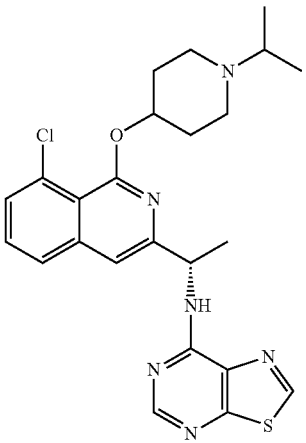 [SMILES: CC(C)N1CCC(Oc2nc([C@H](C)Nc3ncnc4scnc34)cc3cccc(Cl)c23)CC1] | ++++ | ++ | ++ | ++ | +++ | Calcd: 482.17<br>Found: 483.2<br>[M + H]$^+$ |
| 118 | 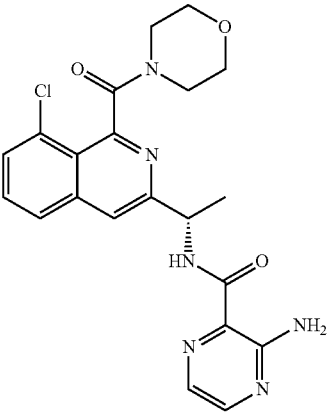 [SMILES: C[C@H](NC(=O)c1nccnc1N)c1cc2cccc(Cl)c2c(C(=O)N2CCOCC2)n1] | +++ | ++ | + | ++ | | Calcd: 440.14<br>Found: 441.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 123 | 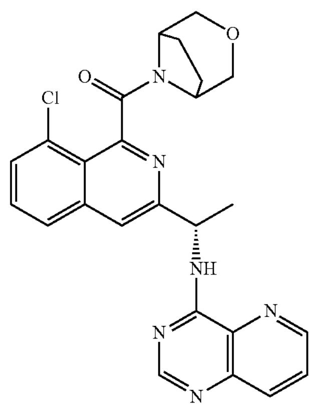 [SMILES: C[C@H](Nc1ncnc2cccnc12)c1cc2cccc(Cl)c2c(C(=O)N2C3CCC2COC3)n1] | ++++ | +++ | ++ | ++ | ++++ | Calcd: 474.16<br>Found: 475.2<br>[M + H]$^+$ |
| 126 | 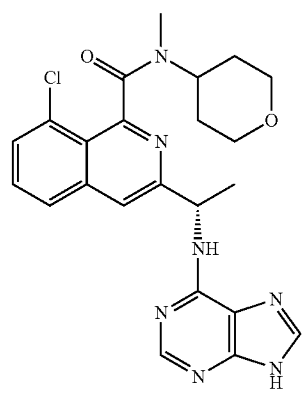 [SMILES: C[C@H](Nc1ncnc2[nH]cnc12)c1cc2cccc(Cl)c2c(C(=O)N(C)C2CCOCC2)n1] | +++ | ++ | + | + | | Calcd: 465.17<br>Found: 466.2<br>[M + H]$^+$ |
| 128 | 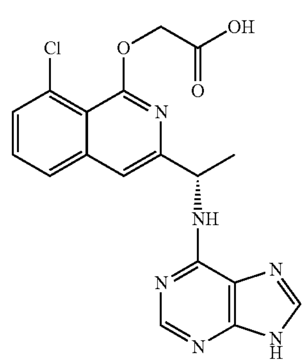 [SMILES: C[C@H](Nc1ncnc2[nH]cnc12)c1cc2cccc(Cl)c2c(OCC(=O)O)n1] | ++ | +++ | + | + | | Calcd: 398.09<br>Found: 399.0<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 129 | 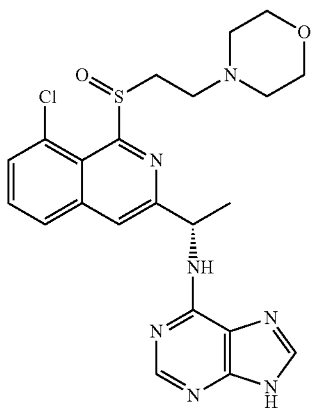 [SMILES: C[C@H](Nc1ncnc2[nH]cnc12)c1cc2cccc(Cl)c2c(S(=O)CCN2CCOCC2)n1] | ++++ | +++ | ++ | +++ | +++ | Calcd: 485.14<br>Found: 486.2<br>[M + H]$^+$ |
| 130 | 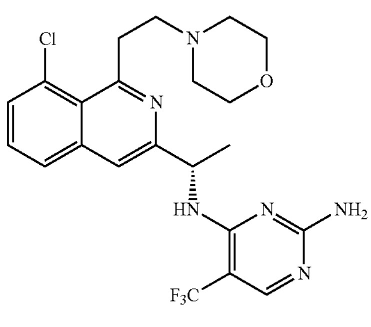 [SMILES: C[C@H](Nc1nc(N)ncc1C(F)(F)F)c1cc2cccc(Cl)c2c(CCN2CCOCC2)n1] | ++++ | ++ | + | ++ | | Calcd: 480.17<br>Found: 481.2<br>[M + H]$^+$ |
| 124 | 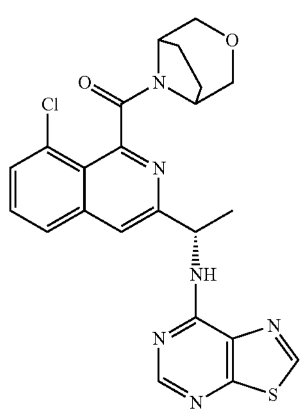 [SMILES: C[C@H](Nc1ncnc2scnc12)c1cc2cccc(Cl)c2c(C(=O)N2C3CCC2COC3)n1] | ++++ | +++ | ++ | +++ | ++++ | Calcd: 480.11<br>Found: 481.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 125 | 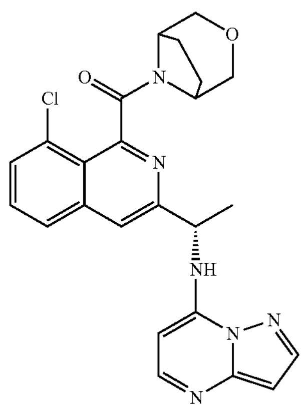 [SMILES: C[C@H](Nc1ccnc2ccnn12)c1cc2cccc(Cl)c2c(C(=O)N2C3CCC2COC3)n1] | ++++ | ++ | + | ++ | ++++ | Calcd: 462.16<br>Found: 463.2<br>[M + H]$^+$ |
| 134 | 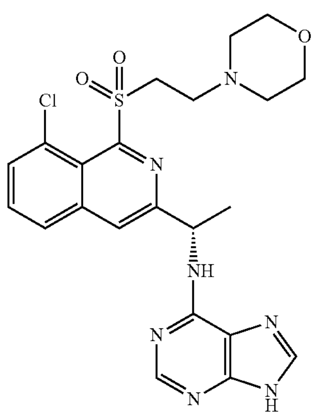 [SMILES: C[C@H](Nc1ncnc2[nH]cnc12)c1cc2cccc(Cl)c2c(S(=O)(=O)CCN2CCOCC2)n1] | +++ | + | + | + |  | Calcd: 501.13<br>Found: 502.2<br>[M + H]$^+$ |
| 135 | 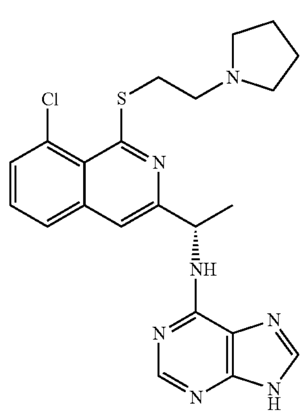 [SMILES: C[C@H](Nc1ncnc2[nH]cnc12)c1cc2cccc(Cl)c2c(SCCN2CCCC2)n1] | ++++ | + | + | ++ | +++ | Calcd: 453.15<br>Found: 454.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 139 | 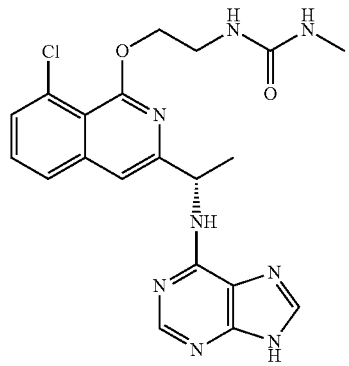 [SMILES: CNC(=O)NCCOc1nc([C@H](C)Nc2ncnc3[nH]cnc23)cc2cccc(Cl)c12] | +++ | ++ | + | ++ | | Calcd: 440.15<br>Found: 441.2<br>[M + H]$^+$ |
| 142 | 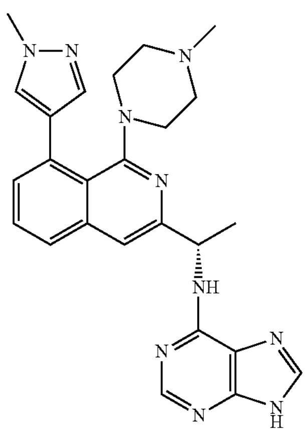 [SMILES: C[C@H](Nc1ncnc2[nH]cnc12)c1cc2cccc(-c3cnn(C)c3)c2c(N2CCN(C)CC2)n1] | +++ | + | + | ++ | | Calcd: 468.25<br>Found: 469.2<br>[M + H]$^+$ |
| 143 | 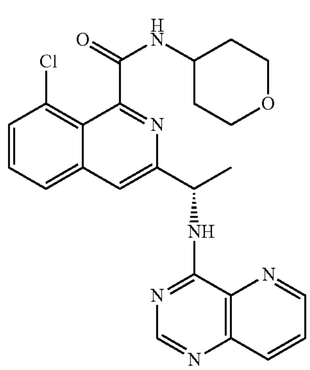 [SMILES: C[C@H](Nc1ncnc2cccnc12)c1cc2cccc(Cl)c2c(C(=O)NC2CCOCC2)n1] | +++ | ++ | + | + | | Calcd: 462.16<br>Found: 463.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 136 | 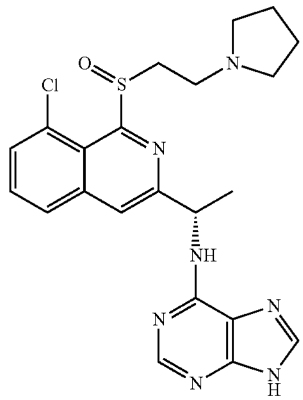 [SMILES: C[C@H](Nc1ncnc2[nH]cnc12)c1cc2cccc(Cl)c2c(S(=O)CCN2CCCC2)n1] | ++++ | ++ | ++ | ++ | ++++ | Calcd: 469.15<br>Found: 470.2<br>[M + H]$^+$ |
| 145 | 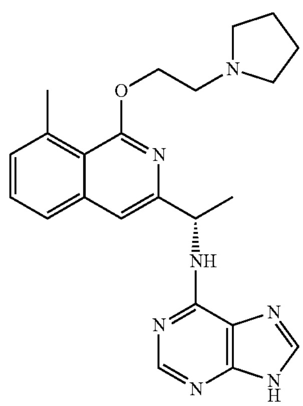 [SMILES: Cc1cccc2cc([C@H](C)Nc3ncnc4[nH]cnc34)nc(OCCN3CCCC3)c12] | ++++ | + | + | ++ | ++++ | Calcd: 417.23<br>Found: 418.2<br>[M + H]$^+$ |
| 243 | 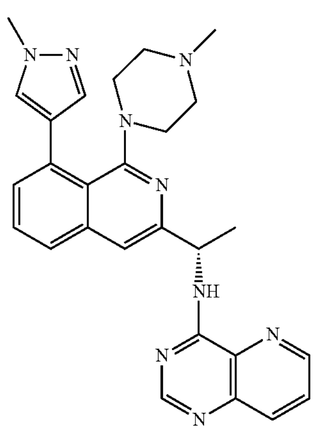 [SMILES: C[C@H](Nc1ncnc2cccnc12)c1cc2cccc(-c3cnn(C)c3)c2c(N2CCN(C)CC2)n1] | +++ | ++ | + | ++ | | Calcd: 479.23<br>Found: 480.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 146 | 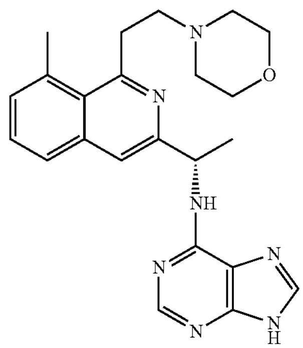 [SMILES: Cc1cccc2cc([C@H](C)Nc3ncnc4[nH]cnc34)nc(CCN3CCOCC3)c12] | ++++ | ++ | + | ++ | ++++ | Calcd: 417.23<br>Found: 418.2<br>[M + H]$^+$ |
| 147 | 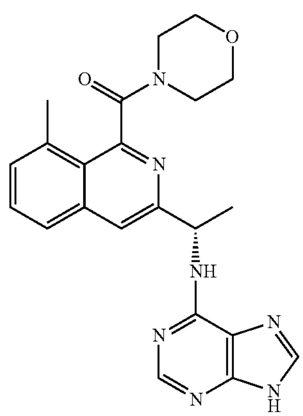 [SMILES: Cc1cccc2cc([C@H](C)Nc3ncnc4[nH]cnc34)nc(C(=O)N3CCOCC3)c12] | +++ | ++ | + | + | | Calcd: 417.19<br>Found: 418.2<br>[M + H]$^+$ |
| 144 | 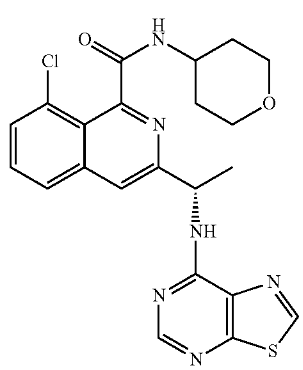 [SMILES: C[C@H](Nc1ncnc2scnc12)c1cc2cccc(Cl)c2c(C(=O)NC2CCOCC2)n1] | ++++ | ++ | + | + | ++++ | Calcd: 468.11<br>Found: 469.0<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 148 | 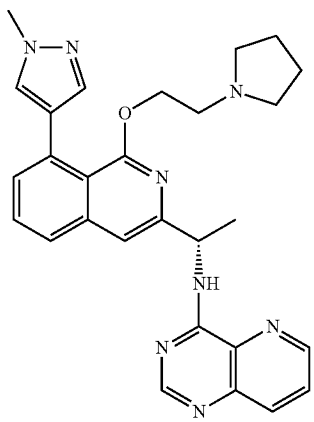 [SMILES: C[C@H](Nc1ncnc2cccnc12)c1cc2cccc(-c3cnn(C)c3)c2c(OCCN2CCCC2)n1] | +++ | ++ | ++ | + | | Calcd: 494.23 Found: 495.2 [M + H]$^+$ |
| 151 | 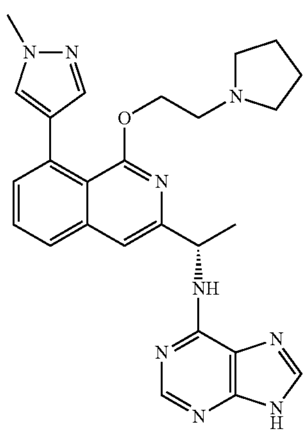 [SMILES: C[C@H](Nc1ncnc2[nH]cnc12)c1cc2cccc(-c3cnn(C)c3)c2c(OCCN2CCCC2)n1] | ++++ | ++ | + | ++ | ++++ | Calcd: 483.25 Found: 484.2 [M + H]$^+$ |
| 154 | 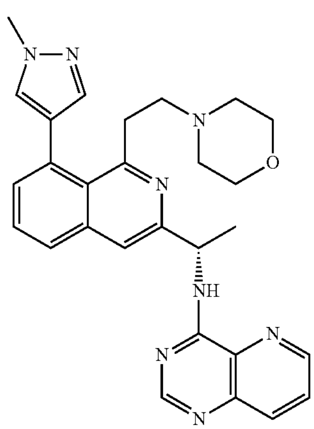 [SMILES: C[C@H](Nc1ncnc2cccnc12)c1cc2cccc(-c3cnn(C)c3)c2c(CCN2CCOCC2)n1] | +++ | ++ | ++ | + | | Calcd: 494.25 Found: 495.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 157 | 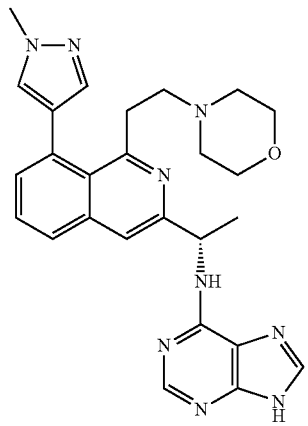 [SMILES: C[C@H](Nc1ncnc2[nH]cnc12)c1cc2cccc(-c3cnn(C)c3)c2c(CCN2CCOCC2)n1] | +++ | ++ | + | + | | Calcd: 483.25<br>Found: 484.2<br>[M + H]$^+$ |
| 158 | 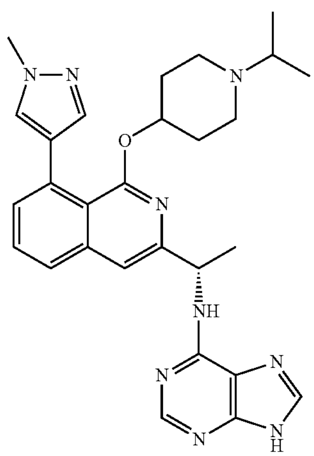 [SMILES: CC(C)N1CCC(Oc2nc([C@H](C)Nc3ncnc4[nH]cnc34)cc3cccc(-c4cnn(C)c4)c23)CC1] | ++++ | + | + | ++ | +++ | Calcd: 511.28<br>Found: 512.2<br>[M + H]$^+$ |
| 149 | 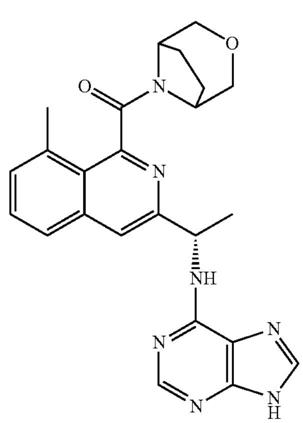 [SMILES: Cc1cccc2cc([C@H](C)Nc3ncnc4[nH]cnc34)nc(C(=O)N3C4CCC3COC4)c12] | ++++ | ++ | + | + | ++++ | Calcd: 443.21<br>Found: 444.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 160 | 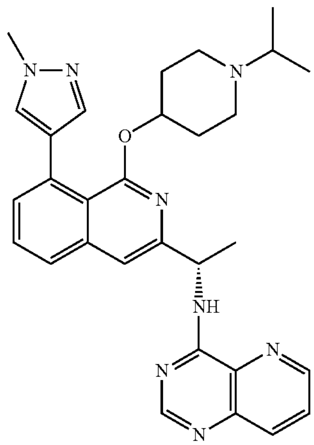 [SMILES: CC(C)N1CCC(Oc2nc([C@H](C)Nc3ncnc4cccnc34)cc3cccc(-c4cnn(C)c4)c23)CC1] | ++++ | ++ | ++ | + | ++++ | Calcd: 522.29<br>Found: 523.2<br>[M + H]$^+$ |
| 162 | 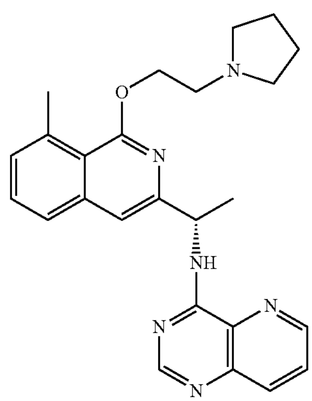 [SMILES: Cc1cccc2cc([C@H](C)Nc3ncnc4cccnc34)nc(OCCN3CCCC3)c12] | ++++ | +++ | +++ | ++ | ++++ | Calcd: 428.23<br>Found: 429.2<br>[M + H]$^+$ |
| 163 | 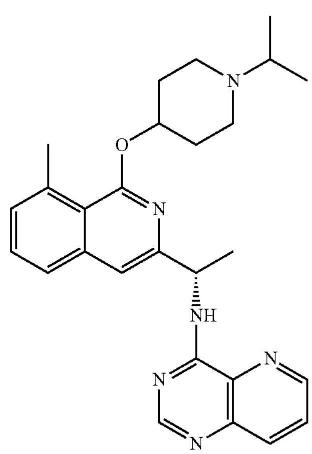 [SMILES: Cc1cccc2cc([C@H](C)Nc3ncnc4cccnc34)nc(OC3CCN(C(C)C)CC3)c12] | ++++ | ++ | ++ | + | ++++ | Calcd: 456.26<br>Found: 457.0<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 164 | 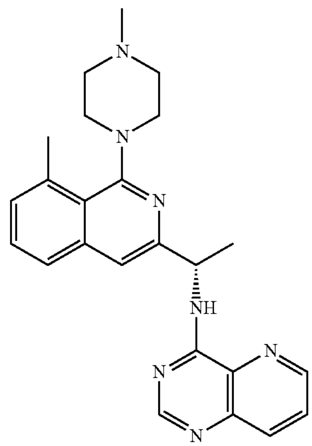 [SMILES: Cc1cccc2cc([C@H](C)Nc3ncnc4cccnc34)nc(N3CCN(C)CC3)c12] | ++++ | ++ | ++ | ++ | ++++ | Calcd: 413.23 Found: 414.2 [M + H]$^+$ |
| 165 | 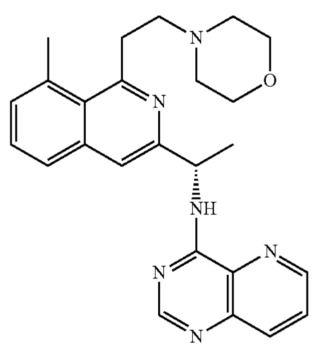 [SMILES: Cc1cccc2cc([C@H](C)Nc3ncnc4cccnc34)nc(CCN3CCOCC3)c12] | ++++ | ++ | ++ | + | ++++ | Calcd: 428.23 Found: 429.2 [M + H]$^+$ |
| 172 | 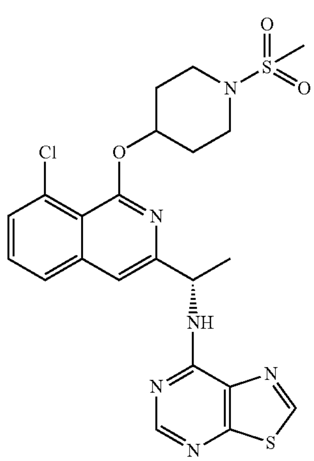 [SMILES: C[C@H](Nc1ncnc2scnc12)c1cc2cccc(Cl)c2c(OC2CCN(S(C)(=O)=O)CC2)n1] | ++++ | ++ | + | ++ | +++ | Calcd: 518.10 Found: 519.0 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 166 | 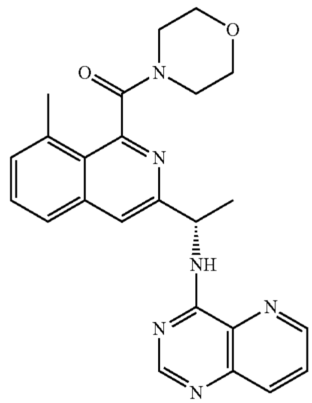 [SMILES: Cc1cccc2cc([C@H](C)Nc3ncnc4cccnc34)nc(C(=O)N3CCOCC3)c12] | ++++ | +++ | ++ | ++ | ++++ | Calcd: 428.20<br>Found: 429.2<br>[M + H]$^+$ |
| 167 | 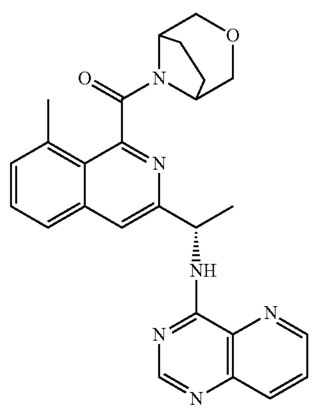 [SMILES: Cc1cccc2cc([C@H](C)Nc3ncnc4cccnc34)nc(C(=O)N3C4CCC3COC4)c12] | ++++ | +++ | ++ | ++ | ++++ | Calcd: 454.21<br>Found: 455.2<br>[M + H]$^+$ |
| 170 | 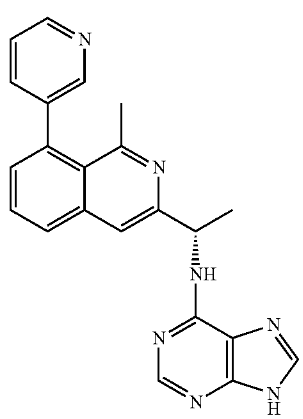 [SMILES: Cc1nc([C@H](C)Nc2ncnc3[nH]cnc23)cc2cccc(-c3cccnc3)c12] | ++++ | ++ | + | + | | Calcd: 381.17<br>Found: 382.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 177 | 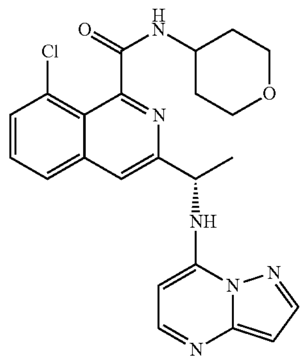 [SMILES: C[C@H](Nc1ccnc2ccnn12)c1cc2cccc(Cl)c2c(C(=O)NC2CCOCC2)n1] | ++++ | + | + | + | ++++ | Calcd: 450.16<br>Found: 451.2<br>[M + H]$^+$ |
| 180 | 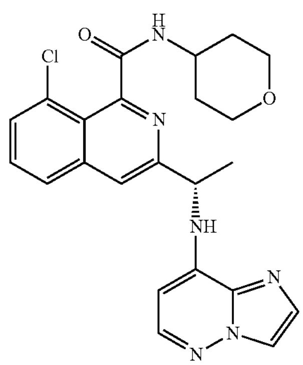 [SMILES: C[C@H](Nc1ccnn2ccnc12)c1cc2cccc(Cl)c2c(C(=O)NC2CCOCC2)n1] | ++++ | + | + | + | ++++ | Calcd: 450.16<br>Found: 451.0<br>[M + H]$^+$ |
| 182 | 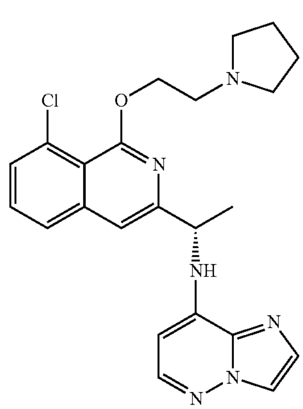 [SMILES: C[C@H](Nc1ccnn2ccnc12)c1cc2cccc(Cl)c2c(OCCN2CCCC2)n1] | ++++ | + | + | + | +++ | Calcd: 436.18<br>Found: 437.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 173 | 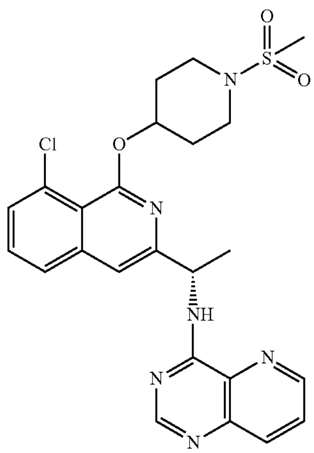 [SMILES: C[C@H](Nc1ncnc2cccnc12)c1cc2cccc(Cl)c2c(OC2CCN(S(C)(=O)=O)CC2)n1] | ++++ | ++ | + | ++ | +++ | Calcd: 512.14 Found: 513.2 [M + H]$^+$ |
| 174 | 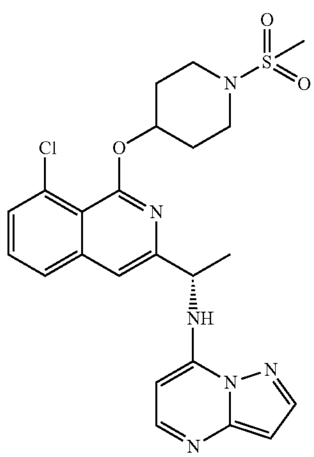 [SMILES: C[C@H](Nc1ccnc2ccnn12)c1cc2cccc(Cl)c2c(OC2CCN(S(C)(=O)=O)CC2)n1] | +++ | + | + | ++ | | Calcd: 500.14 Found: 501.0 [M + H]$^+$ |
| 176 | 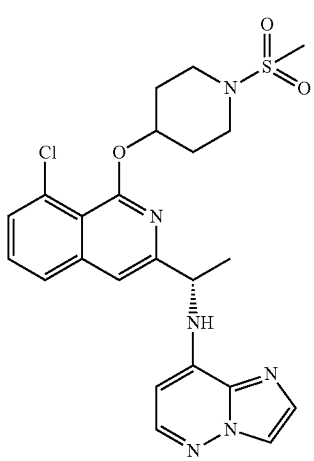 [SMILES: C[C@H](Nc1ccnn2ccnc12)c1cc2cccc(Cl)c2c(OC2CCN(S(C)(=O)=O)CC2)n1] | ++++ | ++ | + | ++ | +++ | Calcd: 500.14 Found: 501.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 171 | 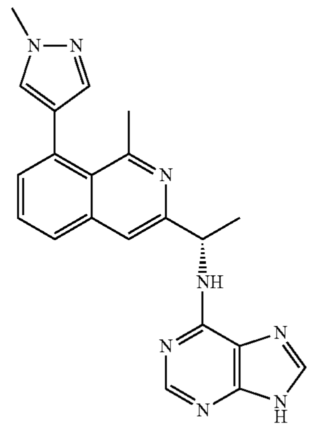 [SMILES: Cc1nc([C@H](C)Nc2ncnc3[nH]cnc23)cc2cccc(-c3cnn(C)c3)c12] | ++++ | ++ | ++ | + | | Calcd: 384.18 Found: 385.2 [M + H]$^+$ |
| 187 | 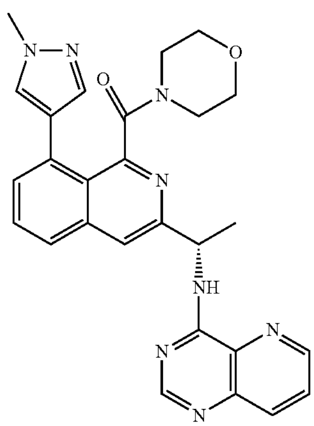 [SMILES: C[C@H](Nc1ncnc2cccnc12)c1cc2cccc(-c3cnn(C)c3)c2c(C(=O)N2CCOCC2)n1] | +++ | ++ | ++ | + | | Calcd: 494.22 Found: 495.2 [M + H]$^+$ |
| 185 | 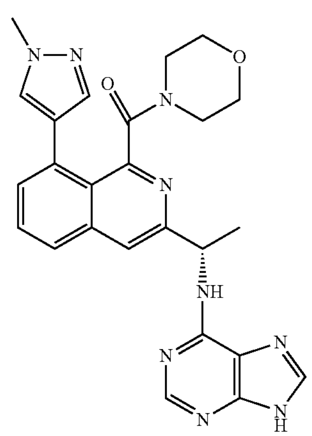 [SMILES: C[C@H](Nc1ncnc2[nH]cnc12)c1cc2cccc(-c3cnn(C)c3)c2c(C(=O)N2CCOCC2)n1] | ++++ | ++ | + | + | ++++ | Calcd: 483.21 Found: 484.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 188 | 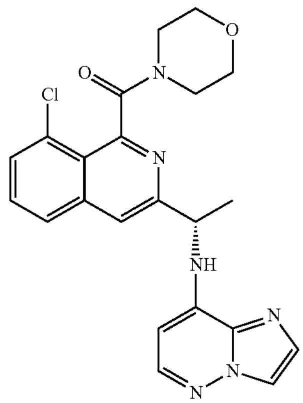 [SMILES: C[C@H](Nc1ccnn2ccnc12)c1cc2cccc(Cl)c2c(C(=O)N2CCOCC2)n1] | ++++ | +++ | ++ | +++ | ++++ | Calcd: 436.14 Found: 437.2 [M + H]$^+$ |
| 193 | 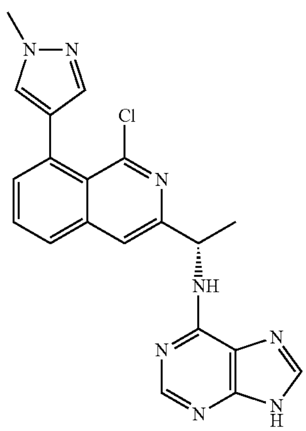 [SMILES: C[C@H](Nc1ncnc2[nH]cnc12)c1cc2cccc(-c3cnn(C)c3)c2c(Cl)n1] | ++++ | +++ | + | + | | Calcd: 404.13 Found: 405.2 [M + H]$^+$ |
| 192 | 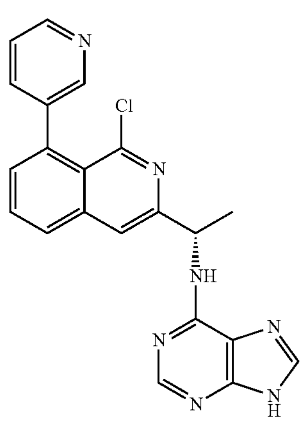 [SMILES: C[C@H](Nc1ncnc2[nH]cnc12)c1cc2cccc(-c3cccnc3)c2c(Cl)n1] | ++++ | +++ | + | + | +++ | Calcd: 401.12 Found: 402.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 198 | 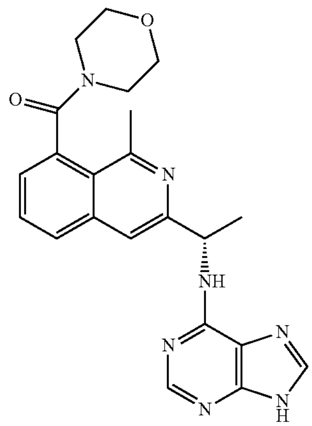 [SMILES: Cc1nc([C@H](C)Nc2ncnc3[nH]cnc23)cc2cccc(C(=O)N3CCOCC3)c12] | +++ | + | + | + | | Calcd: 417.19 Found: 418.2 [M + H]$^+$ |
| 200 | 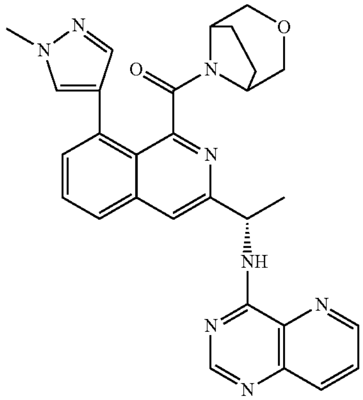 [SMILES: C[C@H](Nc1ncnc2cccnc12)c1cc2cccc(-c3cnn(C)c3)c2c(C(=O)N2C3CCC2COC3)n1] | +++ | + | + | + | | Calcd: 520.23 Found: 521.2 [M + H]$^+$ |
| 189 | 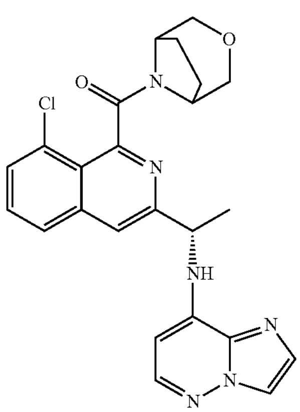 [SMILES: C[C@H](Nc1ccnn2ccnc12)c1cc2cccc(Cl)c2c(C(=O)N2C3CCC2COC3)n1] | ++++ | ++ | + | ++ | ++++ | Calcd: 462.16 Found: 463.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 201 | 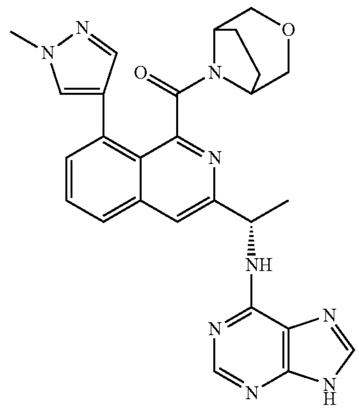 [SMILES: C[C@H](Nc1ncnc2[nH]cnc12)c1cc2cccc(-c3cnn(C)c3)c2c(C(=O)N2C3CCC2COC3)n1] | ++++ | +++ | + | + | | Calcd: 509.23 Found: 510.2 [M + H]$^+$ |
| 199 | 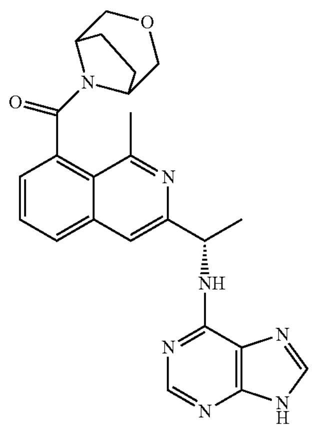 [SMILES: Cc1nc([C@H](C)Nc2ncnc3[nH]cnc23)cc2cccc(C(=O)N3C4CCC3COC4)c12] | ++ | + | + | + | | Calcd: 443.21 Found: 444.2 [M + H]$^+$ |
| 203 | 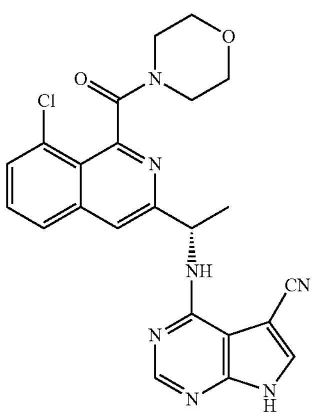 [SMILES: C[C@H](Nc1ncnc2[nH]cc(C#N)c12)c1cc2cccc(Cl)c2c(C(=O)N2CCOCC2)n1] | ++++ | +++ | ++ | ++ | | Calcd: 461.14 Found: 462.0 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 204 | 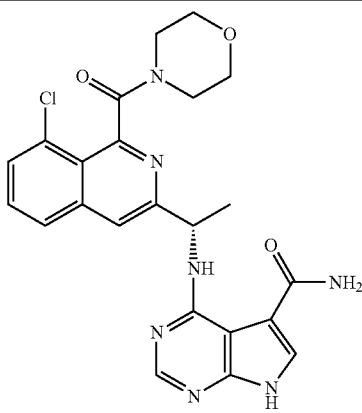 | ++++ | ++++ | ++ | ++ | ++++ | Calcd: 479.15<br>Found: 480.2<br>[M + H]$^+$ |
| 205 | 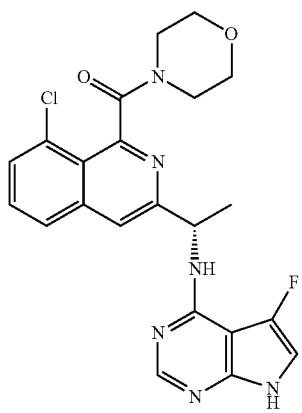 [SMILES: C[C@H](Nc1ncnc2[nH]cc(F)c12)c1cc2cccc(Cl)c2c(C(=O)N2CCOCC2)n1] | ++++ | +++ | ++ | ++ | | Calcd: 454.13<br>Found: 455.2<br>[M + H]$^+$ |
| 202 | 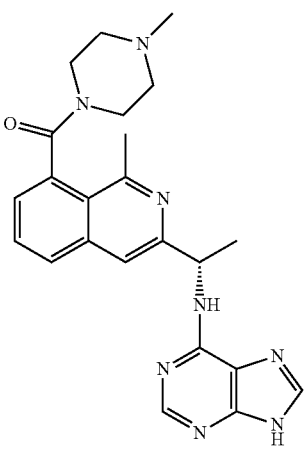 [SMILES: Cc1nc([C@H](C)Nc2ncnc3[nH]cnc23)cc2cccc(C(=O)N3CCN(C)CC3)c12] | + | + | + | + | | Calcd: 430.22<br>Found: 431.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 206 | 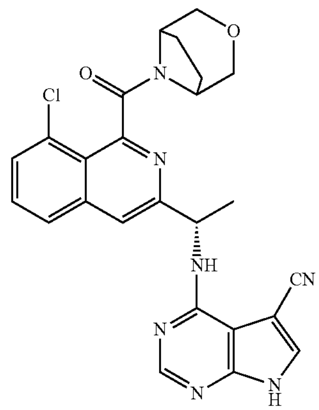 [SMILES: C[C@H](Nc1ncnc2[nH]cc(C#N)c12)c1cc2cccc(Cl)c2c(C(=O)N2C3CCC2COC3)n1] | ++++ | ++ | + | ++ | | Calcd: 487.15 Found: 488.2 [M + H]$^+$ |
| 207 | 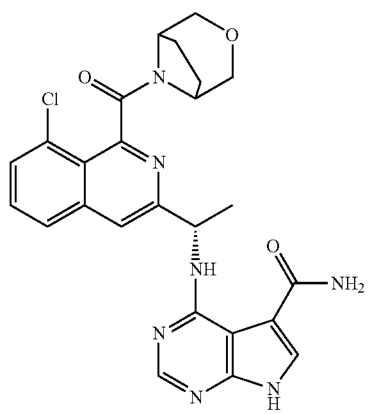 [SMILES: C[C@H](Nc1ncnc2[nH]cc(C(N)=O)c12)c1cc2cccc(Cl)c2c(C(=O)N2C3CCC2COC3)n1] | ++++ | ++++ | ++ | ++ | ++++ | Calcd: 505.15 Found: 506.2 [M + H]$^+$ |
| 208 | 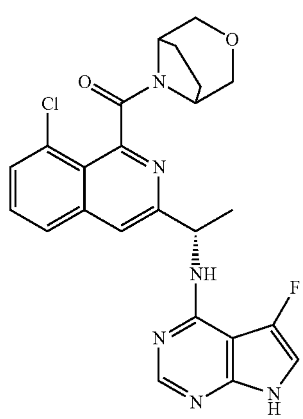 [SMILES: C[C@H](Nc1ncnc2[nH]cc(F)c12)c1cc2cccc(Cl)c2c(C(=O)N2C3CCC2COC3)n1] | ++++ | +++ | ++ | ++ | ++++ | Calcd: 480.15 Found: 481.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 209 | 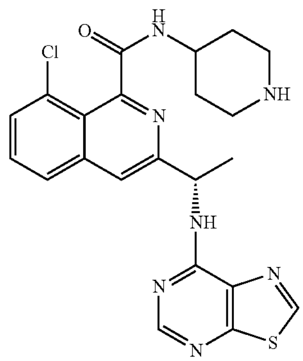 [SMILES: C[C@H](Nc1ncnc2scnc12)c1cc2cccc(Cl)c2c(C(=O)NC2CCNCC2)n1] | ++++ | + | ++ | + | | Calcd: 467.1 Found: 468.2 [M + H]$^+$ |
| 210 | 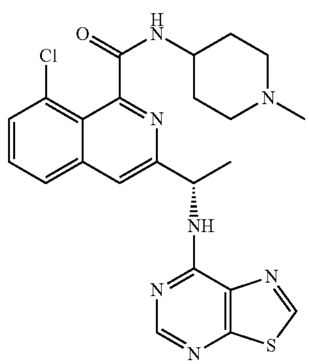 [SMILES: C[C@H](Nc1ncnc2scnc12)c1cc2cccc(Cl)c2c(C(=O)NC2CCN(C)CC2)n1] | ++++ | + | + | + | | Calcd: 481.2 Found: 482.2 [M + H]$^+$ |
| 211 | 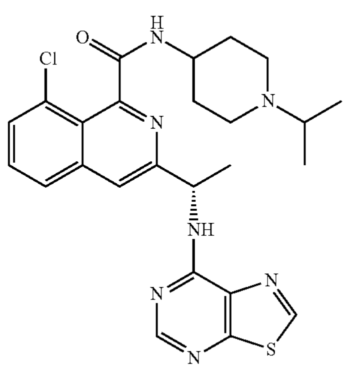 [SMILES: CC(C)N1CCC(NC(=O)c2nc([C@H](C)Nc3ncnc4scnc34)cc3cccc(Cl)c23)CC1] | +++ | + | + | + | | Calcd: 509.2 Found: 510.2 [M + H]$^+$ |
| 212 | 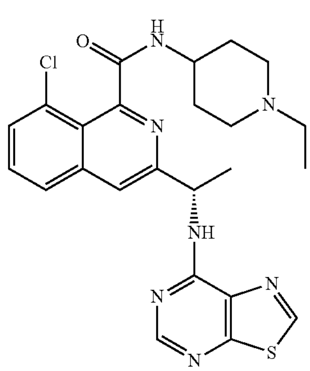 [SMILES: CCN1CCC(NC(=O)c2nc([C@H](C)Nc3ncnc4scnc34)cc3cccc(Cl)c23)CC1] | ++++ | ++ | ++ | ++ | ++++ | Calcd: 495.2 Found: 496.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 213 | 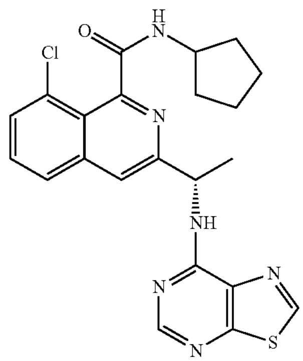 [SMILES: C[C@H](Nc1ncnc2scnc12)c1cc2cccc(Cl)c2c(C(=O)NC2CCCC2)n1] | ++++ | ++ | ++ | + | ++++ | Calcd: 452.1<br>Found: 453.0<br>[M + H]$^+$ |
| 214 | 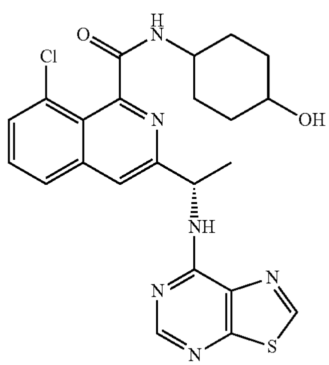 [SMILES: C[C@H](Nc1ncnc2scnc12)c1cc2cccc(Cl)c2c(C(=O)NC2CCC(O)CC2)n1] | ++++ | ++ | ++ | + | ++++ | Calcd: 482.1<br>Found: 483.2<br>[M + H]$^+$ |
| 215 | 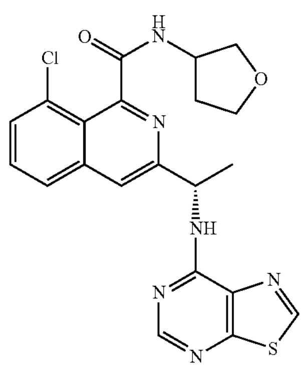 [SMILES: C[C@H](Nc1ncnc2scnc12)c1cc2cccc(Cl)c2c(C(=O)NC2CCOC2)n1] | ++++ | ++ | + | + | | Calcd: 454.1<br>Found: 455.0<br>[M + H]$^+$ |
| 216 | 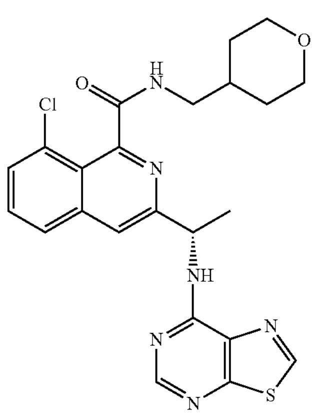 [SMILES: C[C@H](Nc1ncnc2scnc12)c1cc2cccc(Cl)c2c(C(=O)NCC2CCOCC2)n1] | +++ | + | + | + | | Calcd: 482.1<br>Found: 483.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 217 | 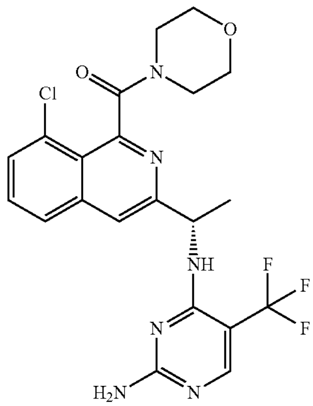 [SMILES: C[C@H](Nc1nc(N)ncc1C(F)(F)F)c1cc2cccc(Cl)c2c(C(=O)N2CCOCC2)n1] | +++ | ++ | + | + | | Calcd: 480.1 Found: 481.2 [M + H]$^+$ |
| 238 | 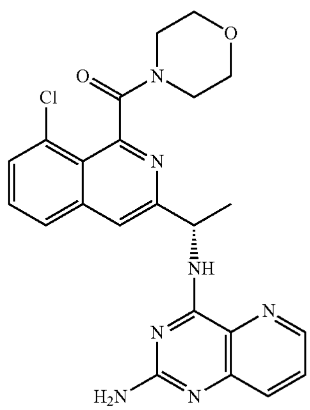 [SMILES: C[C@H](Nc1nc(N)nc2cccnc12)c1cc2cccc(Cl)c2c(C(=O)N2CCOCC2)n1] | ++++ | ++++ | + | ++ | ++++ | Calcd: 463.1 Found: 464.2 [M + H]$^+$ |
| 218 | 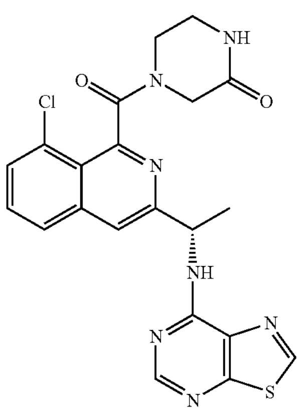 [SMILES: C[C@H](Nc1ncnc2scnc12)c1cc2cccc(Cl)c2c(C(=O)N2CCNC(=O)C2)n1] | ++++ | +++ | + | ++ | | Calcd: 467.1 Found: 468.0 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 219 | 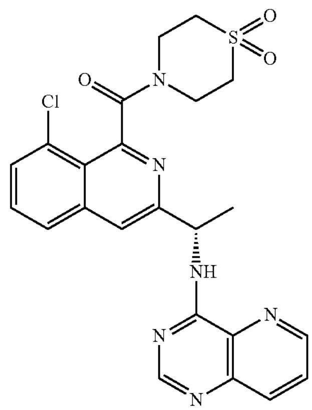 [SMILES: C[C@H](Nc1ncnc2cccnc12)c1cc2cccc(Cl)c2c(C(=O)N2CCS(=O)(=O)CC2)n1] | +++ | +++ | + | + | | Calcd: 496.1 Found: 497.0 [M + H]$^+$ |
| 220 | 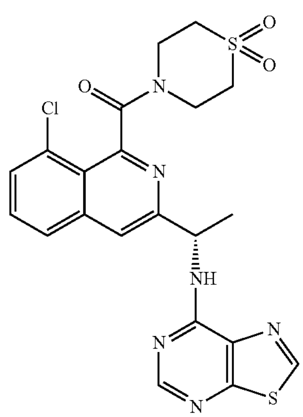 [SMILES: C[C@H](Nc1ncnc2scnc12)c1cc2cccc(Cl)c2c(C(=O)N2CCS(=O)(=O)CC2)n1] | ++++ | +++ | + | ++ | ++++ | Calcd: 502.1 Found: 503.0 [M + H]$^+$ |
| 221 | 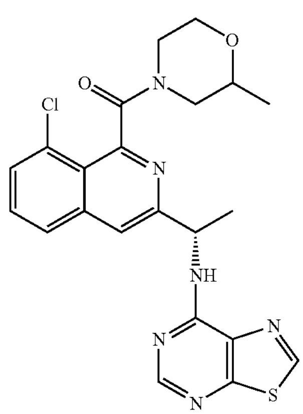 [SMILES: CC1CN(C(=O)c2nc([C@H](C)Nc3ncnc4scnc34)cc3cccc(Cl)c23)CCO1] | ++++ | +++ | + | + | | Calcd: 468.1 Found: 469.0 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 222 | 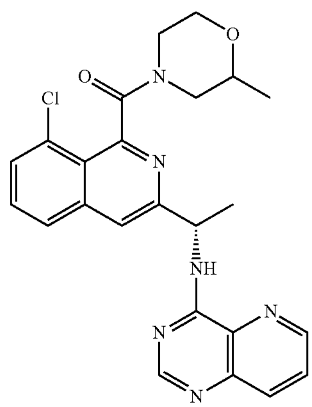 [SMILES: CC1CN(C(=O)c2nc([C@H](C)Nc3ncnc4cccnc34)cc3cccc(Cl)c23)CCO1] | +++ | +++ | ++ | + | | Calcd: 462.2<br>Found: 463.0<br>[M + H]$^+$ |
| 223 | 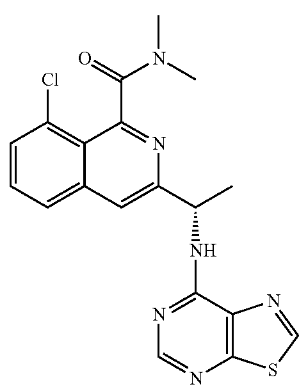 [SMILES: C[C@H](Nc1ncnc2scnc12)c1cc2cccc(Cl)c2c(C(=O)N(C)C)n1] | +++ | +++ | + | ++ | | Calcd: 412.1<br>Found: 413.0<br>[M + H]$^+$ |
| 224 | 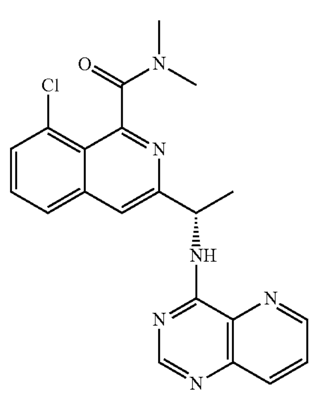 [SMILES: C[C@H](Nc1ncnc2cccnc12)c1cc2cccc(Cl)c2c(C(=O)N(C)C)n1] | ++ | +++ | + | ++ | | Calcd: 406.1<br>Found: 407.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 225 | 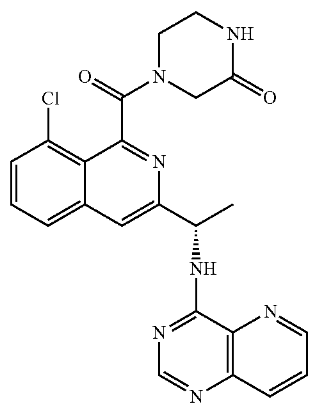 [SMILES: C[C@H](Nc1ncnc2cccnc12)c1cc2cccc(Cl)c2c(C(=O)N2CCNC(=O)C2)n1] | +++ | +++ | ++ | + | | Calcd: 461.1 Found: 462.2 [M + H]$^+$ |
| 226 | 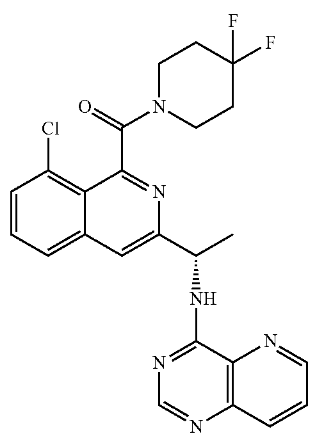 [SMILES: C[C@H](Nc1ncnc2cccnc12)c1cc2cccc(Cl)c2c(C(=O)N2CCC(F)(F)CC2)n1] | +++ | ++ | + | + | | Calcd: 482.1 Found: 483.2 [M + H]$^+$ |
| 227 | 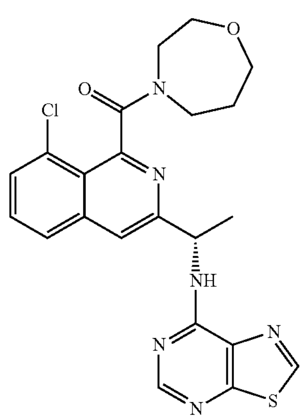 [SMILES: C[C@H](Nc1ncnc2scnc12)c1cc2cccc(Cl)c2c(C(=O)N2CCCOCC2)n1] | ++++ | ++ | ++ | ++ | | Calcd: 468.1 Found: 469.0 [M + H]$^+$ |

… TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 228 | 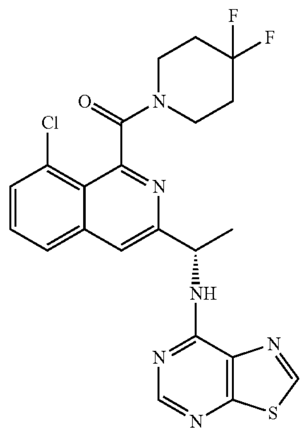 [SMILES: C[C@H](Nc1ncnc2scnc12)c1cc2cccc(Cl)c2c(C(=O)N2CCC(F)(F)CC2)n1] | ++++ | ++ | ++ | ++ | ++++ | Calcd: 488.1<br>Found: 489.0<br>[M + H]$^+$ |
| 229 | 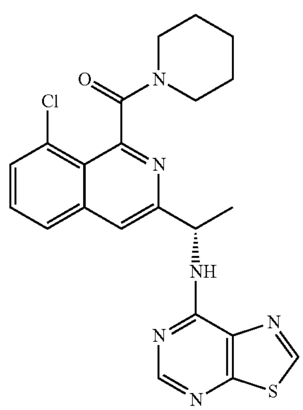 [SMILES: C[C@H](Nc1ncnc2scnc12)c1cc2cccc(Cl)c2c(C(=O)N2CCCCC2)n1] | ++++ | ++ | ++ | +++ | | Calcd: 452.1<br>Found: 453.0<br>[M + H]$^+$ |
| 230 | 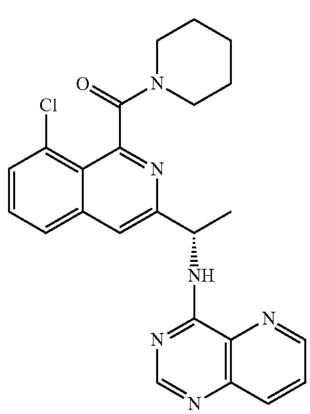 [SMILES: C[C@H](Nc1ncnc2cccnc12)c1cc2cccc(Cl)c2c(C(=O)N2CCCCC2)n1] | +++ | +++ | ++ | + | | Calcd: 446.2<br>Found: 447.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 231 | 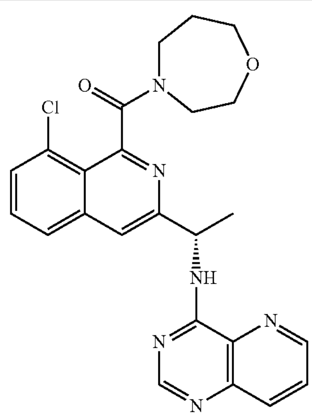 [SMILES: C[C@H](Nc1ncnc2cccnc12)c1cc2cccc(Cl)c2c(C(=O)N2CCCOCC2)n1] | +++ | ++ | ++ | + | | Calcd: 462.2 Found: 463.2 [M + H]$^+$ |
| 232 | 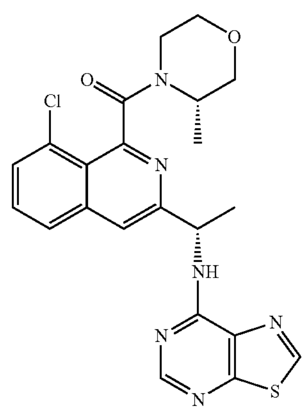 [SMILES: C[C@H](Nc1ncnc2scnc12)c1cc2cccc(Cl)c2c(C(=O)N2CCOC[C@@H]2C)n1] | ++++ | ++ | ++ | ++ | ++++ | Calcd: 468.1 Found: 469.0 [M + H]$^+$ |
| 233 | 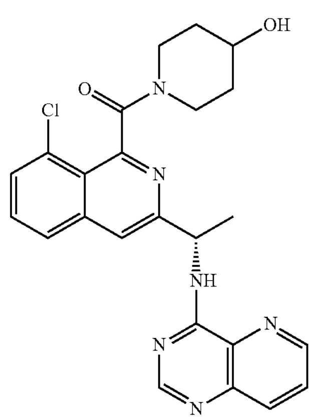 [SMILES: C[C@H](Nc1ncnc2cccnc12)c1cc2cccc(Cl)c2c(C(=O)N2CCC(O)CC2)n1] | +++ | ++ | ++ | + | | Calcd: 462.2 Found: 463.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 234 | 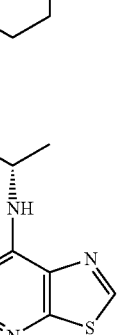 | ++++ | ++ | ++ | ++ | ++++ | Calcd: 468.1 Found: 469.0 [M + H]$^+$ |
| 244 | 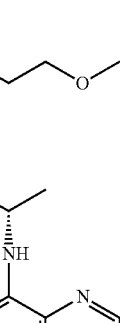 | +++ | ++ | + | + | | |
| 245 | 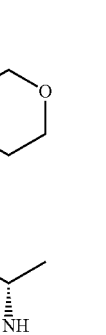 | +++ | +++ | + | + | | |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 246 | 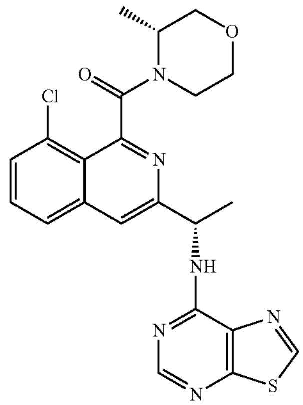 [SMILES: C[C@H](Nc1ncnc2scnc12)c1cc2cccc(Cl)c2c(C(=O)N2CCOC[C@H]2C)n1] | +++ | ++ | ++ | ++ | | |
| 247 | 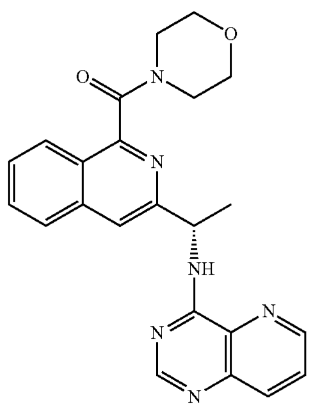 [SMILES: C[C@H](Nc1ncnc2cccnc12)c1cc2ccccc2c(C(=O)N2CCOCC2)n1] | ++++ | + | + | + | +++ | Calcd: 414.2<br>Found: 415.2<br>[M + H]$^+$ |
| 248 | 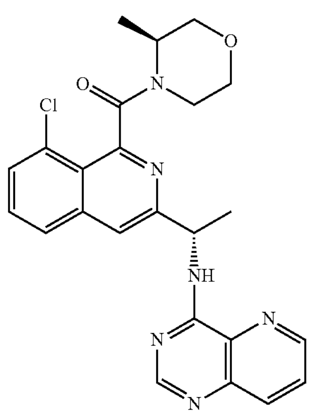 [SMILES: C[C@H](Nc1ncnc2cccnc12)c1cc2cccc(Cl)c2c(C(=O)N2CCOC[C@@H]2C)n1] | ++++ | +++ | ++ | ++ | ++++ | Calcd: 462.2<br>Found: 463.2<br>[M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 249 | 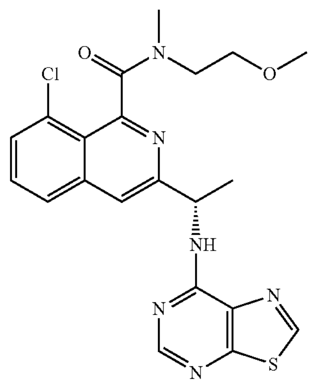 [SMILES: COCCN(C)C(=O)c1nc([C@H](C)Nc2ncnc3scnc23)cc2cccc(Cl)c12] | ++++ | +++ | ++ | ++ | | Calcd: 456.1<br>Found: 457.0<br>[M + H]$^+$ |
| 250 | 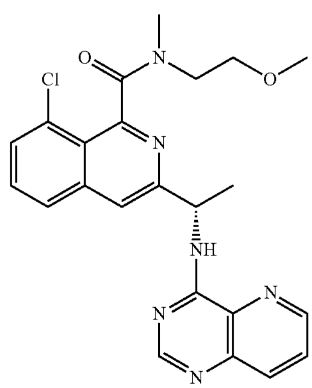 [SMILES: COCCN(C)C(=O)c1nc([C@H](C)Nc2ncnc3cccnc23)cc2cccc(Cl)c12] | +++ | ++ | + | + | | Calcd: 450.2<br>Found: [M + H]$^+$ |
| 251 | 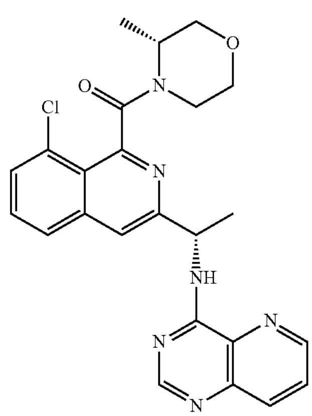 [SMILES: C[C@H](Nc1ncnc2cccnc12)c1cc2cccc(Cl)c2c(C(=O)N2CCOC[C@H]2C)n1] | +++ | +++ | + | + | | Calcd: 462.2<br>Found: [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 252 | 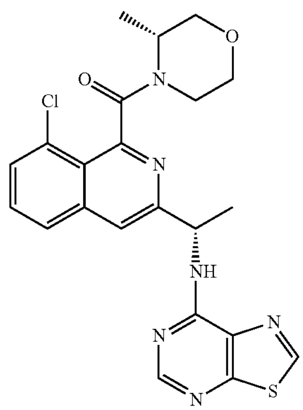 [SMILES: C[C@H](Nc1ncnc2scnc12)c1cc2cccc(Cl)c2c(C(=O)N2CCOC[C@H]2C)n1] | +++ | ++ | ++ | ++ | | Calcd: 468.1 Found: [M + H]$^+$ |
| 253 | 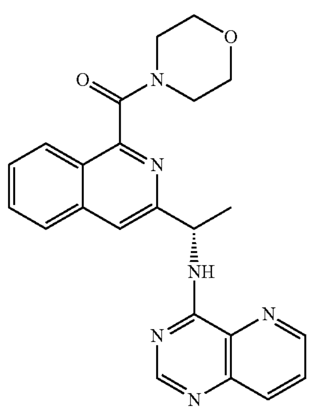 [SMILES: C[C@H](Nc1ncnc2cccnc12)c1cc2ccccc2c(C(=O)N2CCOCC2)n1] | ++++ | + | + | + | +++ | Calcd: 414.2 Found: 415.2 [M + H]$^+$ |
| 254 | 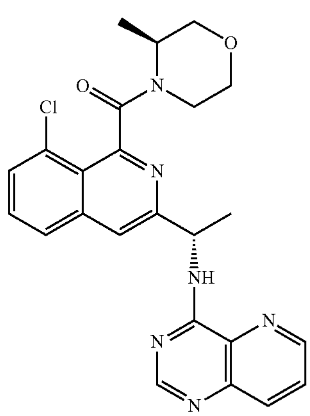 [SMILES: C[C@H](Nc1ncnc2cccnc12)c1cc2cccc(Cl)c2c(C(=O)N2CCOC[C@@H]2C)n1] | ++++ | +++ | ++ | ++ | ++++ | Calcd: 462.2 Found: 463.2 [M + H]$^+$ |

TABLE 3-continued

In Vitro IC$_{50}$ data for selected compounds. The Biological Activity Assessment at the end of Table 3 was used to determine the activites reported herein. The following symbols are used: + (greater than 10 microMolar), ++ (less than 10 microMolar), +++ (less than 1 microMolar), and ++++ (less than 100 nM).

| Compound | Structure | PI3K δ IC$_{50}$ (nM) | PI3K γ IC$_{50}$ (nM) | PI3K α IC$_{50}$ (nM) | PI3K β IC$_{50}$ (nM) | B cell prolif. IC$_{50}$ (nM) | Mass Characterization |
|---|---|---|---|---|---|---|---|
| 255 | 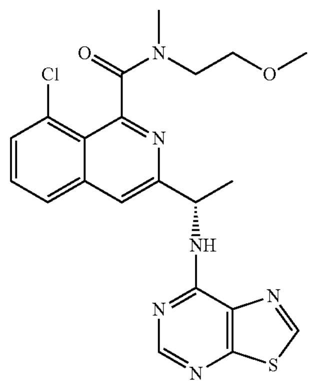 [SMILES: COCCN(C)C(=O)c1nc([C@H](C)Nc2ncnc3scnc23)cc2cccc(Cl)c12] | | | | | | Calcd: 456.1<br>Found: 457.0<br>[M + H]$^+$ |

Biological Activity Assessment

A PI3 Kinase HTRF® assay kit (cat No. 33-016) purchased from Millipore Corporation was used to screen compounds disclosed herein. This assay used specific, high affinity binding of the GRP1 pleckstrin homology (PH) domain to PIP3, the product of a Class 1A or 1B PI3 Kinase acting on its physiological substrate PIP2. During the detection phase of the assay, a complex was generated between the GST-tagged PH domain and biotinylated short chain PIP3. The biotinylated PIP3 and the GST-tagged PH domain recruited fluorophores (Streptavidin-Allophycocyanin and Europium-labeled anti-GST respectively) to form the fluorescence resonance energy transfer (FRET) architecture, generating a stable time-resolved FRET signal. The FRET complex was disrupted in a competitive manner by non-biotinylated PIP3, a product formed in the PI3 Kinase assay.

PI3 Kinase α, β, γ and δ activity was assayed using the PI3 Kinase HTRF® assay kit (catalogue No. 33-016) purchased from Millipore Corporation. Purified recombinant PI3Kα (catalogue No. 14-602-K), PI3Kβ (catalogue No. 14-603-K), PI3Kγ (catalogue No. 14-558-K) and PI3Kδ (catalogue No. 14-604-K) were obtained from Millipore Corporation. Purified recombinant PI3K enzyme was used to catalyze the phosphorylation of phosphatidylinositol 4,5-bisphosphate (PIP2 at 10 μM) to phosphatidylinositol 3,4,5-trisphosphate (PIP3) in the presence of 10 μM ATP. The assay was carried out in 384-well format and detected using a Perkin Elmer EnVision Xcite Multilabel Reader. Emission ratios were converted into percent inhibitions and imported into GraphPad Prism software. The concentration necessary to achieve inhibition of enzyme activity by 50% (IC$_{50}$) was calculated using concentrations ranging from 20 μM to 0.1 nM (12-point curve). IC$_{50}$ values were determined using a nonlinear regression model available in GraphPad Prism 5.

Example 159

Expression and Inhibition Assays of p110α/p85α, p110β/p85α, p110δ/p85α, and p110γ

Class I PI3 Ks can be either purchased (p110α/p85α, p110β/p85α, p110δ/p85α from Upstate, and p110γ from Sigma) or expressed as previously described (Knight et al., 2004). IC50 values are measured using either a standard TLC assay for lipid kinase activity (described below) or a high-throughput membrane capture assay. Kinase reactions are performed by preparing a reaction mixture containing kinase, inhibitor (2% DMSO final concentration), buffer (25 mM HEPES, pH 7.4, 10 mM MgCl2), and freshly sonicated phosphatidylinositol (100 μg/ml). Reactions are initiated by the addition of ATP containing 10 μCi of γ-32P-ATP to a final concentration 10 or 100 μM and allowed to proceed for 5 minutes at room temperature. For TLC analysis, reactions are then terminated by the addition of 105 μl 1N HCl followed by 160 μl CHCl$_3$:MeOH (1:1). The biphasic mixture is vortexed, briefly centrifuged, and the organic phase is transferred to a new tube using a gel loading pipette tip precoated with CHCl$_3$. This extract is spotted on TLC plates and developed for 3-4 hours in a 65:35 solution of n-propanol:1 M acetic acid. The TLC plates are then dried, exposed to a phosphorimager screen (Storm, Amersham), and quantitated. For each compound, kinase activity is measured at 10-12 inhibitor concentrations representing two-fold dilutions from the highest concentration tested (typically, 200 μM). For compounds showing significant activity, IC$_{50}$ determinations are repeated two to four times, and the reported value is the average of these independent measurements.

Other commercial kits or systems for assaying PI3 K activities are available. The commercially available kits or systems can be used to screen for inhibitors and/or agonists of PI3 Ks including but not limited to PI 3-Kinase α, β, δ and γ. And exemplary system is PI 3-Kinase (human) HTRF™ Assay from Upstate. The assay can be carried out according to the procedures suggested by the manufacturer. Briefly, the assay is a time resolved FRET assay that indirectly measures PIP3 product formed by the activity of a PI3 K. The kinase reaction is performed in a microtitre plate (e.g., a 384 well microtitre plate). The total reaction volume is approximately 20 μl per well. In the first step, each well receives 2 μl of test compound in 20% dimethylsulphoxide resulting in a 2% DMSO final concentration. Next, approximately 14.5 μl of a kinase/PIP2 mixture (diluted in 1× reaction buffer) is added per well for a final concentration of 0.25-0.3 ug/ml kinase and 10 uM PIP2. The plate is sealed and incubated for 15 minutes at room temperature. To start the reaction, 3.5 µl of ATP (diluted in 1× reaction buffer) is added per well for a final concentration of 10 µM ATP. The plate is sealed and incubated for 1 hour at room temperature. The reaction is stopped by adding 5 ul of Stop Solution per well and then 5 µl of Detection Mix is added per well. The plate is sealed, incubated for 1 hour at room temperature, and then read on an appropriate plate reader. Data is analyzed and $IC_{50}$s are generated using GraphPad Prism 5.

Example 160

Expression and Inhibition Assays of Abl

The cross-activity or lack thereof of one or more compounds described herein against Abl kinase can be measured according to any procedures known in the art or methods disclosed below. For example, the compounds described herein can be assayed in triplicate against recombinant full-length Abl or Abl (T315I) (Upstate) in an assay containing 25 mM HEPES, pH 7.4, 10 mM $MgCl_2$, 200 µM ATP (2.5 µCi of γ-32P-ATP), and 0.5 mg/mL BSA. The optimized Abl peptide substrate EAIYAAPFAKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 161

Expression and Inhibition Assays of Hck

The cross-activity or lack thereof of one or more compounds as described herein against Hck kinase can be measured according to any procedures known in the art or methods disclosed below. The compounds described herein can be assayed in triplicate against recombinant full-length Hck in an assay containing 25 mM HEPES, pH 7.4, 10 mM $MgCl_2$, 200 µM ATP (2.5 µCi of γ-32P-ATP), and 0.5 mg/mL BSA. The optimized Src family kinase peptide substrate EIYGEFKKK is used as phosphoacceptor (200 µM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 162

Expression and Inhibition Assays of Inulsin Receptor (1R)

The cross-activity or lack thereof of one or more compounds as described herein against IR receptor kinase can be measured according to any procedures known in the art or methods disclosed below. The compounds described herein can be assayed in triplicate against recombinant insulin receptor kinase domain (Upstate) in an assay containing 25 mM HEPES, pH 7.4, 10 mM $MgCl_2$, 10 mM $MnCl_2$, 200 µM ATP (2.5 µCi of γ-32P-ATP), and 0.5 mg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 163

Expression and Inhibition Assays of Src

The cross-activity or lack thereof of one or more compounds as described herein against Src kinase can be measured according to any procedures known in the art or methods disclosed below. The compounds described herein can be assayed in triplicate against recombinant full-length Src or Src (T338I) in an assay containing 25 mM HEPES, pH 7.4, 10 mM $MgCl_2$, 200 µM ATP (2.5 µCi of γ-32P-ATP), and 0.5 mg/mL BSA. The optimized Src family kinase peptide substrate EIYGEFKKK is used as phosphoacceptor (200 µM). Reactions are terminated by spotting onto phosphocellulose sheets, which are washed with 0.5% phosphoric acid (approximately 6 times, 5-10 minutes each). Sheets were dried and the transferred radioactivity quantitated by phosphorimaging.

Example 164

Expression and Inhibition Assays of DNA-PK (DNAK)

The cross-activity or lack thereof of one or more compounds as described herein against DNAK kinase can be measured according to any procedures known in the art. DNA-PK can be purchased from Promega and assayed using the DNA-PK Assay System (Promega) according to the manufacturer's instructions.

Example 165

Expression and Inhibition Assays of mTOR

The cross-activity or lack thereof of one or more compounds as described herein against mTor can be measured according to any procedures known in the art or methods disclosed below. The compounds described herein can be tested against recombinant mTOR (Invitrogen) in an assay containing 50 mM HEPES, pH 7.5, 1 mM EGTA, 10 mM $MgCl_2$, 2.5 mM, 0.01% Tween, 10 µM ATP (2.5 µCi of µ-32P-ATP), and 3 µg/mL BSA. Rat recombinant PHAS-1/4EBP1 (Calbiochem; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Other kits or systems for assaying mTOR activity are commercially available. For instance, one can use Invitrogen's LanthaScreen™ Kinase assay to test the inhibitors of mTOR disclosed herein. This assay is a time resolved FRET platform that measures the phosphorylation of GFP labeled 4EBP1 by mTOR kinase. The kinase reaction is performed in a white 384 well microtitre plate. The total reaction volume is 20 µl per well and the reaction buffer composition is 50 mM HEPES pH7.5, 0.01% Polysorbate 20, 1 mM EGTA, 10 mM $MnCl_2$, and 2 mM DTT. In the first step, each well receives 2 µl of test compound in 20% dimethylsulphoxide resulting in a 2% DMSO final concentration. Next, 8 ul of mTOR diluted in reaction buffer is added per well for a 60 ng/ml final concentration. To start the reaction, 10 ul of an ATP/GFP-4EBP1 mixture (diluted in reaction buffer) is added per well for a final concentration of 10 µM ATP and 0.5 uM GFP-4EBP1. The plate is sealed and incubated for 1 hour at room temperature. The reaction is stopped by adding 10 µl per well of a Tb-anti-pT46 4EBP1 antibody/EDTA mixture (diluted in TR-FRET buffer) for a final concentration of 1.3 nM antibody and 6.7 mM EDTA. The plate is sealed, incubated for 1 hour at room temperature, and then read on a plate reader set up for LanthaScreen™ TR-FRET. Data is analyzed and $IC_{50}$s are generated using GraphPad Prism 5.

Example 166

Expression and Inhibition Assays of Vascular Endothelial Growth Receptor

The cross-activity or lack thereof of one or more compounds as described herein against VEGF receptor can be measured according to any procedures known in the art or methods disclosed below. The compounds described herein can be tested against recombinant KDR receptor kinase domain (Invitrogen) in an assay containing 25 mM HEPES, pH 7.4, 10 mM $MgCl_2$, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 167

Expression and Inhibition Assays of Ephrin Receptor B4 (EphB4)

The cross-activity or lack thereof of one or more compounds as described herein against EphB4 can be measured according to any procedures known in the art or methods disclosed below. The compounds described herein can be tested against recombinant Ephrin receptor B4 kinase domain (Invitrogen) in an assay containing 25 mM HEPES, pH 7.4, 10 mM $MgCl_2$, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 168

Expression and Inhibition Assays of Epidermal Growth Factor Receptor (EGFR)

The cross-activity or lack thereof of one or more compounds as described herein against EGFR kinase can be measured according to any procedures known in the art or methods disclosed below. The compounds described herein can be tested against recombinant EGF receptor kinase domain (Invitrogen) in an assay containing 25 mM HEPES, pH 7.4, 10 mM $MgCl_2$, 0.1% BME, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 169

Expression and Inhibition Assays of KIT Assay

The cross-activity or lack thereof of one or more compounds as described herein against KIT kinase can be measured according to any procedures known in the art or methods disclosed below. The compounds described herein can be tested against recombinant KIT kinase domain (Invitrogen) in an assay containing 25 mM HEPES, pH 7.4, 10 mM $MgCl_2$, 1 mM DTT, 10 mM $MnCl_2$, 10 μM ATP (2.5 μCi of μ-32P-ATP), and 3 μg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 170

Expression and Inhibition Assays of RET

The cross-activity or lack thereof of one or more compounds as described herein against RET kinase can be measured according to any procedures known in the art or methods disclosed below. The compounds described herein can be tested against recombinant RET kinase domain (Invitrogen) in an assay containing 25 mM HEPES, pH 7.4, 10 mM $MgCl_2$, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 171

Expression and Inhibition Assays of Platelet Derived Growth Factor Receptor (PDGFR)

The cross-activity or lack thereof of one or more compounds as described herein against PDGFR kinase can be measured according to any procedures known in the art or methods disclosed below. The compounds described herein can be tested against recombinant PDG receptor kinase domain (Invitrogen) in an assay containing 25 mM HEPES, pH 7.4, 10 mM $MgCl_2$, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 172

Expression and Inhibition Assays of FMS-Related Tyrosine Kinase 3 (FLT-3)

The cross-activity or lack thereof of one or more compounds as described herein against FLT-3 kinase can be measured according to any procedures known in the art or methods disclosed below. The compounds described herein can be tested against recombinant FLT-3 kinase domain (Invitrogen) in an assay containing 25 mM HEPES, pH 7.4, 10 mM $MgCl_2$, 2.5 mM DTT, 10 μM ATP (2.5 μCi of μ-32P-ATP), and 3 μg/mL BSA. The optimized Abl peptide substrate EAIYAAPFAKKK is used as phosphoacceptor (200 μM). Reactions are terminated by spotting onto phosphocellulose sheets, which are washed with 0.5% phosphoric acid (approximately 6 times, 5-10 minutes each). Sheets are dried and the transferred radioactivity quantitated by phosphorimaging.

Example 173

Expression and Inhibition Assays of TEK Receptor Tyrosine Kinase (TIE2)

The cross-activity or lack thereof of one or more compounds as described herein against TIE2 kinase can be measured according to any procedures known in the art or methods disclosed below. The compounds described herein can be tested against recombinant TIE2 kinase domain (Invitrogen) in an assay containing 25 mM HEPES, pH 7.4, 10 mM $MgCl_2$, 2 mM DTT, 10 mM $MnCl_2$, 10 µM ATP (2.5 µCi of µ-32P-ATP), and 3 µg/mL BSA. Poly E-Y (Sigma; 2 mg/mL) is used as a substrate. Reactions are terminated by spotting onto nitrocellulose, which is washed with 1M NaCl/1% phosphoric acid (approximately 6 times, 5-10 minutes each). Sheets are dried and the transferred radioactivity quantitated by phosphorimaging.

Example 174

B Cell Activation and Proliferation Assay

The ability of one or more subject compounds to inhibit B cell activation and proliferation is determined according to standard procedures known in the art. For example, an in vitro cellular proliferation assay is established that measures the metabolic activity of live cells. The assay is performed in a 96 well microtiter plate using Alamar Blue reduction. Balb/c splenic B cells are purified over a Ficoll-Paque™ PLUS gradient followed by magnetic cell separation using a MACS B cell Isolation Kit (Miletenyi). Cells are plated in 90 ul at 50,000 cells/well in B Cell Media (RPMI+10% FBS+Penn/Strep+50 uM bME+5 mM HEPES). A compound disclosed herein is diluted in B Cell Media and added in a 10 µl volume. Plates are incubated for 30 min at 37 C and 5% $CO_2$ (0.2% DMSO final concentration). A 50 µl B cell stimulation cocktail is then added containing either 10 ug/ml LPS or 5 ug/ml F(ab')2 Donkey anti-mouse IgM plus 2 ng/ml recombinant mouse IL4 in B Cell Media. Plates are incubated for 72 hours at 37° C. and 5% $CO_2$. A volume of 15 µl of Alamar Blue reagent is added to each well and plates are incubated for 5 hours at 37 C and 5% $CO_2$. Alamar Blue fluoresce is read at 560Ex/590Em, and $IC_{50}$ or $EC_{50}$ values are calculated using GraphPad Prism 5.

Example 175

Tumor Cell Line Proliferation Assay

The ability of one or more compounds as disclosed herein to inhibit tumor cell line proliferation is determined according to standard procedures known in the art. For instance, an in vitro cellular proliferation assay can be performed to measure the metabolic activity of live cells. The assay is performed in a 96 well microtiter plate using Alamar Blue reduction. Human tumor cell lines are obtained from ATCC (e.g., MCF7, U-87 MG, MDA-MB-468, PC-3), grown to confluency in T75 flasks, trypsinized with 0.25% trypsin, washed one time with Tumor Cell Media (DMEM+10% FBS), and plated in 90 µl at 5,000 cells/well in Tumor Cell Media. A compound disclosed herein is diluted in Tumor Cell Media and added in a 10 µl volume. Plates are incubated for 72 hours at 37 C and 5% $CO_2$. A volume of 10 uL of Alamar Blue reagent is added to each well and plates are incubated for 3 hours at 37 C and 5% $CO_2$. Alamar Blue fluoresce is read at 560Ex/590Em, and $IC_{50}$ values are calculated using GraphPad Prism 5.

Example 176

Antitumor Activity in Vivo

The compounds described herein can be evaluated in a panel of human and murine tumor models.
Paclitaxel-Refractory Tumor Models
 1. Clinically-Derived Ovarian Carcinoma Model.
 This tumor model is established from a tumor biopsy of an ovarian cancer patient. Tumor biopsy is taken from the patient. The compounds described herein are administered to nude mice bearing staged tumors using an every 2 days×5 schedule.
 2. A2780Tax Human Ovarian Carcinoma Xenograft (Mutated Tubulin).
 A2780Tax is a paclitaxel-resistant human ovarian carcinoma model. It is derived from the sensitive parent A2780 line by co-incubation of cells with paclitaxel and verapamil, an MDR-reversal agent. Its resistance mechanism has been shown to be non-MDR related and is attributed to a mutation in the gene encoding the beta-tubulin protein. The compounds described herein can be administered to mice bearing staged tumors on an every 2 days×5 schedule.
 3. HCT116/VM46 Human Colon Carcinoma Xenograft (Multi-Drug Resistant).
 HCT116/VM46 is an MDR-resistant colon carcinoma developed from the sensitive HCT116 parent line. In vivo, grown in nude mice, HCT116/VM46 has consistently demonstrated high resistance to paclitaxel. The compounds described herein can be administered to mice bearing staged tumors on an every 2 days×5 schedule.
 4. M5076 Murine Sarcoma Model
 M5076 is a mouse fibrosarcoma that is inherently refractory to paclitaxel in vivo. The compounds described herein can be administered to mice bearing staged tumors on an every 2 days×5 schedule.

One or more compounds of the invention can be used in combination other therapeutic agents in vivo in the multidrug resistant human colon carcinoma xenografts HCT/VM46 or any other model known in the art including those described herein.

Example 177

Microsome Stability Assay

The stability of one or more compounds as disclosed herein is determined according to standard procedures known in the art. For example, stability of one or more subject compounds is established by an in vitro assay. In particular, an in vitro microsome stability assay is established that measures stability of one or more subject compounds when reacting with mouse, rat or human microsomes from liver. The microsome reaction with compounds is performed in a 1.5 mL Eppendorf tube. Each tube contains 0.1 µL of 10.0 mg/ml NADPH; 75 µL of 20.0 mg/ml mouse, rat or human liver microsome; 0.4 µL of 0.2 M phosphate buffer, and 425 µL of dd$H_2$O, Negative control (without NADPH) tube contains 75 µL of 20.0 mg/ml mouse, rat or human liver microsome; 0.4 µL of 0.2 M phosphate buffer, and 525 µL of dd$H_2$O. The reaction is started by adding 1.0 µL of 10.0 mM tested compound. The reaction tubes are incubated at 37° C. 100 µL sample is collected into new Eppendorf tube containing 300 µL cold methanol at 0, 5, 10, 15, 30 and 60 minutes of reaction. Samples are centrifuged at 15,000 rpm to remove protein. The supernatant of the centrifuged sample is transferred to new tube. Concentration of stable compound after reaction with microsome in the supernatant is measured by Liquid Chromatography/Mass Spectrometry (LC-MS).

Example 178

Plasma Stability Assay

The stability of one or more subject compounds in plasma is determined according to standard procedures known in the art. See, e.g., *Rapid Commun. Mass Spectrom.*, 10: 1019-1026. The following procedure is an HPLC-MS/MS assay using human plasma; other species including monkey, dog, rat, and mouse are also available. Frozen, heparinized human plasma is thawed in a cold water bath and spun for 10 minutes at 2000 rpm at 4° C. prior to use. A subject compound is added from a 400 µM stock solution to an aliquot of pre-warmed plasma to give a final assay volume of 400 µL (or 800 µL for half-life determination), containing 5 µM test compound and 0.5% DMSO. Reactions are incubated, with shaking, for 0 minutes and 60 minutes at 37° C., or for 0, 15, 30, 45 and 60 minutes at 37 C for half life determination. Reactions are stopped by transferring 50 µL of the incubation mixture to 200 µL of ice-cold acetonitrile and mixed by shaking for 5 minutes. The samples are centrifuged at 6000×g for 15 minutes at 4° C. and 120 µL of supernatant removed into clean tubes. The samples are then evaporated to dryness and submitted for analysis by HPLC-MS/MS.

In one embodiment, one or more control or reference compounds (5 µM) are tested simultaneously with the test compounds: one compound, propoxycaine, with low plasma stability and another compound, propantheline, with intermediate plasma stability.

Samples are reconstituted in acetonitrile/methanol/water (1/1/2, v/v/v) and analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 60 minutes relative to the amount remaining at time zero, expressed as percent, is reported as plasma stability. In case of half-life determination, the half-life is estimated from the slope of the initial linear range of the logarithmic curve of compound remaining (%) vs. time, assuming first order kinetics.

Example 179

Chemical Stability

The chemical stability of one or more compounds as disclosed herein is determined according to standard procedures known in the art. The following details an exemplary procedure for ascertaining chemical stability of a disclosed compound. The default buffer used for the chemical stability assay is phosphate-buffered saline (PBS) at pH 7.4; other suitable buffers can be used. A compound is added from a 100 µM stock solution to an aliquot of PBS (in duplicate) to give a final assay volume of 400 µL, containing 5 µM test compound and 1% DMSO (for half-life determination a total sample volume of 700 µL is prepared). Reactions are incubated, with shaking, for 0 minutes and 24 hours at 37° C.; for half-life determination samples are incubated for 0, 2, 4, 6, and 24 hours. Reactions are stopped by adding immediately 100 µL of the incubation mixture to 100 µL of acetonitrile and vortexing for 5 minutes. The samples are then stored at −20° C. until analysis by HPLC-MS/MS. Where desired, a control compound or a reference compound such as chlorambucil (5 µM) is tested simultaneously with a subject compound of interest, as this compound is largely hydrolyzed over the course of 24 hours. Samples are analyzed via (RP)HPLC-MS/MS using selected reaction monitoring (SRM). The HPLC conditions consist of a binary LC pump with autosampler, a mixed-mode, C12, 2×20 mm column, and a gradient program. Peak areas corresponding to the analytes are recorded by HPLC-MS/MS. The ratio of the parent compound remaining after 24 hours relative to the amount remaining at time zero, expressed as percent, is reported as chemical stability. In case of half-life determination, the half-life is estimated from the slope of the initial linear range of the logarithmic curve of compound remaining (%) vs. time, assuming first order kinetics.

Example 180

Akt Kinase Assay

Cells comprising components of the Akt/mTOR pathway, including but not limited to L6 myoblasts, B-ALL cells, B-cells, T-cells, leukemia cells, bone marrow cells, p190 transduced cells, philadelphia chromosome positive cells (Ph+), and mouse embryonic fibroblasts, are typically grown in cell growth media such as DMEM supplemented with fetal bovine serum and/or antibiotics, and grown to confluency.

In order to compare the effect of one or more compounds disclosed herein on Akt activation, said cells are serum starved overnight and incubated with one or more compounds disclosed herein or about 0.1% DMSO for approximately 1 minute to about 1 hour prior to stimulation with insulin (e.g. 100 nM) for about 1 minutes to about 1 hour. Cells are lysed by scraping into ice cold lysis buffer containing detergents such as sodium dodecyl sulfate and protease inhibitors (e.g., PMSF). After contacting cells with lysis buffer, the solution is briefly sonicated, cleared by centrifugation, resolved by SDS-PAGE, transferred to nitrocellulose or PVDF and immunoblotted using antibodies to phospho-Akt 5473, phospho-Akt T308, Akt, and β-actin (Cell Signaling Technologies).

Example 181

Kinase Signaling in Blood

PI3K/Akt/mTor signaling is measured in blood cells using the phosflow method (*Methods Enzymol.* 2007; 434:131-54). The method is by nature a single cell assay so that cellular heterogeneity can be detected rather than population averages. This allows concurrent distinction of signaling states in different populations defined by other markers. Phosflow is also highly quantitative. To test the effects of one or more compounds disclosed herein, unfractionated splenocytes, or peripheral blood mononuclear cells are stimulated with anti-CD3 to initiate T-cell receptor signaling. The cells are then fixed and stained for surface markers and intracellular phosphoproteins. It is expected that inhibitors disclosed herein inhibit anti-CD3 mediated phosphorylation of Akt-S473 and S6, whereas rapamycin inhibits S6 phosphorylation and enhances Akt phosphorylation under the conditions tested.

Similarly, aliquots of whole blood are incubated for 15 minutes with vehicle (e.g. 0.1% DMSO) or kinase inhibitors at various concentrations, before addition of stimuli to crosslink the T cell receptor (TCR) (anti-CD3 with secondary antibody) or the B cell receptor (BCR) using anti-kappa light chain antibody (Fab'2 fragments). After approximately 5 and 15 minutes, samples are fixed (e.g. with cold 4% paraformaldehyde) and used for Phosflow. Surface staining is used to distinguish T and B cells using antibodies directed to cell surface markers that are known to the art. The level of phosphrylation of kinase substrates such as Akt and S6 are then measured by incubating the fixed cells with labeled antibodies specific to the phosphorylated isoforms of these proteins. The population of cells is then analyzed by flow cytometry.

Example 182

Colony Formation Assay

Murine bone marrow cells freshly transformed with a p190 BCR-Abl retrovirus (herein referred to as p190 transduced cells) are plated in the presence of various drug combinations in M3630 methylcellulose media for about 7 days with recombinant human IL-7 in about 30% serum, and the number of colonies formed is counted by visual examination under a microscope.

Alternatively, human peripheral blood mononuclear cells are obtained from Philadelphia chromosome positive (Ph+) and negative (Ph−) patients upon initial diagnosis or relapse. Live cells are isolated and enriched for CD19+CD34+B cell progenitors. After overnight liquid culture, cells are plated in methocult GF+H4435, Stem Cell Tehcnologies) supplemented with cytokines (IL-3, IL-6, IL-7, G-CSF, GM-CSF, CF, Flt3 ligand, and erythropoietin) and various concentrations of known chemotherapeutic agents in combination with either compounds of the present disclosure. Colonies are counted by microscopy 12-14 days later. This method can be used to test for evidence of additive or synergistic activity.

Example 183

In Vivo Effect of Kinase Inhibitors on Leukemic Cells

Female recipient mice are lethally irradiated from a γ source in two doses about 4 hr apart, with approximately 5Gy each. About 1 hr after the second radiation dose, mice are injected i.v. with about $1 \times 10^6$ leukemic cells (e.g. Ph+ human or murine cells, or p190 transduced bone marrow cells). These cells are administered together with a radioprotective dose of about $5 \times 10^6$ normal bone marrow cells from 3-5 week old donor mice. Recipients are given antibiotics in the water and monitored daily. Mice who become sick after about 14 days are euthanized and lymphoid organs are harvested for analysis. Kinase inhibitor treatment begins about ten days after leukemic cell injection and continues daily until the mice become sick or a maximum of approximately 35 days post-transplant. Inhibitors are given by oral lavage.

Peripheral blood cells are collected approximately on day 10 (pre-treatment) and upon euthanization (post treatment), contacted with labeled anti-hCD4 antibodies and counted by flow cytometry. This method can be used to demonstrate that the synergistic effect of one or more compounds disclosed herein in combination with known chemotherapeutic agents significantly reduce leukemic blood cell counts as compared to treatment with known chemotherapeutic agents (e.g. Gleevec) alone under the conditions tested.

Example 184

Treatment of Lupus Disease Model Mice

Mice lacking the inhibitory receptor FcγRIIb that opposes PI3K signaling in B cells develop lupus with high penetrance. FcγRIIb knockout mice (R2KO, Jackson Labs) are considered a valid model of the human disease as some lupus patients show decreased expression or function of FcγRIIb (S. Bolland and J. V. Ravtech 2000. *Immunity* 12:277-285).

The R2KO mice develop lupus-like disease with antinuclear antibodies, glomerulonephritis and proteinurea within about 4-6 months of age. For these experiments, the rapamycin analogue RAD001 (available from LC Laboratories) is used as a benchmark compound, and administered orally. This compound has been shown to ameliorate lupus symptoms in the B6.Sle1z.Sle3z model (T. Wu et al. *J. Clin Invest.* 117:2186-2196).

Lupus disease model mice such as R2KO, BXSB or MLR/lpr are treated at about 2 months old, approximately for about two months. Mice are given doses of: vehicle, RAD001 at about 10 mg/kg, or compounds disclosed herein at approximately 1 mg/kg to about 500 mg/kg. Blood and urine samples are obtained at approximately throughout the testing period, and tested for antinuclear antibodies (in dilutions of serum) or protein concentration (in urine). Serum is also tested for anti-ssDNA and anti-dsDNA antibodies by ELISA. Animals are euthanized at day 60 and tissues harvested for measuring spleen weight and kidney disease. Glomerulonephritis is assessed in kidney sections stained with H&E. Other animals are studied for about two months after cessation of treatment, using the same endpoints.

This established art model can be employed to test that the compounds disclosed herein can suppress or delay the onset of lupus symptoms in lupus disease model mice.

Example 185

Murine Bone Marrow Transplant Assay

Female recipient mice are lethally irradiated from a γ ray source. About 1 hr after the radiation dose, mice are injected with about $1 \times 10^6$ leukemic cells from early passage p190 transduced cultures (e.g. as described in *Cancer Genet Cytogenet.* 2005 August; 161(1):51-6). These cells are administered together with a radioprotective dose of approximately $5 \times 10^6$ normal bone marrow cells from 3-5 wk old donor mice. Recipients are given antibiotics in the water and monitored daily. Mice who become sick after about 14 days are euthanized and lymphoid organs harvested for flow cytometry and/or magnetic enrichment. Treatment begins on approximately day 10 and continues daily until mice become sick, or after a maximum of about 35 days post-transplant. Drugs are given by oral gavage (p.o.). In a pilot experiment a dose of chemotherapeutic that is not curative but delays leukemia onset by about one week or less is identified; controls are vehicle-treated or treated with chemotherapeutic agent, previously shown to delay but not cure leukemogenesis in this model (e.g. imatinib at about 70 mg/kg twice daily). For the first phase p190 cells that express eGFP are used, and postmortem analysis is limited to enumeration of the percentage of leukemic cells in bone marrow, spleen and lymph node (LN) by flow cytometry. In the second phase, p190 cells that express a tailless form of human CD4 are used and the postmortem analysis includes magnetic sorting of hCD4+ cells from spleen followed by immunoblot analysis of key signaling endpoints: p Akt-T308 and S473; pS6 and p4EBP-1. As controls for immunoblot detection, sorted cells are incubated in the presence or absence of kinase inhibitors of the present disclosure inhibitors before lysis. Optionally, "phosflow" is used to detect p Akt-S473 and pS6-S235/236 in hCD4-gated cells without prior sorting. These signaling studies are particularly useful if, for example, drug-treated mice have not developed clinical leukemia at the 35 day time point. Kaplan-Meier plots of survival are generated and statistical analysis done according to methods known in the art. Results from p190 cells are analyzed separated as well as cumulatively.

Samples of peripheral blood (100-200 µl) are obtained weekly from all mice, starting on day 10 immediately prior to commencing treatment. Plasma is used for measuring drug concentrations, and cells are analyzed for leukemia markers (eGFP or hCD4) and signaling biomarkers as described herein.

This general assay known in the art can be used to test that effective therapeutic doses of the compounds disclosed herein can be used for inhibiting the proliferation of leukemic cells.

Example 186

TNP-Ficoll T-Cell Independent B-Cell Activation Assay

To test the effects of the compounds as described herein in suppressing T cell independent antibody production, the TNP-Ficoll B-cell activation assay is used as described herein. Compounds as described herein are dissolved in an appropriate vehicle (e.g. 5% 1-methyl-2-pyrrolidinone, 85% polyethylene glycol 400, 10% Solutor). Compounds are administered orally approximately 1 hr before TNP-Ficoll treatment to 4-10 week old mice. To study the effects of the compounds on B-cell activation, one set of mice are grouped according to the following table:

and the solution is removed. 200 µl/well of blocking buffer (e.g. 1% BSA in PBS) is added to each well and incubated 1 hr at room temperature. The plate is washed once with 200 µl/well of PBS 0.05% Tween-20 (wash buffer). A 1:2 dilution of serum from each mouse in blocking buffer is added to each well in the first column (1) of the microtiter plate. The serum in each well of column 1 is then diluted 3-fold in blocking buffer and added to column 2. The serum in each well of column 2 is diluted 3-fold in blocking buffer and added to column 3. The procedure is repeated across the twelve columns of the microtiter plate. The microtiter plate is incubated 1 hr at room temperature. Serum is removed from the plate and the plate is washed three times with wash buffer. 100 µl/well of goat anti-mouse IgG3-HRP diluted 1:250 in blocking buffer is added to each well and incubated 1 hr at room temperature. The anti-mouse IgG3-HRP is removed from the microtiter plate and the plate is washed six times with wash buffer. HRP substrate (200 µl ABTS solution+30% $H_2O_2$+10 ml citrate buffer) is added to each well at 100 µl/well, incubated 2-20 minutes in the dark and the amount of anti-TNP IgG3 is determined spectrophotometrically at 405 nm. Similarly, anti-TNP IgM and total anti-TNP Ab are determined using anti-mouse IgM-HRP and anti-mouse Ig-HRP respectively.

Example 187

Rat Developing Type II Collagen Induced Arthritis Assay

In order to study the effects of the compounds as described herein on the autoimmune disease arthritis, a collagen induced developing arthritis model is used. Female Lewis rats are given collagen injections at day 0. Bovine type II collagen is prepared as a 4 mg/ml solution in 0.01N acetic acid. Equal volumes of collagen and Freund's incomplete adjuvant are emulsified by hand mixing until a bead of the emulsified material holds its form in water. Each rodent receives a 300 µl

| Group# | Mice/ group | Comp treated | Group | Antigen injection at day-1 TNP-F | Route | Compound Administration from day-1 to day-7 (mg/kg) | Route | Regimen |
|---|---|---|---|---|---|---|---|---|
| 1 | 4 | Vehicle | Antigen only | 200 uL | ip | 0 | Po | BID for 7 days |
| 2 | 8 | — | Antigen only | (0.5 | | 0 | | |
| 3 | 8 | Reference compound #1 | reference | mg/ml) | | 30 | | |
| 4 | 8 | Test | Antigen + | | | 1 | | |
| 5 | 8 | compound | cmp | | | 3 | | |
| 6 | 8 | | | | | 10 | | |
| 7 | 8 | | | | | 30 | | |
| 8 | 8 | | | | | 60 | | |

Four animals in group 1, and eight animals in groups 2 to 7 are euthanized in $CO_2$ 2 hours after the last compound administration on day 7. Blood is immediately collected by cadiopuncture and kept at 37° C. for 1 hr to clot followed by overnight incubation at 4° C. to allow the clot to contract. The following day, serum is collected by decanting and centrifugation at 3000 rpm for 10 min. The collected serum is then frozen at −80° C. for future analysis.

Serum samples are analyzed for anti-TNP antibody titers by ELISA as described herein. TNP-BSA is coated onto a Nunc Maxisorb microtiter plate with 100 µl/well at a concentration of 10 µg/ml in phosphate buffered saline (PBS). The Maxisorb plate is incubated for 1.5 hours at room temperature injection of the mixture at each injection time spread over three subcutaneous sites on the back.

Oral compound administration begins on day 0 and continues through day 16 with vehicle (5% NMP, 85% PEG 400, 10% Solutol) or compounds as described herein in vehicle or control (e.g. methotrexate) at 12 hour intervals daily. Rats are weighed on days 0, 3, 6, 9-17 and caliper measurements of ankles are taken on days 9-17. Final body weights are taken, and then the animals are euthanized on day 17. After euthanization, blood is drawn and hind paws and knees are removed. Blood is further processed for pharmacokinetics experiments as well as an anti-type II collagen antibody ELISA assay. Hind paws are weighed and then, with the knees, preserved in 10% formalin. The paws and knees are subsequently processed for microscopy. Livers, spleen and thymus are weighed. Sciatic nerves are prepared for histopathology.

Knee and ankle joints are fixed for 1-2 days and decalcified for 4-5 days Ankle joints are cut in half longitudinally, and knees are cut in half along the frontal plane. Joints are processed, embedded, sectioned and stained with toluidine blue. Scoring of the joints is done according to the following criteria:
Knee and Ankle Inflammation
0=Normal
1=Minimal infiltration of inflammatory cells in synovium/periarticular tissue
2=Mild infiltration
3=Moderate infiltration with moderate edema
4=Marked infiltration with marked edema
5=Severe infiltration with severe edema
Ankle Pannus
0=Normal
1=Minimal infiltration of pannus in cartilage and subchondral bone
2=Mild infiltration (<¼ of tibia or tarsals at marginal zones)
3=Moderate infiltration (¼ to ⅓ of tibia or small tarsals affected at marginal zones)
4=Marked infiltration (½-¾ of tibia or tarsals affected at marginal zones)
5=Severe infiltration (>¾ of tibia or tarsals affected at marginal zones, severe distortion of overall architecture)
Knee Pannus
0=Normal
1=Minimal infiltration of pannus in cartilage and subchondral bone
2=Mild infiltration (extends over up to ¼ of surface or subchondral area of tibia or femur)
3=Moderate infiltration (extends over >¼ but <½ of surface or subchondral area of tibia or femur)
4=Marked infiltration (extends over ½ to ¾ of tibial or femoral surface)
5=Severe infiltration (covers >¾ of surface)
Cartilage Damage (Ankle, emphasis on small tarsals)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal moderate (depth to middle zone) chondrocyte loss and/or collagen disruption, smaller tarsals affected to ½-¾ depth
4=Marked=marked loss of toluidine blue staining with multifocal marked (depth to deep zone) chondrocyte loss and/or collagen disruption, 1 or more small tarsals have full thickness loss of cartilage
5=Severe=severe diffuse loss of toluidine blue staining with multifocal severe (depth to tide mark) chondrocyte loss and/or collagen disruption
Cartilage Damage (Knee, Emphasis on Femoral Condyles)
0=Normal
1=Minimal=minimal to mild loss of toluidine blue staining with no obvious chondrocyte loss or collagen disruption
2=Mild=mild loss of toluidine blue staining with focal mild (superficial) chondrocyte loss and/or collagen disruption
3=Moderate=moderate loss of toluidine blue staining with multifocal to diffuse moderate (depth to middle zone) chondrocyte loss and/or collagen disruption
4=Marked=marked loss of toluidine blue staining with multifocal to diffuse marked (depth to deep zone) chondrocyte loss and/or collagen disruption or single femoral surface with total or near total loss
5=Severe=severe diffuse loss of toluidine blue staining with multifocal severe (depth to tide mark) chondrocyte loss and/or collagen disruption on both femurs and/or tibias
Bone Resorption (Ankle)
0=Normal
1=Minimal=small areas of resorption, not readily apparent on low magnification, rare osteoclasts
2=Mild=more numerous areas of resorption, not readily apparent on low magnification, osteoclasts more numerous, <¼ of tibia or tarsals at marginal zones resorbed
3=Moderate=obvious resorption of medullary trabecular and cortical bone without full thickness defects in cortex, loss of some medullary trabeculae, lesion apparent on low magnification, osteoclasts more numerous, ¼ to ⅓ of tibia or tarsals affected at marginal zones
4=Marked=Full thickness defects in cortical bone, often with distortion of profile of remaining cortical surface, marked loss of medullary bone, numerous osteoclasts, ½-¾ of tibia or tarsals affected at marginal zones
5=Severe=Full thickness defects in cortical bone, often with distortion of profile of remaining cortical surface, marked loss of medullary bone, numerous osteoclasts, >¾ of tibia or tarsals affected at marginal zones, severe distortion of overall architecture
Bone Resorption (Knee)
0=Normal
1=Minimal=small areas of resorption, not readily apparent on low magnification, rare osteoclasts
2=Mild=more numerous areas of resorption, definite loss of subchondral bone involving ¼ of tibial or femoral surface (medial or lateral)
3=Moderate=obvious resorption of subchondral bone involving >¼ but <½ of tibial or femoral surface (medial or lateral)
4=Marked=obvious resorption of subchondral bone involving ≥½ but <¾ of tibial or femoral surface (medial or lateral)
5=Severe=distortion of entire joint due to destruction involving >¾ of tibial or femoral surface (medial or lateral)

Statistical analysis of body/paw weights, paw AUC parameters and histopathologic parameters were evaluated using a Student's t-test or other appropriate (ANOVA with post-test) with significance set at the 5% significance level. Percent inhibition of paw weight and AUC was calculated using the following formula:

$$\% \text{ Inhibition} = A - B/A \times 100$$

$A$=Mean Disease Control−Mean Normal $B$=Mean Treated−Mean Normal

The assay can determine whether, relative to vehicle only control or to methotrexate control, the compounds as described herein exhibit a significant reduction in arthritis induced ankle diameter increase over time, and reduction of ankle histopathology in at least one or more of the categories of inflammation, pannus, cartilage damage, and bone resorption as described above. A dose dependent reduction in knee histopathology can be measured indicating that compounds as described herein can be useful for the treatment and reduction of arthritis disease symptoms.

A reduction at 10, 20, and 60 mg/kg dosage levels of serum anti-type II collagen levels can be detected, which would suggest that one or more compounds as described herein can not only be useful for the treatment and reduction of arthritis disease symptoms, but can also be useful for the inhibition of the autoimmune reaction itself.

Example 188

Rat Established Type II Collagen Induced Arthritis Assay

In order to examine the dose responsive efficacy of the compounds as described herein in inhibiting the inflammation, cartilage destruction and bone resorption of 10 day established type II collagen induced arthritis in rats, compounds are administered orally daily or twice daily for 6 days.

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is evidence of bilateral disease.

After an animal is selected for enrollment in the study, treatment is initiated by the oral route. Animals are given vehicle, control (Enbrel) or compound doses, twice daily or once daily (BID or QD respectively). Administration is performed on days 1-6 using a volume of 2.5 ml/kg (BID) or 5 ml/kg (QD) for oral solutions. Rats are weighed on days 1-7 following establishment of arthritis and caliper measurements of ankles taken every day. Final body weights are taken on day 7 and animals are euthanized The assay can determine reduction in mean ankle diameter increase over time with a once daily administration or twice daily administration under the conditions tested would suggest that the compounds as described herein can be useful for the treatment of autoimmune diseases such as arthritis.

Example 189

Adjuvant Induced Arthritis Assay

Intrathecal Catheterization of Rats

Isoflurane-anesthetized Lewis rats (200-250 g) are implanted with an intrathecal (IT) catheter. After a 6 d recovery period, all animals except those that appeared to have sensory or motor abnormalities (generally fewer than 5% of the total number) are used for experiments. For IT administration, 10 µl of drug or saline followed by 10 µl of isotonic saline is injected through the catheter.

Adjuvant Arthritis and Drug Treatment

Lewis rats are immunized at the base of the tail with 0.1 ml of complete Freund's adjuvant (CFA) on day 0 several days after catheter implantation (n=6/group). Drug (e.g. one or more compounds as described herein or vehicle) treatment is generally started on day 8 and is continued daily until day 20. Clinical signs of arthritis generally begin on day 10, and paw swelling is determined every second day by water displacement plethysmometry.

The assay can demonstrate a dose dependent reduction in the average paw volume increase as measured in this adjuvant induced arthritis model system which would suggest that one or more of the compounds as described herein can be useful for the treatment of one or more of the diseases or conditions described herein.

Example 190

Rodent Pharmacokinetic Assay

In order to study the pharmacokinetics of the compounds as described herein a set of 4-10 week old mice are grouped according to the following table:

| Group# | Mice/group | Compound Administration from day-1 to day-7 | | |
|---|---|---|---|---|
| | | (mg/kg) | Route | Regimen |
| 1 | 3 | 1 | Po | BID for 7 days |
| 2 | 3 | 3 | | |
| 3 | 3 | 10 | | |
| 4 | 3 | 30 | | |
| 5 | 3 | 60 | | |

Compounds as described herein are dissolved in an appropriate vehicle (e.g. 5% 1-methyl-2-pyrrolidinone, 85% polyethylene glycol 400, 10% Solutor) and administered orally at 12 hour intervals daily. All animals are euthanized in $CO_2$ 2 hours after the final compound is administered. Blood is collected immediately and kept on ice for plasma isolation. Plasma is isolated by centrifuging at 5000 rpm for 10 minutes. Harvested plasma is frozen for pharmacokinetic detection.

The results can demonstrate the pharmacokinetic parameters such as absorption, distribution, metabolism, excretion, and toxicity for the compounds as described herein.

Example 191

Basotest Assay

The basotest assay is performed using Orpegen Pharma Basotest reagent kit. Heparinized whole blood is pre-incubated with test compound or solvent at 37° C. for 20 min. Blood is then incubated with assay kit stimulation buffer (to prime cells for response) followed by allergen (dust mite extract or grass extract) for 20 min. The degranulation process is stopped by incubating the blood samples on ice. The cells are then labeled with anti-IgE-PE to detect basophilic granulocytes, and anti-gp53-FITC to detect gp53 (a glycoprotein expressed on activated basophils). After staining, red blood cells are lysed by addition of Lysing Solution. Cells are washed, and analyzed by flow cytometry. This assay can determine inhibition of allergen induced activation of basophilic granulocytes at sub micromolar range by compounds as disclosed herein.

Example 192

Cell Culture of Epithelial Cells of Ocular Origin

Ocular epithelial cells are obtained within 5 days postmortem from corneas preserved under cold storage conditions in Optisol (Bausch and Lomb, Irvine, Calif.) or from corneal biopsy from living donors. The tissue is washed with phosphate-buffered saline and incubated in Dispase II (Roche Diagnostics, Basel, Switzerland) at 37° C. for 30 minutes, and the epithelial surface is gently scraped to separate the epithelium from the underlying stroma. The separated epithelium is then incubated and pipetted in trypsin-ethylenediaminetetraacetic acid to obtain a single cell suspension. The trypsin is then neutralized with corneal epithelium culture medium. Corneal epithelium culture medium is composed of Dulbecco modified Eagle medium:F12 basal media in a 2:1 ratio containing 10% irradiated fetal bovine serum, hydrocortisone 0.4 µg/mL, cholera toxin 0.1 nmol, recombinant human insulin 5 µg/mL, and epidermal growth factor 10 ng/mL, and the antimicrobials penicillin (100 IU/mL), streptomycin (100 µg/mL), and amphotericin B (0.25 µg/mL). Cells are maintained by sub-culturing at a 1:4 ratio after reaching 80% confluency. Ocular epithelial cells are screened for inhibition of proliferation or toxicity by contacting a test compound with the cells and assaying for viability using the commercially available MTT assay (Promega).

Example 193

Cell Culture of Endothelial Cells of Ocular Origin

All tissues are maintained at 4° C. in storage medium (Optisol; Chiron Vision, Irvine, Calif.) for less than 10 days before study. The tissue is rinsed three times with DMEM containing 50 mg/mL gentamicin and 1.25 mg/mL amphotericin B. The central cornea is removed by a trephine of 8-mm diameter. Afterward, the Descemet's membrane and corneal endothelial cells are stripped from the posterior surface of the peripheral corneoscleral tissue under a dissecting microscope and digested at 37° C. for 1.5 to 16 hours with 2 mg/mL collagenase A in supplemented hormonal epithelial medium (SHEM), which is made of an equal volume of HEPES-buffered DMEM and Ham's F12 supplemented with 5% FBS, 0.5% dimethyl sulfoxide, 2 ng/mL mouse EGF, 5 µg/mL insulin, 5 µg/mL transferrin, 5 ng/mL selenium, 0.5 µg/mL hydrocortisone, 1 nM cholera toxin, 50 µg/mL gentamicin, and 1.25 µg/mL amphotericin B. After digestion, HCECs formed aggregates, which are collected by centrifugation at 2000 rpm for 3 minutes to remove the digestion solution. As a control, Descemet's membrane strips are also digested in 10 mg/mL Dispase II in SHEM and trypsin/EDTA for up to 3 hours.

Preservation of Isolated HCEC Aggregates: The resultant aggregates of HCECs are preserved in KSFM with complete supplement (storage medium 1), DMEM/F12 with KSFM supplements (storage medium 2), or DMEM/F12 with SHEM supplements without FBS (storage medium 3). All these media are serum free, one of the major differences among them is the calcium concentration, which is 0.09 mM in storage medium 1, but is 1.05 mM in storage media 2 and 3. HCEC aggregates are stored in a tissue culture incubator at 37° C. for up to 3 weeks. Cell viability is determined (Live and Dead assay; Invitrogen) and also evaluated by subculturing them in SHEM.

Preservation of Isolated HCEC Aggregates: The resultant HCEC aggregates, either immediately after digestion or after a period of preservation in a storage medium, are then cultured in SHEM with or without additional growth factors such as 40 ng/mL bFGF, 0.1 mg/mL BPE, and 20 ng/mL NGF on a plastic dish under 37° C. and 5% $CO_2$. The media are changed every 2 to 3 days. Some HCEC aggregates are pretreated with trypsin/EDTA at 37° C. for 10 minutes to dissociate endothelial cells before the aforementioned cultivation.

Immunostaining: HCEC aggregates are embedded in OCT and subjected to frozen sectioning. Cryosections of 4 µm are air-dried at room temperature (RT) for 30 minutes, and fixed in cold acetone for 10 minutes at −20° C. Sections used for immunostaining are rehydrated in PBS, and incubated in 0.2% Triton X-100 for 10 minutes. After three rinses with PBS for 5 minutes each and preincubation with 2% BSA to block nonspecific staining, the sections are incubated with anti-laminin 5, type IV collagen, perlecan, ZO-1, and connexin 43 (all at 1:100) antibodies for 1 hour. After three washes with PBS for 15 minutes, the sections are incubated with a FITC-conjugated secondary antibody (goat anti-rabbit or anti-mouse IgG at 1:100) for 45 minutes. After three additional PBS washes, each for 10 minutes, they are counterstained with propidium iodide (1:1000) or Hoechst 33342 (10 µg/mL), then mounted with an antifade solution and analyzed with a fluorescence microscope. HCECs cultured in 24-well plates or chamber slides are fixed in 4% paraformaldehyde for 15 minutes at RT and stained with anti-ZO-1 and connexin 43 antibodies as just described. For immunohistochemical staining of Ki67, endogenous peroxidase activity is blocked by 0.6% hydrogen peroxide for 10 minutes. Nonspecific staining is blocked by 1% normal goat serum for 30 minutes. Cells are then incubated with anti-Ki67 antibody (1:100) for 1 hour. After three washes with PBS for 15 minutes, cells are incubated with biotinylated rabbit anti-mouse IgG (1:100) for 30 minutes, followed by incubation with ABC reagent for 30 minutes. The reaction product is developed with DAB for 5 minutes and examined by light microscope.

Cell-Viability and TUNEL Assays: Cell-viability and terminal deoxyribonucleotidyl transferase-mediated FITC-linked dUTP nick-end DNA labeling (TUNEL) assays are used to determine living and apoptotic cells, respectively. HCEC aggregates are incubated with cell-viability assay reagents for 15 minutes at RT. Live cells are distinguished by green fluorescence staining of the cell cytoplasm, and dead cells are stained with red fluorescence in the nuclei. The TUNEL assay is performed according to the manufacturer's instructions. Briefly, cross-sections of HCEC aggregates are fixed in 4% paraformaldehyde for 20 minutes at RT and permeabilized with 1% Triton X-100. Samples are then incubated for 60 minutes at 37° C. with exogenous TdT and fluorescein-conjugated dUTP, for repair of nicked 3'-hydroxyl DNA ends. Cells are treated with DNase I as the positive control, whereas negative control cells are incubated with a buffer lacking the rTdT enzyme. The apoptotic nuclei are labeled with green fluorescence.

Example 194

Cell Culture of Retinal Cells

Eyes are cut in half along their equator and the neural retina is dissected from the anterior part of the eye in buffered saline solution, according to standard methods known in the art. Briefly, the retina, ciliary body, and vitreous are dissected away from the anterior half of the eye in one piece, and the retina is gently detached from the clear vitreous. Each retina is dissociated with papain (Worthington Biochemical Corporation, Lakewood, N.J.), followed by inactivation with fetal bovine serum (FBS) and addition of 134 Kunitz units/ml of DNaseI. The enzymatically dissociated cells are triturated and collected by centrifugation, resuspended in Dulbecco's modified Eagle's medium (DMEM)/F12 medium (Gibco BRL, Invitrogen Life Technologies, Carlsbad, Calif.) containing 25 µg/ml of insulin, 100 µg/ml of transferrin, 60 µM putrescine, 30 nM selenium, 20 nM progesterone, 100 U/ml of penicillin, 100 µg/ml of streptomycin, 0.05 M Hepes, and 10% FBS. Dissociated primary retinal cells are plated onto Poly-D-lysine- and Matrigel- (BD, Franklin Lakes, N.J.) coated glass coverslips that are placed in 24-well tissue culture plates (Falcon Tissue Culture Plates, Fisher Scientific, Pittsburgh, Pa.). Cells are maintained in culture for 5 days to one month in 0.5 ml of media (as above, except with only 1% FBS) at 37° C. and 5% $CO_2$.

Immunocytochemistry Analysis: The retinal neuronal cells are cultured for 1, 3, 6, and 8 weeks in the presence and absence of test compounds as disclosed herein, and the cells are analyzed by immunohistochemistry at each time point. Immunocytochemistry analysis is performed according to standard techniques known in the art. Rod photoreceptors are identified by labeling with a rhodopsin-specific antibody (mouse monoclonal, diluted 1:500; Chemicon, Temecula, Calif.). An antibody to mid-weight neurofilament (NFM rabbit polyclonal, diluted 1:10,000, Chemicon) is used to identify ganglion cells; an antibody to β3-tubulin (G7121 mouse monoclonal, diluted 1:1000, Promega, Madison, Wis.) is used to generally identify interneurons and ganglion cells, and antibodies to calbindin (AB1778 rabbit polyclonal, diluted 1:250, Chemicon) and calretinin (AB5054 rabbit polyclonal, diluted 1:5000, Chemicon) are used to identify subpopulations of calbindin- and calretinin-expressing interneurons in the inner nuclear layer. Briefly, the retinal cell cultures are fixed with 4% paraformaldehyde (Polysciences, Inc, Warrington, Pa.) and/or ethanol, rinsed in Dulbecco's phosphate buffered saline (DPBS), and incubated with primary antibody for 1 hour at 37° C. The cells are then rinsed with DPBS, incubated with a secondary antibody (Alexa 488- or Alexa 568-conjugated secondary antibodies (Molecular Probes, Eugene, Oreg.)), and rinsed with DPBS. Nuclei are stained with 4',6-diamidino-2-phenylindole (DAPI, Molecular Probes), and the cultures are rinsed with DPBS before removing the glass coverslips and mounting them with Fluoromount-G (Southern Biotech, Birmingham, Ala.) on glass slides for viewing and analysis.

Example 195

Matrigel Plug Angiogenesis Assay

Matrigel containing test compounds are injected subcutaneously or intraocularly, where it solidifies to form a plug. The plug is recovered after 7-21 days in the animal and examined histologically to determine the extent to which blood vessels have entered it. Angiogenesis is measured by quantification of the vessels in histologic sections. Alternatively, fluorescence measurement of plasma volume is performed using fluorescein isothiocyanate (FITC)-labeled dextran 150. The results are expected to indicate one or more compounds disclosed herein that inhibit angiogenesis and are thus expected to be useful in treating ocular disorders related to aberrant angiogenesis and/or vascular permeability.

Example 196

Corneal Angiogenesis Assay

A pocket is made in the cornea, and a plug containing an angiogenesis inducing formulation (e.g., VEGF, FGF, or tumor cells), when introduced into this pocket, elicits the ingrowth of new vessels from the peripheral limbal vasculature. Slow-release materials such as ELVAX (ethylene vinyl copolymer) or Hydron are used to introduce angiogenesis inducing substances into the corneal pocket. Alternatively, a sponge material is used.

The effect of putative inhibitors on the locally induced (e.g., sponge implant) angiogenic reaction in the cornea (e.g., by FGF, VEGF, or tumor cells). The test compound is administered orally, systemically, or directly to the eye. Systemic administration is by bolus injection or, more effectively, by use of a sustained-release method such as implantation of osmotic pumps loaded with the test inhibitor. Administration to the eye is by any of the methods described herein including but not limited to eye drops, topical administration of a cream, emulsion, or gel, intravitreal injection.

The vascular response is monitored by direct observation throughout the course of the experiment using a stereomicroscope in mice. Definitive visualization of the corneal vasculature is achieved by administration of fluorochrome-labeled high-molecular weight dextran. Quantification is performed by measuring the area of vessel penetration, the progress of vessels toward the angiogenic stimulus over time, or in the case of fluorescence, histogram analysis or pixel counts above a specific (background) threshold.

The assay can determine inhibition of angiogenesis and thus can be useful in treating ocular disorders related to aberrant angiogenesis and/or vascular permeability.

Example 197

Microtiter-Plate Angiogenesis Assay

The assay plate is prepared by placing a collagen plug in the bottom of each well with 5-10 cell spheroids per collagen plug each spheroid containing 400-500 cells. Each collagen plug is covered with 1100 µl of storage medium per well and stored for future use (1-3 days at 37° C., 5% $CO_2$). The plate is sealed with sealing. Test compounds are dissolved in 200 µl assay medium with at least one well including a VEGF positive control and at least one well without VEGF or test compound as a negative control. The assay plate is removed from the incubator and storage medium is carefully pipeted away. Assay medium containing the test compounds are pipeted onto the collagen plug. The plug is placed in a humidified incubator for (37° C., 5% $CO_2$) 24-48 hours. Angiogenesis is quantified by counting the number of sprouts, measuring average sprout length, or determining cumulative sprout length. The assay can be preserved for later analysis by removing the assay medium, adding 1 ml of 10% paraformaldehyde in Hanks BSS per well, and storing at 4° C. The assay can determine inhibition of angiogenesis in various cell types tested, including cells of ocular origin.

Example 198

Combination Use of PI3Kδ Inhibitors and Agents that Inhibit IgE Production or Activity The compounds as described herein can present synergistic or additive efficacy when administered in combination with agents that inhibit IgE production or activity. Agents that inhibit IgE production include, for example, one or more of TEI-9874, 2-(4-(6-cyclohexyloxy-2-naphtyloxy)phenylacetamide)benzoic acid, rapamycin, rapamycin analogs (i.e. rapalogs), TORC1 inhibitors, TORC2 inhibitors, and any other compounds that inhibit mTORC1 and mTORC2. Agents that inhibit IgE activity include, for example, anti-IgE antibodies such as Omalizumab and TNX-901.

One or more of the disclosed compounds capable of inhibiting PI3Kδ can be useful in the treatment of autoimmune and inflammatory disorders (AIID) for example rheumatoid arthritis. If any of the compounds causes an undesired level of IgE production, one can choose to administer it in combination with an agent that inhibits IgE production or IgE activity. Additionally, the administration of PI3Kδ or PI3Lδ/γ inhibitors as described herein in combination with inhibitors of mTOR can also exhibit synergy through enhanced inhibition of the PI3K pathway. Various in vivo and in vitro models can be used to establish the effect of such combination treatment on AIID including but not limited to (a) in vitro B-cell antibody production assay, (b) in vivo TNP assay, and (c) rodent collagen induced arthritis model.

(a) B-Cell Assay

Mice are euthanized, and the spleens are removed and dispersed through a nylon mesh to generate a single-cell suspension. The splenocytes are washed (following removal of erythrocytes by osmotic shock) and incubated with anti-CD43 and anti-Mac-1 antibody-conjugated microbeads (Miltenyi Biotec). The bead-bound cells are separated from unbound cells using a magnetic cell sorter. The magnetized column retains the unwanted cells and the resting B cells are collected in the flow-through. Purified B-cells are stimulated with lipopolysaccharide or an anti-CD40 antibody and interleukin 4. Stimulated B-cells are treated with vehicle alone or with compounds as described herein with and without mTOR inhibitors such as rapamycin, rapalogs, or mTORC1/C2 inhibitors. The assay can determine that in the presence of mTOR inhibitors (e.g., rapamycin) alone, there is little to no substantial effect on IgG and IgE response. However, in the presence of PI3Kδ and mTOR inhibitors, the B-cells are expected to exhibit a decreased IgG response as compared to the B-cells treated with vehicle alone, and the B-cells are expected to exhibit a decreased IgE response as compared to the response from B-cells treated with disclosed compounds alone.

(b) TNP Assay

Mice are immunized with TNP-Ficoll or TNP-KHL and treated with: vehicle, a test compound, an mTOR inhibitor, for example rapamycin, or a test compound in combination with an mTOR inhibitor such as rapamycin. Antigen-specific serum IgE is measured by ELISA using TNP-BSA coated plates and isotype specific labeled antibodies. This assay can be used to test that mice treated with an mTOR inhibitor alone exhibit little or no substantial effect on antigen specific IgG3 response and no statistically significant elevation in IgE response as compared to the vehicle control. This assay can also be used to test that mice treated with both test compound and mTOR inhibitor exhibit a reduction in antigen specific IgG3 response as compared to the mice treated with vehicle alone. Additionally, this assay can be employed to test that the mice treated with both test compound and mTOR inhibitor exhibit a decrease in IgE response as compared to the mice treated with PI3Kδ inhibitor alone.

(c) Rat Collagen Induced Arthritis Model

Female Lewis rats are anesthetized and given collagen injections prepared and administered as described previously on day 0. On day 6, animals are anesthetized and given a second collagen injection. Caliper measurements of normal (pre-disease) right and left ankle joints are performed on day 9. On days 10-11, arthritis typically occurs and rats are randomized into treatment groups. Randomization is performed after ankle joint swelling is obviously established and there is good evidence of bilateral disease.

After an animal is selected for enrollment in the study, treatment is initiated. Animals are given vehicle, test compound, or test compound in combination with rapamycin. Dosing is administered on days 1-6. Rats are weighed on days 1-7 following establishment of arthritis and caliper measurements of ankles taken every day. Final body weights are taken on day 7 and animals are euthanized.

This assay can be used to test whether the combination treatment using test compound and rapamycin provides greater efficacy than treatment with test compound alone.

Example 199

Delayed Type Hypersensitivity Model

DTH was induced by sensitizing 60 BALB/c male mice on day 0 and day 1 with a solution of 0.05% 2,4 dinitrofluorobenzene (DNFB) in a 4:1 acetone/olive oil mixture. Mice were gently restrained while 20 μL of solution was applied to the hind foot pads of each mouse. The hind foot pads of the mice were used as they represent an anatomical site that can be easily isolated and immobilized without anesthesia. On day 5, mice were administered a single dose of vehicle, test compound at 10, 3, 1, or 0.3 mg/kg, or dexamethasone at a dose of 5 mg/kg by oral gavage. Thirty minutes later mice were anaesthetized, and a solution of 0.25% DNFB in a 4:1 acetone/olive oil solution was applied to the left inner and outer ear surface. This application resulted in the induction of swelling to the left ear and under these conditions, all animals responded to this treatment with ear swelling. A vehicle control solution of 4:1 acetone/olive oil was applied to the right inner and outer ear. Twenty four hours later, mice were anaesthetized, and measurements of the left and right ear were taken using a digital micrometer. The difference between the two ears was recorded as the amount of swelling induced by the challenge of DNFB. Drug treatment groups were compared to vehicle control to generate the percent reduction in ear swelling. Dexamethasone is routinely used as a positive control as it has broad anti-inflammatory activity.

Example 200

Peptidoglycan-Polysaccharide Rat Arthritic Model (a) Systemic Arthritis Model

All injections are performed under anesthesia. 60 female Lewis rats (150-170) are anesthetized by inhalation isoflurane using a small animal anesthesia machine. The animals are placed in the induction chamber until anesthetized by delivery of 4-5% isoflurane in $O_2$ and then held in that state using a nose cone on the procedure table. Maintenance level of isoflurane is at 1-2%. Animals are injected intraperitoneally (i.p.) with a single injection of purified PG-PS 10S Group A, D58 strain (concentration 25 μg/g of bodyweight) suspended in sterile 0.85% saline. Each animal receives a total volume of 500 microliters administered in the lower left quadrant of the abdomen using a 1 milliliter syringe with a 23 gauge needle. Placement of the needle is critical to avoid injecting the PG-PS 10S into either the stomach or caecum. Animals are under continuous observation until fully recovered from anesthesia and moving about the cage. An acute response of a sharp increase in ankle measurement, typically 20% above baseline measurement can peak in 3-5 days post injection. Treatment with test compounds can be PO, SC, IV or IP. Rats are dosed no more than two times in a 24 hour time span. Treatment can begin on day 0 or any day after that through day 30. The animals are weighed on days 0, 1, 2, 3, 4, 5, 6, 7 and beginning again on day 12-30 or until the study is terminated. Paw/ankle diameter is measured with a digital caliper on the left and right side on day 0 prior to injection and again on day 1, 2, 3, 4, 5, 6 and 7. On day 12, measurements begin again and continue on through day 30. At this time, animals can be anesthetized with isoflurane, as described above, and terminal blood samples can be obtained by tail vein draws for the evaluation of the compound blood levels, clinical chemistry or hematology parameters. Animals are them euthanized with carbon dioxide overdose. A thoracotomy can be conducted as a means of death verification.

(b) Monoarticular Arthritis Model

All injections are performed under anesthesia. 60 female Lewis rats (150-170) are anesthetized by inhalation isoflurane using a small animal anesthesia machine. The animals are placed in the induction chamber until anesthetized by delivery of 4-5% isoflurane in $O_2$ and then held in that state using a nose cone on the procedure table. Maintenance level of isoflurane is at 1-2%. Animals are injected intra-articular (i.a.) with a single injection of purified PG-PS 100P Group A, D58 strain (concentration 500 µg/mL) suspended in sterile 0.85% saline. Each rat receives a total volume of 10 microliters administered into the tibiotalar joint space using a 1 milliliter syringe with a 27 gauge needle. Animals are under continuous observation until fully recovered from anesthesia and moving about the cage. Animals that respond 2-3 days later with a sharp increase in ankle measurement, typically 20% above baseline measurement on the initial i.a. injection, are included in the study. On day 14, all responders are anesthetized again using the procedure previously described. Animals receive an intravenous (I.V.) injection of PG-PS (concentration 250 µL/mL). Each rat receives a total volume of 400 microliters administered slowly into the lateral tail vein using a 1 milliliter syringe with a 27 gauge needle. Baseline ankle measurements are measured prior to IV injection and continue through the course of inflammation or out to day 10. Treatment with test compounds will be PO, SC, IV or IP. Rats are dosed no more than two times in a 24 hour time span. Treatment can begin on day 0 or any day after that through day 24. The animals are weighed on days 0, 1, 2, 3, 4, 5, and beginning again on day 14-24 or until the study is terminated. Paw/ankle diameter is measured with a digital caliper on the left and right side on day 0 prior to injection and again on day 1, 2, 3, 4, 5, and beginning again on day 14-24 or until the study is terminated. At this time, animals can be anesthetized with isoflurane, as described above, and terminal blood samples can be obtained by tail vein draws for the evaluation of the compound blood levels, clinical chemistry or hematology parameters. Animals are them euthanized with carbon dioxide overdose. A thoracotomy can be conducted as a means of death verification.

Example 201

Use of the Compounds as Described Herein for Inhibition of Tumor Growth

Cell Lines

Cell lines of interest (A549, U87, ZR-75-1 and 786-O) are obtained from American Type Culture Collection (ATCC, Manassas, Va.). Cells are proliferated and preserved cryogenically at early passage (e.g. passage 3). One aliquot is used for further proliferation to get enough cells for one TGI study (at about passage 9).

Animals

Female athymic nude mice are supplied by Harlan. Mice are received at 4 to 6 weeks of age. All mice are acclimated for about one day to two weeks prior to handling. The mice are housed in microisolator cages and maintained under specific pathogen-free conditions. The mice are fed with irradiated mouse chow and freely available autoclaved water is provided.

Tumor Xenograft Model

Mice are inoculated subcutaneously in the right flank with 0.01 to 0.5 ml of tumor cells (approximately $1.0 \times 10^5$ to $1.0 \times 10^8$ cells/mouse). Five to 10 days following inoculation, tumors are measured using calipers and tumor weight is calculated, for example using the animal study management software, such as Study Director V.1.6.70 (Study Log). Mice with tumor sizes of about 120 mg are pair-matched into desired groups using Study Director (Day 1). Body weights are recorded when the mice are pair-matched. Tumor volume and bodyweight measurements are taken one to four times weekly and gross observations are made at least once daily. On Day 1, compounds as described herein and reference compounds as well as vehicle control are administered by oral gavage or iv as indicated. At the last day of the experiment, mice are sacrificed and their tumors are collected 1-4 hours after the final dose. The tumors are excised and cut into two sections. One third of the tumor is fixed in formalin and embedded in paraffin blocks and the remaining two thirds of tumor is snap frozen and stored at −80° C.

Data and Statistical Analysis

Mean tumor growth inhibition (TGI) is calculated utilizing the following formula:

$$TGI = \left[1 - \frac{(\bar{X}_{Treated(Final)} - \bar{X}_{Treated(Day1)})}{(\bar{X}_{Control(Final)} - \bar{X}_{Control(Day1)})}\right] \times 100\%$$

Tumors that regress from the Day 1 starting size are removed from the calculations. Individual tumor shrinkage (TS) is calculated using the formula below for tumors that show regression relative to Day 1 tumor weight. The mean tumor shrinkage of each group is calculated and reported.

$$TS = \left[1 - \frac{(\text{Tumor Weight}_{(Final)})}{(\text{Tumor Weight}_{(Day1)})}\right] \times 100\%$$

The model can be employed to show whether the compounds as described herein can inhibit tumor cell growth such as renal carcinomoa cell growth, breast cancer cell growth, lung cancer cell growth, or glioblastoma cell growth under the conditions tested.

What is claimed is:

1. A compound of Formula (Ia):

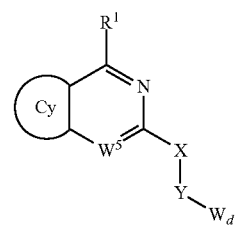

Formula (Ia)

or a pharmaceutically acceptable form thereof, wherein:
 $W^5$ is $CR^4$;
 $R^4$ is hydrogen, alkyl, haloalkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R" wherein R' and R" are taken together with nitrogen to form a cyclic moiety;
 Cy is aryl substituted by 0-4 occurrences of $R^3$;
 $R^1$ is -(L)$_n$-$R^{1'}$;
 each L is independently a bond, alkylene, heteroalkylene, —N($R^2$)—, —S(=O)—, —S(=O)$_2$—, —S—, —C(=O)—, —P(=O)$R^2$—, or —O—;
 $R^{1'}$ is hydrogen, alkyl, heteroalkyl, alkenyl, alkynyl, cycloalkyl, heterocycloalkyl, aryl, arylalkyl, heteroaryl, heteroarylalkyl, alkoxy, heterocyclyloxy, heterocycloalkyloxy, amino, amido, acyl, acyloxy, alkoxycarbonyl, sulfonamido, halo, cyano, nitro, phosphate, urea, carbonate, —(C═O)—NR$^{a1}$R$^{a2}$, or NR$^{a1}$R$^{a2}$;

R$^{a1}$ and R$^{a2}$ are each independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or R$^{a1}$ and R$^{a2}$ are taken together with nitrogen to form a cyclic moiety;

R$^2$ is hydrogen, alkyl, cycloalkyl, heterocycloalkyl, heteroalkyl, aryl, or heteroaryl;

each R$^3$ is independently alkyl, heteroalkyl, haloalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R" wherein R' and R" are taken together with nitrogen to form a cyclic moiety;

X is —(CH(R$^{10}$))$_z$—;

Y is absent, —O—, —S—, —S(═O)—, —S(═O)$_2$—, —N(R$^9$)—, —C(═O)—(CHR$^{10}$)$_z$—, —C(═O)—, —N(R$^9$)—C(═O)—, —C(═O)—N(R$^9$)—, —N(R$^9$)—C(═O)NH—, —N(R$^9$)C(R$^{10}$)$_2$—, —C(═O)—N(R$^9$)—(CHR$^{10}$)$_z$—, or —P(═O)R$^2$—;

each z is an integer of 1, 2, 3, or 4;

n is an integer of 0, 1, 2, 3, or 4;

each R$^9$ is independently hydrogen, alkyl, cycloalkyl, heterocycloalkyl, heterocycloalkylalkyl, heteroalkyl, aryl, or heteroaryl;

W$_d$ is

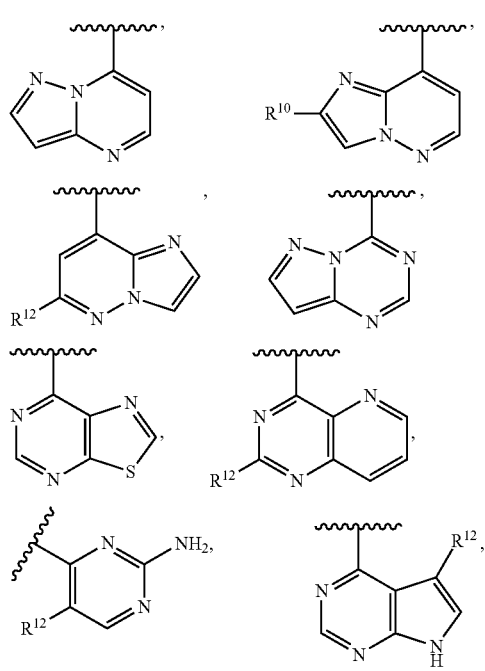

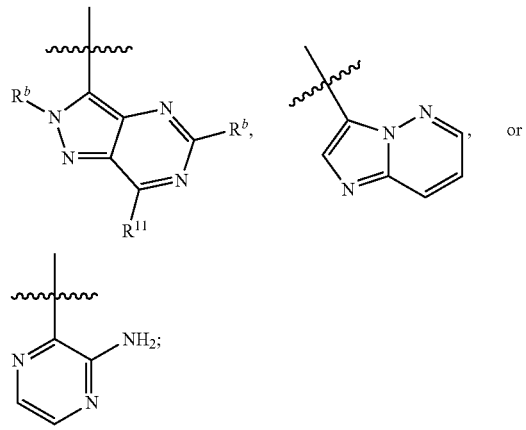

each R$^b$ is independently hydrogen, halo, phosphate, urea, carbonate, alkyl, alkenyl, alkynyl, cycloalkyl, heteroalkyl, or heterocycloalkyl; and each R$^{10}$, R$^{11}$, and R$^{12}$ is independently hydrogen, alkyl, heteroalkyl, alkenyl, alkynyl, cycloalkyl, heterocycloalkyl, aryl, arylalkyl, heteroaryl, heteroarylalkyl, alkoxy, heterocyclyloxy, amido, amino, acyl, acyloxy, alkoxycarbonyl, sulfonamido, halo, haloalkyl, cyano, hydroxyl, nitro, phosphate, urea, carbonate, or NR'R" wherein R' and R" are taken together with nitrogen to form a cyclic moiety.

2. The compound of claim 1, wherein n is 1, 2, or 3.

3. The compound of claim 1, wherein each L is —O—, —C(═O)—, —S(═O)—, —S(═O)$_2$—, —S—, alkylene, or a bond.

4. The compound of claim 1, wherein R$^{1'}$ is alkyl, hydroxy, aryl, heteroaryl, aralkyl, —(C═O)—NR$^{a1}$R$^{a2}$, or NR$^{a1}$R$^{a2}$.

5. The compound of claim 4, wherein R$^{a1}$ is hydrogen or alkyl.

6. The compound of claim 4, wherein R$^{a2}$ is alkyl, cycloalkyl, aryl, aralkyl, heteroaryl, heteroaralkyl, heterocycloalkyl, acyl, or heterocycloalkylalkyl.

7. The compound of claim 4, wherein R$^{a1}$ and R$^{a2}$ are taken together with the nitrogen to which they are attached to form a cyclic moiety.

8. The compound of claim 1, wherein W$^5$ is CH.

9. The compound of claim 1, wherein X is —(CH(R$^{10}$))$_z$— and z is 1 or 2.

10. The compound of claim 1, wherein Y is absent, —O—, —NH(R$^9$)—, or —S(═O)$_2$—.

11. The compound of claim 1, wherein Cy is phenyl substituted with 0-4 occurrences of R$^3$.

12. The compound of claim 1, wherein Cy is phenyl substituted with 1 occurrence of R$^3$.

13. The compound of claim 1, wherein R$^3$ is halo, alkyl, haloalkyl, acyl, or heteroaryl.

14. The compound of claim 1, wherein R$^{10}$ is hydrogen.

15. The compound of claim 1, wherein R$^{12}$ is hydrogen, halo, haloalkyl, cyano, amino, or amido.

16. The compound of claim 1, wherein the compound of Formula (Ia) is a compound of Formula (II):

Formula (II)

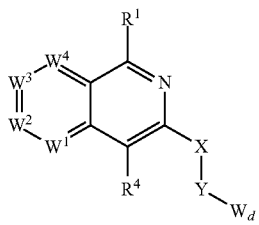

or a pharmaceutically acceptable form thereof, wherein:
W$^1$ is CR$^{14}$, W$^2$ is CR$^6$, W$^3$ is CR$^7$, and W$^4$ is CR$^8$; and
R$^6$, R$^7$, R$^8$ and R$^{14}$ are independently hydrogen, alkyl, haloalkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R", wherein R' and R" are taken together with nitrogen to form a cyclic moiety.

17. The compound of claim 16, wherein R$^{1'}$ is hydrogen, amino, alkoxy, alkyl, heterocycloalkyl, aryl, or NR$^{a1}$R$^{a2}$, wherein R$^{a1}$ and R$^{a2}$ are taken together with nitrogen to form a cyclic moiety.

18. The compound of claim 16, wherein R$^{1'}$ is amino, alkoxy, alkyl, or NR$^{a1}$R$^{a2}$, wherein R$^{a1}$ and R$^{a2}$ are taken together with nitrogen to form a cyclic moiety.

19. The compound of claim 1, wherein the compound of Formula (Ia) is a compound of Formula (IIIa):

Formula (IIIa)

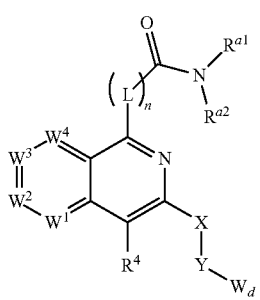

or a pharmaceutically acceptable form thereof, wherein:
W$^1$ is CR$^{14}$, W$^2$ is CR$^6$, W$^3$ is CR$^7$, and W$^4$ is CR$^8$; and
R$^6$, R$^7$, R$^8$ and R$^{14}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR'R", wherein R' and R" are taken together with nitrogen to form a cyclic moiety.

20. The compound of claim 19, wherein R$^{a1}$ and R$^{a2}$ are taken together with nitrogen to form a cyclic moiety.

21. The compound of claim 20, wherein the cyclic moiety is 5- or 6-membered.

22. The compound of claim 19, wherein n is 1 and L is alkylene.

23. The compound of claim 22, wherein L is methylene or ethylene.

24. The compound of claim 19, wherein L is alkylene substituted by aryl, heteroaryl or halo.

25. The compound of claim 1, wherein the compound of Formula (Ia) is a compound of Formula (IV):

Formula (IV)

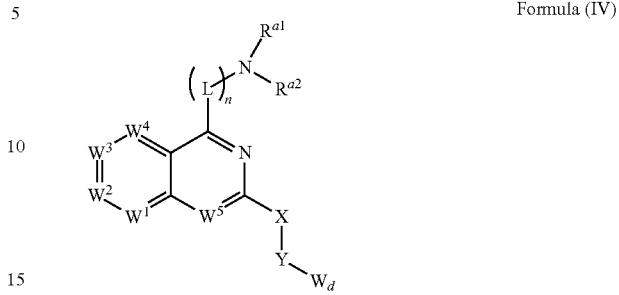

or a pharmaceutically acceptable form thereof, wherein:
W$^1$ is CR$^{14}$, W$^2$ is CR$^6$, W$^3$ is CR$^7$, W$^4$ is CR$^8$, and W$^5$ is CR$^4$; and
R$^6$, R$^7$, R$^8$ and R$^{14}$ are independently hydrogen, alkyl, heteroalkyl, alkenyl, alkynyl, cycloalkyl, heterocycloalkyl, aryl, arylalkyl, heteroaryl, heteroarylalkyl, alkoxy, heterocycloalkyloxy, amido, amino, acyl, acyloxy, alkoxycarbonyl, sulfonamido, thio, sulfoxide, sulfone, halo, cyano, hydroxy, nitro, phosphate, urea, carbonate, or NR/R", wherein R' and R" are taken together with nitrogen to form a cyclic moiety.

26. The compound of claim 16, wherein R$^8$ is hydrogen, alkyl, heteroalkyl, alkenyl, alkynyl, cycloalkyl, heterocycloalkyl, alkoxy, sulfonamido, thio, sulfoxide, sulfone, halo, cyano, hydroxy, or NR'R", wherein R' and R" are taken together with nitrogen to form a cyclic moiety.

27. The compound of claim 26, wherein R$^8$ is hydrogen or alkyl.

28. The compound of claim 27, wherein R$^8$ is alkyl substituted with one or more fluoro.

29. The compound of claim 1, wherein X is —CH$_2$—, —CH(CH$_3$)—, —CH(C$_6$H$_5$)—, or —CH(CH$_2$CH$_3$)—.

30. The compound of claim 29, wherein the CH carbon of —CH(CH$_3$)— or —CH(CH$_2$CH$_3$)— has a predominately (S) stereochemical configuration.

31. The compound of claim 1, wherein Y is absent, —O—, —N(R$^9$)—, N(R$^9$)C(R$^{10}$)$_2$—, or —S(=O)$_2$—.

32. The compound of claim 31, wherein R$^9$ and R$^{10}$ are independently hydrogen, methyl or ethyl.

33. The compound of claim 1, wherein X is —(CHR$^{10}$)$_z$—, is 1, Y is —N(R$^9$)—, and R$^9$ is hydrogen.

34. The compound of claim 1, wherein Y is —N(CH$_2$CH$_3$)CH$_2$— or —N(CH$_3$)CH$_2$—.

35. The compound of claim 1, wherein X—Y is —CH$_2$—N(CH$_3$)—, or —CH$_2$—N(CH$_2$CH$_3$)—.

36. The compound of claim 1, wherein W$_d$ is

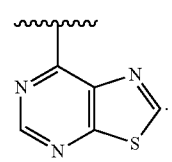 [SMILES: *c1ncnc2scnc12]

37. The compound of claim 1, wherein the compound of Formula (Ia) is a compound of Formula (V):

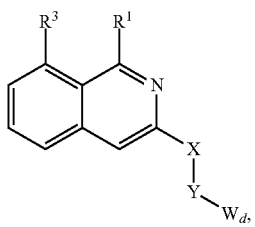

Formula (V)

or a pharmaceutically acceptable form thereof.

38. The compound of claim 37, or a pharmaceutically acceptable form thereof, wherein:

$R^1$ is $-(L)_n-R^{1'}$;

each L is —O—, —C(=O)—, —S(=O)$_2$—, —S—, or alkylene;

$R^{1'}$ is alkyl, hydroxy, aryl, heteroaryl, aralkyl, —(C=O)—$NR^{a1}R^{a2}$, or $NR^{a1}R^{a2}$;

$W_d$ is:

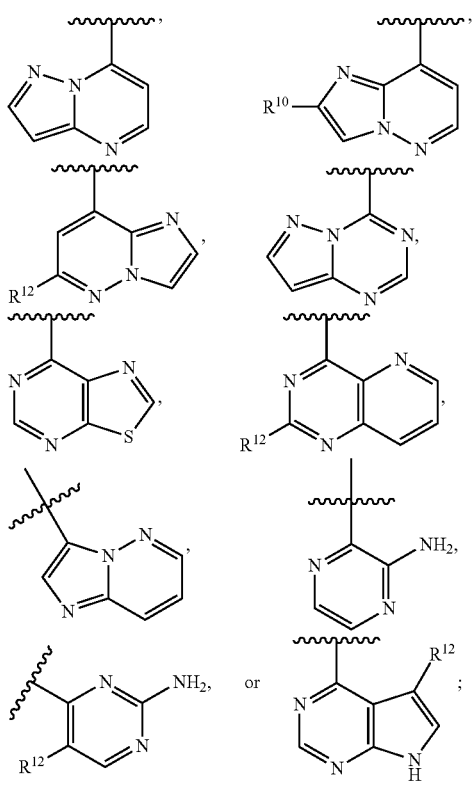

$R^{10}$ is hydrogen;

$R^{12}$ is hydrogen, halo, haloalkyl, cyano, amino, or amido; and n is 0, 1, 2, 3, or 4.

39. The compound of claim 38, wherein L is —O— or alkylene; and n is 0, 1, or 2.

40. A pharmaceutical composition comprising a compound according to claim 1, and one or more pharmaceutically acceptable excipients.

41. The compound of claim 1, wherein the compound of Formula (Ia) is:

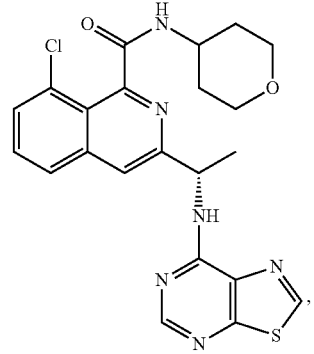 [SMILES: C[C@H](Nc1ncnc2scnc12)c1cc2cccc(Cl)c2c(C(=O)NC2CCOCC2)n1]

or a pharmaceutically acceptable form thereof.

42. The pharmaceutical composition of claim 40, wherein the compound is:

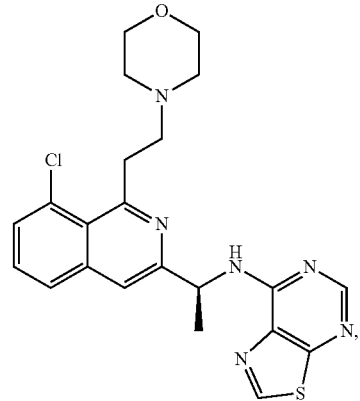

or a pharmaceutically acceptable form thereof.

43. The compound of claim 1, wherein the compound is:

72

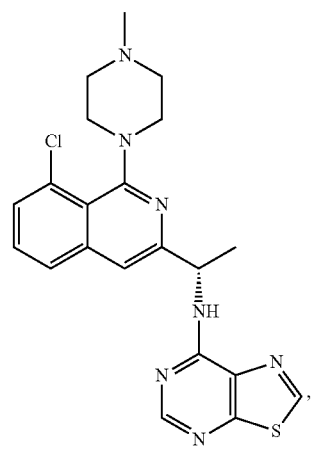

98

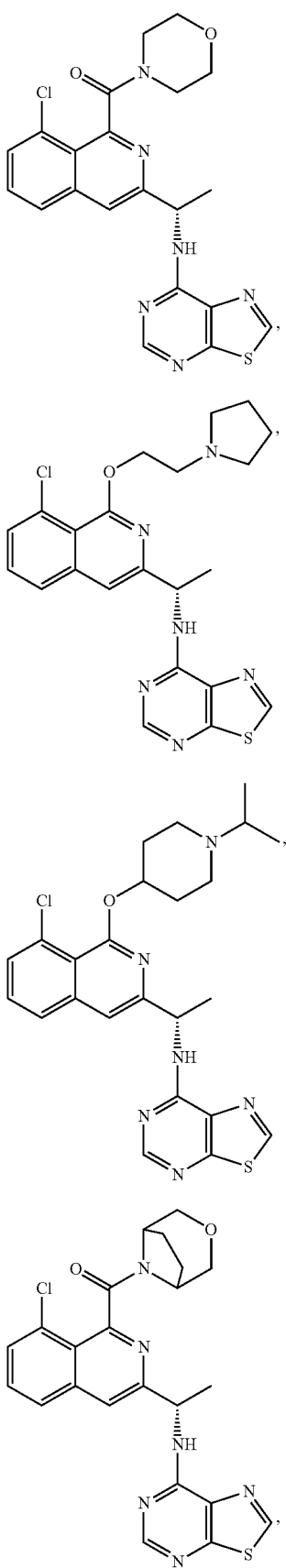
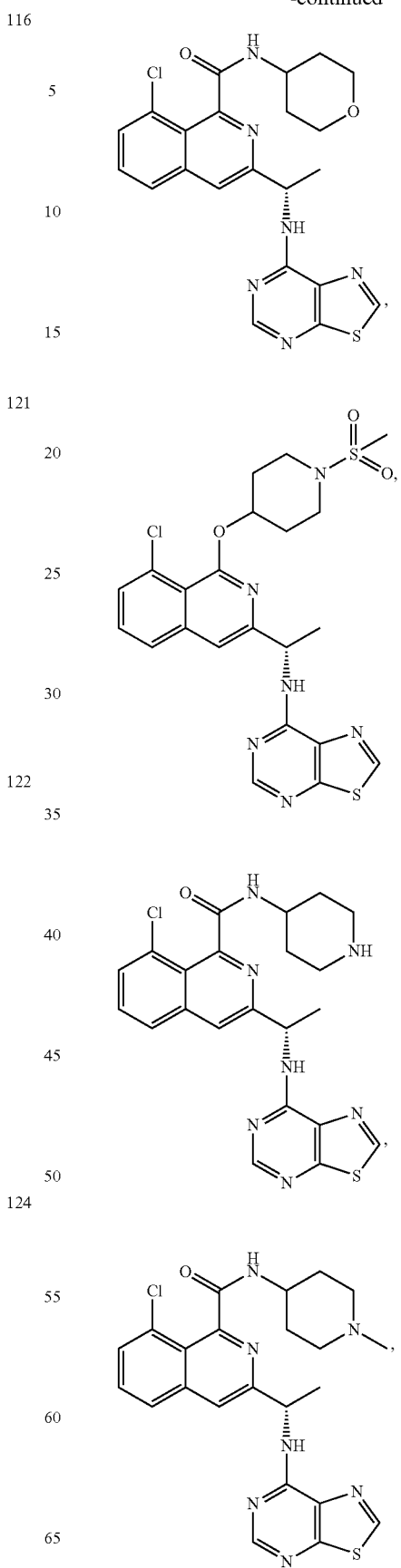

413
-continued
211 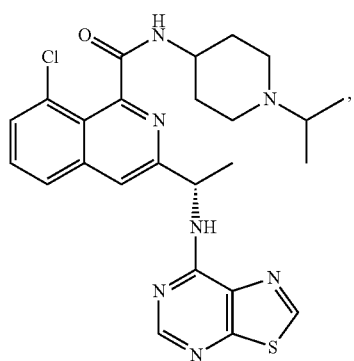
212 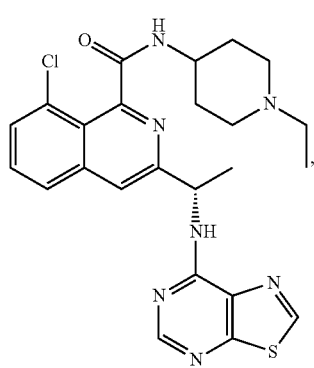
213 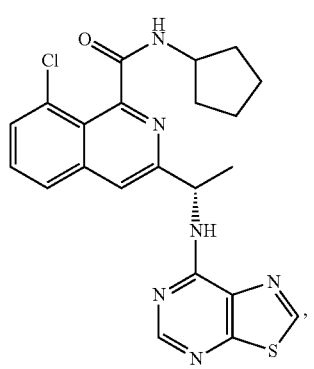
214 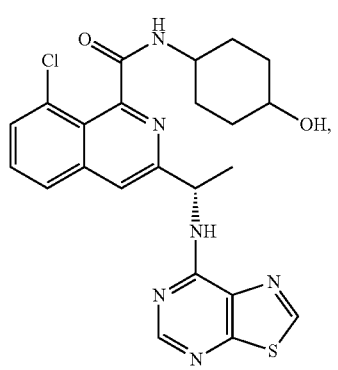
414
-continued
215 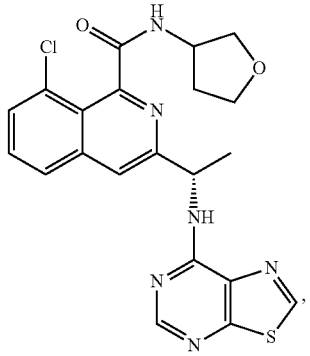
216 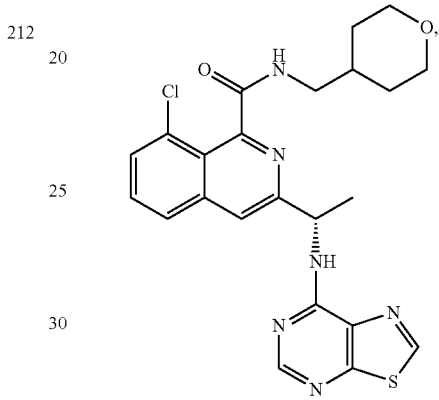
218 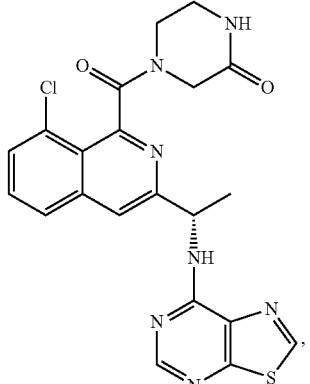
220 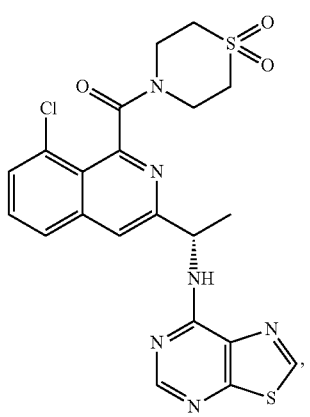

221 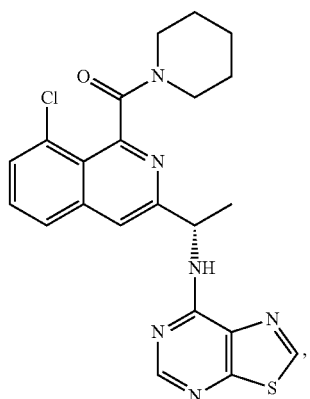
223 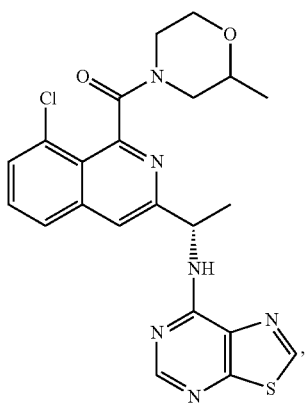
227 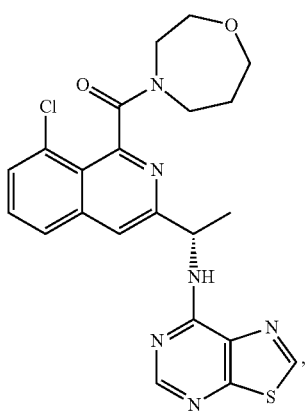
228
229 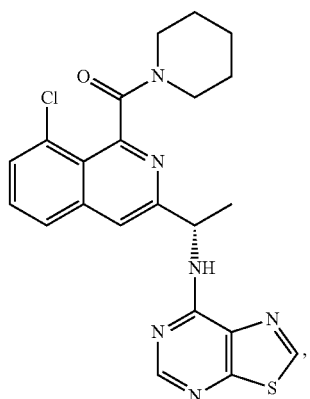
232 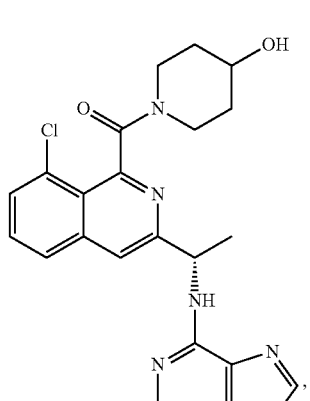
234
246

417
-continued
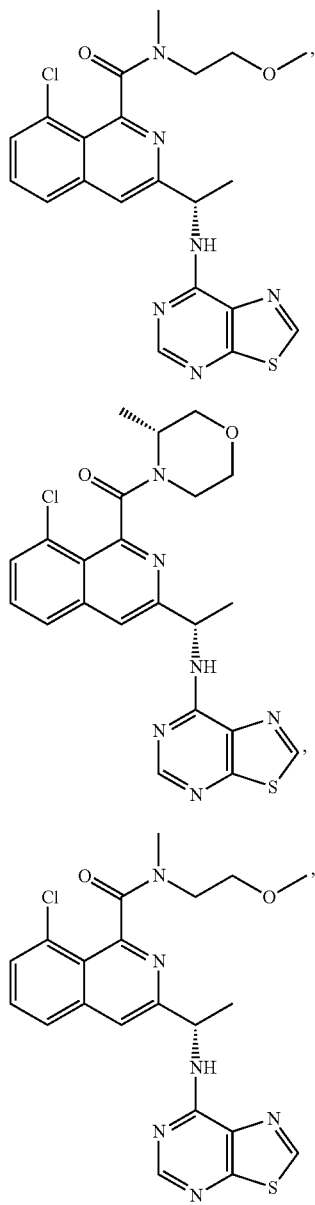
249
252
or
255
or a pharmaceutically acceptable form thereof.
44. The compound of claim 1, wherein the compound is:
105
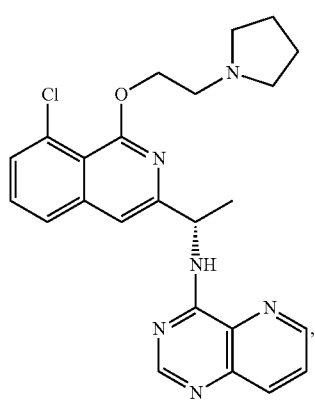
418
-continued
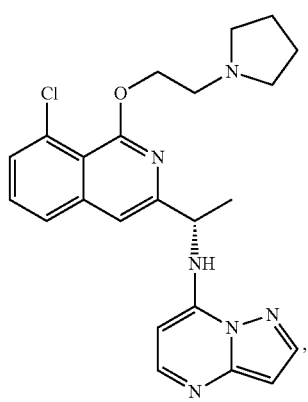
106
107
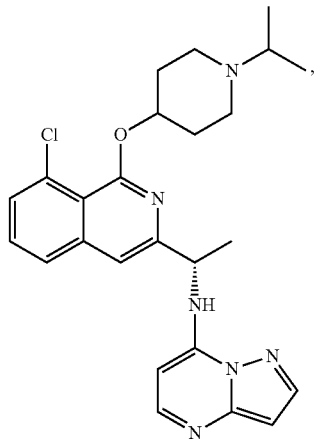
115
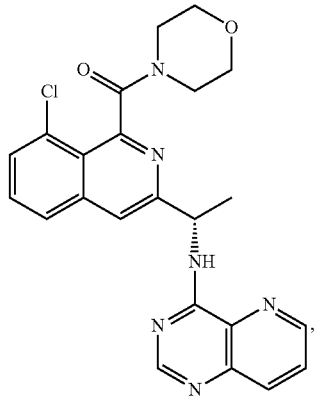

117
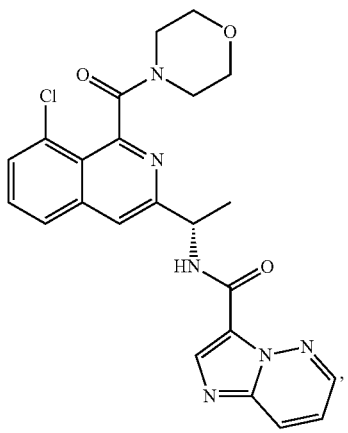
108
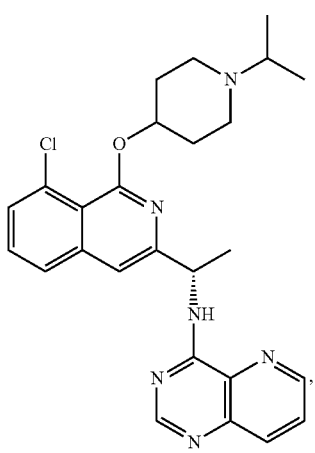
118
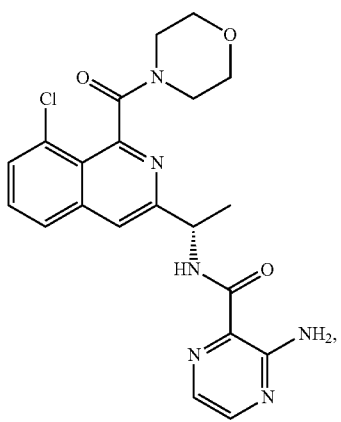
120
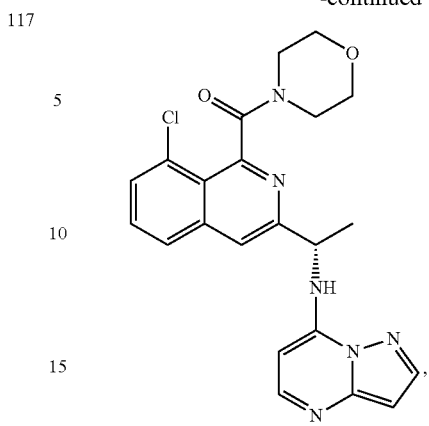
73
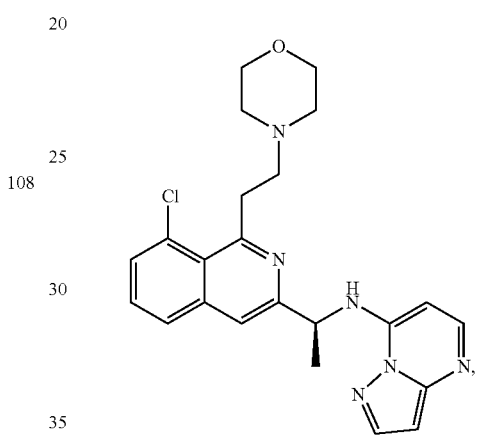
75
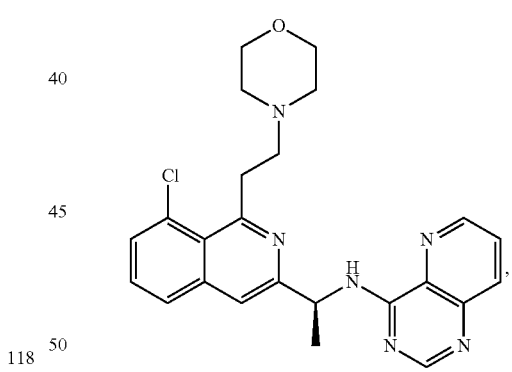
76
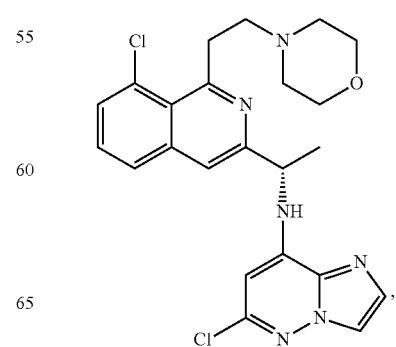

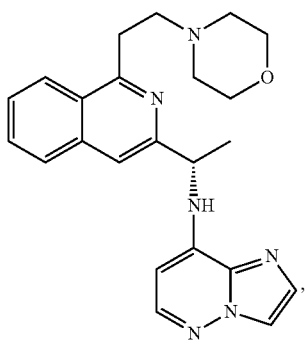
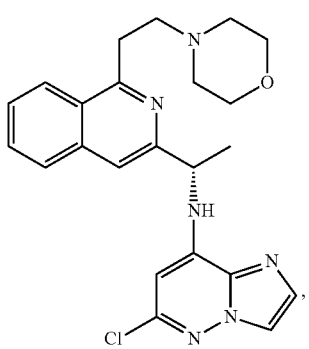
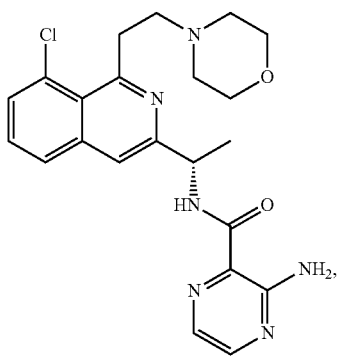
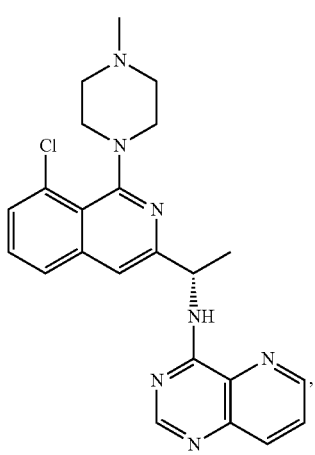
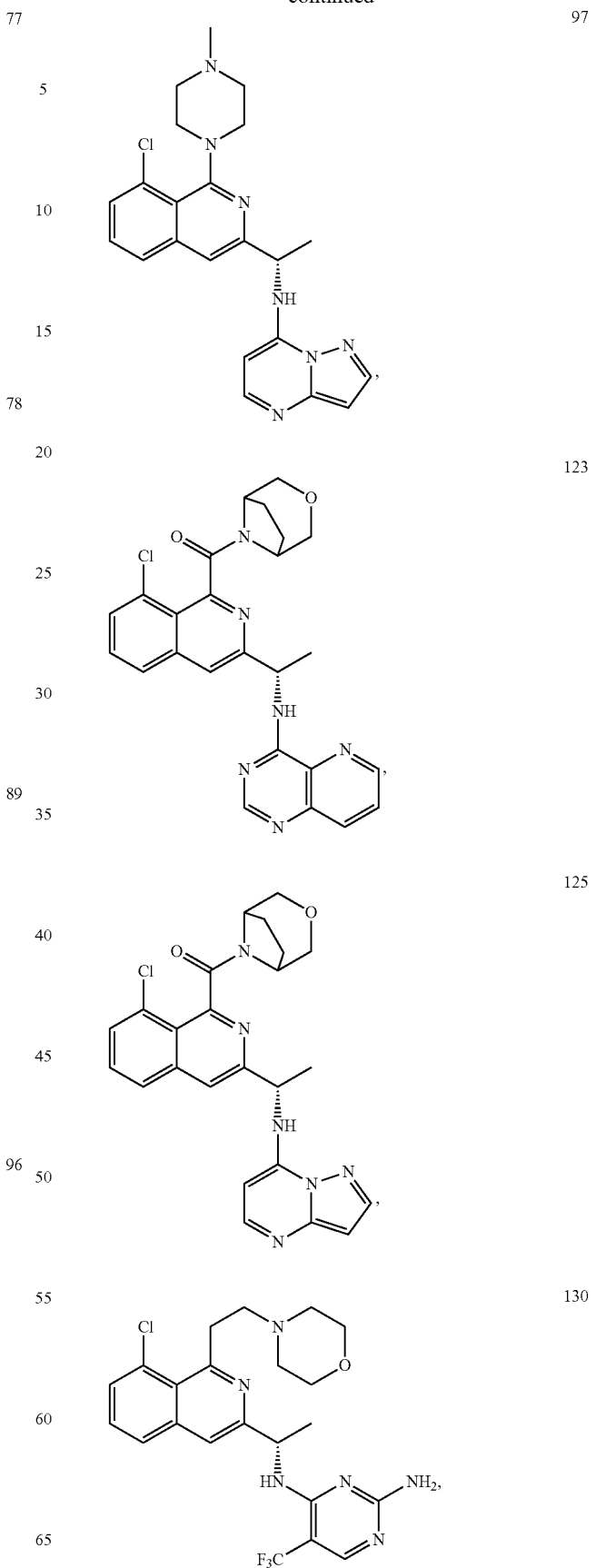

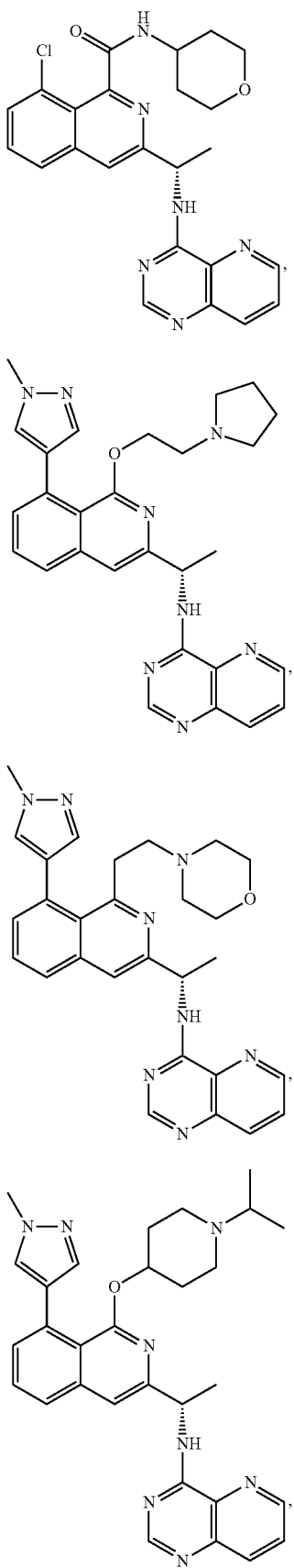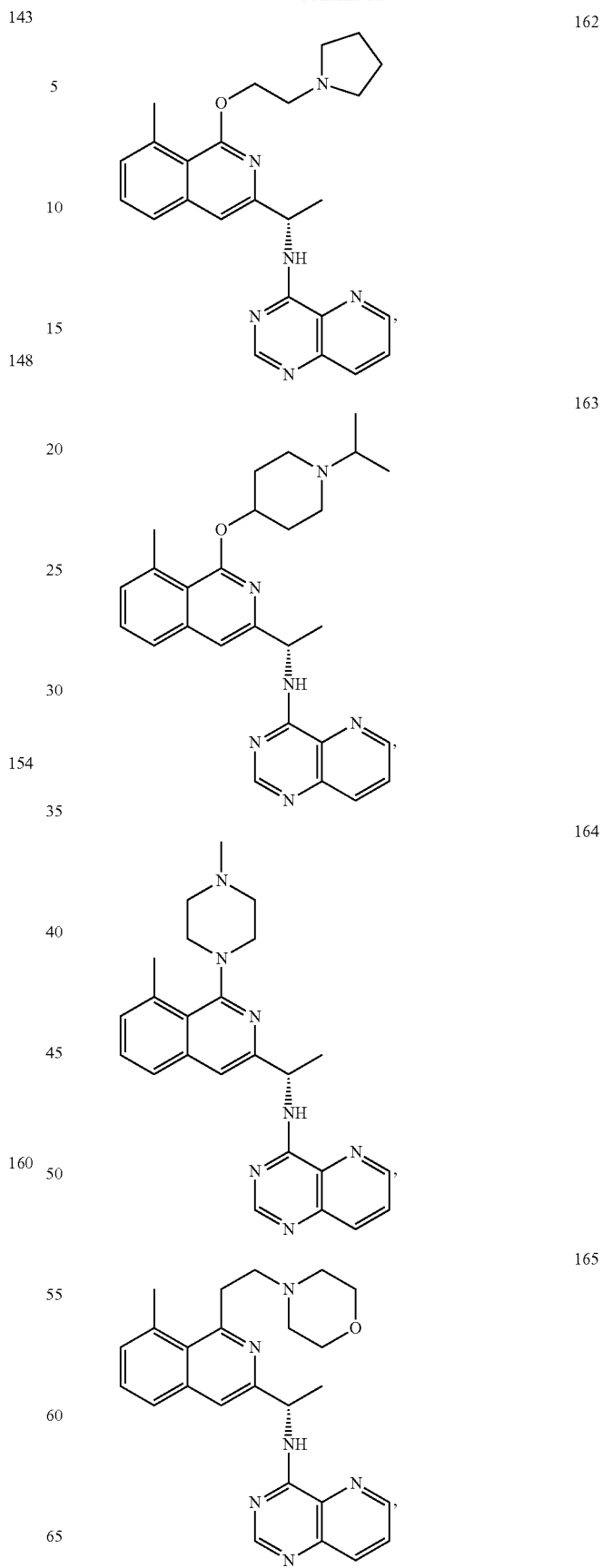

166 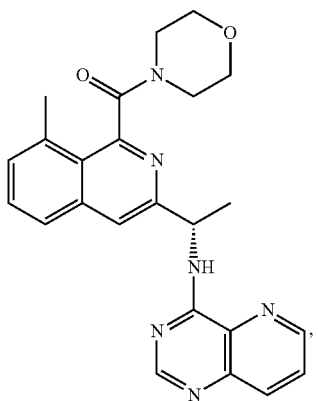
167 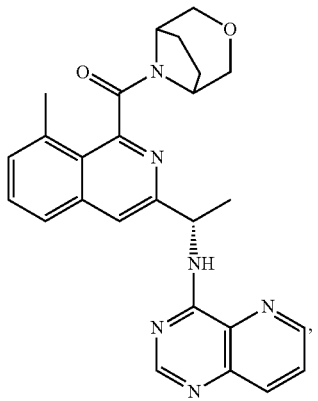
173 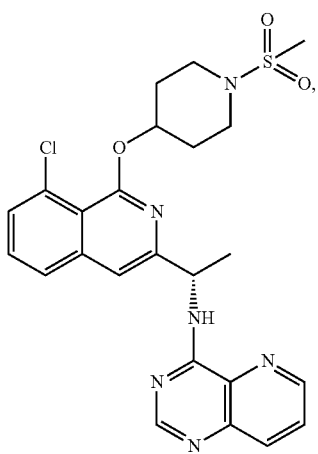
174 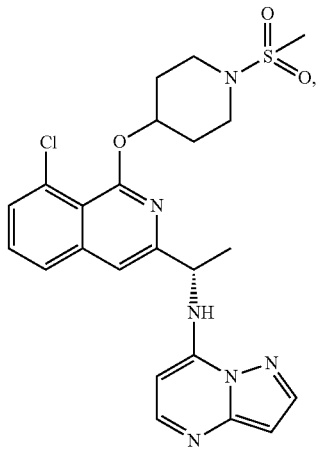
176 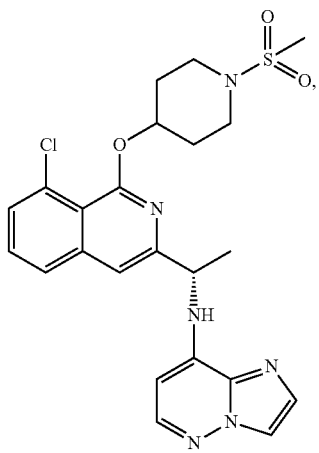
177 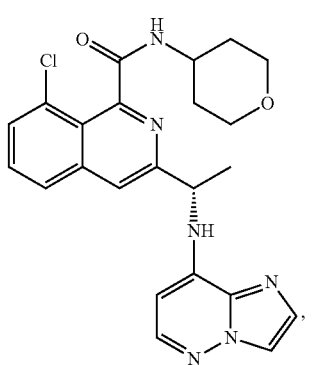
180

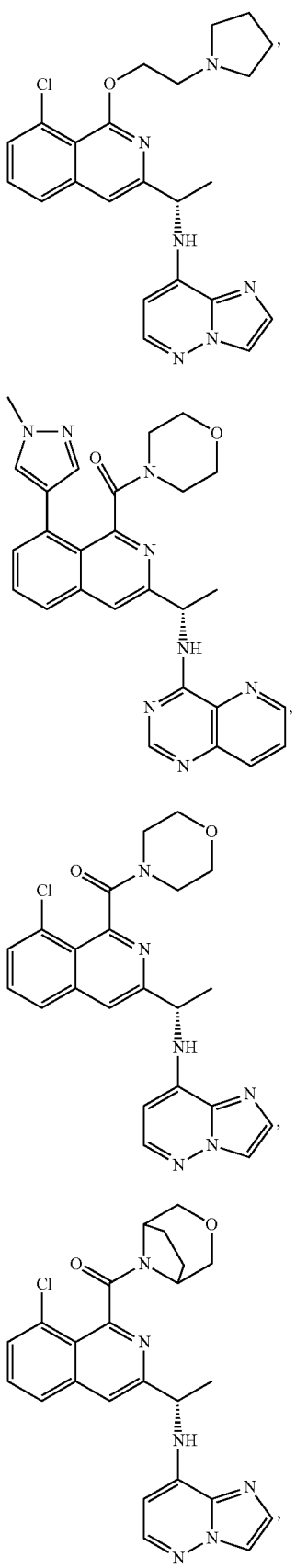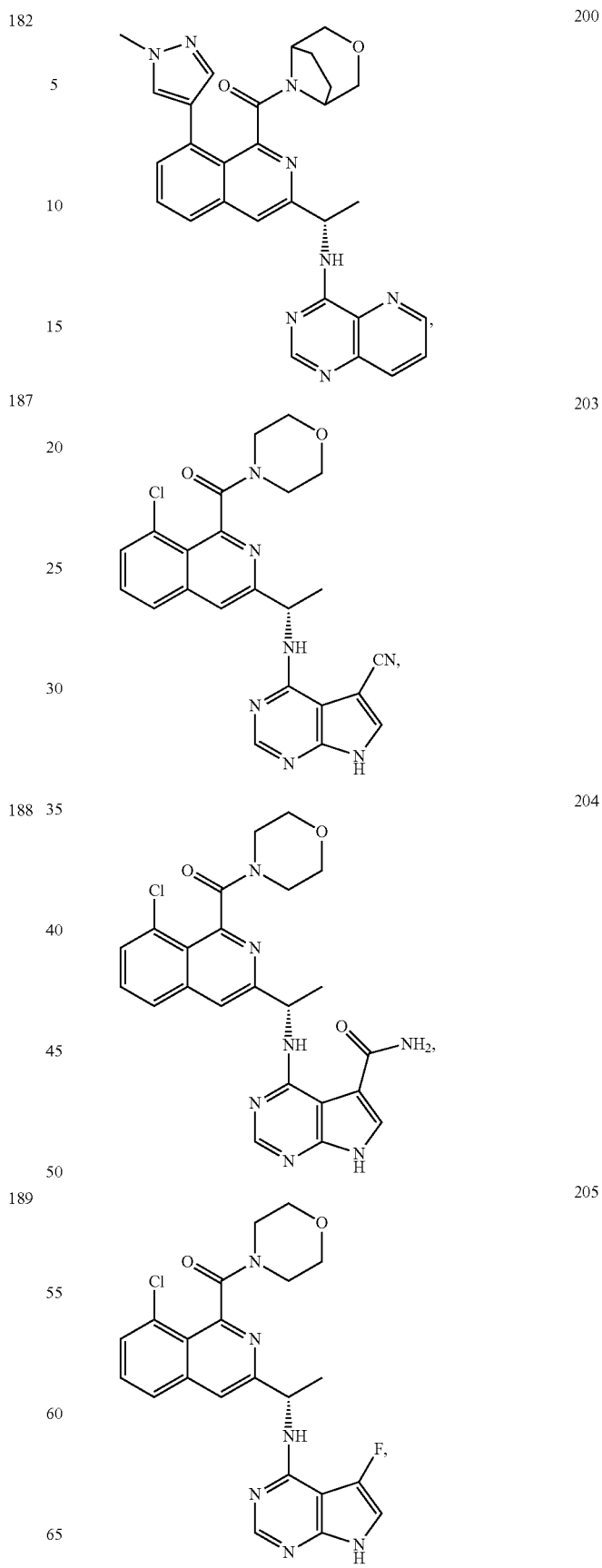

429
-continued
206
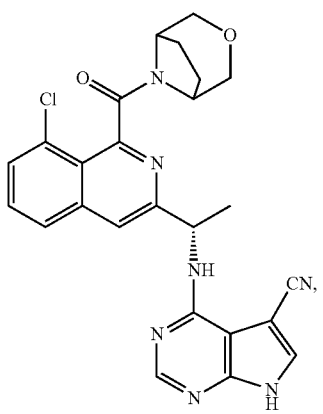
207
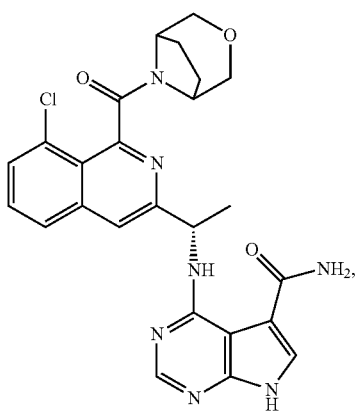
208
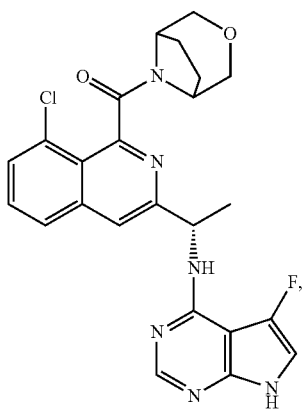
217
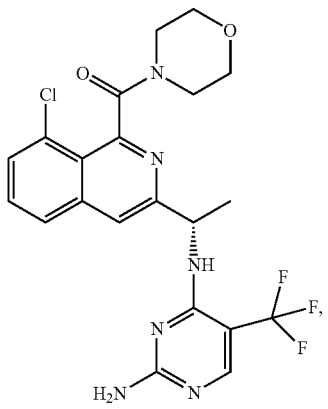
430
-continued
219
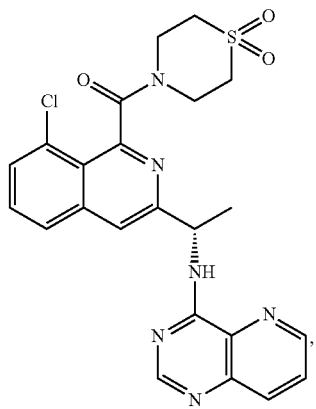
222
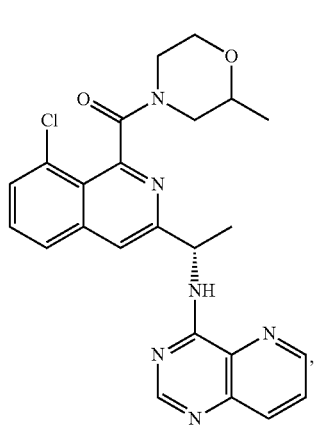
224
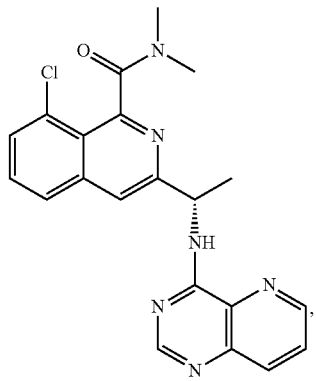
225
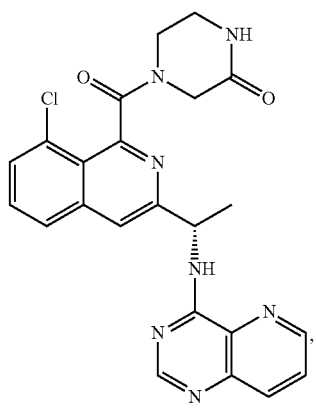

226
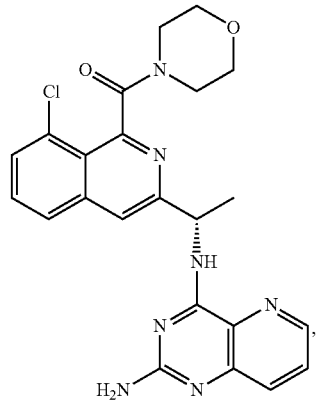
230
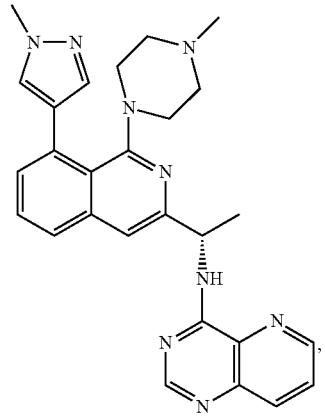
231
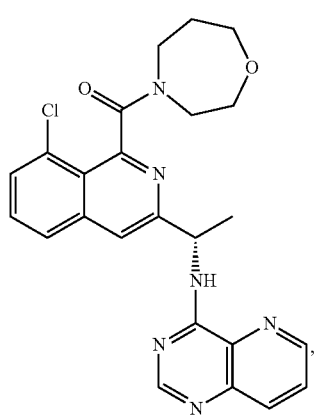
233
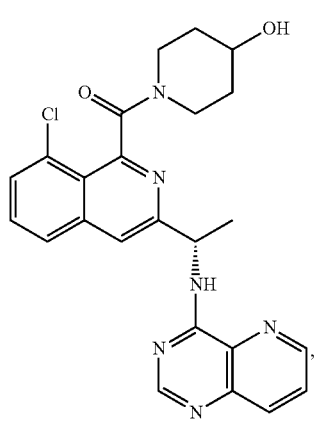
238
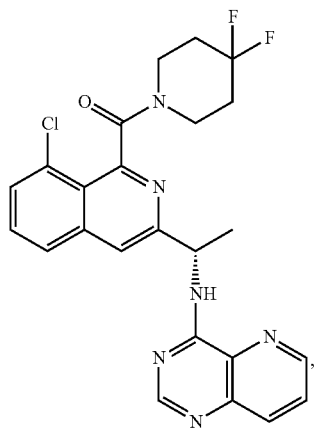
243
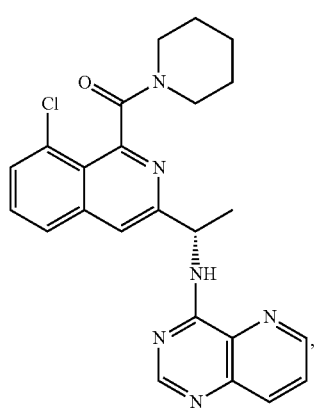
244
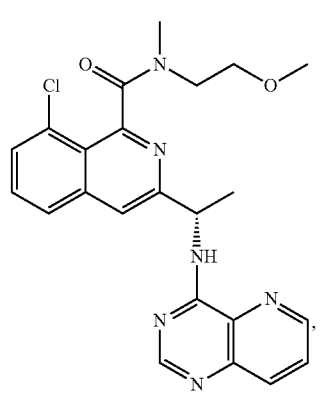
245
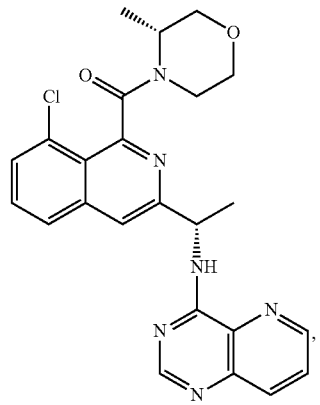

433
-continued
247
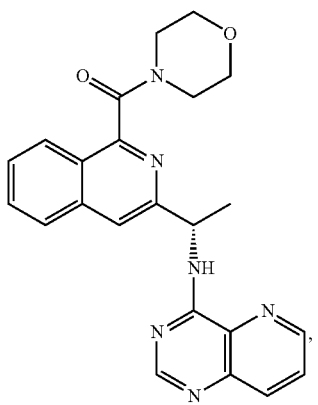
248
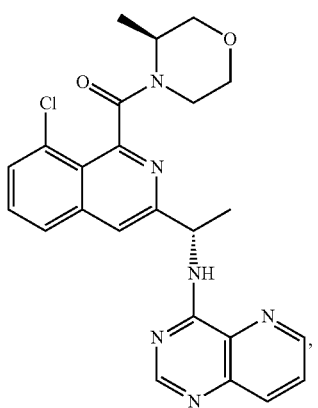
250
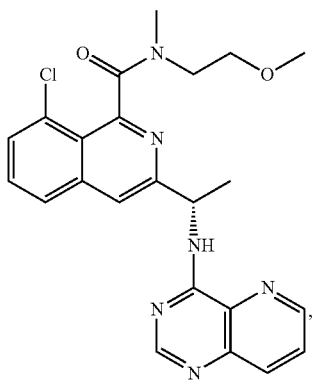
251
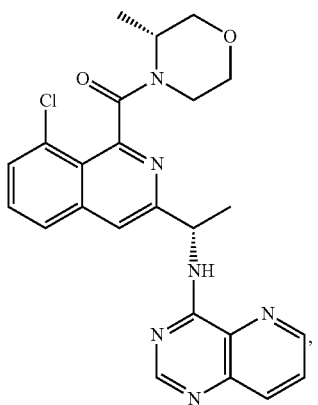
434
-continued
253
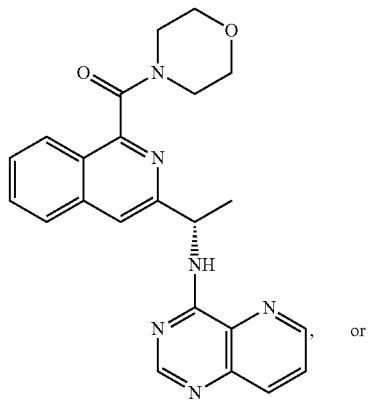, or
254
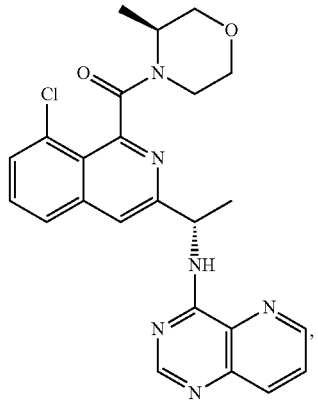,
or a pharmaceutically acceptable form thereof.
45. The compound of claim 1, wherein the compound is:
104
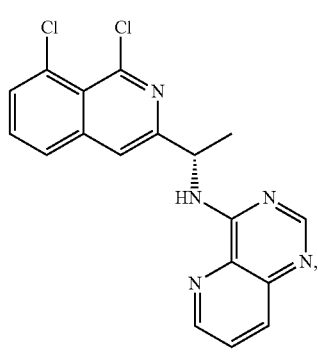,
152
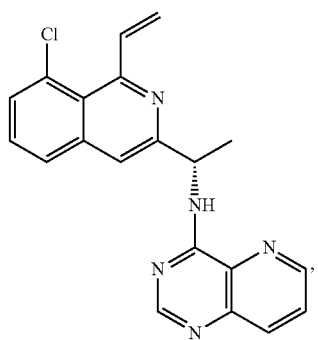, 435
-continued
153
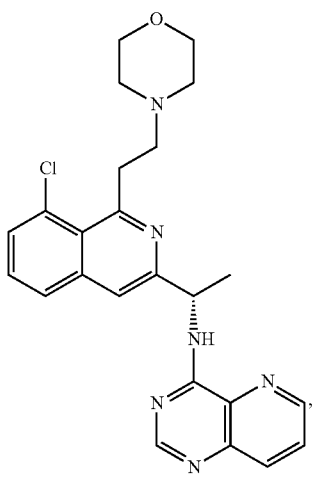
159
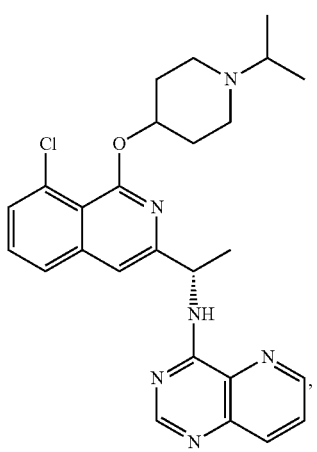
186
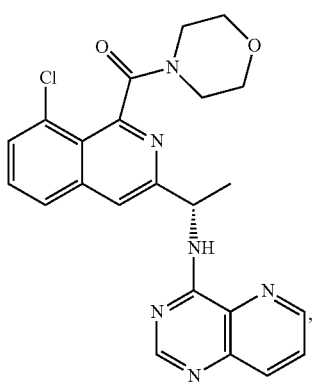
or
436
-continued
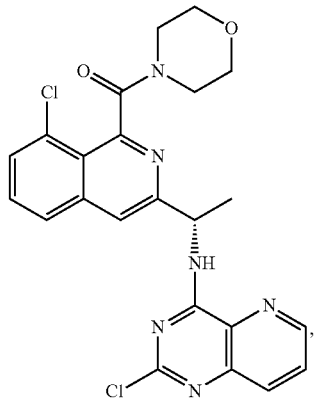
or a pharmaceutically acceptable form thereof.
46. A compound, which is:
119
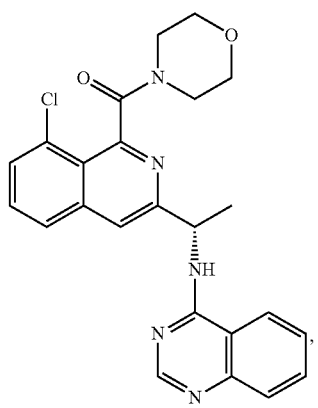
, or
74
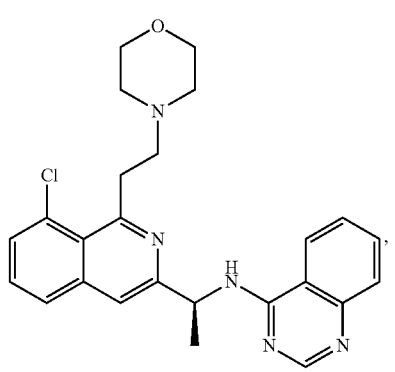
or a pharmaceutically acceptable form thereof.
47. The compound of claim 1, wherein $W_d$ is
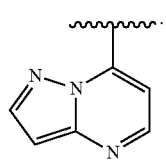 [SMILES: *c1ccnc2ccnn12]
237

48. The compound of claim 1, wherein $W_d$ is

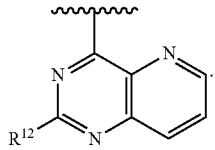

49. The compound of claim 1, wherein $W_d$ is

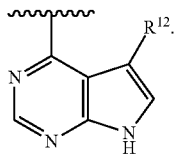

50. The compound of claim 1, wherein $W_d$ is

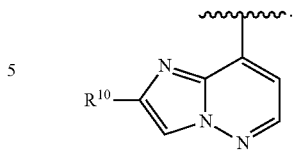

51. A pharmaceutical composition comprising a compound according to claim 43, and one or more pharmaceutically acceptable excipients.

52. A pharmaceutical composition comprising a compound according to claim 44, and one or more pharmaceutically acceptable excipients.

53. A pharmaceutical composition comprising a compound according to claim 45, and one or more pharmaceutically acceptable excipients.

54. A pharmaceutical composition comprising a compound according to claim 46, and one or more pharmaceutically acceptable excipients.

* * * * *

UNITED STATES PATENT AND TRADEMARK OFFICE
CERTIFICATE OF CORRECTION

PATENT NO. : 8,901,133 B2  
APPLICATION NO. : 13/293828  
DATED : December 2, 2014  
INVENTOR(S) : Ren et al.

Page 1 of 1

It is certified that error appears in the above-identified patent and that said Letters Patent is hereby corrected as shown below:

Claims

In column 408, lines 49–50 (part of claim 33), insert a -- ) -- before subscripted z and insert a -- z -- before the term "is 1" to read:

-- wherein X is –(CH($R^{10}$))$_z$-, z is 1 --

In column 409, line 17 (part of claim 38), insert the term -- -S(=O)-, -- before "-S(=O)$_2$-" to read:

-- each L is –O-, -C(=O)-, -S(=O)-, -S(=O)$_2$- --

In column 416 (part of claim 43), delete the last structure, *i.e.*, Compound 246.

In column 417 (part of claim 43), delete the first structure, *i.e.*, Compound 249.

In column 432 (part of claim 44), delete the last two structures, *i.e.*, Compounds 244 and 245.

In column 433 (part of claim 44), delete the first two structures, *i.e.*, Compounds 247 and 248.

Signed and Sealed this  
Twenty-eighth Day of June, 2016

Michelle K. Lee  
*Director of the United States Patent and Trademark Office*